US012630529B2

(12) United States Patent
Sathe et al.

(10) Patent No.: US 12,630,529 B2
(45) Date of Patent: May 19, 2026

(54) GCN2 MODULATOR COMPOUNDS

(71) Applicant: ALESTA THERAPEUTICS BV, Leiden (NL)

(72) Inventors: Balaji Dashrath Sathe, New Delhi (IN); Brahmam Pujala, New Delhi (IN); Gonzalo Andrés Ureta Díaz, Santiago (CL); Sebastian Bernales, San Francisco, CA (US); Jennifer Borthwick, Hertfordshire (GB)

(73) Assignee: Alesta Therapeutics BV, Leiden (NL)

( * ) Notice: Subject to any disclaimer, the term of this patent is extended or adjusted under 35 U.S.C. 154(b) by 946 days.

(21) Appl. No.: 17/796,449

(22) PCT Filed: Feb. 17, 2021

(86) PCT No.: PCT/EP2021/053928

§ 371 (c)(1),
(2) Date: Jul. 29, 2022

(87) PCT Pub. No.: WO2021/165346

PCT Pub. Date: Aug. 26, 2021

(65) Prior Publication Data

US 2023/0143059 A1 May 11, 2023

(30) Foreign Application Priority Data

Feb. 17, 2020 (GB) .................................... 2002144
May 14, 2020 (GB) .................................... 2007163

(51) Int. Cl.

| | |
|---|---|
| ***C07D 401/14*** | (2006.01) |
| ***C07D 403/04*** | (2006.01) |
| ***C07D 409/12*** | (2006.01) |
| ***C07D 417/12*** | (2006.01) |
| ***C07D 471/04*** | (2006.01) |
| ***C07D 487/04*** | (2006.01) |

(52) U.S. Cl.
CPC ......... *C07D 401/14* (2013.01); *C07D 403/04* (2013.01); *C07D 409/12* (2013.01); *C07D 417/12* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 7,501,513 | B2 | 3/2009 | Waer |
| 2013/0324516 | A1 | 12/2013 | Chen et al. |

FOREIGN PATENT DOCUMENTS

| | | | | |
|---|---|---|---|---|
| CA | 2407593 | A1 | 11/2001 | |
| CN | 103814027 | A | 5/2014 | |
| CN | 104507933 | A | 4/2015 | |
| CN | 104507942 | A | 4/2015 | |
| CN | 109311894 | A | 2/2019 | |
| CN | 109790122 | | 6/2019 | |
| EP | 3498693 | A1 | 6/2019 | |
| WO | 2013016197 | A1 | 1/2013 | |
| WO | WO-2014023385 | A1 * | 2/2014 | ............. A61P 35/04 |
| WO | 2017220477 | A1 | 12/2017 | |
| WO | 2018222918 | A1 | 12/2018 | |
| WO | 2020210828 | A1 | 10/2020 | |

OTHER PUBLICATIONS

Angele, M.K. et al. (Jan. 1999). "L-Arginine. A Unique Amino Acid for Restoring the Depressed Macrophage Functions after Trauma-Hemorrhage," J. Trauma 46(1); 34-41, 15 pages.
Bertaggia, E. et al. (2012, e-pub. Nov. 16, 2011). "Posttranslational Modifications Control FoxO3 Activity During Denervation," Am. J. Physiol. Cell Physiol. 302:C587-C596.
Boasso, A. et al. (Apr. 15, 2007, e-pub. Dec. 7, 2006). "HIV Inhibits CD4+ T-Cell Proliferation by Inducing Indoleamine 2,3-Doxygenase in Plasmacytoid Dendritic Cells," Blood 109(8):3351-3359.
Bronte, V. et al. (Aug. 2005). "Regulation of Immune Responses by L-Arginine Metabolism," Nat. Rev. Immunol. 5(8):641-654.
Cederbaum, S.D. et al. (Apr. 2004). "Arginases I and II: Do Their Functions Overlap?," Mol. Gent. Metab. 81(Suppl. 1):S38-S44.
Chen, Y. et al. (Sep. 2012). "Activating Transcription Factor 4 Mediates Hyperglycemia-Induced Endothelial Inflammation and Retinal Vascular Leakage Through Activation of STAT3 in a Mouse Model of Type 1 Diabetes," Diabetologia 55(9):2533-2545, 24 pages.
Costa-Mattioli, M. et al. (Aug. 25, 2005). "Translational Control of Hippocampal Synaptic Plasticity and Memory by the eIF2α Kinase, GCN2," Nature 436(7054);1166-1173., 11 pages.
De Souza Sales, J. et al. (2011). "The Role of Indoleamine 2, 3-Dioxygenase in Lepromatous leprosy Immunosuppression," Clinical and Experimental Immunology 165:251-263.
Feng, W. et al. (Jan. 2019). "GCN2 Deficiency Ameliorates Cardiac Dysfunction in Diabetic Mice by Reducing Lipotoxicity and Oxidative Stress," Free Radic Biol Med. 130:128-139.

(Continued)

*Primary Examiner* — Adam C Milligan
*Assistant Examiner* — Jed A Kucharczk
(74) *Attorney, Agent, or Firm* — MORRISON & FOERSTER LLP

(57) ABSTRACT

The disclosures herein relate to novel compounds of Formula (1): or a salt thereof, wherein X, Y, $R^1$, $R^2$, $R^3$, $R^4$ and $R^5$ are defined herein, and their use in treating, preventing, ameliorating, controlling or reducing the risk of disorders associated with General Control Nondepressible 2 (GCN2).

(1)

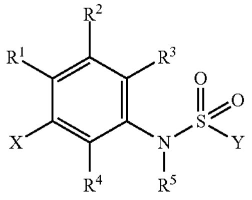

27 Claims, 7 Drawing Sheets

(56) References Cited

OTHER PUBLICATIONS

Fougeray, S. et al. (Sep. 15, 2012, e-pub. Aug. 15, 2012). "Tryptophan Depletion and the Kinase GCN2 Mediate IFN-γ-Induced Autophagy," J. Immunol. 189(6):2954-2964.
Gelin, C. et al. (2021). "Novartis AG: Tetrahydropyrido-Pyridine and Tetahydropyrido-Pyrimidine Compounds and Use Thereof as CSA receptor Modulations, Patent WO-2013/16197-A1," Reaxys 2 pages.
Grohmann, U. et al. (May 2003). "Tolerance, DCs and Tryptophan Much Ado About IDO," Trends in Immunology 24 (5):242-248.
Guo, Y. et al. (Nov. 2018). "GCN2 Deficiency Protects Mice from Denervation-Induced Skeletal Muscle Atrophy via Inhibiting FoxO3a Nuclear Translocation," Protein Cell 9(11):966-970.
International Preliminary Report on Patentability mailed on Sep. 1, 2022, for PCT Application No. PCT/ EP2021/053928, filed on Feb. 17, 2021, 12 pages.
International Search Report and Written Opinion mailed on Apr. 21, 2021, for PCT Application No. PCT/EP2021/053928, filed on Feb. 17, 2021, 22 pages.
Liu, H. et al. (Feb. 2014, e-pub. Nov. 18, 2013). "GCN2-Dependent Metabolic Stress Is Essential for Endotoxemic Cytokine Induction and Pathology," Molecular and Cellular 234(3):428-438.
Liu, S. et al. (Oct. 2018). "GCN2 Deficiency Protects Against High Fat Diet Induced Hepatic Steatosis and Insulin Resistance in Mice," Biochimica et Biphysica Acta (BBA)—Molecular Basis of Diesease1864(10):3257-3267. (Abstract).
Longchamp, A. et al. (Mar. 2018). "Amino Acid Restriction Triggers Angiogenesis via GCN2/ATF4 Regulation of VEGF and H2S Production," Cell 173(1):117-129, 35 pages.
Lough, L. et al (Jan. 1, 2018.e-pub. Sep. 28, 2018). "Triazolo[4,5-d]pyrimidines as Validated General Control Nonderepressible 2 (GCN2) Protein Kinase Inhibitors Reduce Growth of Leukemia Cells," Computational and Structural Biotechnology Journal 16:350-360.
Lu, Z. et al. (Jan. 2014). "Loss of the elF2α Kinase GCN2 Protects Mice from Pressure Overload Induced Congestive Heart Failure Without Affecting Ventricular Hypertrophy," Hypertension 63(1):128-135, 19 pages.
Makala, L.H.C et al. (Mar. 1, 2011). "Leishmania major Attenuates Host Immunity by Stimulating Local Indoleamine 2,3-Dioxygenase Expression," Journal of Infectious Diseases 203:715-725.
Masuoka, H.C. et al. (Feb. 1, 2002). "Targeted Disruption of the Activating Transcription Factor 4 Gene Results in Severe Fetal Anemia in Mice," Blood 99(3):736-745.
Mellor, A.J. et al. (Oct. 2004). "Ido Expression by Dendritic Cells: Tolerance and Tryptophan Catabolism" Nat. Rev. Immunol. 4(10):762-774.
Munn, D.H., et al. (May 2005). "GCN2 kinase in T Cells Mediates Proliferative Arrest and Anergy Induction in Response to Indoleamine 2,3-Dioxygenase," Immunity 22(5):633-642.
Nagasawa, I. et al. (2017). "BRAF-Mutated Cells Activate GCN2-Mediated Integrated Stress Response as a Cytoprotective Mechanism in Response to Vemurafenib," Biochem. Biophys. Res. Commun. 482(4):1491-1497.
Nakamura, A. et al. (2018, e-pub. Jul. 30, 2018). "Inhibition of GCN2 Sensitizes ASNS-Low Cancer Cells to Asparaginase by Disrupting the Amino Acid Response," PNAS 115(33):E7776-E7785.
Ohta, K. et al. (Apr. 2010). "Autophagy Impairment Stimulates PS1 Expression and Gamma-Secretase Activity," Autophagy 6(3):345-352. (Abstract).
O'Connor, T. et al. (Dec. 26, 2008)." Phosphorylation of the Translation Initiation Factor elF2α Increases BACE1 Levels and Promotes Amyloidogenesis," Neuron. 60(6):988-1009, 42 pages.
Rodriguez, P.C. et al. (2007). "L-Arginine Availability Regulates T-Lymphocyte Cell-Cycle Progression," Blood 109:1568-1573.
Rodriguez, P.C. et al. (Aug. 2003). "L-Arginine Consumption by Macrophages Modulates the Expression of CD3 Zeta Chain in T Lymphocytes," J. Immunol 171(3):1232-1239. (Abstract).
Sandri, M. et al. (Apr. 30, 2004). "Foxo Transcription Factors Induce the Atrophy-Related Ubiquitin Ligase Atrogin-1 and Cause Skeletal Muscle Atrophy," Cell 117(3):399-412, 22 pages.
Terwiliger, T. et al. (2017, e-pub. Jun. 30, 2017). "Review. Acute Lymphoblastic Leukemia: a Comprehensive Review and 2017 Update," Blood Cancer Journal 7:e577, 12 pages.
Tsuru, A. et al. (Apr. 7, 2016). "Novel Mechanism of Enhancing IRE1α-XPB1 Signaling via the PERK-ATF4 Pathway," Scientific Reports 6:24217, 8 pages.
Wang, S-F. et al. (Oct. 29, 2018). "Activated Integrated Stress Response Induced by Salubrinal Promotes Cisplatin Resistance in Human Gastric Cancer Cells via Enhanced xCT Expression and Glutathione Biosynthesis," Int. J. Mol. Sci. 19:3389, 19 pages.
Wang, Y. et al. (2013). "Amino Acid Deprivation Promotes Tumor Angiogenesis Through the GCN2/ATF4 Pathway," Neoplasia 15:989-997.
Wei, S-H. et al. (2014). "Disturbance of Autophagy Lysosome Signaling Molecule Expression in Human Gastric Adenocarcinoma," Oncology Letters 7:635-640.
Xu, X. et al. (2013). "GCN2 in the Brain Programs PPARc2 and Triglyceride Storage in the Liver during Perinatal Development in Response to Maternal Dietary Fat," Plos One 8(10):375917, 14 pages.
Ye, J. et al. (2010, e-pub. Apr. 7, 2010). "The GCN2-ATF4 Pathway is Critical for Tumour Cell Survival and Proliferation in Response to Nutrient Deprivation," The EMBO Journal 29(12):2082-2096.
Zea, A.H. et al. (Nov.-Dec. 2004—e-pub. Feb. 23, 2005). "L-Arginine Modulates CD3zeta Expression and T Cell Function in Activated Human T Lymphocytes," Cell Immunol. 232(1-2):21-31.
Zhang, P. et al. (Oct. 2002). "The GCN2 elF2α Kinase Is Required for Adaptation to Amino Acid Deprivation in Mice," Molecular and Cellular Biology 22(19):6681-6688.
Zhang, S.X. et al. (Mar. 2015). "The Unfolded Protein Response in Retinal Vascular Diseases: Implications and Therapeutic Potential Beyond Protein Folding," Prog. Retin Eye Res. 0:111-131, 48 pages.
Zhong, Y. et al. (Feb. 2012). "Activation of Endoplasmic Reticulum Stress by Hyperglycemia Is Essential for Müller Cell-Derived Inflammatory Cytokine Production in Diabetes," Diabetes 61:492-504.

* cited by examiner

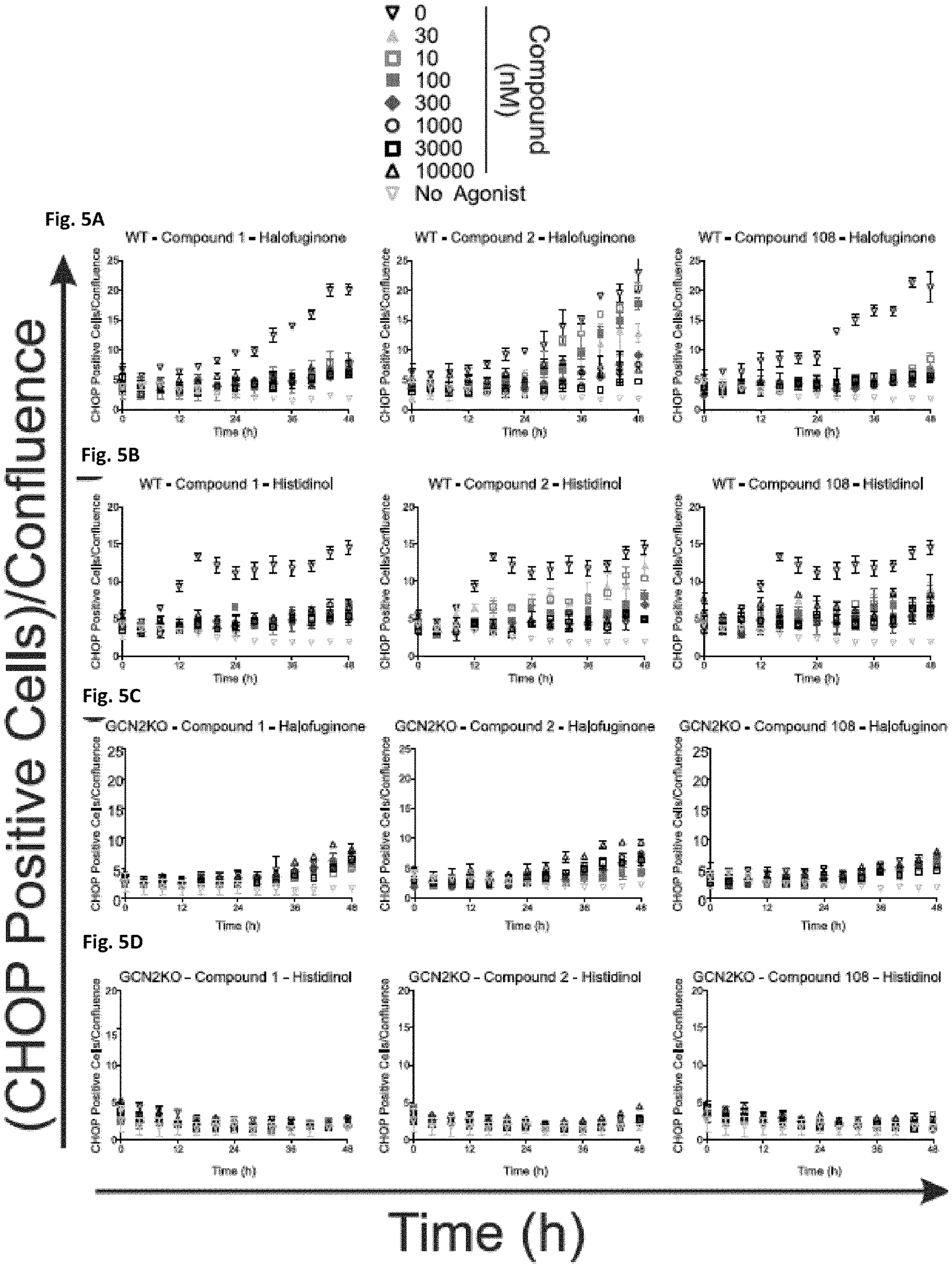

0
30
10
100
300
1000
3000
10000
No Agonist
Compound (nM)
Fig. 5A
WT - Compound 1 - Halofuginone
WT - Compound 2 - Halofuginone
WT - Compound 108 - Halofuginone
Fig. 5B
WT - Compound 1 - Histidinol
WT - Compound 2 - Histidinol
WT - Compound 108 - Histidinol
Fig. 5C
GCN2KO - Compound 1 - Halofuginone
GCN2KO - Compound 2 - Halofuginone
GCN2KO - Compound 108 - Halofuginon
Fig. 5D
GCN2KO - Compound 1 - Histidinol
GCN2KO - Compound 2 - Histidinol
GCN2KO - Compound 108 - Histidinol
CHOP Positive Cells/Confluence
Time (h)
(CHOP Positive Cells)/Confluence
Time (h)

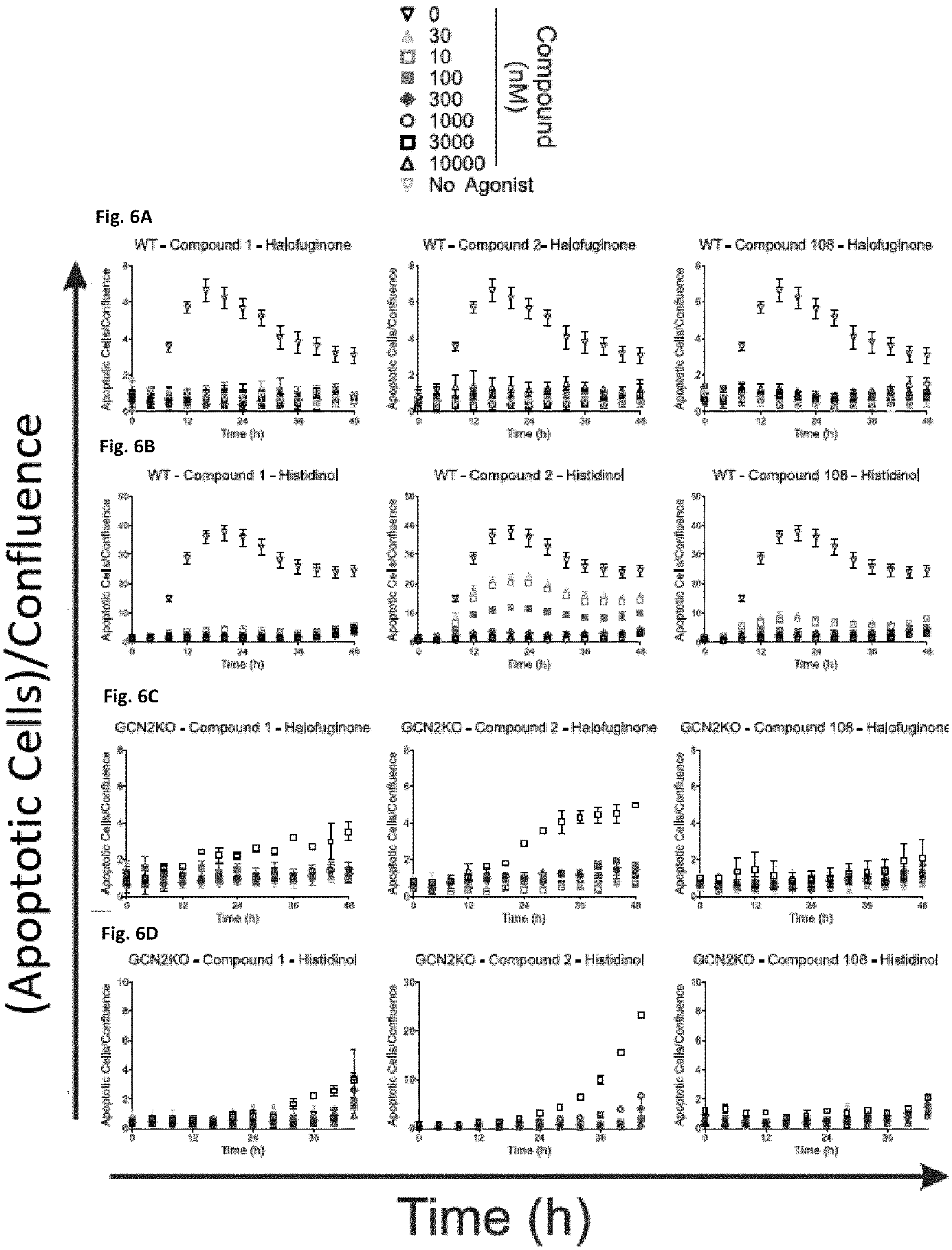
0
30
10
100
300
1000
3000
10000
No Agonist
Compound (nM)
Fig. 6A
WT - Compound 1 - Halofuginone
WT - Compound 2- Halofuginone
WT - Compound 108 - Halofuginone
Fig. 6B
WT - Compound 1 - Histidinol
WT - Compound 2 - Histidinol
WT - Compound 108 - Histidinol
Fig. 6C
GCN2KO - Compound 1 - Halofuginone
GCN2KO - Compound 2 - Halofuginone
GCN2KO - Compound 108 - Halofuginone
Fig. 6D
GCN2KO - Compound 1 - Histidinol
GCN2KO - Compound 2 - Histidinol
GCN2KO - Compound 108 - Histidinol
Apoptotic Cells/Confluence
Time (h)
(Apoptotic Cells)/Confluence
Time (h)

GCN2 MODULATOR COMPOUNDS

CROSS REFERENCE TO RELATED APPLICATIONS

This application is a national stage application under 35 U.S.C. § 371 of International Application No. PCT/EP2021/053928, filed internationally on Feb. 17, 2021, which claims priority benefit of GB Patent Application Nos. 2002144.0, filed Feb. 17, 2020, and 2007163.5, filed May 14, 2020. The disclosures of those applications are hereby incorporated herein by reference in their entirety.

FIELD OF THE INVENTION

This application relates to novel compounds and their use as General Control Nondepressible 2 (GCN2) modulators. Compounds described herein may be useful in the treatment or prevention of diseases in which GCN2 is involved. The application is also directed to pharmaceutical compositions comprising these compounds and the manufacture and use of these compounds and compositions in the prevention or treatment of such diseases in which GCN2 is involved.

BACKGROUND OF THE INVENTION

Diverse cellular conditions and stresses activate a widely conserved signalling pathway termed the Integrated Stress Response (ISR) pathway. The activation of ISR can trigger cell-cycle arrest, differentiation, amino acid biosynthetic and transport pathways, compensatory adaptation, or apoptosis, depending on the cell type and the initiating stress.
General Control
Nonderepressible 2 (GCN2) is one of four stress kinases of the ISR pathway that senses amino acid availability and controls gene expression in response to amino acid deprivation, UV-irradiation, viral infection, proteasome inhibition, hypoxia, glucose deprivation and oxidative stress. In mammals, GCN2 is also called EIF2AK4 (eukaryotic translation initiation factor 2 alpha kinase 4).

GCN2 harbours a eukaryotic kinase domain, a pseudokinase domain and a histidyl-tRNA synthetase (HisRS)-related domain, which binds uncharged tRNAs with higher affinity than it does charged tRNAs. Sequences at both the N- and C-termini of GCN2 have been shown to be important for efficient sensing of the starvation signal. Lysine residues in the C-terminus have also been shown to be required for tRNA binding and kinase activity and residues at the tip of the C-terminal region confer ribosome binding capabilities on GCN2, which are important for translational control.

In eukaryotes, the mechanism for recognizing indispensable amino acid deficiency follows the conserved general control system, wherein uncharged transfer RNA induces first the autophosphorylation of GCN2 and then the phosphorylation of eukaryotic initiation factor 2α (eIF2α), leading to reduced gdlobal protein synthesis and thus to reduced overall utilization of amino acids. Simultaneously, a group of stress-responsive mRNAs with upstream open reading frames (uORF) that include ATF4, CHOP, GADD34 and the (β-secretase BACE-1, are translated more efficiently when eIF2α is phosphorylated, which in turn increases amino acid biosynthetic and transport pathways. GCN2-mediated translational program also controls host responses to infection, responses to immunization, inflammation and other physiological and pathological processes. A significant subset of the genes upregulated by ATF4 are involved in amino acid import and metabolism and a hallmark of ATF4−/−cells is their impaired metabolism of amino acids.

Therefore, modulation of general control nonderepressible 2 (GCN2) may provide a therapeutic strategy for many diseases.

SUMMARY OF THE INVENTION

The present invention provides compounds having activity as general control nonderepressible 2 (GCN2) modulators.

Accordingly, in some embodiments the invention provides a compound of Formula (1):

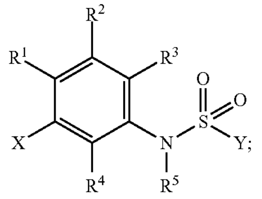

(1)

or a salt thereof, wherein;

$R^1$, $R^2$, $R^3$ and $R^4$ are independently selected from the group consisting of H, halo and $C_{1-3}$ alkyl optionally substituted with 1-6 fluoro, wherein at least one of $R^1$, $R^2$ $R^3$ and $R^4$ is halo or $C_{1-3}$ alkyl optionally substituted with 1-6 fluoro, or $R^4$ is joined to $R^5$ to form 5 or 6-membered heterocyclic ring, wherein the 5 or 6-membered heterocyclic ring is optionally substituted with halo and $C_{1-3}$ alkyl optionally substituted with 1-6 fluoro;

$R^5$ is selected from the group consisting of H and $C_{1-3}$ alkyl optionally substituted with 1-6 fluoro;

X is a 9 or 10-membered fused heterobicyclic ring comprising 1-4 annular heteroatoms being nitrogen, wherein the 9 or 10-membered fused heterobicyclic ring is substituted with $NR^8R^9$ and optionally further substituted with halo, $C_{1-3}$ alkyl or $NH_2$;

$R^8$ and $R^9$ are independently selected from the group consisting of H, $C_{1-6}$ alkyl, —C(O)$NH_2$, —C(O)—$C_{1-6}$ alkyl, and 5 or 6-membered carbocyclic or heterocyclic, wherein the $C_{1-6}$ alkyl, —C(O)—$C_{1-6}$ alkyl, and 5 or 6-membered carbocyclic or heterocyclic are independently optionally substituted with 1-6 substituents selected from the group consisting halo, OH and phenyl, or $R^8$ and $R^9$ taken together with the nitrogen form a 6-membered heterocyclic ring;

Y is a 5, 6, 9 or 10-membered carbocyclic or heterocyclic ring; or $NH_2$, wherein the 5, 6, 9 or 10-membered carbocyclic or heterocyclic ring is optionally substituted with 1-3 substituents selected from the group consisting of halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH;

$R^{13}$ and $R^{14}$ are independently H or $C_{1-3}$ alkyl; and provided that when X is a 9-membered fused heterobicyclic ring comprising 1-4 annular heteroatoms being nitrogen, then the 9 membered fused heterobicyclic ring is substituted with $NR^8R^9$ only, and Y is a 6-membered heterocyclic ring comprising 1-4 annular heteroatoms being nitrogen, wherein the 6-membered heterocyclic ring is optionally substituted with 1-3 substituents selected from the group consisting of halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH; and when X is a 10-membered fused heterobicyclic ring comprising 1-4 annular heteroatoms being nitrogen, wherein the 10 membered fused heterobicyclic ring is substituted with $NH_2$ only, one of $R^1$, $R^2$, $R^3$ and $R^4$ is halo or $C_{1-3}$ alkyl, the remainder of $R^1$, $R^2$, $R^3$ and $R^4$ are H, $R^5$ is H, and Y is 5 or 6-membered carbocyclic or heterocyclic ring, then the 5 or 6-membered carbocyclic or heterocyclic ring is substituted with 2 or 3 substituents selected from the group consisting of halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH.

Compounds of the present invention may be used as GCN2 modulators. Compounds of the present invention may be used as GCN2 inhibitors. Compounds of the present invention may be used as GCN2 antagonists. Compounds of the present invention may be used as GCN2 agonists. Compounds of the present invention may be used in the treatment of a disease or disorder characterised by activation of GCN2. Compounds of the present invention may be used in the manufacture of medicaments. The compounds or medicaments may be for use in treating, preventing, ameliorating, controlling or reducing the risk of diseases or disorders in which GCN2 is involved. Compounds of the present invention may be for use as a single agent or in combination with one or more additional pharmaceutical agents. Additional pharmaceutical agents may include radiotherapy, chemotherapy, immunotherapy or tumor microenvironment modulating agents. Compounds of the present invention may be useful in the treatment of cancer, neurodegenerative diseases, chronic infections or conditions or symptoms related thereto. Compounds of the present invention may be useful in the treatment of breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, adenocarcinoma, hepatocellular carcinoma, thyroid cancer, multiple myeloma, cancer of secretory cells, myelodysplastic syndrome, myeloproliferative neoplasm, malignant glioma, non-Hodgkin's lymphoma, Hodgkin's lymphoma, Burkitt's lymphoma, chronic lymphocytic leukemia, chronic myeloid leukemia, hairy cell leukemia, monoclonal gammopathy of undetermined significance (MGUS), plasmacytoma, lymphoplasmacytic lymphoma, acute lymphoblastic leukemia, acute myeloid leukemia, chronic myelomonocytic leukemia, juvenile myelomonocytic leukemia, large granular lymphocytic leukemia, B-cell prolymphocytic leukemia, T-cell prolymphocytic leukemia. small cell lung cancer, malignant pleural mesothelioma, Head and neck squamous cell carcinoma, glioblastoma multiforme, sarcoma, pediatric neuroblastoma or symptoms related thereto.

DETAILED DESCRIPTION OF THE INVENTION

The invention relates to novel compounds. The invention also relates to the use of novel compounds as modulators of GCN2. The invention further relates to the use of novel compounds in the manufacture of medicaments for use as GCN2 modulators.

The invention further relates to compounds, compositions and medicaments that may be useful in the treatment of cancer, neurodegenerative diseases, chronic infections or conditions or symptoms related thereto.

In one aspect, provided is a compound of Formula (1):

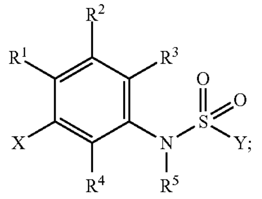

(1)

or a salt thereof, wherein;

$R^1$, $R^2$, $R^3$ and $R^4$ are independently selected from the group consisting of H, halo and $C_{1-3}$ alkyl optionally substituted with 1-6 fluoro, wherein at least one of $R^1$, $R^2$ $R^3$ and $R^4$ is halo or $C_{1-3}$ alkyl optionally substituted with 1-6 fluoro, or $R^4$ is joined to $R^5$ to form 5 or 6-membered heterocyclic ring, wherein the 5 or 6-membered heterocyclic ring is optionally substituted with halo and $C_{1-3}$ alkyl optionally substituted with 1-6 fluoro;

$R^5$ is selected from the group consisting of H and $C_{1-3}$ alkyl optionally substituted with 1-6 fluoro;

X is a 9 or 10-membered fused heterobicyclic ring comprising 1-4 annular heteroatoms being nitrogen, wherein the 9 or 10-membered fused heterobicyclic ring is substituted with NR$^8$R$^9$ and optionally further substituted with halo, $C_{1-3}$ alkyl or $NH_2$;

$R^8$ and $R^9$ are independently selected from the group consisting of H, $C_{1-6}$ alkyl, —C(O)NH$_2$, —C(O)—$C_{1-6}$ alkyl, and 5 or 6-membered carbocyclic or heterocyclic, wherein the $C_{1-6}$ alkyl, —C(O)—$C_{1-6}$ alkyl, and 5 or 6-membered carbocyclic or heterocyclic are independently optionally substituted with 1-6 substituents selected from the group consisting halo, OH and phenyl, or $R^8$ and $R^9$ taken together with the nitrogen form a 6-membered heterocyclic ring;

Y is a 5, 6, 9 or 10-membered carbocyclic or heterocyclic ring; or $NH_2$, wherein the 5, 6, 9 or 10-membered carbocyclic or heterocyclic ring is optionally substituted with 1-3 substituents selected from the group consisting of halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH;

$R^{13}$ and $R^{14}$ are independently H or $C_{1-3}$ alkyl; and provided that when X is a 9-membered fused heterobicyclic ring comprising 1-4 annular heteroatoms being nitrogen, then the 9 membered fused heterobicyclic ring is substituted with NR$^8$R$^9$ only, and Y is a 6-membered heterocyclic ring comprising 1-4 annular heteroatoms being nitrogen, wherein the 6-membered heterocyclic ring is optionally substituted with 1-3 substituents selected from the group consisting of halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH; and when X is a 10-membered fused heterobicyclic ring comprising 1-4 annular heteroatoms being nitrogen, wherein the 10 membered fused heterobicyclic ring is substituted with $NH_2$ only, one of R$^1$, R$^2$, R$^3$ and R$^4$ is halo or $C_{1-3}$ alkyl, the remainder of R$^1$, R$^2$, R$^3$ and R$^4$ are H, R$^5$ is H, and Y is 5 or 6-membered carbocyclic or heterocyclic ring, then the 5 or 6-membered carbocyclic or heterocyclic ring is substituted with 2 or 3 substituents selected from the group consisting of halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH.

In the descriptions herein, it is understood that every description, variation, embodiment, or aspect of a moiety may be combined with every description, variation, embodiment, or aspect of other moieties the same as if each and every combination of descriptions is specifically and individually listed. For example, every description, variation, embodiment, or aspect provided herein with respect to X of formula (1) may be combined with every description, variation, embodiment or aspect of Y of formula (1) the same as if each and every combination were specifically and individually listed.

In the compounds herein, X can be a 9 or 10-membered fused heterobicyclic ring system comprising 1-4 N annular heteroatoms. X can be a 9 or 10-membered fused heterobicyclic ring system comprising 1 N heteroatom. X can be a 9 or 10-membered fused heterobicyclic ring system comprising 2 N annular heteroatoms. X can be a 9 or 10-membered fused heterobicyclic ring system comprising 3 N annular heteroatoms. X can be a 9 or 10-membered fused heterobicyclic ring system comprising 4 N annular heteroatoms. X can be a 9 or 10-membered fused heterobicyclic ring system comprising 1-4 N annular heteroatoms which is substituted with groups R$^6$ and R$^7$; wherein one of R$^6$ and R$^7$ is NR$^8$R$^9$ and the other is H, $NH_2$ or halo.

X can be a 9 or 10-membered fused heterobicyclic ring system comprising 1-4 N annular heteroatoms which is substituted with NR$^8$R$^9$ and optionally further substituted with halo, $C_{1-3}$ alkyl or $NH_2$. The 9 or 10-membered fused heterobicyclic ring can be aromatic or non-aromatic. In some embodiments, the 9 or 10-membered fused heterobicyclic ring is aromatic.

X can be a 9 or 10-membered fused heterobicyclic ring which is substituted with groups R$^6$ and R$^7$, wherein one of R$^6$ and R$^7$ is NR$^8$R$^9$ and the other is H, $NH_2$ or halo. In some embodiments, R$^8$ and R$^9$ are independently selected from the group consisting of H, $C_{1-6}$ alkyl, —C(O)$NH_2$, —C(O)—$C_{1-6}$ alkyl, and 5 or 6-membered carbocyclic or heterocyclic, wherein the $C_{1-6}$ alkyl, —C(O)—$C_{1-6}$ alkyl, and 5 or 6-membered carbocyclic or heterocyclic are independently optionally substituted with 1-6 substituents selected from the group consisting halo, OH and phenyl, or R$^8$ and R$^9$ taken together with the nitrogen form a 6-membered heterocyclic ring. In some embodiments, R$^6$ and R$^7$ are independently selected from the group consisting of: H, $NH_2$, $NHCH_3$, $N(CH_3)_2$, F, $NHCH_2CH_2OH$, $NHCH(CH_3)CH_2OH$, $NHCH(CH_2OH)_2$, $NHCH(CH_2OH)(C_6H_5)$, $NHCOCH_3$, $NHCOCH_2CH_3$, $NHCOCH(CH_3)_2$, $NHCOC(CH_3)_3$,

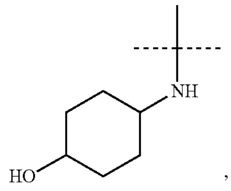
,
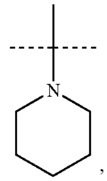
, and
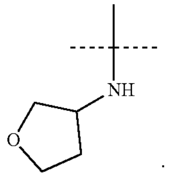
.

X can be a 9 or 10-membered fused heterobicyclic ring system comprising 1-4 N annular heteroatoms which is substituted with $NH_2$.

X can be a 10-membered fused heterobicyclic ring system comprising 2 N annular heteroatoms which is substituted with $NH_2$.

In some embodiments, the heterobicyclic ring system is selected from the group consisting of: quinazoline, quinoline, benzimidazole, isoquinoline, pyrido[2,3-d]pyrimidine, pyrido[3,2-d]pyrimidine, pyrido[2,3-b]pyrazine, pyrido[3,4-b]pyrazine, pteridine, quinoxaline, purine, pyrrolo[2,3-d]pyrimidine, pyrrolo[3,2-d]pyrimidine, indazole and pyrrolo[2,3-b]pyridine; and the optional substituents are the groups R$^6$ and R$^7$; wherein one of R$^6$ and R$^7$ is NR$^8$R$^9$ and the other is H, $NH_2$ or halo.

In some embodiments, the heterobicyclic ring system is selected from the group consisting of: quinazoline, quinoline, benzimidazole, isoquinoline, pyrido[2,3-d]pyrimidine, pyrido[3,2-d]pyrimidine, pyrido[2,3-b]pyrazine, pyrido[3,4-b]pyrazine, pteridine, quinoxaline, purine, pyrrolo[2,3-d]pyrimidine, pyrrolo[3,2-d]pyrimidine, indazole and pyrrolo[2,3-b]pyridine; and the optional substituents are the groups R$^6$ and R$^7$, one of R$^6$ and R$^7$ is NR$^8$R$^9$ and the other is H, $NH_2$ or halo.

In some embodiments, the heterobicyclic ring system is selected from the group consisting of: quinazoline, quinoline, benzimidazole, isoquinoline, pyrido[2,3-d]pyrimidine, pyrido[3,2-d]pyrimidine, pyrido[2,3-b]pyrazine, pyrido[3,4-b]pyrazine, pteridine, quinoxaline, purine, pyrrolo[2,3-d]pyrimidine, pyrrolo[3,2-d]pyrimidine, indazole and pyrrolo[2,3-b]pyridine, each of which is substituted with $NH_2$.

X can be a substituted quinazoline ring system, wherein the substituent is $NH_2$.

X can be selected from the group consisting of:

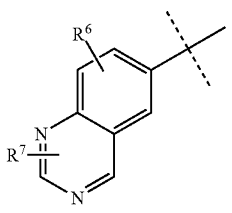
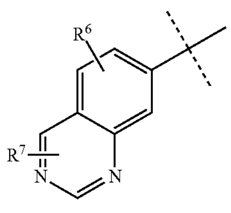

-continued
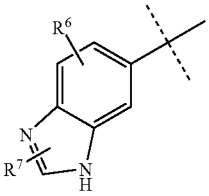
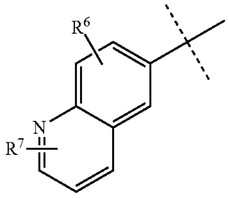
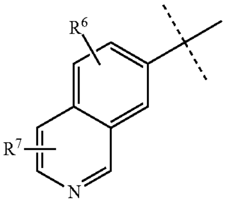
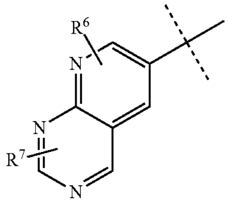
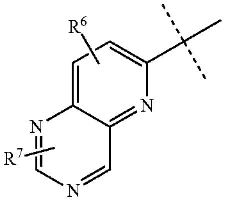
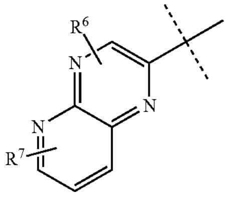
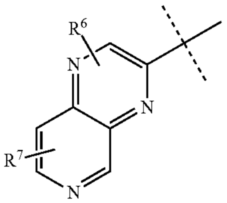
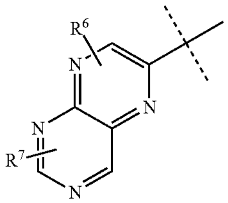
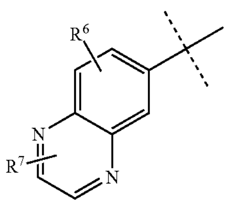
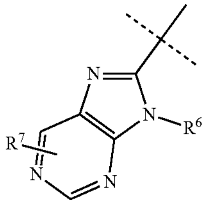
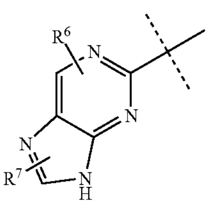
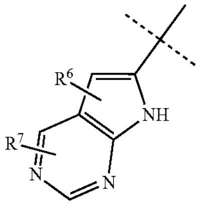
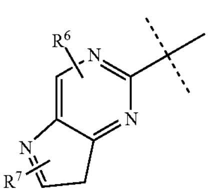
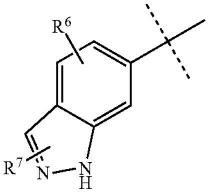
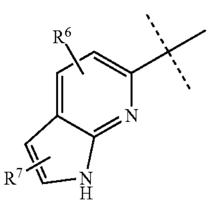
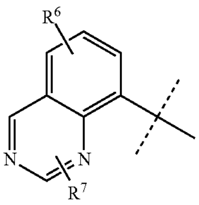
-continued
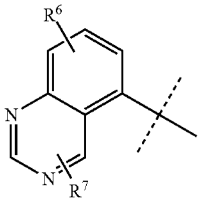
wherein $R^6$ and $R^7$ may be attached at any available position of the bicyclic ring system, one of $R^6$ and $R^7$ is $NR^8R^9$ and the other is H, $NH_2$ or halo.
X can be:
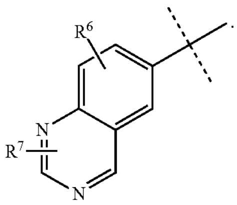
X can be selected from the group consisting of:
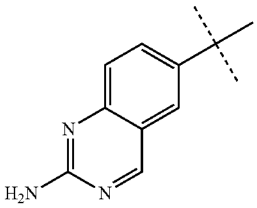
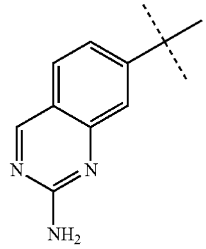
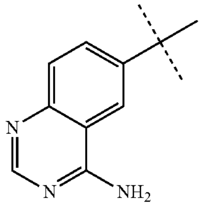
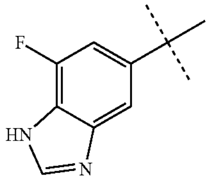
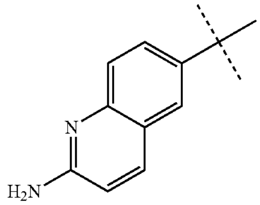
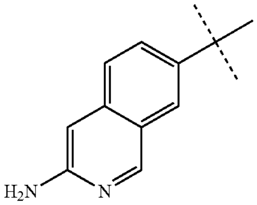
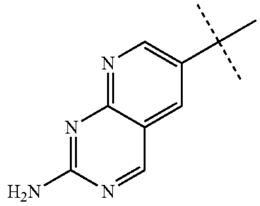
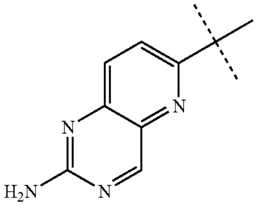

-continued
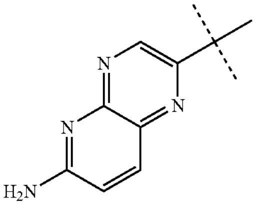
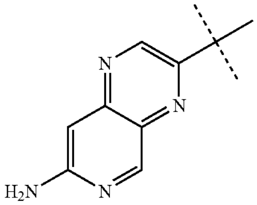
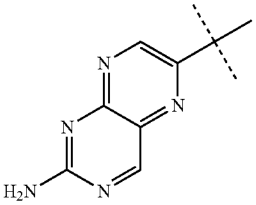
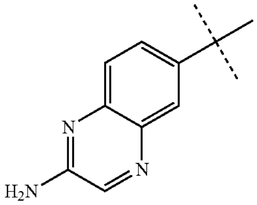
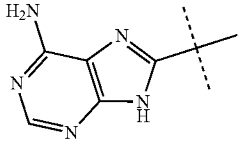
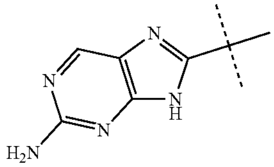
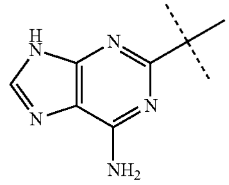
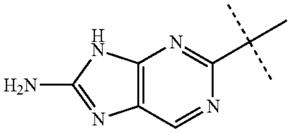
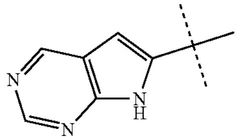
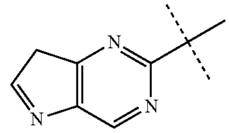
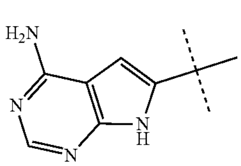
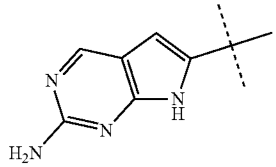
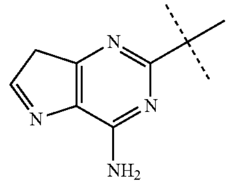
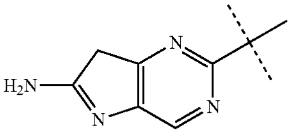
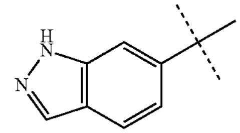
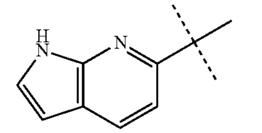
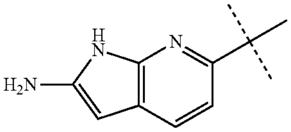
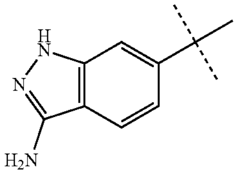
-continued
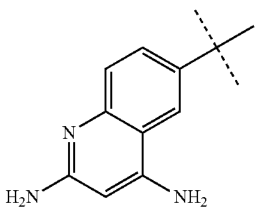
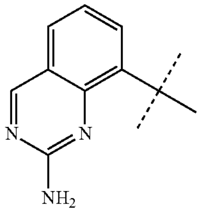
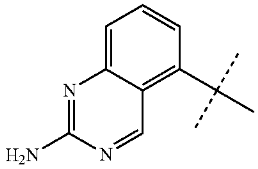
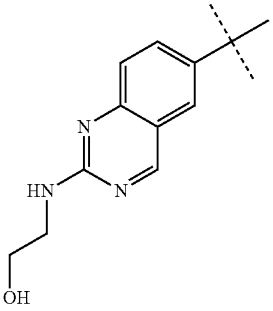
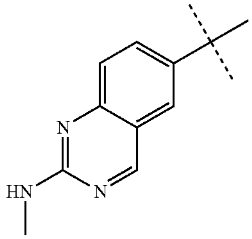
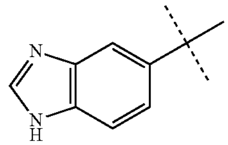
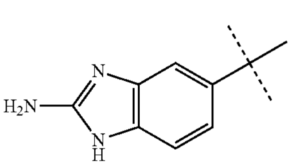
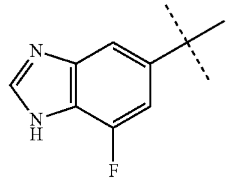
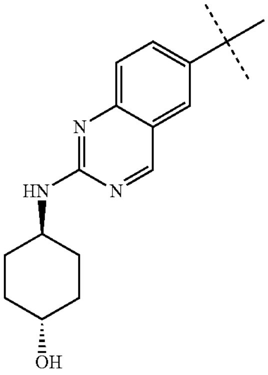
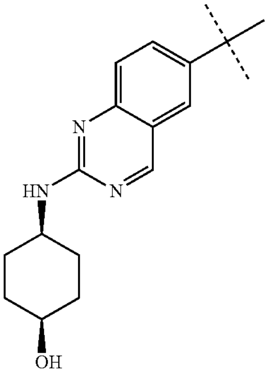
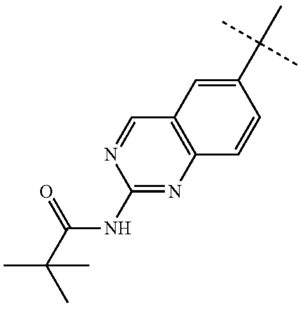
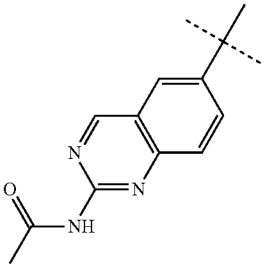

-continued

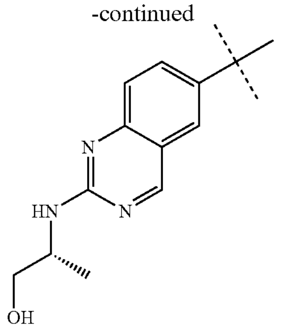

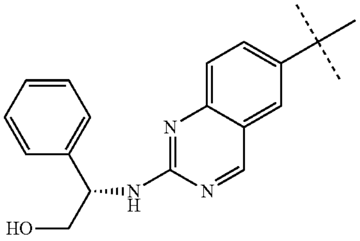

and

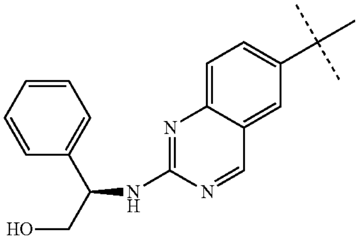

In some embodiments, one of $R^6$ and $R^7$ is $NR^8R^9$ and the other is H, $NH_2$ or halo. $R^6$ and $R^7$ may be independently selected from: H, $NH_2$, $NHCH_3$, $N(CH_3)_2$, F, $NHCH_2CH_2OH$, $NHCH(CH_3)CH_2OH$, $NHCH(CH_2OH)_2$, $NHCH(CH_2OH)(C_6H_5)$, $NHCOCH_3$, $NHCOCH_2CH_3$, $NHCOCH(CH_3)_2$, $NHCOC(CH_3)_3$,

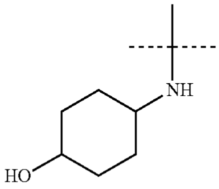
,
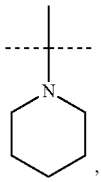
, and
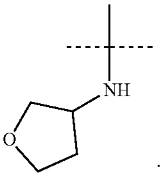
.

$R^6$ can be H and $R^7$ can be $NH_2$.

In the compounds herein, $R^8$ and $R^9$ may be independently selected from the group consisting of H, $C_{1-6}$ alkyl, —C(O)$NH_2$, —C(O)—$C_{1-6}$ alkyl, and 5 or 6-membered carbocyclic or heterocyclic, wherein the $C_{1-6}$ alkyl, —C(O)—$C_{1-6}$ alkyl, and 5 or 6-membered carbocyclic or heterocyclic are independently optionally substituted with 1-6 substituents selected from the group consisting of halo, OH and phenyl, or $R^8$ and $R^9$ taken together with the nitrogen form a 6-membered heterocyclic ring. In some embodiments, $R^8$ and $R^9$ are independently selected from the group consisting of H, $C_{1-6}$ alkyl optionally substituted with 1 to 6 fluorine atoms or optionally substituted with OH and —C(O)—$C_{1-6}$ alkyl optionally substituted with 1 to 6 fluorine atoms or optionally substituted with OH. $R^8$ and $R^9$ may be independently selected from the group consisting of H, $CH_3$, $CH_2CH_2OH$, $CH(CH_3)CH_2OH$, $NHCOCH_3$, $NHCOCH_2CH_3$, $NHCOCH(CH_3)_2$, $NHCOC(CH_3)_3$ and

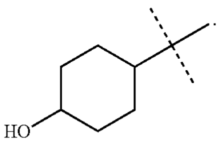

In some embodiments, $NR^8R^9$ is selected from the group consisting of $NH_2$, $NHCH_3$, $N(CH_3)_2$, $NHCH_2CH_2OH$, $NHCH(CH_3)CH_2OH$, $NHCH(CH_2OH)_2$, $NHCH(CH_2OH)(C_6H_5)$, $NHCOCH_3$, $NHCOCH_2CH_3$, $NHCOCH(CH_3)_2$, $NHCOC(CH_3)_3$,

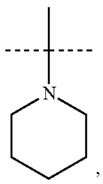
,
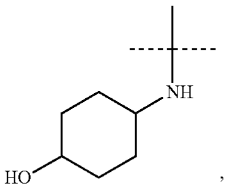
, and
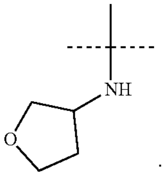
.

In the compounds herein, Y can be a 5, 6, 9 or 10-membered carbocyclic or heterocyclic ring; or $NH_2$, wherein the 5, 6, 9 or 10-membered carbocyclic or heterocyclic ring is optionally substituted with 1-3 substituents selected from the group consisting of halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH, and wherein $R^{13}$ and $R^{14}$ are independently H or $C_{1-3}$ alkyl. The 5, 6, 9 or 10-membered heterocyclic ring can have 1 to 4 annular heteroatoms independently selected from nitrogen, oxygen and sulphur.

The 5 or 6-membered carbocyclic or heterocyclic ring can be aromatic or non-aromatic monocyclic ring. In some embodiments, 5 or 6-membered carbocyclic or heterocyclic ring is aromatic. In some embodiments, 5 or 6-membered carbocyclic or heterocyclic ring is saturated. In some embodiments, 5 or 6-membered carbocyclic or heterocyclic ring is unsaturated non-aromatic.

The 9 or 10-membered carbocyclic or heterocyclic ring can be aromatic or non-aromatic fused bicyclic ring. In some embodiments, 9 or 10-membered carbocyclic or heterocyclic ring is aromatic. In some embodiments, 9 or 10-membered carbocyclic or heterocyclic ring is saturated. In some embodiments, 9 or 10-membered carbocyclic or heterocyclic ring is unsaturated non-aromatic.

Y can be an optionally substituted 6-membered carbocyclic or heterocyclic ring; or $NH_2$. Y can be an optionally substituted 6-membered carbocyclic or heterocyclic ring. Y can be $NH_2$. Y can be an optionally substituted 6-membered carbocyclic ring. Y can be an optionally substituted 6-membered heterocyclic ring.

Y can be selected from: an optionally substituted phenyl ring, an optionally substituted pyridyl ring, an optionally substituted cyclohexane ring, an optionally substituted piperidine ring, an optionally substituted piperazine ring, an optionally substituted tetrahydropyran ring, an optionally substituted thiane ring, an optionally substituted morpholine ring and an optionally substituted thiomorpholine ring; wherein the optional substituents are the groups $R^{10}$, $R^{11}$ and $R^{12}$ which are themselves independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH; wherein $R^{13}$ and $R^{14}$ are independently H or $C_{1-3}$ alkyl.

$R^{13}$ and $R^{14}$ can independently be selected from the group consisting of H and $CH_3$.

In some embodiments, $R^{10}$, $R^{11}$ and $R^{12}$ can be independently selected from the group consisting of: H, halo, —C(O)$NR^{13}R^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH. In some embodiments, $R^{10}$, $R^{11}$ and $R^{12}$ are independently selected from the group consisting of: H, Cl, F, $OCH_3$, $CF_3$, $CH_3$, $CH_2OH$, OH, $CONH_2$, COOH, $CONHCH_3$ and $COOCH_3$. In some embodiments, $R^{10}$, $R^{11}$ and $R^{12}$ are independently selected from the group consisting of: H, Cl, and $OCH_3$.

Y can be an optionally substituted phenyl ring or an optionally substituted pyridyl ring, wherein the optional substituents are the groups $R^{10}$, $R^{11}$ and $R^{12}$ which are as defined above.

Y can be a group of formula:

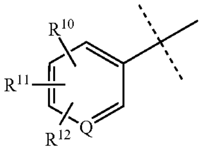
;

wherein Q is C, CH or N and $R^{10}$, $R^{11}$ and $R^{12}$ are as defined above.

Q can be C. Q can be N. Q can be CH. Q can be $CR^{10}$. Q can be $CR^{10}$. Q can be $CR^{12}$. Q can be $CR^{10}$, $CR^{11}$, $CR^{12}$, CH or N.

Y can be selected from the group consisting of:

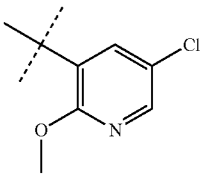
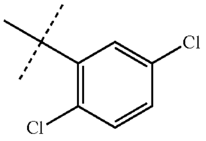
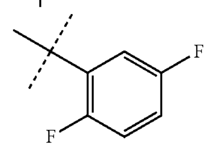
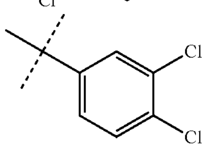

-continued

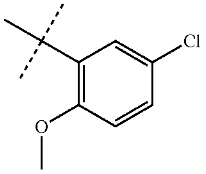
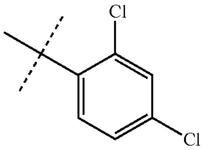
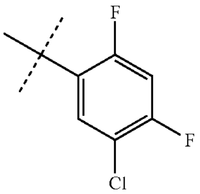
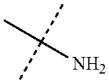
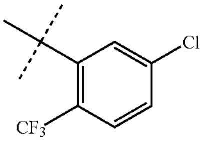
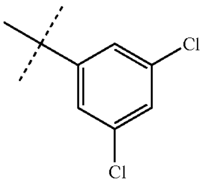
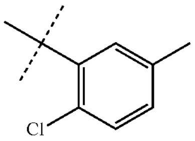
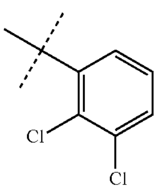
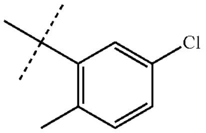
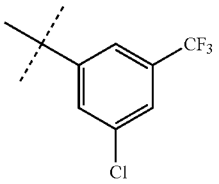
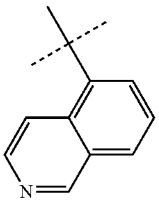
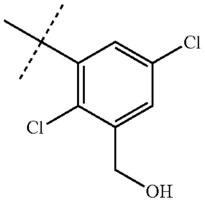
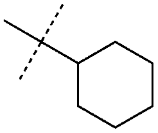
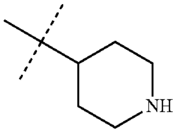
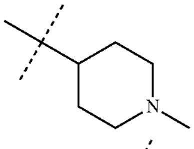
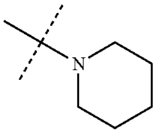
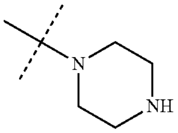
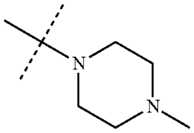
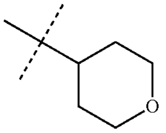
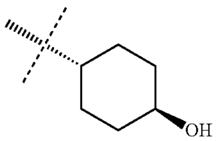
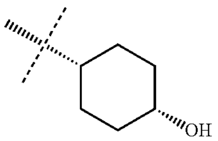
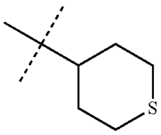
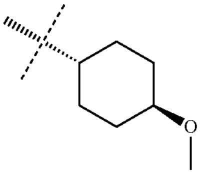

-continued
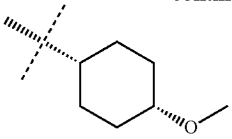
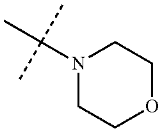
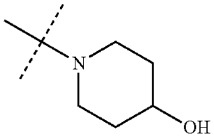
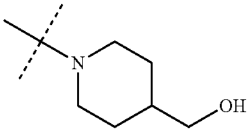
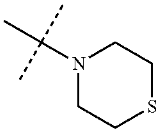
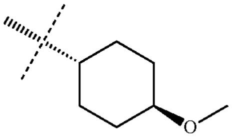
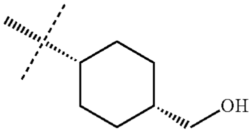
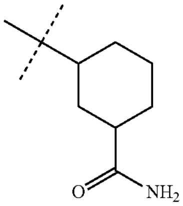
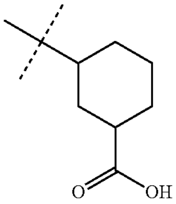
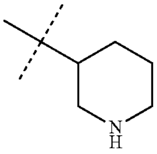
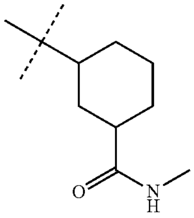
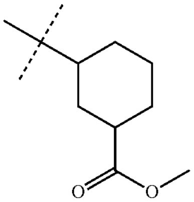
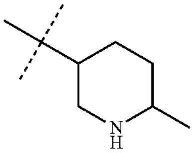
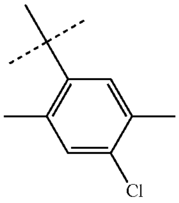
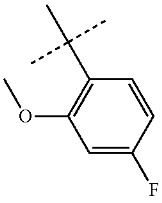
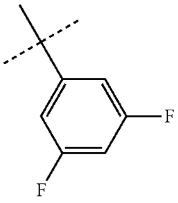
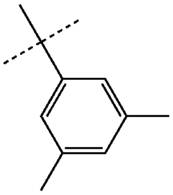
In the compounds herein, the moiety:
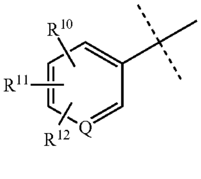
can be selected from the group consisting of:
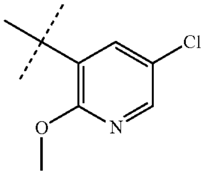
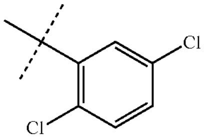
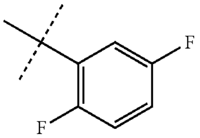
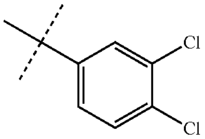
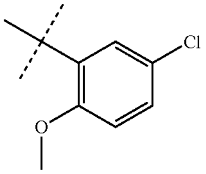
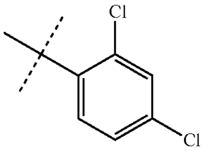
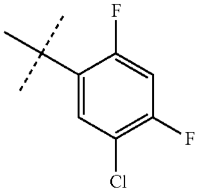
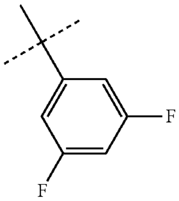
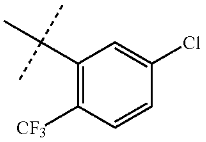
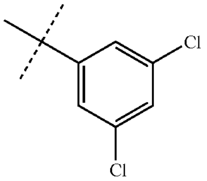
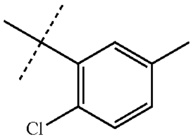
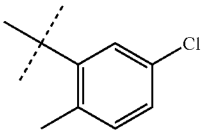
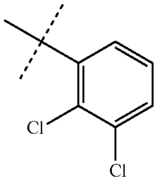
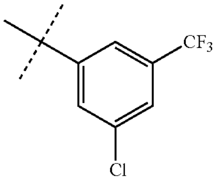
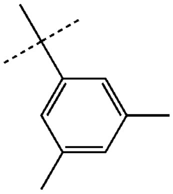
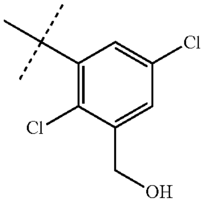
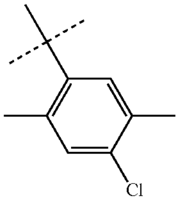
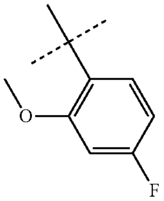

The moiety:

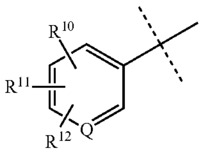

can be:

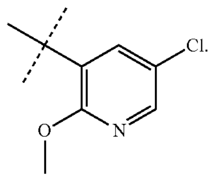

In the compounds herein, $R^1$, $R^2$, $R^3$ and $R^4$ can be independently selected from H, halo and $C_{1-3}$ alkyl optionally substituted with 1-6 fluoro, wherein at least one of $R^1$, $R^2$ $R^3$ and $R^4$ is halo or $C_{1-3}$ alkyl optionally substituted with 1-6 fluoro, or $R^4$ is joined to $R^5$ to form 5 or 6-membered heterocyclic ring, wherein the 5 or 6-membered heterocyclic ring is optionally substituted with halo and $C_{1-3}$ alkyl optionally substituted with 1-6 fluoro; and $R^5$ is selected from H and $C_{1-3}$ alkyl optionally substituted with 1-6 fluoro.

In some embodiments, $R^1$, $R^2$ and $R^3$ can be independently selected from the group consisting of H, halo and $C_{1-3}$ alkyl optionally substituted with 1-6 fluorine atoms. $R^1$, $R^2$ and $R^3$ can be independently selected from the group consisting of H, F and $CH_3$. $R^1$ can be H, F or $CH_3$. $R^2$ can be H, F or $CH_3$. $R^3$ can be H, F or $CH_3$. $R^1$ can be F, $R^2$ can be H and $R^3$ can be H.

In some embodiments, $R^4$ is selected from the group consisting of H, halo and $C_{1-3}$ alkyl optionally substituted with 1-6 fluorine atoms; or is joined to $R^5$ to form an optionally substituted ring. $R^4$ can be selected from the group consisting of H, halo and $C_{1-3}$ alkyl optionally substituted with 1-6 fluorine atoms; or joined to $R^5$ to form a ring. $R^4$ can be selected from the group consisting of H, halo and $C_{1-3}$ alkyl optionally substituted with 1-6 fluorine atoms. $R^4$ can be joined to $R^5$ to form an optionally substituted ring. $R^4$ can be selected from the group consisting of H, F and $CH_3$. $R^4$ can be F. $R^4$ can be joined to $R^5$ to form a 5-membered ring which may be optionally substituted with groups $R^{15}$ and $R^{16}$; wherein $R^{15}$ and $R^{16}$ are independently selected from the group consisting of H, halo and $C_{1-3}$ alkyl optionally substituted with 1 to 6 fluorine atoms.

$R^1$, $R^2$, $R^3$ and $R^4$ can be independently selected from the group consisting of H, F and $CH_3$. $R^1$ can be F, $R^2$ can be H, $R^3$ can be H, and $R^4$ can be F. $R^1$ and $R^4$ can be F and $R^2$ and $R^3$ can be H.

In some embodiments, $R^5$ can be selected from the group consisting of H and $C_{1-3}$ alkyl optionally substituted with 1-6 fluorine atoms; or is joined to $R^4$ to form an optionally substituted ring. $R^5$ can be selected from the group consisting of H and $C_{1-3}$ alkyl optionally substituted with 1-6 fluorine atoms; or joined to $R^4$ to form a ring. $R^5$ can be H. $R^5$ can be joined to $R^4$ to form an optionally substituted ring. $R^5$ can be joined to $R^4$ to form a 5-membered ring which may be optionally substituted with groups $R^{15}$ and $R^{16}$; wherein $R^{15}$ and $R^{16}$ are independently selected from the group consisting of H, halo and $C_{1-3}$ alkyl optionally substituted with 1 to 6 fluorine atoms.

$R^1$, $R^2$ and $R^3$ may be independently selected from the group consisting of H, F and $CH_3$ and $R^4$ may be joined to $R^5$ to form a ring.

In some embodiments, the compound of formula (1) is a compound of formula (1a):

(1a)

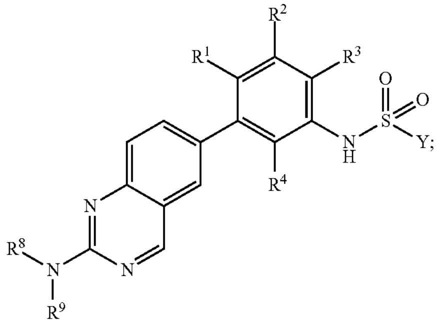

or a salt thereof, wherein:

$R^1$, $R^2$, $R^3$, $R^4$, $R^8$, $R^9$ and Y are as defined in formula (1), and provided that when one of $R^1$, $R^2$, $R^3$ and $R^4$ is halo or $C_{1-3}$ alkyl, the remainder of $R^1$, $R^2$, $R^3$ and $R^4$ are H, $R^5$ is H, and Y is 5 or 6-membered carbocyclic or heterocyclic ring, then the 5 or 6-membered carbocyclic or heterocyclic ring is substituted with 2 or 3 substituents selected from the group consisting of halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH.

In some embodiments, the compound of formula (1) is a compound of formula (1b):

(1b)

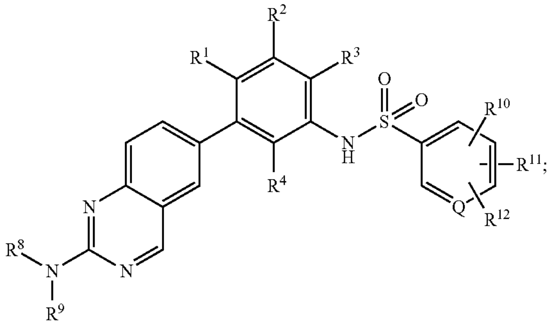

or a salt thereof, wherein:

$R^1$, $R^2$, $R^3$, $R^4$, $R^8$ and $R^9$ are as defined in formula (1);

Q is C or N;

$R^{10}$, $R^{11}$ and $R^{12}$ are independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH;

wherein $R^{13}$ and $R^{14}$ are independently H or $C_{1-3}$ alkyl, and provided that when one of $R^1$, $R^2$, $R^3$ and $R^4$ is halo or $C_{1-3}$ alkyl, the remainder of $R^1$, $R^2$, $R^3$ and $R^4$ are H, then 2 or 3 of $R^{10}$, $R^{11}$ and $R^{12}$ are independently selected from the group consisting of halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH.

The compound may be a compound of formula (2):

(2)

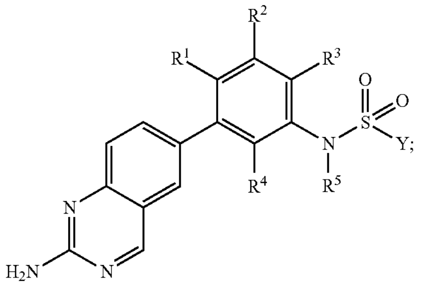

or a salt thereof, wherein Y, $R^1$, $R^2$, $R^3$, $R^4$ and $R^5$ are as defined in formula (1).

The compound may be a compound of formula (3):

(3)

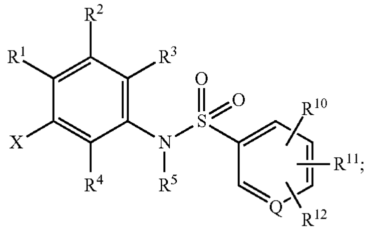

or a salt thereof, wherein:

X, $R^1$, $R^2$, $R^3$, $R^4$ and $R^5$ are as defined in formula (1);

Q is C or N;

$R^{10}$, $R^{11}$ and $R^{12}$ are independently selected from the group consisting of: H, halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH;

wherein $R^{13}$ and $R^{14}$ are independently H or $C_{1-3}$ alkyl, provided that when X is a 9-membered fused heterobicyclic ring comprising 1-4 annular heteroatoms being nitrogen, then the 9 membered fused heterobicyclic ring is substituted with NR$^8$R$^9$ only, and Q is N; and when X is a 10-membered fused heterobicyclic ring comprising 1-4 annular heteroatoms being nitrogen, wherein the 10 membered fused heterobicyclic ring is substituted with $NH_2$ only, one of $R^1$, $R^2$, $R^3$ and $R^4$ is halo or $C_{1-3}$ alkyl, the remainder of $R^1$, $R^2$, $R^3$ and $R^4$ are H, and $R^5$ is H, then 2 or 3 of $R^{10}$, $R^{11}$ and $R^{12}$ are independently selected from the group consisting of halo, OH, CN, —C(O)NR$^{13}$R$^{14}$, —NR$^{13}$COR$^{14}$, —C(O)OR$_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH.

In some embodiments, the compound of formula (3) is a compound of formula (3a):

(3a)

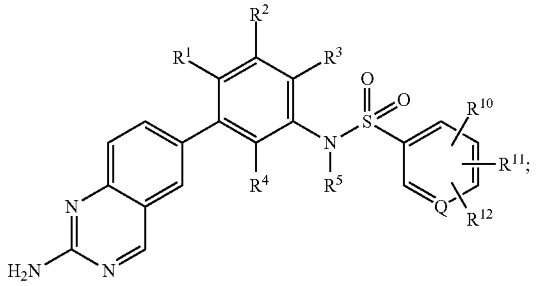

or a salt thereof, wherein $R^1$, $R^2$, $R^3$, $R^4$, $R^5$, $R^{10}$, $R^{11}$ and $R^{12}$ are as defined above.

In some embodiments, the compound of formula (3) is a compound of formula (4a):

(4a)

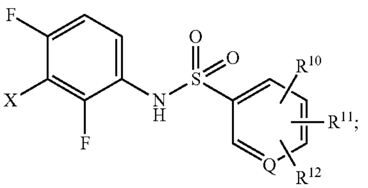

or a salt thereof, wherein X, Q, $R^{10}$, $R^{11}$ and $R^{12}$ are as defined above.

In some embodiments, the compound of formula (3) is a compound of formula (4b):

(4b)

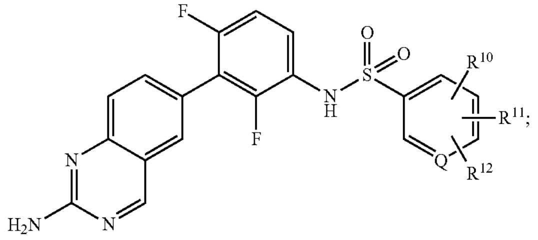

or a salt thereof, wherein Q, $R^{10}$, $R^{11}$ and $R^{12}$ are as defined above.

The compound may be a compound of formula (5) or (5a):

(5)

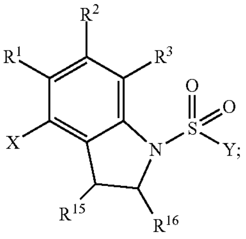

-continued (5a)

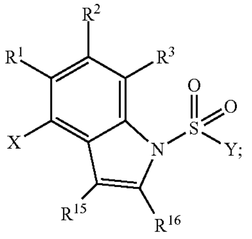

or a salt thereof, wherein X, Y, $R^1$, $R^2$ and $R^3$ are as defined in formula (1); and $R^{15}$ and $R^{16}$ are independently selected from the group consisting of H, halo and $C_{1-3}$ alkyl optionally substituted with 1 to 6 fluoro.

The compound may be a compound of formula (5b) or (5c):

(5b)

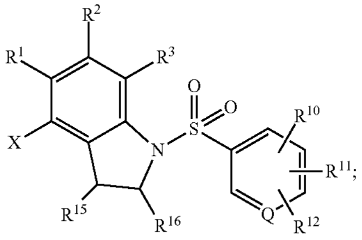

(5c)

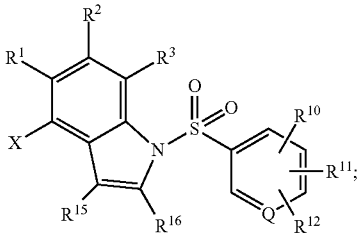

or a salt thereof, wherein X, $R^1$, $R^2$, $R^3$, Q, $R^{10}$, $R^{11}$, $R^{12}$, $R^{15}$ and $R^{16}$ are as defined above.

The compound may be a compound of formula (5d) or (5e):

(5d)

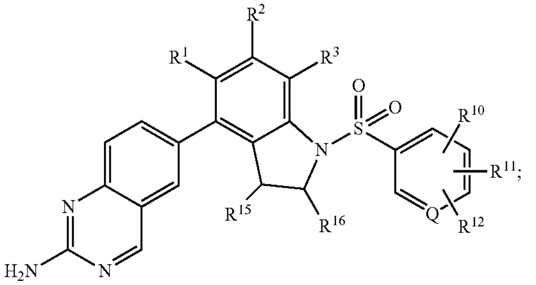

-continued (5e)

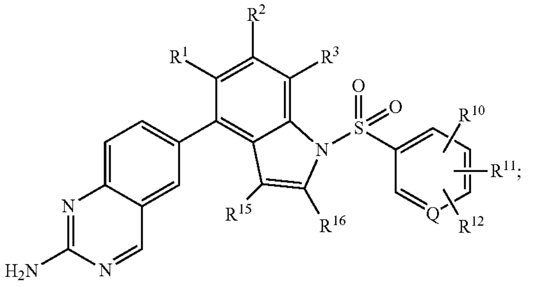

or a salt thereof, wherein $R^1$, $R^2$, $R^3$, Q, $R^{10}$, $R^{11}$, $R^{12}$, $R^{15}$ and $R^{16}$ are as defined above.

The compound may be a compound of formula (6) or (6a):

(6)

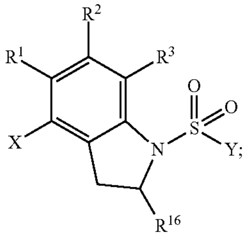

(6a)

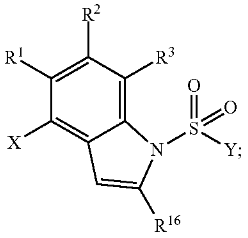

or a salt thereof, wherein X, Y, $R^1$, $R^2$ and $R^3$ are as defined above.

The compound may be a compound of formula (6b) or (6c):

(6b)

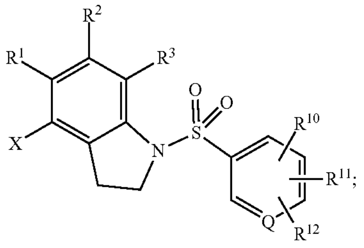

-continued (6c)

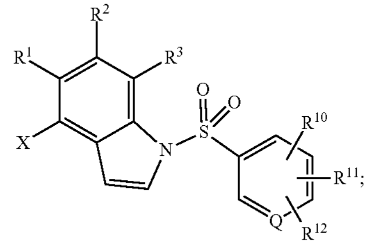

or a salt thereof, wherein X, $R^1$, $R^2$. $R^3$, Q, $R^{10}$, $R^{11}$ and $R^{12}$ are as defined above.

The compound may be a compound of formula (6d) or (6e):

(6d)

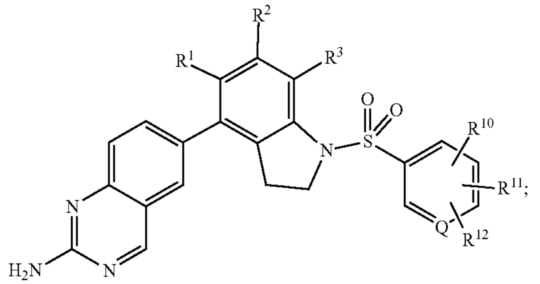

(6e)

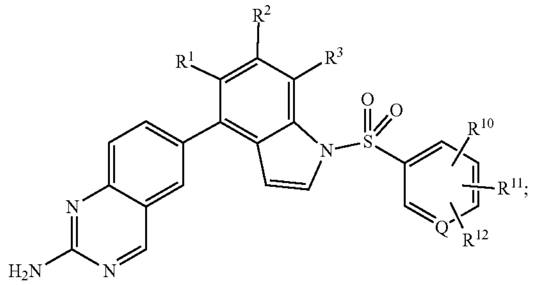

or a salt thereof, wherein X, $R^1$, $R^2$. $R^3$, Q, $R^{10}$, $R^{11}$ and $R^{12}$ are as defined above.

The compound may be a compound of formula (7):

(7)

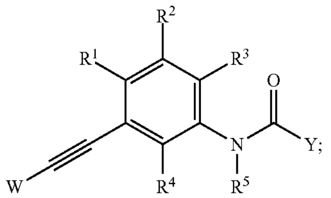

or a salt thereof, wherein;

$R^1$, $R^2$, $R^3$, $R^4$, $R^5$ and Y are as defined above;

and W is an optionally substituted 6-membered heteroaryl ring comprising 1-3 N heteroatoms.

The compound may be a compound of formula (7a):

(7a)

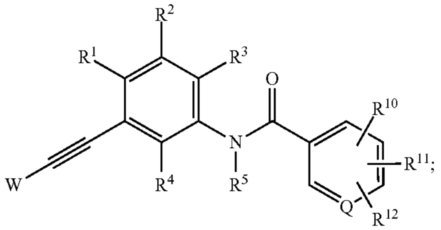

or a salt thereof, wherein;

$R^1$, $R^2$, $R^3$, $R^4$, $R^5$, $R^{10}$, $R^{11}$, $R^{12}$ and Q are as defined above;

and W is an optionally substituted 6-membered heteroaryl ring comprising 1-3 N heteroatoms.

The compound may be a compound of formula (7b):

(7b)

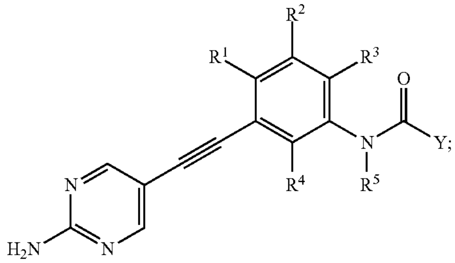

or a salt thereof, wherein;

$R^1$, $R^2$, $R^3$, $R^4$, $R^5$ and Y are as defined above.

The compound may be a compound of formula (7c):

(7c)

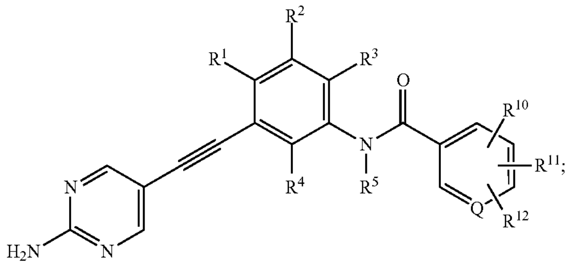

or a salt thereof, wherein;

$R^1$, $R^2$, $R^3$, $R^4$, $R^5$, $R^{10}$, $R^{11}$, $R^{12}$ and Q are as defined above.

The compound may be a compound of formula (7d) or (7e):

(7d)

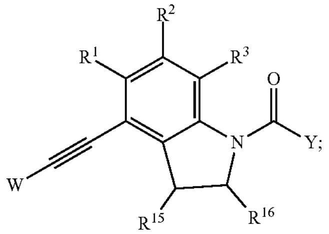

(7e)

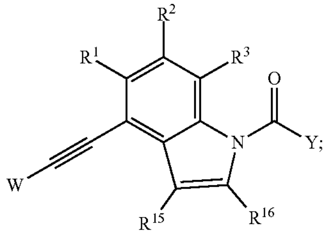

or a salt thereof, wherein;

$R^1$, $R^2$, $R^3$, $R^{15}$, $R^{16}$ and Y are as defined above;

and W is an optionally substituted 6-membered heteroaryl ring comprising 1-3 N heteroatoms.

The compound may be a compound of formula (7f) or (7g):

(7f)

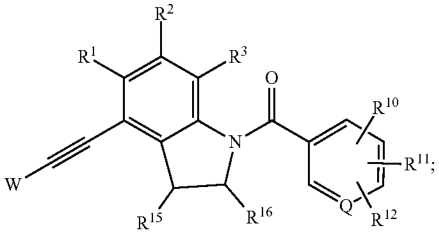

(7g)

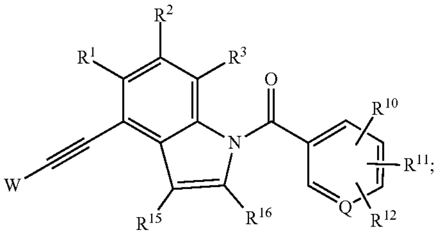

or a salt thereof, wherein;

$R^1$, $R^2$, $R^3$, $R^{10}$, $R^{11}$, $R^{12}$, $R^{15}$, $R^{16}$ and Q are as defined above;

and W is an optionally substituted 6-membered heteroaryl ring comprising 1-3 N heteroatoms.

The compound may be a compound of formula (7h) or (7i):

(7h)

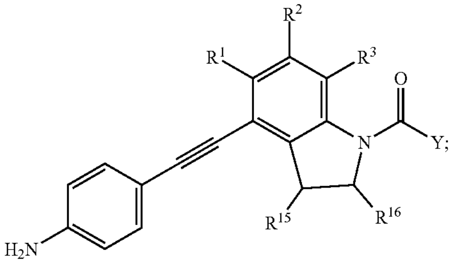

(7i)

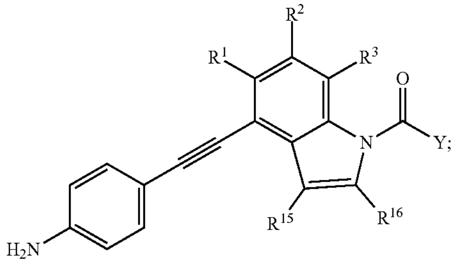

or a salt thereof, wherein;

$R^1$, $R^2$, $R^3$, $R^{15}$, $R^{16}$ and Y are as defined above.

The compound may be a compound of formula (7j) or (7k):

(7j)

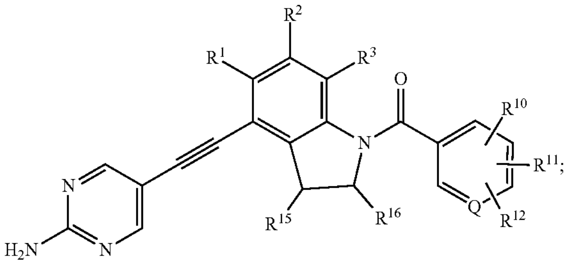

(7h)

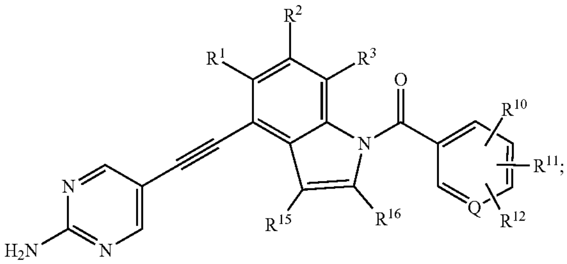

or a salt thereof, wherein;

$R^1$, $R^2$, $R^3$, $R^{10}$, $R^{11}$, $R^{12}$, $R^{15}$, $R^{16}$ and Q are as defined above.

The compound may be a compound of formula (8):

(8)

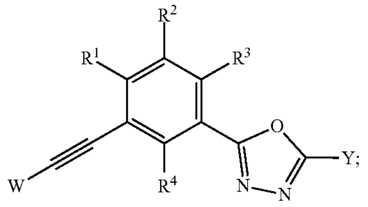

or a salt thereof, wherein;

$R^1$, $R^2$, $R^3$, $R^4$ and Y are as defined above;

and W is an optionally substituted 6-membered heteroaryl ring comprising 1-3 N heteroatoms.

The compound may be a compound of formula (8a):

(8a)

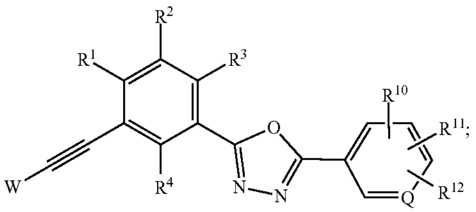

or a salt thereof, wherein;

$R^1$, $R^2$, $R^3$, $R^4$, $R^{10}$, $R^{11}$, $R^{12}$ and Q are as defined above;

and W is an optionally substituted 6-membered heteroaryl ring comprising 1-3 N heteroatoms.

The compound may be a compound of formula (8b):

(8b)

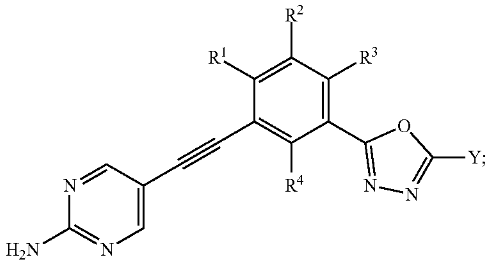

or a salt thereof, wherein;

$R^1$, $R^2$, $R^3$, $R^4$ and Y are as defined above.

The compound may be a compound of formula (8c):

(8c)

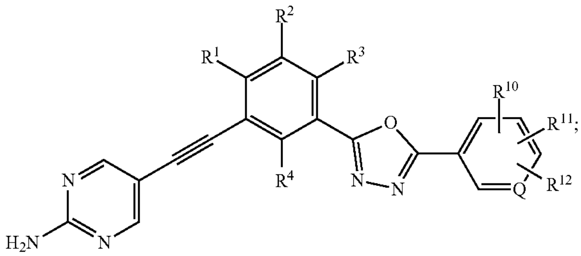

or a salt thereof, wherein;

$R^1$, $R^2$, $R^3$, $R^4$, $R^{10}$, $R^{11}$, $R^{12}$ and Q are as defined above.

The compound may be a compound of formula (9):

(9)

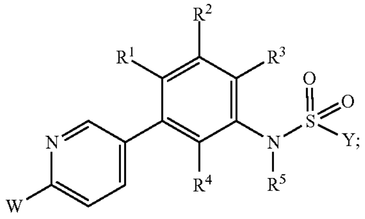

or a salt thereof, wherein;

$R^1$, $R^2$, $R^3$, $R^4$, $R^5$ and Y are as defined above;

and W is an optionally substituted 6-membered heteroaryl ring comprising 1-3 N heteroatoms.

The compound may be a compound of formula (9a):

(9c)

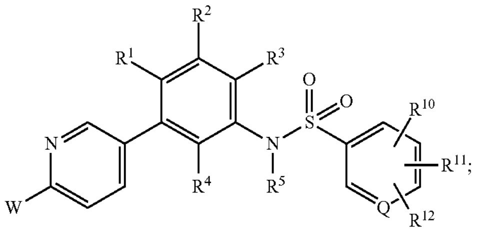

or a salt thereof, wherein;

$R^1$, $R^2$, $R^3$, $R^4$, $R^5$, $R^{10}$, $R^{11}$, $R^{12}$ and Q are as defined above;

and W is an optionally substituted 6-membered heteroaryl ring comprising 1-3 N heteroatoms.

The compound may be a compound of formula (9b):

(9b)

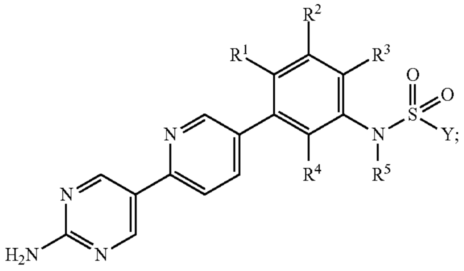

or a salt thereof, wherein;

$R^1$, $R^2$, $R^3$, $R^4$, $R^5$ and Y are as defined above.

The compound may be a compound of formula (9c):

(9c)

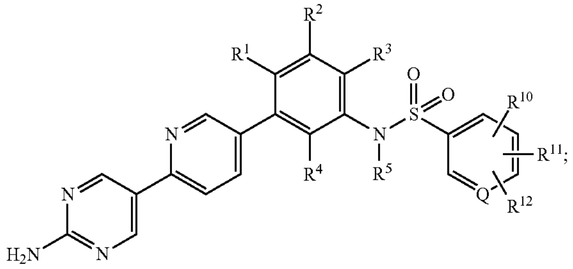

or a salt thereof, wherein;

$R^1$, $R^2$, $R^3$, $R^4$, $R^5$, $R^{10}$, $R^{11}$, $R^{12}$ and Q are as defined above.

The compound may be a compound of formula (9d) or (9e):

(9d)

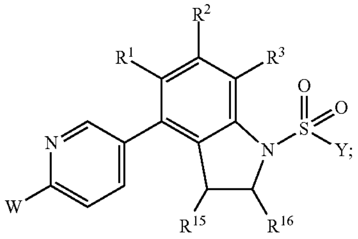

(9e)

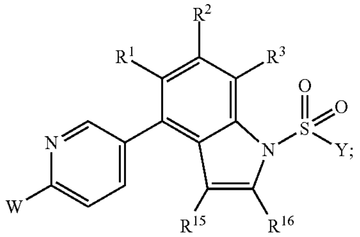

or a salt thereof, wherein;

$R^1$, $R^2$, $R^3$, $R^{15}$, $R^{16}$ and Y are as defined above;

and W is an optionally substituted 6-membered heteroaryl ring comprising 1-3 N heteroatoms.

The compound may be a compound of formula (9f) or (9g):

(9f)

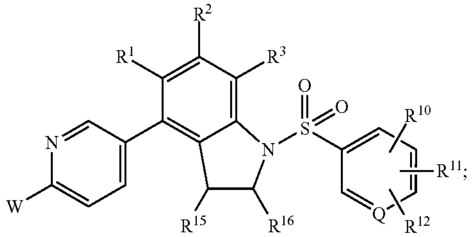

(9g)

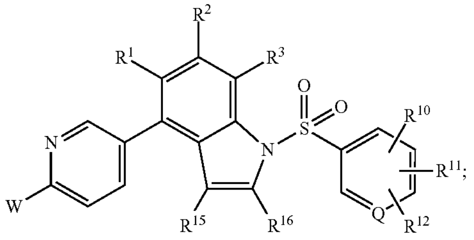

or a salt thereof, wherein;

$R^1$, $R^2$, $R^3$, $R^{10}$, $R^{11}$, $R^{12}$, $R^{15}$, $R^{16}$ and Q are as defined above;

and W is an optionally substituted 6-membered heteroaryl ring comprising 1-3 N heteroatoms.

The compound may be a compound of formula (9h) or (9i):

(9h)

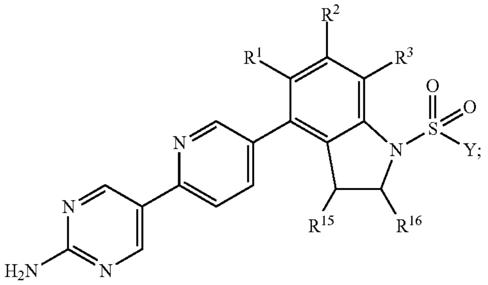

(9i)

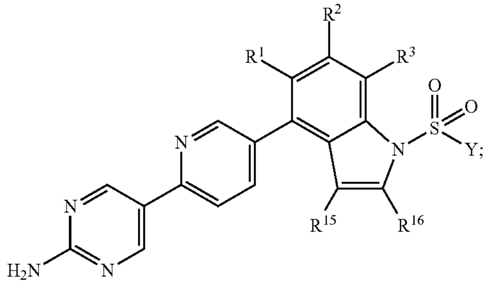

or a salt thereof, wherein;

$R^1$, $R^2$, $R^3$, $R^{15}$, $R^{16}$ and Y are as defined above.

The compound may be a compound of formula (9j) or (9k):

(9j)

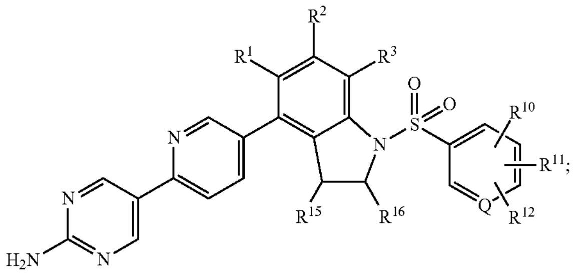

(9k)

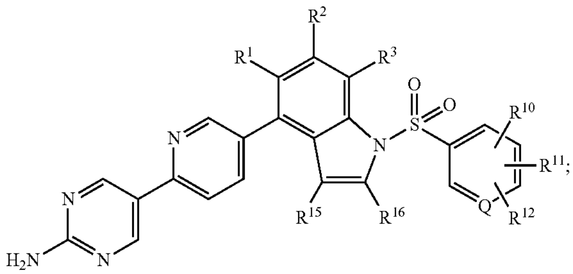

or a salt thereof, wherein;

$R^1$, $R^2$, $R^3$, $R^{10}$, $R^{11}$, $R^{12}$, $R^{15}$, $R^{16}$ and Q are as defined above.

In the compounds herein, W can be a substituted 6-membered heteroaryl ring comprising 1-3 N heteroatoms. W can be an optionally substituted 6-membered heteroaryl ring comprising 2 N heteroatoms. W can be a substituted 6-membered heteroaryl ring comprising 2 N heteroatoms. W can be a 6-membered heteroaryl ring comprising 1-3 N heteroatoms which is substituted with $R^6$, wherein $R^6$ is as defined above. W can be a 6-membered heteroaryl ring comprising 2 N heteroatoms which is substituted with $R^6$, wherein $R^6$ is as defined above. W can be a 6-membered heteroaryl ring comprising 1-3 N heteroatoms which is substituted with $NH_2$. W can be a 6-membered heteroaryl ring comprising 2 N heteroatoms which is substituted with $NH_2$. W can be an optionally substituted pyrimidine ring. W can be a substituted pyrimidine ring. W can be a pyrimidine ring substituted with $R^6$, wherein $R^6$ is as defined above. W can be a pyrimidine ring substituted with $NH_2$. W can be 2-amino-pyrimidine.

W can be:

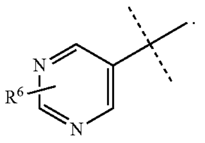

W can be:

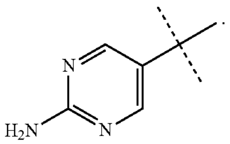

The compound can be selected from any one of exemplary compounds as shown in Table 1 or a salt thereof.

The compound can be selected from the group consisting of:

N-(3-(2-aminoquinazolin-6-yl)-2,4-difluorophenyl)-5-chloro-2-methoxypyridine-3-sulfonamide,
N-[3-(2-aminoquinazolin-6-yl)-2,4-difluorophenyl]-2,5-dichlorobenzene-1-sulfonamide,
N-[3-(2-aminoquinazolin-7-yl)-2,4-difluorophenyl]-2,5-dichlorobenzene-1-sulfonamide
N-[3-(2-aminoquinazolin-7-yl)-2,4-difluorophenyl]-5-chloro-2-methoxypyridine-3-sulfonamide,
N-[3-(2-aminoquinazolin-6-yl)-2,4-difluorophenyl]-2,5-difluorobenzene-1-sulfonamide,
N-[3-(2-aminoquinazolin-6-yl)-2,4-difluorophenyl]-3,4-dichlorobenzene-1-sulfonamide,
N-[3-(2-aminoquinazolin-6-yl)-2,4-difluorophenyl]-5-chloro-2-methoxybenzene-1-sulfonamide,
N-[3-(2-aminoquinazolin-6-yl)-2-methylphenyl]-2,5-dichlorobenzene-1-sulfonamide,
N-[3-(2-aminoquinazolin-6-yl)-2,6-difluorophenyl]-2,5-dichlorobenzene-1-sulfonamide,
N-[3-(2-aminoquinazolin-6-yl)-2-fluorophenyl]-2,5-dichlorobenzene-1-sulfonamide,
N-[3-(2-aminoquinazolin-6-yl)-5-fluorophenyl]-2,5-dichlorobenzene-1-sulfonamide,
N-[3-(2-aminoquinazolin-6-yl)-2,4-difluorophenyl]-2,4-dichlorobenzene-1-sulfonamide,
N-[3-(2-aminoquinazolin-6-yl)-4-methylphenyl]-2,5-dichlorobenzene-1-sulfonamide,
N-[3-(4-aminoquinazolin-6-yl)-2,4-difluorophenyl]-2,5-dichlorobenzene-1-sulfonamide,
2,5-dichloro-N-[2,4-difluoro-3-(7-fluoro-1H-benzimidazol-5-yl)phenyl]benzene-1-sulfonamide,
N-[3-(2-aminoquinazolin-6-yl)-4-fluorophenyl]-5-chloro-2-methoxypyridine-3-sulfonamide,
N-[3-(2-aminoquinolin-6-yl)-2,4-difluorophenyl]-5-chloro-2-methoxypyridine-3-sulfonamide,
N-[3-(3-aminoisoquinolin-7-yl)-2,4-difluorophenyl]-5-chloro-2-methoxypyridine-3-sulfonamide,
N-[3-(2-aminopyrido[2,3-d]pyrimidin-6-yl)-2,4-difluorophenyl]-5-chloro-2-methoxypyridine-3-sulfonamide,
N-[3-(2-aminopyrido[3,2-d]pyrimidin-6-yl)-2,4-difluorophenyl]-5-chloro-2-methoxypyridine-3-sulfonamide,
N-[3-(6-aminopyrido[2,3-b]pyrazin-2-yl)-2,4-difluorophenyl]-5-chloro-2-methoxypyridine-3-sulfonamide,
N-[3-(7-aminopyrido[3,4-b]pyrazin-3-yl)-2,4-difluorophenyl]-5-chloro-2-methoxypyridine-3-sulfonamide, -continued N-[3-(2-aminopteridin-6-yl)-2,4-difluorophenyl]-5-chloro-2-methoxypyridine-3-sulfonamide,
N-[3-(2-aminoquinoxalin-6-yl)-2,4-difluorophenyl]-5-chloro-2-methoxypyridine-3-sulfonamide,
N-[3-(6-amino-9H-purin-8-yl)-2,4-difluorophenyl]-5-chloro-2-methoxypyridine-3-sulfonamide,
N-[3-(2-amino-9H-purin-8-yl)-2,4-difluorophenyl]-5-chloro-2-methoxypyridine-3-sulfonamide,
N-[3-(6-amino-9H-purin-2-yl)-2,4-difluorophenyl]-5-chloro-2-methoxypyridine-3-sulfonamide,
N-[3-(8-amino-9H-purin-2-yl)-2,4-difluorophenyl]-5-chloro-2-methoxypyridine-3-sulfonamide,
5-chloro-N-[2,4-difluoro-3-(7H-pyrrolo[2,3-d]pyrimidin-6-yl)phenyl]-2-methoxypyridine-3-sulfonamide,
5-chloro-N-[2,4-difluoro-3-(7H-pyrrolo[3,2-d]pyrimidin-2-yl)phenyl]-2-methoxypyridine-3-sulfonamide,
N-[3-(4-amino-7H-pyrrolo[2,3-d]pyrimidin-6-yl)-2,4-difluorophenyl]-5-chloro-2-methoxypyridine-3-sulfonamide,
N-[3-(2-amino-7H-pyrrolo[2,3-d]pyrimidin-6-yl)-2,4-difluorophenyl]-5-chloro-2-methoxypyridine-3-sulfonamide,
N-[3-(4-amino-7H-pyrrolo[3,2-d]pyrimidin-2-yl)-2,4-difluorophenyl]-5-chloro-2-methoxypyridine-3-sulfonamide,
N-[3-(6-amino-7H-pyrrolo[3,2-d]pyrimidin-2-yl)-2,4-difluorophenyl]-5-chloro-2-methoxypyridine-3-sulfonamide,
5-chloro-N-[2,4-difluoro-3-(1H-indazol-6-yl)phenyl]-2-methoxypyridine-3-sulfonamide,
5-chloro-N-[2,4-difluoro-3-(1H-pyrrolo[2,3-b]pyridin-6-yl)phenyl]-2-methoxypyridine-3-sulfonamide,
N-[3-(2-amino-1H-pyrrolo[2,3-b]pyridin-6-yl)-2,4-difluorophenyl]-5-chloro-2-methoxypyridine-3-sulfonamide,
N-[3-(4-aminoquinazolin-6-yl)-2,4-difluorophenyl]-5-chloro-2-methoxypyridine-3-sulfonamide,
N-[3-(3-amino-1H-indazol-6-yl)-2,4-difluorophenyl]-5-chloro-2-methoxypyridine-3-sulfonamide,
5-chloro-N-[3-(2,4-diaminoquinolin-6-yl)-2,4-difluorophenyl]-2-methoxypyridine-3-sulfonamide,
N-[3-(2-aminoquinazolin-8-yl)-2,4-difluorophenyl]-5-chloro-2-methoxypyridine-3-sulfonamide,
N-[3-(2-aminoquinazolin-5-yl)-2,4-difluorophenyl]-5-chloro-2-methoxypyridine-3-sulfonamide,
5-chloro-N-(2,4-difluoro-3-{2-[(2-hydroxyethyl)amino]quinazolin-6-yl}phenyl)-2-methoxypyridine-3-sulfonamide,
5-chloro-N-{2,4-difluoro-3-[2-(methylamino)quinazolin-6-yl]phenyl}-2-methoxypyridine-3-sulfonamide,
N-[3-(1H-benzimidazol-5-yl)-2,4-difluorophenyl]-5-chloro-2-methoxypyridine-3-sulfonamide,
N-[3-(2-amino-1H-benzimidazol-5-yl)-2,4-difluorophenyl]-5-chloro-2-methoxypyridine-3-sulfonamide,
5-chloro-N-[2,4-difluoro-3-(7-fluoro-1H-benzimidazol-5-yl)phenyl]-2-methoxypyridine-3-sulfonamide,
N-[3-(2-aminoquinazolin-6-yl)-2-methylphenyl]-5-chloro-2-methoxypyridine-3-sulfonamide,
N-[3-(2-aminoquinazolin-6-yl)-2-fluorophenyl]-5-chloro-2-methoxypyridine-3-sulfonamide,
N-[3-(2-aminoquinazolin-6-yl)-5-fluorophenyl]-5-chloro-2-methoxypyridine-3-sulfonamide,
N-[3-(2-aminoquinazolin-6-yl)-2,6-difluorophenyl]-5-chloro-2-methoxypyridine-3-sulfonamide,
N-[3-(2-aminoquinazolin-6-yl)-2,4-difluorophenyl]-5-chloro-2,4-difluorobenzene-1-sulfonamide,
N-[3-(2-aminoquinazolin-6-yl)-2,4-difluorophenyl]sulfuric diamide,
N-[3-(2-aminoquinazolin-6-yl)-4-fluorophenyl]-2,5-dichlorobenzene-1-sulfonamide,
N-[3-(2-aminoquinazolin-6-yl)-2,4-difluorophenyl]-5-chloro-2-(trifluoromethyl)benzene-1-sulfonamide,
N-[3-(2-aminoquinazolin-6-yl)-2,4-difluorophenyl]-3,5-dichlorobenzene-1-sulfonamide,
N-[3-(2-aminoquinazolin-6-yl)-2,4-difluorophenyl]-2-chloro-5-methylbenzene-1-sulfonamide,
N-[3-(2-aminoquinazolin-6-yl)-2,4-difluorophenyl]-5-chloro-2-methylbenzene-1-sulfonamide,
N-[3-(2-aminoquinazolin-6-yl)-2,4-difluorophenyl]-2,3-dichlorobenzene-1-sulfonamide,
N-[3-(2-aminoquinazolin-6-yl)-2,4-difluorophenyl]-3-chloro-5-(trifluoromethyl)benzene-1-sulfonamide,
N-[3-(2-aminoquinazolin-6-yl)-2,4-difluorophenyl]isoquinoline-5-sulfonamide,
5-chloro-N-[2,4-difluoro-3-(2-{[(1r,4r)-4-hydroxycyclohexyl]amino}quinazolin-6-yl)phenyl]-2-methoxypyridine-3-sulfonamide,
5-chloro-N-[2,4-difluoro-3-(2-{[(2R)-1-hydroxypropan-2-yl]amino}quinazolin-6-yl)phenyl]-2-methoxypyridine-3-sulfonamide,
2,5-dichloro-N-[2,4-difluoro-3-(2-{[(1r,4r)-4-hydroxycyclohexyl]amino}quinazolin-6-yl)phenyl]benzene-1-sulfonamide, -continued 2,5-dichloro-N-[2,4-difluoro-3-(2-{[(2R)-1-hydroxypropan-2-yl]amino}quinazolin-6-yl)phenyl]benzene-1-sulfonamide,
2,5-dichloro-N-[2,4-difluoro-3-(2-{[(1r,4r)-4-hydroxycyclohexyl]amino}quinazolin-6-yl)phenyl]-3-(hydroxymethyl)benzene-1-sulfonamide,
2,5-dichloro-N-[2,4-difluoro-3-(2-{[(2R)-1-hydroxypropan-2-yl]amino}quinazolin-6-yl)phenyl]-3-(hydroxymethyl)benzene-1-sulfonamide,
6-[1-(5-chloro-2-methoxypyridine-3-sulfonyl)-5-fluoro-1H-indol-4-yl]quinazolin-2-amine,
6-[1-(5-chloro-2-methoxypyridine-3-sulfonyl)-1H-indol-4-yl]quinazolin-2-amine,
6-[1-(5-chloro-2-methoxypyridine-3-sulfonyl)-5-fluoro-2,3-dihydro-1H-indol-4-yl]quinazolin-2-amine,
6-[1-(5-chloro-2-methoxypyridine-3-sulfonyl)-2,3-dihydro-1H-indol-4-yl]quinazolin-2-amine,
6-[1-(2,5-dichlorobenzene-1-sulfonyl)-5-fluoro-1H-indol-4-yl]quinazolin-2-amine,
6-[1-(2,5-dichlorobenzene-1-sulfonyl)-1H-indol-4-yl]quinazolin-2-amine,
{3-[4-(2-aminoquinazolin-6-yl)-5-fluoro-1H-indole-1-sulfonyl]-2,5-dichlorophenyl}methanol,
6-[1-(2,5-dichlorobenzene-1-sulfonyl)-5-fluoro-2,3-dihydro-1H-indol-4-yl]quinazolin-2-amine,
6-[1-(2,5-dichlorobenzene-1-sulfonyl)-2,3-dihydro-1H-indol-4-yl]quinazolin-2-amine,
{3-[4-(2-aminoquinazolin-6-yl)-5-fluoro-2,3-dihydro-1H-indole-1-sulfonyl]-2,5-dichlorophenyl}methanol,
N-[3-(2-aminoquinazolin-6-yl)-2,4-difluorophenyl]cyclohexanesulfonamide,
N-[3-(2-aminoquinazolin-6-yl)-2,4-difluorophenyl]piperidine-4-sulfonamide,
N-[3-(2-aminoquinazolin-6-yl)-2,4-difluorophenyl]-1-methylpiperidine-4-sulfonamide,
N-[3-(2-aminoquinazolin-6-yl)-2,4-difluorophenyl]piperidine-1-sulfonamide,
N-[3-(2-aminoquinazolin-6-yl)-2,4-difluorophenyl]piperazine-1-sulfonamide,
N-[3-(2-aminoquinazolin-6-yl)-2,4-difluorophenyl]-4-methylpiperazine-1-sulfonamide,
N-[3-(2-aminoquinazolin-6-yl)-2,4-difluorophenyl]oxane-4-sulfonamide,
(1r,4r)-N-[3-(2-aminoquinazolin-6-yl)-2,4-difluorophenyl]-4-hydroxycyclohexane-1-sulfonamide,
(1s,4s)-N-[3-(2-aminoquinazolin-6-yl)-2,4-difluorophenyl]-4-hydroxycyclohexane-1-sulfonamide,
N-[3-(2-aminoquinazolin-6-yl)-2,4-difluorophenyl]thiane-4-sulfonamide
(1r,4r)-N-[3-(2-aminoquinazolin-6-yl)-2,4-difluorophenyl]-4-methoxycyclohexane-1-sulfonamide,
(1s,4s)-N-[3-(2-aminoquinazolin-6-yl)-2,4-difluoropheny1]-4-methoxycyclohexane-1-sulfonamide,
N-[3-(2-aminoquinazolin-6-yl)-2,4-difluorophenyl]morpholine-4-sulfonamide,
N-[3-(2-aminoquinazolin-6-yl)-2,4-difluorophenyl]-4-hydroxypiperidine-1-sulfonamide,
N-[3-(2-aminoquinazolin-6-yl)-2,4-difluorophenyl]-4-(hydroxymethyl)piperidine-1-sulfonamide,
N-[3-(2-aminoquinazolin-6-yl)-2,4-difluorophenyl]thiomorpholine-4-sulfonamide,
(1r,4r)-N-[3-(2-aminoquinazolin-6-yl)-2,4-difluorophenyl]-4-(hydroxymethyl)cyclohexane-1-sulfonamide,
(1s,4s)-N-[3-(2-aminoquinazolin-6-yl)-2,4-difluorophenyl]-4-(hydroxymethyl)cyclohexane-1-sulfonamide,
3-{[3-(2-aminoquinazolin-6-yl)-2,4-difluorophenyl]sulfamoyl}cyclohexane-1-carboxamide,
3-{[3-(2-aminoquinazolin-6-yl)-2,4-difluorophenyl]sulfamoyl}cyclohexane-1-carboxylic acid,
N-[3-(2-aminoquinazolin-6-yl)-2,4-difluorophenyl]piperidine-3-sulfonamide,
3-{[3-(2-aminoquinazolin-6-yl)-2,4-difluorophenyl]sulfamoyl}-N-methylcyclohexane-1-carboxamide,
methyl 3-{[3-(2-aminoquinazolin-6-yl)-2,4-difluorophenyl]sulfamoyl}cyclohexane-1-carboxylate,
N-[3-(2-aminoquinazolin-6-yl)-2,4-difluorophenyl]-6-methylpiperidine-3-sulfonamide,
N-(6-(3-((5-chloro-2-methoxypyridine)-3-sulfonamido)-2,6-difluorophenyl)quinazolin-2-yl)pivalamide,
N-(6-(3((2,5-dichlorophenyl)sulfonamido)2,6-difluorophenyl)quinazolin-2-yl)acetamide,
N-(3-(2-aminoquinolin-6-yl)-2,4-difluorophenyl)-2,5-dichlorobenzenesulfonamide,
N-(3-(2-aminoquinazolin-6-yl)-2,4-difluorophenyl)-2,5-dichloro-3-(hydroxymethyl)benzenesulfonamide,
N-(3-(2-aminoquinazolin-6-yl)-2,4-difluorophenyl)-4-chloro-2,5-dimethylbenzenesulfonamide,
N-(3-(2-aminoquinazolin-6-yl)-2,4-difluorophenyl)-5-fluoro-2-methoxybenzenesulfonamide,
N-(3-(2-aminoquinazolin-5-yl)-2,4-difluorophenyl)-2,5-dichlorobenzenesulfonamide,
N-(3-(2-aminoquinazolin-6-yl)-2,4-difluorophenyl)-3,5-difluorobenzenesulfonamide,
N-(3-(2-aminoquinazolin-6-yl)-2,4-difluorophenyl)-3,5-dimethylbenzenesulfonamide,
N-(5-(3-((5-chloro-2-methoxypyridine)-3-sulfonamido)-2,6-difluorophenyl)quinazolin-2-yl)pivalamide,
N-(3-(2-aminoquinazolin-6-yl)-2,4-difluorophenyl)-3,4-dimethoxybenzenesulfonamide,
N-(3-(2-aminoquinazolin-6-yl)-2,4-difluorophenyl)-3-fluorobenzenesulfonamide,
N-(3-(2-aminoquinazolin-6-yl)-2,4-difluorophenyl)-4-methoxy-3-methylbenzenesulfonamide,
N-(3-(2-aminoquinazolin-6-yl)-2,4-difluorophenyl)-2-methoxy-5-methylbenzenesulfonamide, -continued N-(3-(2-aminoquinazolin-6-yl)-2,4-difluorophenyl)-2,5-dimethoxybenzenesulfonamide,
N-(3-(2-aminoquinazolin-6-yl)-2,4-difluorophenyl)-5-ethyl-2-methoxybenzenesulfonamide,
N-(3-(2-aminoquinazolin-6-yl)-2,4-difluorophenyl)-2,5-bis(trifluoromethyl)benzenesulfonamide,
N-(3-(2-aminoquinazolin-6-yl)-2,4-difluorophenyl)benzofuran-5-sulfonamide,
N-(3-(2-aminoquinazolin-6-yl)-2,4-difluorophenyl)-3-fluoro-5-(trifluoromethyl)benzenesulfonamide,
N-(3-(2-aminoquinazolin-6-yl)-2,4-difluorophenyl)-2,3-difluorobenzenesulfonamide,
N-(3-(2-aminoquinazolin-6-yl)-2,4-difluorophenyl)-3-methylbenzenesulfonamide,
2,5-dichloro-N-(3,5-difluoro-4-(2-((2-hydroxyethyl)amino)quinazolin-6-yl)pheny) benzenesulfonamide,
5-chloro-N-(2,4-difluoro-3-(2-(((1s,4s)-4-hydroxycyclohexyl)amino)quinazolin-6-yl)phenyl)-2-methoxypyridine-3-sulfonamide,
N-(3-(2-aminoquinazolin-6-yl)-2,4-difluorophenyl)pyridine-3-sulfonamide,
N-(3-(2-aminoquinazolin-6-yl)-2,4-dichlorophenyl)-5-chloro-2-methoxypyridine-3-sulfonamide,
N-(3-(2-aminoquinazolin-6-yl)-2,4-difluorophenyl)-3,4-difluorobenzenesulfonamide,
N-(3-(2-aminoquinazolin-6-yl)-2,4-difluorophenyl)-5-fluoro-2-methylbenzenesulfonamide,
2,5-dichloro-N-(2,4-difluoro-3-(2-((2-hydroxyethyl)amino)quinazolin-6-yl)phenyl)-3-(hydroxymethyl)benzenesulfonamide,
N-(3-(2-aminoquinazolin-6-yl)-2,4-difluorophenyl)-2-fluoro-5-(trifluoromethyl)benzenesulfonamide,
N-(3-(2-aminoquinazolin-6-yl)-2,4-difluorophenyl)-4-fluoro-3-(trifluoromethyl)benzenesulfonamide,
N-(3-(2-aminoquinazolin-6-yl)-2,4-difluorophenyl)-4-chloro-2-(trifluoromethyl)benzenesulfonamide,
N-(3-(2-aminoquinazolin-6-yl)-2,4-difluorophenyl)quinoxaline-5-sulfonamide,
N-(3-(2-aminoquinazolin-6-yl)-2,4-difluorophenyl)-3-(trifluoromethoxy)benzenesulfonamide,
N-(3-(2-aminoquinazolin-6-yl)-2,4-difluorophenyl)thiophene-3-sulfonamide,
N-(3-(2-aminoquinazolin-6-yl)-2,4-difluorophenyl)-3-isopropylbenzenesulfonamide,
N-(3-(2-aminoquinazolin-6-yl)-2,4-difluorophenyl)thiophene-2-sulfonamide,
N-(3-(2-aminoquinazolin-6-yl)-2,4-difluorophenyl)-4-fluoro-3-methoxybenzenesulfonamide,
N-(3-(2-aminoquinazolin-6-yl)-2,4-difluorophenyl)-3,5-bis(trifluoromethyl)benzenesulfonamide,
N-(3-(2-aminoquinazolin-6-yl)-2,4-difluorophenyl)-3-(trifluoromethyl)benzenesulfonamide,
N-(3-(2-aminoquinazolin-6-yl)-2,4-difluorophenyl)-4-chloro-3-fluorobenzenesulfonamide,
N-(3-(2-aminoquinazolin-6-yl)-2,4-difluorophenyl)-3-chloro-4-methylbenzenesulfonamide,
N-(3-(2-aminoquinazolin-6-yl)-2,4-difluorophenyl)-3-chloro-4-methoxybenzenesulfonamide,
N-(3-(2-aminoquinazolin-6-yl)-2,4-difluorophenyl)-4-chloro-3-(trifluoromethyl)benzenesulfonamide,
N-(3-(2-aminoquinazolin-6-yl)-2,4-difluorophenyl)-2,4,5-trichlorobenzenesulfonamide,
5-chloro-N-(3-(2-((1,3-dihydroxypropan-2-yl)amino)quinazolin-6-yl)-2,4-difluorophenyl)-2-methoxypyridine-3-sulfonamide,
(R)-5-chloro-N-(2,4-difluoro-3-(2-((2-hydroxy-1-phenylethyl)amino)quinazolin-6-yl)phenyl)-2-methoxypyridine-3-sulfonamide,
5-chloro-N-(3-(2-(dimethylamino)quinazolin-6-yl)-2,4-difluorophenyl)-2-methoxypyridine-3-sulfonamide,
5-chloro-N-(2,4-difluoro-3-(2-(piperidin-1-yl)quinazolin-6-yl)phenyl)-2-methoxypyridine-3-sulfonamide,
(S)-5-chloro-N-(2,4-difluoro-3-(2-((1-hydroxypropan-2-yl)amino)quinazolin-6-yl)phenyl)-2-methoxypyridine-3-sulfonamide,
N-(3-(2-aminoquinazolin-6-yl)-2,4-difluorophenyl)-3-chloro-4-fluorobenzenesulfonamide,
N-(3-(2-aminoquinazolin-6-yl)-2,4-difluorophenyl)-3-fluoro-4-methylbenzenesulfonamide,
N-(3-(2-aminoquinazolin-6-yl)-2,4-difluorophenyl)-4-fluoro-3-methylbenzenesulfonamide,
N-(3-(2-aminoquinazolin-6-yl)-2,4-difluorophenyl)-2,3-dihydro-1H-indene-5-sulfonamide,
2,5-dichloro-N-(2,4-difluoro-3-(2-(methylamino)quinazolin-6-yl)phenyl)-3-(hydroxymethyl)benzenesulfonamide,
(S)-5-chloro-N-(2,4-difluoro-3-(2-((2-hydroxy-1-phenylethyl)amino)quinazolin-6-yl)phenyl)-2-methoxypyridine-3-sulfonamide,
5-chloro-N-(2,4-difluoro-3-(2-(((1r,4r)-4-hydroxycyclohexyl)amino)quinazolin-6-yl)phenyl)-2-(trifluoromethyl)benzenesulfonamide,
5-chloro-N-(2,4-difluoro-3-(2-(((1s,4s)-4-hydroxycyclohexyl)amino)quinazolin-6-yl)phenyl)-2-(trifluoromethyl)benzenesulfonamide,
(S)-5-chloro-N-(2,4-difluoro-3-(2-((2-hydroxy-1-phenylethyl)amino)quinazolin-6-yl)phenyl)-2-(trifluoromethyl)benzenesulfonamide, -continued

| |
|---|
| (R)-5-chloro-N-(2,4-difluoro-3-(2-((2-hydroxy-1-phenylethyl)amino)quinazolin-6-yl)phenyl)-2-(trifluoromethyl)benzenesulfonamide, |
| 2,5-dichloro-N-(2,4-difluoro-3-(2-((tetrahydrofuran-3-yl)amino)quinazolin-6-yl)phenyl)benzenesulfonamide, |

or a salt thereof.

Methods of Treatment

Further embodiments of the invention include the use of a compound of Formula (1) or a salt thereof or a pharmaceutical composition comprising a compound of Formula (1) as a GCN2 modulator. Compounds of the present invention may be used as GCN2 modulators. Compounds of the present invention may be used as GCN2 inhibitors, antagonists or agonists. Compounds of the present invention may be used in the treatment of a disease or disorder characterised by activation of GCN2.

Compounds of the present invention may be used in the treatment of cancer, neurodegenerative diseases, chronic infections or conditions or symptoms related thereto. Other aspects of the invention relate more generally to compounds or compositions, for example compounds of Formula (I) or compositions containing them, for use in therapy, for example compounds or compositions for use in a method of treatment of the human or animal body by therapy. Some embodiments include compounds or compositions, for example compounds of Formula (I) or compositions containing them, for use in a method of treatment of the human body by therapy.

Compounds of the present invention may be used in the treatment of cancer. In some embodiments, compounds of the present invention are used to treat breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, adenocarcinoma, hepatocellular carcinoma, thyroid cancer, multiple myeloma, cancer of secretory cells, myelodysplastic syndrome, myeloproliferative neoplasm, malignant glioma, non-Hodgkin's lymphoma, Hodgkin's lymphoma, Burkitt's lymphoma, chronic lymphocytic leukemia, chronic myeloid leukemia, hairy cell leukemia, monoclonal gammopathy of undetermined significance (MGUS), plasmacytoma, lymphoplasmacytic lymphoma, acute lymphoblastic leukemia, acute myeloid leukemia, chronic myelomonocytic leukemia, juvenile myelomonocytic leukemia, large granular lymphocytic leukemia, B-cell prolymphocytic leukemia, T-cell prolymphocytic leukemia. small cell lung cancer, malignant pleural mesothelioma, Head and neck squamous cell carcinoma, glioblastoma multiforme, sarcoma, pediatric neuroblastoma or conditions or symptoms related thereto.

In some embodiments, compounds and compositions detailed herein are used as modulators of GCN2. Provided herein is a method of treating a disease in an individual comprising administering an effective amount of a compound of Formula (I) or any embodiment, variation or aspect thereof.

It was demonstrated that GCN2 may be used as an immune regulator. GCN2 senses tryptophan and L-arginine deficiency. Indoleamine 2,3-dioxygenase (IDO) is a potent immunoregulatory enzyme that mediates conversion of the essential amino acid tryptophan (Trp) to kyneurines and its expression allows certain macrophages and dendritic cells (DCs) to inhibit T cell proliferation (Grohmann et al., 2003, Mellor and Munn, 2004). IDO and the subsequent tryptophan starvation triggers a GCN2-dependent stress signalling pathway that induced profound anergy in responding T cells. GCN2-knockout cells are refractory to IDO-induced cell cycle arrest and anergy. IDO-expressing plasmacytoid DCs are found in tumor-draining lymph nodes and activates the GCN2 kinase pathway in responding T cells. T cells with a targeted disruption of GCN2 are not susceptible to IDO-mediated suppression of proliferation. (Munn et al., 2005). GCN2 activation through accumulation of unloaded tRNAs leads to inhibition of CD8+ effector T-cells and increase in generation and activation of regulatory T-cells.

IFN-γ is a cytokine that is produced mostly by activated T cells and NK cells and has complex effects on immune and nonimmune cells. IFN-γ plays important roles in inflammation, making it particularly relevant to transplantation and autoimmune diseases. IFN-γ induces Trp metabolism, which then activates GCN2 kinase, leading to the phosphorylation of the eIF2α, an activator of autophagy. Conversely, Trp supplementation reduces the activation of the GCN2-eIF2α pathway and inhibits autophagy. Further, targeting of GCN2 expression by RNA interference also inhibits IFN-γ-induced autophagy (Fougeray et al., 2012).

GCN2 plays a central role in regulating the cell-cycle arrest induced by L-Arginine (L-Arg) starvation. L-Arg is a nonessential amino acid that plays a central role in regulating the immune response (Bronte and Zanovello, 2005). In tumor-infiltrating myeloid cells, L-Arg is converted by arginase I and arginase II to urea and ornithine and oxidized by the inducible form of nitric oxide synthase to citrulline and nitric oxide. Thus, L-Arg is profoundly reduced in cancer patients, following liver transplantation, or in severe trauma by an increased production of arginase I (Zea et al., 2005; Roth et al., 1994; Angele et al., 1999). Increased arginase activity is frequently observed in patients with breast, prostate, lung and colon cancer (Cederbaum et al., 2004). This results in a decreased T-cell proliferation and an impaired T-cell function. GCN2-knockout T cells did not show a decreased proliferation in the absence of L-Arg (Rodriguez et al., 2006).

GCN2 activation via L-Arg deprivation was also shown to occur in astrocytes, similar to how activation of GCN2 kinase mediates proliferative arrest and T-cell anergy induction in response to Trp deprivation by IDO. L-Arg consumption by arginase 1 in tumor-conditioned ges mediated GCN2 kinase-dependent cell cycle arrest in the G0-G1 phase and downregulation of the (chain of the TCR/CD3 complex in antigen-activated T cells (Rodriguez et al., 2002).

Activation of GCN2 through amino acid deficient-conditions promotes macrophage inflammation and mortality in a mouse model of septicemia. GCN2 knockout macrophages had a significant reduction of cytokine gene expression after lipopolysaccharide (LPS) stimulation. When monocytic-lineage-specific GCN2 knockout mice were challenged with a lethal dose of LPS, mice showed reduced inflammatory responses, with decreased IL-6 and IL-12 expression correlating with significant reduction in animal mortality (Liu et al., 2014).

In some embodiments, provided herein is a method of treating a disease mediated by the GCN2 pathway in an individual comprising administering an effective amount of a compound of Formula (I), or a pharmaceutically acceptable salt thereof, to the individual.

In some embodiments, provided herein is a method of treating a disease characterised by activation of the GCN2 pathway in an individual comprising administering an effective amount of a compound of Formula (I), or a pharmaceutically acceptable salt thereof, to the individual.

In some embodiments, provided herein is a method of treating a disease in an individual, wherein the individual has a low level of an amino acid. In some embodiments, the individual has a low level of a nonessential amino acid. In some embodiments, the individual has a low level of L-arginine. In some embodiments, the individual has a low level of L-tryptophan. In some embodiments, the disease results in a low level of arginine in a specific tissue or cell type, such as a tumor or an immune cell. In some embodiments, the disease results in a low level of tryptophan in a specific tissue or cell type, such as a tumor or an immune cell. In some embodiments, the level of L-tryptophan is less than 200 μM, less than 100 μM, less than 75 μM, less than 50 μM, or less than 25 μM. In some embodiments, the level of L-tryptophan is 10 μM to 75 μM. In some embodiments, the level of L-arginine is less than 200 μM, less than 100 μM, less than 75 μM, less than 50 μM, or less than 25 μM. In some embodiments, the level of L-arginine is 10 μM to 75 μM.

Also provided herein is a method of treating a disease in an individual, wherein the disease involves overexpression of GCN2. In some embodiments, provided herein is a method of treating a disease in an individual, wherein the disease involves activation of GCN2. In some embodiments, GCN2 is overexpressed and/or activated in a in specific tissue or cell type, such as a tumor or an immune cell.

In some embodiments, the methods provided herein inhibit a stress response in a cell. In some embodiments, the stress response is involved protecting cancer cells. In some embodiments, the stress response relates to amino acid starvation. In some embodiments, the stress response is a the unfolded protein response. In some embodiments, the stress response is an ER stress response.

In some embodiments, the methods provided herein result in reduced phosphorylation of GCN2. In some embodiments, downstream signalling by GCN2 is reduced. In some embodiments, phosphorylation of eIF2α kinase is reduced.

It was described that persistent parasite or viral infections are associated to the local induction of IDO expression affecting the activation of a proper immune response. It was also demonstrated that cutaneous *Leishmania major* infection stimulated expression of IDO in local lymph nodes. Induced IDO attenuated the T cell stimulatory functions of dendritic cells and suppressed local T cell responses to exogenous and nominal parasite antigens (Makala et al., 2011).

It was also demonstrated the role of IDO in leprosy. An increased number of macrophages/dendritic cells expressing IDO were found in lepromatous compared to reversal reaction patients. Furthermore, an increased IDO message in *Mycobacterium leprae*-stimulated peripheral blood mononuclear cells were also found. These data suggest that *M. leprae* chronic infection activates the suppressive molecule IDO which, in turn, contributes to the specific immunosuppression observed in lepromatous leprosy (de Souza et al., 2011).

It was described that HIV inhibits CD4+ T-cell proliferation by inducing IDO in plasmacytoid dendritic cells and that in vitro inhibition of IDO results in increased CD4(+) T-cell proliferative response in peripheral blood mononuclear cells from HIV-infected patients (Boasso et al., 2007).

Accordingly, inhibitors of the IDO/GCN2 pathway as disclosed herein could be used to enhance immune responses to chronic and persistent infections. In some embodiments, a compound or salt thereof described herein or a composition described herein may be used in a method of treating or preventing a viral infection. In some embodiments, the viral infection is an African swine fever virus, a dengue virus, an enterovirus, a hepatitis B virus, a hepatitis C virus, influenza virus, a tick-borne encephalitis virus, or a West Nile virus infection. In some embodiments, the viral infection is caused by a virus that activates GCN2 in an infected cell.

The basic mechanism of nutritional stress management mediated by GCN2 pathway functions primarily to couple cell growth to amino acid availability (Zhang et al., 2002).

In the tumor microenvironment, the abnormal development of vasculature results in insufficient blood supply and deprivation of glucose and amino acids. Both amino acid and glucose deprivation, stresses found in solid tumors, activated GCN2 to upregulate ATF4 target genes involved in amino acid synthesis and transport. GCN2 activation/overexpression and increased phospho-eIF2α were observed in human and mouse tumors compared with normal tissues and abrogation of ATF4 or GCN2 expression significantly inhibited tumor growth in vivo (Ye et al., 2010).

ATF4 is necessary for tumor cells to maintain homeostasis of amino acid metabolism and that activation of GCN2-ATF4-asparagine synthetase (ASNS) pathway promotes tumor cell survival under nutrient (amino acid or glucose) deprivation. GCN2-eIF2α pathway is activated in various human and mouse tumor tissues. Deficiency of ATF4 or GCN2 severely inhibits tumor growth in vivo. Together, these results suggest that GCN2-ATF4-ASNS pathway is a promising target for tumor therapy.

Tumor xenograft studies of head and neck squamous cell carcinoma (HNSCC), or fibrosarcoma (HT1080) cell lines with GCN2 deletions prevented tumor growth and survival (Ye et al., 2010; Wang et al., 2013). Additionally, in response to vemurafenib, BRAF-mutated melanoma and colorectal cancer cells rapidly induced the ISR as a cytoprotective mechanism through activation of GCN2. The vemurafenib-triggered ISR, an event independent of downstream MEK inhibition, was specifically prevented by silencing GCN2, but not other eIF2α kinases. Interestingly, ATF4 silencing by siRNA rendered BRAF-mutated melanoma cells sensitive to vemurafenib. Thus, the GCN2-mediated ISR can promote cellular adaptation to vemurafenib-induced stress, providing an insight into the development of drug resistance (Nagasawa et al., 2017).

It was reported that amino acid deficiency, glucose deprivation and hypoxia promote tumor growth and angiogenesis through the GCN2/eIF2α/ATF4 pathway (Wang et al., 2013). GCN2 expression is elevated in human tumors to overcome the stress associated to amino acid deprivation by stimulating vascular endothelial growth factor (VEGF)-mediated angiogenesis.

Leukemia cells lack the ability to synthesize asparagine. Thus, asparaginase, which functions by depletion of asparagine and glutamine, is a first line of treatment for B-Cell-derived acute lymphoblastic leukemia (B-ALL) (Terwilliger et al., 2017). It has been demonstrated that treatment with asparaginase activates GCN2 pathway in several leukemia cells and this is a mechanism by which tumor cells cope with nutrient stress by reversing chemotherapeutic amino acid deprivation (Lough et al., 2018). The inhibition of GCN2 sensitizes cancer cells with low basal-level expression of asparagine synthetase (ASNS) to the anti-leukemic agent asparaginase (Nakamura et al., 2018). Thus, GCN2 inhibitors could be exploited as a single agent therapy or in combination with asparaginase.

Without being bound to any particular theory, the GCN2-eIF2α-ATF4 pathway is important for maintaining metabolic homeostasis in tumor cells, making it a novel and attractive target for anti-tumor approaches.

Compounds as GCN2 modulators as disclosed herein can be useful as a prophylactic or therapeutic agent for many GCN2 associated diseases such as cancer: colorectal cancer, gastrointestinal stromal tumor, lung cancer (e.g. small and non-small cell lung cancer, malignant mesothelioma, primary lung cancer), hematologic cancer (e.g. multiple myeloma, leukemia (e.g. acute myeloid leukemia, acute lymphocytic leukemia, chronic leukemia), malignant lymphoma, Hodgkin's disease, non-Hodgkin's leukemia, chronic myeloproliferative disease), cancer metastasis, precancerous lesions (e.g. bone marrow myelodysplastic syndrome), pancreatic cancer (e.g. pancreatic duct cancer, pancreatic endocrine tumor), pharyngeal cancer, laryngeal cancer, esophagus cancer, gastric cancer (e.g. papillary adenocarcinoma, adenosquamous carcinoma), duodenal cancer, small intestinal cancer, breast cancer (e.g. ductal carcinoma in situ, inflammatory breast cancer, invasive ductal carcinoma), ovarian cancer (e.g. ovarian epithelial carcinoma, ovarian germ cell tumor), testis tumor, prostate cancer (e.g. hormone and non-hormone dependent prostate cancer, castration-resistant prostate cancer), liver cancer (e.g. hepatoma, primary liver cancer), extrahepatic bile duct cancer, thyroid cancer, renal cancer (e.g. renal cell carcinoma, clear cell renal carcinoma), uterine cancer (e.g. cervix cancer, uterine body cancer, uterus sarcoma), brain tumor (e.g. glioma, glioblastoma, medulloblastoma, astrocytoma, hypophyseal adenoma), retinoblastoma, skin cancer (e.g. melanoma, basal cell carcinoma), sarcoma (e.g. rhabdomyosarcoma, leiomyosarcoma, soft tissue sarcoma, osteosarcoma, spindle cell sarcoma), malignant bone tumor, urinary bladder cancer. In some embodiments, a compound or salt thereof described herein or a composition described herein may be used in a method of treating cancer, such as breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma, hepatocellular carcinoma, thyroid cancer, multiple myeloma, cancer of secretory cells, myelodysplastic syndrome, myeloproliferative neoplasm, malignant glioma, non-Hodgkin's lymphoma, Hodgkin's lymphoma, Burkitt's lymphoma, chronic lymphocytic leukemia, chronic myeloid leukemia, hairy cell leukemia, monoclonal gammopathy of undetermined significance (MGUS), plasmacytoma, lymphoplasmacytic lymphoma, acute lymphoblastic leukemia, acute myeloid leukemia, chronic myelomonocytic leukemia, juvenile myelomonocytic leukemia, large granular lymphocytic leukemia, B-cell prolymphocytic leukemia, T-cell prolymphocytic leukemia. small cell lung cancer, malignant pleural mesothelioma, Head and neck squamous cell carcinoma, glioblastoma multiforme, sarcoma or pediatric neuroblastoma. In some embodiments, the compound, salt, or composition may be used in a method of treating metastatic kidney cancer, chronic lymphocytary leukemia, pancreatic adenocarcinoma, or non-small cell lung cancer.

The GCN2 modulation provides the opportunity for interfering with the tumor growth metabolism at the same time what may enhance the efficacy of a monotherapy or a combination therapy with other anticancer agents. In some embodiments, a compound or salt thereof described herein or a composition described herein may be used in treating tumor in combination with other anticancer agents such as an anti-neoplastic agent, an immune checkpoint inhibitor, or any other suitable anti-cancer agent. Exemplary immune checkpoint inhibitors include anti-PD-1, anti-PD-L1, anti GITR, anti-OX-40, anti-LAG3, anti-TIM-3, anti-41BB, anti-CTLA-4 antibodies. Exemplary anti-neoplastic agents can include, for example, anti-microtubule agents, platinum coordination complexes, alkylating agents, topoisomerase II inhibitors, topoisomerase I inhibitors, antimetabolites, antibiotic agents, hormones and hormonal analogs, signal transduction pathway inhibitors, non-receptor tyrosine kinase angiogenesis inhibitors, proteasome inhibitors, and inhibitors of cancer metabolism. Other anti-cancer agents can include one or more of an immuno-stimulant, an antibody or fragment thereof (e.g. an anti-CD20, anti-HER2, anti-CD52, or anti-VEGF antibody or fragment thereof), or an immunotoxin (e.g. an anti-CD33 antibody or fragment thereof, an anti-CD22 antibody or fragment thereof, a calicheamicin conjugate, or a *pseudomonas* exotoxin conjugate).

In some embodiments, a compound or salt thereof described herein or a composition described herein may be used in a method of treating cancer in an individual, wherein one or more cancer cells in the individual are dormant cancer cells. In some embodiments, one or more of the dormant cancer cells are disseminated tumor cells or circulating tumor cells. In some embodiments, one or more of the dormant cancer cells are disseminated tumor cells.

In some embodiments, a compound or salt thereof described herein or a composition described herein may be used in a method of treating cancer in an individual, wherein the individual has had a prior treatment. In some embodiments, the cancer is resistant or refractory to the prior treatment. In some embodiments, the cancer has progressed on the prior treatment. In the embodiments, the cancer is a recurrent cancer. In some embodiments, the prior treatment was treatment with a ubiquitin-proteasome pathway inhibitor (e.g., bortezomib), a taxane (e.g., paclitaxel or docetaxel), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), an mTOR inhibitor (e.g., rapamycin), an immune-check point inhibitor, or an agent that is used in immune oncology. In some embodiments, the cancer is resistant to treatment with a ubiquitin-proteasome pathway inhibitor (e.g., bortezomib), a taxane (e.g., paclitaxel or docetaxel), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), an mTOR inhibitor (e.g., rapamycin), an immune-check point inhibitor, or an agent that is used in immune oncology. In some embodiments, the cancer is resistant to treatment with doxorubicin and/or rapamycin.

In some embodiments, the administration of the compound, salt, or composition reduces tumor growth, tumor proliferation, or tumorigenicity in the individual. In some embodiments, the compound, salt, or composition may be used in a method of reducing tumor growth, tumor proliferation, or tumorigenicity in an individual in need thereof. In some embodiments, tumor growth is slowed or arrested. In some embodiments, tumor growth is reduced at least about 10%, 20%, 30%, 40%, 50%, 60%, 70%, 80%, or 90%. In some embodiments, the tumor is reduced in size. In some embodiments, tumor size is reduced at least about 10%, 20%, 30%, 40%, 50%, 60%, 70%, 80%, or 90%. In some embodiments, tumor metastasis is prevented or slowed. In some embodiments, the tumor growth, tumor proliferation, or tumorigenicity is compared to the tumor growth, tumor proliferation, or tumorigenicity in the individual prior to the administration of the compound, salt, or composition. In some embodiments, the tumor growth, tumor proliferation, or tumorigenicity is compared to the tumor growth, tumor proliferation, or tumorigenicity in a similar individual or group of individuals. Methods of measuring tumor growth, tumor proliferation, and tumorigenicity are known in the art, for example by repeated imaging of the individual.

In some embodiments, the administration of the compound, salt, or composition induces apoptosis of cancer cells. In some embodiments, apoptosis of cancer cells is increased at least 10%, at least 20%, at least 30%, at least 40% or at least 50% upon administration.

In some embodiments, the administration of the compound, salt, or composition reduces CHOP induction. In some embodiments, CHOP induction is reduced at least 10%, at least 20%, at least 30%, at least 40% or at least 50% upon administration.

In some embodiments, the administration of the compound, salt, or composition does not induce PERK activation. In some embodiments, CHOP production caused by PERK is not inhibited upon administration.

It was recently demonstrated that hepatic GCN2 is activated in fatty livers, and GCN2 deficiency protects against high-fat diet (HFD)-induced hepatic steatosis and insulin resistance, indicating that the role of GCN2 in lipid metabolism regulation is context dependent.

After high fat diet (HFD) feeding for 12 weeks, Gcn2−/− mice were less obese than wild-type (WT) mice, and Gcn2−/− significantly attenuated HFD-induced liver dysfunction, hepatic steatosis and insulin resistance. In the livers of the HFD-fed mice, GCN2 deficiency resulted in higher levels of lipolysis genes, lower expression of genes related to fatty acid synthesis, transport and lipogenesis, and less induction of oxidative stress. In this work it was also reported that knockdown of GCN2 attenuated, whereas overexpression of GCN2 exacerbated, palmitic acid-induced steatosis, oxidative & ER stress, and changes of peroxisome proliferator-activated receptor gamma (PPARy), fatty acid synthase and metallothionein expression in HepG2 cells (Liu et al., 2018). These findings suggest that strategies to inhibit GCN2 activity in the liver may provide a novel approach to attenuate Nonalcoholic fatty liver disease (NAFLD) development.

When mice are reared with a medium fat (22 kcal % fat) diet during perinatal development, GCN2 deficiency reduced hepatic triglyceride storage (Xu et al., 2013).

It was reported that GCN2 deficiency attenuated cardiac dysfunction and hyperlipidemia in both type 1 diabetes (T1D) and Type 2 diabetes (T2D) mice, and the improved cardiac function in diabetic GCN2−/− mice was associated with reduced hypertrophy, fibrosis, lipid accumulation, oxidative stress, inflammation and apoptosis. The pathological role of GCN2 in diabetic cardiomyopathy (DCM) was also validated in high glucose or palmitic acid treated H9C2 rat cardio-myoblast cell line (Feng et al., 2019).

GCN2 deficiency attenuated transverse aortic constriction (TAC)-induced cardiac dysfunction and cardiomyocyte apoptosis by decreasing cardiomyocyte apoptosis and myocardial oxidative stress. GCN2 activation impairs adaptative responses to congestive heart failure (Lu et al., 2014). After doxorubicin-induced cardiac dysfunction, Gcn2−/− mice developed less contractile dysfunction, myocardial fibrosis, apoptosis, and oxidative stress compared with WT mice. In the hearts of the Dox-treated mice, GCN2 deficiency attenuated eIF2α phosphorylation and induction of its downstream targets, activating transcription factor 4 (ATF4) and C/EBP homologous protein (CHOP), and preserved the expression of anti-apoptotic factor Bcl-2 and mitochondrial uncoupling protein-2 (UCP2) (Wang et al., 2018). These data suggest that strategies to inhibit GCN2 activity in cardiomyocyte may provide a novel approach to attenuate Dox-related cardiotoxicity.

Accordingly, in some embodiments, a compound or salt thereof described herein or a composition described herein may be used in treating or preventing metabolic and cardiac diseases.

It was demonstrated that GCN2 deletion attenuates denervation-induced muscle atrophy. GCN2 deficiency also significantly attenuated the muscle mass loss in atrophied gastrocnemius and extensor digitorum longus muscles. Similar results were observed on day 14 after denervation. Wheat germ agglutinin staining of muscle cryosections demonstrated that GCN2-deficient TA muscles had a better preservation of myofiber size in response to denervation (Guo et al., 2018). Furthermore, the detrimental effect of GCN2 in denervation-induced muscle atrophy was related to FoxO3a activation, which upregulates genes involved in both the ubiquitin-proteasome pathway and autophagy in muscle atrophy (Sandri et al., 2004; Bertaggia et al., 2012; Wei et al., 2013; Guo et al., 2016).

Accordingly, in some embodiments, a compound or salt thereof described herein or a composition described herein may be used in treating or preventing muscle atrophy.

Expression of long-lasting synaptic plasticity and long-term memory (LTM) requires protein synthesis, which can be repressed by phosphorylation of eIF2α. In mice lacking the eIF2α kinase, GCN2, the reduction in phosphorylated eIF2α is associated with altered synaptic plasticity and memory. GCN2 deficient mice, in which both eIF2α phosphorylation and ATF4 levels are reduced, the threshold for long-lasting long-term potentiation (L-LTP) and LTM in hippocampus is lowered and it is associated with an improved spatial memory of weak conditioning (Costa-Mattioli et al., 2005). This model is supported by the increase of ATF4 expression upon treatment with an inhibitor of eIF2α phosphatases, Sal003, which leads to an impairment of L-LTP and LTM.

Accordingly, in some embodiments, a compound or salt thereof described herein or a composition described herein may be used in treating or preventing memory loss.

Elevated phosphorylation of eIF2α has been observed in the brains of Alzheimer's disease (AD) patients and Alzheimer's disease model mice. Suppressing GCN2 prevents amyloid-β-induced synaptic plasticity impairments by diminishing eIF2α phosphorylation. Senile plaques are primarily composed of β-amyloid peptides (Aβ) derived from amyloid precursor protein (APP) that has undergone proteolytic processing by β-secretase (BACE-1) and γ-secretase. It was also reported that BACE-1 levels are translationally increased by phosphorylation of eIF2α (O'Connor et al., 2008). Inhibition of GCN2 under such disease conditions that promote activation of γ-secretase or induction of BACE-1 with consequence of accumulation of Aβ and plaque formation in the brain would provide a valuable avenue to cope with or even stop the progression of neurodegenerative diseases.

Deletion of GCN2 prevented impairments of synaptic plasticity and defects in spatial memory in mice that express familial AD-related mutations in amyloid precursor protein (APP) and presenilin-1 (PS1). PS1 is essential for γ-secretase activity and GCN2/eIF2α/ATF4 signalling has an important role in the regulation of γ-secretase activity in autophagy impaired cells (Ohata et al., 2010).

Furthermore, hippocampal LTP deficits in APP-PS1 mice were normalized in APP-PS1 GCN2-deficient mice. The impairments in spatial learning and memory displayed by the APP-PS1 mice were prevented in the APP-PS1 GCN2-deficient mice as observed in a Morris Water Maze task by decreased escape latency, increased platform crossings as well as target quadrant occupancy that were close to those displayed by wild-type mice (Ma et al., 2013). Taken together, these findings indicate that genetic removal of the eIF2α kinase GCN2 prevents Alzheimer's disease-associated LTP failure and spatial memory impairments.

Accordingly, in some embodiment, a compound or salt thereof described herein or a composition described herein may be used in treating neurodegenerative diseases.

Angiogenesis, the formation of new blood vessels by endothelial cells (ECs), is an adaptive response to oxygen/nutrient deprivation sensed by GCN2 and orchestrated by vascular endothelial growth factor (VEGF) upon ischemia or exercise. Neovascularization in the retina and the choroid is a major cause of vision loss in severe eye diseases, such as diabetic retinopathy, age-related macular degeneration, retinopathy of prematurity, and central and branch retinal vein occlusion. Amino acid restriction triggers angiogenesis via GCN2/ATF4 regulation of VEGF and hydrogen sulfide production (Longchamp et al., 2018).

Yet, retinal neovascularization is causally and dynamically associated with vasodegeneration, ischemia, and vascular remodeling in retinal tissues (Zhang et al., 2015). ATF4 has been shown to function as an oxygen sensor and interacts with HIF-1α to regulate VEGF production (Zhong et al., 2012). Global knockout of ATF4 disturbs lens development, resulting in microphthalmia (Masuoka and Townes, 2002). Genetic inhibition of ATF4 activity attenuates diabetic-induced retinal inflammation and vascular leakage, suggesting that up-regulation of ATF4 contributes to retinal inflammation and endothelial barrier dysfunction in diabetic retinopathy (Chen et al., 2012).

Accordingly, in some embodiment, a compound or salt thereof described herein or a composition described herein may be used in treating ocular diseases.

Since there is accumulating evidence showing that the GCN2 pathway strongly influences the function of the immune system, the present invention encompasses the use of GCN2 modulators for the treatment or prevention of immune related disorders. In some embodiment, a compound or salt thereof described herein or a composition described herein may be used in treating or preventing immune related disorders. In some embodiment, a compound or salt thereof described herein or a composition described herein may be used in treating or preventing an autoimmune disease selected from the group consisting of arthritis, graft-versus-host disease, Crohn's disease, multiple sclerosis, lupus, type 1 diabetes mellitus, rheumatoid arthritis, Grave's disease, autoimmune hemolytic anemia, Wegener's granulomatosis, ankylosing spondylitis, aplastic anemia, Behcet's disease, hyper IgE syndrome, idiopathic thrombocytopenia purpura, Myasthenia gravis and psoriasis.

In some embodiment, a compound or salt thereof described herein or a composition described herein may be used in transplantation proceeding to treat organ rejection, myeloablative and non-myeloablative bone marrow transplant rejection.

In some embodiment, a compound or salt thereof described herein or a composition described herein may be used to inhibit the phosphorylation of GCN2. In some embodiments, a compound or salt thereof described herein or a composition described herein can be used to promote the recovery protein synthesis under amino acid deprived condition. In some embodiments, a compound or salt thereof described herein or a composition described herein can be used to enhance protein synthesis, and thus can be used in diseases or disorders that are mediated by a decrease in protein synthesis such as muscle atrophy, muscle dystrophy, cachexia, synaptic plasticity and long-term memory, among others.

In accordance with the present disclosure, in some embodiments, the individual is a mammal. In some embodiments, the individual is a primate, bovine, ovine, porcine, equine, canine, feline, rabbit, or rodent. In some embodiments, the individual is a human. In some embodiments, the individual has any of the diseases or disorders disclosed herein. In some embodiments, the individual is a risk for developing any of the diseases or disorders disclosed herein.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by the GCN2 pathway.

In some embodiments, a compound or salt thereof described herein or a composition described herein may be used in a method as either a stand-alone therapy, or as a conjunctive therapy with other agents that are either palliative (e.g., agents that relieve the symptoms of the disorder to be treated), and/or agents that target the etiology of the disorder. Compounds or compositions of the present invention may be used or administered in combination with a second therapeutic agent. Compounds or compositions of the present invention may be used or administered in combination with an anticancer agent, anti-angiogenesis agent or an agent that targets an immune checkpoint protein. Compounds or compositions of the present invention may be used or administered in combination with a second therapeutic agent selected from: PEG-arginase, asparaginase, anti-angiogenic factors, cysteinase or sulfasalazine.

As provided herein, compounds or salts thereof described herein and compositions described herein may be administered with an agent to treat any of the diseases and disorders disclosed herein. In some embodiments, the agent is an anti-angiogenesis agent. In some embodiments, the agent is an anticancer agent. In some embodiments, the agent targets an immune checkpoint protein.

In some embodiments, (a) a compound described herein, or a pharmaceutically acceptable salt thereof, or a pharmaceutical composition described herein and (b) an agent are sequentially administered, concurrently administered or simultaneously administered. In certain embodiments, (a) a compound described herein, or a pharmaceutically acceptable salt thereof, or a pharmaceutical composition described herein and (b) an agent are administered with a time separation of about 15 minutes or less, such as about any of 10, 5, or 1 minutes or less. In certain embodiments, (a) a compound described herein, or a pharmaceutically acceptable salt thereof, or a pharmaceutical composition described herein and (b) an agent are administered with a time separation of about 15 minutes or more, such as about any of 20, 30, 40, 50, 60, or more minutes. Either (a) a compound described herein, or a pharmaceutically acceptable salt thereof, or a pharmaceutical composition described herein and (b) an agent may be administered first. In certain embodiments, (a) a compound described herein, or a pharmaceutically acceptable salt thereof, or a pharmaceutical composition described herein and (b) an agent are administered simultaneously.

Provided herein is a method of enhancing an immune response in an individual comprising administering to the individual (a) a compound described herein, or a pharmaceutically acceptable salt thereof, or a pharmaceutical composition described herein and (b) an agent that targets an immune checkpoint protein. In some embodiments, the individual has cancer. In some embodiments, the enhanced immune response is directed to a tumor or cancerous cell.

Also provided herein are methods of treating cancer in an individual in need thereof comprising administering to the individual (a) a compound described herein, or a pharmaceutically acceptable salt thereof, or a pharmaceutical composition described herein and (b) an agent that targets an immune checkpoint protein, wherein an immune response of the individual is increased.

In some embodiments, the agent is an anticancer agent. In some embodiments, anticancer agent is an ubiquitin-proteasome pathway inhibitor (e.g., bortezomib), a taxane (e.g., paclitaxel or docetaxil), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), or an agent that modulates the Unfolded Protein Response or the Integrated Stress Response (e.g. an IRE1/XBP1 inhibitor or a PERK inhibitor). In some embodiments, the anticancer agent is oxaliplatin, 5-fluorouracil, or gemcitabine. In some embodiments, the anticancer agent is an immune-check point inhibitor, or an agent that is used in immune oncology.

In some embodiments, an effective amount of a compound described herein, or a pharmaceutically acceptable salt thereof, or a pharmaceutical composition described herein is administered to an individual with cancer to increase sensitivity to one or more anticancer treatments.

In some embodiments, an effective amount of a compound described herein, or a pharmaceutically acceptable salt thereof, or a pharmaceutical composition described herein is administered to an individual with cancer to increase sensitivity to radiation. In some embodiments, provided herein are methods of treating cancer in an individual in need thereof comprising administering to the individual (a) a compound described herein, or a pharmaceutically acceptable salt thereof, or a pharmaceutical composition described herein and (b) radiation.

In some embodiments, an effective amount of a compound described herein, or a pharmaceutically acceptable salt thereof, or a pharmaceutical composition described herein is administered to an individual with cancer to increase sensitivity to one or more anticancer agents. In some embodiments, the anticancer agent is an ubiquitin-proteasome pathway inhibitor (e.g., bortezomib), a taxane (e.g., paclitaxel or docetaxil), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), or an agent that modulates the Unfolded Protein Response or the Integrated Stress Response (e.g. an IRE1/XBP1 inhibitor or a PERK inhibitor). In some embodiments, the anticancer agent is oxaliplatin, 5-fluorouracil, or gemcitabine. In some embodiments, the anticancer agent is an immune-check point inhibitor, or an agent that is used in immune oncology.

Definitions

In this application, the following definitions apply, unless indicated otherwise.

The term "GCN2 modulator" as used herein refers to any compound which binds to and modulates the function of GCN2. The term "modulator" should be interpreted to include modulation by modalities including, but not limited to, antagonists, agonists, partial agonists and inverse agonists.

The term "treatment", in relation to the uses of any of the compounds described herein, including those of Formula (1) is used to describe any form of intervention where a compound is administered to a subject suffering from, or at risk of suffering from, or potentially at risk of suffering from the disease or disorder in question, such as cancer or an immunological disease. Thus, the term "treatment" covers both preventative (prophylactic) treatment and treatment where measurable or detectable symptoms of the disease or disorder are being displayed. Treatment also encompasses decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient.

In some variations, treatment does not include prevention. Thus, it is understood that in some variations, treatment refers to uses of any of the compounds described herein, including those of Formula (1) is used to describe any form of intervention where a compound is administered to a subject suffering from, or at risk of suffering from, or potentially at risk of suffering from the disease or disorder in question, such as cancer or an immunological disease.

"Individual" refers to mammals and includes humans and non-human mammals. Examples of individuals include, but are not limited to, mice, rats, hamsters, guinea pigs, pigs, rabbits, cats, dogs, goats, sheep, cows, and humans. In some embodiments, individual refers to a human.

The term "effective therapeutic amount" (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain. With respect to the treatment, if the condition is cancer, then the effective therapeutic amount is an amount sufficient to reduce one or more symptoms associated with cancer, for example reduction of tumour size or rate of metastasis.

As used herein, "about" a parameter or value includes and describes that parameter or value per se. For example, "about X" includes and describes X per se.

Terms such as "heterobicyclic", "heteroaryl", "bicyclic", "heterocyclic", "carbocyclic", "alkyl", "alkoxy" and "halo" are all used in their conventional sense (e.g. as defined in the IUPAC Gold Book), unless indicated otherwise. "optionally substituted" as applied to any group means that the said group may if desired be substituted with one or more substituents, which may be the same or different.

To the extent that any of the compounds described have chiral centres, the present invention extends to all optical isomers of such compounds, whether in the form of racemates or resolved enantiomers. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-1 0-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, Ind., USA, 1999, ISBN 0-967-06710-3.

The term "pharmaceutical composition" in the context of this invention means a composition comprising an active agent and comprising additionally one or more pharmaceutically acceptable carriers that is suitable for administration to an individual. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in some embodiments of the invention, there is provided a pharmaceutical composition comprising at least one compound of Formula (1) as defined above together with at least one pharmaceutically acceptable excipient.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term “pharmaceutically acceptable” as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be “acceptable” in the sense of being compatible with the other ingredients of the formulation.

Pharmaceutical compositions containing compounds of the Formula (1) can be formulated in accordance with known techniques, see for example, Remington’s Pharmaceutical Sciences, Mack Publishing Company, Easton, Pa., USA. The pharmaceutical compositions can be in any form suitable for oral, parenteral, intravenous, intramuscular, intrathecal, subcutaneous, topical, intranasal, intrabronchial, sublingual, buccal, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

The composition may be a tablet composition or a capsule composition. Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

The composition may be a parenteral composition. Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in “patient packs” containing an entire course of treatment in a single package, usually a blister pack.

The compounds of the Formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the following examples shown in Table 1.

TABLE 1

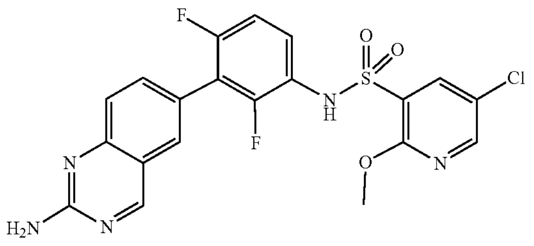 [SMILES: COc1ncc(Cl)cc1S(=O)(=O)Nc1ccc(F)c(-c2ccc3nc(N)ncc3c2)c1F]

Compound 1

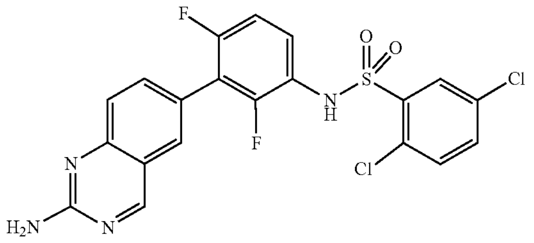 [SMILES: Nc1ncc2cc(-c3c(F)ccc(NS(=O)(=O)c4cc(Cl)ccc4Cl)c3F)ccc2n1]

Compound 2

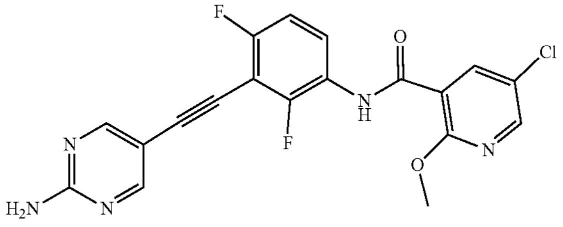 [SMILES: COc1ncc(Cl)cc1C(=O)Nc1ccc(F)c(C#Cc2cnc(N)nc2)c1F]

Compound 3

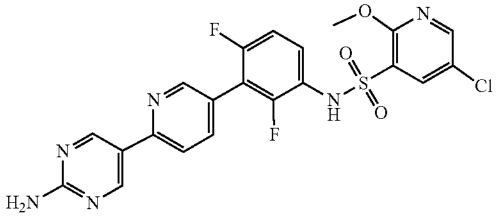 [SMILES: COc1ncc(Cl)cc1S(=O)(=O)Nc1ccc(F)c(-c2ccc(-c3cnc(N)nc3)nc2)c1F]

Compound 4

TABLE 1-continued

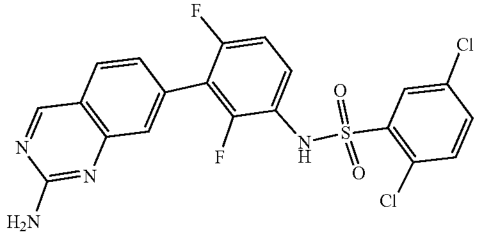 [SMILES: Nc1ncc2ccc(-c3c(F)ccc(NS(=O)(=O)c4cc(Cl)ccc4Cl)c3F)cc2n1]

Compound 5

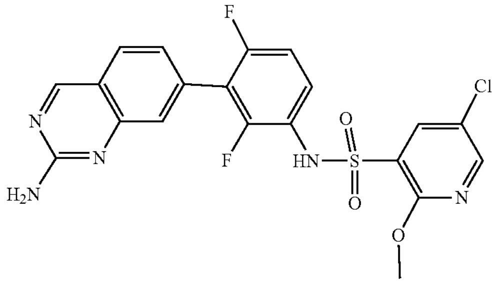 [SMILES: COc1ncc(Cl)cc1S(=O)(=O)Nc1ccc(F)c(-c2ccc3cnc(N)nc3c2)c1F]

Compound 6

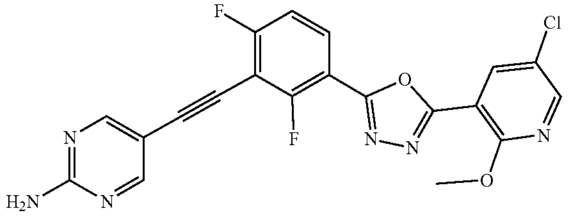 [SMILES: COc1ncc(Cl)cc1-c1nnc(-c2ccc(F)c(C#Cc3cnc(N)nc3)c2F)o1]

Compound 7

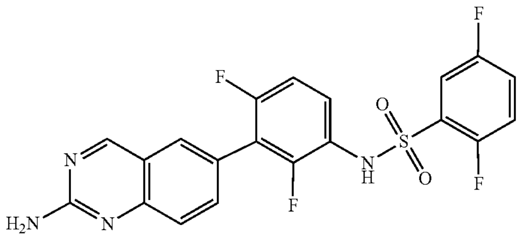 [SMILES: Nc1ncc2cc(-c3c(F)ccc(NS(=O)(=O)c4cc(F)ccc4F)c3F)ccc2n1]

Compound 8

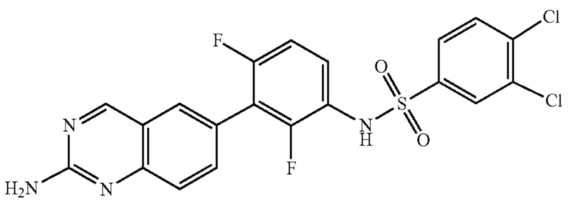 [SMILES: Nc1ncc2cc(-c3c(F)ccc(NS(=O)(=O)c4ccc(Cl)c(Cl)c4)c3F)ccc2n1]

Compound 9

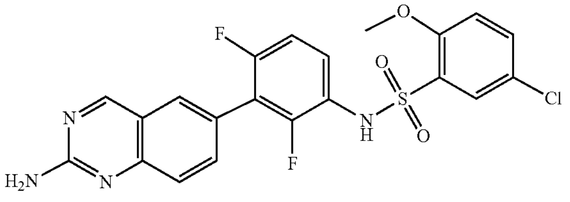 [SMILES: COc1ccc(Cl)cc1S(=O)(=O)Nc1ccc(F)c(-c2ccc3nc(N)ncc3c2)c1F]

TABLE 1-continued
Compound 10
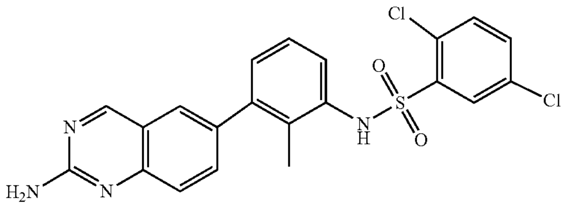 [SMILES: Cc1c(NS(=O)(=O)c2cc(Cl)ccc2Cl)cccc1-c1ccc2nc(N)ncc2c1]
Compound 11
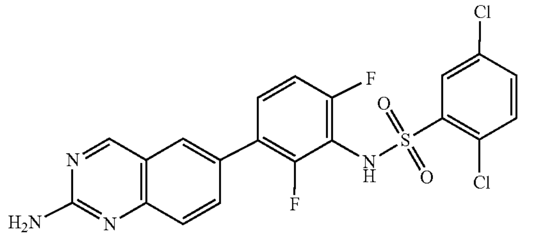 [SMILES: Nc1ncc2cc(-c3ccc(F)c(NS(=O)(=O)c4cc(Cl)ccc4Cl)c3F)ccc2n1]
Compound 12
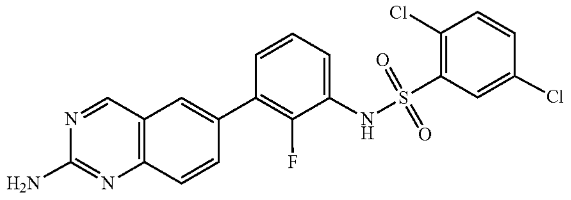 [SMILES: Nc1ncc2cc(-c3cccc(NS(=O)(=O)c4cc(Cl)ccc4Cl)c3F)ccc2n1]
Compound 13
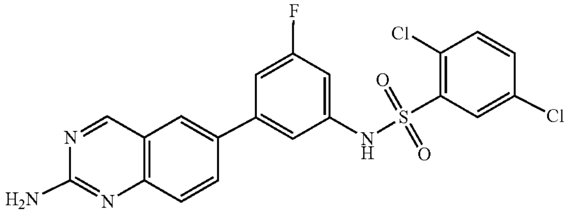 [SMILES: Nc1ncc2cc(-c3cc(F)cc(NS(=O)(=O)c4cc(Cl)ccc4Cl)c3)ccc2n1]
Compound 14
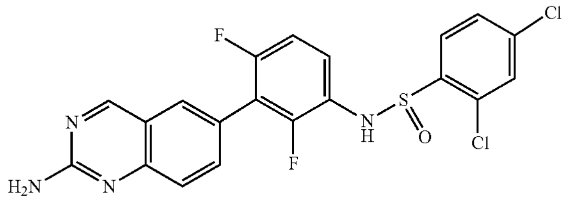 [SMILES: Nc1ncc2cc(-c3c(F)ccc(NS(=O)c4ccc(Cl)cc4Cl)c3F)ccc2n1]
Compound 15
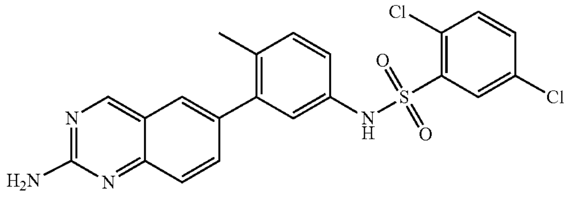 [SMILES: Cc1ccc(NS(=O)(=O)c2cc(Cl)ccc2Cl)cc1-c1ccc2nc(N)ncc2c1]
Compound 16
TABLE 1-continued
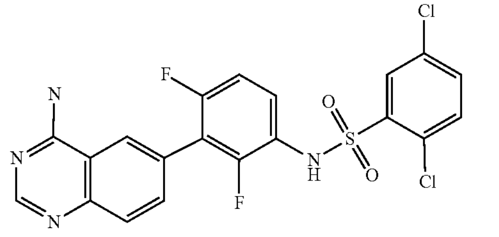
Compound 17
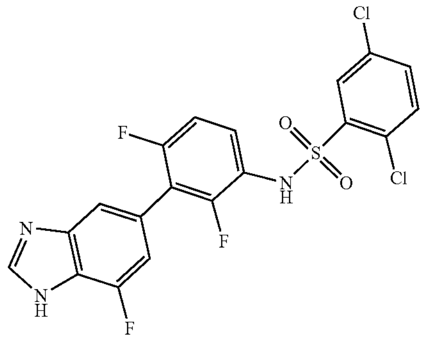 [SMILES: O=S(=O)(Nc1ccc(F)c(-c2cc(F)c3[nH]cnc3c2)c1F)c1cc(Cl)ccc1Cl]
Compound 18
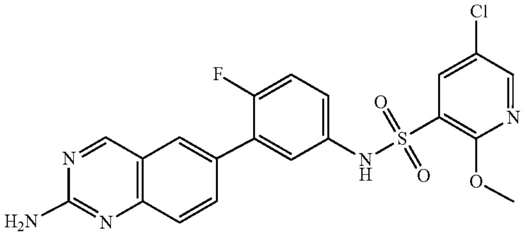 [SMILES: COc1ncc(Cl)cc1S(=O)(=O)Nc1ccc(F)c(-c2ccc3nc(N)ncc3c2)c1]
Compound 19
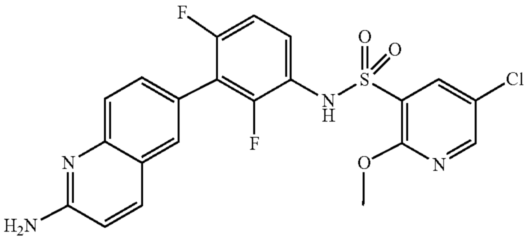 [SMILES: COc1ncc(Cl)cc1S(=O)(=O)Nc1ccc(F)c(-c2ccc3nc(N)ccc3c2)c1F]
Compound 20
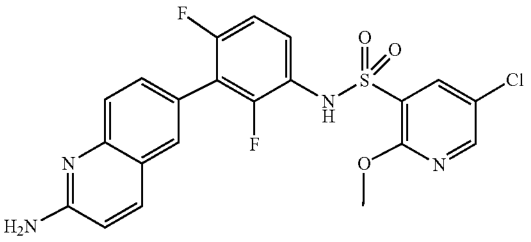 [SMILES: COc1ncc(Cl)cc1S(=O)(=O)Nc1ccc(F)c(-c2ccc3nc(N)ccc3c2)c1F]
Compound 21

TABLE 1-continued
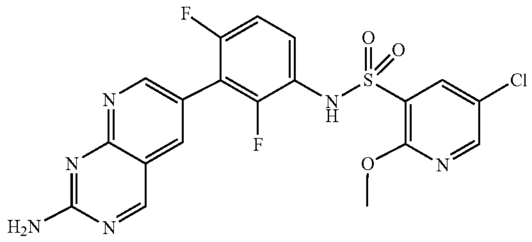 [SMILES: COc1ncc(Cl)cc1S(=O)(=O)Nc1ccc(F)c(-c2cnc3nc(N)ncc3c2)c1F]
Compound 22
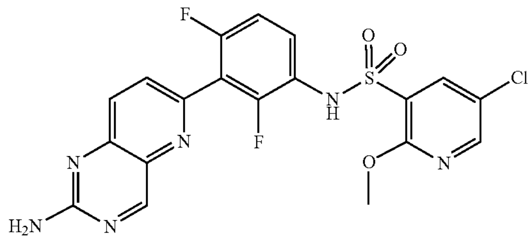 [SMILES: COc1ncc(Cl)cc1S(=O)(=O)Nc1ccc(F)c(-c2ccc3nc(N)ncc3n2)c1F]
Compound 23
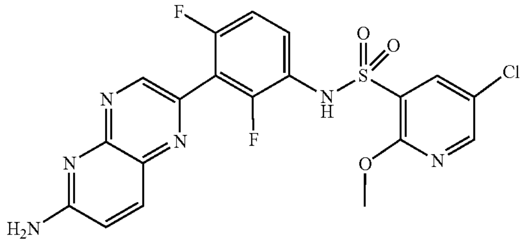 [SMILES: COc1ncc(Cl)cc1S(=O)(=O)Nc1ccc(F)c(-c2cnc3nc(N)ccc3n2)c1F]
Compound 24
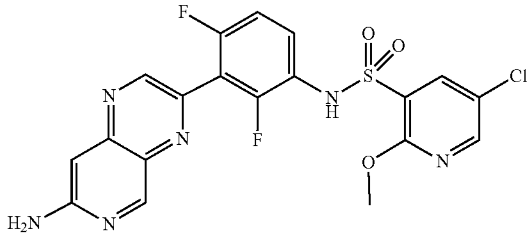
Compound 25
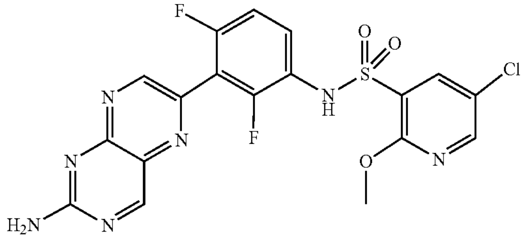 [SMILES: COc1ncc(Cl)cc1S(=O)(=O)Nc1ccc(F)c(-c2cnc3nc(N)ncc3n2)c1F]
Compound 26
TABLE 1-continued
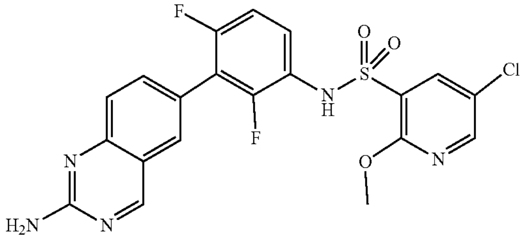 [SMILES: COc1ncc(Cl)cc1S(=O)(=O)Nc1ccc(F)c(-c2ccc3nc(N)ncc3c2)c1F]
Compound 27
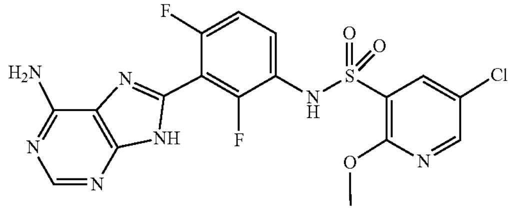 [SMILES: COc1ncc(Cl)cc1S(=O)(=O)Nc1ccc(F)c(-c2nc3c(N)ncnc3[nH]2)c1F]
Compound 28
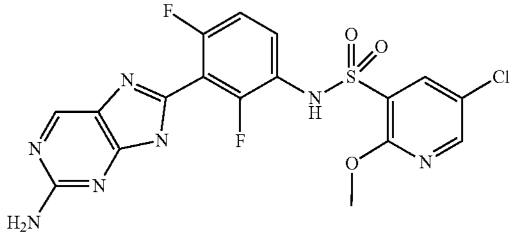
Compound 29
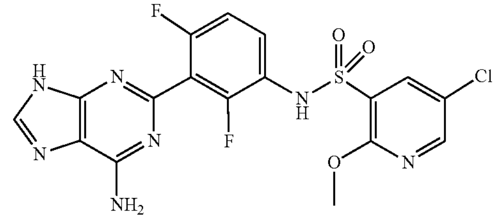 [SMILES: COc1ncc(Cl)cc1S(=O)(=O)Nc1ccc(F)c(-c2nc(N)c3nc[nH]c3n2)c1F]
Compound 30
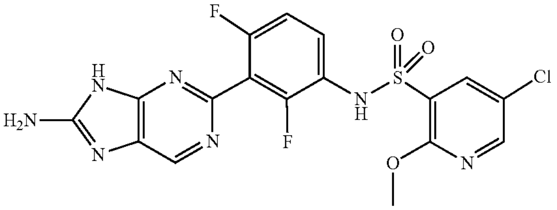 [SMILES: COc1ncc(Cl)cc1S(=O)(=O)Nc1ccc(F)c(-c2ncc3nc(N)[nH]c3n2)c1F]
Compound 31
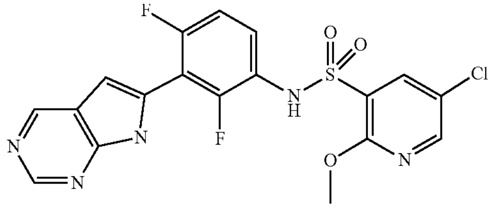
Compound 32

TABLE 1-continued
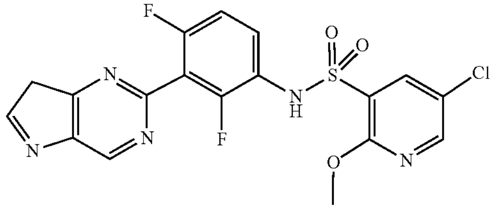 [SMILES: COc1ncc(Cl)cc1S(=O)(=O)Nc1ccc(F)c(-c2ncc3c(n2)CC=N3)c1F]
Compound 33
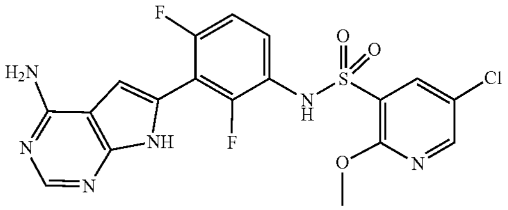 [SMILES: COc1ncc(Cl)cc1S(=O)(=O)Nc1ccc(F)c(-c2cc3c(N)ncnc3[nH]2)c1F]
Compound 34
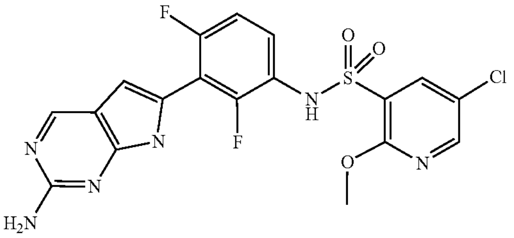
Compound 35
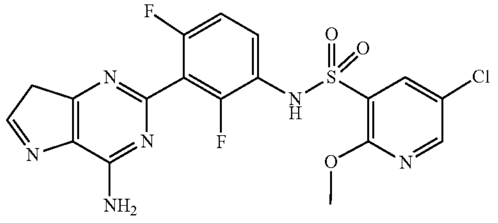 [SMILES: COc1ncc(Cl)cc1S(=O)(=O)Nc1ccc(F)c(-c2nc(N)c3c(n2)CC=N3)c1F]
Compound 36
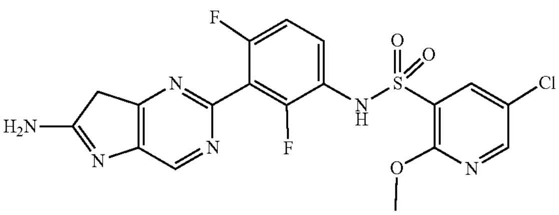 [SMILES: COc1ncc(Cl)cc1S(=O)(=O)Nc1ccc(F)c(-c2ncc3c(n2)CC(N)=N3)c1F]
Compound 37
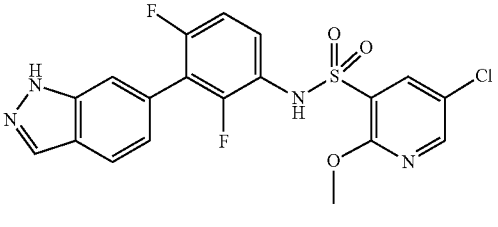 [SMILES: COc1ncc(Cl)cc1S(=O)(=O)Nc1ccc(F)c(-c2ccc3cn[nH]c3c2)c1F]
Compound 38
TABLE 1-continued
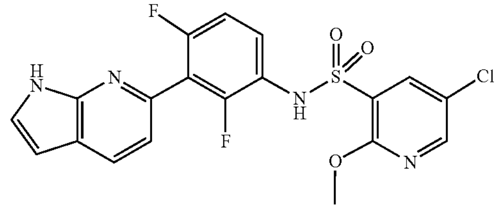 [SMILES: COc1ncc(Cl)cc1S(=O)(=O)Nc1ccc(F)c(-c2ccc3cc[nH]c3n2)c1F]
Compound 39
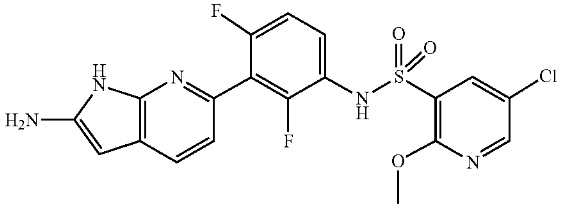 [SMILES: COc1ncc(Cl)cc1S(=O)(=O)Nc1ccc(F)c(-c2ccc3cc(N)[nH]c3n2)c1F]
Compound 40
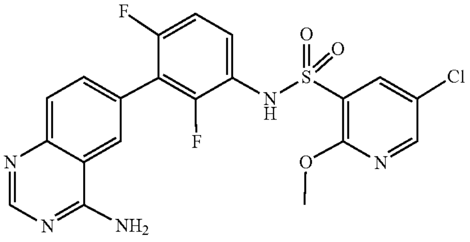 [SMILES: COc1ncc(Cl)cc1S(=O)(=O)Nc1ccc(F)c(-c2ccc3ncnc(N)c3c2)c1F]
Compound 41
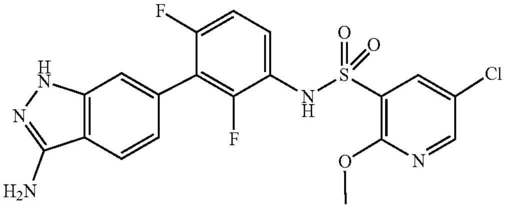 [SMILES: COc1ncc(Cl)cc1S(=O)(=O)Nc1ccc(F)c(-c2ccc3c(N)n[nH]c3c2)c1F]
Compound 42
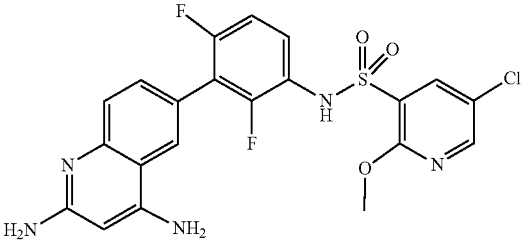 [SMILES: COc1ncc(Cl)cc1S(=O)(=O)Nc1ccc(F)c(-c2ccc3nc(N)cc(N)c3c2)c1F]
Compound 43
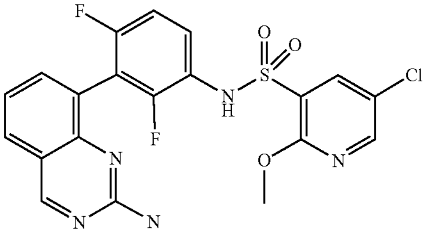
Compound 44

TABLE 1-continued
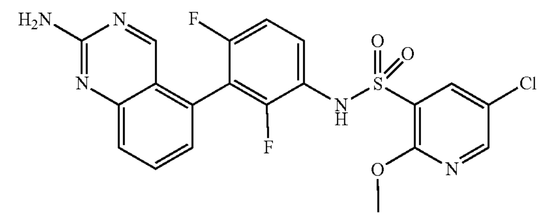 [SMILES: COc1ncc(Cl)cc1S(=O)(=O)Nc1ccc(F)c(-c2cccc3nc(N)ncc23)c1F]
Compound 45
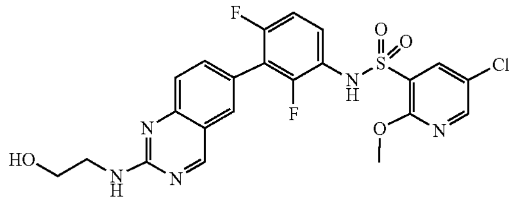 [SMILES: COc1ncc(Cl)cc1S(=O)(=O)Nc1ccc(F)c(-c2ccc3nc(NCCO)ncc3c2)c1F]
Compound 46
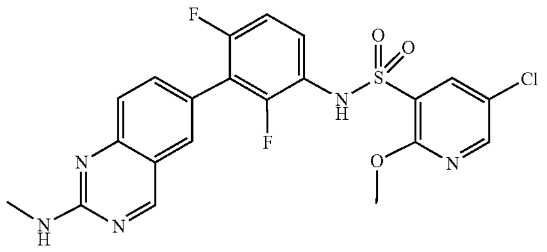 [SMILES: CNc1ncc2cc(-c3c(F)ccc(NS(=O)(=O)c4cc(Cl)cnc4OC)c3F)ccc2n1]
Compound 47
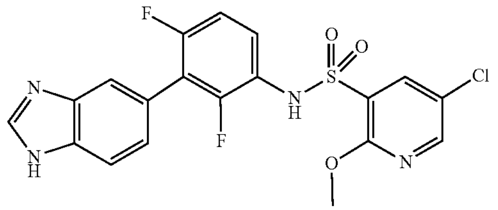 [SMILES: COc1ncc(Cl)cc1S(=O)(=O)Nc1ccc(F)c(-c2ccc3[nH]cnc3c2)c1F]
Compound 48
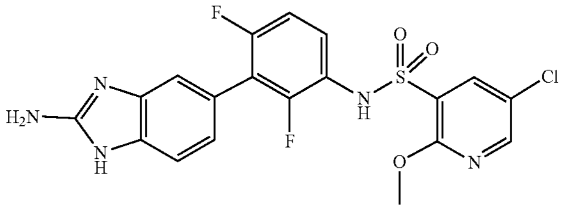 [SMILES: COc1ncc(Cl)cc1S(=O)(=O)Nc1ccc(F)c(-c2ccc3[nH]c(N)nc3c2)c1F]
Compound 49
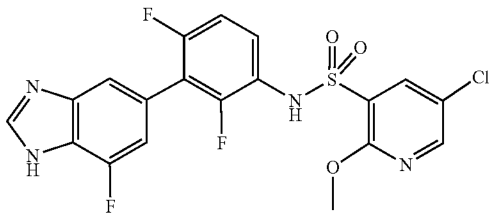 [SMILES: COc1ncc(Cl)cc1S(=O)(=O)Nc1ccc(F)c(-c2cc(F)c3[nH]cnc3c2)c1F]
Compound 50
TABLE 1-continued
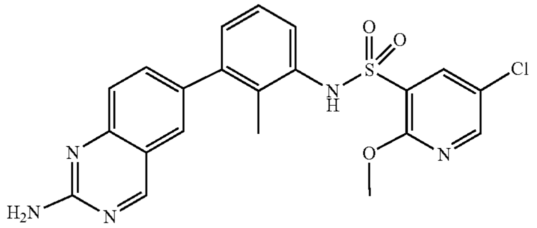 [SMILES: COc1ncc(Cl)cc1S(=O)(=O)Nc1cccc(-c2ccc3nc(N)ncc3c2)c1C]
Compound 51
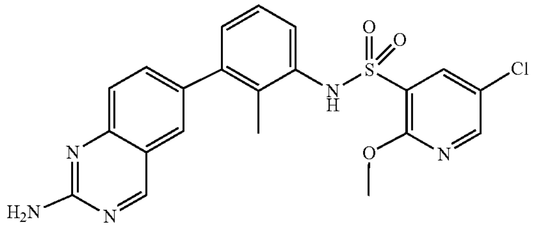 [SMILES: COc1ncc(Cl)cc1S(=O)(=O)Nc1cccc(-c2ccc3nc(N)ncc3c2)c1C]
Compound 52
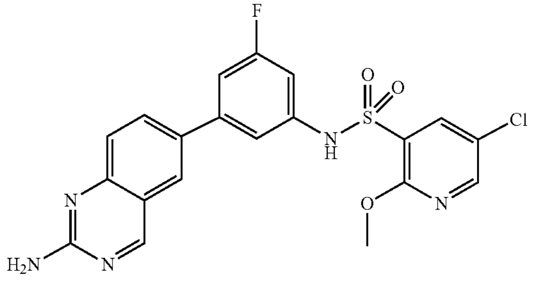 [SMILES: COc1ncc(Cl)cc1S(=O)(=O)Nc1cc(F)cc(-c2ccc3nc(N)ncc3c2)c1]
Compound 53
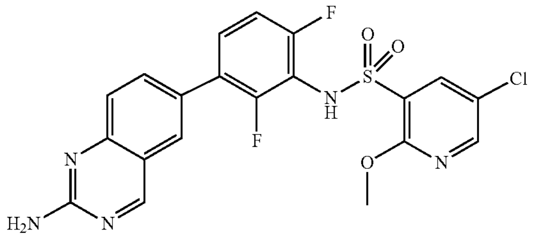 [SMILES: COc1ncc(Cl)cc1S(=O)(=O)Nc1c(F)ccc(-c2ccc3nc(N)ncc3c2)c1F]
Compound 54
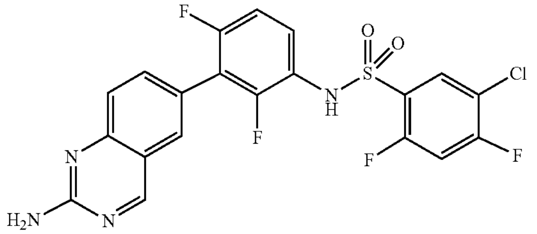 [SMILES: Nc1ncc2cc(-c3c(F)ccc(NS(=O)(=O)c4cc(Cl)c(F)cc4F)c3F)ccc2n1]
Compound 55

TABLE 1-continued
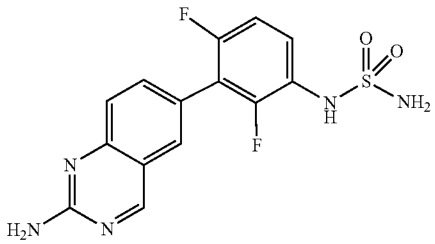 [SMILES: Nc1ncc2cc(-c3c(F)ccc(NS(N)(=O)=O)c3F)ccc2n1]
Compound 56
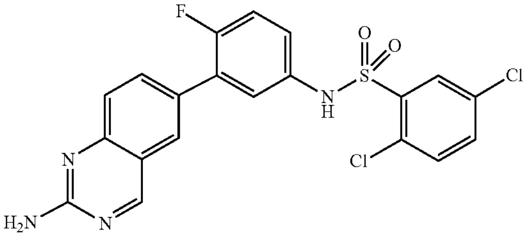 [SMILES: Nc1ncc2cc(-c3cc(NS(=O)(=O)c4cc(Cl)ccc4Cl)ccc3F)ccc2n1]
Compound 57
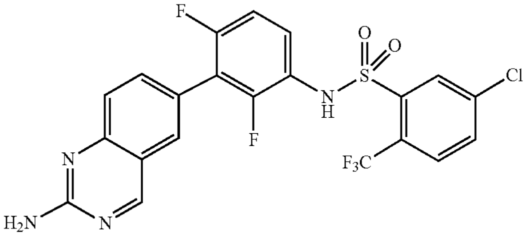 [SMILES: Nc1ncc2cc(-c3c(F)ccc(NS(=O)(=O)c4cc(Cl)ccc4C(F)(F)F)c3F)ccc2n1]
Compound 58
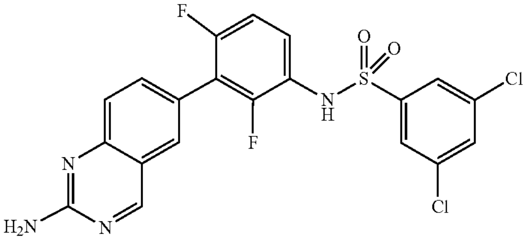 [SMILES: Nc1ncc2cc(-c3c(F)ccc(NS(=O)(=O)c4cc(Cl)cc(Cl)c4)c3F)ccc2n1]
Compound 59
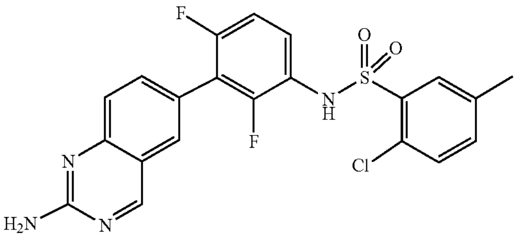 [SMILES: Cc1ccc(Cl)c(S(=O)(=O)Nc2ccc(F)c(-c3ccc4nc(N)ncc4c3)c2F)c1]
Compound 60
TABLE 1-continued
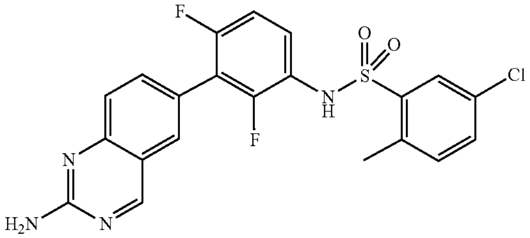 [SMILES: Cc1ccc(Cl)cc1S(=O)(=O)Nc1ccc(F)c(-c2ccc3nc(N)ncc3c2)c1F]
Compound 61
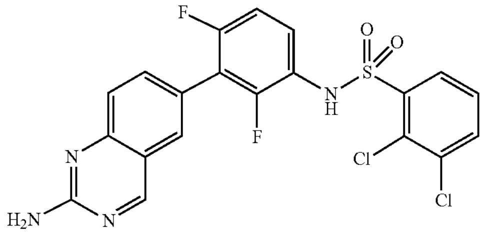 [SMILES: Nc1ncc2cc(-c3c(F)ccc(NS(=O)(=O)c4cccc(Cl)c4Cl)c3F)ccc2n1]
Compound 62
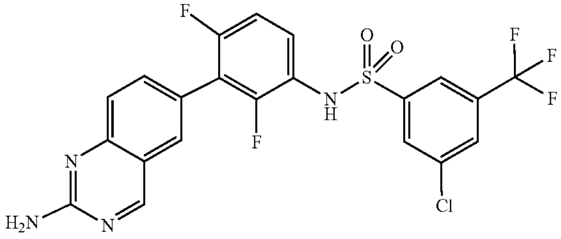 [SMILES: Nc1ncc2cc(-c3c(F)ccc(NS(=O)(=O)c4cc(Cl)cc(C(F)(F)F)c4)c3F)ccc2n1]
Compound 63
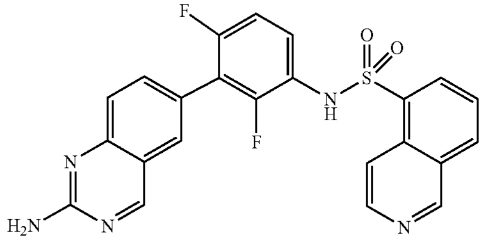 [SMILES: Nc1ncc2cc(-c3c(F)ccc(NS(=O)(=O)c4cccc5cnccc45)c3F)ccc2n1]
Compound 64
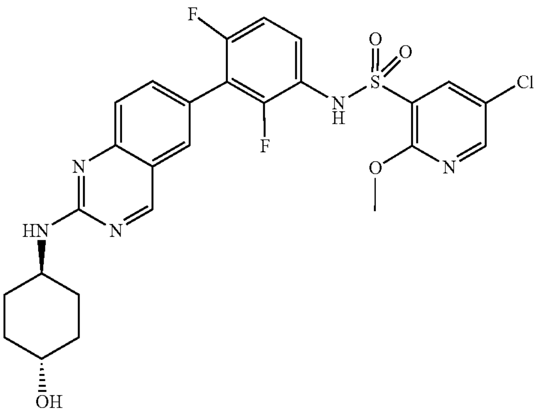 [SMILES: COc1ncc(Cl)cc1S(=O)(=O)Nc1ccc(F)c(-c2ccc3nc(N[C@H]4CC[C@H](O)CC4)ncc3c2)c1F]
Compound 65

TABLE 1-continued
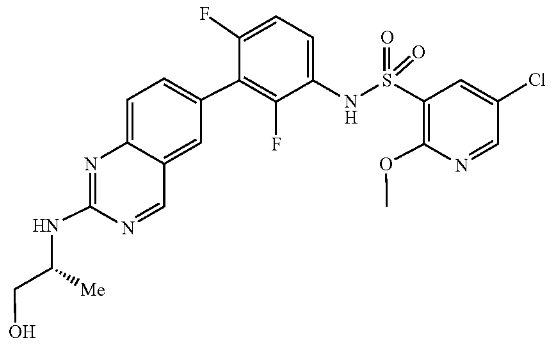 [SMILES: COc1ncc(Cl)cc1S(=O)(=O)Nc1ccc(F)c(-c2ccc3nc(N[C@H](C)CO)ncc3c2)c1F]
Compound 66
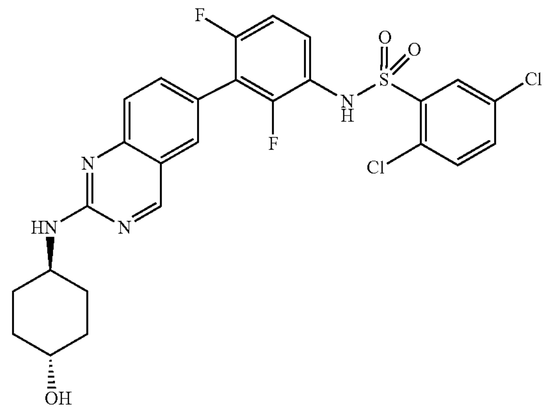 [SMILES: O=S(=O)(Nc1ccc(F)c(-c2ccc3nc(N[C@H]4CC[C@H](O)CC4)ncc3c2)c1F)c1cc(Cl)ccc1Cl]
Compound 67
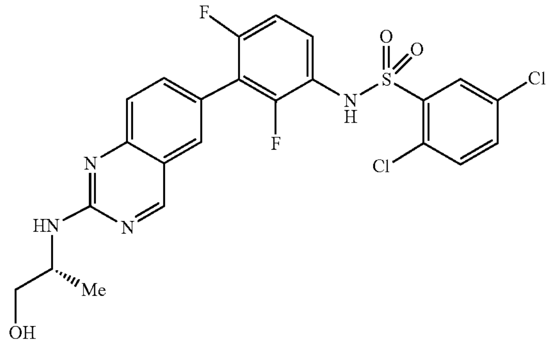 [SMILES: C[C@H](CO)Nc1ncc2cc(-c3c(F)ccc(NS(=O)(=O)c4cc(Cl)ccc4Cl)c3F)ccc2n1]
Compound 68
TABLE 1-continued
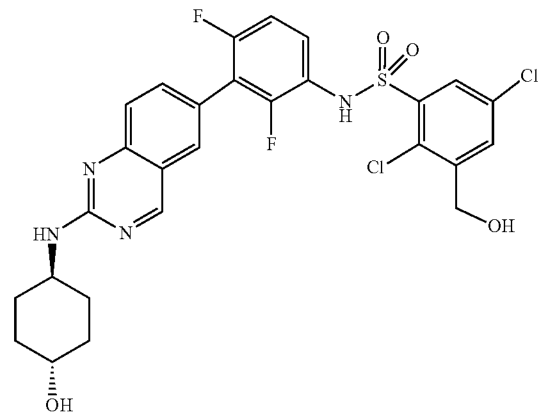 [SMILES: O=S(=O)(Nc1ccc(F)c(-c2ccc3nc(N[C@H]4CC[C@H](O)CC4)ncc3c2)c1F)c1cc(Cl)cc(CO)c1Cl]
Compound 69
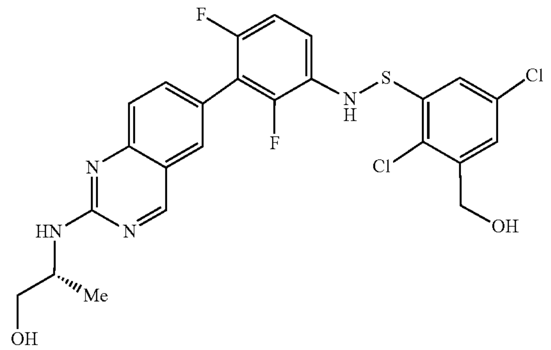 [SMILES: C[C@H](CO)Nc1ncc2cc(-c3c(F)ccc(NSc4cc(Cl)cc(CO)c4Cl)c3F)ccc2n1]
Compound 70
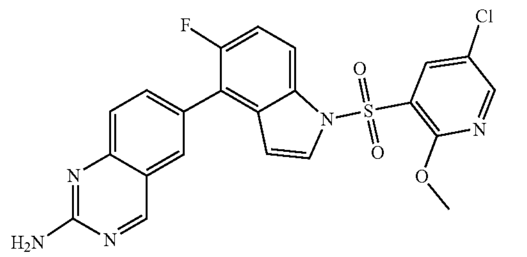 [SMILES: COc1ncc(Cl)cc1S(=O)(=O)n1ccc2c(-c3ccc4nc(N)ncc4c3)c(F)ccc21]
Compound 71
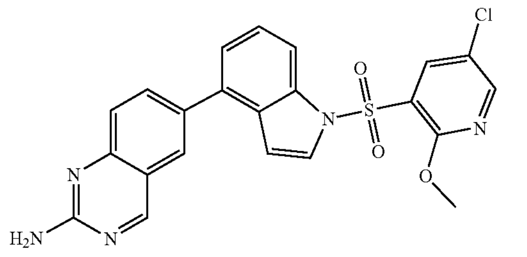 [SMILES: COc1ncc(Cl)cc1S(=O)(=O)n1ccc2c(-c3ccc4nc(N)ncc4c3)cccc21]
Compound 72

TABLE 1-continued
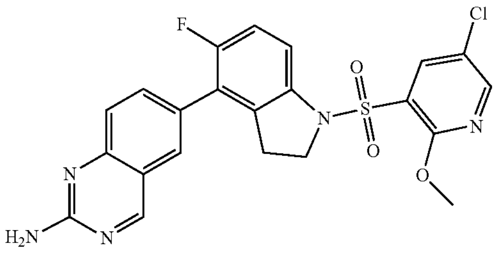 [SMILES: COc1ncc(Cl)cc1S(=O)(=O)N1CCc2c1ccc(F)c2-c1ccc2nc(N)ncc2c1]
Compound 73
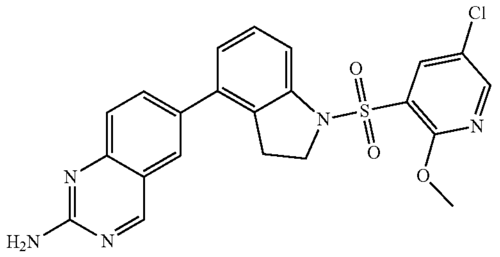 [SMILES: COc1ncc(Cl)cc1S(=O)(=O)N1CCc2c(-c3ccc4nc(N)ncc4c3)cccc21]
Compound 74
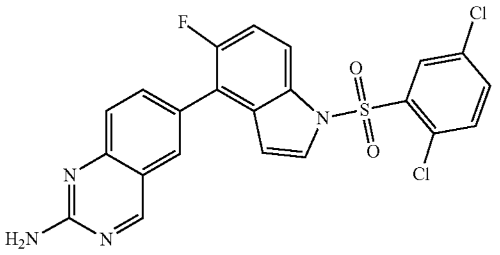 [SMILES: Nc1ncc2cc(-c3c(F)ccc4c3ccn4S(=O)(=O)c3cc(Cl)ccc3Cl)ccc2n1]
Compound 75
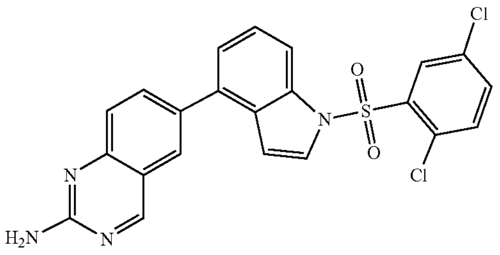 [SMILES: Nc1ncc2cc(-c3cccc4c3ccn4S(=O)(=O)c3cc(Cl)ccc3Cl)ccc2n1]
Compound 76
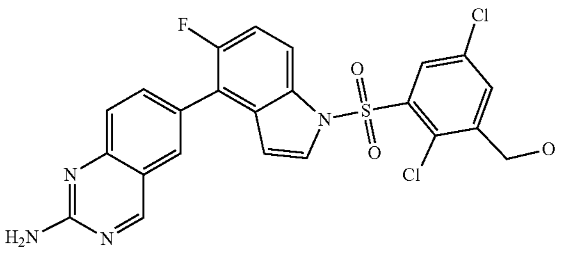
Compound 77
TABLE 1-continued
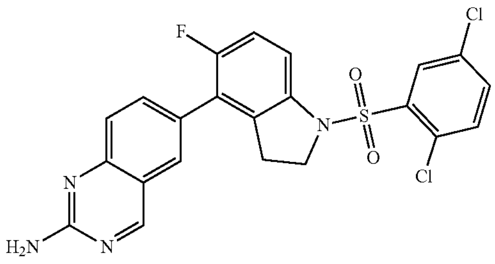 [SMILES: Nc1ncc2cc(-c3c(F)ccc4c3CCN4S(=O)(=O)c3cc(Cl)ccc3Cl)ccc2n1]
Compound 78
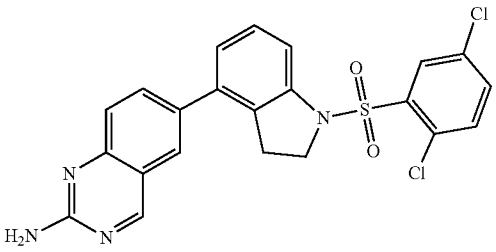 [SMILES: Nc1ncc2cc(-c3cccc4c3CCN4S(=O)(=O)c3cc(Cl)ccc3Cl)ccc2n1]
Compound 79
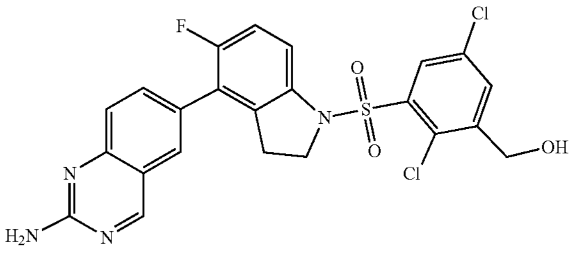 [SMILES: Nc1ncc2cc(-c3c(F)ccc4c3CCN4S(=O)(=O)c3cc(Cl)cc(CO)c3Cl)ccc2n1]
Compound 80
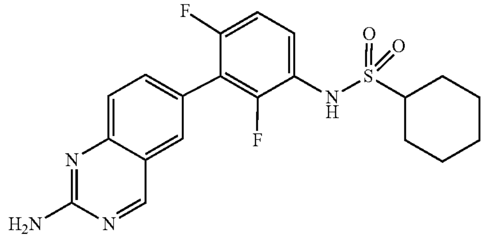 [SMILES: Nc1ncc2cc(-c3c(F)ccc(NS(=O)(=O)C4CCCCC4)c3F)ccc2n1]
Compound 81
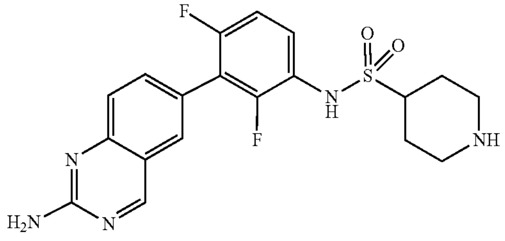 [SMILES: Nc1ncc2cc(-c3c(F)ccc(NS(=O)(=O)C4CCNCC4)c3F)ccc2n1]
Compound 82

TABLE 1-continued
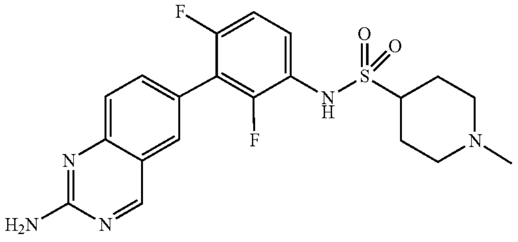
Compound 83
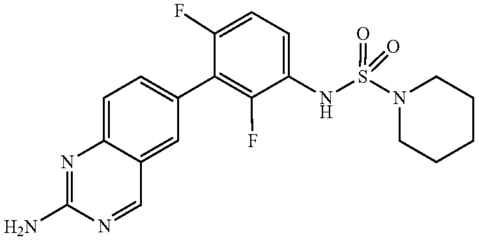 [SMILES: Nc1ncc2cc(-c3c(F)ccc(NS(=O)(=O)N4CCCCC4)c3F)ccc2n1]
Compound 84
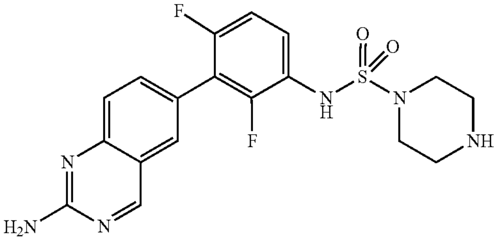 [SMILES: Nc1ncc2cc(-c3c(F)ccc(NS(=O)(=O)N4CCNCC4)c3F)ccc2n1]
Compound 85
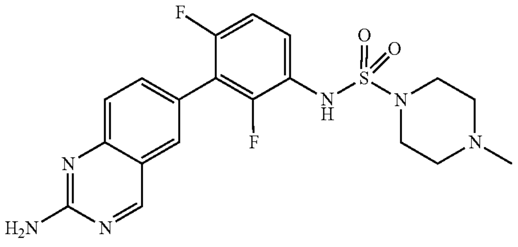 [SMILES: CN1CCN(S(=O)(=O)Nc2ccc(F)c(-c3ccc4nc(N)ncc4c3)c2F)CC1]
Compound 86
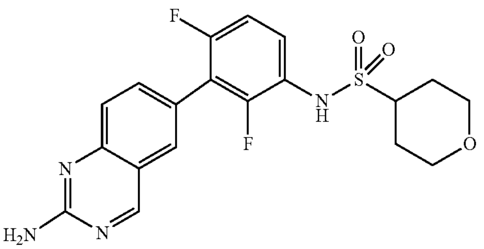 [SMILES: Nc1ncc2cc(-c3c(F)ccc(NS(=O)(=O)C4CCOCC4)c3F)ccc2n1]
Compound 87
TABLE 1-continued
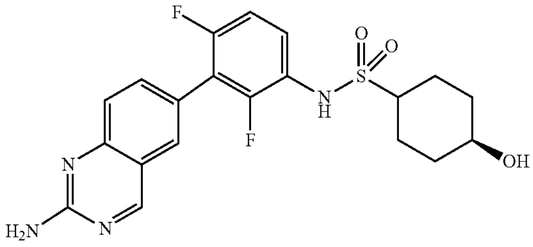
Compound 88
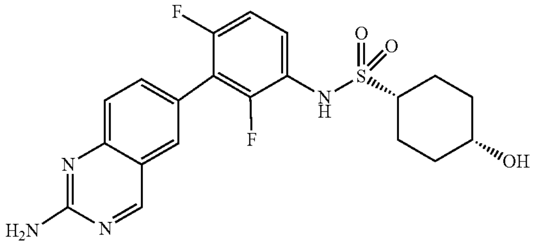 [SMILES: Nc1ncc2cc(-c3c(F)ccc(NS(=O)(=O)[C@H]4CC[C@@H](O)CC4)c3F)ccc2n1]
Compound 89
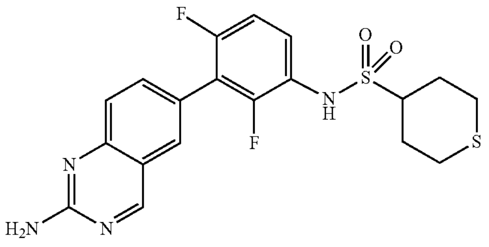 [SMILES: Nc1ncc2cc(-c3c(F)ccc(NS(=O)(=O)C4CCSCC4)c3F)ccc2n1]
Compound 90
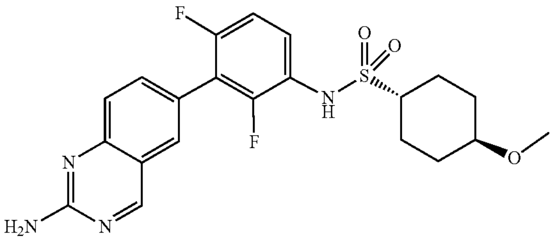 [SMILES: CO[C@H]1CC[C@H](S(=O)(=O)Nc2ccc(F)c(-c3ccc4nc(N)ncc4c3)c2F)CC1]
Compound 91
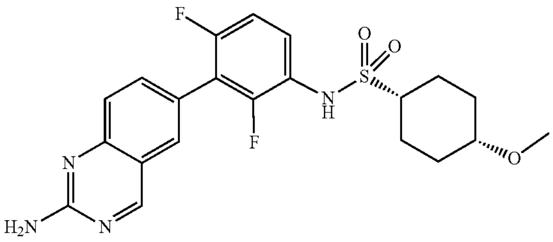 [SMILES: CO[C@H]1CC[C@@H](S(=O)(=O)Nc2ccc(F)c(-c3ccc4nc(N)ncc4c3)c2F)CC1]
Compound 92

TABLE 1-continued
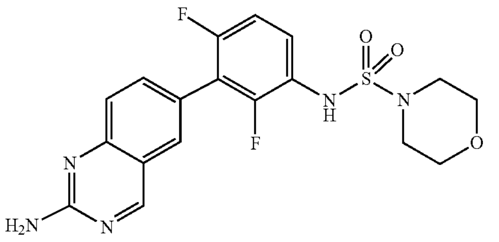 [SMILES: Nc1ncc2cc(-c3c(F)ccc(NS(=O)(=O)N4CCOCC4)c3F)ccc2n1]
Compound 93
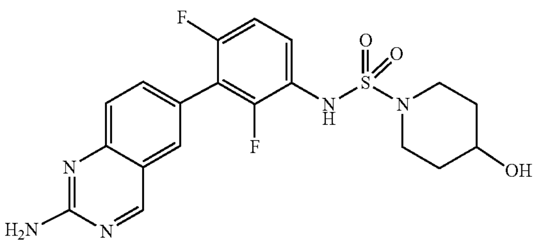 [SMILES: Nc1ncc2cc(-c3c(F)ccc(NS(=O)(=O)N4CCC(O)CC4)c3F)ccc2n1]
Compound 94
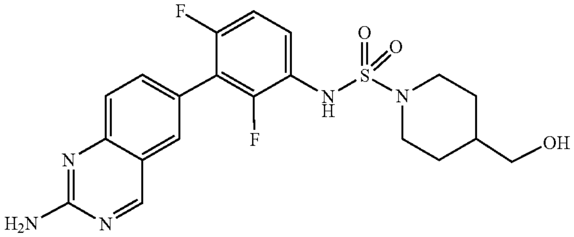 [SMILES: Nc1ncc2cc(-c3c(F)ccc(NS(=O)(=O)N4CCC(CO)CC4)c3F)ccc2n1]
Compound 95
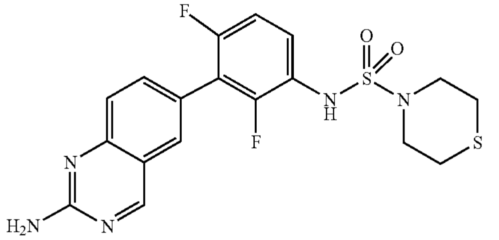 [SMILES: Nc1ncc2cc(-c3c(F)ccc(NS(=O)(=O)N4CCSCC4)c3F)ccc2n1]
Compound 96
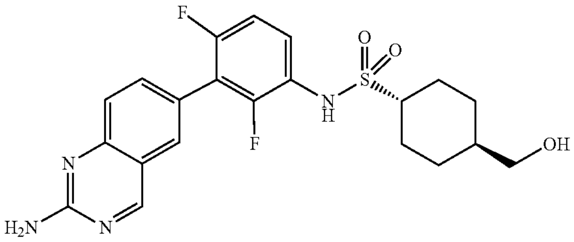 [SMILES: Nc1ncc2cc(-c3c(F)ccc(NS(=O)(=O)[C@H]4CC[C@H](CO)CC4)c3F)ccc2n1]
Compound 97
TABLE 1-continued
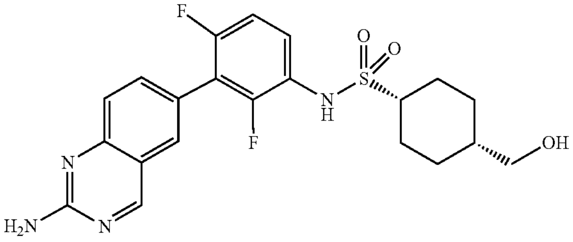 [SMILES: Nc1ncc2cc(-c3c(F)ccc(NS(=O)(=O)[C@H]4CC[C@@H](CO)CC4)c3F)ccc2n1]
Compound 98
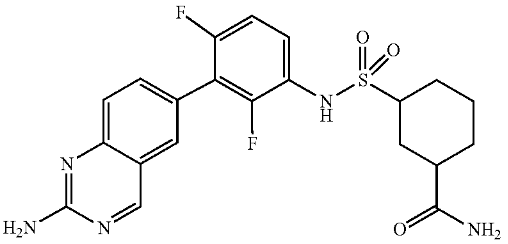 [SMILES: NC(=O)C1CCCC(S(=O)(=O)Nc2ccc(F)c(-c3ccc4nc(N)ncc4c3)c2F)C1]
Compound 99
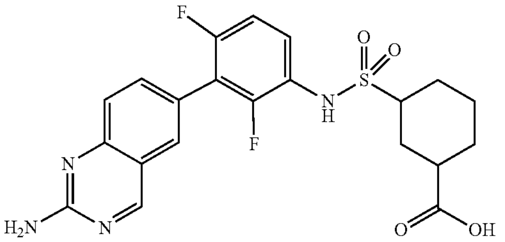 [SMILES: Nc1ncc2cc(-c3c(F)ccc(NS(=O)(=O)C4CCCC(C(=O)O)C4)c3F)ccc2n1]
Compound 100
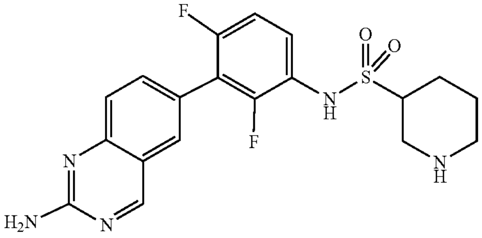 [SMILES: Nc1ncc2cc(-c3c(F)ccc(NS(=O)(=O)C4CCCNC4)c3F)ccc2n1]
Compound 101
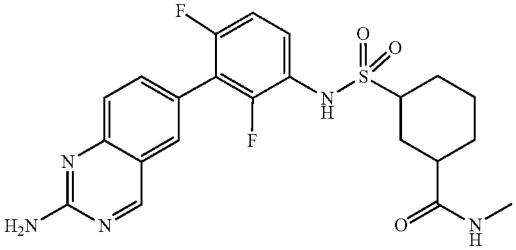 [SMILES: CNC(=O)C1CCCC(S(=O)(=O)Nc2ccc(F)c(-c3ccc4nc(N)ncc4c3)c2F)C1]
Compound 102

TABLE 1-continued
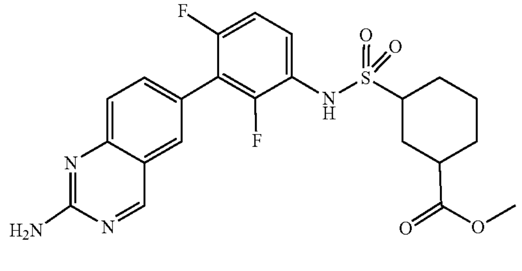 [SMILES: COC(=O)C1CCCC(S(=O)(=O)Nc2ccc(F)c(-c3ccc4nc(N)ncc4c3)c2F)C1]
Compound 103
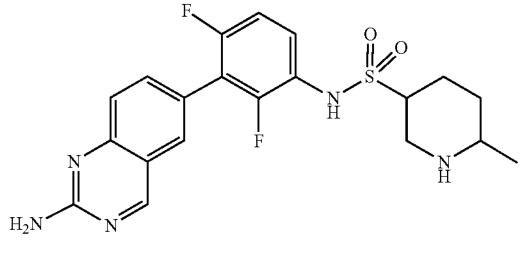 [SMILES: CC1CCC(S(=O)(=O)Nc2ccc(F)c(-c3ccc4nc(N)ncc4c3)c2F)CN1]
Compound 104
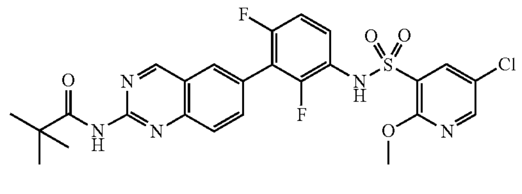 [SMILES: COc1ncc(Cl)cc1S(=O)(=O)Nc1ccc(F)c(-c2ccc3nc(NC(=O)C(C)(C)C)ncc3c2)c1F]
Compound 105
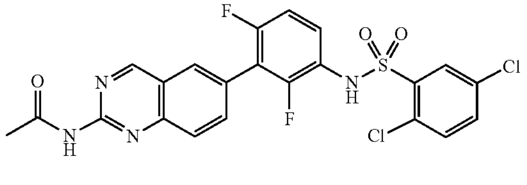 [SMILES: CC(=O)Nc1ncc2cc(-c3c(F)ccc(NS(=O)(=O)c4cc(Cl)ccc4Cl)c3F)ccc2n1]
Compound 106
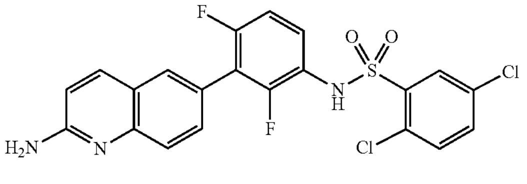 [SMILES: Nc1ccc2cc(-c3c(F)ccc(NS(=O)(=O)c4cc(Cl)ccc4Cl)c3F)ccc2n1]
Compound 107
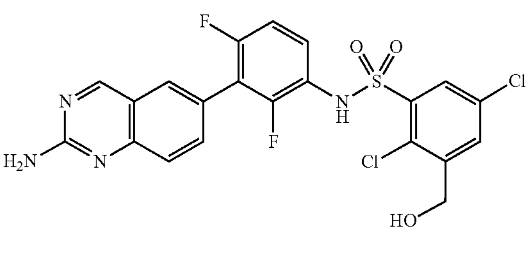 [SMILES: Nc1ncc2cc(-c3c(F)ccc(NS(=O)(=O)c4cc(Cl)cc(CO)c4Cl)c3F)ccc2n1]
Compound 108
TABLE 1-continued
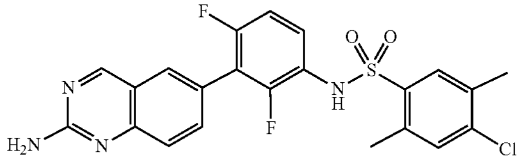 [SMILES: Cc1cc(S(=O)(=O)Nc2ccc(F)c(-c3ccc4nc(N)ncc4c3)c2F)c(C)cc1Cl]
Compound 109
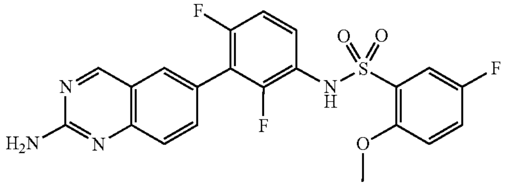 [SMILES: COc1ccc(F)cc1S(=O)(=O)Nc1ccc(F)c(-c2ccc3nc(N)ncc3c2)c1F]
Compound 110
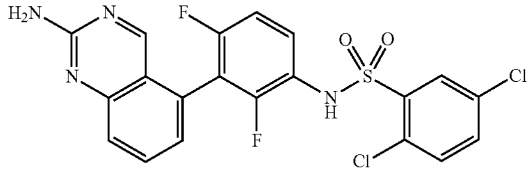 [SMILES: Nc1ncc2c(-c3c(F)ccc(NS(=O)(=O)c4cc(Cl)ccc4Cl)c3F)cccc2n1]
Compound 111
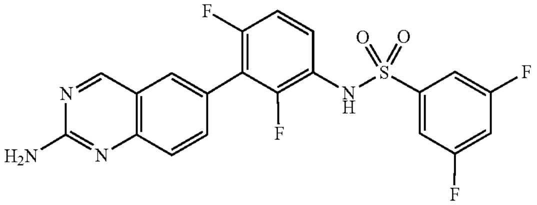 [SMILES: Nc1ncc2cc(-c3c(F)ccc(NS(=O)(=O)c4cc(F)cc(F)c4)c3F)ccc2n1]
Compound 112
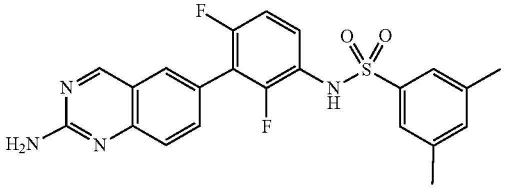 [SMILES: Cc1cc(C)cc(S(=O)(=O)Nc2ccc(F)c(-c3ccc4nc(N)ncc4c3)c2F)c1]
Compound 113
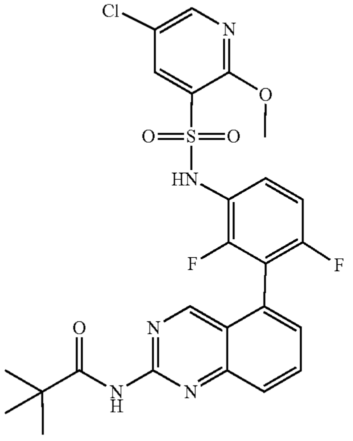 [SMILES: COc1ncc(Cl)cc1S(=O)(=O)Nc1ccc(F)c(-c2cccc3nc(NC(=O)C(C)(C)C)ncc23)c1F]
Compound 114

TABLE 1-continued
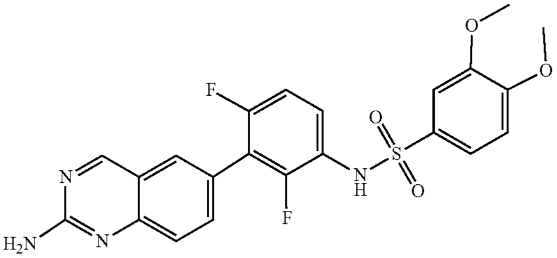 [SMILES: COc1ccc(S(=O)(=O)Nc2ccc(F)c(-c3ccc4nc(N)ncc4c3)c2F)cc1OC]
Compound 115
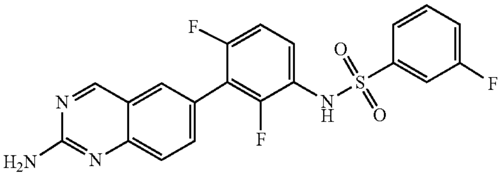 [SMILES: Nc1ncc2cc(-c3c(F)ccc(NS(=O)(=O)c4cccc(F)c4)c3F)ccc2n1]
Compound 116
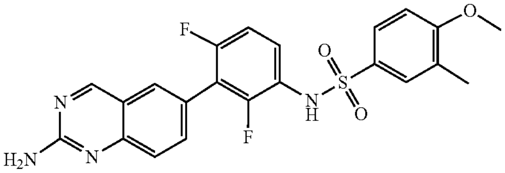 [SMILES: COc1ccc(S(=O)(=O)Nc2ccc(F)c(-c3ccc4nc(N)ncc4c3)c2F)cc1C]
Compound 117
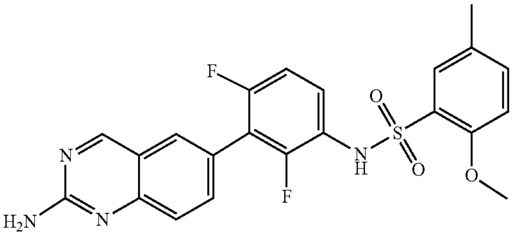 [SMILES: COc1ccc(C)cc1S(=O)(=O)Nc1ccc(F)c(-c2ccc3nc(N)ncc3c2)c1F]
Compound 118
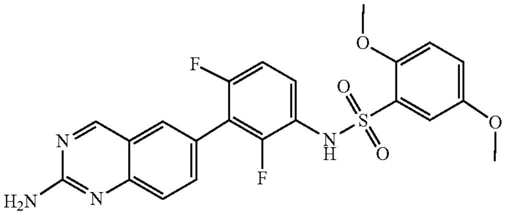 [SMILES: COc1ccc(OC)c(S(=O)(=O)Nc2ccc(F)c(-c3ccc4nc(N)ncc4c3)c2F)c1]
Compound 119
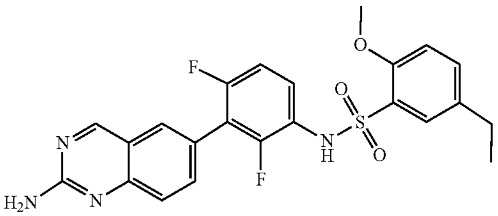 [SMILES: CCc1ccc(OC)c(S(=O)(=O)Nc2ccc(F)c(-c3ccc4nc(N)ncc4c3)c2F)c1]
Compound 120
TABLE 1-continued
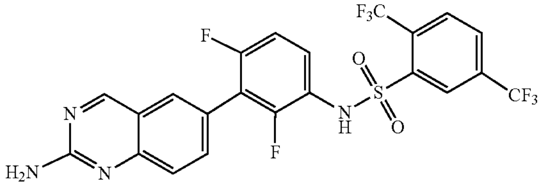 [SMILES: Nc1ncc2cc(-c3c(F)ccc(NS(=O)(=O)c4cc(C(F)(F)F)ccc4C(F)(F)F)c3F)ccc2n1]
Compound 121
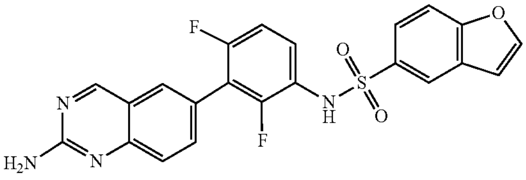 [SMILES: Nc1ncc2cc(-c3c(F)ccc(NS(=O)(=O)c4ccc5occc5c4)c3F)ccc2n1]
Compound 122
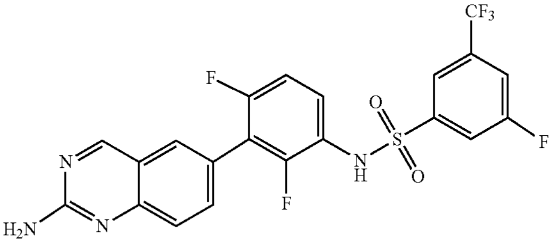 [SMILES: Nc1ncc2cc(-c3c(F)ccc(NS(=O)(=O)c4cc(F)cc(C(F)(F)F)c4)c3F)ccc2n1]
Compound 123
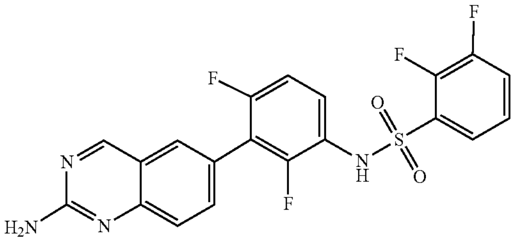 [SMILES: Nc1ncc2cc(-c3c(F)ccc(NS(=O)(=O)c4cccc(F)c4F)c3F)ccc2n1]
Compound 124
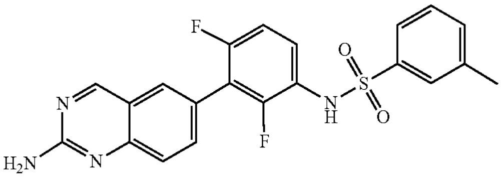 [SMILES: Cc1cccc(S(=O)(=O)Nc2ccc(F)c(-c3ccc4nc(N)ncc4c3)c2F)c1]
Compound 125
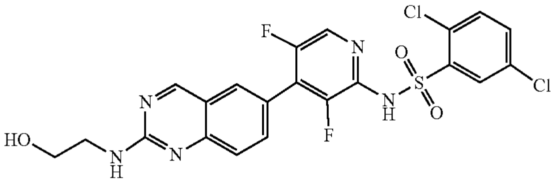 [SMILES: O=S(=O)(Nc1ncc(F)c(-c2ccc3nc(NCCO)ncc3c2)c1F)c1cc(Cl)ccc1Cl]
Compound 128

TABLE 1-continued
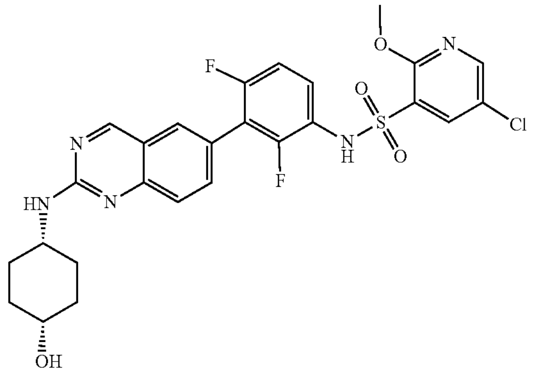 [SMILES: COc1ncc(Cl)cc1S(=O)(=O)Nc1ccc(F)c(-c2ccc3nc(N[C@H]4CC[C@@H](O)CC4)ncc3c2)c1F]
Compound 129
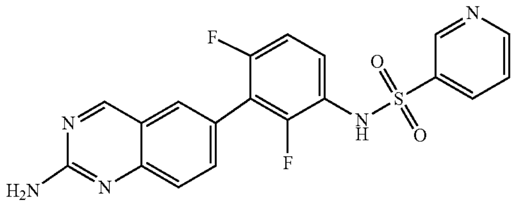 [SMILES: Nc1ncc2cc(-c3c(F)ccc(NS(=O)(=O)c4cccnc4)c3F)ccc2n1]
Compound 130
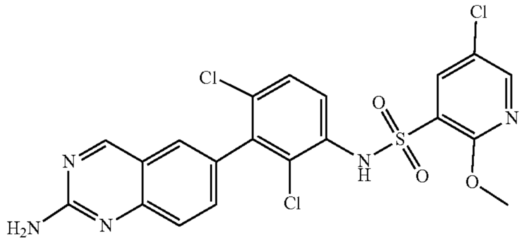 [SMILES: COc1ncc(Cl)cc1S(=O)(=O)Nc1ccc(Cl)c(-c2ccc3nc(N)ncc3c2)c1Cl]
Compound 131
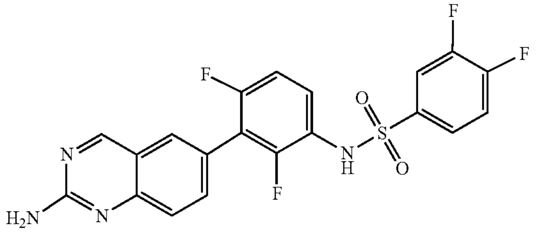 [SMILES: Nc1ncc2cc(-c3c(F)ccc(NS(=O)(=O)c4ccc(F)c(F)c4)c3F)ccc2n1]
Compound 132
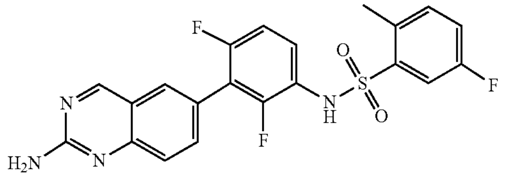 [SMILES: Cc1ccc(F)cc1S(=O)(=O)Nc1ccc(F)c(-c2ccc3nc(N)ncc3c2)c1F]
Compound 133
TABLE 1-continued
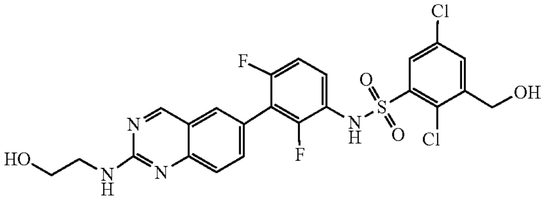 [SMILES: O=S(=O)(Nc1ccc(F)c(-c2ccc3nc(NCCO)ncc3c2)c1F)c1cc(Cl)cc(CO)c1Cl]
Compound 134
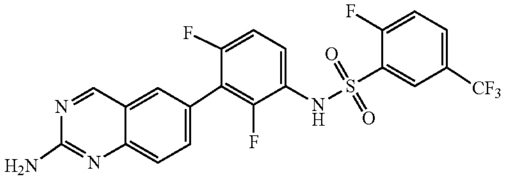 [SMILES: Nc1ncc2cc(-c3c(F)ccc(NS(=O)(=O)c4cc(C(F)(F)F)ccc4F)c3F)ccc2n1]
Compound 135
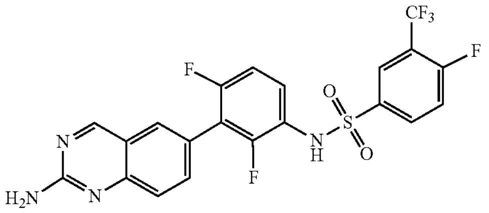 [SMILES: Nc1ncc2cc(-c3c(F)ccc(NS(=O)(=O)c4ccc(F)c(C(F)(F)F)c4)c3F)ccc2n1]
Compound 136
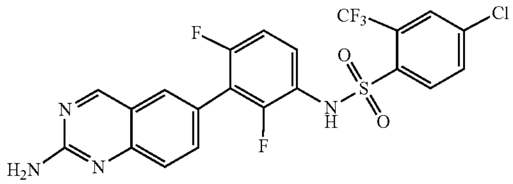 [SMILES: Nc1ncc2cc(-c3c(F)ccc(NS(=O)(=O)c4ccc(Cl)cc4C(F)(F)F)c3F)ccc2n1]
Compound 137
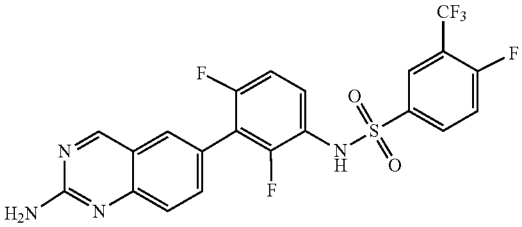 [SMILES: Nc1ncc2cc(-c3c(F)ccc(NS(=O)(=O)c4ccc(F)c(C(F)(F)F)c4)c3F)ccc2n1]
Compound 138
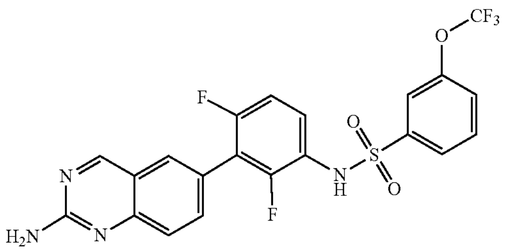 [SMILES: Nc1ncc2cc(-c3c(F)ccc(NS(=O)(=O)c4cccc(OC(F)(F)F)c4)c3F)ccc2n1]
Compound 139

TABLE 1-continued
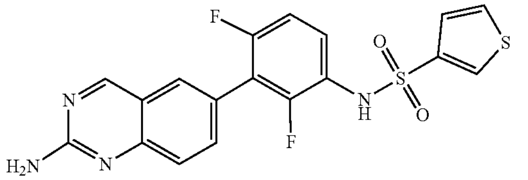 [SMILES: Nc1ncc2cc(-c3c(F)ccc(NS(=O)(=O)c4ccsc4)c3F)ccc2n1]
Compound 140
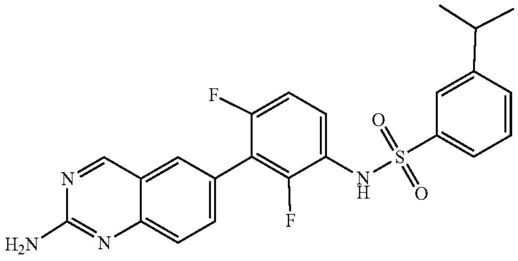 [SMILES: CC(C)c1cccc(S(=O)(=O)Nc2ccc(F)c(-c3ccc4nc(N)ncc4c3)c2F)c1]
Compound 141
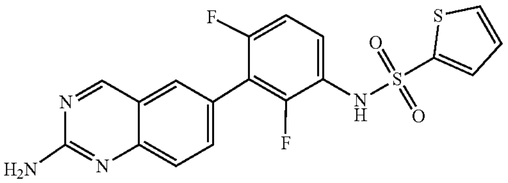
Compound 142
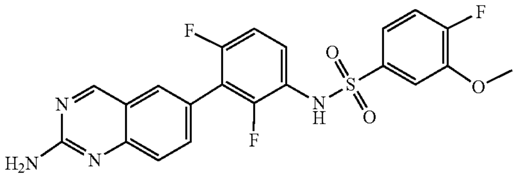 [SMILES: COc1cc(S(=O)(=O)Nc2ccc(F)c(-c3ccc4nc(N)ncc4c3)c2F)ccc1F]
Compound 143
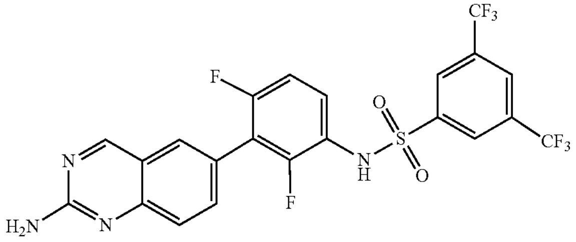 [SMILES: Nc1ncc2cc(-c3c(F)ccc(NS(=O)(=O)c4cc(C(F)(F)F)cc(C(F)(F)F)c4)c3F)ccc2n1]
Compound 144
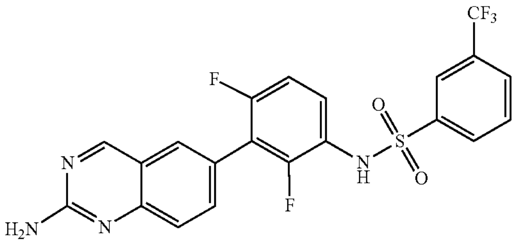 [SMILES: Nc1ncc2cc(-c3c(F)ccc(NS(=O)(=O)c4cccc(C(F)(F)F)c4)c3F)ccc2n1]
Compound 145
TABLE 1-continued
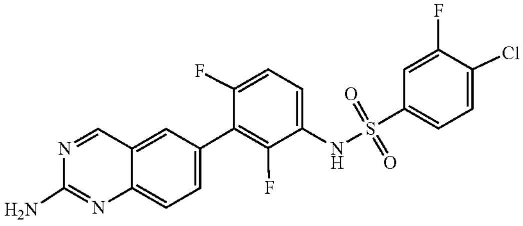 [SMILES: Nc1ncc2cc(-c3c(F)ccc(NS(=O)(=O)c4ccc(Cl)c(F)c4)c3F)ccc2n1]
Compound 146
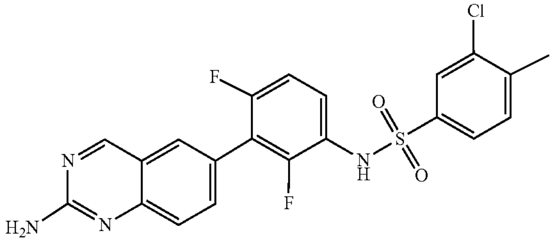 [SMILES: Cc1ccc(S(=O)(=O)Nc2ccc(F)c(-c3ccc4nc(N)ncc4c3)c2F)cc1Cl]
Compound 147
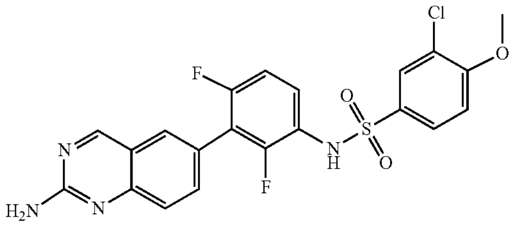 [SMILES: COc1ccc(S(=O)(=O)Nc2ccc(F)c(-c3ccc4nc(N)ncc4c3)c2F)cc1Cl]
Compound 148
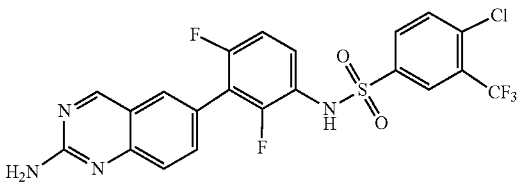 [SMILES: Nc1ncc2cc(-c3c(F)ccc(NS(=O)(=O)c4ccc(Cl)c(C(F)(F)F)c4)c3F)ccc2n1]
Compound 149
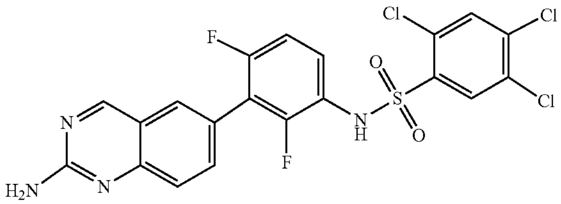 [SMILES: Nc1ncc2cc(-c3c(F)ccc(NS(=O)(=O)c4cc(Cl)c(Cl)cc4Cl)c3F)ccc2n1]
Compound 150
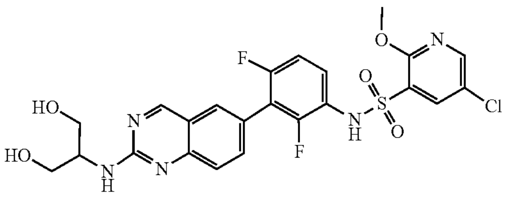 [SMILES: COc1ncc(Cl)cc1S(=O)(=O)Nc1ccc(F)c(-c2ccc3nc(NC(CO)CO)ncc3c2)c1F]
Compound 153

TABLE 1-continued
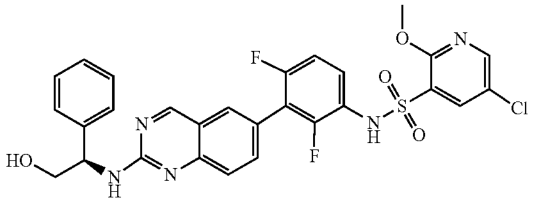 [SMILES: COc1ncc(Cl)cc1S(=O)(=O)Nc1ccc(F)c(-c2ccc3nc(N[C@@H](CO)c4ccccc4)ncc3c2)c1F]
Compound 154
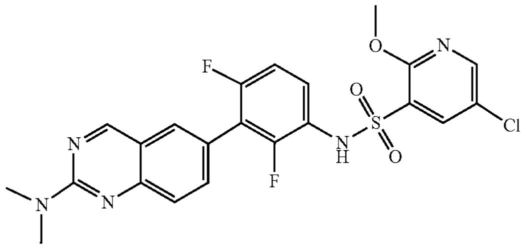 [SMILES: COc1ncc(Cl)cc1S(=O)(=O)Nc1ccc(F)c(-c2ccc3nc(N(C)C)ncc3c2)c1F]
Compound 155
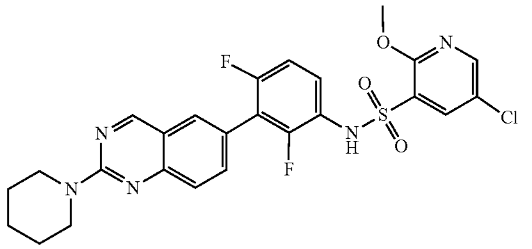 [SMILES: COc1ncc(Cl)cc1S(=O)(=O)Nc1ccc(F)c(-c2ccc3nc(N4CCCCC4)ncc3c2)c1F]
Compound 156
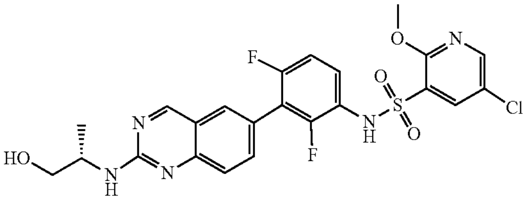 [SMILES: COc1ncc(Cl)cc1S(=O)(=O)Nc1ccc(F)c(-c2ccc3nc(N[C@@H](C)CO)ncc3c2)c1F]
Compound 157
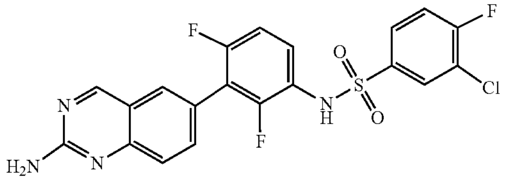 [SMILES: Nc1ncc2cc(-c3c(F)ccc(NS(=O)(=O)c4ccc(F)c(Cl)c4)c3F)ccc2n1]
Compound 158
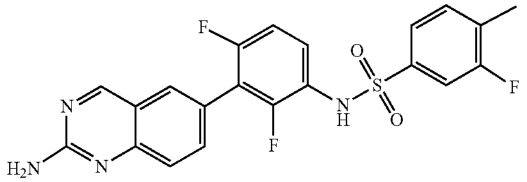 [SMILES: Cc1ccc(S(=O)(=O)Nc2ccc(F)c(-c3ccc4nc(N)ncc4c3)c2F)cc1F]
Compound 159
TABLE 1-continued
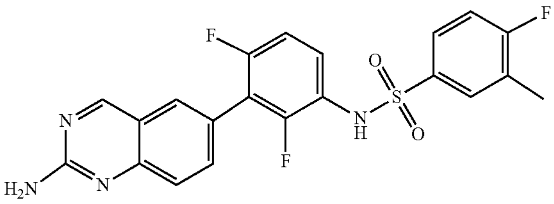 [SMILES: Cc1cc(S(=O)(=O)Nc2ccc(F)c(-c3ccc4nc(N)ncc4c3)c2F)ccc1F]
Compound 160
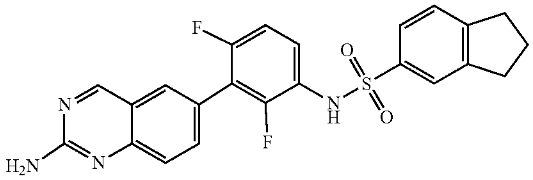 [SMILES: Nc1ncc2cc(-c3c(F)ccc(NS(=O)(=O)c4ccc5c(c4)CCC5)c3F)ccc2n1]
Compound 161
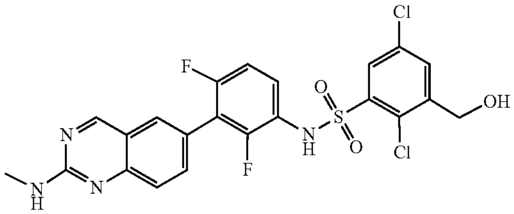 [SMILES: CNc1ncc2cc(-c3c(F)ccc(NS(=O)(=O)c4cc(Cl)cc(CO)c4Cl)c3F)ccc2n1]
Compound 162
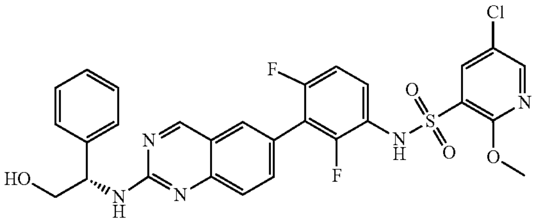 [SMILES: COc1ncc(Cl)cc1S(=O)(=O)Nc1ccc(F)c(-c2ccc3nc(N[C@H](CO)c4ccccc4)ncc3c2)c1F]
Compound 163
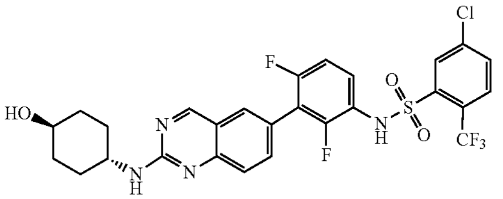 [SMILES: O=S(=O)(Nc1ccc(F)c(-c2ccc3nc(N[C@H]4CC[C@H](O)CC4)ncc3c2)c1F)c1cc(Cl)ccc1C(F)(F)F]
Compound 164

TABLE 1-continued

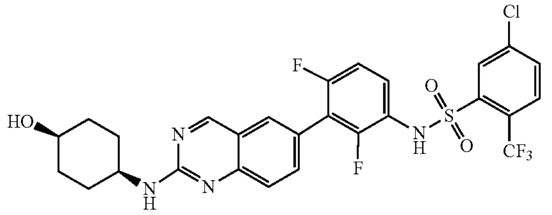 [SMILES: O=S(=O)(Nc1ccc(F)c(-c2ccc3nc(N[C@H]4CC[C@@H](O)CC4)ncc3c2)c1F)c1cc(Cl)ccc1C(F)(F)F]

Compound 165

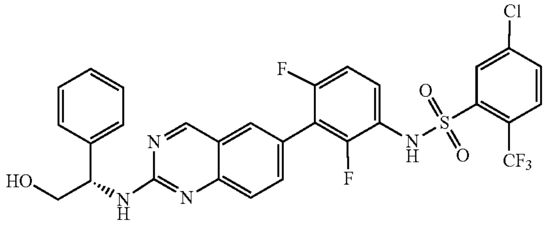 [SMILES: O=S(=O)(Nc1ccc(F)c(-c2ccc3nc(N[C@H](CO)c4ccccc4)ncc3c2)c1F)c1cc(Cl)ccc1C(F)(F)F]

Compound 166

TABLE 1-continued

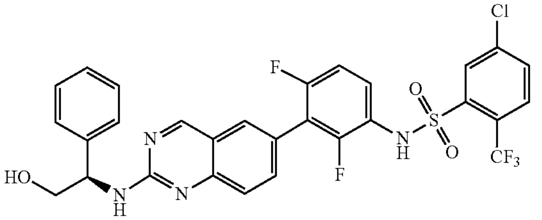 [SMILES: O=S(=O)(Nc1ccc(F)c(-c2ccc3nc(N[C@@H](CO)c4ccccc4)ncc3c2)c1F)c1cc(Cl)ccc1C(F)(F)F]

Compound 167

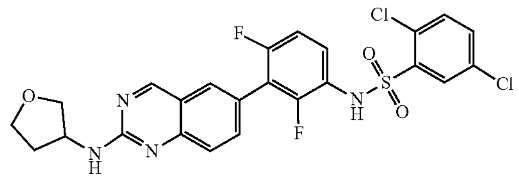 [SMILES: O=S(=O)(Nc1ccc(F)c(-c2ccc3nc(NC4CCOC4)ncc3c2)c1F)c1cc(Cl)ccc1Cl]

Compound 168

Preparation of the Compounds of the Invention

Some compounds of Formula (1) and derivatives or synthetic intermediates thereof can be prepared in accordance with synthetic methods known to the skilled person. In some embodiments, the invention provides a process for the preparation of a compound as defined in Formula (1) above. Certain compounds of the invention may be prepared according to the methods described below.

Compound 1

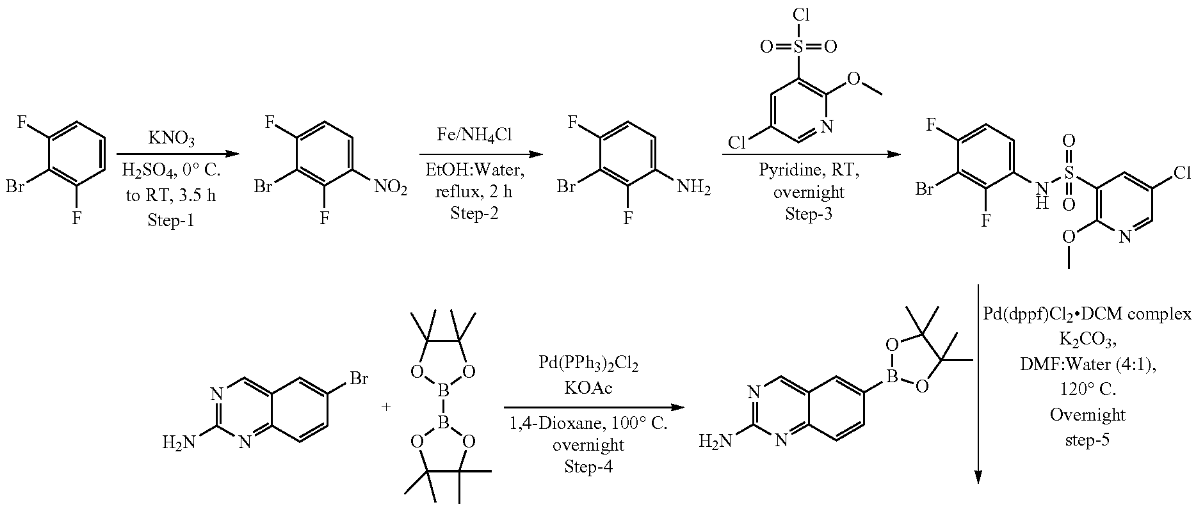

-continued

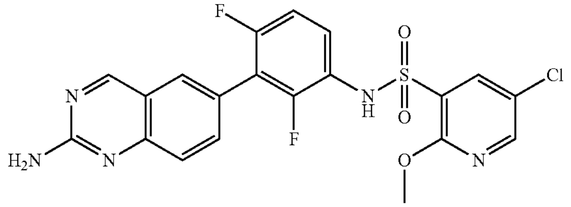

Step-1: Synthesis of 2-bromo-1,3-difluoro-4-nitrobenzene

To a stirred solution of 2-bromo-1,3-difluorobenzene (1.0 g, 5.18 mmol, 1.0 equiv) in conc. sulfuric acid (5 mL) at 0° C. was added potassium nitrate (1.046 g, 10.36 mmol, 2.0 equiv) and the mixture was stirred at 0° C. for 30 min and at room temperature for 3.5 hr. The reaction mixture was added to ice water (50 mL). The precipitated solid was filtered and washed with excess of water and was dried under vacuum to obtain title compound. Analytical Data: LCMS: 238 $[M+H]^+$.

Step-2: Synthesis of 3-bromo-2,4-difluoroaniline

To a stirred solution of 1,3-difluoro-2-Bromo-6-nitrobenzene (2.0 g, 8.40 mmol, 1.0 equiv.) in EtOH:water (1:1, 20 mL) was added Fe (2.37 g, 42.01 mmol, 5.0 equiv.) and ammonium chloride (2.19 g, 42.01 mmol, 5.0 equiv.). The resulting reaction mixture was stirred under reflux for 2 h. The progress of the reaction was monitored by TLC. After completion of the reaction, the reaction mixture was cooled, filtered through celite bed and washed with methanol. Methanol layer was collected evaporated under reduced pressure to obtain crude which was added water and EtOAc, organic layer was collected, dried over anhydrous sodium sulphate and concentrated under reduced pressure to obtain crude solid. The solid was purified through flash chromatography using EtOAc/hexane (10%) as eluent to obtain title product as solid. Analytical Data: LCMS: 208 $[M+H]^+$.

Step-3: Synthesis of N-(3-bromo-2,4-difluorophenyl)-5-chloro-2-methoxypyridine-3-sulfonamide The mixture of 3-bromo-2,4-difluoroaniline (300 mg, 1.44 mmol. 1.0 equiv.) and 5-chloro-2-methoxypyridine-3-sulfonyl chloride (180 mg, 1.009 mmol, and 0.7 equiv.) in pyridine was stirred at room temperature for overnight. MeOH (10 mL) was added to the mixture and the mixture was stirred at room temperature for 10 min. The mixture was concentrated in rotary. The residue was purified by silica flash chromatography (n-hexane-ethyl acetate=100:0-80:20) to give crude 6 (400 mg) as solid. This material was used in the next reaction without further purification. Analytical Data: LCMS: 413 $[M+H]^+$.

Step-4: Synthesis of 6-(4,4,5,5-tetramethyl-1,3,2-dioxaborolan-2-yl)quinazolin-2-amine To a stirred solution of 6-bromoquinazolin-2-amine (50 mg, 0.223 mmol, 1.0 equiv) in 1,4-Dioxane (5 mL) was added potassium acetate (33 mg, 0.334 mmol, 1.5 equiv.) and 4,4,5,5-tetramethyl-2-(4,4,5,5-tetramethyl-1,3,2-dioxaborolan-2-yl)-1,3,2-dioxaborolane (85 mg, 0.334 mmol, 1.5 equiv.). The reaction mixture was degassed with nitrogen for 20 min followed by addition of $Pd(PPh_3)_2Cl_2$ (8 mg, 0.011 mmol), 0.05 eq). The reaction mixture was again degassed for 10 min and then stirred at 100° C. for overnight. Reaction mass was diluted with water and extracted by Ethyl acetate (3×50 mL). The combined organic layer was dried over anhydrous sodium sulphate and concentrated under reduced pressure and purified by column chromatography to obtain the title compound. Analytical Data: LCMS: 272 $[M+H]^+$.

Step-5: Synthesis of N-(3-(2-aminoquinazolin-6-yl)-2,4-difluorophenyl)-5-chloro-2-methoxypyridine-3-sulfonamide To the stirred solution of N-(3-bromo-2,4-difluorophenyl)-5-chloro-2-methoxypyridine-3-sulfonamide (100 mg, 0.24 mmol, 1.0 equiv) and 6-(4,4,5,5-tetramethyl-1,3,2-dioxaborolan-2-yl)quinazolin-2-amine (66 mg, 0.24 mmol, 1.0 equiv) in DMF:Water (4:1, 5 mL) was added $K_2CO_3$ (99 mg, 0.72 mmol, 3.0 equiv.). The resulting reaction mixture was purged with nitrogen for 15 minutes followed by the addition of $Pd(dppf)Cl_2 \cdot DCM$ complex (10 mg, 0.012 mmol, 0.05 equiv.). The reaction mixture was again purged with nitrogen for 5 minutes. The reaction mixture was heated to 120° C. for overnight. The progress of reaction was monitored through TLC and LCMS. After completion of reaction, water was added to the reaction mixture, extracted with EtOAc (5×100 mL). The organic layers were combined, dried over anhydrous $Na_2SO_4$ and evaporated under reduced pressure to obtain title product as crude residue which was purified by flash chromatography using EtOAc/Hexane (50-100%) as eluent to obtain title product as liquid residue. The residue was further purified by reverse phase HPLC to obtain title product as solid (2.23 mg), Analytical Data: LCMS: 478 $[M+H]^+$, $^1H$ NMR: (400 MHz, DMSO-$d_6$) δ ppm 10.41 (br. s., 1H) 9.16 (s, 1H) 8.51 (d, J=2.63 Hz, 1H) 8.07 (d, J=2.63 Hz, 1H) 7.79 (s, 1H) 7.59 (d, J=9.21 Hz, 1H) 7.49 (d, J=8.33 Hz, 1H) 7.33 (d, J=5.70 Hz, 1H) 7.23 (d, J=9.21 Hz, 1H) 7.04 (s, 2H) 3.91 (s, 3H).

Compound 2

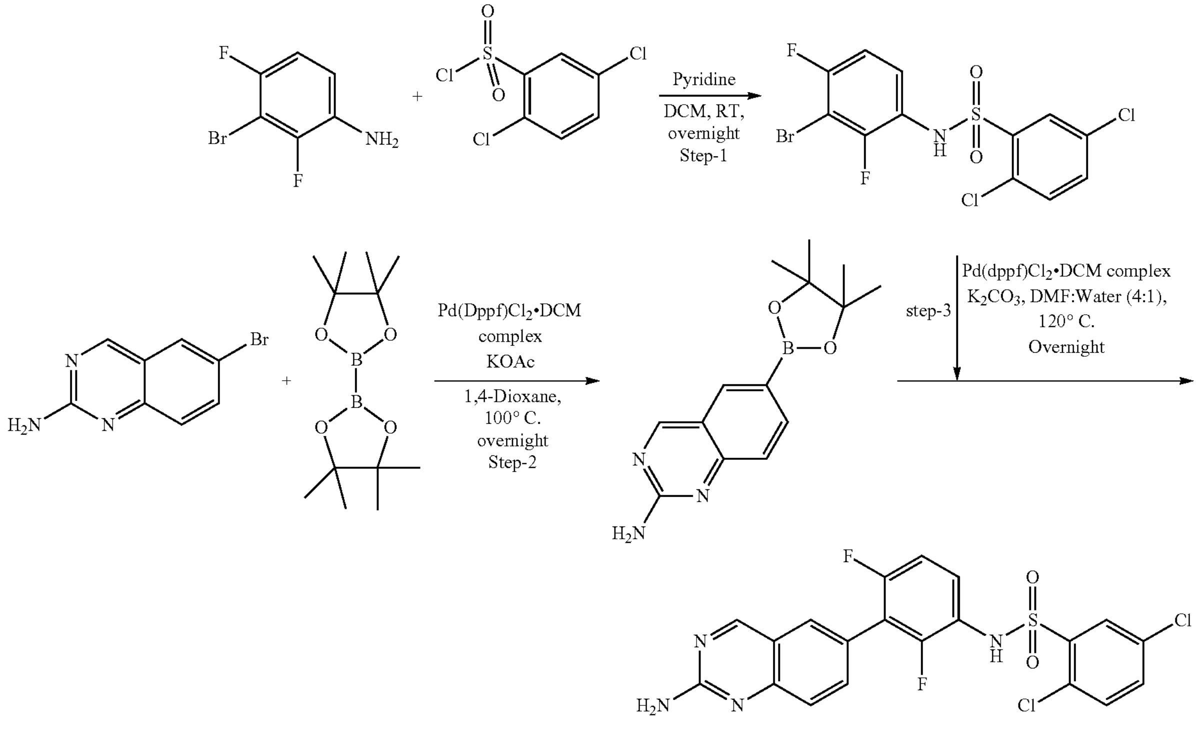

Step-1: Synthesis of N-(3-bromo-2,4-difluorophenyl)-2,5-dichlorobenzenesulfonamide The mixture of 3-bromo-2,4-difluoroaniline (200 mg, 0.96 mmol. 1.0 equiv.) in DCM (15 mL) at room temperature was added pyridine (0.4 mL, 4.80 mmol, 5.0 equiv.). The reaction mixture was stirred at room temperature for 10 minutes followed by the addition of 2,5-dichlorobenzenesulfonyl chloride (233 mg, 0.96 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure to obtain title compound (200 mg). This material was used in the next reaction without further purification. Analytical Data: LCMS: 416 $[M+H]^+$.

Step-2: Synthesis of 6-(4,4,5,5-tetramethyl-1,3,2-dioxaborolan-2-yl)quinazolin-2-amine To a stirred solution of 6-bromoquinazolin-2-amine (100 mg, 0.446 mmol, 1.0 equiv) in 1,4-Dioxane (5 mL) was added potassium acetate (88 mg, 0.90 mmol, 2.0 equiv.) and 4,4,5,5-tetramethyl-2-(4,4,5,5-tetramethyl-1,3,2-dioxaborolan-2-yl)-1,3,2-dioxaborolane (137 mg, 0.669 mmol, 1.5 equiv.). The reaction mixture was degassed with nitrogen for 20 min followed by addition of $Pd(dppf)Cl_2DCM$ complex (19 mg, 0.022 mmol, 0.05 equiv). The reaction mixture was again degassed for 10 min and then stirred at 85° C. for overnight. Reaction mass was treated with $K_2CO_3$ (125 mg, 0.892 mmol, 2.0 equiv.) and reaction mixture was added ethyl acetate and filtered through a short plug of celite. The celite layer was washed with 2×50 mL of ethyl acetate. The combined organic layers were dried over anhydrous sodium sulphate and concentrated under reduced pressure and the crude was used for next step without further purification.

Step-3: Synthesis of N-(3-(2-aminoquinazolin-6-yl)-2,4-difluorophenyl)-2,5-dichlorobenzenesulfonamide To the stirred solution of N-(3-bromo-2,4-difluorophenyl)-2,5-dichlorobenzenesulfonamide (100 mg, 0.239 mmol, 1.0 equiv) and 6-(4,4,5,5-tetramethyl-1,3,2-dioxaborolan-2-yl)quinazolin-2-amine (66 mg, 0.239 mmol, 1.0 equiv) in DMF:Water (4:1, 5 mL) was added $K_2CO_3$ (99 mg, 0.717 mmol, 3.0 equiv.). The resulting reaction mixture was purged with nitrogen for 15 minutes followed by the addition of $Pd(dppf)Cl_2{\cdot}DCM$ complex (10 mg, 0.012 mmol, 0.05 equiv.). The reaction mixture was again purged with nitrogen for 5 minutes. The reaction mixture was heated to 120° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure to obtain title product as crude residue which was purified by reverse phase HPLC to obtain title product as solid (3.80 mg), Analytical Data: LCMS: 481 $[M+H]^+$, $^1H$ NMR (400 MHz, DMSO-d6) δ ppm 10.66 (br. s., 1H) 9.21 (s, 1H) 7.79-7.89 (m, 2H) 7.70-7.79 (m, 2H) 7.62 (br. s., 1H) 7.52 (d, J=8.77 Hz, 1H) 7.15-7.44 (m, 4H).

Compound 3

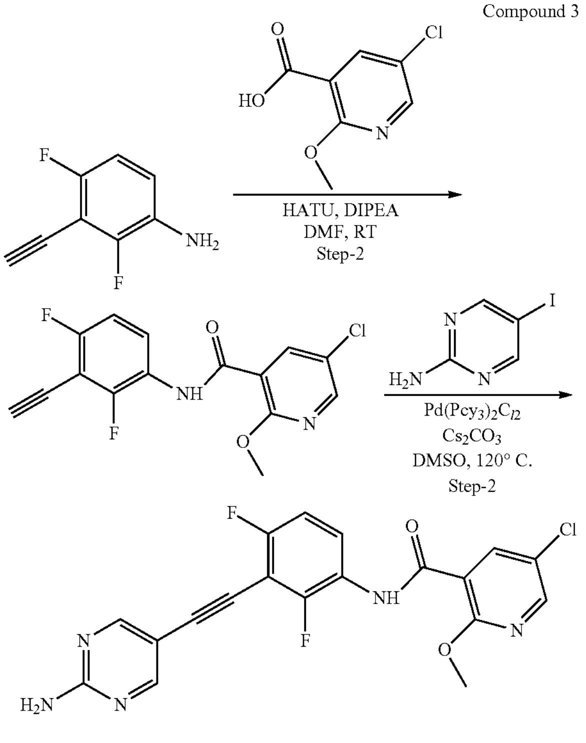

Step-1: Synthesis of 5-chloro-N-(3-ethynyl-2,4-difluorophenyl)-2-methoxynicotinamide To a stirred solution of 5-chloro-2-methoxynicotinic acid (100 mg, 0.531 mmol, 1 equiv.), in DMF (2 mL) was added HATU (304 mg, 0.797 mmol, 1.5 equiv.). The mixture was allowed to stir for 5 minutes, followed by the addition of DIPEA (172 mg, 1.33 mmol, 2.5 equiv.) and 3-ethynyl-2,4-difluoroaniline (81 mg, 0.53 mmol, 1 equiv.) The reaction mixture was kept under stirring for overnight at RT. Product formation was confirmed with TLC and LCMS and reaction mixture was diluted water (30 mL) and the precipitated solid was filtered, washed with water and dried under vacuum to obtain title compound as solid. Analytical Data: LCMS: 323 $[M+H]^+$ Step-2: Synthesis of N-(3-((2-aminopyrimidin-5-yl)ethynyl)-2,4-difluorophenyl)-5-chloro-2-methoxynicotinamide:

To the stirred solution of 5-chloro-N-(3-ethynyl-2,4-difluorophenyl)-2-methoxynicotinamide (100 mg, 0.310 mmol, 1.0 equiv.) and 5-iodopyrimidin-2-amine (68 mg, 0.310 mmol, 1.0 equiv.) in DMSO (5 mL) was added cesium carbonate (403 mg, 1.24 mmol, 4.0 equiv.). The reaction mixture was purged with nitrogen for 15 minutes followed by the addition of $Pd(PCy_3)_2Cl_2$ (11 mg, 0.015 mmol, 0.05 equiv.). The reaction mixture was stirred at 120° C. for 4 h. The mixture was diluted with water and brine and extracted with EtOAc (2×50 mL). The organic layers were collected, washed with brine, dried over anhydrous $Na_2SO_4$, and concentrated under reduced pressure to obtain residue which was purified using flash chromatography (40-50% EtOAc/Hexane as eluent) to obtain title compound as off-white solid. The solid was again purified using reverse phase HPLC TO obtain title product as pure solid (5 mg).

Analytical Data: LCMS: 416 $[M+H]^+$, $^1H$ NMR (400 MHz, DMSO-$d_6$) δ ppm 4.03 (s, 3H) 7.01 (br. s., 1H) 7.14-7.42 (m, 2H) 7.90-8.08 (m, 1H) 8.22 (d, J=2.63 Hz, 1H) 8.35-8.62 (m, 2H) 8.70 (br. s., 1H) 10.22 (s, 1H).

Compound 4

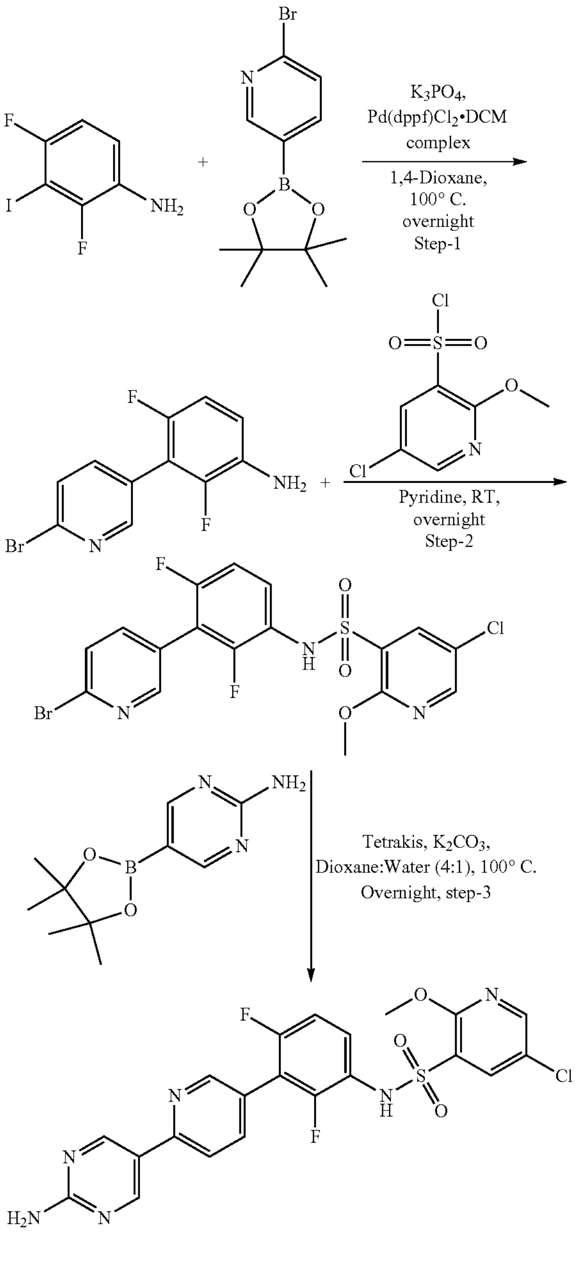

Step-1: Synthesis of 3-(6-bromopyridin-3-yl)-2,4-difluoroaniline

To the stirred solution of 2,4-difluoro-3-iodoaniline (500 mg, 1.96 mmol, 1.0 equiv) in 1,4-Dioxane (5 mL) was added potassium phosphate (1.2 g, 5.88 mmol, 3.0 equiv.) and 2-bromo-5-(4,4,5,5-tetramethyl-1,3,2-dioxaborolan-2-yl) pyridine (660 mg, 2.352 mmol, 1.2 equiv.). The reaction mixture was degassed with nitrogen for 20 min followed by addition of $Pd(dppf)Cl_2$·DCM complex (8 mg, 0.098 mmol). The reaction mixture was again degassed for 10 min and then stirred at 100° C. for overnight. Reaction mass was diluted with water and extracted by Ethyl acetate (3×50 mL).

The combined organic layers were dried over anhydrous sodium sulphate and concentrated under reduced pressure and purified by column chromatography to obtain the title compound (140 mg). LCMS: 285 $[M+H]^+$.

Step-2: Synthesis of N-(3-(6-bromopyridin-3-yl)-2,4-difluorophenyl)-5-chloro-2-methoxypyridine-3-sulfonamide To the stirred solution of 3-(6-bromopyridin-3-yl)-2,4-difluoroaniline (140 mg, 0.498 mmol. 1.0 equiv.) in pyridine was added 5-chloro-2-methoxypyridine-3-sulfonyl chloride (118 mg, 0.491 mmol, 1.0 equiv.) and the reaction mixture was stirred at room temperature overnight. MeOH (10 mL) was added to the mixture, and the mixture was stirred at room temperature for 10 min. The mixture was concentrated under reduced pressure. Then crude was washed with 2N HCl sol., extracted using ethyl acetate (3×50 ml) and reduced under pressure to obtain residue to give the title product as (150 mg) as brown solid. This material was used in the next reaction without further purification. LCMS: 490 $[M+H]^+$.

Step-3: Synthesis of N-(3-(6-(2-aminopyrimidin-5-yl)pyridin-3-yl)-2,4-difluorophenyl)-5-chloro-2-methoxypyridine-3-sulfonamide To the stirred solution of N-(3-(6-bromopyridin-3-yl)-2,4-difluorophenyl)-5-chloro-2-methoxypyridine-3-sulfonamide (150 mg, 0.305 mmol, 1.0 equiv) and 5-(4,4,5,5-tetramethyl-1,3,2-dioxaborolan-2-yl)pyrimidin-2-amine (130 mg, 0.458 mmol, 1.5 equiv) in Dioxane:Water (4:1, 5 mL) was added $K_2CO_3$ (124 mg, 0.917 mmol, 3.0 equiv.). The resulting reaction mixture was purged with nitrogen for 15 minutes followed by the addition of Tetrakis (17 mg, 0.0152 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (5×100 mL). The organic layers were combined, dried over anhydrous $Na_2SO_4$ and evaporated under reduced pressure to obtain title product as crude residue which was purified by reverse phase HPLC chromatography using EtOAc/Hexane (50-100%) as eluent to obtain title product. The residue was further purified by normal phase silica gel chromatography in order to remove TPPO to obtain title product as white solid (18 mg). Analytical Data: LCMS: 505 $[M+H]^+$, $^1H$ NMR (400 MHz, DMSO-$d_6$) δ ppm 3.92 (s, 3H) 7.06 (s, 2H) 7.25 (t, J=9.65 Hz, 1H) 7.32-7.51 (m, 1H) 7.83 (d, J=8.77 Hz, 1H) 8.01 (d, J=8.33 Hz, 1H) 8.08 (s, 1H) 8.44-8.70 (m, 2H) 8.97 (s, 2H) 10.44 (s, 1H).

Compound 5

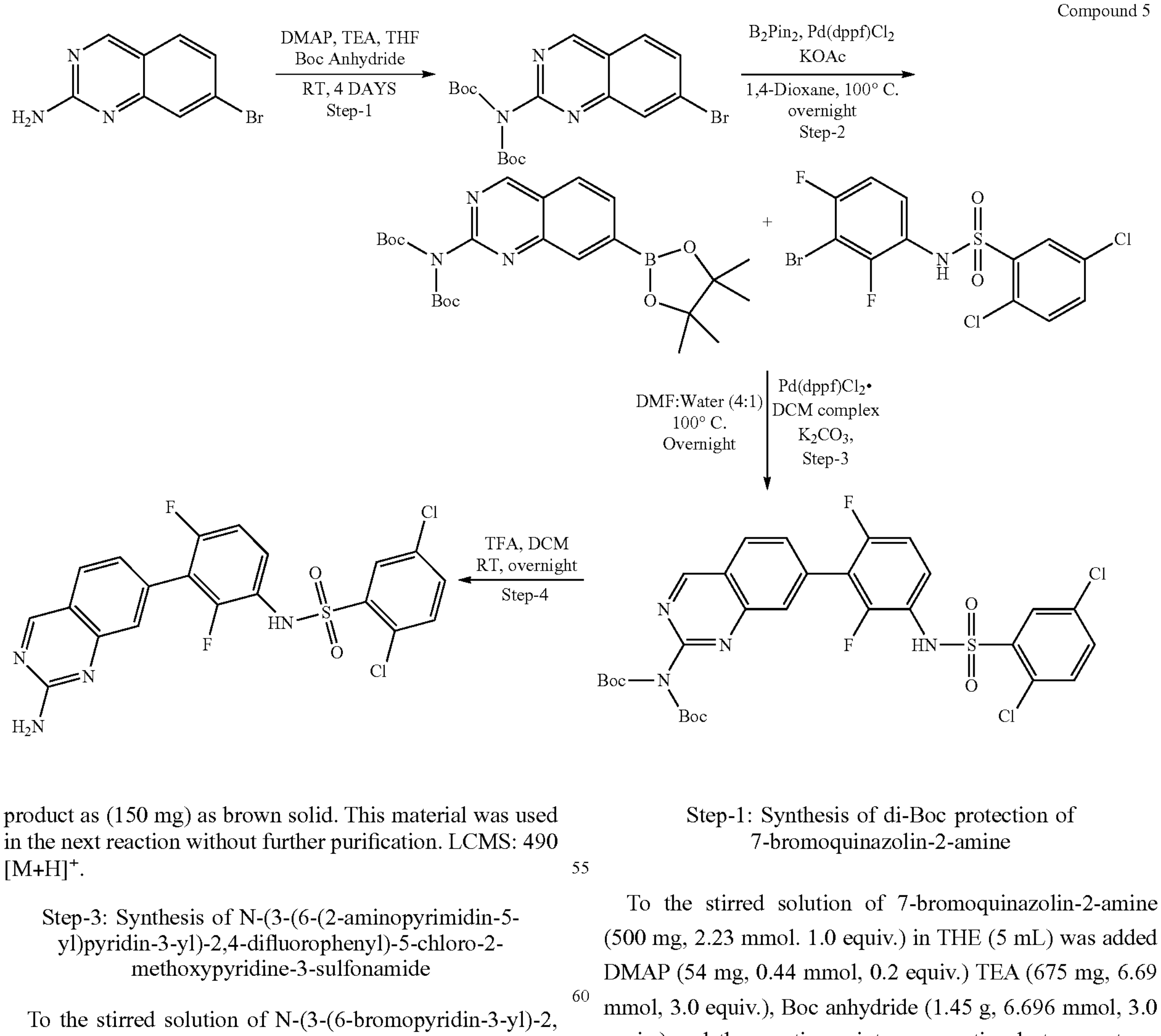

Step-1: Synthesis of di-Boc protection of 7-bromoquinazolin-2-amine

To the stirred solution of 7-bromoquinazolin-2-amine (500 mg, 2.23 mmol. 1.0 equiv.) in THF (5 mL) was added DMAP (54 mg, 0.44 mmol, 0.2 equiv.) TEA (675 mg, 6.69 mmol, 3.0 equiv.), Boc anhydride (1.45 g, 6.696 mmol, 3.0 equiv.) and the reaction mixture was stirred at room temperature for 4 days. The mixture was extracted by using ethyl acetate (3×50 ml) and reduced under pressure to obtain residue to give the title product as (700 mg). This material was used in the next reaction without further purification.

Step-2: Synthesis of boronate of di-Boc protection of 7-bromoquinazolin-2-amine

To the stirred solution of tert-butyl (7-bromoquinazolin-2-yl)(tert-butoxycarbonyl)carbamate (200 mg, 0.472 mmol, 1.0 equiv) and bis(pinacolato)diboron (144 mg, 0.56 mmol, 1.0 equiv) in dioxane (3 mL) was added KOAc (138 mg, 1.41 mmol, 3.0 equiv.). The resulting reaction mixture was purged with nitrogen for 15 minutes followed by the addition of Pd(dppf)$Cl_2$ (10 mg, 0.014 mmol, 0.03 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (5×100 mL). The organic layers were combined, dried over anhydrous $Na_2SO_4$ and evaporated under reduced pressure to obtain title product as crude residue (250 mg).

Step-3: Synthesis of tert-butyl (tert-butoxycarbonyl)(7-(3-((2,5-dichlorophenyl)sulfonamido)-2,6-difluorophenyl)quinazolin-2-yl)carbamate To the stirred solution of N-(3-bromo-2,4-difluorophenyl)-2,5-dichlorobenzenesulfonamide (150 mg, 0.36 mmol, 1.0 equiv) and (2-(2-(bis(tert-butoxycarbonyl)amino)quinazolin-7-yl)-4,5,5-trimethyl-1,3,2-dioxaborolan-4-yl) methylium (204 mg, 0.43 mmol, 1.2 equiv) in DMF:Water (4:1, 5 mL) was added $K_2CO_3$ (147 mg, 1.08 mmol, 3.0 equiv.). The resulting reaction mixture was purged with nitrogen for 15 minutes followed by the addition of Pd(dppf)$Cl_2$·DCM complex (15 mg, 0.05 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (5×100 mL). The organic layers were combined, dried over anhydrous $Na_2SO_4$ and evaporated under reduced pressure to obtain title product as crude residue (300 mg).

Step-4: Synthesis of N-(3-(2-aminoquinazolin-7-yl)-2,4-difluorophenyl)-2,5-dichlorobenzenesulfonamide To a stirred solution of tert-butyl (tert-butoxycarbonyl)(7-(3-((2,5-dichlorophenyl)sulfonamido)-2,6-difluorophenyl)quinazolin-2-yl)carbamate (300 mg, 0.44 mmol, 1.0 equiv) in DCM (5 mL) was added TFA (2 mL). Then, the reaction mixture was allowed to stir at RT overnight. After completion of reaction, the solvent was evaporated, washed with pentane (5 mL) and ether (5 mL) to obtain solid which was purified by reverse phase chromatography to obtain N-(3-(2-aminoquinazolin-7-yl)-2,4-difluorophenyl)-2,5-dichlorobenzenesulfonamide (7 mg). Analytical Data: LCMS: 481 $[M+H]^+$, $^1$H NMR (400 MHz, DMSO-$d_6$) δ ppm 6.94 (br. s., 2H) 7.14-7.29 (m, 3H) 7.34 (br. s., 1H) 7.61 (br. s., 2H) 7.77-7.95 (m, 2H) 8.14 (s, 1H) 9.15 (s, 1H).

Compound 6

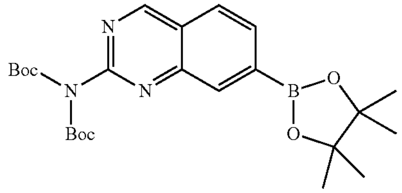

+

-continued

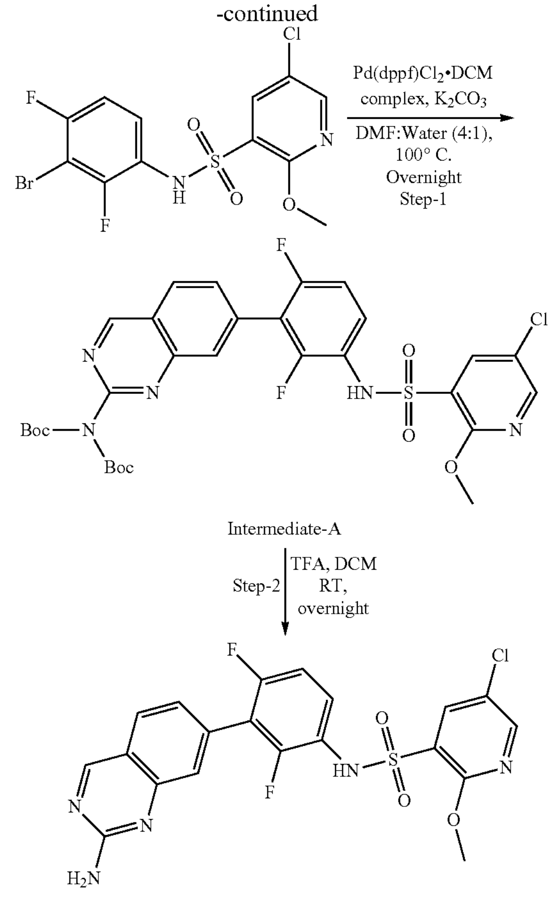

Intermediate-A

Step-1: Synthesis of Intermediate A

To the stirred solution of N-(3-bromo-2,4-difluorophenyl)-5-chloro-2-methoxypyridine-3-sulfonamide (150 mg, 0.362 mmol, 1.0 equiv) and diboc-2-amino-quinazoline-7-bronate ester (206 mg, 0.43 mmol, 1.2 equiv) in DMF:Water (4:1, 5 mL) was added $K_2CO_3$ (150 mg, 1.09 mmol, 3.0 equiv.). The resulting reaction mixture was purged with nitrogen for 15 minutes followed by the addition of Pd(dppf)$Cl_2$·DCM complex (15 mg, 0.018 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure to obtain title product as crude residue (300 mg) which was carried forward to next step without further purification.

Step-2: Synthesis of N-(3-(2-aminoquinazolin-7-yl)-2,4-difluorophenyl)-5-chloro-2-methoxypyridine-3-sulfonamide To a stirred solution of intermediate A (300 mg, 0.44 mmol, 1.0 equiv) in DCM (5 mL) was added TFA (2 mL). Then, the reaction mixture was allowed to stir at RT overnight. After completion of reaction, the solvent was evaporated, washed with pentane (5 mL) and diethyl ether (5 mL) to obtain solid which was purified by reverse phase chromatography to obtain title product N-(3-(2-aminoquinazolin-7-yl)-2,4-difluorophenyl)-2,5-dichlorobenzenesulfonamide as free base (14 mg). Analytical Data: LCMS: 478 $[M+H]^+$, $^1H$ NMR (400 MHz, DMSO-$d_6$) δ ppm 3.90 (s, 3H) 6.96 (s, 2H) 7.12 (d, J=7.45 Hz, 1H) 7.21 (br. s., 1H) 7.33 (s, 1H) 7.39 (bs, 1H), 7.88 (d, J=8.33 Hz, 1H) 8.07 (d, J=2.63 Hz, 1H) 8.48 (br. s., 1H) 9.16 (s, 1H) 10.42 (br. s., 1H).

Step-3 Synthesis of 5-chloro-2-methoxynicotinohydrazide

To a stirred solution of ethyl 5-chloro-2-methoxynicotinate (2.85 g, 13.19 mmol 1 eq) in THF was added hydrazine hydrate (2.53 ml, 79.14 mmol 6 eq) at RT. The mixture was stirred at RT for overnight. After completion of reaction, Compound 7

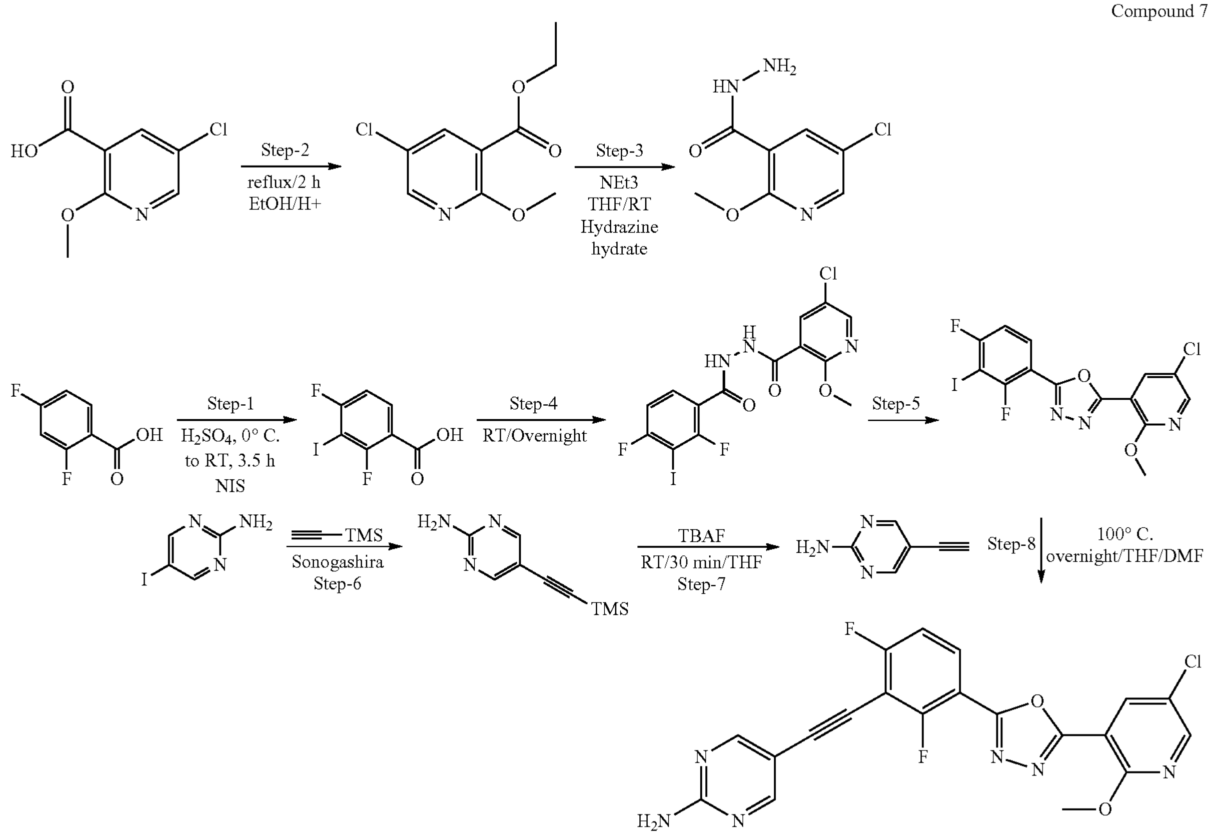

Step-1: Synthesis of 2,4-difluoro-3-iodobenzoic acid

To a stirred solution of 2,4-difluorobenzoic acid (3.0 g, 18.97 mmol, 1.0 equiv.) in $H_2SO_4$ (50 mL) at a 0° C. was added drop wise NIS (8.5 g 37.97 mmol, 2 equiv.) and the reaction was allowed to stir at 25° C. for 2 h. After completion of reaction, reaction mixture was diluted with cold water (500 mL), the precipitated solid was filtered and dried under vacuum to obtain title compound as white solid (3.5 g).

Step-2: Synthesis of ethyl 5-chloro-2-methoxynicotinate

To a stirred solution of 5-chloro-2-methoxynicotinic acid (2.5 g, 13.29 mmol, 1.0 equiv.) in EtOH (20 mL) was added hydrochloric acid (2 ml), the reaction was heated at 100° C. for 2 h. The reaction mixture was cooled to room temperature and solvent was evaporated under vacuum to obtain crude which was diluted with ethyl acetate (50 mL) and water (50 ml). Organic layers were washed with saturated brine and dried over $Na_2SO_4$, concentrated under vacuum to obtain desired product (2.85 g).

reaction mixture was evaporated under vacuum to obtain crude which was added water (25 mL) and ethyl acetate (50 mL). The layers were separated and the aqueous layer extracted with ethyl acetate (2×25 mL). The combined organic layers were washed with saturated brine dried over $Na_2SO_4$, concentrated under vacuum to obtain desired product (2.5 g).

Step-4: Synthesis of 5-chloro-N'-(2,4-difluoro-3-iodobenzoyl)-2-methoxynicotinohydrazide To a stirred solution of 2,4-difluoro-3-iodobenzoic acid (1 g, 3.52 mmol 1 eq) in DMF was added HATU (2 g, 5.28 mmol 1.5 eq) & DIPEA (10.56 mmol 1.5 ml 3 eq) at 25° C. stir for over 10 min & was added 5-chloro-2-methoxynicotinohydrazide (711 mg, 3.52 mmol 1 eq). The mixture was stirred at room temperature for overnight. The mixture was diluted with water and extracted with EtOAc. The organic layer was washed with brine, dried over anhydrous $Na_2SO_4$, and concentrated under reduced pressure to obtain crude residue which was purified by flash chromatography (EtOAc in Hexane; 30%) to yield the title compound as off-white solid (800 mg).

Step-5 Synthesis of 2-(5-chloro-2-methoxypyridin-3-yl)-5-(2,4-difluoro-3-iodophenyl)-1,3,4-oxadiazole To a stirred solution of 5-chloro-N'-(2,4-difluoro-3-iodobenzoyl)-2-methoxynicotinohydrazide (800 mg, 1.70 mmol, 1.0 equiv.) in DCM (15 mL) at 0° C. was added. $NEt_3$ (0.7 ml, 5.1 mmol, 3.0 equiv.) and the mixture was stirred at 0° C. for 30 min and added p-toluenesulfonyl chloride (0162 mg, 0.85 mmol, 0.5 eq). The reaction mixtures were stirred overnight. After completion of reaction, reaction mixture was added aqueous sodium hydroxide, extracted twice with DCM (2×25 mL), organic layer was washed with saturated brine, dried over anhydrous $Na_2SO_4$ and concentrated under reduced pressure to give the title compound (500 mg).

Step-6: Synthesis 5-((trimethylsilyl)ethynyl)pyrimidin-2-amine

To the solution of 5-iodopyrimidin-2-amine (500 mg, 2.26 mmol, 1 eq.) in THF/DMF was added triethylamine (0.85 ml, 6.78 mmol, 3 eq.) was purged with nitrogen 2-3 times was added ethynyltriisopropylsilane (0.7 ml, 4.52 mmol, 2 eq.), CuCl (61 mg, 0.452 mmol, 0.2 eq.) dikis (793 mg 1.13 mmol, 0.5 eq). Reaction mixture stirred at 100° C. for 12 h. After completion of reaction, reaction mixture was diluted with water (50 mL) and extracted with ethyl acetate (50 ml) and organic layer was collected and concentrated to give crude product, which was purified by combiflash chromatography to obtain pure product (500 mg).

Step-7: Synthesis of 5-ethynylpyrimidin-2-amine

To a solution of 5-((trimethylsilyl)ethynyl)pyrimidin-2-amine (500 mg, 2.60 mmol, 1.0 equiv.) in THE (10 mL) was added TBAF (0.4 ml, 1.3 mmol, 0.5 Eq). The reaction mixture was purged with nitrogen. The mixture was stirred at RT for 30 min. The reaction mixtures diluted with water (25 mL) and extracted with ethyl acetate (3×10 mL). The obtained organic layer was washed with saturated brine, dried over sodium sulfate and concentrated under reduced pressure to obtain title compound as a crude product which was purified by combi-flash to get pure compound (400 mg).

Step-8: Synthesis of 5-((3-(5-(5-chloro-2-methoxypyridin-3-yl)-1,3,4-oxadiazol-2-yl)-2,6-difluorophenyl)ethynyl)pyrimidin-2-amine To a stirred solution of 2-(5-chloro-2-methoxypyridin-3-yl)-5-(2,4-difluoro-3-iodophenyl)-1,3,4-oxadiazole (120 mg 0.27 mmol, 1.0 equiv) in THE (10 mL) was added triethylamine (0.3 mL, 1.66 mmol, 6 equiv.) and CuCl (6 mg, 0.054 mmol, 0.2 equiv). The reaction mixture was purged with nitrogen for 15 minutes followed by the addition of 5-((trimethylsilyl)ethynyl)pyrimidin-2-amine (60 mg, 0.54 mmol, 2 equiv.) & dichlorobis(triphenylphosphine)palladium (95 mg, 0.13 mmol 0.05 eq). The mixture was stirred at 100° C. for overnight. The reaction mixtures added to water (25 mL) and the mixture was extracted with ethyl acetate (3×50 mL). The obtained organic layer was washed with saturated brine, dried over sodium sulfate and concentrated under reduced pressure to obtain crude product which was purified by combiflash to obtain desired product. Analytical data: LCMS: 441.3 (M+H)+, $^1H$ NMR (400 MHz, DMSO-$d_6$) δ ppm 8.60 (d, J=2.63 Hz, 1H) 8.53 (d, J=2.63 Hz, 1H) 8.50 (s, 1H) 8.43 (t, J=7.67 Hz, 1H) 7.81 (t, J=10.09 Hz, 1H) 7.51-7.67 (m, 1H) 7.29 (s, 2H) 4.05 (s, 3H).

Compound 8

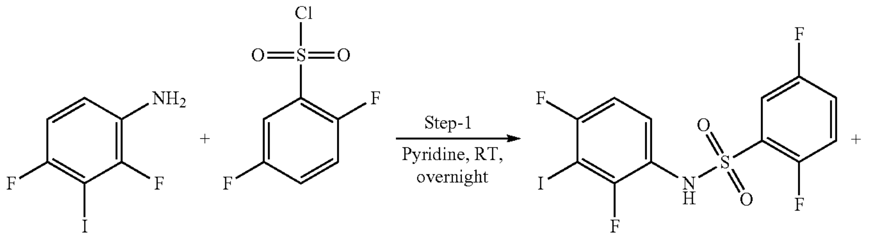

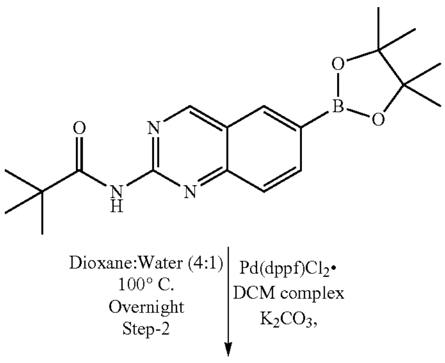

-continued

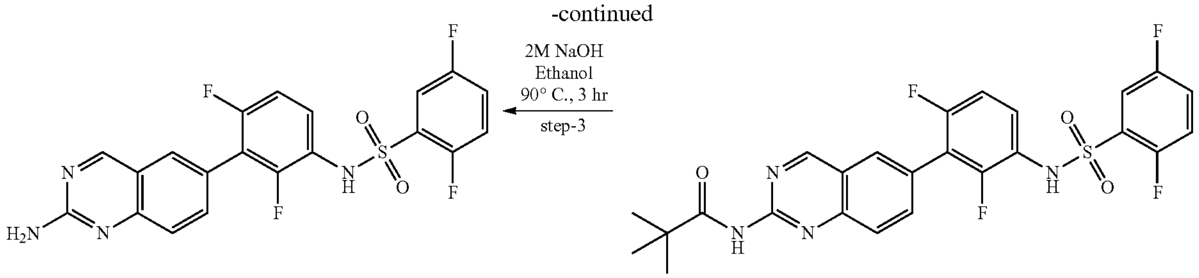

Step-1 Synthesis of N-(2,4-difluoro-3-iodophenyl)-2,5-difluorobenzenesulfonamide To a stirred solution of 2,4-difluoro-3-iodoaniline (300 mg, 1.4111 mmol. 1.0 equiv.) in pyridine (1.5 mL) at room temperature was added 2,5-difluorobenzenesulfonyl chloride (360 mg, 1.4111 mmol. 1.0 equiv.). The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure to obtain title compound. This material was further purified by flash chromatography to obtain desired compound (530 mg).

Step-2: Synthesis of N-(6-(3-((2,5-difluorophenyl)sulfonamido)-2,6-difluorophenyl)quinazolin-2-yl)pivalamide To a stirred solution of N-(2,4-difluoro-3-iodophenyl)-2,5-difluorobenzenesulfonamide (100 mg, 0.2320 mmol, 1.0 equiv) and N-(6-(4,4,5,5-tetramethyl-1,3,2-dioxaborolan-2-yl)quinazolin-2-yl)pivalamide (164.9 mg, 0.4641 mmol, 2.0 equiv) in dioxane:water (4:1, 5 mL) was added $K_2CO_3$ (96 mg, 0.6962 mmol, 3.0 equiv.). The resulting reaction mixture was purged with nitrogen for 15 minutes followed by the addition of $Pd(dppf)Cl_2$ DCM complex (9.48 mg, 0.0116 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3x100 mL). The organic layers were combined, dried over anhydrous $Na_2SO_4$ and evaporated under reduced pressure to obtain title compound. This compound was used in further reaction without purification (190 mg), Analytical Data: LCMS: 533.3 $[M+H]^+$.

Step-3: Synthesis of N-(3-(2-aminoquinazolin-6-yl)-2,4-difluorophenyl)-2,5-difluorobenzenesulfonamide To a stirred solution of N-(6-(3-((2,5-difluorophenyl)sulfonamido)-2,6-difluorophenyl)quinazolin-2-yl)pivalamide (170 mg, crude) in ethanol (6 mL) at room temperature was added 2M NaOH (4 mL). Then, the reaction mixture was allowed to stir at 90° C. overnight. After completion of reaction, the solvent was evaporated and water was added to the reaction mixture, extracted with EtOAc (1x50 mL). The organic layers were combined, dried over anhydrous $Na_2SO_4$ and evaporated under reduced pressure, washed with ether (2 ml) and pentane (3 ml) to obtain N-(3-(2-aminoquinazolin-6-yl)-2,4-difluorophenyl)-2,5-difluorobenzenesulfonamide (11 mg), Analytical Data: LCMS: 449.08 $[M+H]^+$, NMR: $^1H$ NMR (400 MHz, DMSO-$d_6$) δ 10.70 (br. s., 1H), 9.15 (s, 1H), 7.77 (s, 1H), 7.46-7.65 (m, 5H), 7.32 (d, J=6.58 Hz, 1H), 7.24 (d, J=9.65 Hz, 1H), 7.03 (s, 2H).

Compound 9

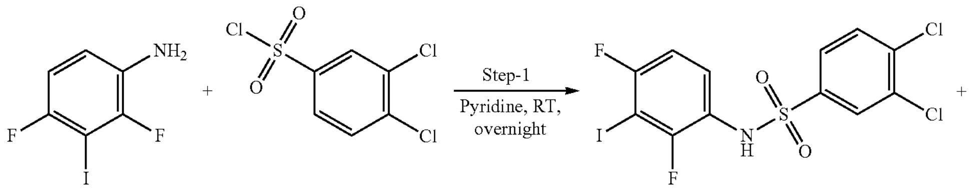

-continued

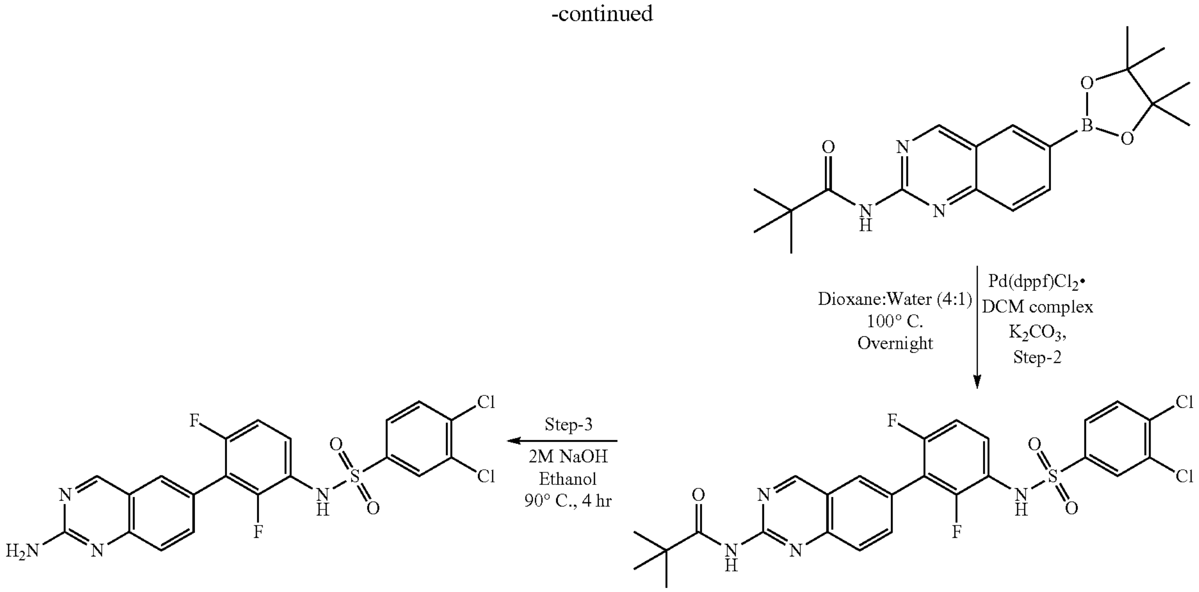

Step-1: Synthesis of 3,4-dichloro-N-(2,4-difluoro-3-iodophenyl)benzenesulfonamide To a stirred solution of 2,4-difluoro-3-iodoaniline (300 mg, 1.2219 mmol. 1.0 equiv.) in pyridine (2 mL) at room temperature was added 3,4-dichlorobenzenesulfonyl chloride (311.6 mg, 1.2219 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc, dried over sodium sulphate and concentrated under vacuum to obtain crude product was triturated with hexanes to obtain desired product (220 mg).

Step-2: Synthesis of N-(6-(3-((3,4-dichlorophenyl)sulfonamido)-2,6-difluorophenyl)quinazolin-2-yl)pivalamide To a stirred solution of 3,4-dichloro-N-(2,4-difluoro-3-iodophenyl)benzenesulfonamide (200 mg, 0.4310 mmol, 1.0 equiv) and N-(6-(4,4,5,5-tetramethyl-1,3,2-dioxaborolan-2-yl)quinazolin-2-yl)pivalamide (306.25 mg, 0.8620 mmol, 2.0 equiv) in dioxane:water (4:1, 5 mL) was added $K_2CO_3$ (178.7 mg, 1.2931 mmol, 3.0 equiv.). The resulting reaction mixture was purged with nitrogen for 15 minutes followed by the addition of $Pd(dppf)Cl_2 \cdot DCM$ complex (17.59 mg, 0.0215 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure to obtain title product. This compound was used next step without purification (350 mg), Analytical Data: LCMS: 565.2 $[M+H]^+$.

Step-3: Synthesis of N-(3-(2-aminoquinazolin-6-yl)-2,4-difluorophenyl)-3,4-dichlorobenzenesulfonamide To a stirred solution of N-(6-(3-((3,4-dichlorophenyl)sulfonamido)-2,6-difluorophenyl)quinazolin-2-yl)pivalamide (350 mg, crude) in ethanol (6 mL) at room temperature was added 2M NaOH (4 mL). Then, the reaction mixture was allowed to stir at 90° C. overnight. After completion of reaction, the solvent was evaporated and water was added to the reaction mixture, extracted with EtOAc (1×50 mL). The organic layers were combined, dried over anhydrous $Na_2SO_4$ and evaporated under reduced pressure to obtain crude which was purified by flash chromatography to obtain product which was triturated with ether (2 ml) and pentane (3 ml) to obtain as title compound N-(3-(2-aminoquinazolin-6-yl)-2,4-difluorophenyl)-3,4-dichlorobenzenesulfonamide (45 mg), Analytical Data: LCMS: 481$[M+H]^+$, NMR: $^1H$ NMR (400 MHz, DMSO-$d_6$) δ10.47 (s, 1H), 9.14 (s, 1H), 7.88-7.93 (m, 2H), 7.75 (s, 1H), 7.67 (dd, J=1.97, 8.55 Hz, 1H), 7.58 (d, J=9.21 Hz, 1H), 7.48 (d, J=8.77 Hz, 1H), 7.20-7.32 (m, 2H), 7.04 (s, 2H).

Compound 10

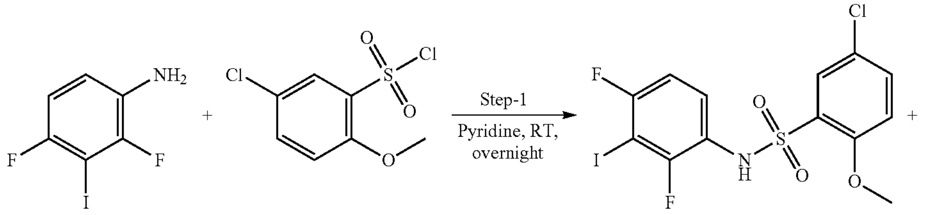

-continued

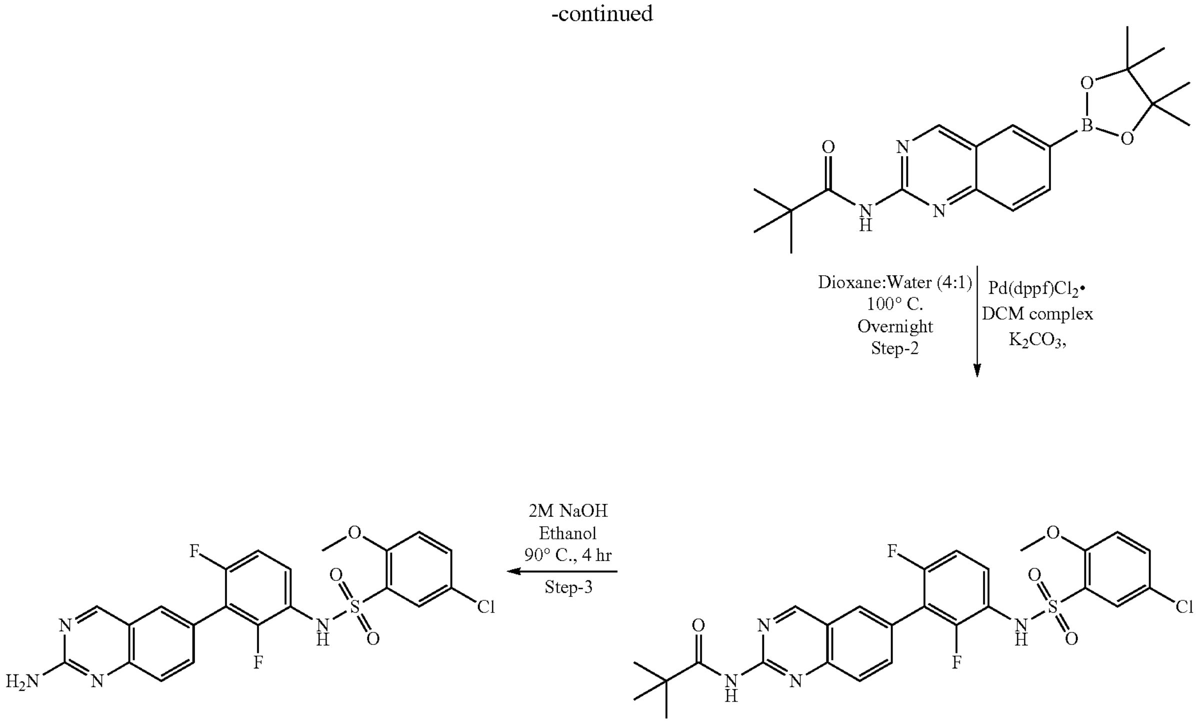

Step-1: Synthesis of 5-chloro-N-(2,4-difluoro-3-iodophenyl)-2-methoxybenzenesulfonamide To a stirred solution of 2,4-difluoro-3-iodoaniline (500 mg, 2.0738 mmol. 1.0 equiv.) in pyridine (3 mL) at room temperature was added 5-chloro-2-methoxybenzenesulfonyl chloride (528.8 mg, 2.0738 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure and further purified by flash chromatography to obtain the desired product (250 mg).

Step-2: Synthesis of N-(6-(3-((5-chloro-2-methoxyphenyl)sulfonamido)-2,6-difluorophenyl)quinazolin-2-yl)pivalamide To a stirred solution of 5-chloro-N-(2,4-difluoro-3-iodophenyl)-2-methoxybenzenesulfonamide (200 mg, 0.4351 mmol, 1.0 equiv) and N-(6-(4,4,5,5-tetramethyl-1,3,2-dioxaborolan-2-yl)quinazolin-2-yl)pivalamide (309.2 mg, 0.8702 mmol, 2.0 equiv) in dioxane:water (5:2, 7 mL) was added $K_2CO_3$ (180.4 mg, 1.3053 mmol, 3.0 equiv.). The resulting reaction mixture was purged with nitrogen for 15 minutes followed by the addition of Pd(dppf)$Cl_2$·DCM complex (17.76 mg, 0.0217 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure. This compound was used in further reaction without purification (350 mg), Analytical Data: LCMS: 561.1 $[M+H]^+$.

Step-3: Synthesis of N-(3-(2-aminoquinazolin-6-yl)-2,4-difluorophenyl)-5-chloro-2-methoxybenzenesulfonamide To a stirred solution of N-(6-(3-((5-chloro-2-methoxyphenyl)sulfonamido)-2,6-difluorophenyl)quinazolin-2-yl)pivalamide (60 mg, crude) in ethanol (5 mL) was added 2M NaOH (3 mL). Then, the reaction mixture was allowed to stir at 90° C. overnight. After completion of reaction, the solvent was evaporated and water was added to the reaction mixture, extracted with EtOAc (1×50 mL). The organic layers were combined, dried over anhydrous $Na_2SO_4$ and evaporated under reduced pressure to obtain crude which was purified by flash chromatography to obtain product which was triturated with ether (2 mL) and pentane (3 mL) to obtain as title compound N-(3-(2-aminoquinazolin-6-yl)-2,4-difluorophenyl)-5-chloro-2-methoxybenzenesulfonamide (30 mg), Analytical Data: LCMS: 477.05$[M+H]^+$, NMR: $^1$H NMR (400 MHz, DMSO-$d_6$) δ 10.10 (s, 1H), 9.16 (s, 1H), 7.79 (s, 1H), 7.69 (dd, J=2.63, 8.77 Hz, 1H), 7.59 (br. s., 1H), 7.49 (d, J=8.77 Hz, 1H), 7.10-7.40 (m, 3H), 7.03 (s, 2H), 3.82 (s, 3H).

Compound 11

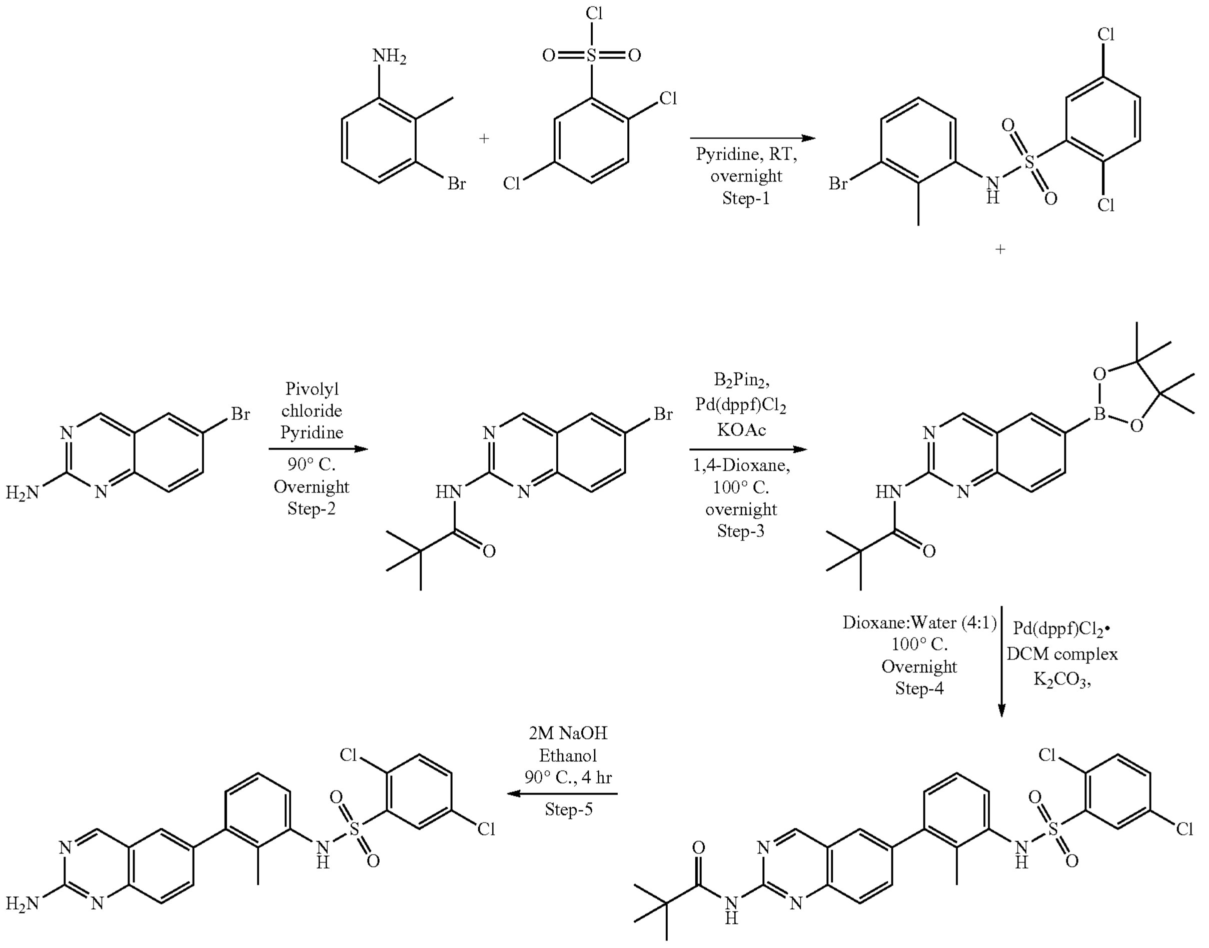

Step-1: Synthesis of N-(3-bromo-2-methylphenyl)-2,5-dichlorobenzenesulfonamide

To a stirred solution of 3-bromo-2-methylaniline (500 mg, 2.7 mmol. 1.0 equiv.) in pyridine (5 mL) at room temperature was added 2,5-dichlorobenzenesulfonyl chloride (663 mg, 2.7 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure to obtain title compound. This material was used in the next reaction without further purification (700 mg).

Step-2: Synthesis of N-(6-bromoquinazolin-2-yl)pivalamide

To a stirred solution of 6-bromoquinazolin-2-amine (1.0 g, 4.46 mmol. 1.0 equiv.) in pyridine (5 mL) was added pivolyl chloride (1.61 g, 1.33 mmol, 3.0 equiv.). The reaction mixture was stirred at 90° C. for overnight. After completion of reaction, reaction mixture was diluted with water (100 mL) and extracted with ethyl acetate (3×500 mL), organic layer was washed with 1N HCl (100 mL X 3 times) to remove pyridine, organic layer was dried over anhydrous sodium sulfate and evaporated under reduced pressure to obtain title compound. This crude product was washed with hexane (20 mL) and used in the next reaction without further purification (1.2 g).

Step-3: Synthesis of N-(6-(4,4,5,5-tetramethyl-1,3,2-dioxaborolan-2-yl)quinazolin-2-yl)pivalamide To a stirred solution of N-(6-bromoquinazolin-2-yl)pivalamide (1.2 g, 3.90 mmol, 1.0 equiv) and bis(pinacolato) diboron (1.48 g, 5.86 mmol, 1.5 equiv) in dioxane (20 mL) was added KOAc (1.14 g, 11.7 mmol, 3.0 equiv.). The resulting reaction mixture was purged with nitrogen for 15 minutes followed by the addition of $Pd(dppf)Cl_2$ (142 mg, 0.195 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (5×100 mL). The organic layers were combined, dried over anhydrous $Na_2SO_4$ and evaporated under reduced pressure and washed with hexane (20 mL) to obtain title product as crude residue (1.1 g).

Step-4: Synthesis of N-(6-(3-((2,5-dichlorophenyl) sulfonamido)-2-methylphenyl)quinazolin-2-yl)pivalamide To the stirred solution of N-(3-bromo-2-methylphenyl)-2,5-dichlorobenzenesulfonamide (200 mg, 0.50 mmol, 1.0 equiv) and N-(6-(4,4,5,5-tetramethyl-1,3,2-dioxaborolan-2-yl)quinazolin-2-yl)pivalamide (359 mg, 1.01 mmol, 2.0 equiv) in Dioxane:Water (8:2, 10 mL) was added $K_2CO_3$ (207 mg, 1.5 mmol, 3.0 equiv.). The resulting reaction mixture was purged with nitrogen for 15 minutes followed by the addition of Pd(dppf)$Cl_2$·DCM complex (20 mg, 0.025 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure which was purified by flash chromatography to obtain title product (130 mg).

Step-5: Synthesis of N-(3-(2-aminoquinazolin-6-yl)-2-methylphenyl)-2,5 dichlorobenzenesulfonamide To a stirred solution of N-(6-(3-((2,5-dichlorophenyl) sulfonamido)-2-methylphenyl)quinazolin-2-yl)pivalamide (130 mg, 0.533 mmol, 1.0 equiv) in ethanol (6 mL) was added 2M NaOH (4 mL). Then, the reaction mixture was allowed to stir at 90 degree celsius overnight. After completion of reaction, the solvent was evaporated and water was added to the reaction mixture, extracted with EtOAc (2×100 mL). The organic layers were combined, dried over anhydrous $Na_2SO_4$ and evaporated under reduced pressure which was purified by flash chromatography, washed with ether (5 ml) and pentane (5 ml) to obtain as title compound N-(3-(2-aminoquinazolin-6-yl)-2,4-difluorophenyl)-5-chloro-2-methoxypyridine-3-sulfonamide (70 mg). Analytical Data: LCMS: 459 $[M+H]^+$, NMR: $^1H$ NMR (400 MHz, DMSO-$d_6$) δ ppm 2.12 (s, 3H) 6.90 (s, 3H) 7.17 (br. s., 2H) 7.45 (d, J=8.77 Hz, 1H) 7.51-7.63 (m, 1H) 7.68 (d, J=1.75 Hz, 1H) 7.78 (s, 2H) 7.83 (s, 1H) 9.14 (s, 1H) 10.18 (s, 1H).

Compound 12

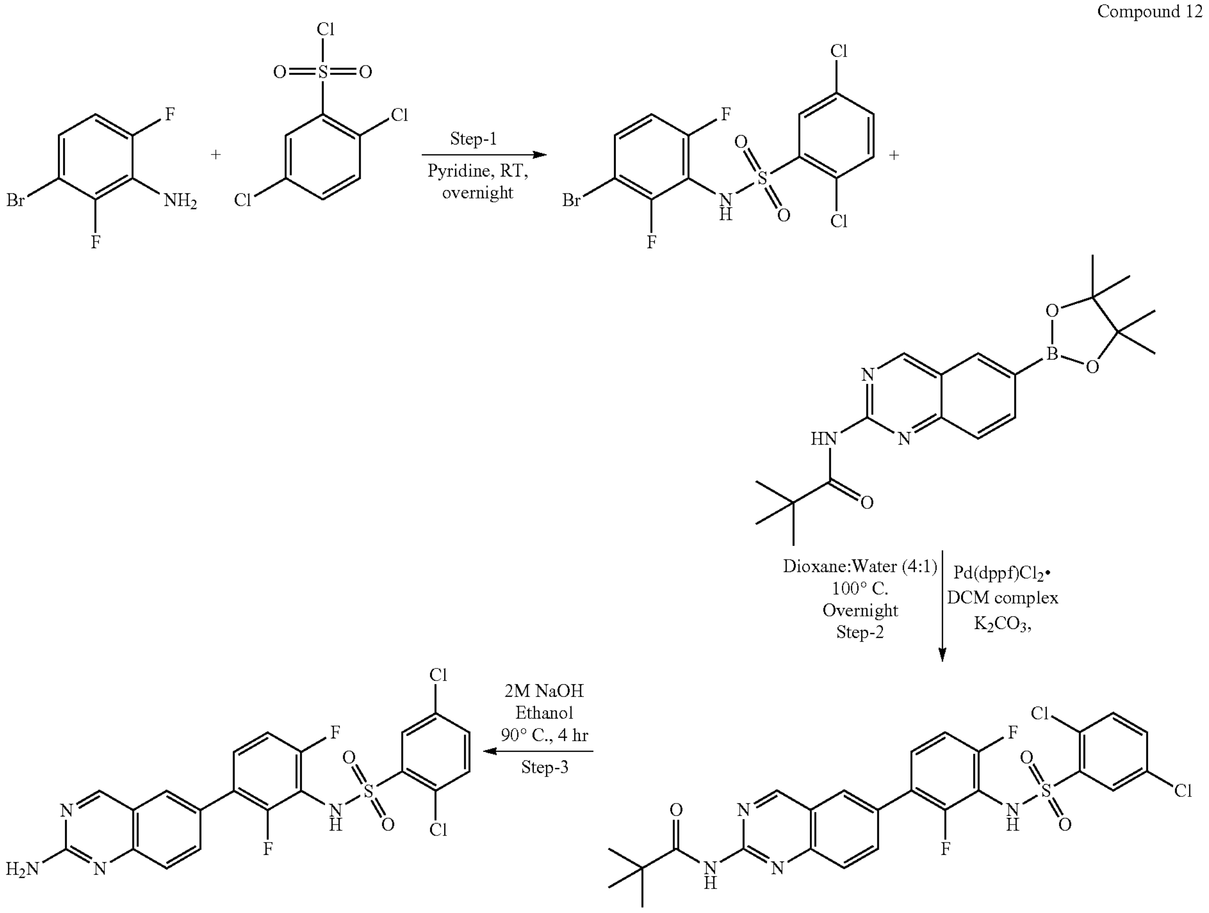

Step-1: Synthesis of N-(3-bromo-2,6-difluorophenyl)-2,5-dichlorobenzenesulfonamide To a stirred solution of 3-bromo-2,6-difluoroaniline (100 mg, 0.480 mmol. 1.0 equiv.) in pyridine (1.5 mL) at room temperature was added pyridine of 2,5-dichlorobenzenesulfonyl chloride (141 mg, 0.576 mmol. 1.2 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure to obtain title compound. This material was used in the next reaction without further purification (150 mg).

Step-2: Synthesis of N-(6-(3-((2,5-dichlorophenyl) sulfonamido)-2,4-difluorophenyl)quinazolin-2-yl) pivalamide To a stirred solution of N-(3-bromo-2,6-difluorophenyl)-2,5-dichlorobenzenesulfonamide (120 mg, 0.289 mmol, 1.0 equiv) and N-(6-(4,4,5,5-tetramethyl-1,3,2-dioxaborolan-2-yl)quinazolin-2-yl)pivalamide (206 mg, 0.578 mmol, 2.0 equiv) in Dioxane:Water (4:1, 5 mL) was added $K_2CO_3$ (111 mg, 0.867 mmol, 3.0 equiv.). The resulting reaction mixture was purged with nitrogen for 15 minutes followed by the addition of Pd(dppf)$Cl_2$·DCM complex (11 mg, 0.014 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure to obtain crude which was purified by flash chromatography to obtain title product (50 mg).

Step-3: Synthesis of N-(3-(2-aminoquinazolin-6-yl)-2,6-difluorophenyl)-2,5-dichlorobenzenesulfonamide To a stirred solution of N-(6-(3-((2,5-dichlorophenyl) sulfonamido)-2,4-difluorophenyl)quinazolin-2-yl)pivalamide (50 mg, 0.0886 mmol, 1.0 equiv) in ethanol (4 mL) was added 2M NaOH (4 mL) at room temperature. Then, the reaction mixture was allowed to stir at 90° C. for overnight. After completion of reaction, the solvent was evaporated and water was added to the reaction mixture, extracted with EtOAc (2×50 mL). The organic layers were combined, dried over anhydrous $Na_2SO_4$ and evaporated under reduced pressure to obtain crude washed with ether (2 ml) and pentane (3 ml) to obtain as title compound N-(3-(2-aminoquinazolin-6-yl)-2,6-difluorophenyl)-2,5-dichlorobenzenesulfonamide (22 mg). Analytical Data: LCMS: 481$[M+H]^+$, NMR: $^1H$ NMR (400 MHz, DMSO-$d_6$) δ ppm 7.27 (s, 2H) 7.29 (t, J=8.77 Hz, 1H) 7.51 (d, J=8.77 Hz, 1H) 7.57-7.64 (m, 1H) 7.67-7.83 (m, 3H) 7.84-7.98 (m, 2H) 9.21 (s, 1H) 10.59 (br. s., 1H).

Compound 13

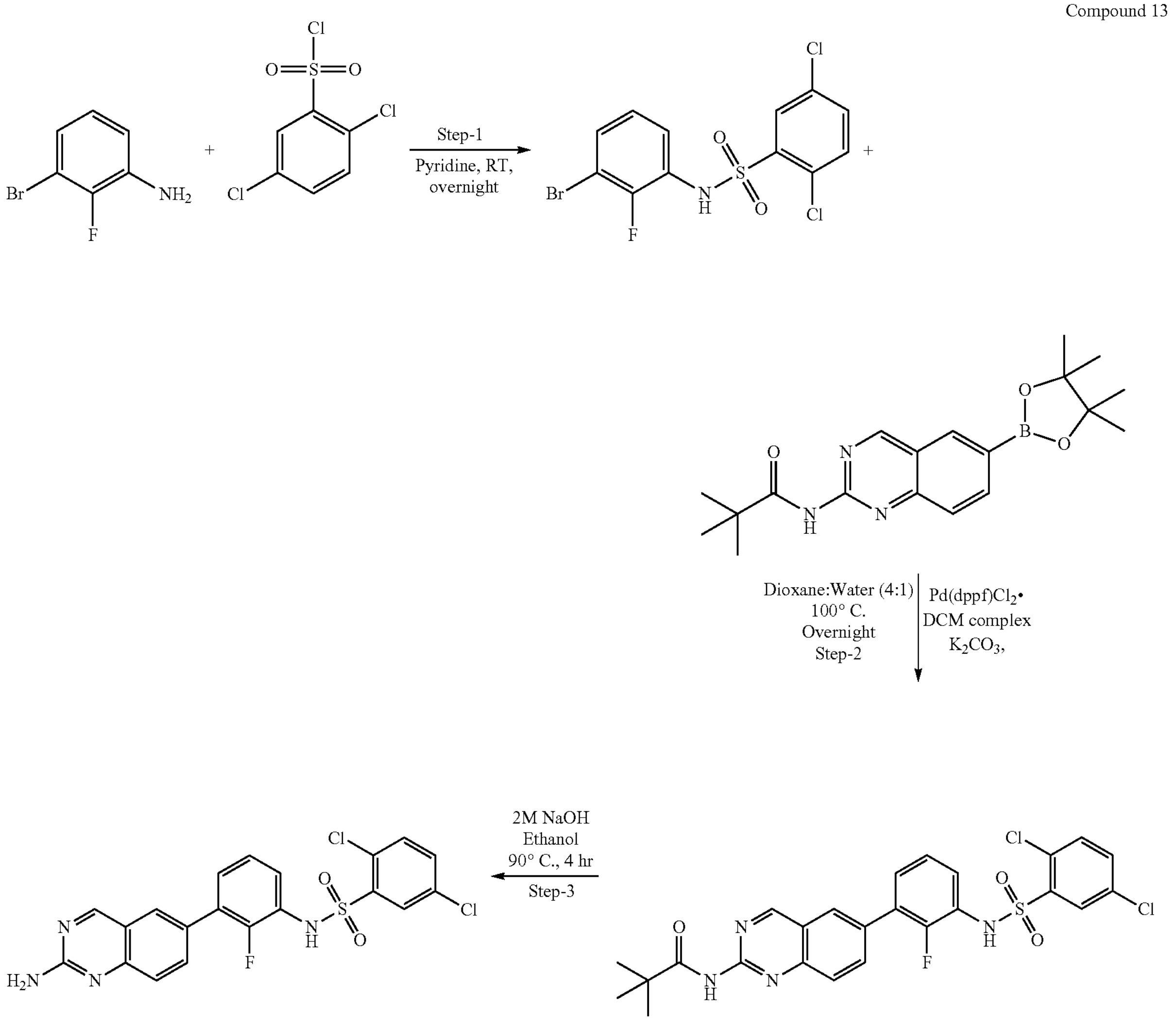

Step-1 Synthesis of N-(3-bromo-2-fluorophenyl)-2,5-dichlorobenzenesulfonamide

To a stirred solution of 3-bromo-2-fluoroaniline (500 mg, 2.631 mmol. 1.0 equiv.) in pyridine (2.0 mL) at room temperature was added 2,5-dichlorobenzenesulfonyl chloride (645.984 mg, 2.631 mmol. 1.0 equiv.) The resultant reaction mixture was stirred at room temperature for overnight. The progress of reaction was monitored by TLC. After completion of the reaction, the water (100 ml) was added and filtered, residue washed with water and hexanes to used next step without further purification (710 mg).

Step-2: Synthesis of N-(6-(3-((2,5-dichlorophenyl)sulfonamido)-2-fluorophenyl)quinazolin-2-yl)pivalamide To a stirred solution of N-(3-bromo-2-fluorophenyl)-2,5-dichlorobenzenesulfonamide (200 mg, 0.501 mmol, 1.0 equiv.) and N-(6-(4,4,5,5-tetramethyl-1,3,2-dioxaborolan-2-yl)quinazolin-2-yl)pivalamide (178.043 mg, 0.501 mmol, 1.0 equiv.) in Dioxane:Water (4:1, 5 mL) was added $K_2CO_3$ (207.52 mg, 1.503 mmol, 3.0 equiv.). The resulting reaction mixture was purged with nitrogen for 15 minutes followed by the addition of $Pd(dppf)Cl_2 \cdot DCM$ complex (40.93 mg, 0.0501 mmol, 0.1 equiv.). The reaction mixture was again purged with nitrogen for 5 minutes. The reaction mixture was heated to 100° C. for overnight. The progress of reaction was monitored by TLC and LCMS. After completion of reaction, reaction mixture was filtered through celite bed and filtrate was dried over anhydrous sodium sulfate and evaporated under reduced pressure to obtain title compound used next step without further purification. Analytical Data: LCMS: 547.07 $[M+H]^+$.

Step-3: Synthesis of N-(3-(2-aminoquinazolin-6-yl)-2-fluorophenyl)-2,5-dichlorobenzenesulfonamide To a stirred solution of N-(6-(3-((2,5-dichlorophenyl)sulfonamido)-2-fluorophenyl)quinazolin-2-yl)pivalamide (200 mg) in ethanol (4 mL) was added 2M NaOH (4 mL). Then, the reaction mixture was allowed to stir at 90° C. for overnight. After completion of reaction, the solvent was evaporated and water (20 mL) was added to the reaction mixture, extracted with EtOAc (2×50 mL). The organic layers were combined, dried over anhydrous $Na_2SO_4$ and evaporated under reduced pressure to obtain crude which was purified by reverse phase HPLC to obtained title compound N-(3-(2-aminoquinazolin-6-yl)-2-fluorophenyl)-2,5-dichlorobenzenesulfonamide (4 mg). Analytical Data: LCMS: 463.01 $[M+H]^+$, $^1H$ NMR (400 MHz, DMSO-$d_6$) δ 9.15 (s, 1H), 7.85-7.93 (m, 2H), 7.76 (d, J=8.77 Hz, 1H), 7.54 (s, 2H), 7.46 (d, J=8.77 Hz, 1H), 7.08-7.15 (m, 1H), 6.87-7.02 (m, 5H).

Compound 14

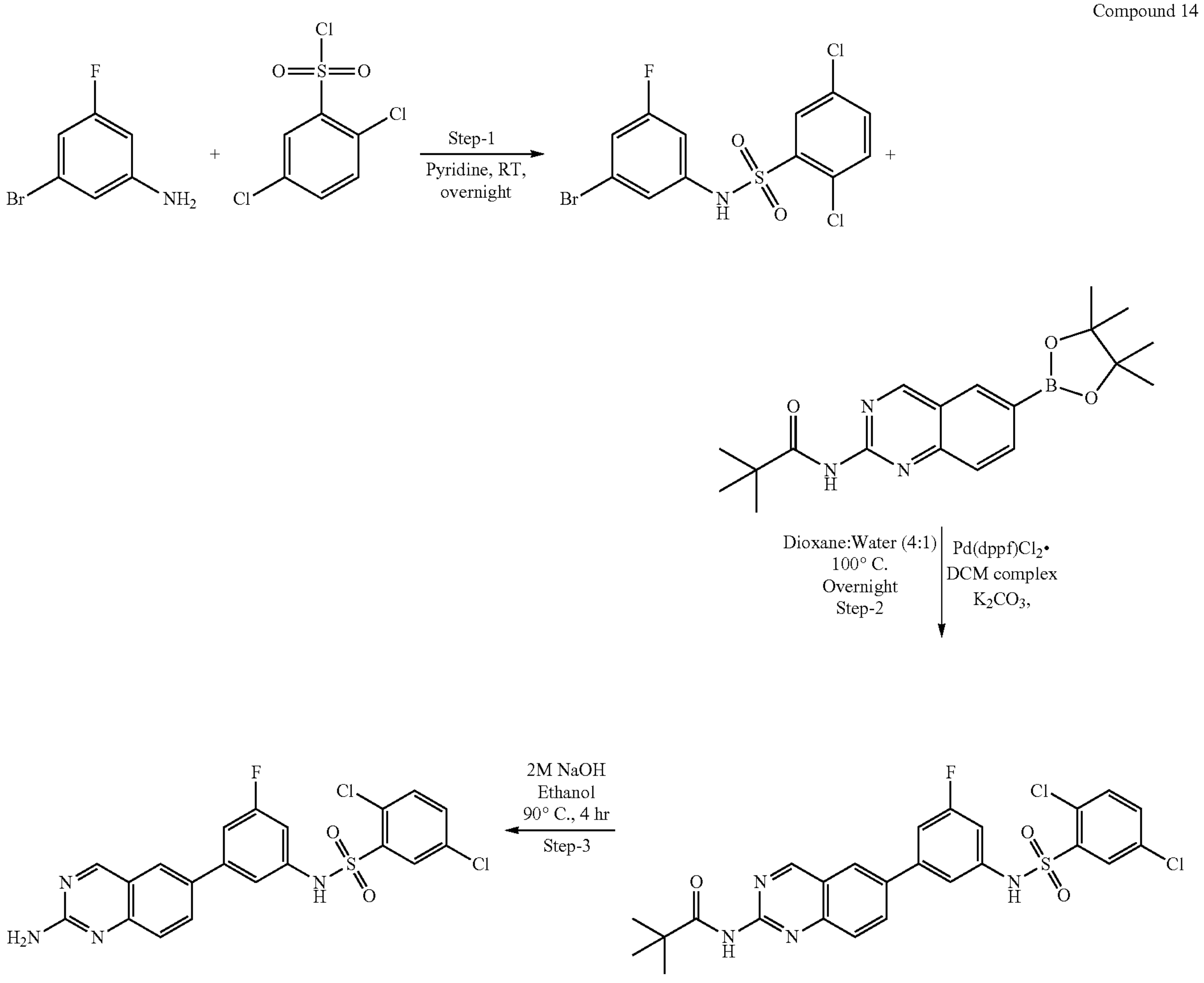

Step-1 Synthesis of N-(3-bromo-5-fluorophenyl)-2,5-dichlorobenzenesulfonamide

To a stirred solution of 3-bromo-5-fluoroaniline (500 mg, 2.64 mmol. 1.0 equiv.) in pyridine (15 mL) at room temperature was added 3-bromo-5-fluoroaniline (774 mg, 3.17 mmol. 1.2 equiv.) The resultant reaction mixture was stirred at 90° C. for overnight. The progress of reaction was monitored by TLC. After completion of the reaction, water was added to the reaction mixture, extracted with EtOAc (5×100 mL). The organic layers were combined treated with 1N HCl to remove pyridine. The organic layer was dried over anhydrous sodium sulfate and evaporated under reduced pressure to obtain crude compound used next step without further purification (0.200 g), Analytical Data: LCMS: 398 [M+H]$^+$.

Step-2: Synthesis of N-(6-(3-((2,5-dichlorophenyl)sulfonamido)-5-fluorophenyl)quinazolin-2-yl)pivalamide To a stirred solution of N-(3-bromo-5-fluorophenyl)-2,5-dichlorobenzenesulfonamide (500 mg, 1.26 mmol, 1.0 equiv.) and N-(6-(4,4,5,5-tetramethyl-1,3,2-dioxaborolan-2-yl)quinazolin-2-yl)pivalamide (894 mg, 2.51 mmol, 2.0 equiv.) in Dioxane:Water (4:1, 10 mL) was added $K_2CO_3$ (521 mg, 3.77 mmol, 3.0 equiv.). The resulting reaction mixture was purged with nitrogen for 15 minutes followed by the addition of Pd(dppf)$Cl_2$·DCM complex (51 mg, 0.062 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, quench water (2×100 mL) extracted with EtOAc (5×100 mL). The organic layers were combined, dried over anhydrous $Na_2SO_4$ and evaporated under reduced pressure to obtain crude product which was purified by flash chromatography to obtain title product N-(6-(3-((2,5-dichlorophenyl)sulfonamido)-5-fluorophenyl)quinazolin-2-yl)pivalamide (0.300 g), Analytical Data: LCMS: 547 [M+H]$^+$.

Step-3: Synthesis of N-(3-(2-aminoquinazolin-6-yl)-5-fluorophenyl)-2,5-dichlorobenzenesulfonamide To a stirred solution of N-(6-(3-((2,5-dichlorophenyl)sulfonamido)-5-fluorophenyl)quinazolin-2-yl)pivalamide (500 mg, 0.915 mmol) in ethanol (12 mL) was added 2M NaOH (12 mL). Then, the reaction mixture was allowed to stir at 90° C. for 6 h. After completion of reaction, the solvent was evaporated dissolved with EtOAc (2×100 mL) wash with brine (2×50 mL). The organic layers were combined, dried over anhydrous $Na_2SO_4$ and evaporated under reduced pressure to obtain crude which was purified by flash chromatography to obtained title compound N-(3-(2-aminoquinazolin-6-yl)-5-fluorophenyl)-2,5-dichlorobenzenesulfonamide (0.150 g), Analytical Data: LCMS: 463.01 [M+H]$^+$, $^1$H NMR (400 MHz, DMSO-$d_6$) δ ppm 11.24 (br. s., 1H) 9.17 (s, 1H) 8.21 (d, J=2.19 Hz, 1H) 7.96 (s, 1H) 7.85 (d, J=8.77 Hz, 1H) 7.68-7.82 (m, 2H) 7.48 (d, J=8.33 Hz, 1H) 7.22-7.35 (m, 2H) 7.01 (br. s., 2H) 6.88 (d, J=10.09 Hz, 1H).

Compound 15

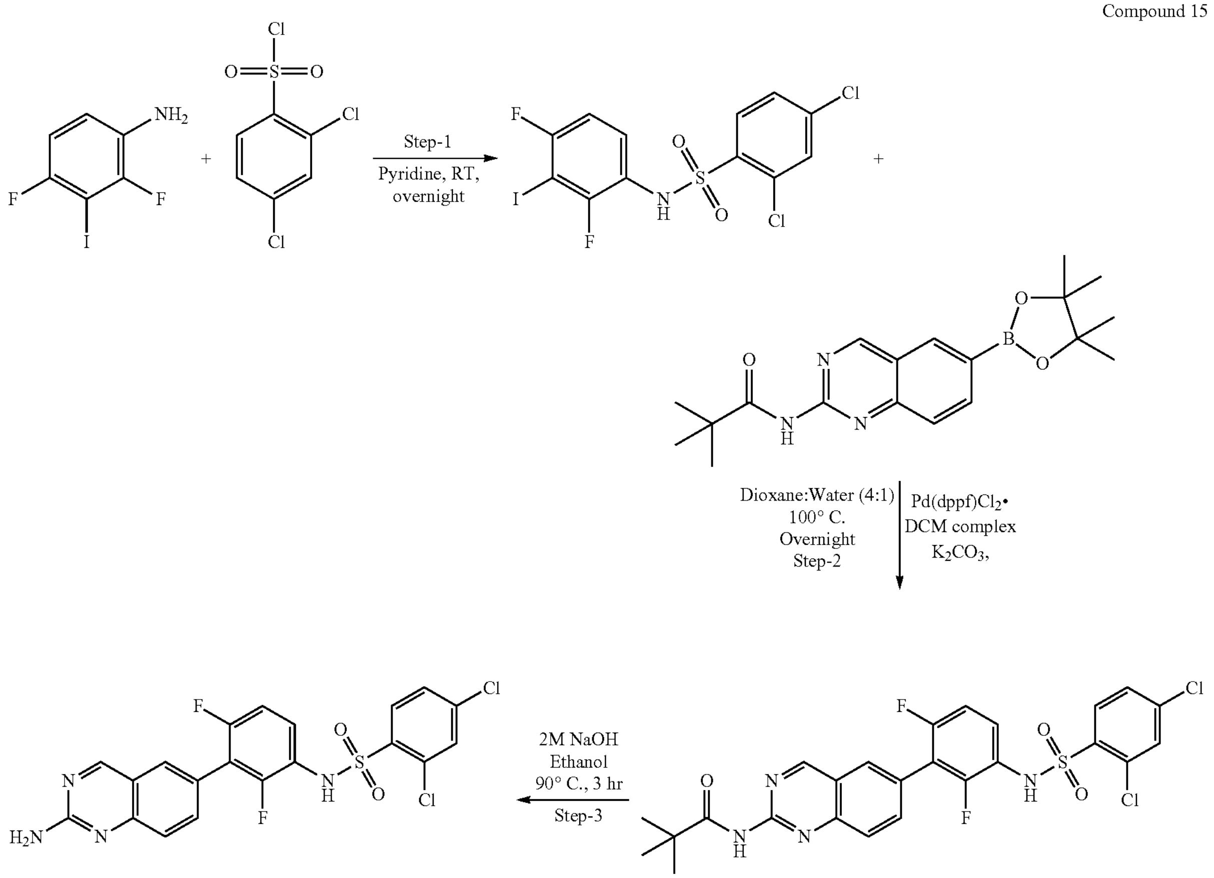

Step-1 Synthesis of 2, 4-dichloro-N-(2,4-difluoro-3-iodophenyl)benzenesulfonamide To a stirred solution of 2,4-difluoro-3-iodoaniline (415.41 mg, 1.6293 mmol. 1.0 equiv.) in pyridine (2 mL) at room temperature was added 2,4-dichlorobenzenesulfonyl chloride (400 mg, 1.6293 mmol, 1.0 equiv.) The resultant reaction mixture was stirred at 90 deg C. for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure to obtain title compound. This material was further purified by flash chromatography to obtain desired compound (1.2 g).

Step-2: Synthesis of N-(6-(3-((2,4-dichlorophenyl)sulfonamido)-2,6-difluorophenyl)quinazolin-2-yl)pivalamide To a stirred solution of 2,4-dichloro-N-(2,4-difluoro-3-iodophenyl)benzenesulfonamide (200 mg, 0.4310 mmol, 1.0 equiv) and N-(6-(4,4,5,5-tetramethyl-1,3,2-dioxaborolan-2-yl)quinazolin-2-yl)pivalamide (306.2 mg, 0.8620 mmol, 2.0 equiv) in dioxane:water (4:1, 5 mL) was added $K_2CO_3$ (178.7 mg, 1.2931 mmol, 3.0 equiv.). The resulting reaction mixture was purged with nitrogen for 15 minutes followed by the addition of $Pd(dppf)Cl_2$·DCM complex (17.59 mg, 0.0215 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure to obtain title compound. This compound is used in further reaction without purification (250 mg), Analytical Data: LCMS: 565.1 $[M+H]^+$.

Step-3: Synthesis of N-(3-(2-aminoquinazolin-6-yl)-2,4-difluorophenyl)-2,4-dichlorobenzenesulfonamide To a stirred solution of N-(6-(3-((2,4-dichlorophenyl)sulfonamido)-2,6-difluorophenyl)quinazolin-2-yl)pivalamide (250 mg, 0.4432 mmol, 1.0 equiv) in ethanol (6 mL) at room temperature was added 2M NaOH (6 mL). Then, the reaction mixture was allowed to stir at 90° C. for 4 hr. Progress of the reaction was analyzed by TLC and LCMS. After completion of reaction, reaction mixture was concentrated under reduced pressure and was extracted with EtOAc (2×30 mL). The organic layers were combined, dried over anhydrous $Na_2SO_4$ and evaporated under reduced pressure and further purified under flash chromatography to obtain N-(3-(2-aminoquinazolin-6-yl)-2,4-difluorophenyl)-2,4-dichlorobenzenesulfonamide (49 mg), Analytical Data: LCMS: 481.0 $[M+H]^+$, $^1H$ NMR (400 MHz, DMSO-$d_6$) δ 10.58 (s, 1H), 9.15 (s, 1H), 7.93 (d, J=2.19 Hz, 1H), 7.89 (d, J=8.33 Hz, 1H), 7.76 (s, 1H), 7.52-7.64 (m, 2H), 7.48 (d, J=8.77 Hz, 1H), 7.24-7.33 (m, 1H), 7.16-7.24 (m, 1H), 7.03 (s, 2H).

Compound 16

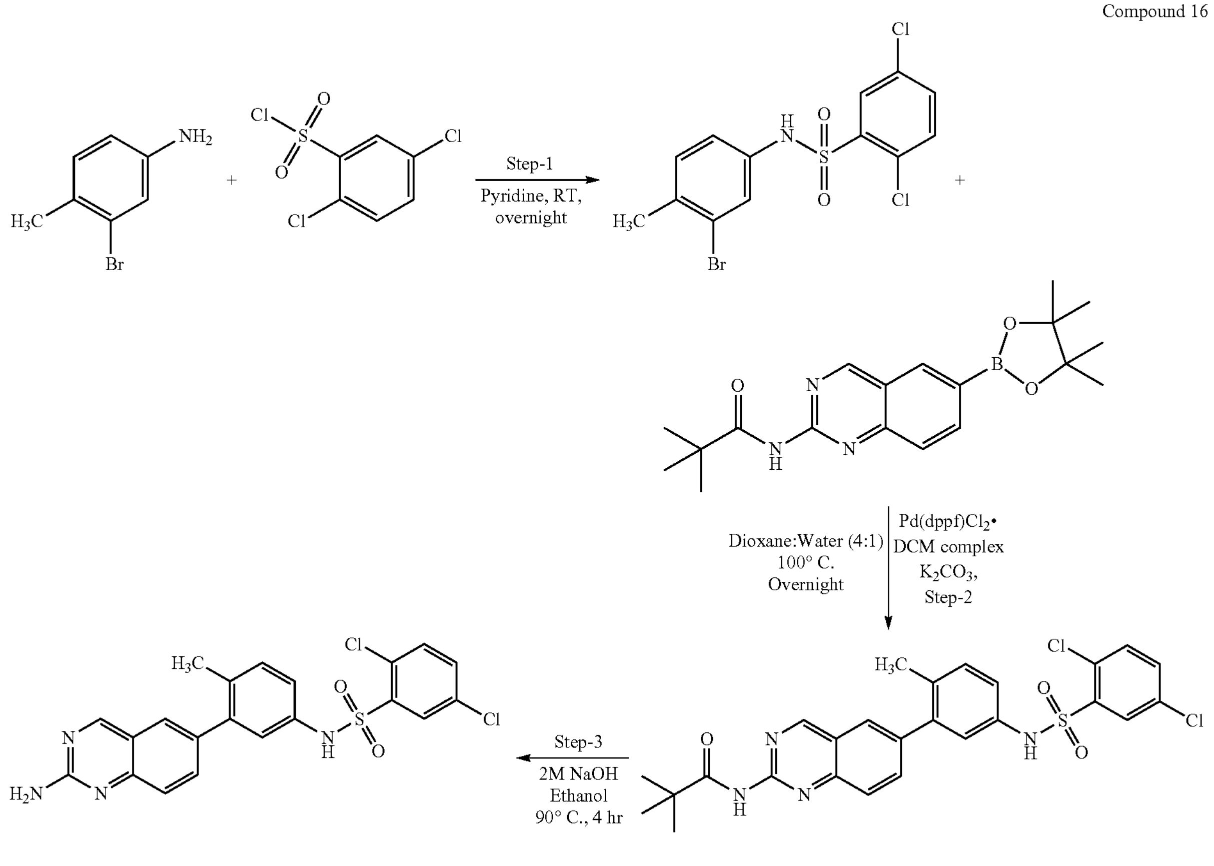

Step-1 Synthesis of N-(3-bromo-4-methylphenyl)-2,5-dichlorobenzenesulfonamide

To a stirred solution of 3-bromo-4-methylaniline (379.02 mg, 2.0366 mmol. 1.0 equiv.) in pyridine (3 mL) at room temperature was added 2,5-dichlorobenzenesulfonyl chloride (500 mg, 2.0366 mmol. 1.0 equiv.). The resultant reaction mixture was stirred at 90 deg C. for 3 h. The progress of reaction was monitored through TLC. After completion of the reaction, the solvent was concentrated under reduced pressure to obtain crude residue which was treated with 1N HCl to remove pyridine. The product was extracted with EtOAc, organic layer dried over sodium sulphate and concentrated under vacuum to obtain desired product N-(3-bromo-4-methylphenyl)-2,5-dichlorobenzenesulfonamide (600 mg).

Step-2: Synthesis of N-(6-(5-((2,5-dichlorophenyl)sulfonamido)-2-methylphenyl)quinazolin-2-yl)pivalamide To a stirred solution of N-(3-bromo-4-methylphenyl)-2,5-dichlorobenzenesulfonamide (500 mg, 1.2725 mmol, 1.0 equiv) and N-(6-(4,4,5,5-tetramethyl-1,3,2-dioxaborolan-2-yl)quinazolin-2-yl)pivalamide (904.17 mg, 2.5451 mmol, 2.0 equiv) in dioxane:water (6:2, 8 mL) was added $K_2CO_3$ (527.6 mg, 3.8177 mmol, 3.0 equiv.). The resulting reaction mixture was purged with nitrogen for 15 minutes followed by the addition of Pd(dppf)$Cl_2$·DCM complex (51.9 mg, 0.0636 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure and further purified using flash chromatography to obtain desired compound N-(6-(5-((2,5-dichlorophenyl)sulfonamido)-2-methylphenyl)quinazolin-2-yl)pivalamide (400 mg), LCMS: 543.1[M+H]$^+$.

Step-3: Synthesis of N-(3-(2-aminoquinazolin-6-yl)-4-methylphenyl)-2,5-dichlorobenzenesulfonamide To a stirred solution of N-(6-(5-((2,5-dichlorophenyl)sulfonamido)-2-methylphenyl)quinazolin-2-yl)pivalamide (230 mg, 0.4242 mmol, 1.0 equiv) in ethanol (6 mL) at room temperature was added 2M NaOH (5 mL). Then, the reaction mixture was allowed to stir at 90° C. for 4 h. After completion of reaction, the reaction mixture was concentrated under reduced pressure to obtain crude product extracted with EtOAc (50 mL×2), dried over sodium sulphate, concentrated under reduced pressure and further purified by using flash chromatography to obtain N-(3-(2-aminoquinazolin-6-yl)-4-methylphenyl)-2,5-dichlorobenzenesulfonamide (120 mg), Analytical Data: LCMS: 459.0 [M+H]$^+$, $^1$H NMR (400 MHz, DMSO-$d_6$) δ10.76 (s, 1H), 9.13 (s, 1H), 8.01 (d, J=2.63 Hz, 1H), 7.75-7.80 (m, 1H), 7.71 (d, J=8.77 Hz, 1H), 7.59 (d, J=1.75 Hz, 1H), 7.53 (dd, J=1.75, 8.77 Hz, 1H), 7.45 (d, J=8.77 Hz, 1H), 7.20 (d, J=8.33 Hz, 1H), 7.03 (dd, J=2.19, 8.33 Hz, 1H), 6.99 (d, J=2.19 Hz, 1H), 6.92 (s, 2H), 2.14 (s, 3H).

Compound 17

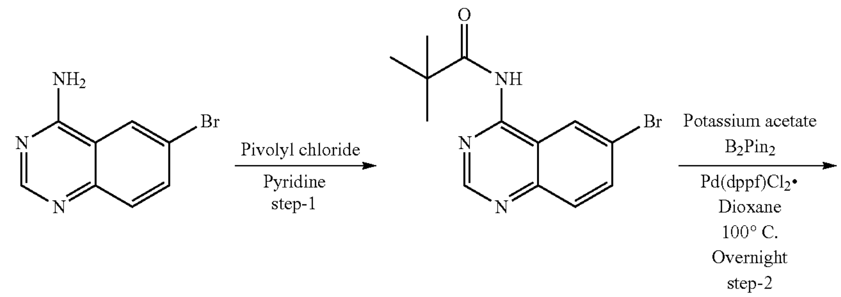

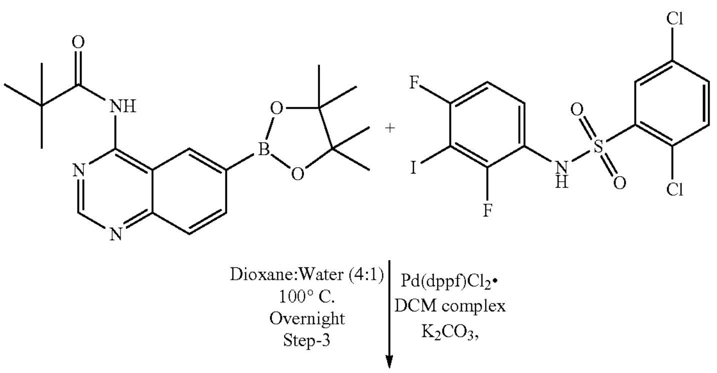

-continued

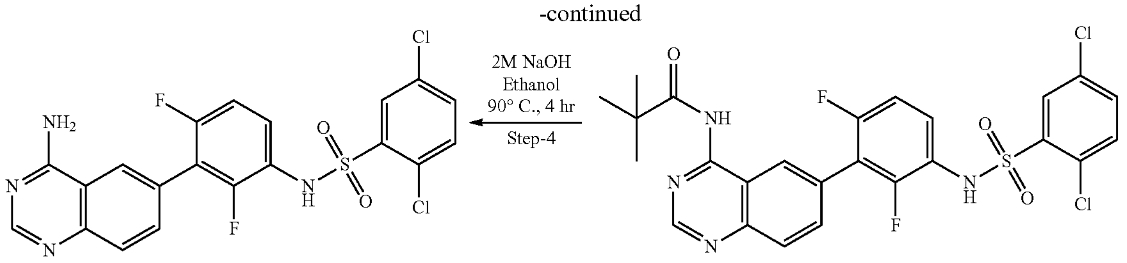

Step-1: Synthesis of N-(6-bromoquinazolin-4-yl)pivalamide

To a stirred solution of 6-bromoquinazolin-4-amine (1 g, 4.4642 mmol, 1.0 equiv.) in pyridine (4 mL) at room temperature was added pivolyl chloride (1.6 mL, 13.3928 mmol. 1.0 equiv.) The resultant reaction mixture was stirred at 90 deg C. for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure and further purified by flash chromatography to obtain the desired product (650 mg).

Step-2: Synthesis of N-(6-(4,4,5,5-tetramethyl-1,3,2-dioxaborolan-2-yl)quinazolin-4-yl)pivalamide To a stirred solution of N-(6-bromoquinazolin-4-yl)pivalamide (500 mg, 1.6286 mmol, 1.0 equiv.) in dioxane (7 mL) was added potassium acetate (478.8 mg, 4.8859 mmol, 3.0 equiv.) and $B_2Pin_2$ (620.2 mg, 2.4429 mmol, 1.5 equiv.) and was purged at room temperature under nitrogen atmosphere for 15 min. After 15 min, Pd(dppf)$Cl_2$ (59.5 mg, 0.0814 mmol, 0.05 equiv.) was added to the reaction mixture and was again purged for 5 min, reaction mixture was then heated at 100° C. for overnight. Progress of the reaction was analyzed by TLC and $^1$H NMR. After the completion of reaction, reaction mixture was passed through a celite bed, then extracted with EtOAc (70 mL×2), dried over sodium sulphate and concentrated under reduced pressure to obtain the desired product N-(6-(4,4,5,5-tetramethyl-1,3,2-dioxaborolan-2-yl)quinazolin-4-yl)pivalamide (800 mg) used next step without any purification.

Step-3: Synthesis of N-(6-(3-(2,5-dichlorophenylsulfonamido)-2,6-difluorophenyl)quinazolin-4-yl) pivalamide To a stirred solution of 2,5-dichloro-N-(2,4-difluoro-3-iodophenyl)benzenesulfonamide (522.4 mg, 1.1258 mmol, 1.0 equiv) and N-(6-(4,4,5,5-tetramethyl-1,3,2-dioxaborolan-2-yl)quinazolin-4-yl)pivalamide (800 mg, 2.2519 mmol, 2.0 equiv) in dioxane:water (6:2, 8 mL) was added $K_2CO_3$ (466.7 mg, 3.3775 mmol, 3.0 equiv.). The resulting reaction mixture was purged with nitrogen for 15 minutes followed by the addition of Pd(dppf)$Cl_2$·DCM complex (45.9 mg, 0.0562 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. This compound was used in further reaction without purification (600 mg).

Step-4: Synthesis of N-(3-(4-aminoquinazolin-6-yl)-2,4-difluorophenyl)-2,5-dichlorobenzenesulfonamide To a stirred solution of N-(6-(3-(2,5-dichlorophenylsulfonamido)-2,6-difluorophenyl)quinazolin-4-yl)pivalamide (500 mg, 0.8864 mmol, 1.0 equiv) in ethanol (7 mL) was added 2M NaOH (6 mL). Then, the reaction mixture was allowed to stir at 90° C. overnight. Progress of the reaction was analyzed by TLC and LCMS. After completion of reaction, reaction mixture was concentrated under reduced pressure to obtain crude diluted with water and extracted with EtOAc (2×50 mL). The organic layers were combined, dried over anhydrous $Na_2SO_4$ and evaporated under reduced pressure to obtain crude which was purified by flash chromatography (50% EtOAc:Hexanes) to obtain as title compound N-(3-(4-aminoquinazolin-6-yl)-2,4-difluorophenyl)-2,5-dichlorobenzenesulfonamide, Analytical Data: LCMS: 481.0 [M+H]$^+$, $^1$H NMR (400 MHz, DMSO-$d_6$) δ 10.84 (br. s., 1H), 8.44 (s, 1H), 8.31 (br. s., 1H), 7.89 (br. s., 3H), 7.75 (br. s., 3H), 7.66 (d, J=8.33 Hz, 1H), 7.11-7.40 (m, 2H).

Compound 18

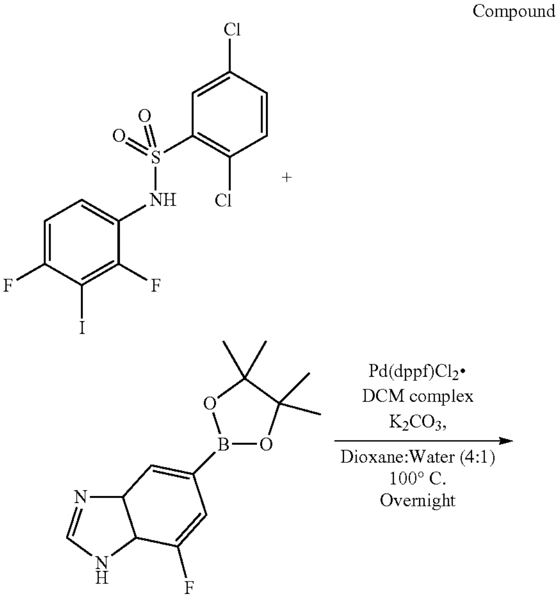

-continued

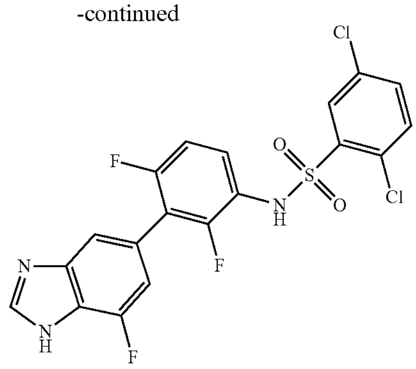

Step-1: Synthesis of 2,5-dichloro-N-(2,4-difluoro-3-(7-fluoro-1H-benzo[d]imidazol-5-yl)phenyl)benzenesulfonamide To a stirred solution of 2,5-dichloro-N-(2,4-difluoro-3-iodophenyl)benzenesulfonamide (500 mg, 1.07 mmol, 1.0 equiv) and 7-fluoro-5-(4,4,5,5-tetramethyl-1,3,2-dioxaborolan-2-yl)-3a,7a-dihydro-1H-benzo[d]imidazole (395 mg, 1.61 mmol, 1.5 equiv) in Dioxane:Water (4:1, 10 mL) was added $K_2CO_3$ (440 mg, 3.23 mmol, 3.0 equiv.). The resulting reaction mixture was purged with nitrogen for 15 minutes followed by the addition of Pd(dppf)$Cl_2$·DCM complex (88 mg, 0.107 mmol, 0.1 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (5×100 mL). The organic layers were combined, dried over anhydrous $Na_2SO_4$ and evaporated under reduced pressure which was purified by reverse phase chromatography to obtain title product 2,5-dichloro-N-(2,4-difluoro-3-(7-fluoro-1H-benzo[d]imidazol-5-yl)phenyl) benzenesulfonamide (200 mg). Analytical Data: LCMS: 472 $[M+H]^+$, $^1H$ NMR (400 MHz, DMSO-$d_6$) δ ppm 12.92 (br. s., 1H) 10.66 (s, 1H) 8.37 (s, 1H) 7.86 (d, J=2.19 Hz, 1H) 7.72-7.80 (m, 2H) 7.29-7.37 (m, 2H) 7.18-7.24 (m, 1H) 6.96 (d, J=10.96 Hz, 1H).

Compound 19

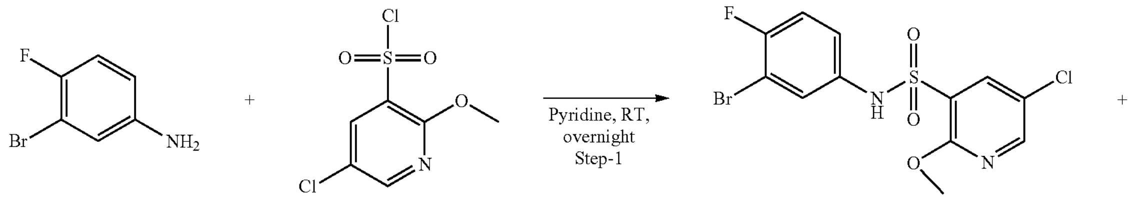

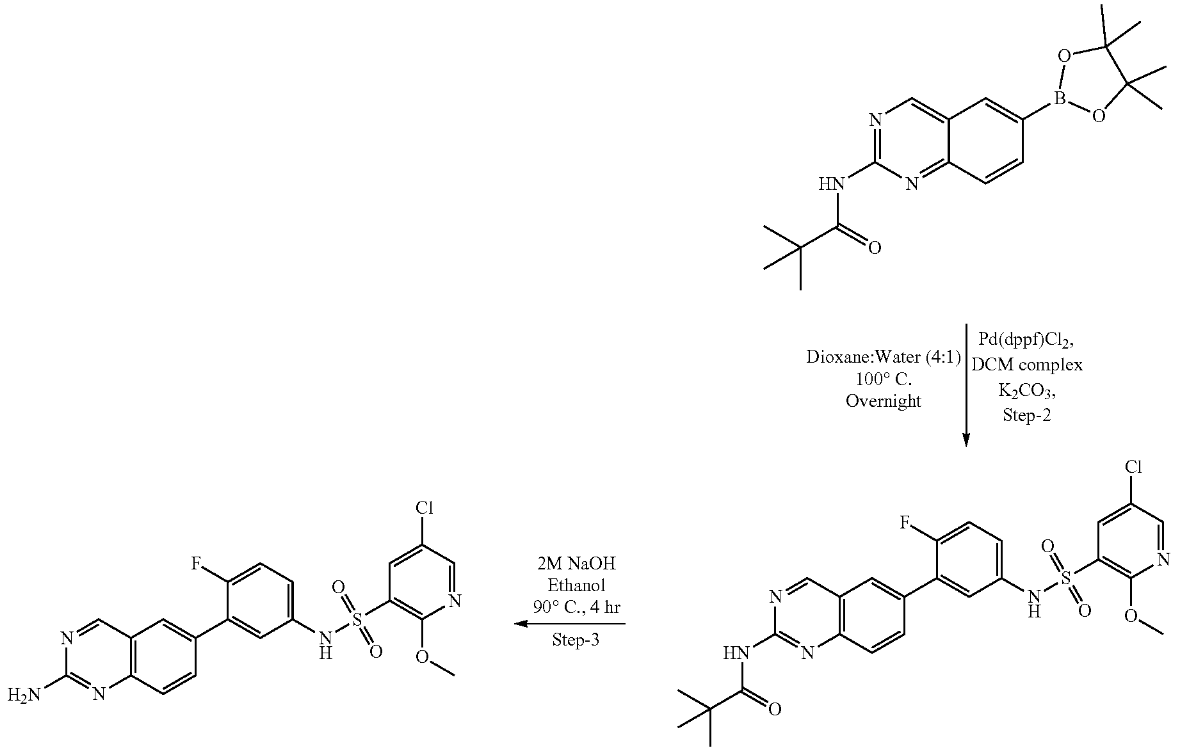

Step-1: Synthesis of N-(3-bromo-4-fluorophenyl)-5-chloro-2-methoxypyridine-3-sulfonamide To a stirred solution of 3-bromo-4-fluoroaniline (500 mg, 2.6 mmol. 1.0 equiv.) in pyridine (3.0 mL) at room temperature was added 5-chloro-2-methoxypyridine-3-sulfonyl chloride (634 mg, 2.6 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc. The organic layer was dried over anhydrous sodium sulfate and evaporated under reduced pressure to obtain title compound. This material was used in the next reaction without further purification (200 mg), Analytical Data: LCMS: 395 $[M+H]^+$.

Step-2: Synthesis of N-(6-(5-((5-chloro-2-methoxypyridine)-3-sulfonamido)-2-fluorophenyl)quinazolin-2-yl)pivalamide To the stirred solution of N-(3-bromo-4-fluorophenyl)-5-chloro-2-methoxypyridine-3-sulfonamide (200 mg, 0.508 mmol, 1.0 equiv) and N-(6-(4,4,5,5-tetramethyl-1,3,2-dioxaborolan-2-yl)quinazolin-2-yl)pivalamide (360 mg, 1.0 mmol, 2.0 equiv) in Dioxane:Water (8:2, 10 mL) was added $K_2CO_3$ (207 mg, 1.5 mmol, 3.0 equiv.). The resulting reaction mixture was purged with nitrogen for 15 minutes followed by the addition of $Pd(dppf)Cl_2 \cdot DCM$ complex (20 mg, 0.025 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure which was purified by flash chromatography to obtain title product. (120 mg) Analytical Data: LCMS: 544.1 $[M+H]^+$.

Step-3: Synthesis of N-(3-(2-aminoquinazolin-6-yl)-4-fluorophenyl)-5-chloro-2-methoxypyridine-3-sulfonamide To a stirred solution of N-(6-(5-((5-chloro-2-methoxypyridine)-3-sulfonamido)-2-fluorophenyl)quinazolin-2-yl) pivalamide (120 mg, 0.219 mmol, 1.0 equiv) in ethanol (6 mL) was added 2M NaOH (4 mL). Then, the reaction mixture was allowed to stir at 90 degree Celsius for 4 hr. After completion of reaction, the solvent was evaporated under vacuum to obtain crude was added water extracted with EtOAc (2×50 mL). The organic layers were combined, dried over anhydrous $Na_2SO_4$ and evaporated under reduced pressure. The crude product was then purified by reverse phase silica gel chromatography to obtain as title compound N-(3-(2-aminoquinazolin-6-yl)-2,6-difluorophenyl)-2,5-dichlorobenzenesulfonamide (9 mg), Analytical Data: LCMS: 460 $[M+H]^+$, NMR: $^1H$ NMR (400 MHz, DMSO-$d_6$) δ 10.58 (br. s., 1H), 9.18 (s, 1H), 8.48 (d, J=2.63 Hz, 1H), 8.22 (d, J=2.63 Hz, 1H), 7.84 (s, 1H), 7.72 (d, J=9.21 Hz, 1H), 7.50 (d, J=8.77 Hz, 1H), 7.17-7.38 (m, 2H), 7.09 (d, J=7.89 Hz, 1H), 7.00 (s, 2H), 3.97 (s, 3H).

Compound 20

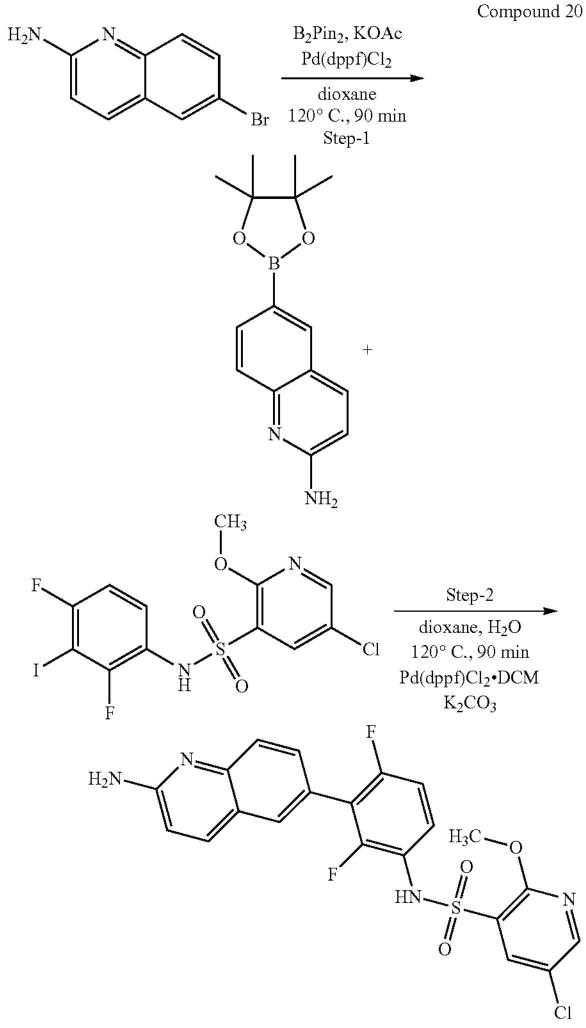

Step-1 Synthesis of 6-(4,4,5,5-tetramethyl-1,3,2-dioxaborolan-2-yl)quinolin-2-amine To a stirred solution of 6-bromoquinolin-2-amine (200 mg, 0.8964 mmol. 1.0 equiv.) in dioxane (3 mL) was added $B_2Pin_2$ (341.4 mg, 1.3446 mmol. 1.5 equiv.) and potassium acetate (263.5 mg, 2.6893 mmol. 3.0 equiv.) and reaction mixture was purged with nitrogen gas at room temperature for 10 min. After 10 min $Pd(dppf)Cl_2$ (32.7 mg, 0.0448 mmol. 0.05 equiv.) was added to RM and was again purged under nitrogen atmosphere for 5 min. The resultant reaction mixture was heated at 120° C. in a microwave for 90 min. The progress of reaction was monitored through TLC and LCMS. After completion of the reaction, RM was extracted with 2×times EtOAc (50 mL). The organic layer was dried over anhydrous sodium sulfate and evaporated under reduced pressure to obtain title compound (400 mg).

Step-2: Synthesis of N-(3-(2-aminoquinolin-6-yl)-2,4-difluorophenyl)-5-chloro-2-methoxypyridine-3-sulfonamide To a stirred solution of 5-chloro-N-(2,4-difluoro-3-iodophenyl)-2-methoxypyridine-3-sulfonamide (330 mg, 0.7164 mmol, 1.0 equiv) and 6-(4,4,5,5-tetramethyl-1,3,2-dioxaborolan-2-yl)quinolin-2-amine (387 mg, 1.4328 mmol, 2.0 equiv) in dioxane:water (4:1, 5 mL) was added $K_2CO_3$ (297 mg, 2.1492 mmol, 3.0 equiv.). The resulting reaction mixture was purged with nitrogen for 15 minutes followed by the addition of Pd(dppf)$Cl_2$ DCM complex (29.25 mg, 0.0358 mmol, 0.05 equiv.). The reaction mixture was again purged with nitrogen for 5 minutes. The reaction mixture was heated to 120° C. in a microwave for 90 min. The progress of reaction was monitored through TLC and LCMS. After completion of reaction, water was added to the reaction mixture, extracted with EtOAc (2×50 mL). The organic layers were combined, dried over anhydrous $Na_2SO_4$, evaporated under reduced pressure and purified using flash chromatography to obtain desired compound. The compound was then triturated using pentane (3 mL) to obtain desired compound N-(3-(2-aminoquinolin-6-yl)-2,4-difluorophenyl)-5-chloro-2-methoxypyridine-3-sulfonamide (47 mg). Analytical Data: LCMS: 477.3[M+H]$^+$, $^1$H NMR (400 MHz, DMSO-$d_6$) δ 11.96 (br. s., 1H), 10.42 (br. s., 1H), 8.51 (d, J=2.19 Hz, 1H), 8.06 (d, J=2.19 Hz, 1H), 7.92 (d, J=8.33 Hz, 1H), 7.59 (br. s., 1H), 7.51 (br. s., 1H), 7.26-7.41 (m, 2H), 7.19 (t, J=9.21 Hz, 1H), 6.81 (br. s., 1H), 6.64 (br. s., 1H), 3.91 (s, 3H).

Compound 44

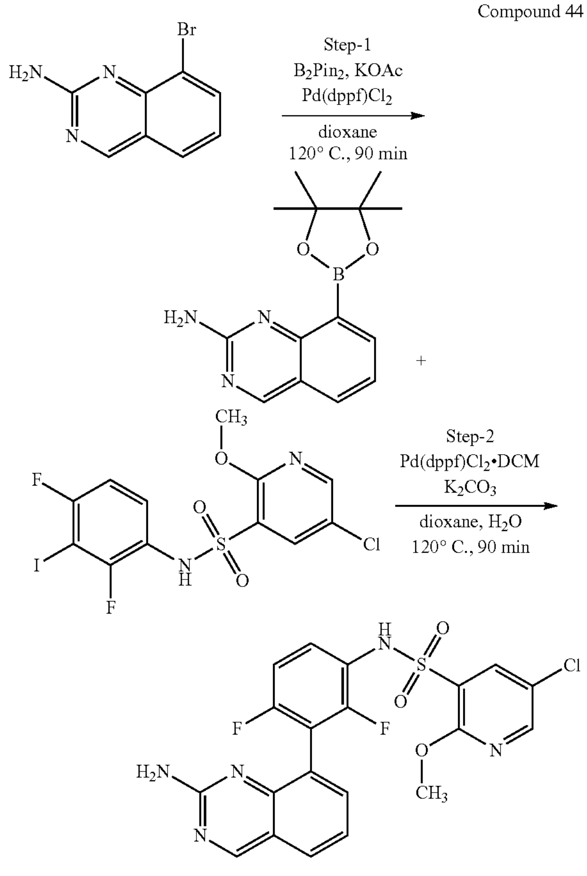

Step-1 Synthesis of 8-(4,4,5,5-tetramethyl-1,3,2-dioxaborolan-2-yl)quinazolin-2-amine To a stirred solution of 8-bromoquinazolin-2-amine (200 mg, 0.8926 mmol. 1.0 equiv.) in dioxane (4 mL) was added $B_2Pin_2$ (339.9 mg, 1.3389 mmol. 1.5 equiv.) and potassium acetate (262.4 mg, 2.6778 mmol. 3.0 equiv.) and reaction mixture was purged with nitrogen gas at room temperature for 10 min. After 10 min Pd(dppf)$Cl_2$ (32.6 mg, 0.0446 mmol. 0.05 equiv.) was added to RM and was again purged under nitrogen atmosphere for 5 min. The resultant reaction mixture was heated at 120° C. in a microwave for 90 min. The progress of reaction was monitored through TLC and LCMS. After completion of the reaction, RM was extracted with EtOAc (50 mL×2). The organic layer was dried over anhydrous sodium sulfate and evaporated under reduced pressure to obtain title compound (420 mg).

Step-2: Synthesis of N-(3-(2-aminoquinazolin-8-yl)-2,4-difluorophenyl)-5-chloro-2-methoxypyridine-3-sulfonamide To a stirred solution of 5-chloro-N-(2,4-difluoro-3-iodophenyl)-2-methoxypyridine-3-sulfonamide (330 mg, 0.7164 mmol, 1.0 equiv) and 8-(4,4,5,5-tetramethyl-1,3,2-dioxaborolan-2-yl)quinazolin-2-amine (388.4 mg, 1.4328 mmol, 2.0 equiv) in dioxane:water (4:1, 5 mL) was added $K_2CO_3$ (297 mg, 2.1492 mmol, 3.0 equiv.). The resulting reaction mixture was purged with nitrogen for 15 minutes followed by the addition of Pd(dppf)$Cl_2$ DCM complex (29.2 mg, 0.0358 mmol, 0.05 equiv.). The reaction mixture was again purged with nitrogen for 5 minutes. The reaction mixture was heated to 120° C. in a microwave for 90 min. The progress of reaction was monitored through TLC and LCMS. After completion of reaction, water was added to the reaction mixture, extracted with EtOAc (2×50 mL). The organic layers were combined, dried over anhydrous $Na_2SO_4$, evaporated under reduced pressure and purified using flash chromatography to obtain desired compound which was triturated with pentane (3 mL) and diethyl ether (2 mL) to obtain desired compound N-(3-(2-aminoquinazolin-8-yl)-2,4-difluorophenyl)-5-chloro-2-methoxypyridine-3-sulfonamide (13 mg). Analytical Data: LCMS: 478.3 [M+H]$^+$, $^1$H NMR (400 MHz, DMSO-$d_6$) δ 10.36 (s, 1H), 9.17 (s, 1H), 8.48 (d, J=2.63 Hz, 1H), 8.10 (d, J=2.63 Hz, 1H), 7.90 (dd, J=1.32, 7.89 Hz, 1H), 7.51 (d, J=5.70 Hz, 1H), 7.25-7.39 (m, 2H), 7.15 (t, J=8.11 Hz, 1H), 6.82 (br. s., 2H), 3.90 (s, 3H).

Compound 45 and 114

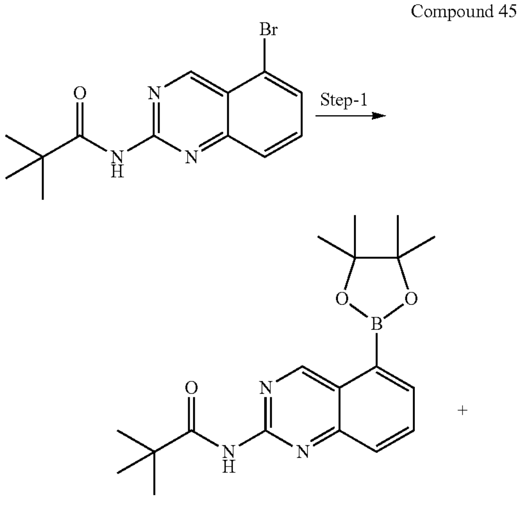

-continued

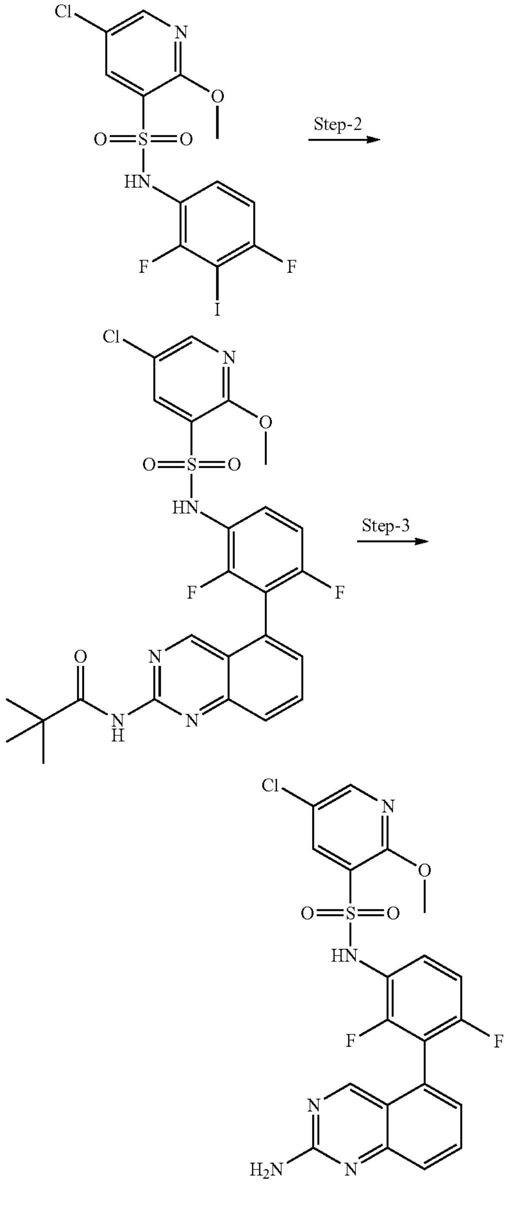

Step-1: Synthesis of N-(5-(4,4,5,5-tetramethyl-1,3,2-dioxaborolan-2-yl)quinazolin-2-yl)pivalamide To a stirred solution of N-(5-bromoquinazolin-2-yl)pivalamide (500 mg, 1.6224 mmol. 1.0 equiv.) in dioxane (6 mL) was added $B_2Pin_2$ (617.9 mg, 2.4336 mmol. 1.5 equiv.) and potassium acetate (476.9 mg, 4.8672 mmol. 3.0 equiv.) and reaction mixture was purged with nitrogen gas at room temperature for 10 min. After 10 min Pd(dppf)$Cl_2$ (59.2 mg, 0.0811 mmol. 0.05 equiv.) was added to RM and was again purged under nitrogen atmosphere for 5 min. The resultant reaction mixture was heated at 100° C. for overnight. The progress of reaction was monitored through TLC and LCMS. After completion of the reaction, RM was extracted with EtOAc (100 mL×2). The organic layers were dried over anhydrous sodium sulfate and evaporated under reduced pressure to obtain title compound (960 mg).

Step-2: Synthesis of N-(5-(3-((5-chloro-2-methoxypyridine)-3-sulfonamido)-2,6-difluorophenyl)quinazolin-2-yl)pivalamide To a stirred solution of 5-chloro-N-(2,4-difluoro-3-iodophenyl)-2-methoxypyridine-3-sulfonamide (250 mg, 0.5439 mmol, 1.0 equiv) and N-(5-(4,4,5,5-tetramethyl-1,3,2-dioxaborolan-2-yl)quinazolin-2-yl)pivalamide (386.4 mg, 1.0878 mmol, 2.0 equiv) in dioxane:water (4:1, 5 mL) was added $K_2CO_3$ (225.5 mg, 1.6317 mmol, 3.0 equiv.). The resulting reaction mixture was purged with nitrogen for 15 minutes followed by the addition of Pd(dppf)$Cl_2$ DCM complex (22.2 mg, 0.0271 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×70 mL). The organic layers were combined, dried over anhydrous $Na_2SO_4$ and evaporated under reduced pressure to obtain title compound. This compound is used in next step without purification (400 mg). Analytical Data: LCMS: 562.1 $[M+H]^+$ Step-3: Synthesis of N-(3-(2-aminoquinazolin-5-yl)-2,4-difluorophenyl)-5-chloro-2-methoxypyridine-3-sulfonamide To a stirred solution of N-(5-(3-((5-chloro-2-methoxypyridine)-3-sulfonamido)-2,6-difluorophenyl)quinazolin-2-yl)pivalamide (400 mg, 0.7677 mmol, 1.0 equiv) in ethanol (6 mL) at room temperature was added 2M NaOH (4 mL). Then, the reaction mixture was allowed to stir at 90° C. overnight. Progress of the reaction was analyzed by TLC and LCMS. After completion of reaction, RM was concentrated under reduced pressure and was extracted with EtOAc (2×30 mL). The organic layers were combined, dried over anhydrous $Na_2SO_4$ and evaporated under reduced and further purified under flash chromatography to obtain N-(3-(2-aminoquinazolin-5-yl)-2,4-difluorophenyl)-5-chloro-2-methoxypyridine-3-sulfonamide (6 mg), Analytical Data: LCMS: 481.3 $[M+H]^+$, $^1H$ NMR (400 MHz, DMSO-$d_6$) δ 10.46 (s, 1H), 8.52 (d, J=2.63 Hz, 1H), 8.32 (br. s., 1H), 8.06 (d, J=2.63 Hz, 1H), 7.76 (dd, J=7.24, 8.55 Hz, 1H), 7.40-7.57 (m, 2H), 7.29 (t, J=8.77 Hz, 1H), 7.10 (d, J=7.02 Hz, 1H), 7.02 (s, 2H), 3.90 (s, 3H).

Compound 46

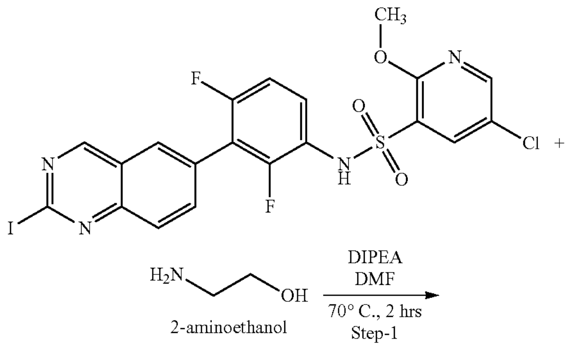

-continued

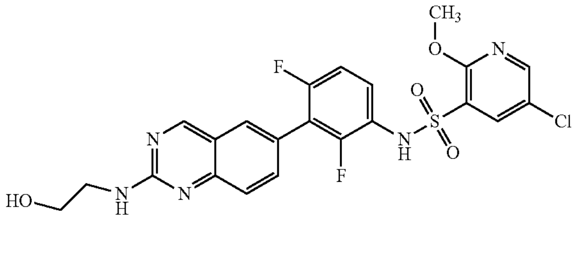

Step-1: Synthesis of 5-chloro-N-(2,4-difluoro-3-(2-((2-hydroxyethyl)amino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (60 mg, 0.10 mmol, 1.0 equiv.) in DMF (0.3 mL) was added 2-aminoethanol (7 mg, 0.12 mmol, 1.2 equiv.), DIPEA (40 mg, 0.31 mmol, 3.0 equiv.). The reaction was allowed to stir at 70° C. for 2 h. Progress of reaction was monitored by TLC. After completion of reaction, ethanol was evaporated and then work up of reaction had been carried out using ethyl acetate (2×50 ml) and water (20 ml). The separated organic layer was dried over $Na_2SO_4$, filtered and concentrated. The crude product was purified by reverse phase HPLC to obtain 5-chloro-N-(2,4-difluoro-3-(2-((2-hydroxyethyl)amino)quinazolin-6-yl)phenyl)-2-methoxypyridine-3-sulfonamide (11 mg), Analytical Data: LCMS: 522.06 $[M+H]^+$. $^1H$ NMR (400 MHz, DMSO-$d_6$) δ ppm 3.43-3.53 (m, 2H) 3.59 (br. s., 2H) 3.88 (s, 3H) 4.75 (br. s., 1H) 7.15 (d, J=8.33 Hz, 1H) 7.28 (d, J=6.14 Hz, 1H) 7.44 (br. s., 1H) 7.53 (br. s., 1H) 7.60 (d, J=8.33 Hz, 1H) 7.79 (br. s., 1H) 8.05 (br. s., 1H) 8.44 (br. s., 1H) 9.14 (br. s., 1H) 10.42 (br. s., 1H).

Compound 47

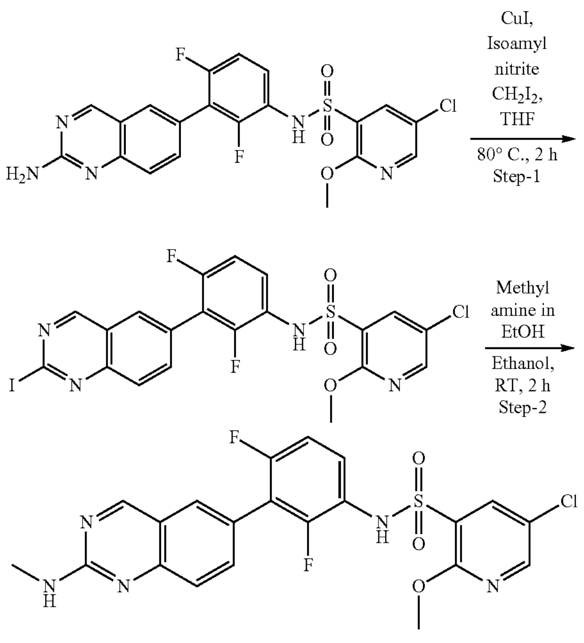

Step-1: Synthesis of 5-chloro-N-(2,4-difluoro-3-(2-iodoquinazolin-6-yl)phenyl)-2-methoxypyridine-3-sulfonamide To a stirred solution N-(3-(2-aminoquinazolin-6-yl)-2,4-difluorophenyl)-5-chloro-2-methoxypyridine-3-sulfonamide (100 mg, 0.209 mmol, 1.0 equi.) was added CuI (55.8 mg, 0.293 mmol, 1.4 equi.) and purged with N2 gas was added Isoamyl nitrite (39 mg, 0.334 mmol, 1.6 equiv.), $CH_2I_2$ (335 mg, 1.25 mmol, 6.0 equiv.) to reaction mixture. After addition, reaction mixture was allowed to stir at 80° C. After completion of reaction, was added water (20 ml) and extracted with ethyl acetate (2×50 ml). The separated organic layer was dried over $Na_2SO_4$, filtered and concentrated under vacuum to obtain desired product (190 mg)., LCMS: $589[M+H]^+$

Step-2: Synthesis of 5-chloro-N-(2,4-difluoro-3-(2-(methylamino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (120 mg, 0.415 mmol, 1.0 equiv.) was added methyl amine solution in ethanol (33% by wt, 1 mL) and allowed to stir at RT 2 hr. Progress of reaction was monitored by TLC. After completion of reaction, ethanol evaporated under vacuum to obtain crude was added water (20 ml) and extracted with ethyl acetate (2×50 ml). The separated organic layer was dried over Na2SO4, filtered and concentrated under vacuum to obtain crude product which was purified by reverse phase silica gel chromatography (6 mg), Analytical Data: LCMS: 492 $[M+H]^+$, $^1H$ NMR (400 MHz, DMSO-$d_6$) δ 9.13 (br. s., 1H), 8.17 (d, J=2.63 Hz, 1H), 7.97 (d, J=2.63 Hz, 1H), 7.80 (br. s., 1H), 7.64 (d, J=9.21 Hz, 1H), 7.54 (br. s., 1H), 7.41 (br. s., 1H), 7.11 (d, J=5.26 Hz, 1H), 6.72-6.86 (m, 2H), 3.78 (s, 3H), 2.91 (d, J=4.82 Hz, 3H).

Compound 51

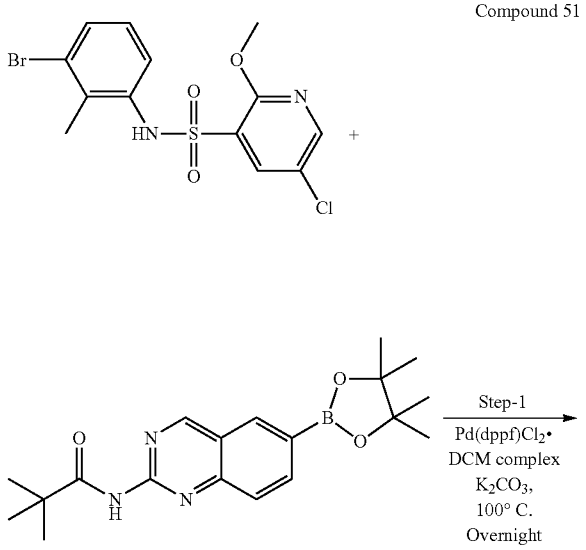

-continued

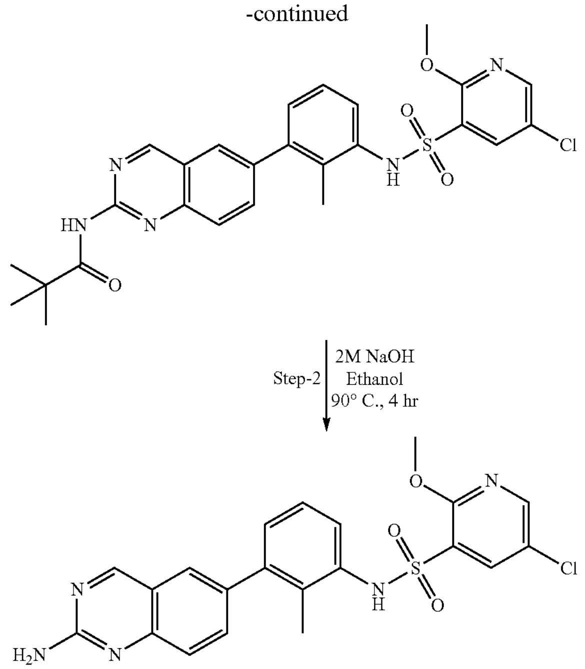

Step-1: Synthesis of N-(6-(3-((5-chloro-2-methoxypyridine)-3-sulfonamido)-2-methylphenyl)quinazolin-2-yl)pivalamide To the stirred solution of N-(3-bromo-2-methylphenyl)-5-chloro-2-methoxypyridine-3-sulfonamide (200 mg, 0.512 mmol, 1.0 equiv) and N-(6-(4,4,5,5-tetramethyl-1,3,2-dioxaborolan-2-yl)quinazolin-2-yl)pivalamide (218 mg, 0.615 mmol, 1.2 equiv) in Dioxane:Water (4:1, 5 mL) was added $K_2CO_3$ (212 mg, 1.536 mmol, 3.0 equiv.). The resulting reaction mixture was purged with nitrogen for 15 minutes followed by the addition of $Pd(dppf)Cl_2 \cdot DCM$ complex (21 mg, 0.025 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure. The crude was used in next step without purification (400 mg), LCMS: 544[M+H]$^+$

Step 2: Synthesis of N-(3-(2-aminoquinazolin-6-yl)-2-methylphenyl)-5-chloro-2-methoxypyridine-3-sulfonamide To a stirred solution of N-(6-(3-((5-chloro-2-methoxypyridine)-3-sulfonamido)-2-methylphenyl)quinazolin-2-yl)pivalamide (400 mg, 0.74 mmol, 1.0 equiv) in ethanol (6 mL) was added 2M NaOH (4 mL). Then, the reaction mixture was allowed to stir at 90° C. for 4 h. After completion of reaction, the solvent was evaporated and water was added to the reaction mixture, extracted with EtOAc (2×100 mL). The organic layers were combined, dried over anhydrous $Na_2SO_4$ and evaporated under reduced which was purified by reverse phase chromatography to obtain N-(3-(2-aminoquinazolin-6-yl)-2-methylphenyl)-5-chloro-2-methoxypyridine-3-sulfonamide as title compound (30 mg). Analytical Data: LCMS: 456[M+H]$^+$, $^1$H NMR (400 MHz, DMSO-$d_6$) δ 9.11 (s, 1H), 8.17 (br. s., 1H), 7.93 (br. s., 1H), 7.48-7.73 (m, 3H), 7.42 (d, J=8.77 Hz, 1H), 7.28 (br. s., 1H), 6.99 (d, J=8.33 Hz, 1H), 6.74-6.94 (m, 3H), 6.68 (br. s., 1H), 6.51 (br. s., 2H), 3.82 (s, 3H).

Compound 52

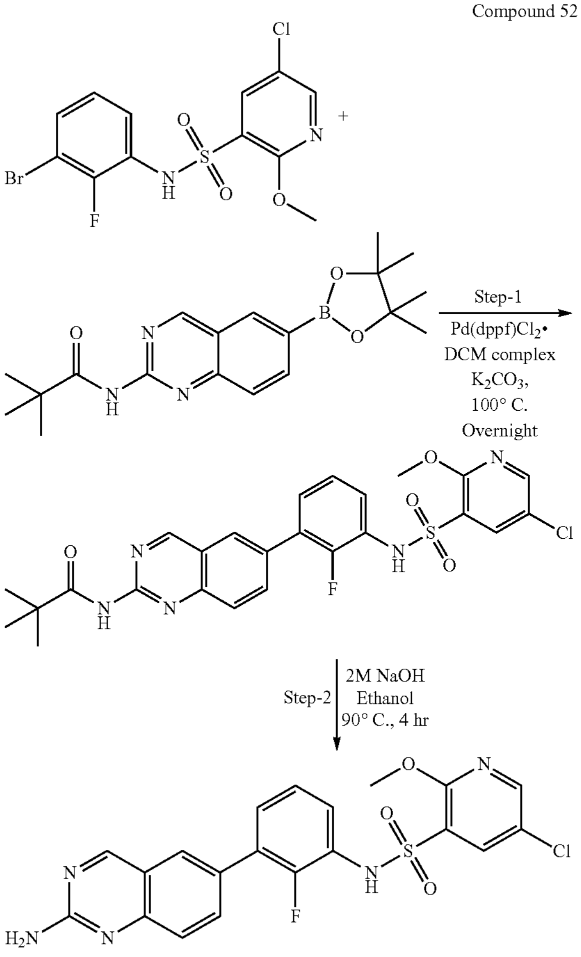

Step 1: Synthesis of N-(6-(3-((5-chloro-2-methoxypyridine)-3-sulfonamido)-2-fluorophenyl)quinazolin-2-yl)pivalamide To the stirred solution N-(3-bromo-2-fluorophenyl)-5-chloro-2-methoxypyridine-3-sulfonamide (200 mg, 0.508 mmol, 1.0 equiv) and N-(6-(4,4,5,5-tetramethyl-1,3,2-dioxaborolan-2-yl)quinazolin-2-yl)pivalamide (217 mg, 0.609 mmol, 1.2 equiv) in Dioxane:Water (4:1, 5 mL) was added $K_2CO_3$ (210 mg, 1.5 mmol, 3.0 equiv.). The resulting reaction mixture was purged with nitrogen for 15 minutes followed by the addition of $Pd(dppf)Cl_2 \cdot DCM$ complex (20 mg, 0.025 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (3×100 mL). The organic layers were combined, dried over anhydrous $Na_2SO_4$ and evaporated under reduced pressure. This material was used in the next reaction without further purification (170 mg), LCMS: 544[M+H]$^+$ Step 2: Synthesis of N-(3-(2-aminoquinazolin-6-yl)-2-fluorophenyl)-5-chloro-2-methoxypyridine-3-sulfonamide To a stirred solution of N-(6-(3-((5-chloro-2-methoxy-pyridine)-3-sulfonamido)-2-fluorophenyl)quinazolin-2-yl) pivalamide (170 mg, 0.312 mmol, 1.0 equiv) in ethanol (4 mL) was added 2M NaoH (4 mL). Then, the reaction mixture was allowed to stir at 90° C. for 4 h. After completion of reaction, the solvent was evaporated and water was added to the reaction mixture, extracted with EtOAc (2×50 mL). The organic layers were combined, dried over anhydrous $Na_2SO_4$ and evaporated under reduced pressure. The crude product which was purified by reverse phase HPLC to obtain as title compound N-(3-(2-aminoquinazolin-6-yl)-2-fluorophenyl)-5-chloro-2-methoxypyridine-3-sulfonamide (11 mg), Analytical Data: LCMS: 460[M+H]$^+$, $^1$H NMR (400 MHz, DMSO-$d_6$) δ 10.43 (s, 1H), 9.16 (s, 1H), 8.50 (d, J=2.63 Hz, 1H), 8.09 (d, J=2.63 Hz, 1H), 7.65 (d, 1H), 7.87 (s, 1H), 7.48 (d, J=8.77 Hz, 1H), 7.35 (m, 1H), 7.26 (d, J=7.45 Hz, 2H), 6.99 (s, 2H), 3.91 (s, 3H).

ice/acetone bath. Part B: hydrochloric acid (26.5 ml) was added, with agitation, to 5-chloro-2-(trifluoromethyl)aniline (3.0 g) maintaining the temperature of the mixture below 30° C. with ice cooling. The reaction mixture was cooled to −5° C. using an ice/acetone bath and a solution of sodium nitrite (3.10 g) in water (40 ml) was added drop wise over 45 minutes, maintaining the temperature of the reaction mixture between −5 and 0 C. The resultant slurry was cooled to −2° C. and stirred for 15 minutes. Part C: The slurry from Part B was cooled to −5° C. and added to the solution obtained from Part A over 95 minutes, maintaining the reaction temperature between −3° to 0° after completion of reaction, Reaction mass was diluted with water and extracted by Ethyl acetate (3×50 mL). The combined organic layers were dried over anhydrous sodium sulphate and concentrated under reduced pressure and purified by column chromatography to obtain the title compound 5-chloro-2-(trifluoromethyl)benzene-1-sulfonyl chloride (1.3 g).

Compound 58

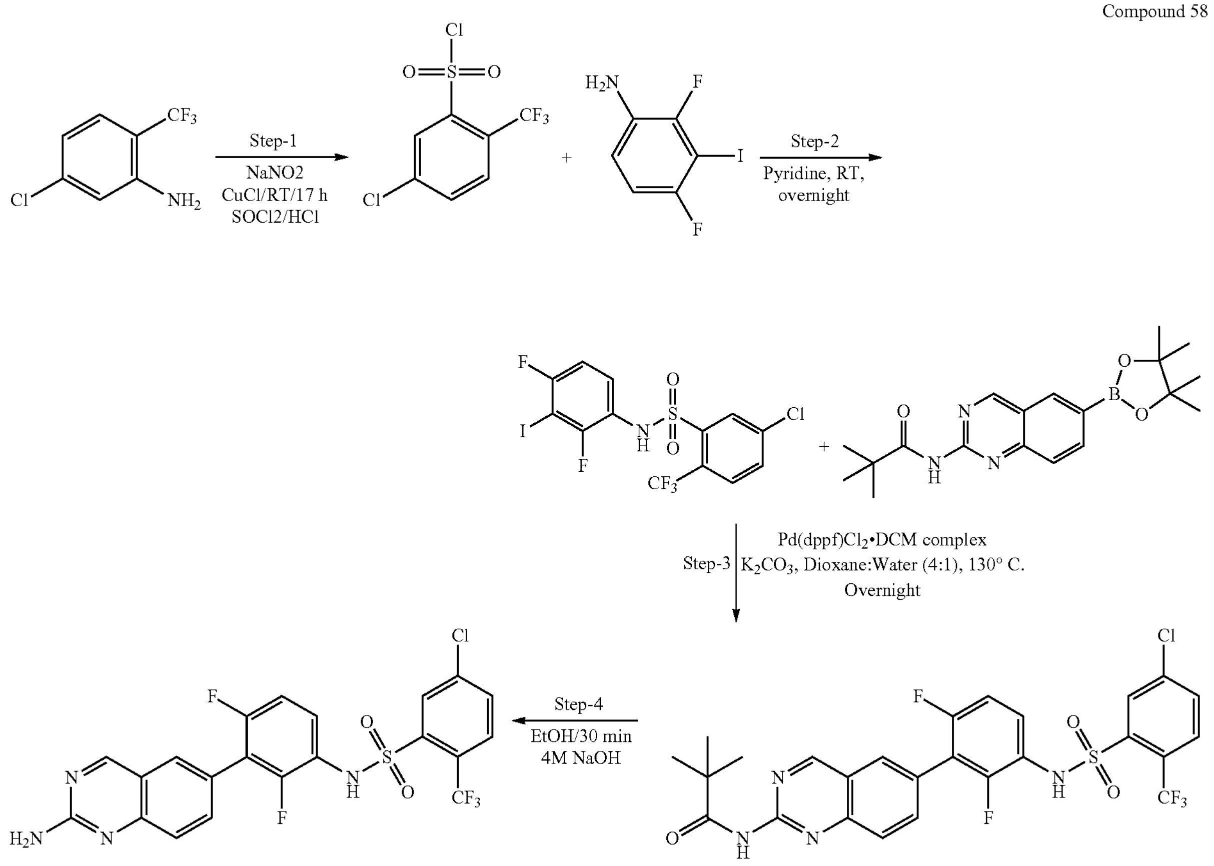

Step-1 Synthesis of 5-chloro-2-(trifluoromethyl)benzene-1-sulfonyl chloride

Part A: Thionyl chloride (8.4 ml) was added drop wise over 60 minutes to water (50 ml) at 5° C., maintaining the temperature of the mixture between 0-7° C. The solution was allowed to warm to 18° C. over 17 hours. Copper (I) chloride (0.003 g) was added to the mixture and the resultant yellow-green solution was cooled to −3 deg C. using an Step-2: Synthesis of 5-chloro-N-(2,4-difluoro-3-iodophenyl)-2-(trifluoromethyl)benzenesulfonamide The mixture of 3-Iodo-2,4-difluoroaniline (300 mg, 1.25 mmol. 1.0 equiv.) and 5-chloro-2-(trifluoromethyl)benzene-1-sulfonyl chloride (450 mg, 1.76 mmol, and 1.5 equiv.) in pyridine were stirred at room temperature for overnight. After completion of reaction was added 2N HCl (10 mL) and the mixture was stirred at room temperature for 10 min reaction mass was diluted with water and extracted by Ethyl acetate (3×50 mL). The combined organic layers were dried over anhydrous sodium sulphate and concentrated under reduced pressure and purified by combi-flash to obtain the title compound (1.03 g).

Step-3: Synthesis of N-(6-(3-(5-chloro-2-(trifluoromethyl)phenylsulfonamido)-2,6-difluorophenyl)quinazolin-2-yl)pivalamide To the stirred solution of 5-chloro-N-(2,4-difluoro-3-iodophenyl)-2-(trifluoromethyl)benzenesulfonamide (650 mg, 1.30 mmol, 1.0 equiv) and N-(6-(4,4,5,5-tetramethyl-1,3,2-dioxaborolan-2-yl)quinazolin-2-yl)pivalamide (700 mg, 1.95 mmol, 1.5 equiv) in Dioxane:Water (4:1, 5 mL) was added K2CO3 (270 mg, 1.95 mmol, 1.5 equiv.) The resulting reaction mixture was purged with nitrogen for 15 minutes followed by the addition of Pd(dppf)Cl2·DCM complex (56 mg, 0.065 mmol, 0.05 equiv.). The reaction mixture was again purged with nitrogen for 5 minutes. The reaction mixture was heated to 130° C. for overnight. The progress of reaction was monitored through TLC and LCMS. After completion of reaction, water was added to the reaction mixture, extracted with EtOAc (5×100 mL). The organic layers were combined, dried over anhydrous sodium sulphate and evaporated under reduced pressure to obtain title product as crude residue which was purified by flash chromatography using EtOAc/Hexane (50-100%) as eluent to obtain title product (250 mg).

Step-4: Synthesis of N-(3-(2-aminoquinazolin-6-yl)-2,4-difluorophenyl)-5-chloro-2-(trifluoromethyl)benzenesulfonamide To a stirred solution of N-(6-(3-(5-chloro-2-(trifluoromethyl)phenylsulfonamido)-2,6-difluorophenyl)quinazolin-2-yl)pivalamide (200 mg, 0.34 mmol, 1.0 equiv) in ethanol (5 mL) at room temperature was added 2M NaOH (2 mL). Then, the reaction mixture was allowed to stir at 100° C. for 30 min. Progress of the reaction was monitored by TLC and LCMS. After completion of the reaction, RM was concentrated under reduced pressure to evaporate ethanol, then extracted with EtOAc (2×50 mL). The organic layers were combined, dried over anhydrous $Na_2SO_4$, evaporated under reduced pressure to obtain crude product. This product was purified by using reverse phase chromatography technique to obtain desired compound N-(3-(2-aminoquinazolin-6-yl)-2,4-difluorophenyl)-5-chloro-2-(trifluoromethyl)benzenesulfonamide (34 mg), Analytical Data: LCMS: 515.2 $[M+H]^+$, $^1H$ NMR (400 MHz, DMSO-$d_6$) 7.02 (s, 2H) 7.15 (br. s., 2H) 7.48 (d, J=9.21 Hz, 2H) 7.58 (d, J=8.33 Hz, 1H) 7.76 (s, 2H) 8.01 (s, 1H) 9.15 (s, 1H) 10.65 (br. s., 1H).

Compound 59

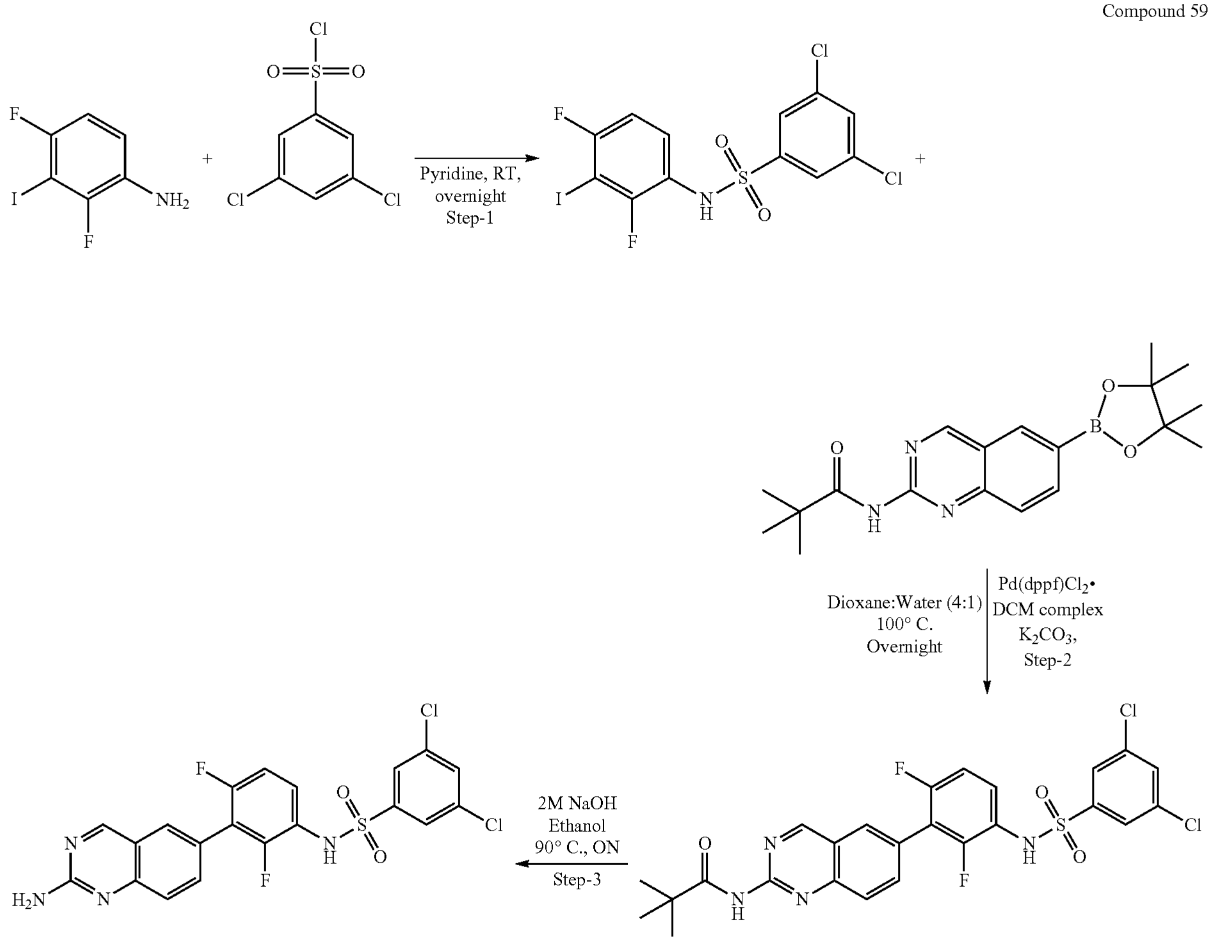

Step-1 Synthesis of 3,5-dichloro-N-(2,4-difluoro-3-iodophenyl)benzenesulfonamide To a stirred solution of 2,4-difluoro-3-iodoaniline (100 mg, 0.392 mmol. 1.0 equiv.) in pyridine (1.0 mL) at room temperature was added pyridine of 3,5-dichlorobenzenesulfonyl chloride (96 mg, 0.392 mmol. 1.0 equiv.) The resultant reaction mixture was stirred at room temperature for overnight. The progress of reaction was monitored through by TLC. After completion of the reaction, ice cold water had been added to reaction mixture. The precipitate formed was filtered using Buchner funnel and washed the product with 1N HCl to remove pyridine. This material was used in the next reaction without further purification. (130 mg)

Step 2: Synthesis of N-(6-(3-((3,5-dichlorophenyl)sulfonamido)-2,6-difluorophenyl)quinazolin-2-yl)pivalamide To a stirred solution of 3,5-dichloro-N-(2,4-difluoro-3-iodophenyl)benzenesulfonamide (125 mg, 0.269 mmol, 1.0 equiv) and N-(6-(4,4,5,5-tetramethyl-1,3,2-dioxaborolan-2-yl)quinazolin-2-yl)pivalamide (114 mg, 0.323 mmol, 1.2 equiv) in Dioxane:Water (4:1, 5 mL) was added $K_2CO_3$ (111 mg, 0.807 mmol, 3.0 equiv.). The resulting reaction mixture was purged with nitrogen for 15 minutes followed by the addition of Pd(dppf)$Cl_2$·DCM complex (10.9 mg, 0.0134 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×150 mL). The organic layers were combined, dried over anhydrous $Na_2SO_4$ and evaporated under reduced pressure to crude product which was used in the next reaction without further purification (115 mg) LCMS: 565 $[M+H]^+$.

Step 3: Synthesis of N-(3-(2-aminoquinazolin-6-yl)-2,4-difluorophenyl)-3,5-dichlorobenzenesulfonamide To a stirred solution of N-(6-(3-((3,5-dichlorophenyl)sulfonamido)-2,6-difluorophenyl)quinazolin-2-yl)pivalamide (115 mg, 0.0203 mmol, 1.0 equiv) in ethanol (5 mL) was added 2M NaOH (4 mL). Then, the reaction mixture was allowed to stir at 90° C. overnight. After completion of reaction, the solvent was evaporated and water was added to the reaction mixture, extracted with EtOAc (2×50 mL). The organic layers were combined, dried over anhydrous $Na_2SO_4$ and evaporated under reduced pressure to obtain crude product which was purified by reverse phase HPLC to obtain as title compound N-(3-(2-aminoquinazolin-6-yl)-2,4-difluorophenyl)-3,5-dichlorobenzenesulfonamide (15 mg), Analytical Data: LCMS: 481 $[M+H]^+$ $^1H$ NMR (400 MHz, DMSO-$d_6$) δ 10.52 (br. s., 1H) 9.14 (s, 1H), 7.85 (br. s., 1H), 7.78 (s, 1H), 7.54-7.71 (m, 3H), 7.48 (d, J=8.77 Hz, 1H), 7.21 (d, J=6.14 Hz, 1H), 7.05 (br. s., 1H), 7.00 (s, 2H).

Compound 63

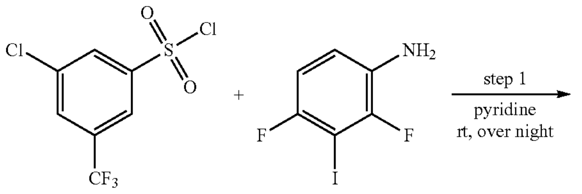

-continued

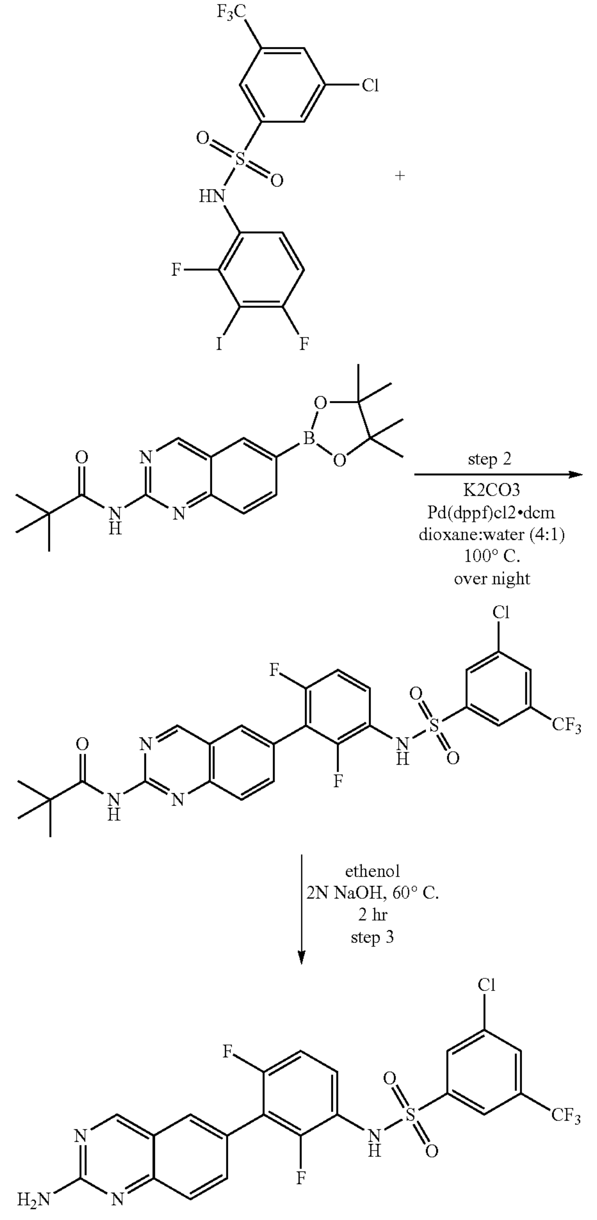

Step-1: Synthesis of 3-chloro-N-(2,4-difluoro-3-iodophenyl)-5-(trifluoromethyl)benzenesulfonamide To the stirred solution of 2,4-difluoro-3-iodoaniline (136 mg, 0.53 mmol. 1.0 equiv.) in pyridine (2 mL) at room temperature was added 3-chloro-5-(trifluoromethyl)benzene-1-sulfonyl chloride (150 mg, 0.53 mmol, 1.0 eq.), After addition reaction mixture was stirred for overnight at room temperature. The progress of reaction was monitored through TLC and LCMS, After completion of reaction added 2N HCl (5 mL) and the mixture was stirred at room temperature for 10 min reaction mass was diluted with water and extracted by Ethyl acetate (2×15 mL). The combined organic layers were dried over anhydrous $Na_2SO_4$ and concentrated under reduced pressure, This material was used in the next reaction without further purification (260 mg).

Step-2: Synthesis N-(6-(3-(3-chloro-5-(trifluoromethyl)phenylsulfonamido)-2,6-difluorophenyl)quinazolin-2-yl)pivalamide To the stirred solution of 3-chloro-N-(2,4-difluoro-3-iodophenyl)-5-(trifluoromethyl)benzenesulfonamide (260 mg, 0.52 mmol. 1.0 equiv.) and N-(6-(4,4,5,5-tetramethyl-1,3,2-dioxaborolan-2-yl)quinazolin-2-yl)pivalamide (204 mg, 0.57 mmol, and 1.1 eq.) in Dioxane:Water (4:1, 5 mL) was added $K_2CO_3$ (216 mg, 1.57 mmol, 3.0 equiv.) The resulting reaction mixture was purged with nitrogen for 15 minutes followed by the addition of Pd(dppf)$Cl_2$·DCM complex (21 mg, 0.026 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×10 mL). The organic layers were combined, dried over anhydrous $Na_2SO_4$ and evaporated under reduced pressure to obtain crude residue which was purified by flash chromatography to obtain title product N-(6-(3-(3-chloro-5-(trifluoromethyl)phenylsulfonamido)-2,6-difluorophenyl)quinazolin-2-yl)pivalamide (422 mg), Analytical Data: LCMS: 599 $[M+H]^+$ Step-3: Synthesis of N-(3-(2-aminoquinazolin-6-yl)-2,4-difluorophenyl)-3-chloro-5-(trifluoromethyl) benzenesulfonamide To a stirred solution of N-(6-(3-(3-chloro-5-(trifluoromethyl)phenylsulfonamido)-2,6-difluorophenyl)quinazolin-2-yl)pivalamide (422 mg, 0.705 mmol, 1.0 equiv) in ethanol (5 mL) at room temperature was added 2N NaOH (2 mL). Then the reaction mixture was allowed to stir at 60° C. for 2 h, Progress of the reaction was monitored by TLC and LCMS. After completion of the reaction, solvent was evaporated and water was added to the reaction mixture, extracted with EtOAc (2×10 mL), The organic layers were combined, dried over anhydrous $Na_2SO_4$, evaporated under reduced pressure to obtain crude product which was purified by using reverse phase chromatography technique to obtain N-(3-(2-aminoquinazolin-6-yl)-2,4-difluorophenyl)-3-chloro-5-(trifluoromethyl)benzenesulfonamide (50 mg), Analytical Data: LCMS: 515 $[M+H]^+$, $^1$H NMR (400 MHz, DMSO-$d_6$) δ ppm 10.75 (br. s., 1H) 9.15 (s, 1H) 8.19 (s, 1H) 8.02 (s, 1H) 7.78 (s, 1H) 7.60 (d, J=8.77 Hz, 1H) 7.49 (d, J=8.77 Hz, 1H) 7.15-7.35 (m, 3H) 7.04 (s, 2H).

Compound 64

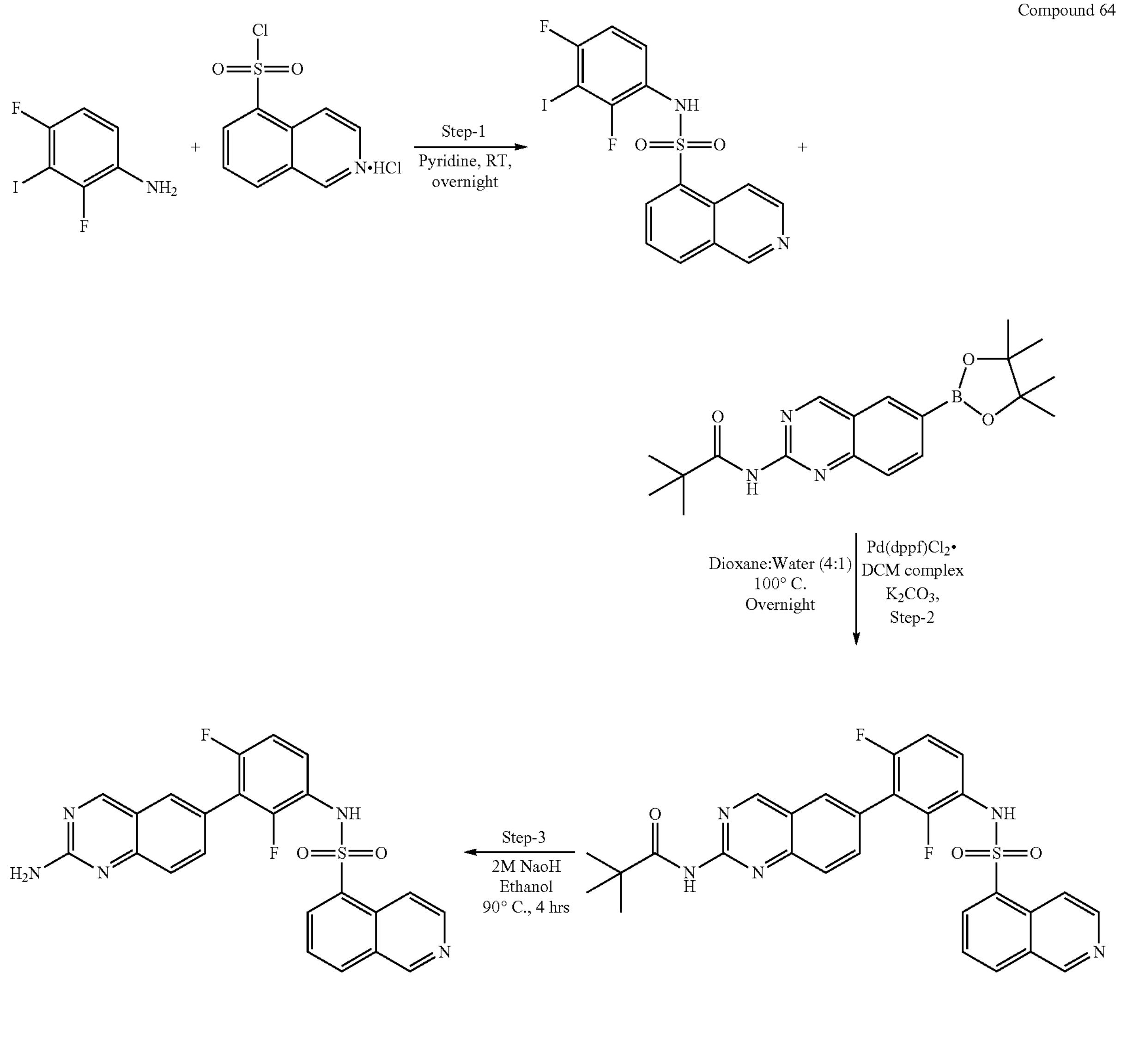

Step-1: Synthesis of N-(2,4-difluoro-3-iodophenyl) isoquinoline-5-sulfonamide

To a stirred solution of 2,4-difluoro-3-iodoaniline (200 mg, 0.7843 mmol. 1.0 equiv.) in pyridine (1 mL) at room temperature was added isoquinoline-5-sulfonyl chloride hydrochloride (248.5 mg, 0.7843 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc, dried over sodium sulphate and concentrated under vacuum to obtain crude product which was triturated with hexanes to obtain desired product N-(2,4-difluoro-3-iodophenyl)isoquinoline-5-sulfonamide (220 mg).

Step-2: Synthesis of N-(6-(2,6-difluoro-3-(isoquinoline-5-sulfonamido)phenyl)quinazolin-2-yl)pivalamide To a stirred solution of N-(2,4-difluoro-3-iodophenyl) isoquinoline-5-sulfonamide (220 mg, 0.4930 mmol, 1.0 equiv) and N-(6-(4,4,5,5-tetramethyl-1,3,2-dioxaborolan-2-yl)quinazolin-2-yl)pivalamide (210 mg, 0.5916 mmol, 1.2 equiv) in dioxane:water (4:1, 5 mL) was added $K_2CO_3$ (204.4 mg, 1.4791 mmol, 3.0 equiv.). The resulting reaction mixture was purged with nitrogen for 10 minutes followed by the addition of $Pd(dppf)Cl_2 \cdot DCM$ complex (20.13 mg, 0.0246 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure to obtain title product N-(6-(2,6-difluoro-3-(isoquinoline-5-sulfonamido)phenyl)quinazolin-2-yl)pivalamide (354 mg), this product was used in next step without further purification. LCMS: 548.4 $[M+H]^+$ Step-3: Synthesis of N-(3-(2-aminoquinazolin-6-yl)-2,4-difluorophenyl)isoquinoline-5-sulfonamide To a stirred solution of N-(6-(2,6-difluoro-3-(isoquinoline-5-sulfonamido)phenyl)quinazolin-2-yl)pivalamide (350 mg, 0.6391 mmol, 1.0 equiv) in ethanol (6 mL) at room temperature was added 2M NaOH (4 mL). Then, the reaction mixture was allowed to stir at 90° C. for 4 hrs. Progress of the reaction was monitored by TLC and LCMS. After completion of the reaction, RM was concentrated under reduced pressure to evaporate ethanol, extracted with EtOAc (2×100 mL). The organic layers were combined, dried over anhydrous $Na_2SO_4$, evaporated under reduced pressure to obtain crude product which was purified by using reverse phase chromatography technique to obtain desired compound N-(3-(2-aminoquinazolin-6-yl)-2,4-difluorophenyl) isoquinoline-5-sulfonamide (40 mg), Analytical Data: LCMS: 464.3 $[M+H]^+$, $^1H$ NMR (400 MHz, DMSO-$d_6$) δ ppm 10.61 (br. s., 1H) 9.39 (s, 1H) 9.08 (s, 1H) 8.49-8.61 (m, 2H) 8.23-8.35 (m, 2H) 7.73 (t, J=7.89 Hz, 1H) 7.59 (s, 1H) 7.36-7.46 (m, 2H) 7.12-7.21 (m, 1H) 6.96 (s, 3H).

Compound 65:
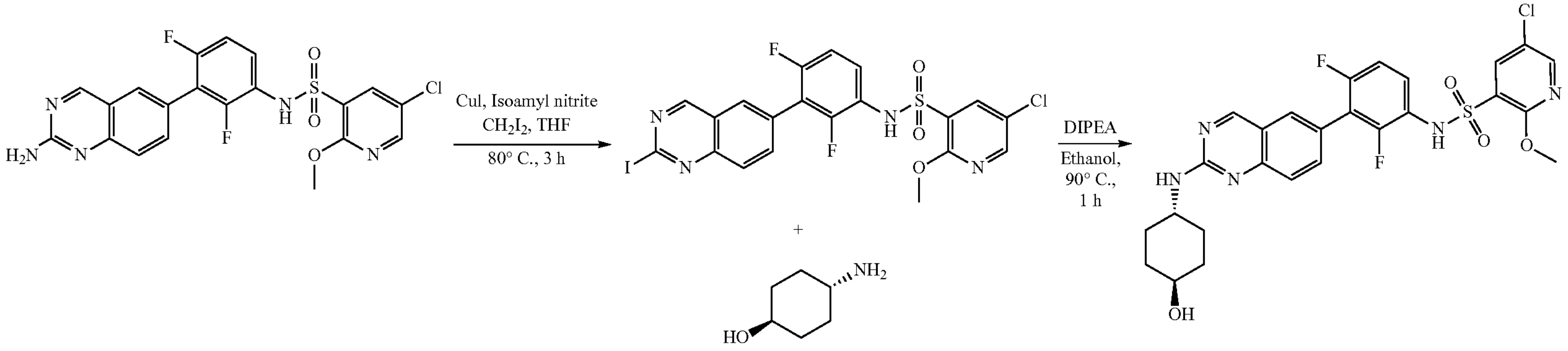

Step-1: Synthesis of 5-chloro-N-(2,4-difluoro-3-(2-iodoquinazolin-6-yl)phenyl)-2-methoxypyridine-3-sulfonamide To a stirred solution N-(3-(2-aminoquinazolin-6-yl)-2,4-difluorophenyl)-5-chloro-2-methoxypyridine-3-sulfonamide (100 mg, 0.21 mmol, 1.0 equiv.) was added CuI (556 mg, 0.29 mmol, 1.4 equiv.) and purged with $N_2$ gas. Under $N_2$ atmosphere was added isoamyl nitrite (39 mg, 0.33 mmol, 1.6 equiv.), $CH_2I_2$ (335 mg, 1.25 mmol, 6.0 equiv.) to reaction mixture. After addition, reaction mixture was allowed to stir at 80° C. for 3 h. After completion of reaction, was added ice water and extracted with ethyl acetate (2×50 ml). The separated organic layer was dried over $Na_2SO_4$, filtered and concentrated under vacuum to obtain crude product which was purified by using combi-flash (Eluent System: 20% EA:Hexanes) to obtain desired product (60 mg), LCMS: 589[M+H]$^+$ Step-2: Synthesis of 5-chloro-N-(2,4-difluoro-3-(2-(((1r,4r)-4-hydroxycyclohexyl)amino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (50 mg, 0.085 mmol, 1.0 equiv.) in ethanol was added (1r,4r)-4-aminocyclohexanol (20 mg, 0.169 mmol, 1.0 equiv.), DIPEA (32.8 mg, 0.25 mmol, 3.0 equiv.). After addition reaction was heated at 90° C. for 1 h. Progress of reaction was monitored by TLC. After completion of reaction, evaporated ethanol and was added work up of reaction had been carried out using ethyl acetate (2×50 ml) and water (20 ml). The separated organic layer was dried over $Na_2SO_4$, filtered and concentrated. The crude product was purified by reverse phase silica gel chromatography to obtain desired product (16 mg). Analytical Data: LCMS: 576 [M+H]$^+$, NMR: $^1$H NMR (400 MHz, DMSO-$d_6$) δ ppm 1.16-1.44 (m, 5H) 1.77-2.04 (m, 4H) 3.84 (br. s., 2H) 3.91 (s, 3H) 7.16-7.26 (m, 1H) 7.29-7.41 (m, 1H) 7.62 (br. s., 3H) 7.82 (br. s., 1H) 8.08 (d, J=2.19 Hz, 1H) 8.52 (d, J=2.63 Hz, 1H) 9.19 (br. s., 1H) 10.41 (s, 1H).

Compound 66:

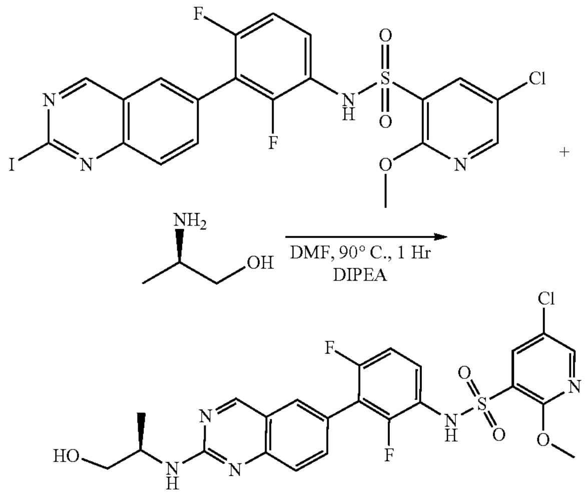

Step-1: Synthesis of (R)-5-chloro-N-(2,4-difluoro-3-(2-(1-hydroxypropan-2-ylamino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (080 mg, 0.136 mmol, 1.0 equi.) in DMF (1.0 ml) was added (R)-2-aminopropan-1-ol (20 mg, 0.272 mmol, 2.0 equi.), DIPEA (52.6 mg, 0.408 mmol, 3.0 equi.). After addition, reaction was heated at 90° C. for 1 h. Progress of reaction was monitored by TLC. After completion of reaction, water (50 ml) was added & extracted ethyl acetate (2×50 ml). The separated organic layer was dried over $Na_2SO_4$, filtered and concentrated. The crude product which was purified by reverse phase chromatography to obtain desired product (18 mg), Analytical Data: LCMS: 536[M+H]$^+$, $^1$H NMR (400 MHz, DMSO-$d_6$) □=10.43 (s, 1H), 9.14 (br. s., 1H), 8.39 (br. s., 1H), 8.04 (d, J=2.2 Hz, 1H), 7.78 (s, 1H), 7.60 (d, J=8.8 Hz, 1H), 7.51 (d, J=7.9 Hz, 1H), 7.35-7.16 (m, 2H), 7.07 (br. s., 1H), 4.73 (br. s., 1H), 4.12 (s, 1H), 4.14 (s, 3H), 3.86 (s, 1H), 3.53 (d, J=5.3 Hz, 1H), 1.31-1.03 (m, 3H).

Compound 67:

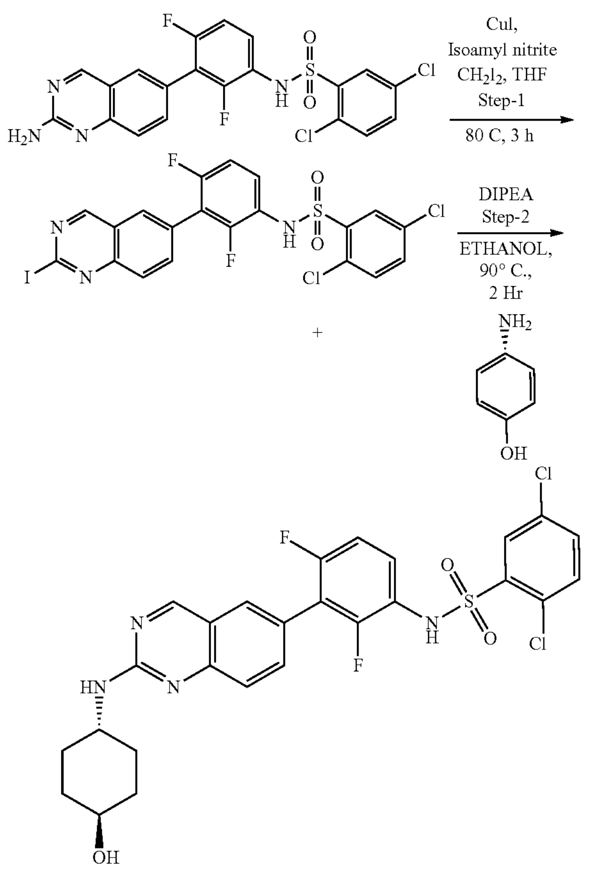

Step-1: Synthesis of 2,5-dichloro-N-(2,4-difluoro-3-(2-iodoquinazolin-6-yl)phenyl)benzenesulfonamide To a stirred solution of N-(3-(2-aminoquinazolin-6-yl)-2,4-difluorophenyl)-2,5-dichloro benzene sulfonamide (300 mg, 0.625 mmol, 1.0 equi.) was added CuI (166 mg, 0.875 mmol, 1.4 equi.) and purged with N2 gas. Under N2 atmosphere was added isoamyl nitrite (117 mg, 1.0 mmol, 1.6 equi.), $CH_2I_2$ (1.0 g, 3.75 mmol, 6.0 equiv.) to reaction mixture. After addition, reaction mixture was allowed to stir at 80° C. for 3 h. After completion of reaction, was added ice water and extracted with ethyl acetate (2×50 ml). The separated organic layer was dried over $Na_2SO_4$, filtered and concentrated under vacuum to obtain crude product which was purified by using combi-flash (Eluent System: 20% EA:Hexanes) to obtain desired product (190 mg), LCMS: 593[M+H]$^+$ Step-2: Synthesis of 2,5-dichloro-N-(2,4-difluoro-3-(2-(((1r,4r)-4-hydroxycyclohexyl)amino)quinazolin-6-yl)phenyl)benzenesulfonamide To a stirred solution of 2,5-dichloro-N-(2,4-difluoro-3-(2-iodoquinazolin-6-yl)phenyl)benzene sulfonamide (40 mg, 0.0679 mmol, 1.0 equi.) in ethanol was added (1r,4r)-4-aminocyclohexanol (15 mg, 0.135 mmol, 2.0 equi.), DIPEA (26 mg, 0.203 mmol, 3.0 equi.). After addition, reaction mixture was heated at 90° C. for 2 h. Progress of reaction was monitored by TLC. After completion of reaction, evaporated ethanol and was added water (20 ml), extracted with ethyl acetate (2×50 ml). The separated organic layers was dried over $Na_2SO_4$, concentrated. The crude product was purified by combi flash to obtain desired product (4 mg), Analytical Data: LCMS: 579 [M+H]$^+$, NMR: $^1$H NMR (400 MHz, DMSO-$d_6$) δ ppm 1.13-1.41 (m, 4H) 1.88 (br. s., 3H) 1.94 (br. s., 2H) 3.42 (br. s., 1H), 3.91 (br. s., 1H), 7.21 (br. s., 1H) 7.29 (d, J=6.14 Hz, 1H) 7.43 (d, J=8.77 Hz, 2H) 7.49-7.61 (m, 2H) 7.68-7.81 (m, 2H) 7.86 (d, J=1.75 Hz, 1H), 9.21 (bs, 1H), 10.67 (br. s., 1H).

Compound 69:
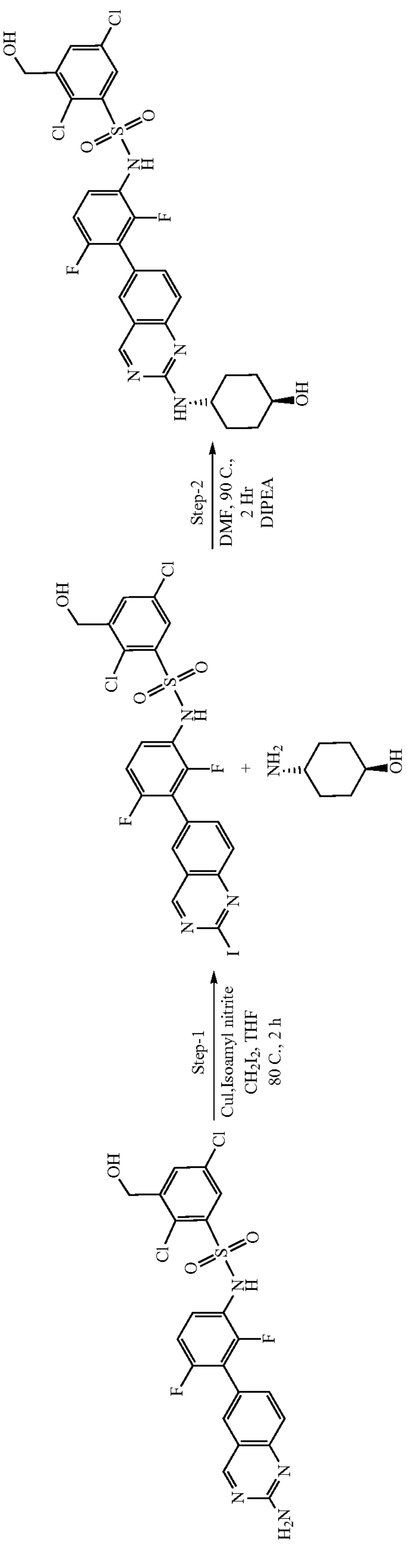

Step-1: Synthesis of 2,5-dichloro-N-(2,4-difluoro-3-(2-iodoquinazolin-6-yl)phenyl)-3-(hydroxymethyl) benzenesulfonamide To a stirred solution of N-(3-(2-aminoquinazolin-6-yl)-2,4-difluorophenyl)-2,5-dichloro-3-(hydroxymethyl)benzenesulfonamide (380 mg, 0.7431 mmol, 1.0 equi.) in THE (10 ml) was added CuI (212.3 mg, 1.1147 mmol, 1.5 equi.) and purged with N2 gas. Under N2 atmosphere was added Isoamyl nitrite (130.59 mg, 1.1147 mmol, 1.5 equi.), $CH_2I_2$ (0.36 mL, 4.4589 mmol, 6.0 equiv.) to reaction mixture. After addition, reaction mixture was allowed to stir at 80° C. for 2 h. After completion of reaction, was added ice water and extracted with ethyl acetate (2×100 ml). The separated organic layer was dried over $Na_2SO_4$, filtered and concentrated under vacuum to obtain crude product which was purified by using combi-flash (Eluent System: 20% EA:Hexanes) to obtain desired product (60 mg).

Step-2: Synthesis of 2,5-dichloro-N-(2,4-difluoro-3-(2-((1r,4r)-4-hydroxycyclohexylamino)quinazolin-6-yl)phenyl)-3-(hydroxymethyl)benzenesulfonamide To a stirred solution of 2,5-dichloro-N-(2,4-difluoro-3-(2-iodoquinazolin-6-yl)phenyl)-3-(hydroxymethyl)benzenesulfonamide (60 mg, 0.0964 mmol, 1.0 equi.) in DMF was added (1r,4r)-4-aminocyclohexanol (22.2 mg, 0.1928 mmol, 2.0 equi.), DIPEA (37.39 mg, 0.2892 mmol, 3.0 equi.). After addition reaction was heated at 90° C. for 2 h. Progress of reaction was monitored by TLC. After completion of reaction, reaction mixture was evaporated under vacuum and was added water (20 ml) and extracted with acetate (2×50 ml) and). The separated organic layer was dried over $Na_2SO_4$, filtered and concentrated under vacuum to obtain crude which was purified by combi flash silica gel chromatography to obtain desired product (10 mg), Analytical Data: LCMS: 609.4 $[M+H]^+$, NMR: $^1H$ NMR (400 MHz, DMSO-$d_6$) δ ppm 10.68 (s, 1H) 9.12 (br. s., 1H) 7.64-7.92 (m, 3H) 7.47-7.63 (m, 2H) 7.42 (d, J=7.45 Hz, 1H) 7.25 (d, J=6.58 Hz, 1H) 7.17 (br. s., 1H) 5.75 (t, J=5.70 Hz, 1H) 4.42-4.68 (m, 3H) 3.83 (br. s., 1H) 3.17 (d, J=4.82 Hz, 1H) 1.80-2.06 (m, 4H) 1.15-1.40 (m, 4H).

Compound 76:

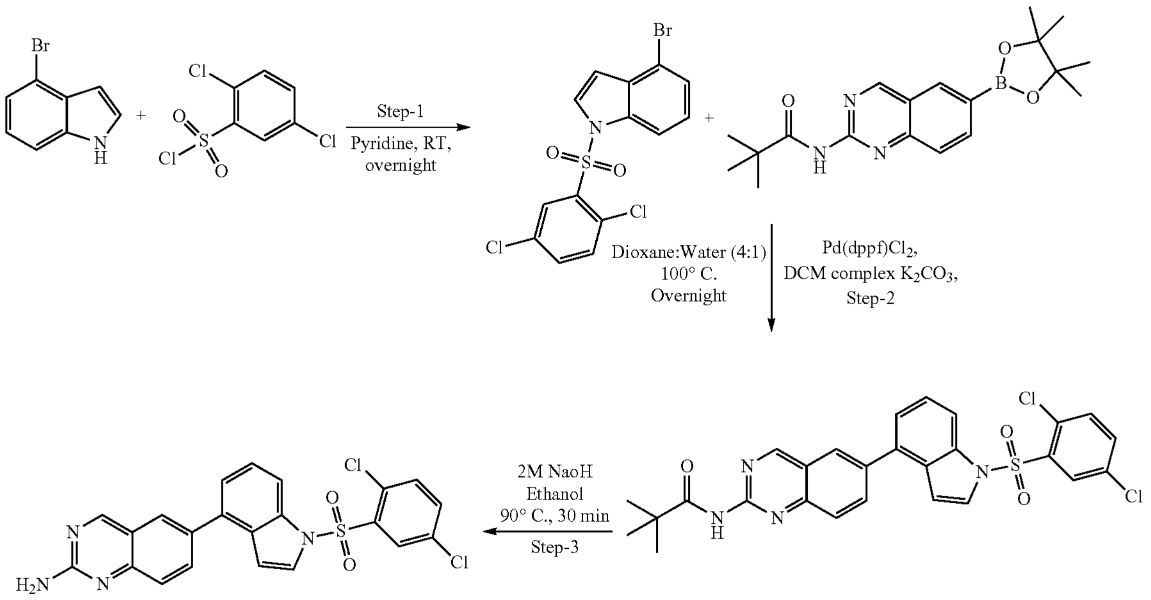

Step-1 Synthesis of 4-bromo-1-(2,5-dichlorophenylsulfonyl)-1H-indole

To a stirred solution of 4-bromo-1H-indole (600 mg, 3.0461 mmol, 1.0 equiv) in THF (6 mL) at 0° C. under nitrogen atmosphere was added NaH (43.8 mg, 1.8276 mmol, 0.6 equiv) and stirred for 10-15 min followed by the drop wise addition of 2,5-dichlorobenzene-1-sulfonyl chloride (1121.7 mg, 4.5692 mmol, 1.5 equiv.). Reaction mixture was then allowed to stir at room temperature for overnight. Progress of the reaction was monitored by TLC and HNMR. After completion of reaction ammonium chloride solution was added and workup of the reaction was carried out by ethyl acetate (2×100 ml). The organic layers were combined, dried over sodium sulphate and concentrated under reduced pressure to obtain crude product which was purified using flash chromatography to obtain 4-bromo-1-(2,5-dichlorophenylsulfonyl)-1H-indole (410 mg).

Step 2: Synthesis of N-(6-(1-(2,5-dichlorophenylsulfonyl)-1H-indol-4-yl)quinazolin-2-yl)pivalamide To a stirred solution of 4-bromo-1-(2,5-dichlorophenylsulfonyl)-1H-indole (300 mg, 0.7405 mmol, 1.0 equiv) and N-(6-(4,4,5,5-tetramethyl-1,3,2-dioxaborolan-2-yl)quinazolin-2-yl)pivalamide (315.7 mg, 0.8886 mmol, 1.2 equiv) in dioxane:Water (4:1, 5 mL) was added $K_2CO_3$ (307.04 mg, 2.2217 mmol, 3.0 equiv.). The resulting reaction mixture was purged with nitrogen for 10 minutes followed by the addition of $Pd(dppf)Cl_2 \cdot DCM$ complex (30.23 mg, 0.0370 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used in the next reaction without further purification (340 mg), LCMS: 553.2 $[M+H]^+$.

Step 3: Synthesis of 6-(1-(2,5-dichlorophenylsulfonyl)-1H-indol-4-yl)quinazolin-2-amine To a stirred solution of N-(6-(1-(2,5-dichlorophenylsulfonyl)-1H-indol-4-yl)quinazolin-2-yl)pivalamide (150 mg, 0.0.2710 mmol, 1.0 equiv) in ethanol (4 mL) was added 2M NaoH (1 mL). Then, the reaction mixture was allowed to stir at 90° C. for 30 min. After completion of reaction, the solvent was evaporated and water was added to the reaction mixture, extracted with EtOAc (2×50 mL). The organic layers were combined, dried over anhydrous $Na_2SO_4$ and evaporated under reduced pressure and purified by reverse phase chromatography to obtain as title compound 6-(1-(2,5-dichlorophenylsulfonyl)-1H-indol-4-yl)quinazolin-2-amine (20 mg), Analytical Data: LCMS: 469.4 $[M+H]^+$, NMR: $^1H$ NMR (400 MHz, DMSO-$d_6$) δ ppm 9.25 (s, 1H) 8.38 (d, J=2.19 Hz, 1H) 8.06 (s, 1H) 8.00 (d, J=3.51 Hz, 1H) 7.94 (d, J=8.77 Hz, 1H) 7.88 (dd, J=8.77, 2.19 Hz, 1H) 7.68-7.80 (m, 2H) 7.56 (d, J=8.77 Hz, 1H) 7.39-7.48 (m, 2H) 7.12 (br. s., 1H) 6.93-7.07 (m, 2H).

Compound 81:
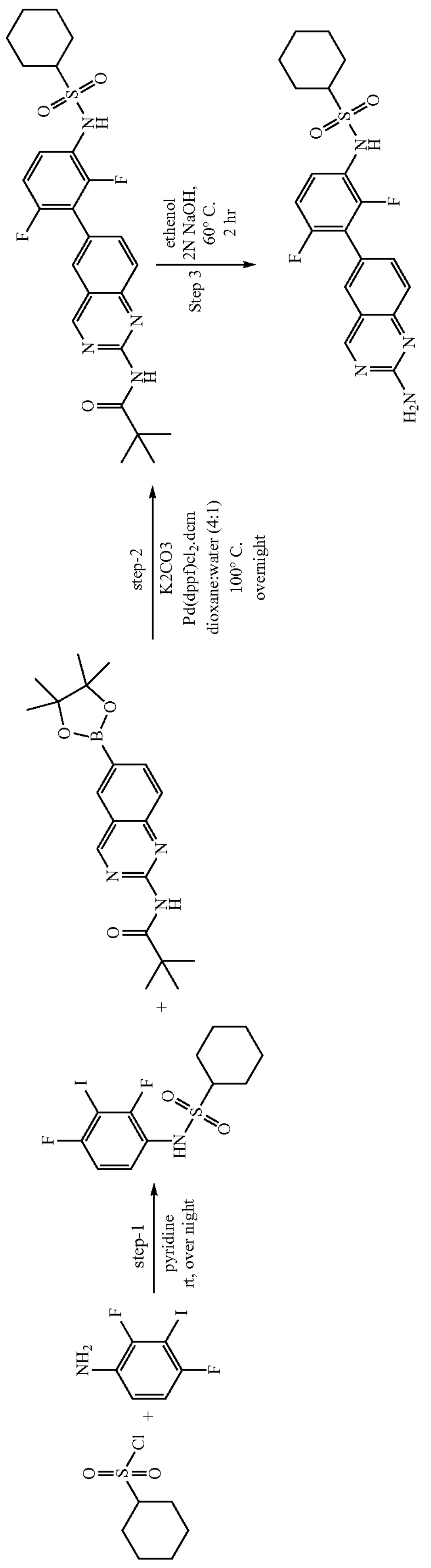

Step-1: Synthesis of N-(2,4-difluoro-3-iodophenyl)cyclohexane sulfonamide

To a stirred solution of 2,4-difluoro-3-iodoaniline (0.153 g, 0.60 mmol, and 1.1 eq) in 2 mL pyridine at room temperature was added cyclohexane sulfonyl chloride (100 mg, 0.54 mmol. 1.0 equiv.). After addition reaction mixture was stirred at room temperature for overnight. The progress of reaction was monitored through TLC and LCMS, After completion of reaction added 2N HCl (5 mL) and the reaction mixture was stirred at room temperature for 10 min, reaction mass was diluted with water and extracted by Ethyl acetate (2×10 mL). The combined organic layers were dried over anhydrous $Na_2SO_4$ and concentrated under reduced pressure, This material was used in the next reaction without further purification (153 mg).

Step-2: Synthesis of N-(6-(3-(cyclohexanesulfonamido)-2,6-difluorophenyl)quinazolin-2-yl)pivalamide To a stirred solution of N-(2,4-difluoro-3-iodophenyl) cyclohexane sulfonamide (0.133 gm, 0.33 mmol. 1.0 equiv.) and N-(6-(4,4,5,5-tetramethyl-1,3,2-dioxaborolan-2-yl)quinazolin-2-yl)pivalamide (129 mg, 0.36 mmol, and 1.1 eq.) in Dioxane:Water (4:1, 5 mL) was added $K_2CO_3$ (137 mg, 0.99 mmol, 3.0 equiv.). The resulting reaction mixture was purged with nitrogen for 15 minutes followed by the addition of Pd(dppf)$Cl_2$·DCM complex (13 mg, 0.016 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×10 mL). The organic layers were combined, dried over anhydrous $Na_2SO_4$ and evaporated under reduced pressure to obtain crude residue which was purified by flash chromatography to obtain title product N-(6-(3-(cyclohexanesulfonamido)-2,6-difluorophenyl)quinazolin-2-yl) pivalamide (170 mg), Analytical Data: LCMS: 503 $[M+H]^+$

Step-3: Synthesis of N-(3-(2-aminoquinazolin-6-yl)-2,4-difluorophenyl)cyclohexanesulfonamide To a stirred solution of N-(6-(3-(cyclohexanesulfonamido)-2,6-difluorophenyl)quinazolin-2-yl)pivalamide (170 mg, 0.33 mmol, 1.0 equiv) in ethanol (5 mL) at room temperature was added 2N NaOH (2 mL). Then the reaction mixture was allowed to stir at 60° C. for 2 hr, Progress of the reaction was monitored by TLC and LCMS. After completion of the reaction, solvent was evaporated and water was added to the reaction mixture, extracted with EtOAc (2×10 mL). The organic layers were combined, dried over anhydrous $Na_2SO_4$, evaporated under reduced pressure to obtain crude product which was purified using reverse phase chromatography technique to obtain desired compound N-(3-(2-aminoquinazolin-6-yl)-2,4-difluorophenyl)cyclohexanesulfonamide (20 mg), Analytical Data: LCMS: 419$[M+H]^+$, $^1H$ NMR (400 MHz, DMSO-$d_6$) δ ppm 1.21-1.33 (m, 3H) 1.34-1.47 (m, 3H) 1.78 (d, J=11.84 Hz, 2H) 2.11 (d, J=10.52 Hz, 2H) 7.03 (s, 2H) 7.24 (t, J=9.21 Hz, 1H) 7.43-7.56 (m, 2H) 7.72 (d, J=8.77 Hz, 1H) 7.90 (s, 1H) 9.19 (s, 1H) 9.66 (br. s., 1H).

Compound 105

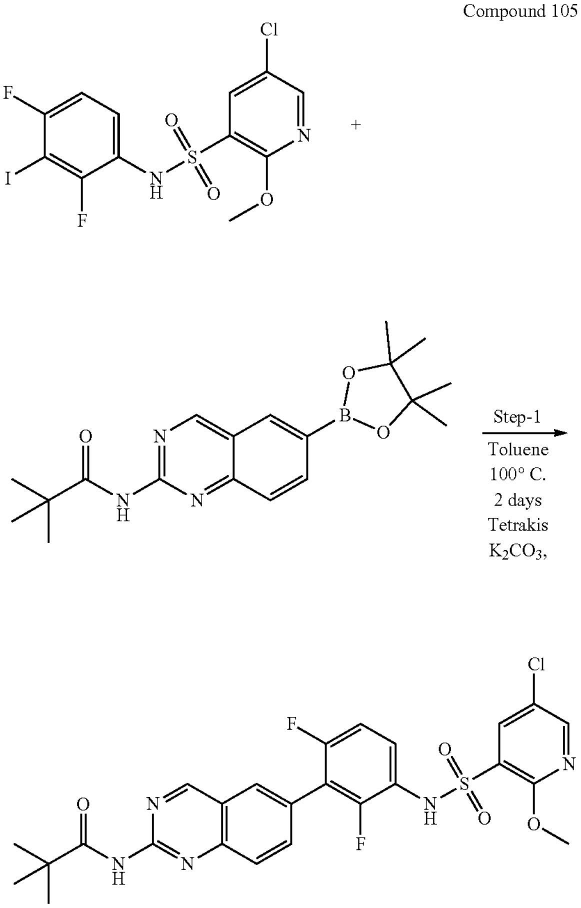

Step-1: Synthesis of N-(6-(3-((5-chloro-2-methoxypyridine)-3-sulfonamido)-2,6-difluorophenyl)quinazolin-2-yl)pivalamide To a stirred solution of 5-chloro-N-(2,4-difluoro-3-iodophenyl)-2-methoxypyridine-3-sulfonamide (5 g, 10.85 mmol, 1.0 equiv) and N-(6-(4,4,5,5-tetramethyl-1,3,2-dioxaborolan-2-yl)quinazolin-2-yl)pivalamide (5.4 g, 15.19 mmol, 1.4 equiv) in Toluene (30 mL) was added $K_2CO_3$ (2.3 g, 16.27 mmol, 1.5 equiv.). The resulting reaction mixture was purged with nitrogen for 15 minutes followed by the addition of Pd$(PPh_3)_4$ (626 mg, 0.54 mmol, 0.05 equiv.). The reaction mixture was again purged with nitrogen for 5 minutes. The reaction mixture was heated to 100° C. for 2 days. The progress of reaction was monitored through TLC and LCMS. After completion of reaction, water (150 mL) was added to the reaction mixture, extracted with EtOAc (2×200 mL). The organic layers were combined, dried over anhydrous $Na_2SO_4$ and evaporated under reduced pressure to obtain crude compound which was purified column chromatography (Eluent System: THF/Hexanes) to obtain desired product (3.8 g) Analytical Data: LCMS: 562.1 $[M+H]^+$, $^1H$ NMR (400 MHz, DMSO-$d_6$) δ ppm 10.47 (s, 1H) 10.32 (s, 1H) 9.57 (s, 1H) 8.51 (d, J=2.63 Hz, 1H) 8.08-8.13 (m, 2H) 7.87-7.93 (m, 2H) 7.38 (d, J=6.14 Hz, 1H) 7.27 (s, 1H) 3.91 (s, 3H) 1.27 (s, 9H).

Compound 106:

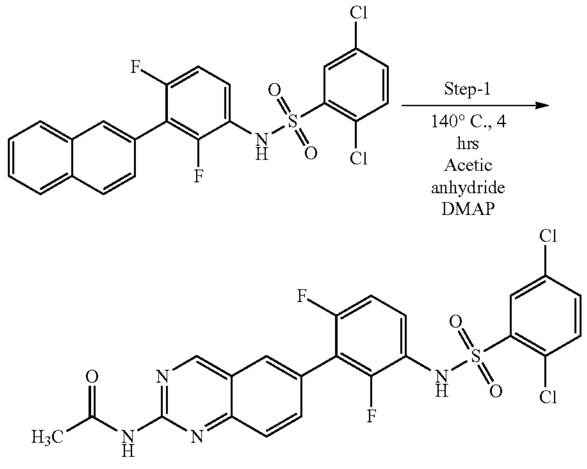

Step 1: Synthesis of N-(6-(3((2,5-dichlorophenyl) sulfonamido)2,6-difluorophenyl)quinazolin-2-yl) acetamide To a stirred solution of N-(3-(2-aminoquinazolin-6-yl)-2,4-difluorophenyl)-2,5-dichlorobenzenesulfonamide (40 mg, 0.0831 mmol, 1.0 equiv.) in acetic anhydride (0.8 ml) was added DMAP (0.2 mg) and the reaction mixture was heated at 140° C. for 4 h. Progress of the reaction was monitored by TLC and LCMS. After completion of reaction, water was added to the reaction mixture, extracted with EtOAc (2×20 mL). The organic layers were combined, dried over anhydrous $Na_2SO_4$ and evaporated under reduced pressure to obtain crude product which was purified by using flash chromatography to obtain N(6(3(2,5dichlorophenylsulfonamido)-2,6-difluorophenyl)quinazolin-2-yl)acetamide. Analytical Data: LCMS: 523.0 $[M+H]^+$, $^1H$ NMR (400 MHz, DMSO-$d_6$) δ 11.93 (s, 1H), 8.18 (d, J=2.63 Hz, 1H), 7.98 (d, J=9.65 Hz, 1H), 7.75-7.93 (m, 4H), 7.63 (d, J=8.33 Hz, 1H), 7.40-7.49 (m, 2H), 6.57 (d, J=9.21 Hz, 1H), 2.01-2.12 (m, 3H).

Compound 107:

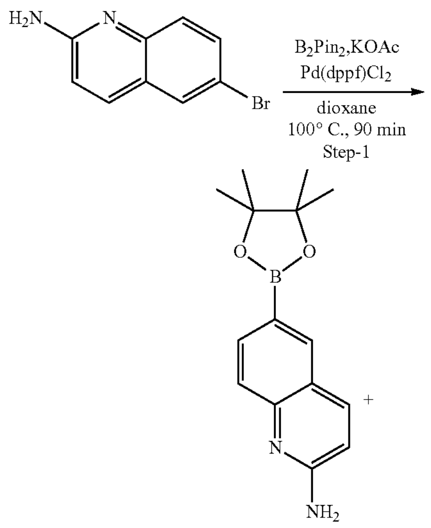

-continued

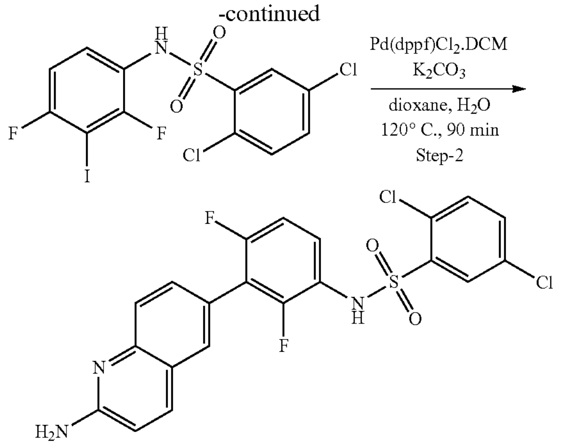

Step-1: Synthesis of 6-(4,4,5,5-tetramethyl-1,3,2-dioxaborolan-2-yl)quinolin-2-amine To a stirred solution of 6-bromoquinolin-2-amine (200 mg, 0.8964 mmol. 1.0 equiv.) in dioxane (3 mL) was added $B_2Pin_2$ (341.4 mg, 1.3446 mmol. 1.5 equiv.) and potassium acetate (263.5 mg, 2.6893 mmol. 3.0 equiv.) and reaction mixture was purged with nitrogen gas at room temperature for 10 min. After 10 min Pd(dppf)$Cl_2$ (32.7 mg, 0.0448 mmol. 0.05 equiv.) was added to RM and was again purged under nitrogen atmosphere for 5 min. The resultant reaction mixture was heated at 120° C. in a microwave for 90 min. The progress of reaction was monitored through TLC and LCMS. After completion of the reaction, RM was extracted with 2×times EtOAc (50 mL). The organic layer was dried over anhydrous sodium sulfate and evaporated under reduced pressure to obtain title compound (340 mg).

Step-2: Synthesis of N-(3-(2-aminoquinolin-6-yl)-2,4-difluorophenyl)-2,5-dichlorobenzenesulfonamide To a stirred solution of 2,5-dichloro-N-(2,4-difluoro-3-iodophenyl)benzenesulfonamide (290 mg, 0.6249 mmol, 1.0 equiv) and 6-(4,4,5,5-tetramethyl-1,3,2-dioxaborolan-2-yl)quinolin-2-amine (337.6 mg, 1.2498 mmol, 2.0 equiv) in dioxane:water (3:1, 4 mL) was added $K_2CO_3$ (259 mg, 1.8747 mmol, 3.0 equiv.). The resulting reaction mixture was purged with nitrogen for 15 minutes followed by the addition of Pd(dppf)$Cl_2$ DCM complex (25.5 mg, 0.0312 mmol, 0.05 equiv.). The reaction mixture was again purged with nitrogen for 5 minutes. The reaction mixture was heated to 120° C. in a microwave for 90 min. The progress of reaction was monitored through TLC and LCMS. After completion of reaction, water was added to the reaction mixture, extracted with EtOAc (2×50 mL). The organic layers were combined, dried over anhydrous $Na_2SO_4$, evaporated under reduced pressure and purified using flash chromatography to obtain desired compound which was triturated by using hexanes (3 mL) and pentane (2 mL) to obtain desired compound N-(3-(2-aminoquinolin-6-yl)-2,4-difluorophenyl)-2,5-dichlorobenzenesulfonamide (13.6 mg). Analytical Data: LCMS: 480.3 $[M+H]^+$, $^1H$ NMR (400 MHz, DMSO-$d_6$) δ10.72 (br. s., 1H), 8.31 (br. s., 1H), 7.85-7.96 (m, 2H), 7.70-7.80 (m, 3H), 7.74 (m, 1H), 7.28-7.40 (m, 2H), 7.24 (s, 1H), 7.06 (d, J=8.77 Hz, 2H).

Compound 108:
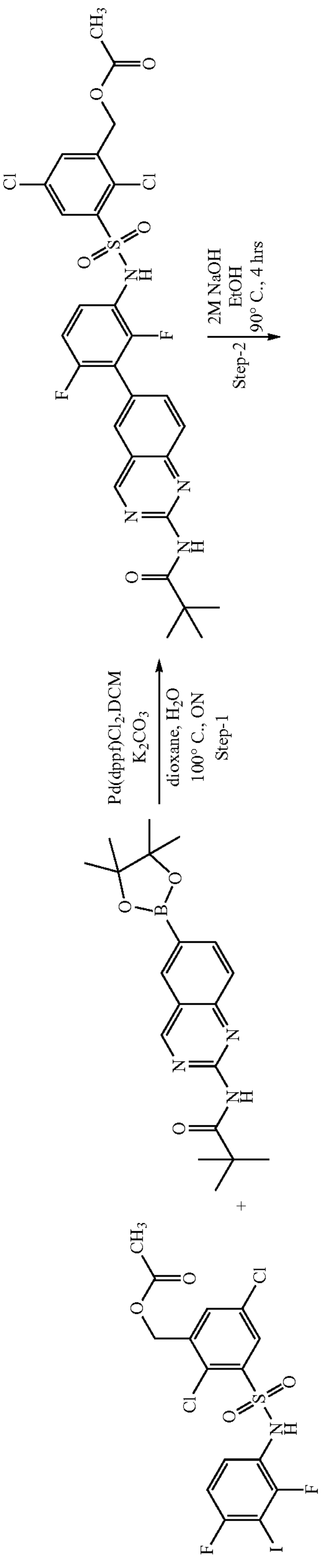

Step-1: Synthesis of 2,5-dichloro-3-(N-(2,4-difluoro-3-(2-pivalamidoquinazolin-6-yl)phenyl)sulfamoyl)benzyl acetate To a stirred solution of 2,5-dichloro-3-(N-(2,4-difluoro-3-iodophenyl)sulfamoyl)benzyl acetate (150 mg, 0.2797 mmol, 1.0 equiv) and N-(6-(4,4,5,5-tetramethyl-1,3,2-dioxaborolan-2-yl)quinazolin-2-yl)pivalamide (198.79 mg, 0.5595 mmol, 2.0 equiv) in dioxane:water (4:1, 5 mL) was added $K_2CO_3$ (116 mg, 0.8393 mmol, 3.0 equiv.). The resulting reaction mixture was purged with nitrogen for 15 minutes followed by the addition of Pd(dppf)$Cl_2$·DCM complex (11.42 mg, 0.0139 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$, evaporated under reduced pressure to obtain desired compound which was used to next step without purification (260 mg). Analytical Data: LCMS: 637.2 $[M+H]^+$

Step-2: Synthesis of N-(3-(2-aminoquinazolin-6-yl)-2,4-difluorophenyl)-2,5-dichloro-3-(hydroxymethyl)benzenesulfonamide To a stirred solution of 2,5-dichloro-3-(N-(2,4-difluoro-3-(2-pivalamidoquinazolin-6-yl)phenyl)sulfamoyl)benzyl acetate (260 mg, 0.4078 mmol, 1.0 equiv) in ethanol (4 mL) at room temperature was added 2M NaOH (6 mL). Then, the reaction mixture was allowed to stir at 90° C. for 4 h. Progress of the reaction was analyzed by TLC and LCMS. After completion of reaction, RM was concentrated under reduced pressure and was extracted with EtOAc (2×50 mL). The organic layers were combined, dried over anhydrous $Na_2SO_4$ and evaporated under reduced and further purified under flash chromatography to obtain desired compound which was triturated with hexane (3 mL) and pentane (2 mL) to obtain desired compound N-(3-(2-aminoquinazolin-6-yl)-

2,4-difluorophenyl)-2,5-dichloro-3-(hydroxymethyl)benzenesulfonamide (2 mg), Analytical Data: LCMS: 511.3 $[M+H]^+$, $^1H$ NMR (400 MHz, DMSO-$d_6$) δ 10.67 (br. s., 1H), 9.15 (s, 1H), 7.73-7.84 (m, 2H), 7.59 (br. s., 1H), 7.48 (d, J=8.33 Hz, 1H), 7.25 (br. s., 2H), 7.03 (br. s., 2H), 5.76 (s, 2H), 4.61 (d, J=5.70 Hz, 2H).

Compound 109:

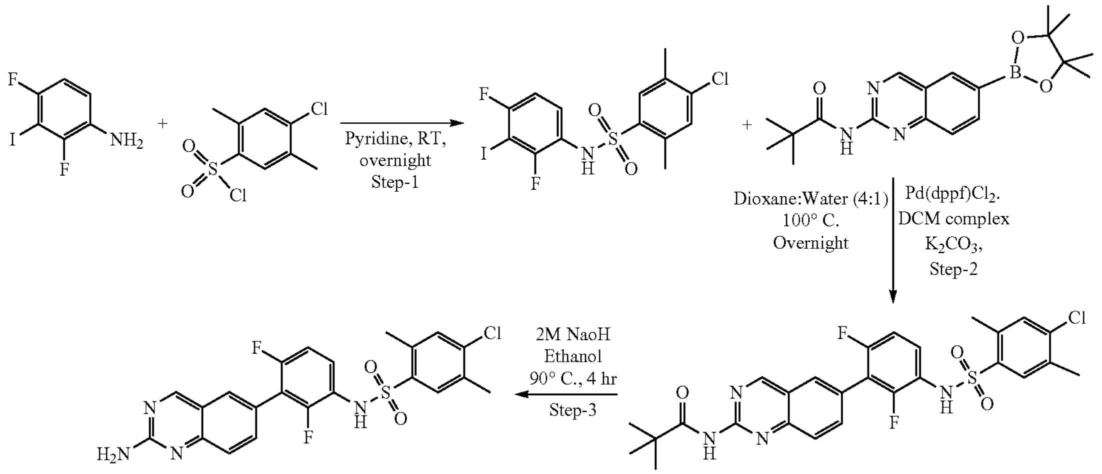

Step-1: Synthesis of 4-chloro-N-(2,4-difluoro-3-iodophenyl)-2,5-dimethylbenzenesulfonamide To a stirred solution of 2,4-difluoro-3-iodoaniline (100 mg, 0.0.392 mmol. 1.0 equiv.) in pyridine (1.5 mL) at room temperature was added 4-chloro-2,5-dimethylbenzenesulfonyl chloride (93.7 mg, 0.392 mmol. 1.0 equiv.) The resultant reaction mixture was stirred at room temperature for overnight. The progress of reaction was monitored through by TLC. After completion of the reaction, ice cold water had been added to reaction mixture. The precipitate formed was filtered using Buchner funnel and washed the product with 1N HCl to remove pyridine. This material was used to next reaction without further purification (128 mg).

Step 2: Synthesis of N-(6-(3-((4-chloro-2,5-dimethylphenyl)sulfonamido)-2,6-difluorophenyl)quinazolin-2-yl)pivalamide To a stirred solution of 4-chloro-N-(2,4-difluoro-3-iodophenyl)-2,5-dimethylbenzenesulfonamide (125 mg, 0.273 mmol, 1.0 equiv) and N-(6-(4,4,5,5-tetramethyl-1,3,2-dioxaborolan-2-yl)quinazolin-2-yl)pivalamide (116 mg, 0.327 mmol, 1.2 equiv) in Dioxane:Water (4:1, 5 mL) was added $K_2CO_3$ (113 mg, 0.819 mmol, 3.0 equiv.). The resulting reaction mixture was purged with nitrogen for 15 minutes followed by the addition of Pd(dppf)$Cl_2$·DCM complex (11 mg, 0.0136 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×150 mL). The organic layers were combined, dried over anhydrous $Na_2SO_4$ and evaporated under reduced pressure to obtain crude product which was used in to next reaction without further purification (117 mg).

Step 3: Synthesis of N-(3-(2-aminoquinazolin-6-yl)-2,4-difluorophenyl)-4-chloro-2,5-dimethylbenzenesulfonamide To a stirred solution of N-(6-(3-((4-chloro-2,5-dimethylphenyl)sulfonamido)-2,6-difluorophenyl)quinazolin-2-yl) pivalamide (117 mg, 0.0209 mmol, 1.0 equiv) in ethanol (5 mL) was added 2M NaOH (4 mL). Then, the reaction mixture was allowed to stir at 90° C. for 4 h. After completion of reaction, the solvent was evaporated and water was added to the reaction mixture, extracted with EtOAc (1×50 mL). The organic layers were combined, dried over anhydrous $Na_2SO_4$ and evaporated under reduced pressure to obtain crude product which was purified by reverse phase HPLC to obtain as title compound N-(3-(2-aminoquinazolin-6-yl)-2,4-difluorophenyl)-4-chloro-2,5-dimethylbenzenesulfonamide (15 mg), Analytical Data: LCMS: 475[M+H]$^+$, $^1$H NMR (400 MHz, DMSO-$d_6$) δ 10.41 (br. s., 1H), 9.14 (s, 1H), 7.77 (s, 2H), 7.63 (d, J=9.21 Hz, 1H), 7.46 (d, J=9.21 Hz, 1H), 7.19 (s, 1H), 7.07 (dd, J=9.65, 15.35 Hz, 1H), 6.92 (s, 2H), 6.69 (t, J=9.21 Hz, 1H), 2.12-2.36 (m, 3H), 1.82 (br. s., 3H).

Step 2: Synthesis of N-(6-(2,6-difluoro-3-(5-fluoro-2-methoxyphenylsulfonamido)phenyl)quinazolin-2-yl)pivalamide To a stirred solution of N-(2,4-difluoro-3-iodophenyl)-5-fluoro-2-methoxybenzenesulfonamide (125 mg, 0.28 mmol, 1.0 equiv) and N-(6-(4,4,5,5-tetramethyl-1,3,2-dioxaborolan-2-yl)quinazolin-2-yl)pivalamide (120 mg, 0.34 mmol, 1.2 equiv) in Dioxane:Water (4:1, 5 mL) was added $K_2CO_3$ (116 mg, 0.85 mmol, 3.0 equiv.). The resulting reaction mixture was purged with nitrogen for 15 minutes followed by the addition of Pd(dppf)$Cl_2$·DCM complex (11.5 mg, 0.014 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×150 mL). The organic layers were combined, dried over anhydrous $Na_2SO_4$ and evaporated under reduced pressure. The crude product was used in the next reaction without further purification (110 mg).

Compound 110:

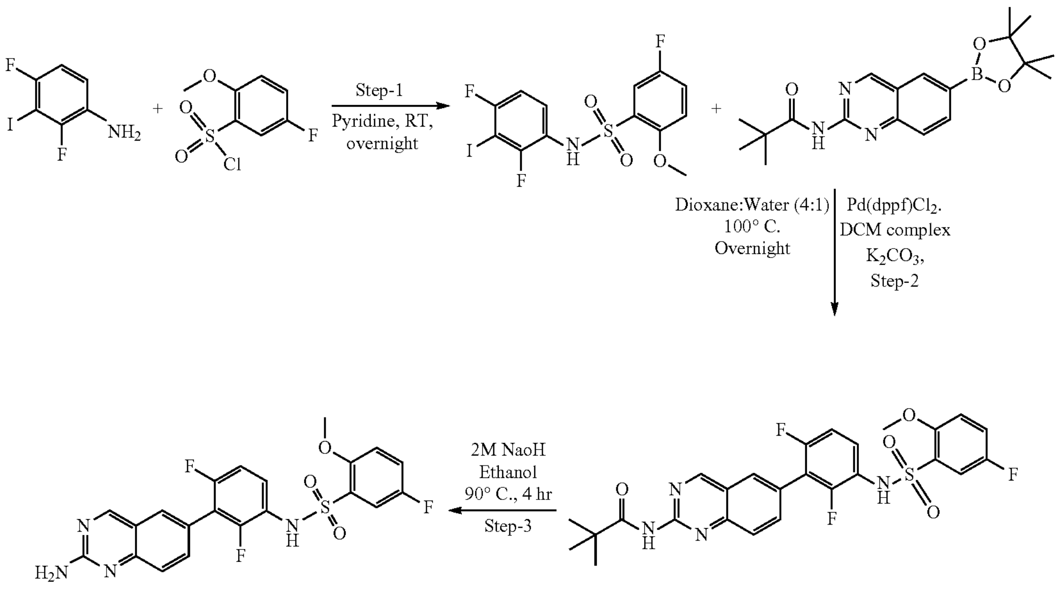

Step-1 Synthesis of N-(2,4-difluoro-3-iodophenyl)-5-fluoro-2-methoxybenzenesulfonamide To a stirred solution of 2,4-difluoro-3-iodoaniline (100 mg, 0.39 mmol. 1.0 equiv.) in pyridine (1.5 mL) at room temperature was added 5-fluoro-2-methoxybenzene-1-sulfonyl chloride (88 mg, 0.39 mmol. 1.0 equiv.) The resultant reaction mixture was stirred at room temperature for overnight. The progress of reaction was monitored by TLC. After completion of the reaction, ice cold water was added to the reaction mixture. The precipitate formed was filtered by using Buchner funnel and the product was washed with 1N HCl. This material was used in the next reaction without further purification (130 mg).

Step 3: Synthesis of N-(3-(2-aminoquinazolin-6-yl)-2,4-difluorophenyl)-5-fluoro-2-methoxybenzenesulfonamide To a stirred solution of N-(6-(2,6-difluoro-3-(5-fluoro-2-methoxyphenylsulfonamido)phenyl)quinazolin-2-yl)pivalamide (110 mg, 0.020 mmol, 1.0 equiv) in ethanol (5 mL) was added 2M NaOH (4 mL). Then, the reaction mixture stirred at 90° C. for overnight. After completion of reaction, the solvent was evaporated and water was added to the reaction mixture, extracted with EtOAc (1×50 mL). The organic layers were combined, dried over anhydrous $Na_2SO_4$ and evaporated under reduced pressure and purified by reverse phase silica gel chromatography to obtain title compound N-(3-(2-aminoquinazolin-6-yl)-2,4-difluorophenyl)-5-fluoro-2-methoxybenzenesulfonamide (15 mg), Analytical Data: LCMS: 461[M+H]$^+$, NMR: $^1$H NMR (400 MHz, DMSO-$d_6$) δ ppm 1.89 (s, 1H) 3.75 (s, 3H) 6.98 (s, 3H) 7.07-7.26 (m, 2H) 7.36 (br. s., 1H) 7.42-7.57 (m, 2H) 7.61 (d, J=8.77 Hz, 1H) 7.79 (s, 1H) 9.15 (s, 1H).

completion of reaction, reaction mixture was extracted with EtOAc (2×100 mL). The organic layers were combined, dried over anhydrous $Na_2SO_4$ and evaporated under reduced pressure to obtain title compound. This compound is used in further reaction without purification (705 mg).

Compound 111:

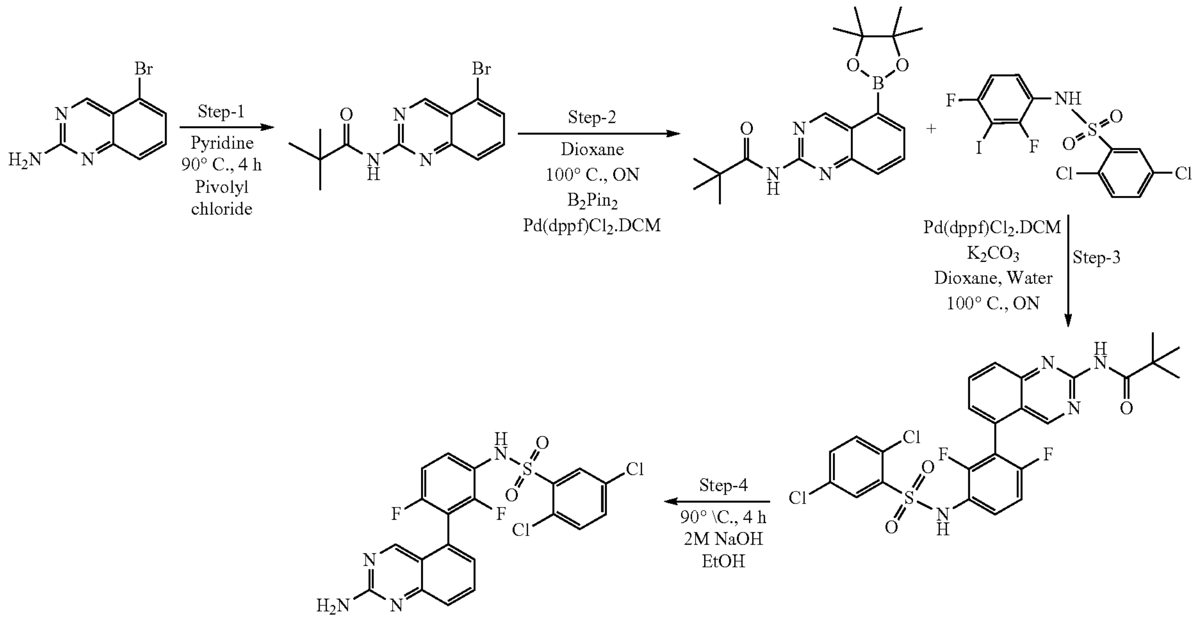

Step-1 Synthesis of N-(5-bromoquinazolin-2-yl)pivalamide

To a stirred solution of 5-bromoquinazolin-2-amine (1 g, 4.46 mmol. 1.0 equiv.) in pyridine (4 mL) at room temperature was added pivaloyl chloride (1.64 mL, 13.39 mmol. 3.0 equiv.) The resultant reaction mixture was heated at 90° C. for overnight. The progress of reaction was monitored through TLC and LCMS. After completion of the reaction, RM was quenched with 1N HCl to remove excess of pyridine, then was extracted with EtOAc (150 mL x 2 times) and was dried over sodium sulphate and concentrated under reduced pressure to obtain crude product which was further triturated with hexane (2 ml) and pentane (3 ml) to obtain desired compound N-(5-bromoquinazolin-2-yl)pivalamide (1.1 g).

Step-2: Synthesis of N-(5-(4,4,5,5-tetramethyl-1,3,2-dioxaborolan-2-yl)quinazolin-2-yl)pivalamide To a stirred solution of N-(5-bromoquinazolin-2-yl)pivalamide (400 mg, 1.30 mmol, 1.0 equiv) in dioxane (5 mL) was added $B_2Pin_2$ (494 mg, 1.95 mmol, 1.5 equiv) and potassium acetate (381.5 mg, 3.89 mmol, 3.0 equiv) and the RM was purged under nitrogen atmosphere for 10 min at RT followed by the addition of Pd(dppf)$Cl_2$ (47.4 mg, 0.065 mmol, 0.05 equiv.). The resulting reaction mixture was again purged with nitrogen for 5 minutes. The reaction mixture was heated to 100° C. for overnight. The progress of reaction was monitored through TLC and LCMS. After Step-3: Synthesis of N-(5-(3-(2,5-dichlorophenylsulfonamido)-2,6-difluorophenyl)quinazolin-2-yl)pivalamide To a stirred solution of 2,5-dichloro-N-(2,4-difluoro-3-iodophenyl)benzenesulfonamide (460 mg, 0.99 mmol, 1.0 equiv) and N-(5-(4,4,5,5-tetramethyl-1,3,2-dioxaborolan-2-yl)quinazolin-2-yl)pivalamide (704 mg, 1.98 mmol, 2.0 equiv)) in dioxane:water (6:2, 8 mL) was added $K_2CO_3$ (411 mg, 2.97 mmol, 3.0 equiv.). The resulting reaction mixture was purged with nitrogen for 15 minutes followed by the addition of Pd(dppf)$Cl_2$·DCM complex (40.4 mg, 0.0495 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure and further purified using flash chromatography to obtain desired compound N-(5-(3-(2,5-dichlorophenylsulfonamido)-2,6-difluorophenyl)quinazolin-2-yl)pivalamide (340 mg).

Step-4: Synthesis of N-(3-(2-aminoquinazolin-5-yl)-2,4-difluorophenyl)-2,5-dichlorobenzenesulfonamide To a stirred solution of N-(5-(3-(2,5-dichlorophenylsulfonamido)-2,6-difluorophenyl)quinazolin-2-yl)pivalamide (340 mg, 0.60 mmol, 1.0 equiv) in ethanol (6 mL) at room temperature was added 2M NaOH (5 mL). Then, the reaction mixture was allowed to stir at 90° C. for 4 hrs. Progress of the reaction was monitored by TLC and LCMS. After completion of the reaction, RM was extracted with EtOAc (2×100 mL) and dried over sodium sulphate. The organic layers were combined and concentrated under reduced pressure to obtain crude product. The compound was purified by using reverse phase chromatography technique to obtain desired compound N-(3-(2-aminoquinazolin-5-yl)-2,4-difluorophenyl)-2,5-dichlorobenzenesulfonamide (20 mg). Analytical Data: LCMS: 481.0 $[M+H]^+$, $^1H$ NMR (400 MHz, DMSO-$d_6$) δ ppm 6.96 (br. s., 3H) 7.12 (d, J=7.45 Hz, 1H) 7.20 (br. s., 1H) 7.38-7.58 (m, 3H) 7.70-7.78 (m, 1H) 7.90 (s, 1H) 8.52 (br. s., 1H) 11.95 (br. s., 1H).

Compound 112:
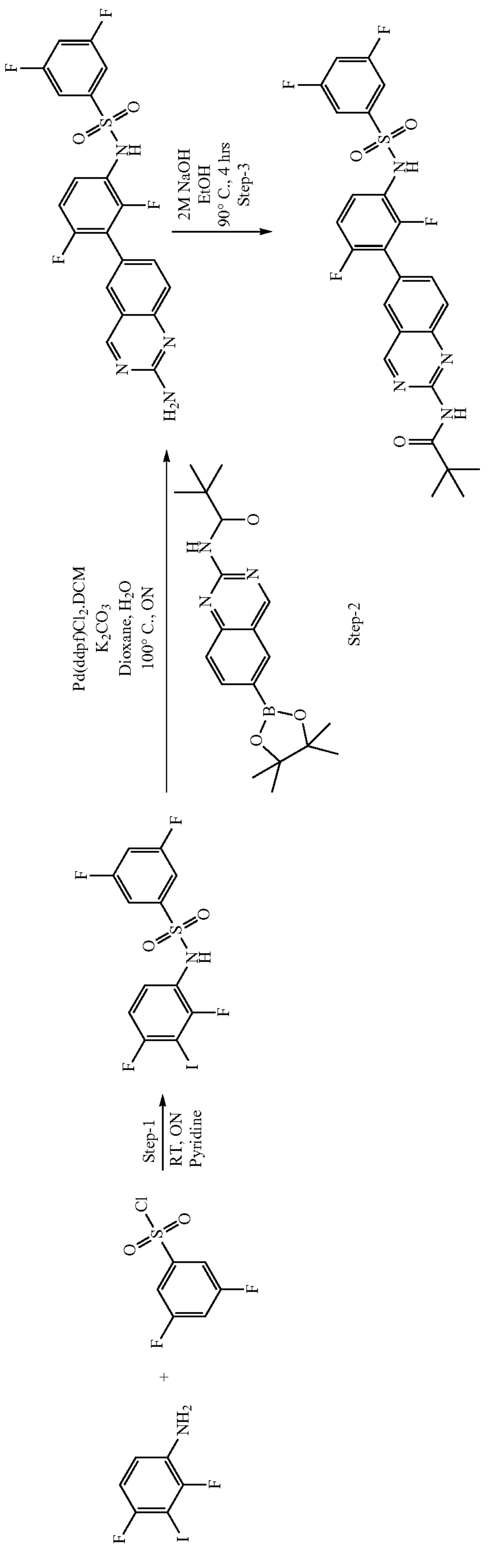

Step-1 Synthesis of N-(2,4-difluoro-3-iodophenyl)-3,5-difluorobenzenesulfonamide To a stirred solution of 2,4-difluoro-3-iodoaniline (100 mg, 0.39 mmol. 1.0 equiv.) in pyridine (1 mL) at room temperature was added 3,5-difluorobenzene-1-sulfonyl chloride (83.3 mg, 0.39 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc, dried over sodium sulphate and concentrated under vacuum to obtain crude product which was triturated with hexanes to obtain desired product N-(2,4-difluoro-3-iodophenyl)-3,5-difluorobenzenesulfonamide (105 mg).

Step 2: Synthesis of N-(6-(3-(3,5-difluorophenylsulfonamido)-2,6-difluorophenyl)quinazolin-2-yl) pivalamide To a stirred solution of N-(2,4-difluoro-3-iodophenyl)-3,5-difluorobenzenesulfonamide (105 mg, 0.24 mmol, 1.0 equiv) and N-(6-(4,4,5,5-tetramethyl-1,3,2-dioxaborolan-2-yl)quinazolin-2-yl)pivalamide (173 mg, 0.49 mmol, 2.0 equiv) in dioxane:water (3:1, 4 mL) was added $K_2CO_3$ (101 mg, 0.73 mmol, 3.0 equiv.). The resulting reaction mixture was purged with nitrogen for 10 minutes followed by the addition of $Pd(dppf)Cl_2{\cdot}DCM$ complex (10 mg, 0.012 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure to obtain title product N-(6-(3-(3,5-difluorophenylsulfonamido)-2,6-difluorophenyl)quinazolin-2-yl)pivalamide (230 mg). This product was used in next step without further purification.

Step-3: Synthesis of N-(3-(2-aminoquinazolin-6-yl)-2,4-difluorophenyl)-3,5-difluorobenzenesulfonamide To a stirred solution of N-(6-(3-(3,5-difluorophenylsulfonamido)-2,6-difluorophenyl)quinazolin-2-yl)pivalamide (230 mg, 0.43 mmol, 1.0 equiv) in ethanol (4 mL) at room temperature was added 2M NaOH (6 mL). Then, the reaction mixture was allowed to stir at 90° C. for 4 hrs. Progress of the reaction was monitored by TLC and LCMS. After completion of the reaction, RM was concentrated under reduced pressure to evaporate ethanol, extracted with EtOAc (2×50 mL). The organic layers were combined, dried over anhydrous $Na_2SO_4$, evaporated under reduced pressure to obtain crude product. This product was purified by using reverse phase chromatography technique to obtain desired compound N-(3-(2-aminoquinazolin-6-yl)-2,4-difluorophenyl)-3,5-difluorobenzenesulfonamide (10 mg), Analytical Data: LCMS: 449.06 $[M+H]^+$, $^1H$ NMR (400 MHz, DMSO-$d_6$) δ ppm 6.81 (br. s., 1H) 6.94 (s, 2H) 7.12 (d, J=6.14 Hz, 1H) 7.29 (d, J=6.58 Hz, 3H) 7.47 (d, J=8.77 Hz, 1H) 7.64 (d, J=7.89 Hz, 1H) 7.80 (s, 1H) 9.14 (s, 1H) 11.95 (br. s., 1H).

Compound 113:

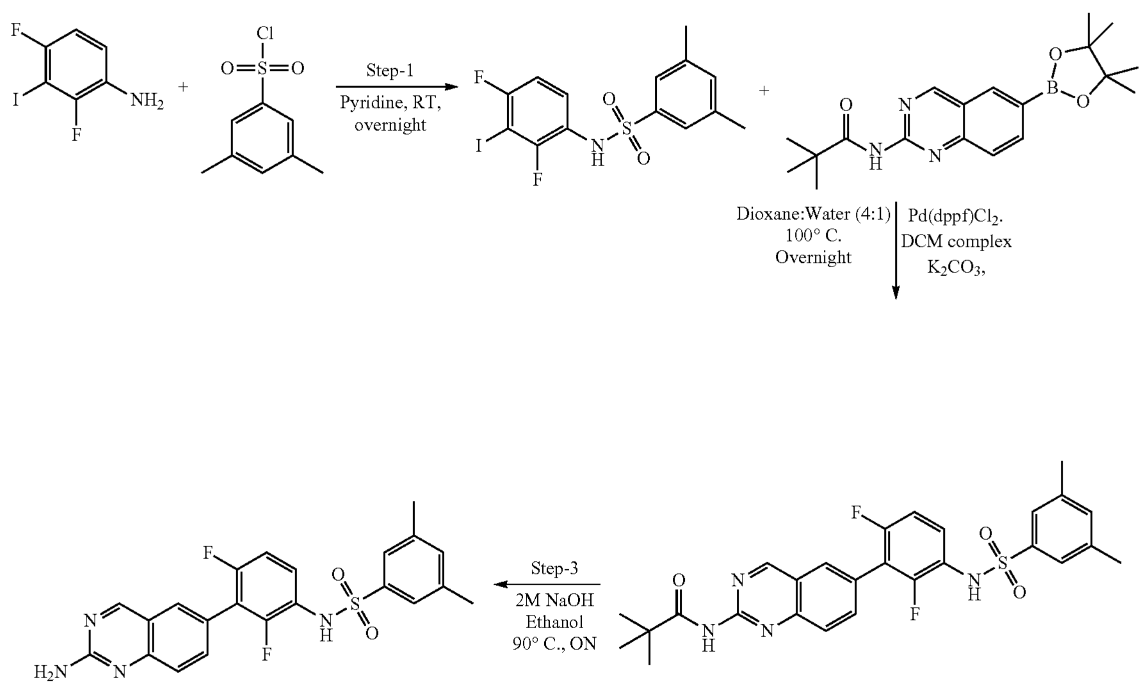

Step-1 Synthesis of 3,5-dimethyl-N-(2,4-difluoro-3-iodophenyl)benzenesulfonamide To a stirred solution of 2,4-difluoro-3-iodoaniline (100 mg, 0.39 mmol. 1.0 equiv.) in pyridine (1.0 mL) at room temperature was added 3,5-dimethylbenzenesulfonyl chloride (80 mg, 0.39 mmol. 1.0 equiv.) The resultant reaction mixture was stirred at room temperature for overnight. The progress of reaction was monitored by TLC. After completion of the reaction, ice cold water had been added to reaction mixture. The precipitate formed was filtered using Buchner funnel and washed the product with 1N HCl to remove pyridine. This material was used in the next reaction without further purification. (128 mg).

Step 2: Synthesis of N-(6-(3-((3,5-dimethylphenyl) sulfonamido)-2,6-difluorophenyl)quinazolin-2-yl) pivalamide To a stirred solution of 3,5-dimethyl-N-(2,4-difluoro-3-iodophenyl)benzenesulfonamide (125 mg, 0.30 mmol, 1.0

Step 3: Synthesis of N-(3-(2-aminoquinazolin-6-yl)-2,4-difluorophenyl)-3,5-dimethylbenzenesulfonamide To a stirred solution of N-(6-(3-((3,5-dimethylphenyl) sulfonamido)-2,6-difluorophenyl)quinazolin-2-yl)pivalamide (115 mg, 0.021 mmol, 1.0 equiv) in ethanol (5 mL) was added 2M NaOH (4 mL). Then, the reaction mixture was allowed to stir at 90° C. overnight. After completion of reaction, the solvent was evaporated and water was added to the reaction mixture, extracted with EtOAc (2×50 mL). The organic layers were combined, dried over anhydrous $Na_2SO_4$ and evaporated under reduced and purified by reverse phase silica gel chromatography to obtain as title compound N-(3-(2-aminoquinazolin-6-yl)-2,4-difluorophenyl)-3,5-dimethylbenzenesulfonamide (23 mg), Analytical Data: LCMS: 441 $[M+H]^+$, NMR: $^1H$ NMR (400 MHz, DMSO-$d_6$) δ ppm 2.31 (s, 6H) 7.01 (s, 2H) 7.14 (br. s., 1H) 7.22-7.29 (m, 2H) 7.34 (s, 2H) 7.48 (d, J=8.77 Hz, 1H) 7.59 (br. s., 1H) 7.76 (s, 1H) 9.14 (s, 1H) 10.12 (br. s., 1H).

Compound 115:

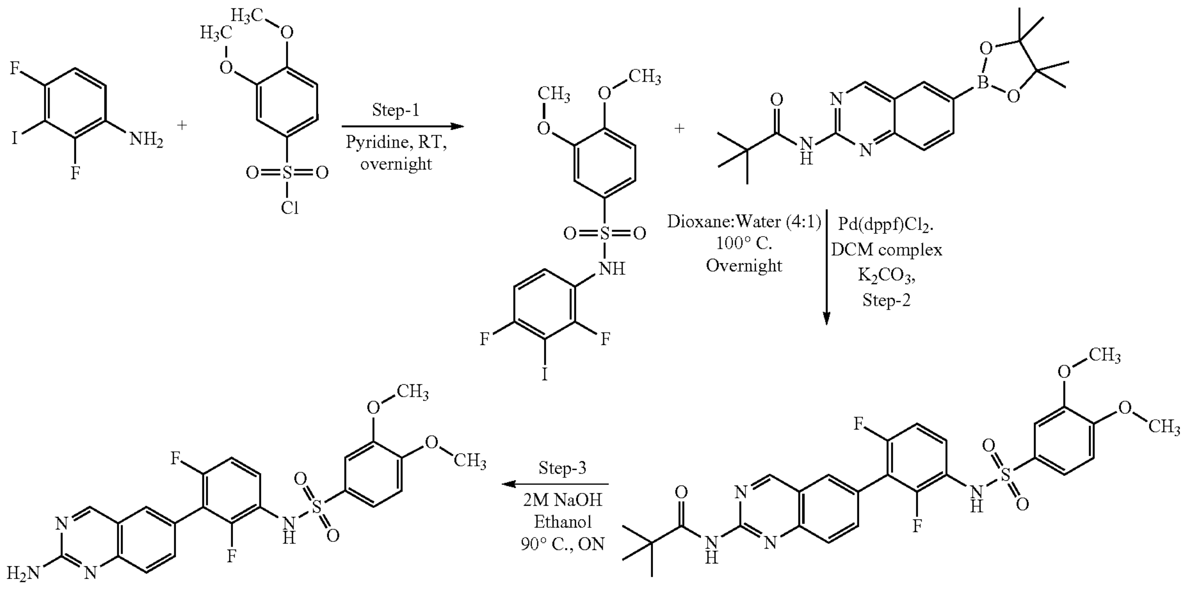

equiv) and (4,5,5-trimethyl-2-(2-pivalamidoquinazolin-6-yl)-1,3,2-dioxaborolan-4-yl)methylium (125 mg, 0.35 mmol, 1.2 equiv) in dioxane:Water (4:1, 5 mL) was added $K_2CO_3$ (122 mg, 0.89 mmol, 3.0 equiv.). The resulting reaction mixture was purged with nitrogen for 15 minutes followed by the addition of Pd(dppf)$Cl_2$·DCM complex (12 mg, 0.015 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×150 mL). The organic layers were combined, dried over anhydrous $Na_2SO_4$ and evaporated under reduced pressure. The crude product was used in the next reaction without further purification (115 mg), LCMS: 525 $[M+H]^+$.

Step-1 Synthesis of N-(2,4-difluoro-3-iodophenyl)-3,4-dimethoxybenzenesulfonamide To a stirred solution of 2,4-difluoro-3-iodoaniline (100 mg, 0.392 mmol. 1.0 equiv.) in pyridine (1.0 mL) at room temperature was added 3,4-dimethoxybenzene-1-sulfonyl chloride (92.8 mg, 0.3921 mmol. 1.0 equiv.) The resultant reaction mixture was stirred at room temperature for overnight. The progress of reaction was monitored through by TLC. After completion of the reaction, ice cold water was added to reaction mixture. The precipitate formed which was filtered by using Buchner funnel and washed the product with 1N HCl. This material was used to next step without further purification (156 mg).

Step-2: Synthesis of N-(6-(3-(3,4-dimethoxyphenylsulfonamido)-2,6-difluorophenyl)quinazolin-2-yl) pivalamide To a stirred solution of N-(2,4-difluoro-3-iodophenyl)-3,4-dimethoxybenzenesulfonamide (156 mg, 0.3426 mmol, 1.0 equiv) and N-(6-(4,4,5,5-tetramethyl-1,3,2-dioxaborolan-2-yl)quinazolin-2-yl)pivalamide (243.4 mg, 0.6853 mmol, 2.0 equiv) in Dioxane:Water (4:2, 6 mL) was added $K_2CO_3$ (142 mg, 1.0280 mmol, 3.0 equiv.). The resulting reaction mixture was purged with nitrogen for 15 minutes followed by the addition of Pd(dppf)$Cl_2$·DCM complex (11.5 mg, 0.014 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure to obtain crude product which was used to next step without further purification (300 mg). LCMS: 557.3[M+H]$^+$ Step 3: Synthesis of N-(3-(2-aminoquinazolin-6-yl)-2,4-difluorophenyl)-3,4-dimethoxybenzenesulfonamide To a stirred solution of N-(6-(3-(3,4-dimethoxyphenylsulfonamido)-2,6-difluorophenyl)quinazolin-2-yl)pivalamide (300 mg, 0.5390 mmol, 1.0 equiv) in ethanol (6 mL) was added 2M NaoH (4 mL). Then, the reaction mixture was allowed to stir at 90 degree Celsius for 3H. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase silica gel chromatography to obtain title compound N-(3-(2-aminoquinazolin-6-yl)-2,4-difluorophenyl)-3,4-dimethoxybenzenesulfonamide (3 mg), Analytical Data: LCMS: 473.4[M+H]$^+$, NMR: $^1$H NMR (400 MHz, DMSO-$d_6$) δ ppm 3.74 (s, 3H) 3.82 (s, 3H) 7.03 (s, 2H) 7.11 (d, J=8.33 Hz, 1H) 7.15-7.32 (m, 4H) 7.47 (d, J=8.77 Hz, 1H) 7.56 (d, J=8.33 Hz, 1H) 7.74 (s, 1H) 9.13 (s, 1H) 10.03 (br. s., 1H)

Compound 116

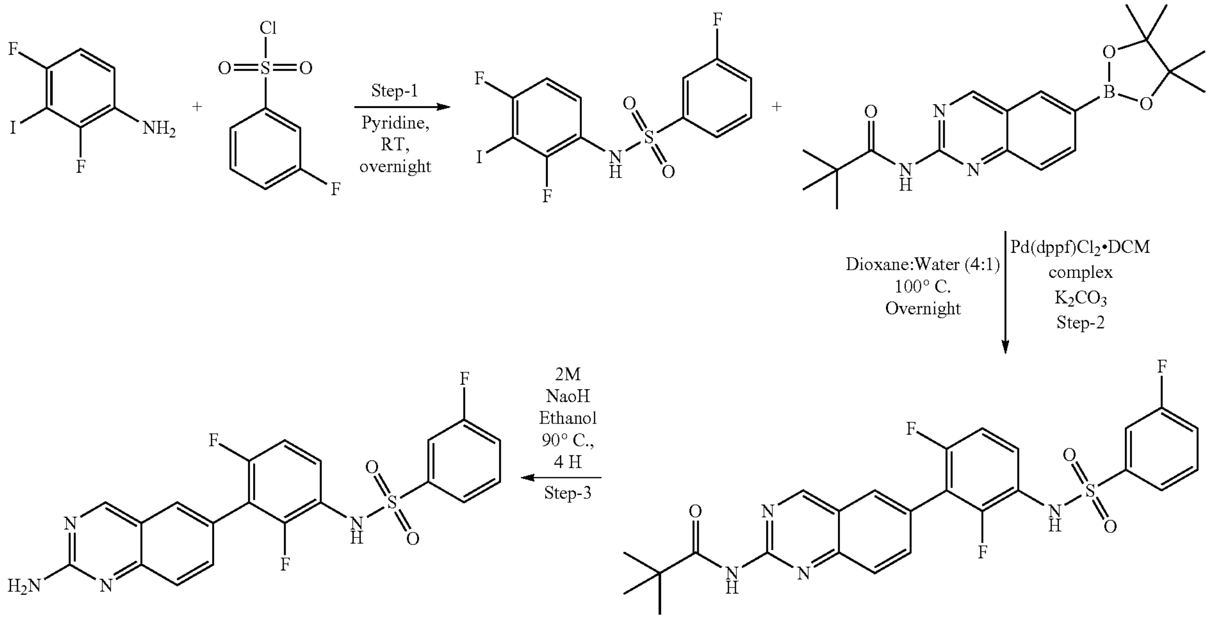

Step-1 Synthesis of N-(2,4-difluoro-3-iodophenyl)-3-fluorobenzenesulfonamide

To a stirred solution of 2,4-difluoro-3-iodoaniline (150 mg, 0.5882 mmol. 1.0 equiv.) in pyridine (1.0 mL) at room temperature was added 3-fluorobenzene-1-sulfonyl chloride (144.4 mg, 0.5882 mmol. 1.0 equiv.) The resultant reaction mixture was stirred at room temperature for overnight. The progress of reaction was monitored by TLC. After completion of the reaction, ice cold water had been added to reaction mixture. The precipitate formed which was filtered by using Buchner funnel and washed the product with 1N HCl. This material was used to next step without further purification (192 mg).

Step-2: Synthesis of N-(6-(2,6-difluoro-3-(3-fluorophenylsulfonamido)phenyl)quinazolin-2-yl)pivalamide To a stirred solution of N-(2,4-difluoro-3-iodophenyl)-3-fluorobenzenesulfonamide (180 mg, 0.4356 mmol, 1.0 equiv) and N-(6-(4,4,5,5-tetramethyl-1,3,2-dioxaborolan-2-yl)quinazolin-2-yl)pivalamide (185.7 mg, 0.5228 mmol, 1.2 equiv) in Dioxane:Water (3:1, 4 mL) was added $K_2CO_3$ (180.6 mg, 1.3070 mmol, 3.0 equiv.). The resulting reaction mixture was purged with nitrogen for 10 minutes followed by the addition of Pd(dppf)$Cl_2$·DCM complex (17.7 mg, 0.0217 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next step without further purification (320 mg). LCMS: 515.3[M+H]$^+$ Step-3: Synthesis of N-(3-(2-aminoquinazolin-6-yl)-2,4-difluorophenyl)-3-fluorobenzenesulfonamide To a stirred solution of N-(6-(2,6-difluoro-3-(3-fluorophenylsulfonamido)phenyl)quinazolin-2-yl)pivalamide (320 mg, 0.6219 mmol, 1.0 equiv) in ethanol (6 mL) was added 2M NaoH (5 mL). Then, the reaction mixture was allowed to stir at 90 degree Celsius for 2H. After completion of reaction, the solvent was evaporated and water was added to the reaction mixture, extracted with EtOAc (2×100 mL). The organic layers were combined, dried over anhydrous $Na_2SO_4$ and evaporated under reduced, evaporated under reduced and purified by reverse phase HPLC to obtain as title compound N-(3-(2-aminoquinazolin-6-yl)-2,4-difluorophenyl)-3-fluorobenzenesulfonamide (20 mg), Analytical Data: LCMS: 431.2[M+H]$^+$, NMR: $^1$H NMR (400 MHz, DMSO-$d_6$) δ ppm 7.00 (s, 2H) 7.09 (t, J=9.21 Hz, 1H) 7.18-7.27 (m, 1H) 7.41-7.64 (m, 7H) 7.76 (s, 1H) 9.14 (s, 1H).

Compound 117

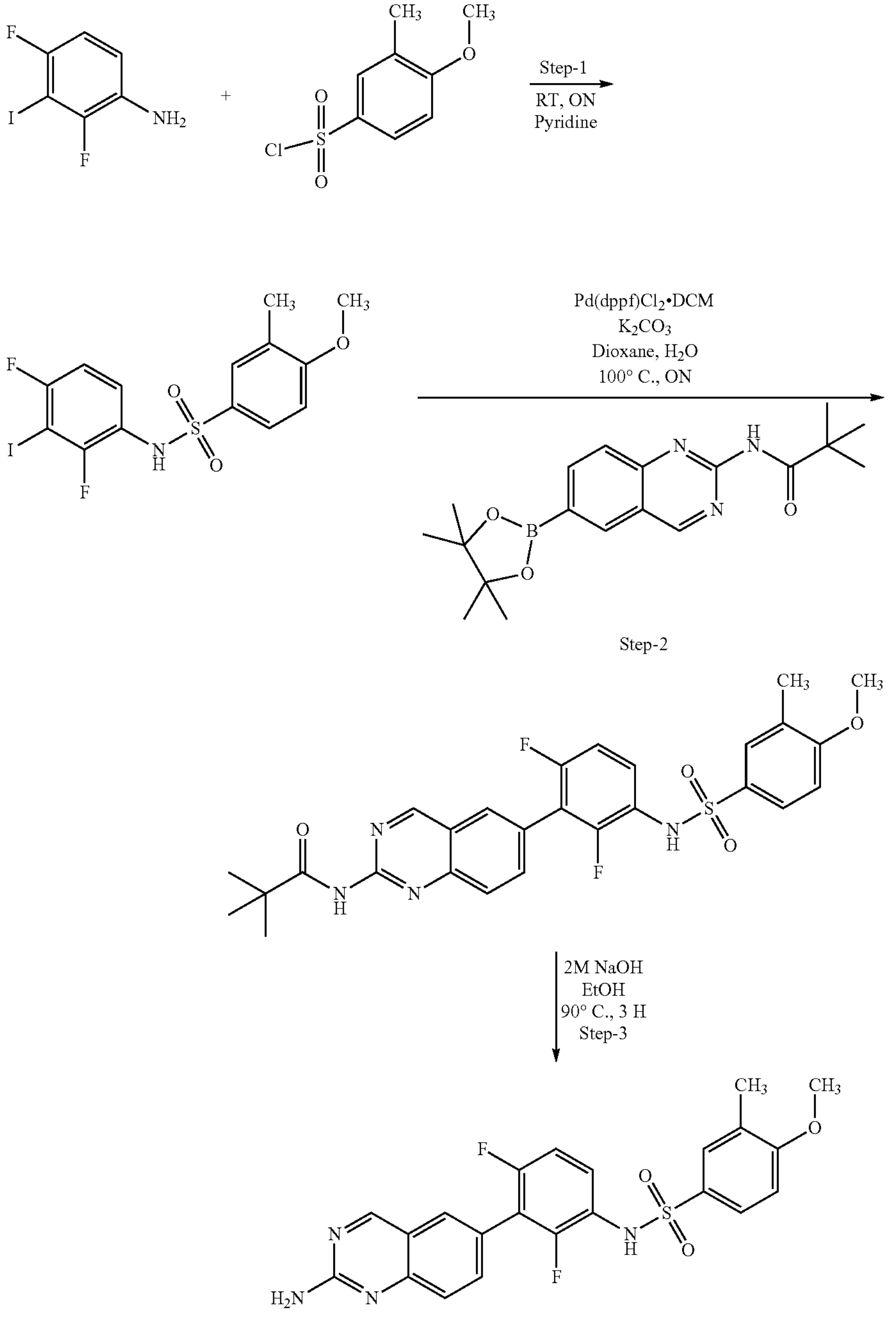

Step-1 Synthesis of N-(2,4-difluoro-3-iodophenyl)-4-methoxy-3-methylbenzenesulfonamide To a stirred solution of 2,4-difluoro-3-iodoaniline (200 mg, 0.7843 mmol. 1.0 equiv.) in pyridine (2 mL) at room temperature was added 4-methoxy-3-methylbenzene-1-sulfonyl chloride (173.07 mg, 0.7843 mmol, 1.0 equiv.) The resultant reaction mixture was stirred at room temperature for overnight. The progress of reaction was monitored by TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc, dried over sodium sulphate and concentrated under vacuum to obtain crude product which was triturated with hexanes to obtain desired product N-(2,4-difluoro-3-iodophenyl)-4-methoxy-3-methylbenzenesulfonamide (340 mg).

Step-2: Synthesis of N-(6-(2,6-difluoro-3-(4-methoxy-3 methylphenylsulfonamido)phenyl)quinazolin-2-yl)pivalamide To a stirred solution of N-(2,4-difluoro-3-iodophenyl)-4-methoxy-3-methylbenzenesulfonamide (340 mg, 0.7740 mmol, 1.0 equiv) and N-(6-(4,4,5,5-tetramethyl-1,3,2-dioxaborolan-2-yl)quinazolin-2-yl)pivalamide (329.9 mg, 0.9289 mmol, 1.2 equiv) in dioxane:water (4:1, 5 mL) was added $K_2CO_3$ (320.9 mg, 2.3222 mmol, 3.0 equiv.). The resulting reaction mixture was purged with nitrogen for 10 minutes followed by the addition of $Pd(dppf)Cl_2{\cdot}DCM$ complex (31.6 mg, 0.0387 mmol, 0.05 equiv.). The reaction mixture was again purged with nitrogen for 5 minutes. The reaction mixture was heated to 100° C. for overnight. The progress of reaction was monitored by TLC and LCMS. After completion of reaction, water was added to the reaction mixture, extracted with EtOAc (2×100 mL). The organic layers were combined, dried over anhydrous $Na_2SO_4$ and evaporated under reduced pressure to obtain title product N-(6-(2,6-difluoro-3-(4-methoxy-3-methylphenylsulfonamido)phenyl)quinazolin-2-yl)pivalamide (600 mg). This product was used in next step without further purification. LCMS: 541.16[M+H]$^+$ Step-3: Synthesis of N-(3-(2-aminoquinazolin-6-yl)-2,4-difluorophenyl)-4-methoxy-3-methylbenzenesulfonamide To a stirred solution of N-(6-(2,6-difluoro-3-(4-methoxy-3-methylphenylsulfonamido)phenyl)quinazolin-2-yl)pivalamide (600 mg, 1.1098 mmol, 1.0 equiv) in ethanol (4 mL) at room temperature was added 2M NaOH (6 mL). Then, the reaction mixture was allowed to stir at 90° C. for 3 h. Progress of the reaction was monitored by TLC and LCMS. After completion of the reaction, RM was concentrated under reduced pressure to evaporate ethanol, extracted with EtOAc (2×100 mL). The organic layers were combined, dried over anhydrous $Na_2SO_4$, evaporated under reduced pressure to obtain crude product. This product was purified by using reverse phase chromatography technique to obtain desired compound N-(3-(2-aminoquinazolin-6-yl)-2,4-difluorophenyl)-4-methoxy-3-methylbenzenesulfonamide (53 mg), Analytical Data: LCMS: 457.4 [M+H]$^+$, $^1$H NMR (400 MHz, DMSO-$d_6$) δ ppm 2.15 (s, 3H) 3.84 (s, 3H) 7.00 (s, 2H) 7.04 (s, 1H) 7.05-7.11 (m, 2H) 7.16-7.26 (m, 1H) 7.45-7.60 (m, 4H) 7.75 (s, 1H) 9.13 (s, 1H)

Compound 118

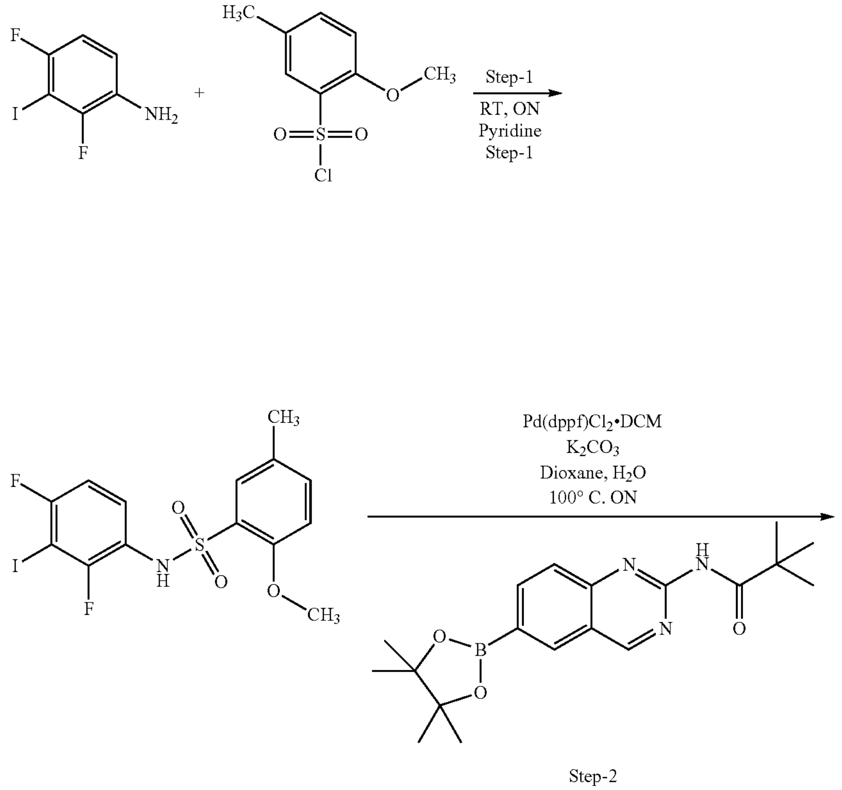

-continued

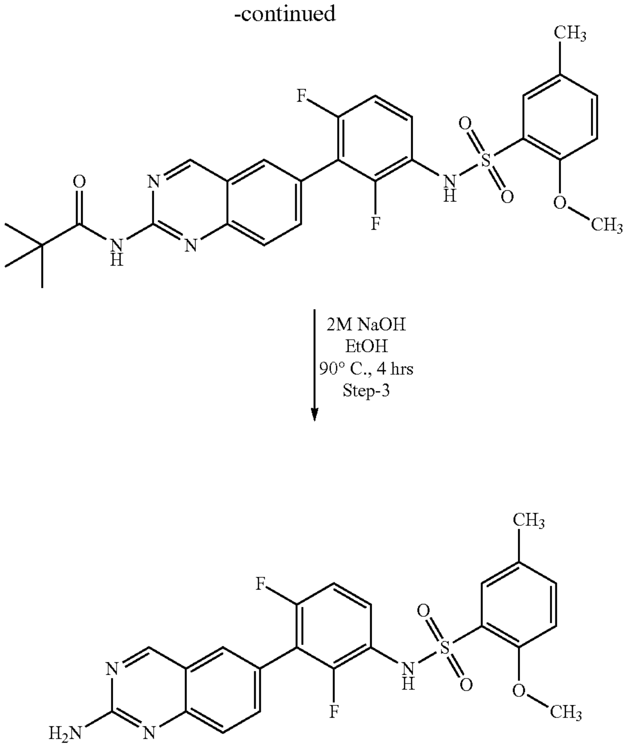

Step-1 Synthesis of N-(2,4-difluoro-3-iodophenyl)-2-methoxy-5-methylbenzenesulfonamide To a stirred solution of 2,4-difluoro-3-iodoaniline (200 mg, 0.7843 mmol. 1.0 equiv.) in pyridine (2 mL) at room temperature was added 2-methoxy-5-methylbenzene-1-sulfonyl chloride (173.07 mg, 0.7843 mmol. 1.0 equiv.) The resultant reaction mixture was stirred at room temperature for overnight. The progress of reaction was monitored by TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc, dried over sodium sulphate and concentrated under vacuum to obtain crude product which was triturated with hexanes to obtain desired product N-(2,4-difluoro-3-iodophenyl)-2-methoxy-5-methylbenzenesulfonamide (315 mg).

Step-2: Synthesis of N-(6-(2,6-difluoro-3-(2-methoxy-5-methylphenylsulfonamido)phenyl)quinazolin-2-yl)pivalamide To a stirred solution of N-(2,4-difluoro-3-iodophenyl)-2-methoxy-5-methylbenzenesulfonamide (315 mg, 0.7171 mmol, 1.0 equiv) and N-(6-(4,4,5,5-tetramethyl-1,3,2-dioxaborolan-2-yl)quinazolin-2-yl)pivalamide (305.7 mg, 0.8606 mmol, 1.2 equiv) in dioxane:water (4:1, 5 mL) was added $K_2CO_3$ (297.3 mg, 2.1515 mmol, 3.0 equiv.). The resulting reaction mixture was purged with nitrogen for 10 minutes followed by the addition of Pd(dppf)$Cl_2$·DCM complex (29.28 mg, 0.0358 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure to obtain title product N-(6-(2,6-difluoro-3-(2-methoxy-5-methylphenylsulfonamido)phenyl)quinazolin-2-yl)pivalamide (560 mg). This product was used in next step without further purification. LCMS: 541.4 $[M+H]^+$ Step-3: Synthesis of N-(3-(2-aminoquinazolin-6-yl)-2,4-difluorophenyl)-2-methoxy-5-methylbenzenesulfonamide To a stirred solution of N-(6-(2,6-difluoro-3-(2-methoxy-5-methylphenylsulfonamido)phenyl)quinazolin-2-yl)pivalamide (560 mg, 1.0359 mmol, 1.0 equiv) in ethanol (6 mL) at room temperature was added 2M NaOH (7 mL). Then, the reaction mixture was allowed to stir at 90° C. for 4 hrs. Progress of the reaction was monitored by TLC and LCMS. After completion of the reaction, RM was concentrated under reduced pressure to evaporate ethanol, extracted with EtOAc (2×100 mL). The organic layers were combined, dried over anhydrous $Na_2SO_4$, evaporated under reduced pressure to obtain crude product. This product was purified by using reverse phase chromatography technique to obtain desired compound N-(3-(2-aminoquinazolin-6-yl)-2,4-difluorophenyl)-2-methoxy-5-methylbenzenesulfonamide (70 mg), Analytical Data: LCMS: 457.4 $[M+H]^+$, $^1H$ NMR (400 MHz, DMSO-$d_6$) δ ppm 2.24 (s, 3H) 3.76 (s, 3H) 7.01 (br. s., 2H) 7.03-7.14 (m, 2H) 7.14-7.30 (m, 2H) 7.36 (d, J=8.33 Hz, 1H) 7.43-7.53 (m, 2H) 7.59 (d, J=8.33 Hz, 1H) 7.78 (br. s., 1H) 9.15 (s, 1H)

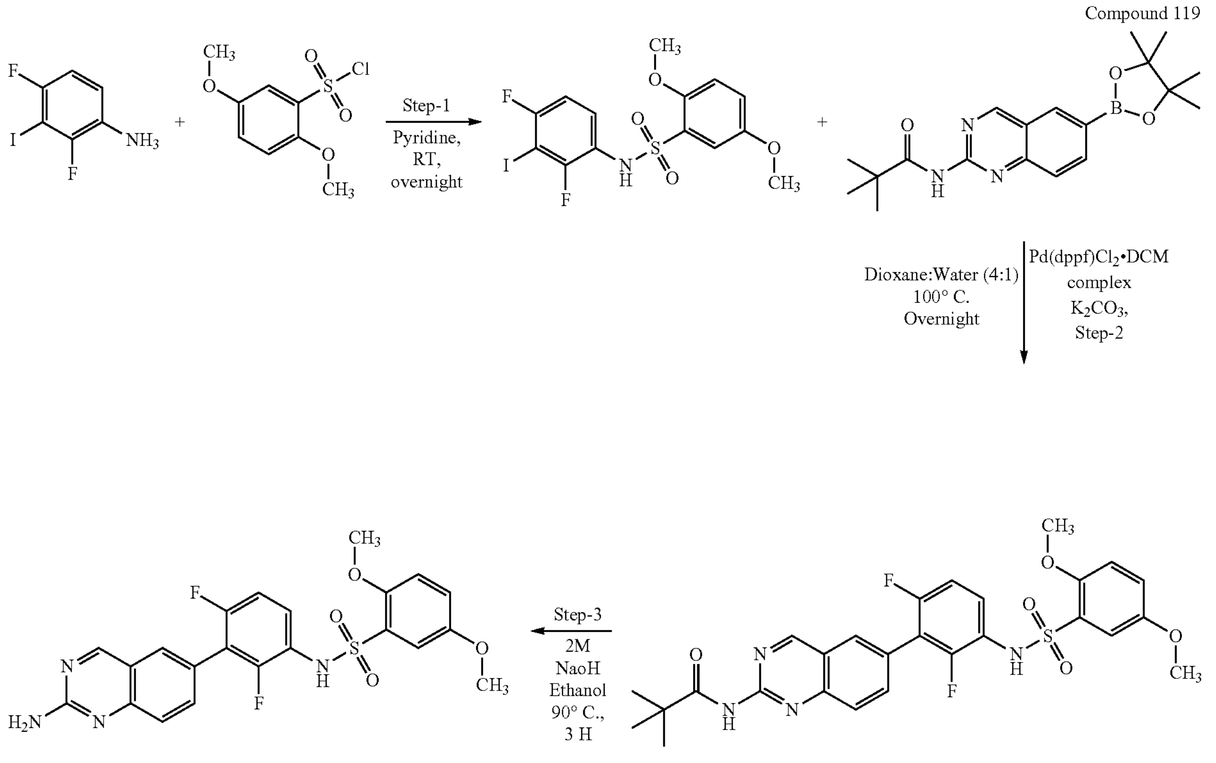 [SMILES: Nc1ccc(F)c(I)c1F ; COc1ccc(OC)c(S(=O)(=O)Cl)c1 ; COc1ccc(OC)c(S(=O)(=O)Nc2ccc(F)c(I)c2F)c1 ; CC(C)(C)C(=O)Nc1ncc2cc(B3OC(C)(C)C(C)(C)O3)ccc2n1 ; COc1ccc(OC)c(S(=O)(=O)Nc2ccc(F)c(-c3ccc4nc(N)ncc4c3)c2F)c1 ; COc1ccc(OC)c(S(=O)(=O)Nc2ccc(F)c(-c3ccc4nc(NC(=O)C(C)(C)C)ncc4c3)c2F)c1]

Step-1: Synthesis of N-(2,4-difluoro-3-iodophenyl)-2,5-dimethoxybenzenesulfonamide To a stirred solution of 2,4-difluoro-3-iodoaniline (200 mg, 0.7843 mmol. 1.0 equiv.) in pyridine (2.0 mL) at room temperature was added 2,5-dimethoxybenzene-1-sulfonyl chloride (185.6 mg, 0.7843 mmol. 1.0 equiv.) The resultant reaction mixture was stirred at room temperature for overnight. The progress of reaction was monitored by TLC. After completion of the reaction, ice cold water had been added to reaction mixture. The precipitate formed was filtered using Buchner funnel and washed the product with 1N HCl to remove pyridine. This material was used in the next reaction without further purification (287 mg).

Step 2: Synthesis of N-(6-(3-(2,5-dimethoxyphenylsulfonamido)-2,6-difluorophenyl)quinazolin-2-yl) pivalamide To a stirred solution of N-(2,4-difluoro-3-iodophenyl)-2,5-dimethoxybenzenesulfonamide (287 mg, 0.6304 mmol, 1.0 equiv) and N-(6-(4,4,5,5-tetramethyl-1,3,2-dioxaborolan-2-yl)quinazolin-2-yl)pivalamide (268.7 mg, 0.7565 mmol, 1.2 equiv) in dioxane:Water (4:1, 5 mL) was added $K_2CO_3$ (261.3 mg, 1.8914 mmol, 3.0 equiv.). The resulting reaction mixture was purged with nitrogen for 10 minutes followed by the addition of $Pd(dppf)Cl_2 \cdot DCM$ complex (25.7 mg, 0.0315 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used to next step without further purification (500 mg), LCMS: 557.3 $[M+H]^+$.

Step-3: Synthesis of N-(3-(2-aminoquinazolin-6-yl)-2,4-difluorophenyl)-2,5-dimethoxybenzenesulfonamide To a stirred solution of N-(6-(3-(2,5-dimethoxyphenylsulfonamido)-2,6-difluorophenyl)quinazolin-2-yl)pivalamide (500 mg, 0.8983 mmol, 1.0 equiv) in ethanol (4 mL) was added 2M NaOH (6 mL). Then, the reaction mixture was allowed to stir at 90° C. for 3H. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)-2,5-dimethoxybenzenesulfonamide (90 mg), Analytical Data: LCMS: 473.4 $[M+H]^+$, NMR: $^1H$ NMR (400 MHz, DMSO-$d_6$) δ ppm 3.72 (s, 3H) 3.70 (s, 3H) 6.93-7.09 (m, 5H) 7.18-7.28 (m, 2H) 7.48 (d, J=8.77 Hz, 1H) 7.61 (d, J=8.77 Hz, 1H) 7.79 (s, 1H) 9.16 (s, 1H) 10.03 (s, 1H).

Compound 120

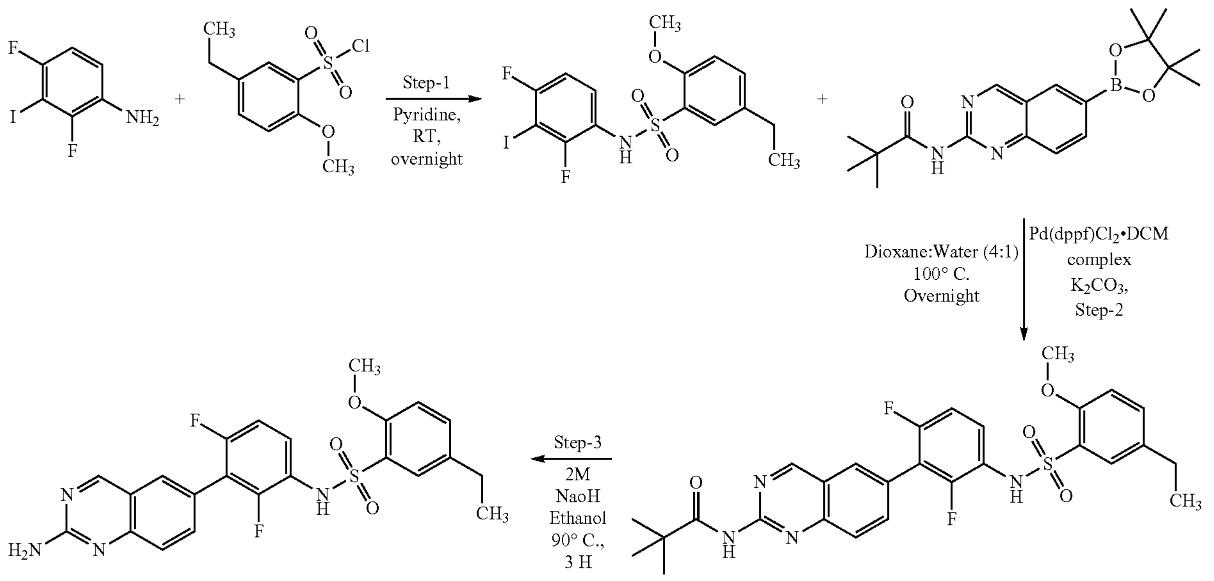

Step-1: Synthesis of N-(2,4-difluoro-3-iodophenyl)-5-ethyl-2-methoxybenzenesulfonamide To a stirred solution of 2,4-difluoro-3-iodoaniline (200 mg, 0.7843 mmol. 1.0 equiv.) in pyridine (2.0 mL) at room temperature was added 5-ethyl-2-methoxybenzene-1-sulfonyl chloride (184.07 mg, 0.7843 mmol. 1.0 equiv.) The resultant reaction mixture was stirred at room temperature for overnight. The progress of reaction was monitored by TLC. After completion of the reaction, ice cold water was added to reaction mixture. The precipitate formed was filtered using Buchner funnel and washed the product with 1N HCl to remove pyridine. This material was used to next reaction without further purification (212 mg).

Step 2: Synthesis of N-(6-(3-(5-ethyl-2-methoxy-phenylsulfonamido)-2,6-difluorophenyl)quinazolin-2-yl)pivalamide To a stirred solution of N-(2,4-difluoro-3-iodophenyl)-5-ethyl-2-methoxybenzenesulfonamide (200 mg, 0.4412 mmol, 1.0 equiv) and N-(6-(4,4,5,5-tetramethyl-1,3,2-dioxaborolan-2-yl)quinazolin-2-yl)pivalamide (188.1 mg, 0.5295 mmol, 1.2 equiv) in dioxane:Water (4:1, 5 mL) was added $K_2CO_3$ (182.9 mg, 1.3238 mmol, 3.0 equiv.). The resulting reaction mixture was purged with nitrogen for 10 minutes followed by the addition of Pd(dppf)$Cl_2$·DCM complex (18.01 mg, 0.0220 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next reaction without further purification (493 mg), LCMS: 555.4 $[M+H]^+$.

Step 3: Synthesis of N-(3-(2-aminoquinazolin-6-yl)-2,4-difluorophenyl)-5-ethyl-2-methoxybenzenesulfonamide To a stirred solution of N-(6-(3-(5-ethyl-2-methoxyphenylsulfonamido)-2,6-difluorophenyl)quinazolin-2-yl)pivalamide (490 mg, 0.8835 mmol, 1.0 equiv) in ethanol (4 mL) was added 2M NaoH (6 mL). Then, the reaction mixture was allowed to stir at 90° C. for 3H. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)-5-ethyl-2-methoxybenzenesulfonamide (14 mg), Analytical Data: LCMS: 471.4 $[M+H]^+$, NMR: $^1$H NMR (400 MHz, DMSO-$d_6$) δ ppm 1.09 (t, J=7.24 Hz, 3H) 2.54 (d, J=8.33 Hz, 2H) 3.76 (br. s., 3H) 7.01 (br. s., 2H) 7.10 (d, J=8.77 Hz, 2H) 7.12 (s, 1H) 7.27 (d, J=5.70 Hz, 1H) 7.41 (d, J=7.45 Hz, 1H) 7.46-7.53 (m, 2H) 7.58 (d, J=8.33 Hz, 1H) 7.77 (br. s., 1H) 9.15 (br. s., 1H).

Compound 121

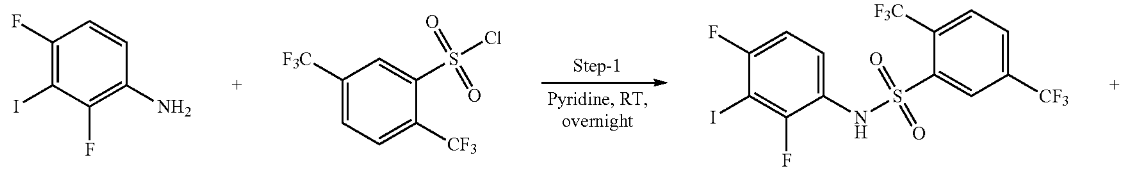

-continued

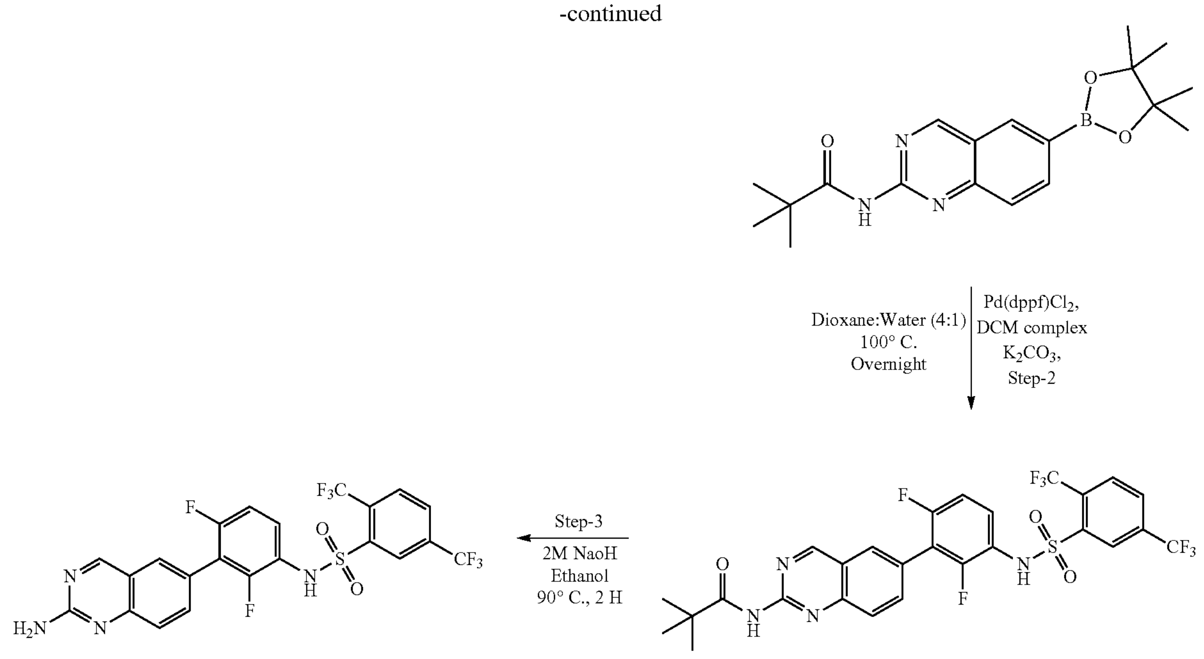

Step-1 Synthesis of N-(2,4-difluoro-3-iodophenyl)-2,5-bis(trifluoromethyl)benzenesulfonamide To a stirred solution of 2,4-difluoro-3-iodoaniline (200 mg, 0.7843 mmol. 1.0 equiv.) in pyridine (2.0 mL) at room temperature was added 2,5-bis(trifluoromethyl)benzene-1-sulfonyl chloride (245.18 mg, 0.7843 mmol. 1.0 equiv.) The resultant reaction mixture was stirred at room temperature for overnight. The progress of reaction was monitored through by TLC. After completion of the reaction, ice cold water was added to reaction mixture. The precipitate formed was filtered using Buchner funnel and washed the product with 1N HCl to remove pyridine. This material was used to next step without further purification. (370 mg).

Step 2: Synthesis of N-(6-(3-(2,5-bis(trifluoromethyl)phenylsulfonamido)-2,6-difluorophenyl)quinazolin-2-yl)pivalamide To a stirred solution of N-(2,4-difluoro-3-iodophenyl)-2,5-bis(trifluoromethyl)benzenesulfonamide (370 mg, 0.6965 mmol, 1.0 equiv) and N-(6-(4,4,5,5-tetramethyl-1,3,2-dioxaborolan-2-yl)quinazolin-2-yl)pivalamide (296.9 mg, 0.8359 mmol, 1.2 equiv) in dioxane:Water (4:1, 5 mL) was added $K_2CO_3$ (288.8 mg, 2.0780 mmol, 3.0 equiv.). The resulting reaction mixture was purged with nitrogen for 10 minutes followed by the addition of Pd(dppf)$Cl_2$·DCM complex (28.4 mg, 0.0348 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used to next step without further purification (610 mg), LCMS: 633.3 $[M+H]^+$.

Step 3: Synthesis of N-(3-(2-aminoquinazolin-6-yl)-2,4-difluorophenyl)-2,5-bis(trifluoromethyl)benzene-sulfonamide To a stirred solution of N-(6-(3-(2,5-bis(trifluoromethyl) phenylsulfonamido)-2,6-difluorophenyl)quinazolin-2-yl) pivalamide (610 mg, 0.9643 mmol, 1.0 equiv) in ethanol (4 mL) was added 2M NaoH (6 mL). Then, the reaction mixture was allowed to stir at 90° C. for 2H. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)-2,5-bis(trifluoromethyl)benzenesulfonamide (39 mg), Analytical Data: LCMS: 549.5 $[M+H]^+$, $^1H$ NMR (400 MHz, DMSO-$d_6$) δ ppm 7.04 (s, 2H) 7.25 (d, J=8.77 Hz, 1H) 7.35 (d, J=6.14 Hz, 1H) 7.42-7.54 (m, 2H) 7.69 (s, 1H) 8.25 (d, J=6.58 Hz, 3H) 9.13 (s, 1H) 10.80 (br. s., 1H).

Compound 122

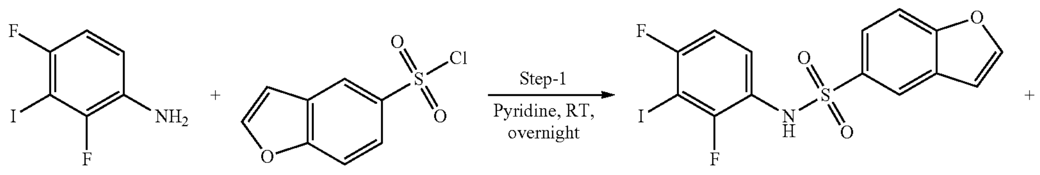

-continued

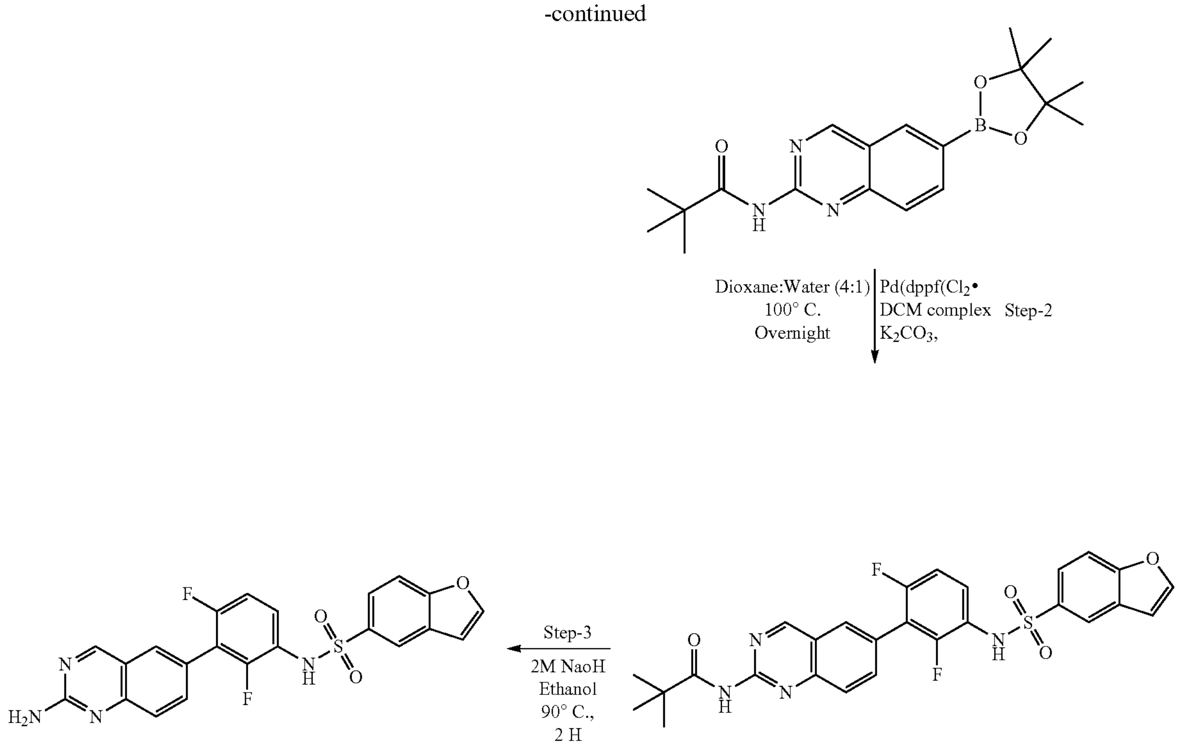

Step-1: Synthesis of N-(2,4-difluoro-3-iodophenyl) benzofuran-5-sulfonamide

To a stirred solution of 2,4-difluoro-3-iodoaniline (200 mg, 0.7843 mmol. 1.0 equiv.) in pyridine (2.0 mL) at room temperature was added benzofuran-5-sulfonyl chloride (169.8 mg, 0.7843 mmol. 1.0 equiv.) The resultant reaction mixture was stirred at room temperature for overnight. The progress of reaction was monitored by TLC. After completion of the reaction, ice cold water had been added to reaction mixture. The precipitate formed was filtered using Buchner funnel and washed the product with 1N HCl to remove pyridine. This material was used in the next reaction without further purification (280 mg).

Step 2: Synthesis of N-(6-(3-(benzofuran-5-sulfonamido)-2,6-difluorophenyl)quinazolin-2-yl)pivalamide To a stirred solution of N-(2,4-difluoro-3-iodophenyl) benzofuran-5-sulfonamide (280 mg, 0.6434 mmol, 1.0 equiv) and N-(6-(4,4,5,5-tetramethyl-1,3,2-dioxaborolan-2-yl)quinazolin-2-yl)pivalamide (274.2 mg, 0.7720 mmol, 1.2 equiv) in dioxane:Water (4:1, 5 mL) was added $K_2CO_3$ (266.7 mg, 1.9302 mmol, 3.0 equiv.). The resulting reaction mixture was purged with nitrogen for 10 minutes followed by the addition of Pd(dppf)$Cl_2$·DCM complex (26.27 mg, 0.0321 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used to next step without further purification (595 mg), LCMS: 537.3 $[M+H]^+$.

Step 3: Synthesis of N-(3-(2-aminoquinazolin-6-yl)-2,4-difluorophenyl)benzofuran-5-sulfonamide To a stirred solution of N-(6-(3-(benzofuran-5-sulfonamido)-2,6-difluorophenyl)quinazolin-2-yl)pivalamide (595 mg, 1.1089 mmol, 1.0 equiv) in ethanol (6 mL) was added 2M NaOH (6 mL). Then, the reaction mixture was allowed to stir at 90° C. for 2H. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)benzofuran-5-sulfonamide (9 mg), Analytical Data: LCMS: 453.3 $[M+H]^+$, $^1H$ NMR (400 MHz, DMSO-$d_6$) δ ppm 7.02 (br. s., 2H) 7.09-7.19 (m, 2H) 7.20-7.30 (m, 1H) 7.39-7.53 (m, 2H) 7.63-7.74 (m, 2H) 7.81 (d, J=8.77 Hz, 1H) 8.06 (br. s., 1H) 8.17 (br. s., 1H) 9.08 (s, 1H) 10.30 (br. s., 1H)

Compound 123

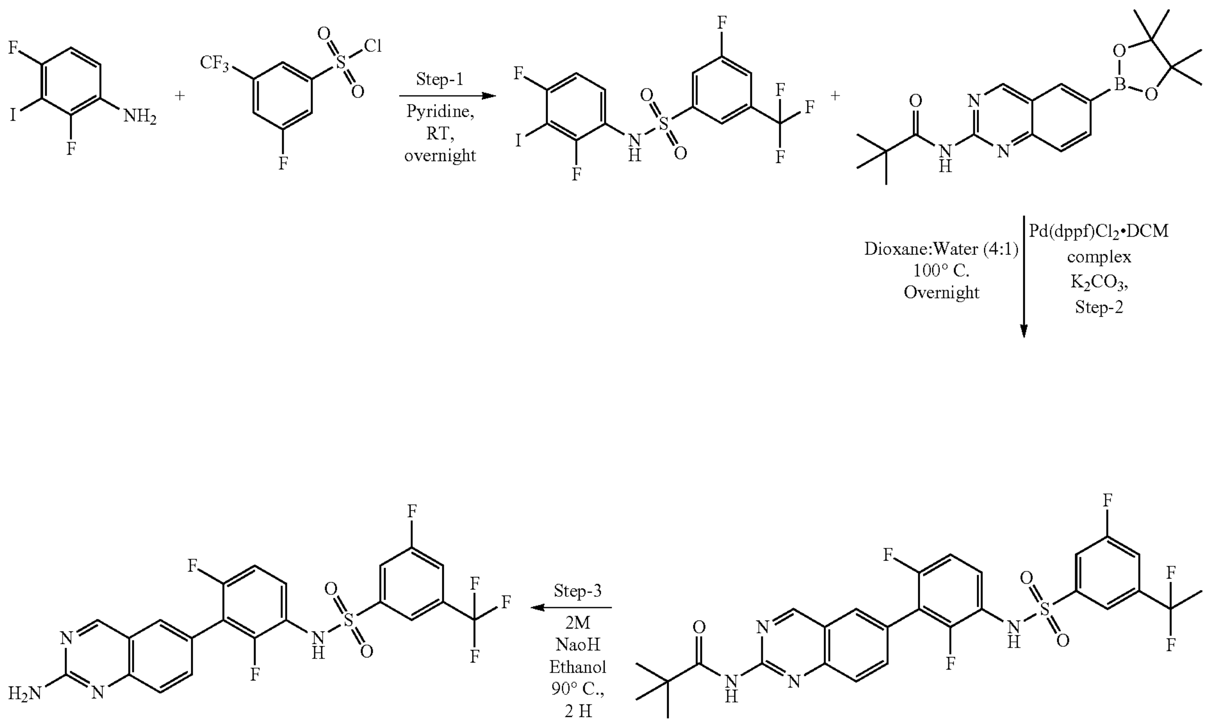

Step-1: Synthesis of N-(2,4-difluoro-3-iodophenyl)-3-fluoro-5-(trifluoromethyl)benzenesulfonamide To a stirred solution of 2,4-difluoro-3-iodoaniline (200 mg, 0.7843 mmol. 1.0 equiv.) in pyridine (1 mL) at room temperature was added 3-fluoro-5-(trifluoromethyl)benzene-1-sulfonyl chloride (205.9 mg, 0.7843 mmol. 1.0 equiv.) The resultant reaction mixture was stirred at room temperature for overnight. The progress of reaction was monitored through by TLC. After completion of the reaction, ice cold water had been added to reaction mixture. The precipitate formed was filtered using Buchner funnel and washed the product with 1N HCl to remove pyridine. This material was used to next step without further purification (227 mg).

Step 2: Synthesis of N-(6-(2,6-difluoro-3-(3-fluoro-5-(trifluoromethyl)phenylsulfonamido)phenyl)quinazolin-2-yl)pivalamide To a stirred solution of N-(2,4-difluoro-3-iodophenyl)-3-fluoro-5-(trifluoromethyl)benzenesulfonamide (227 mg, 0.4717 mmol, 1.0 equiv) and N-(6-(4,4,5,5-tetramethyl-1,3,2-dioxaborolan-2-yl)quinazolin-2-yl)pivalamide (200.9 mg, 0.5661 mmol, 1.2 equiv) in dioxane:Water (4:1, 5 mL) was added $K_2CO_3$ (195.6 mg, 1.4153 mmol, 3.0 equiv.). The resulting reaction mixture was purged with nitrogen for 10 minutes followed by the addition of Pd(dppf)$Cl_2$·DCM complex (19.26 mg, 0.0235 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used to next reaction without further purification (320 mg), LCMS: 583.12 $[M+H]^+$.

Step 3: Synthesis of N-(3-(2-aminoquinazolin-6-yl)-2,4-difluorophenyl)-3-fluoro-5-(trifluoromethyl)benzenesulfonamide To a stirred solution of N-(6-(2,6-difluoro-3-(3-fluoro-5-(trifluoromethyl)phenylsulfonamido)phenyl)quinazolin-2-yl)pivalamide (320 mg, 0.5493 mmol, 1.0 equiv) in ethanol (5 mL) was added 2M NaoH (5 mL). Then, the reaction mixture was allowed to stir at 90° C. for 2 h. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)-3-fluoro-5-(trifluoromethyl)benzenesulfonamide (48 mg), Analytical Data: LCMS: 498.06 $[M+H]^+$, $^1H$ NMR (400 MHz, DMSO-$d_6$) δ ppm 7.00 (s, 2H) 7.08-7.19 (m, 1H) 7.19-7.31 (m, 1H) 7.45 (d, J=8.77 Hz, 1H) 7.55 (d, J=8.33 Hz, 1H) 7.72 (s, 1H) 7.79 (s, 1H) 7.84 (d, J=7.89 Hz, 1H) 8.04 (d, J=8.33 Hz, 1H) 9.11 (s, 1H) 10.60 (br. s., 1H).

Compound 124

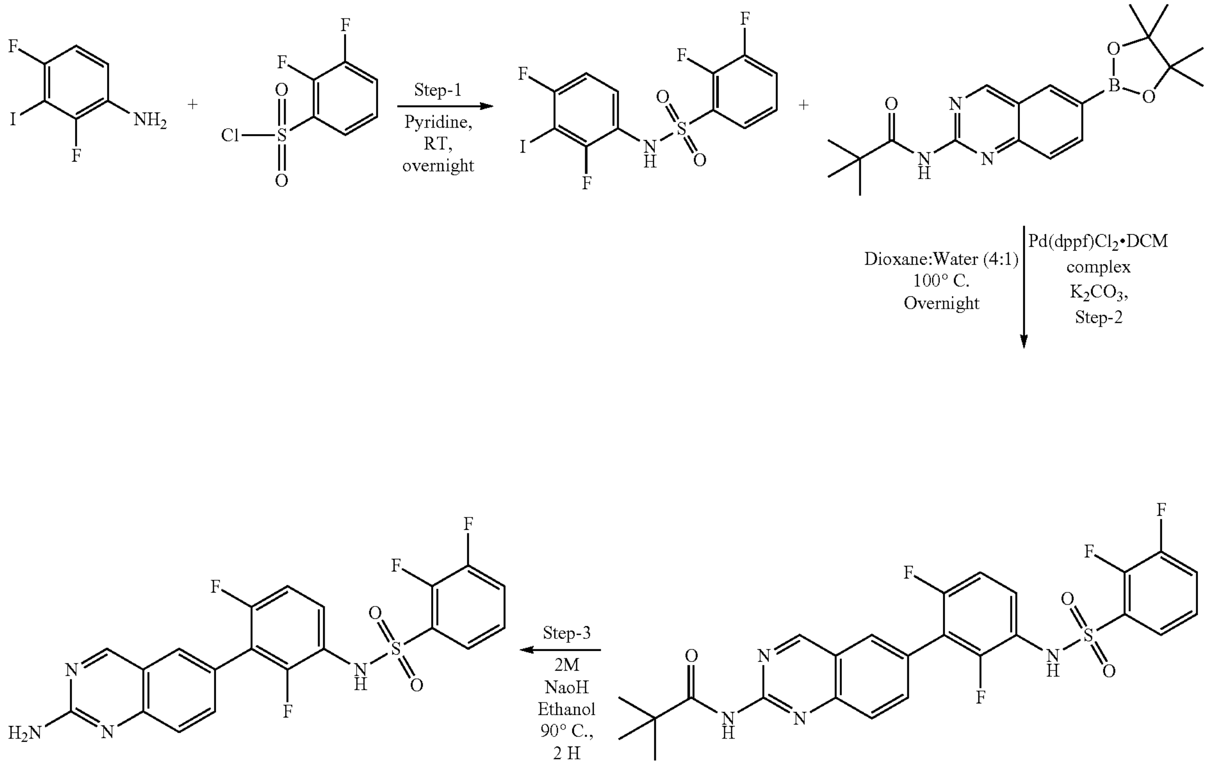

Step-1: Synthesis of N-(2,4-difluoro-3-iodophenyl)-2,3-difluorobenzenesulfonamide To a stirred solution of 2,4-difluoro-3-iodoaniline (200 mg, 0.7843 mmol. 1.0 equiv.) in pyridine (1.0 mL) at room temperature was added 2,3-difluorobenzene-1-sulfonyl chloride (166.7 mg, 0.7843 mmol. 1.0 equiv.) The resultant reaction mixture was stirred at room temperature for overnight. The progress of reaction was monitored by TLC. After completion of the reaction, ice cold water had been added to reaction mixture. The precipitate formed was filtered using Buchner funnel and washed the product with 1N HCl to remove pyridine. This material was used in the next reaction without further purification (266 mg).

Step 2: Synthesis of N-(6-(3-(2,3-difluorophenylsulfonamido)-2,6-difluorophenyl)quinazolin-2-yl) pivalamide To a stirred solution of N-(2,4-difluoro-3-iodophenyl)-2,3-difluorobenzenesulfonamide (266 mg, 0.6169 mmol, 1.0 equiv) and N-(6-(4,4,5,5-tetramethyl-1,3,2-dioxaborolan-2-yl)quinazolin-2-yl)pivalamide (262.8 mg, 0.7403 mmol, 1.2 equiv) in dioxane:Water (4:1, 5 mL) was added $K_2CO_3$ (255.7 mg, 1.8509 mmol, 3.0 equiv.). The resulting reaction mixture was purged with nitrogen for 10 minutes followed by the addition of $Pd(dppf)Cl_2 \cdot DCM$ complex (25.19 mg, 0.0308 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used to next step without further purification (644 mg), LCMS: 533.2 $[M+H]^+$.

Step 3: Synthesis of N-(3-(2-aminoquinazolin-6-yl)-2,4-difluorophenyl)-2,3-difluorobenzenesulfonamide To a stirred solution of N-(6-(3-(2,3-difluorophenylsulfonamido)-2,6-difluorophenyl)quinazolin-2-yl)pivalamide (644 mg, 1.2093 mmol, 1.0 equiv) in ethanol (6 mL) was added 2M NaOH (6 mL). Then, the reaction mixture was allowed to stir at 90° C. for 2 h. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)-2,3-difluorobenzenesulfonamide (40 mg), Analytical Data: LCMS: 449.2 $[M+H]^+$, $^1H$ NMR (400 MHz, DMSO-$d_6$) δ ppm 7.02 (br. s., 2H) 7.16 (t, J=8.99 Hz, 1H) 7.23-7.39 (m, 2H) 7.41-7.59 (m, 3H) 7.74 (br. s., 2H) 9.13 (s, 1H) 10.74 (br. s., 1H)

Compound 125

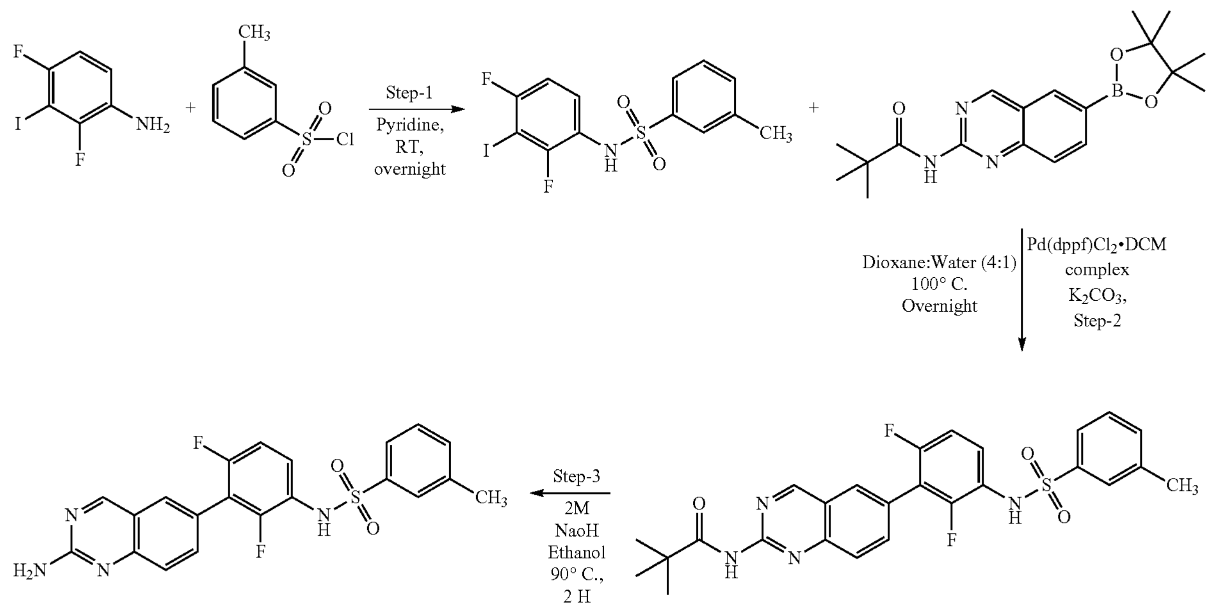

Step-1: Synthesis of N-(2,4-difluoro-3-iodophenyl)-3-methylbenzenesulfonamide

To a stirred solution of 2,4-difluoro-3-iodoaniline (200 mg, 0.7843 mmol. 1.0 equiv.) in pyridine (1.0 mL) at room temperature was added 3-methylbenzene-1-sulfonyl chloride (149.5 mg, 0.7843 mmol. 1.0 equiv.) The resultant reaction mixture was stirred at room temperature for overnight. The progress of reaction was monitored through by TLC. After completion of the reaction, ice cold water had been added to reaction mixture. The precipitate formed was filtered using Buchner funnel and washed the product with 1N HCl to remove pyridine. This material was used to next step without further purification (254 mg).

Step 2: Synthesis of N-(6-(2,6-difluoro-3-(3-methylphenylsulfonamido)phenyl)quinazolin-2-yl)pivalamide To a stirred solution of N-(2,4-difluoro-3-iodophenyl)-3-methylbenzenesulfonamide (254 mg, 0.6207 mmol, 1.0 equiv) and N-(6-(4,4,5,5-tetramethyl-1,3,2-dioxaborolan-2-yl)quinazolin-2-yl)pivalamide (264.4 mg, 0.7448 mmol, 1.2 equiv) in dioxane:Water (4:1, 5 mL) was added $K_2CO_3$ (257.3 mg, 1.8622 mmol, 3.0 equiv.). The resulting reaction mixture was purged with nitrogen for 10 minutes followed by the addition of $Pd(dppf)Cl_2 \cdot DCM$ complex (25.3 mg, 0.0310 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used to next step without further purification (600 mg), LCMS: 511.3 $[M+H]^+$.

Step 3: Synthesis of N-(3-(2-aminoquinazolin-6-yl)-2,4-difluorophenyl)-3-methylbenzenesulfonamide To a stirred solution of N-(6-(2,6-difluoro-3-(3-methylphenylsulfonamido)phenyl)quinazolin-2-yl)pivalamide (600 mg, 1.1751 mmol, 1.0 equiv) in ethanol (6 mL) was added 2M NaoH (6 mL). Then, the reaction mixture was allowed to stir at 90° C. for 2 h. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)-3-methylbenzenesulfonamide (25 mg), Analytical Data: LCMS: 427.3 $[M+H]^+$, $^1H$ NMR (400 MHz, DMSO-$d_6$) δ ppm 10.44 (br. s., 1H), 7.00 (br. s., 2H) 7.07 (t, J=8.77 Hz, 1H) 7.21 (d, J=6.14 Hz, 1H) 7.40 (br. s., 2H) 7.43-7.66 (m, 4H) 7.76 (br. s., 1H) 9.14 (s, 1H), 2.34 (s, 3H).

Compound 128

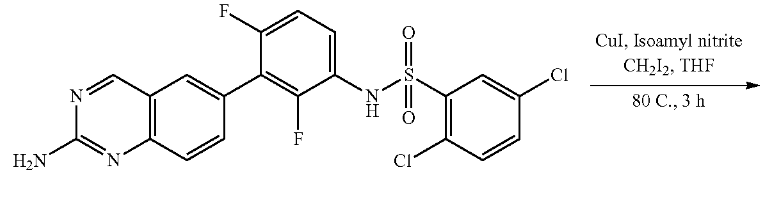

-continued

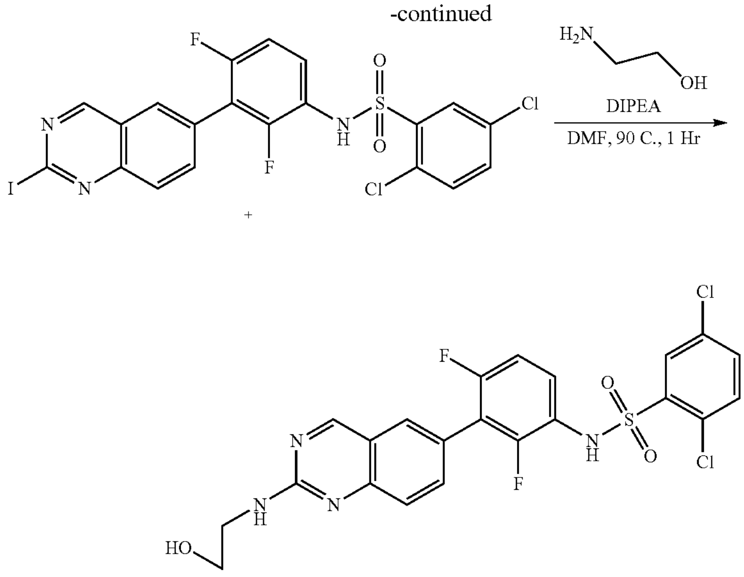

Step-1: Synthesis of 2,5-dichloro-N-(2,4-difluoro-3-(2-iodoquinazolin-6-yl)phenyl)benzenesulfonamide To a stirred solution of N-(3-(2-aminoquinazolin-6-yl)-2,4-difluorophenyl)-2,5-dichloro benzene sulfonamide (300 mg, 0.625 mmol, 1.0 equi.) was added CuI (166 mg, 0.875 mmol, 1.4 equi.) and purged with N2 gas. Under N2 atmosphere was added isoamyl nitrite (117 mg, 1.0 mmol, 1.6 equi.), $CH_2I_2$ (1.0 g, 3.75 mmol, 6.0 equiv.) to reaction mixture. After addition, reaction mixture was allowed to stir at 80° C. for 3 h. After completion of reaction, was added ice water and extracted with ethyl acetate (2×50 ml). The separated organic layer was dried over $Na_2SO_4$, filtered and concentrated under vacuum to obtain crude product which was purified by using combi-flash (Eluent System: 20% EA:Hexanes) to obtain desired product (190 mg), LCMS: 593[M+H]$^+$

Step-2: Synthesis of 2,5-dichloro-N-(2,4-difluoro-3-(2-(2-hydroxyethylamino)quinazolin-6-yl)phenyl) benzenesulfonamide To a stirred solution of 2,5-dichloro-N-(2,4-difluoro-3-(2-iodoquinazolin-6-yl)phenyl)benzene sulfonamide (40 mg, 0.067 mmol, 1.0 equi.) in DMF (1 ml) was added 2-aminoethanol (8 mg, 0.135 mmol, 2.0 equi.), DIPEA (26 mg, 0.203 mmol, 3.0 equi.). After addition, reaction was heated at 90° C. for 1 h. Progress of reaction was monitored by TLC. After completion of reaction, was added water (10 ml), extracted with ethyl acetate (lx 50 ml). The separated organic layer was dried over $Na_2SO_4$, filtered and concentrated. The crude product was purified by reverse phase HPLC to obtain desired product (7 mg), Analytical Data: LCMS: 525 [M+H]$^+$, NMR: $^1$H NMR (400 MHz, DMSO-$d_6$) δ ppm 3.47 (d, J=5.26 Hz, 3H) 3.59 (br. s., 2H) 7.20 (br. s., 1H) 7.28 (br. s., 1H) 7.46 (br. s., 2H) 7.53 (br. s., 1H) 7.59 (d, J=7.89 Hz, 1H) 7.78 (s, 1H) 7.75 (s, 1H) 7.87 (d, J=1.75 Hz, 1H) 9.14 (br. s., 1H) 10.67 (br. s., 1H).

Compound 129

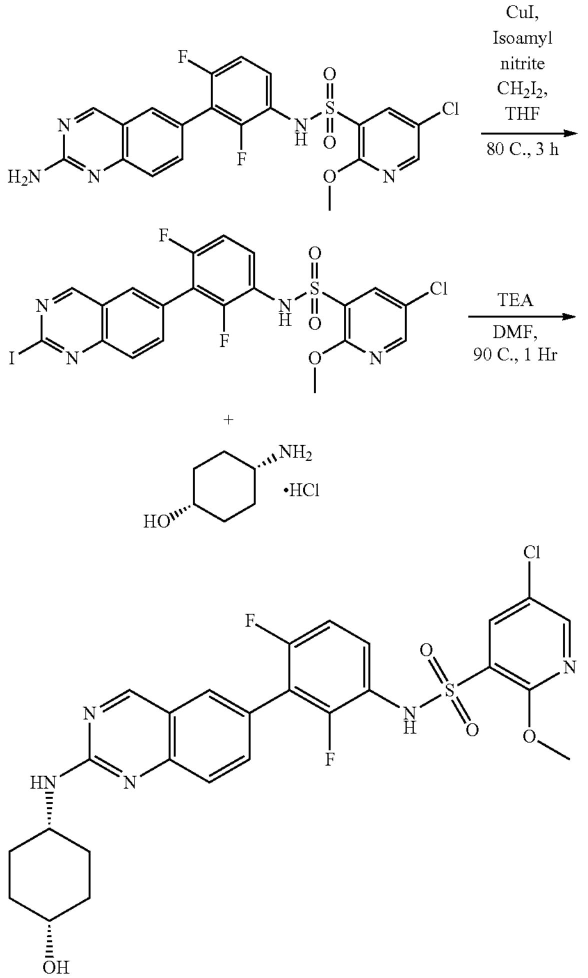

Step-1: Synthesis of 5-chloro-N-(2,4-difluoro-3-(2-iodoquinazolin-6-yl)phenyl)-2-methoxypyridine-3-sulfonamide To a stirred solution N-(3-(2-aminoquinazolin-6-yl)-2,4-difluorophenyl)-5-chloro-2-methoxypyridine-3-sulfonamide (100 mg, 0.209 mmol, 1.0 equi.) was added CuI (55.8 mg, 0.293 mmol, 1.4 equi.) and purged with N2 gas. Under N2 atmosphere was added Isoamyl nitrite (39 mg, 0.334 mmol, 1.6 equi.), $CH_2I_2$ (335 mg, 1.25 mmol, 6.0 equiv.) to reaction mixture. After addition, reaction mixture was allowed to stir at 80° C. for 3 h. After completion of reaction, was added ice water and extracted with ethyl acetate (2×50 ml). The separated organic layer was dried over $Na_2SO_4$, concentrated under vacuum to obtain crude product which was purified by using reverse phase HPLC to obtain desired product (60 mg), LCMS: 589[M+H]$^+$ Step-2: Synthesis of 5-chloro-N-(2,4-difluoro-3-(2-(((1s,4s)-4-hydroxycyclohexyl)amino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (30 mg, 0.051 mmol, 1.0 equi.) in DMF (1 ml) was added (1s,4s)-4-aminocyclohexanol hydrochloride (15.4 mg, 0.102 mmol, 1.0 equi.), TEA (15.4 mg, 0.153 mmol, 3.0 equi.). After addition reaction mixture was heated at 90° C. for 1 h. Progress of reaction was monitored by TLC. After completion of reaction, evaporated ethanol and was added water and extracted by using ethyl acetate (2×50 ml). The separated organic layer was dried over $Na_2SO_4$, filtered and concentrated. The crude product was purified by Combi flash to obtain desired product (9 mg), Analytical Data: LCMS: 576 [M+H]$^+$, NMR: $^1$H NMR (400 MHz, DMSO-$d_6$) δ ppm 1.54 (d, J=12.28 Hz, 3H) 1.66 (br. s., 4H) 1.75 (br. s., 2H) 3.84 (br. s., 2H) 3.91 (s, 3H) 7.16-7.26 (m, 1H) 7.29-7.41 (m, 1H) 7.62 (br. s., 3H) 7.82 (br. s., 1H) 8.08 (d, J=2.19 Hz, 1H) 8.52 (d, J=2.63 Hz, 1H) 9.19 (br. s., 1H) 10.39 (s, 1H).

Step-1: Synthesis of N-(2,4-difluoro-3-iodophenyl)pyridine-3-sulfonamide

To a stirred solution of 2,4-difluoro-3-iodoaniline (200 mg, 0.7843 mmol. 1.0 equiv.) in pyridine (1.0 mL) at room temperature was added pyridine-3-sulfonyl chloride (167.1 mg, 0.9411 mmol. 1.0 equiv.) The resultant reaction mixture was stirred at room temperature for overnight. The progress of reaction was monitored by TLC. After completion of the reaction, ice cold water was added to reaction mixture. The precipitate formed was filtered using Buchner funnel and washed the product with 1N HCl to remove pyridine. This material was used in the next reaction without further purification (165 mg).

Step-2: Synthesis of N-(6-(2,6-difluoro-3-(pyridine-3-sulfonamido)phenyl)quinazolin-2-yl)pivalamide To a stirred solution of N-(2,4-difluoro-3-iodophenyl)pyridine-3-sulfonamide (165 mg, 0.4165 mmol, 1.0 equiv) and N-(6-(4,4,5,5-tetramethyl-1,3,2-dioxaborolan-2-yl)quinazolin-2-yl)pivalamide (177.4 mg, 0.4998 mmol, 1.2 equiv) in dioxane:Water (4:1, 5 mL) was added $K_2CO_3$ (172.68 mg, 1.2495 mmol, 3.0 equiv.). The resulting reaction mixture was purged with nitrogen for 10 minutes followed by the addition of Pd(dppf)$Cl_2$·DCM complex (17 mg, 0.0208 mmol, 0.05 equiv.). The reaction mixture was again purged with nitrogen for 5 minutes. The reaction mixture was heated at 100° C. for overnight. The progress of reaction was monitored by TLC and LCMS. After completion of reaction, water was added to the reaction mixture, Compound 130

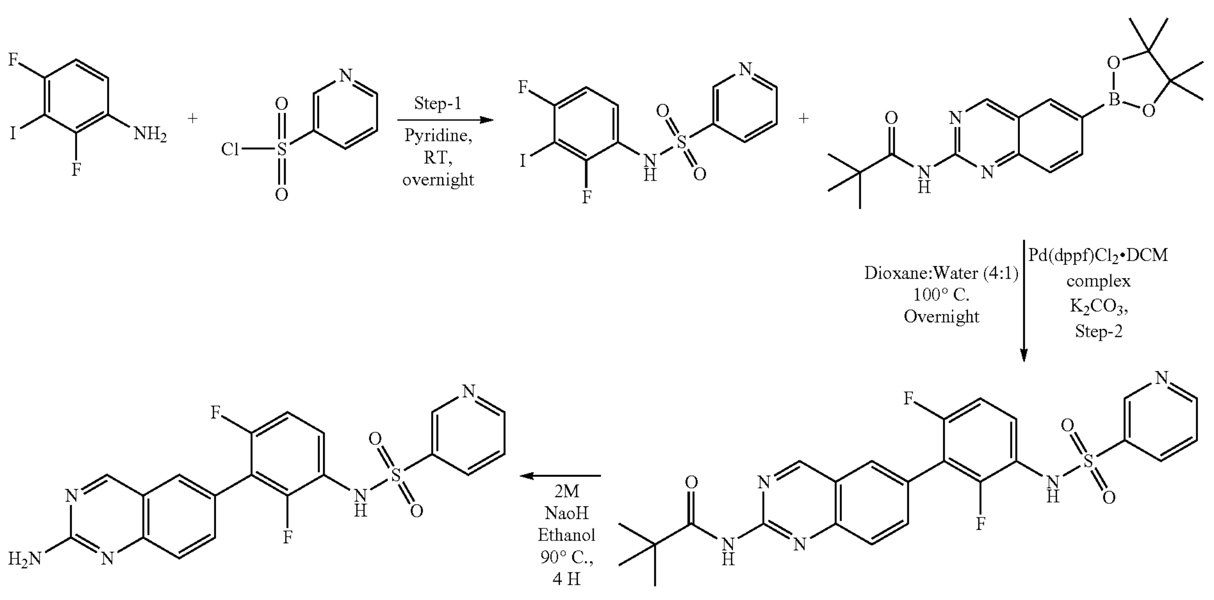

extracted with EtOAc (2×50 mL). The organic layers were combined, dried over anhydrous $Na_2SO_4$ and evaporated under reduced pressure. The crude product was used to next step without further purification (265 mg), LCMS: 498.3 $[M+H]^+$.

Step 3: Synthesis of N-(3-(2-aminoquinazolin-6-yl)-2,4-difluorophenyl)pyridine-3-sulfonamide To a stirred solution of N-(6-(2,6-difluoro-3-(pyridine-3-sulfonamido)phenyl)quinazolin-2-yl)pivalamide (260 mg, 0.5225 mmol, 1.0 equiv) in ethanol (6 mL) was added 2M NaoH (6 mL). Then, the reaction mixture was allowed to stir at 90° C. for 4H. After completion of reaction, the solvent was evaporated and water was added to the reaction mixture, extracted with EtOAc (2×50 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)pyridine-3-sulfonamide (40 mg), Analytical Data: LCMS: 414.2 $[M+H]^+$, $^1H$ NMR (400 MHz, DMSO-$d_6$) δ ppm 6.90-7.12 (m, 3H) 7.23 (br. s., 1H) 7.48 (br. s., 1H) 7.56 (br. s., 2H) 7.76 (br. s., 1H) 8.06 (br. s., 1H) 8.71 (br. s., 1H) 8.85 (br. s., 1H) 9.14 (br. s., 1H) 11.22 (br. s., 1H)

Step-1: Synthesis of N-(2,4-dichlorophenyl)acetamide

To a stirred solution of 2,4-dichloroaniline (1.00 g, 6.25 mmol, 1.0 eq) in 10 mL DCM was added TEA (2.55 mL 18.75 mmol 3.0 eq), then reaction mixture was cooled to 0° C. was added acetyl chloride (0.44 mL 6.25 mmol 1.0 eq) drop wise & stir the reaction mixture at RT for 2 h. The progress of reaction was monitored through TLC and LCMS. After completion of reaction, water was added to the reaction mixture, extracted with DCM (2×10 mL). The organic layers were combined, dried over anhydrous $Na_2SO_4$ and evaporated under reduced pressure to obtain crude residue which was purified by combi flash chromatography to obtain N-(2,4-dichlorophenyl)acetamide (1 g), Analytical Data. LCMS: 204 $[M+H]^+$

Step-2: Synthesis of N-(2,4-dichloro-3-iodophenyl)acetamide

To a stirred solution of N-(2,4-dichlorophenyl)acetamide (600 mg, 2.970, mmol 1.0 eq) in THF (5 mL) at −70° C. was added n-BuLi (1.5 M in THF, 6.0 mL, 8.910 mmol 3.0 eq) under anhydrous condition & stir the reaction mixture for 2

Compound 131

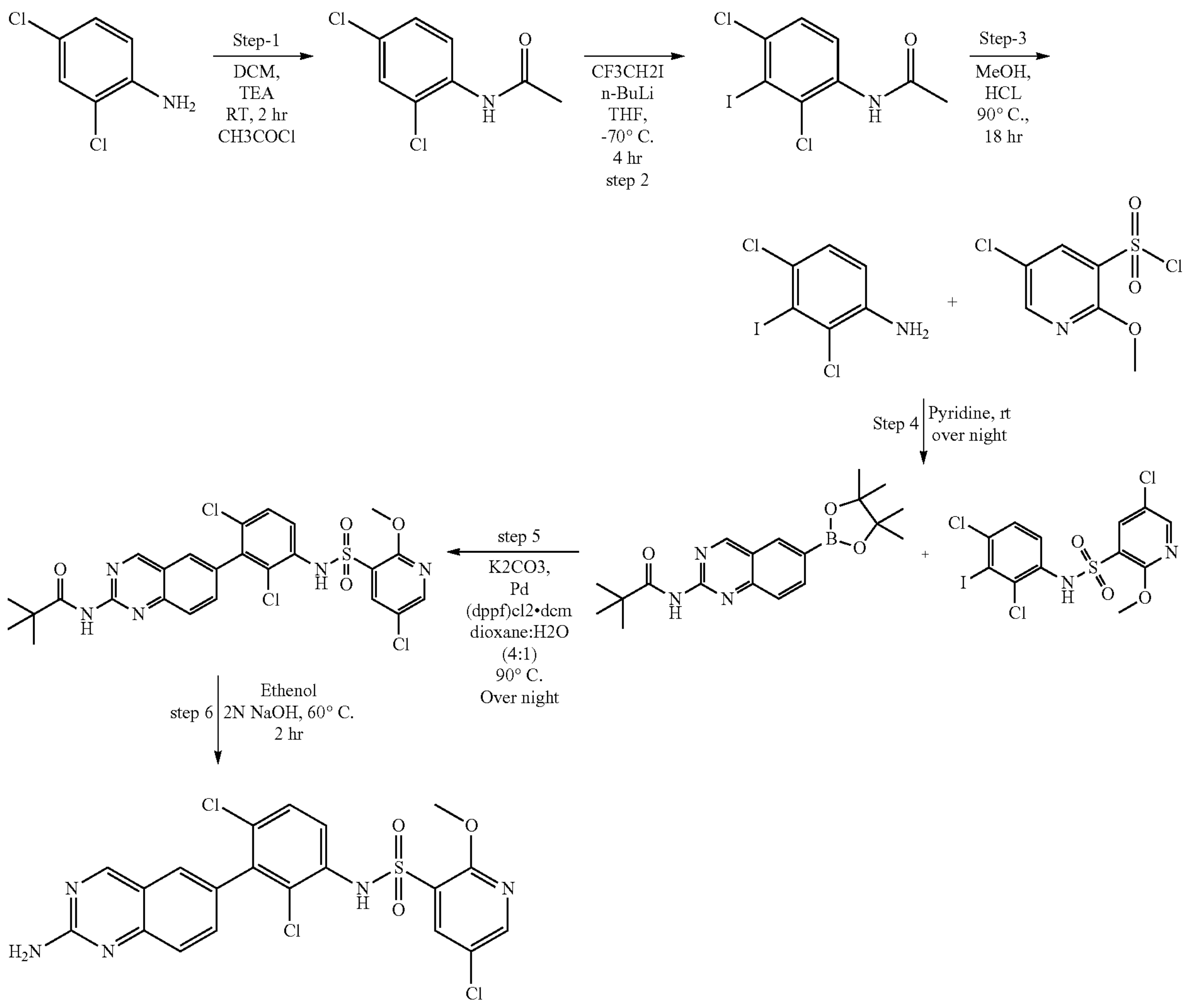

hr at −70° C., was added 1,1,1-trifluoro-2-iodoethane (1.862 mL, 8.910, mmol 3.0 eq) drop wise, after all addition stir the reaction mixture for 1.5 h at −70° C., The progress of reaction was monitored by TLC and LCMS. After completion of reaction, 3N HCl (10 mL) solution is added slowly, the reaction mixture was allowed to warm up to room temperature & extracted with ethyl acetate (2×10 mL). The organic layers were combined, washed with water (20 mL), dried over anhydrous $Na_2SO_4$ and evaporated under reduced pressure to obtain crude residue which was purified by flash chromatography to obtain N-(2,4-dichloro-3-iodophenyl) acetamide (525 mg), Analytical Data: LCMS: 330.0 $[M+H]^+$ Step-3: Synthesis of 2,4-dichloro-3-iodoaniline To a stirred solution of N-(2,4-dichloro-3-iodophenyl) acetamide (525 mg, 1.6 mmol, 1.0 eq) in MeOH (7 mL) was added concentrated HCl (0.61 mL) drop wise after addition, reaction mixture was heated at 70° C. for 18 hours, The progress of reaction was monitored through TLC and LCMS. After completion of reaction, the mixture cooled and solvent were removed under reduced pressure (water bath below 45° C.). The residue was cooled with an ice bath and 3N NaOH solution was added to adjust pH to between 9-10, extracted with ethyl acetate (2×10 mL). The organic layers were combined, dried over anhydrous $Na_2SO_4$ and evaporated under reduced pressure to obtain as crude residue which was purified by flash chromatography to get title product 2,4-dichloro-3-iodoaniline (400 mg), Analytical Data: LCMS: 288 $[M+H]^+$ Step-4: Synthesis of 5-chloro-N-(2,4-dichloro-3-iodophenyl)-2-methoxypyridine-3-sulfonamide To a stirred solution of 2,4-dichloro-3-iodoaniline (400 mg, 1.39 mmol, 1.0 eq) in pyridine (6 mL) at room temperature was 5-chloro-2-methoxypyridine-3-sulfonyl chloride (1.00 g, 4.19 mmol, and 3.0 eq.) were stirred at room temperature for overnight. The progress of reaction was monitored through TLC and LCMS, after completion of reaction, was added 2N HCl (10 mL) and the mixture was stirred at room temperature for 10 min, reaction mass was diluted with water and extracted by Ethyl acetate (2×15 mL). The combined organic layers were dried over anhydrous $Na_2SO_4$ and concentrated under reduced pressure and purified by combi-flash to obtain the title compound 5-chloro-N-(2,4-dichloro-3-iodophenyl)-2-methoxypyridine-3-sulfonamide (460 mg), Analytical Data: LCMS: 493 $[M+H]^+$ Step-5: Synthesis of N-(6-(2,6-dichloro-3-(5-chloro-2-methoxypyridine-3-sulfonamido)phenyl)quinazolin-2-yl)pivalamide To the stirred solution of 5-chloro-N-(2,4-dichloro-3-iodophenyl)-2-methoxypyridine-3-sulfonamide (235 mg, 0.47 mmol, 1.0 equiv.) and N-(6-(4,4,5,5-tetramethyl-1,3,2-dioxaborolan-2-yl)quinazolin-2-yl)pivalamide (186 mg, 0.52 mmol, and 1.1 eq.) in Dioxane:Water (4:1, 5 mL) was added $K_2CO_3$ (197 mg, 1.43 mmol, 3.0 equiv.) The resulting reaction mixture was purged with nitrogen for 15 minutes followed by the addition of Pd(dppf)$Cl_2$·DCM complex (20 mg, 0.023 mmol, 0.05 equiv.). The reaction mixture was again purged with nitrogen for 5 minutes. The reaction mixture was heated to 90° C. for overnight. The progress of reaction was monitored through TLC and LCMS. After completion of reaction, water was added to the reaction mixture, extracted with EtOAc (2×15 mL). The organic layers were combined, dried over anhydrous $Na_2SO_4$ and evaporated under reduced pressure to obtain title product as crude residue which was purified by flash chromatography to obtain title product N-(6-(2,6-dichloro-3-(5-chloro-2-methoxypyridine-3-sulfonamido)phenyl)quinazolin-2-yl) pivalamide (400 mg), Analytical Data: LCMS: 594 $[M+H]^+$ Step-6: Synthesis of N-(3-(2-aminoquinazolin-6-yl)-2,4-dichlorophenyl)-5-chloro-2-methoxypyridine-3-sulfonamide To a stirred solution of N-(6-(2,6-dichloro-3-(5-chloro-2-methoxypyridine-3-sulfonamido)phenyl)quinazolin-2-yl) pivalamide (300 mg, 0.50 mmol, 1.0 equiv) in ethanol (5 mL) at room temperature was added 2N NaOH (2 mL). Then the reaction mixture was allowed to stir at 60° C. for 2 hr, Progress of the reaction was monitored by TLC and LCMS. After completion of reaction, the solvent was evaporated and water was added to the reaction mixture, extracted with EtOAc (2×15 mL). The organic layers were combined, dried over anhydrous $Na_2SO_4$ & evaporated under reduced pressure to obtain crude product which was purified by chromatography technique to obtain desired compound N-(3-(2-aminoquinazolin-6-yl)-2,4-dichlorophenyl)-5-chloro-2-methoxypyridine-3-sulfonamide (25 mg), Analytical Data: LCMS: 510 $[M+H]^+$, $^1H$ NMR (400 MHz, DMSO-$d_6$) δ ppm 3.85 (s, 3H) 7.00 (s, 2H) 7.38-7.52 (m, 3H) 7.60-7.66 (m, 2H) 8.08 (d, J=2.19 Hz, 1H) 8.50 (d, J=2.19 Hz, 1H) 9.14 (s, 1H) 10.42 (br. s., 1H).

Compound 132

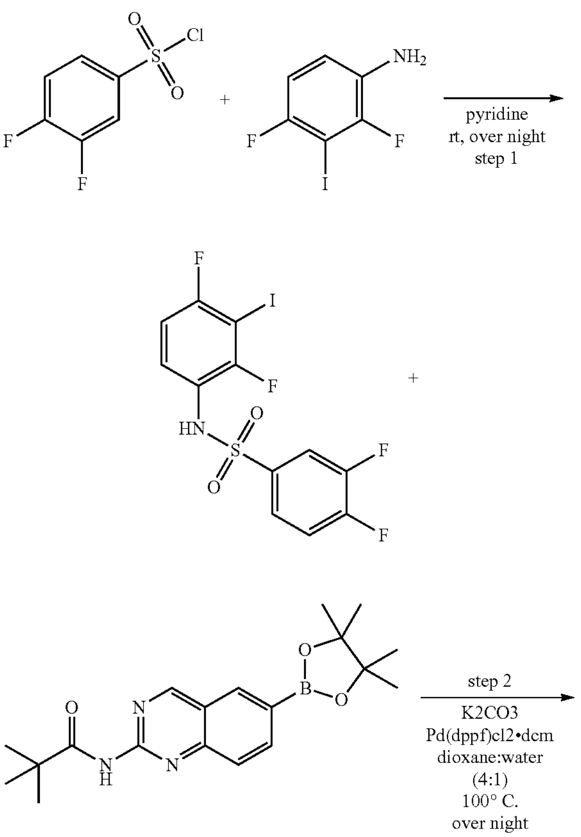

-continued

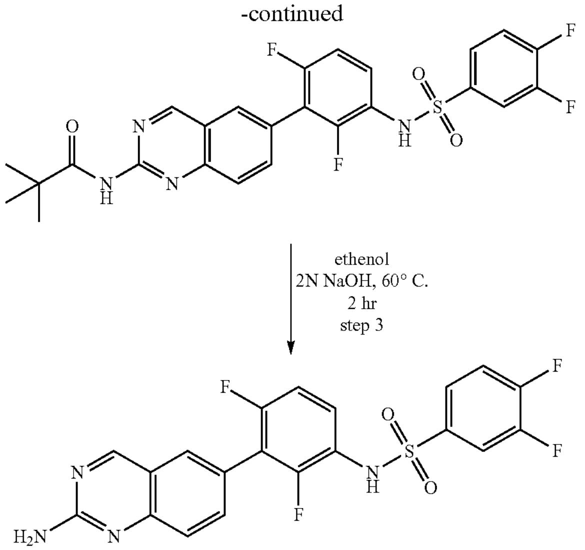

Step-1: Synthesis of N-(2,4-difluoro-3-iodophenyl)-3,4-difluorobenzenesulfonamide To a stirred solution of 3,4-difluorobenzene-1-sulfonyl chloride (100 mg, 0.47 mmol., 1.0 equiv.) & 2,4-difluoro-3-iodoaniline (119 mg, 0.47 mmol, and 1.0 eq.) in 0.3 mL pyridine were stirred at room temperature for overnight, The progress of reaction was monitored through TLC and LCMS. After completion of reaction added 2N HCl (5 mL) and the mixture were stirred at room temperature for 10 min reaction mass was diluted with water and extracted by Ethyl acetate (3×10 mL). The combined organic layers were dried over anhydrous $Na_2SO_4$ and concentrated under reduced pressure. This material was used in the next reaction without further purification (210 mg).

Step-2: Synthesis of N-(6-(3-(3,4-difluorophenylsulfonamido)-2,6-difluorophenyl)quinazolin-2-yl) pivalamide To the stirred solution of N-(2,4-difluoro-3-iodophenyl)-3,4-difluorobenzenesulfonamide (200 mg, 0.46 mmol, 1.0 equiv.) and N-(6-(4,4,5,5-tetramethyl-1,3,2-dioxaborolan-2-yl)quinazolin-2-yl)pivalamide (181 mg, 0.51 mmol, and 1.1 eq.) in Dioxane:Water (4:1, 5 mL) was added $K_2CO_3$ (192 mg, 1.39 mmol, 3.0 equiv.) The resulting reaction mixture was purged with nitrogen for 15 minutes followed by the addition of Pd(dppf)$Cl_2$·DCM complex (20 mg, 0.023 mmol, 0.05 equiv.). The reaction mixture was again purged with nitrogen for 5 minutes. The reaction mixture was heated to 100° C. for overnight. The progress of reaction was monitored by TLC and LCMS. After completion of reaction, water was added to the reaction mixture, extracted with EtOAc (2×15 mL). The organic layers were combined, dried over anhydrous $Na_2SO_4$ and evaporated under reduced pressure to obtain crude residue which was purified by flash chromatography to obtain title product N-(6-(3-(3,4-difluorophenylsulfonamido)-2,6-difluorophenyl)quinazolin-2-yl) pivalamide (350 mg), Analytical Data: LCMS: 533 $[M+H]^+$ Step-3: Synthesis of N-(3-(2-aminoquinazolin-6-yl)-2,4-difluorophenyl)-3,4-difluorobenzenesulfonamide To a stirred solution of N-(6-(3-(3,4-difluorophenylsulfonamido)-2,6-difluorophenyl)quinazolin-2-yl)pivalamide (350 mg, 0.65 mmol, 1.0 equiv) in ethanol (5 mL) at room temperature was added 2N NaOH (2 mL). Then the reaction mixture was allowed to stir at 60° C. for 2 hr, Progress of the reaction was monitored by TLC and LCMS. After completion of the reaction, solvent was evaporated and water was added to the reaction mixture, extracted with EtOAc (2×10 mL). The organic layers were combined, dried over anhydrous $Na_2SO_4$, evaporated under reduced pressure to obtain crude product. This product was purified using reverse phase chromatography technique to obtain desired compound N-(3-(2-aminoquinazolin-6-yl)-2,4-difluorophenyl)-3,4-difluorobenzenesulfonamide (13 mg), Analytical Data: LCMS: 449 $[M+H]^+$, $^1$H NMR (400 MHz, DMSO-$d_6$) δ ppm 7.02 (s, 2H) 7.12-7.48 (d, J=8.33 Hz, 3H) 7.59 (d, J=7.02 Hz, 2H) 7.78-7.08 (s, 3H) 9.14 (s, 1H) 10.4 (s, 1H).

Compound 133

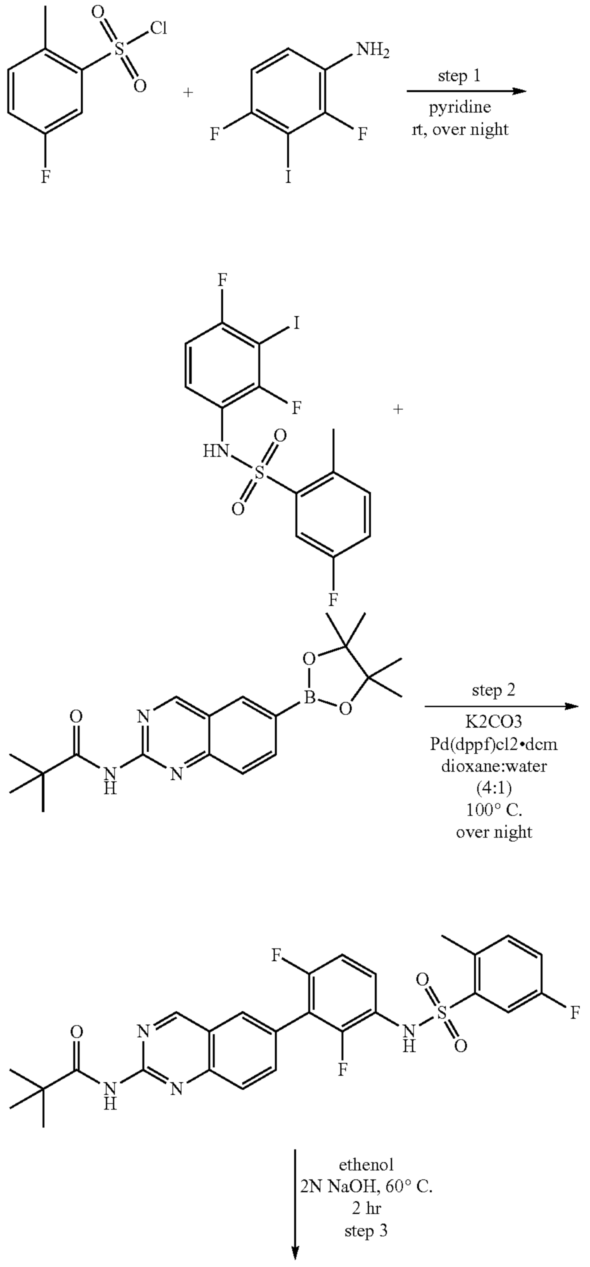

-continued

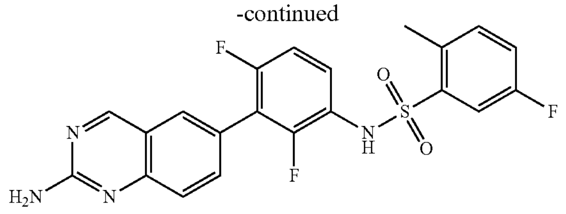

Step-1: Synthesis of N-(2,4-difluoro-3-iodophenyl)-5-fluoro-2-methylbenzenesulfonamide To the stirred solution of 2,4-difluoro-3-iodoaniline (122 mg, 0.47 mmol, and 1.0 eq.) in 2 mL pyridine at room temperature was added 5-fluoro-2-methylbenzene-1-sulfonyl chloride (100 mg, 0.47 mmol. 1.0 equiv.). After addition reaction mixture was stirred for overnight at room temperature. The progress of reaction was monitored through TLC and LCMS, After completion of reaction added 2N HCl (5 mL) and the mixture was stirred at room temperature for 10 min reaction mass was diluted with water and extracted by Ethyl acetate (2×15 mL). The combined organic layers were dried over anhydrous $Na_2SO_4$ and concentrated under reduced pressure, This material was used in the next reaction without further purification (128 mg).

Step-2: Synthesis of N-(6-(2,6-difluoro-3-(5-fluoro-2-methylphenylsulfonamido)phenyl)quinazolin-2-yl) pivalamide To the stirred solution of N-(2,4-difluoro-3-iodophenyl)-5-fluoro-2-methylbenzenesulfonamide (128 mg, 0.29 mmol. 1.0 equiv.) and N-(6-(4,4,5,5-tetramethyl-1,3,2-dioxaborolan-2-yl)quinazolin-2-yl)pivalamide (117 mg, 0.32 mmol, and 1.1 eq.) in Dioxane:Water (4:1, 5 mL) was added $K_2CO_3$ (124 mg, 0.89 mmol, 3.0 equiv.) The resulting reaction mixture was purged with nitrogen for 15 minutes followed by the addition of Pd(dppf)$Cl_2$·DCM complex (12 mg, 0.014 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×10 mL). The organic layers were combined, dried over anhydrous $Na_2SO_4$ and evaporated under reduced pressure to obtain crude residue which was purified by flash chromatography to obtain title product N-(6-(2,6-difluoro-3-(5-fluoro-2-methylphenylsulfonamido)phenyl)quinazolin-2-yl)pivalamide (150 mg), Analytical Data: LCMS: 529 $[M+H]^+$ Step-3: Synthesis of N-(3-(2-aminoquinazolin-6-yl)-2,4-difluorophenyl)-5-fluoro-2-methylbenzenesulfonamide To a stirred solution of product N-(6-(2,6-difluoro-3-(5-fluoro-2-methylphenylsulfonamido)phenyl)quinazolin-2-yl) pivalamide (129 mg, 0.24 mmol, 1.0 equiv) in ethanol (5 mL) at room temperature was added 2N NaOH (2 mL). Then the reaction mixture was allowed to stir at 60° C. for 2 h, Progress of the reaction was monitored by TLC and LCMS. After completion of the reaction, solvent was evaporated and water was added to the reaction mixture, extracted with EtOAc (2×10 mL), The organic layers were combined, dried over anhydrous $Na_2SO_4$ evaporated under reduced pressure to obtain crude product which was purified by using reverse phase chromatography technique to obtain N-(3-(2-aminoquinazolin-6-yl)-2,4-difluorophenyl)-5-fluoro-2-methylbenzenesulfonamide (10 mg), Analytical Data: LCMS: 445 $[M+H]^+$, $^1H$ NMR (400 MHz, DMSO-$d_6$) δ ppm 2.56 (s, 3H) 7.04 (s, 2H) 7.14-7.36 (m, 2H) 7.39-7.60 (m, 5H) 7.74 (s, 1H) 9.14 (s, 1H) 10.45 (s, 1H).

Compound 134

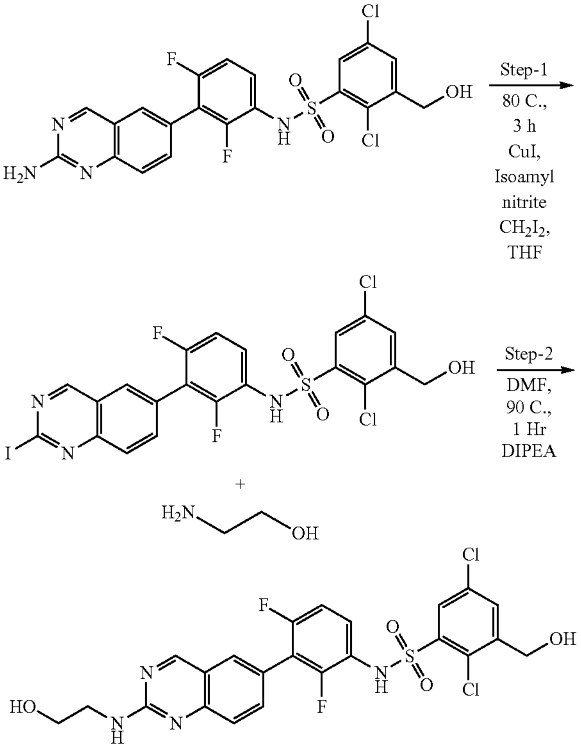

Step-1: Synthesis of 2,5-dichloro-N-(2,4-difluoro-3-(2-iodoquinazolin-6-yl)phenyl)-3-(hydroxymethyl) benzenesulfonamide To a stirred solution of N-(3-(2-aminoquinazolin-6-yl)-2,4-difluorophenyl)-2,5-dichloro-3-(hydroxymethyl)benzenesulfonamide (120 mg, 0.234 mmol, 1.0 equi.) was added CuI (62 mg, 0.328 mmol, 1.4 equi.) and purged with N2 gas. Under N2 atmosphere was added isoamyl nitrite (43.8 mg, 0.374 mmol, 1.6 equi.), $CH_2I_2$ (381 mg, 1.428 mmol, 6.0 equiv.) to reaction mixture. After addition, reaction mixture was allowed to stir at 80° C. for 3 h. After completion of reaction, was added ice water and extracted with ethyl acetate (2×50 ml). The separated organic layer was dried over $Na_2SO_4$, filtered and concentrated under vacuum to obtain crude product which was purified by using combi-flash (Eluent System: 20% EA:Hexanes) to obtain desired product (60 mg). LCMS: 622$[M+H]^+$ Step-2: Synthesis of 2,5-dichloro-N-(2,4-difluoro-3-(2-(2-hydroxyethylamino)quinazolin-6-yl)phenyl)-3-(hydroxymethyl)benzenesulfonamide To a stirred solution of 2,5-dichloro-N-(2,4-difluoro-3-(2-iodoquinazolin-6-yl)phenyl)-3-(hydroxymethyl)benzenesulfonamide (50 mg, 0.0806 mmol, 1.0 equi.) in DMF (1 ml)

at room temperature was added 2-aminoethanol (10.6 mg, 0.161 mmol, 2.0 equi.), DIPEA (31 mg, 0.241 mmol, 3.0 equi.). After addition reaction was heated at 90° C. for 1 h. Progress of reaction was monitored by TLC. After completion of reaction, reaction mixture was diluted with water (20 ml) and extracted with ethyl acetate (2×50 ml) and water (20 ml). The separated organic layer was dried over $Na_2SO_4$, filtered and concentrated. The crude product was purified by reverse phase chromatography to obtain desired product (9 mg), Analytical Data: LCMS: 555$[M+H]^+$, NMR: $^1H$ NMR (400 MHz, DMSO-$d_6$) δ ppm 11.91 (br. s., 1H) 9.14 (br. s., 1H) 7.75-7.90 (m, 2H) 7.65 (d, J=7.45 Hz, 1H) 7.45-7.55 (m, 2H) 7.36 (br. s., 1H) 7.03 (dd, J=15.57, 8.99 Hz, 1H) 6.77 (t, J=8.99 Hz, 1H) 5.56 (t, J=5.92 Hz, 1H) 4.75 (br. s., 1H) 4.54 (d, J=5.26 Hz, 2H) 3.58 (br. s., 2H) 3.39-3.53 (m, 2H).

0.274 mmol, 1.1 equiv) in Dioxane:Water (4:1, 5 mL) was added $K_2CO_3$ (103 mg, 0.747 mmol, 3.0 equiv.). The resulting reaction mixture was purged with nitrogen for 15 minutes followed by the addition of Pd(dppf)$Cl_2$·DCM complex (10 mg, 0.0124 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next reaction without further purification (170 mg). LCMS: 583$[M+H]^+$.

Compound 135

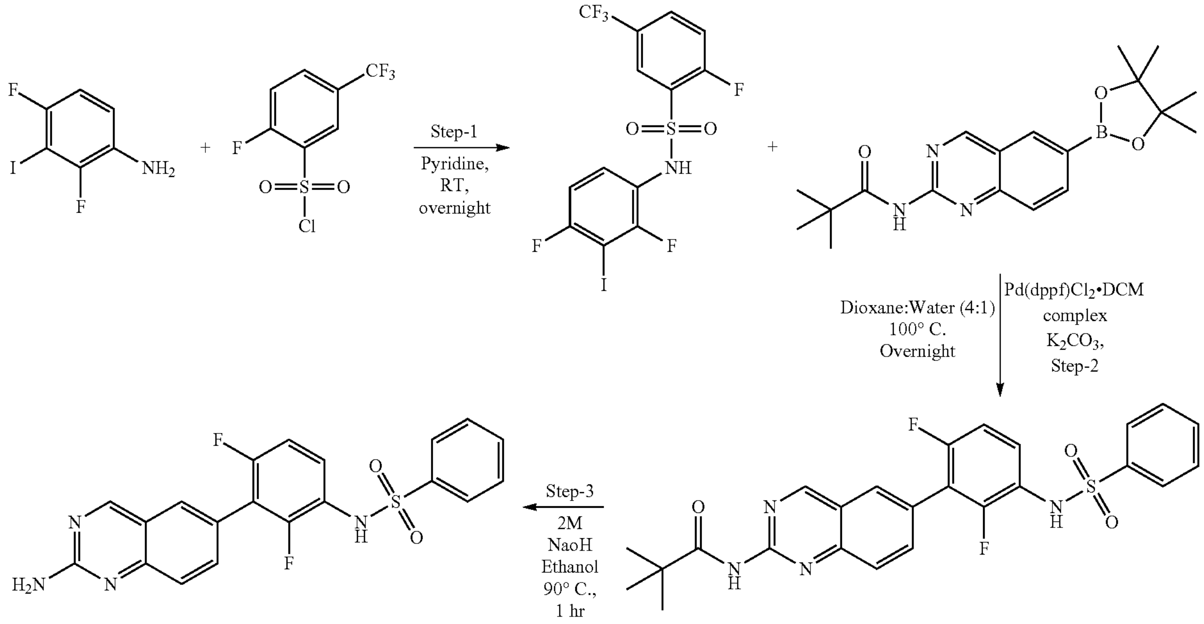

Step-1: Synthesis of N-(2,4-difluoro-3-iodophenyl)-2-fluoro-5-(trifluoromethyl)benzenesulfonamide To a stirred solution of 2,4-difluoro-3-iodoaniline (100 mg, 0.392 mmol. 1.0 equiv.) in pyridine (1.0 mL) at room temperature was added 2-fluoro-5-(trifluoromethyl)benzene-1-sulfonyl chloride (103 mg, 0.392 mmol. 1.0 equiv.) The resultant reaction mixture was stirred at room temperature for overnight. The progress of reaction was monitored through by TLC. After completion of the reaction, ice cold water was added to reaction mixture. The precipitate formed which was filtered by using Buchner funnel and washed the product with 1N HCl. This material was used in the next reaction without further purification (125 mg).

Step-2: Synthesis of N-(6-(2,6-difluoro-3-(2-fluoro-5-(trifluoromethyl)phenylsulfonamido)phenyl)quinazolin-2-yl)pivalamide To a stirred solution of N-(2,4-difluoro-3-iodophenyl)-2-fluoro-5-(trifluoromethyl)benzenesulfonamide (120 mg, 0.249 mmol, 1.0 equiv) and N-(6-(4,4,5,5-tetramethyl-1,3,2-dioxaborolan-2-yl)quinazolin-2-yl)pivalamide (97 mg, Step-3: Synthesis of N-(3-(2-aminoquinazolin-6-yl)-2,4-difluorophenyl)-2-fluoro-5-(trifluoromethyl) benzenesulfonamide To a stirred solution of N-(6-(2,6-difluoro-3-(2-fluoro-5-(trifluoromethyl)phenylsulfonamido)phenyl)quinazolin-2-yl)pivalamide (160 mg, 0.274 mmol, 1.0 equiv) in ethanol (5 mL) was added 2M NaOH (2 mL). Then, the reaction mixture was allowed to stir at 90 degree Celsius for 1 hr. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase chromatography to obtain N-(3-(2-aminoquinazolin-6-yl)-2,4-difluorophenyl)-2-fluoro-5-(trifluoromethyl)benzenesulfonamide (6 mg). Analytical Data: LCMS: 499$[M+H]^+$, NMR: $^1H$ NMR (400 MHz, DMSO-$d_6$) δ ppm 11.89 (br. s., 1H) 9.14 (br. s., 1H) 8.02 (br. s., 1H) 7.78 (br. s., 2H) 7.61 (br. s., 1H) 7.33-7.54 (m, 2H) 7.11 (br. s., 1H) 6.94 (br. s., 2H) 6.79 (br. s., 1H)

Compound 136

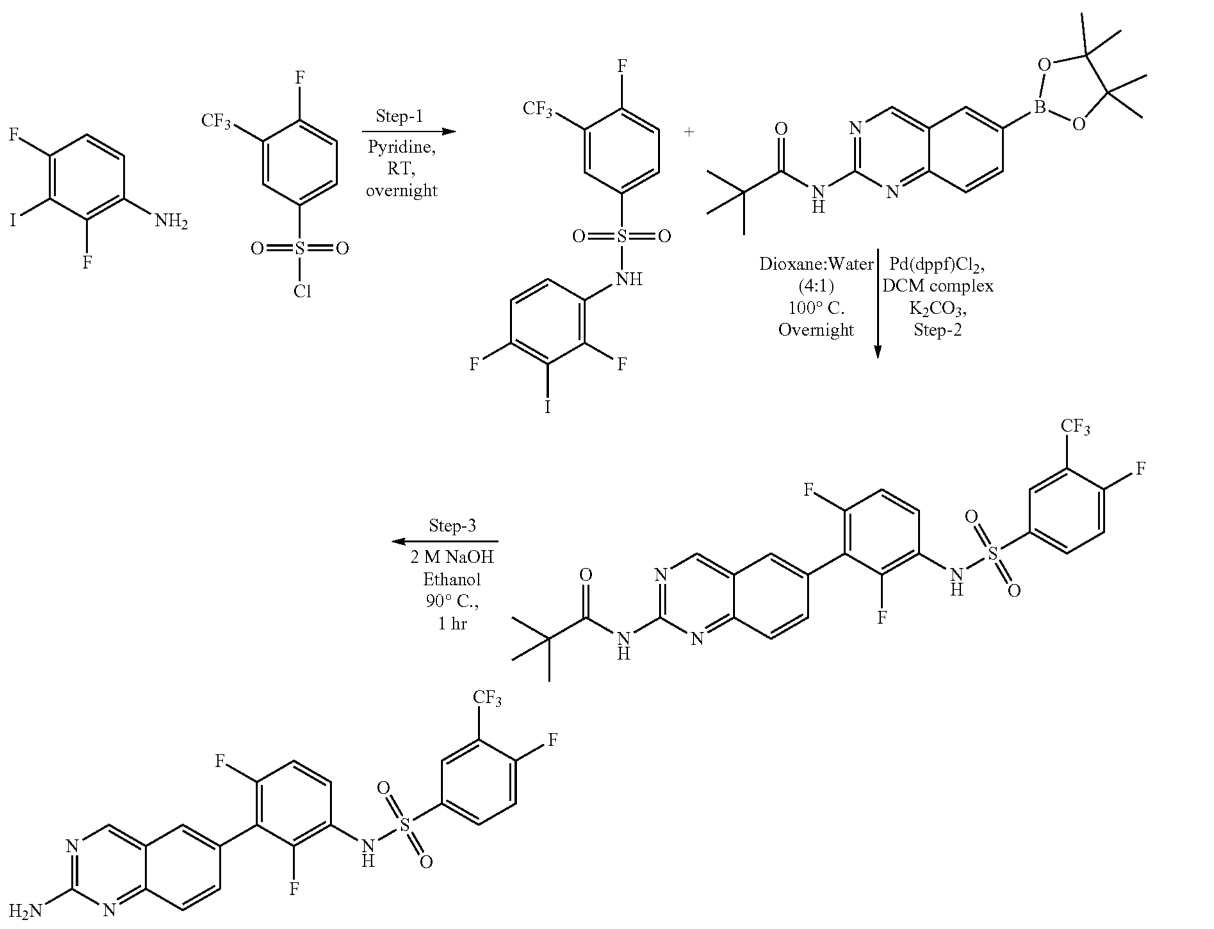

Step-1 Synthesis of N-(2,4-difluoro-3-iodophenyl)-4-fluoro-3-(trifluoromethyl)benzenesulfonamide To a stirred solution of 2,4-difluoro-3-iodoaniline (100 mg, 0.392 mmol. 1.0 equiv.) in pyridine (0.5 mL) at room temperature was added 4-fluoro-3-(trifluoromethyl)benzene-1-sulfonyl chloride (103 mg, 0.3921 mmol. 1.0 equiv.) The resultant reaction mixture was stirred at room temperature for overnight. The progress of reaction was monitored through by TLC. After completion of the reaction, ice cold water was added to reaction mixture. The precipitate formed which was filtered by using Buchner funnel and washed the product with 1N HCl. This material was used in the next reaction without further purification (130 mg).

Step-2: Synthesis of N-(6-(2,6-difluoro-3-(4-fluoro-3-(trifluoromethyl)phenylsulfonamido)phenyl)quinazolin-2-yl)pivalamide To a stirred solution of N-(2,4-difluoro-3-iodophenyl)-4-fluoro-3-(trifluoromethyl)benzenesulfonamide (120 mg, 0.249 mmol, 1.0 equiv) and N-(6-(4,4,5,5-tetramethyl-1,3,2-dioxaborolan-2-yl)quinazolin-2-yl)pivalamide (97 mg, 0.274 mmol, 1.1 equiv) in Dioxane:Water (4:1, 5 mL) was added $K_2CO_3$ (103 mg, 0.747 mmol, 3.0 equiv.). The resulting reaction mixture was purged with nitrogen for 15 minutes followed by the addition of Pd(dppf)$Cl_2$·DCM complex (10 mg, 0.0124 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next reaction without further purification (190 mg), LCMS: 583[M+H]$^+$.

Step-3: Synthesis of N-(3-(2-aminoquinazolin-6-yl)-2,4-difluorophenyl)-4-fluoro-3-(trifluoromethyl) benzenesulfonamide To a stirred solution of N-(6-(2,6-difluoro-3-(4-fluoro-3-(trifluoromethyl)phenylsulfonamido)phenyl)quinazolin-2-yl)pivalamide (160 mg, 0.274 mmol, 1.0 equiv) in ethanol (5 mL) was added 2M NaOH (2 mL). Then, the reaction mixture was allowed to stir at 90 degree Celsius for 1 hr. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase chromatography to obtain as title compound N-(3-(2-aminoquinazolin-6-yl)-2,4-difluorophenyl)-4-fluoro-3-(trifluoromethyl)benzenesulfonamide (5 mg), Analytical Data: LCMS: 499[M+H]+, NMR: $^1$H NMR (400 MHz, DMSO-$d_6$) δ ppm 11.54 (br. s., 1H) 9.14 (s, 1H) 7.91-8.09 (m, 2H) 7.78 (s, 1H) 7.63 (d, J=8.77 Hz, 1H) 7.36-7.55 (m, 2H) 7.05-7.15 (m, 1H) 6.94 (s, 2H) 6.77 (t, J=9.21 Hz, 1H).

added $K_2CO_3$ (99.7 mg, 0.723 mmol, 3.0 equiv.). The resulting reaction mixture was purged with nitrogen for 15 minutes followed by the addition of Pd(dppf)$Cl_2$·DCM complex (9.8 mg, 0.0120 mmol, 0.05 equiv.). The reaction mixture was again purged with nitrogen for 5 minutes. The Compound 137

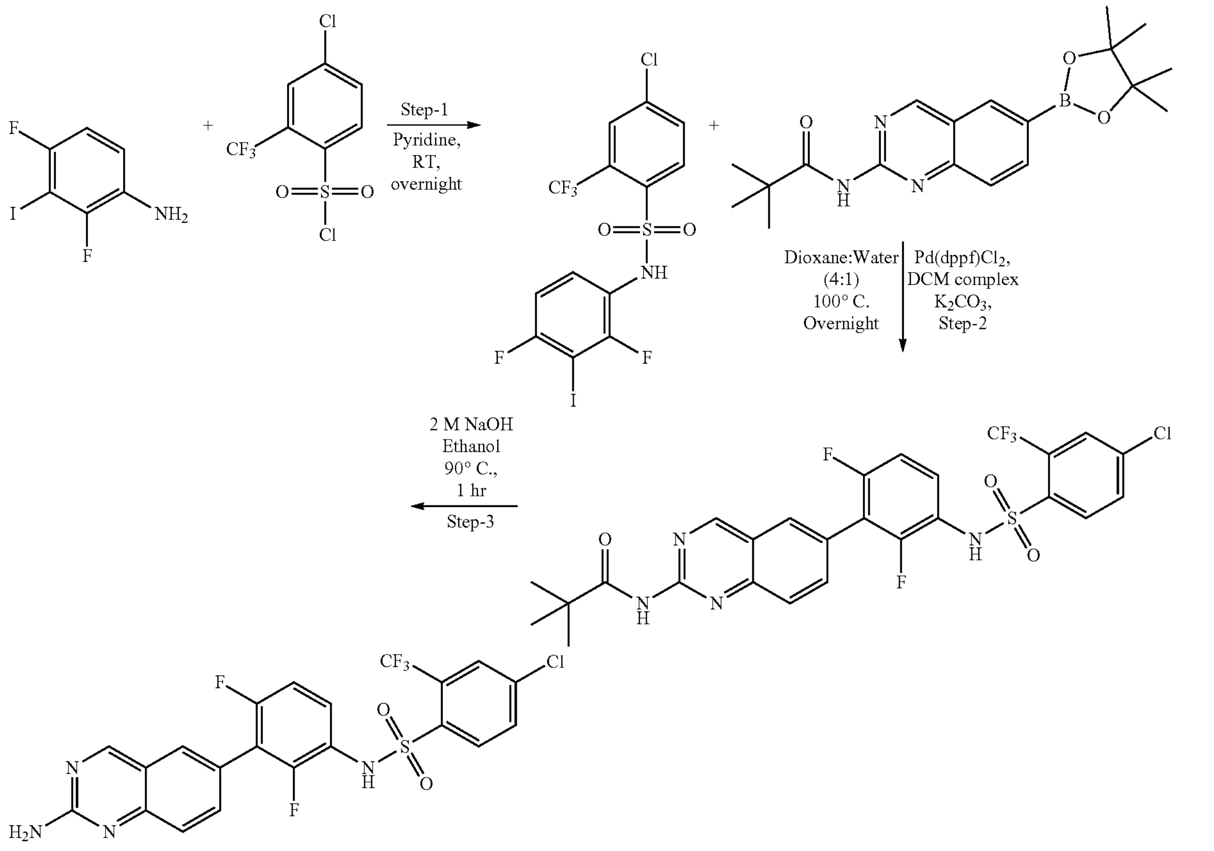

Step-1: Synthesis of 4-chloro-N-(2,4-difluoro-3-iodophenyl)-2-(trifluoromethyl)benzenesulfonamide To a stirred solution of 2,4-difluoro-3-iodoaniline (100 mg, 0.392 mmol. 1.0 equiv.) in pyridine (0.5 mL) at room temperature was added 4-chloro-2-(trifluoromethyl)benzene-1-sulfonyl chloride (109 mg, 0.392 mmol. 1.0 equiv.) The resultant reaction mixture was stirred at room temperature for overnight. The progress of reaction was monitored through by TLC. After completion of the reaction, ice cold water had been added to reaction mixture. The precipitate formed which was filtered by using Buchner funnel and washed the product with 1N HCl. This material was used in the next reaction without further purification (150 mg).

Step-2: Synthesis of N-(6-(3-(4-chloro-2-(trifluoromethyl)phenylsulfonamido)-2,6-difluorophenyl)quinazolin-2-yl)pivalamide To a stirred solution of 4-chloro-N-(2,4-difluoro-3-iodophenyl)-2-(trifluoromethyl)benzenesulfonamide (120 mg, 0.241 mmol, 1.0 equiv) and N-(6-(4,4,5,5-tetramethyl-1,3,2-dioxaborolan-2-yl)quinazolin-2-yl)pivalamide (94 mg, 0.265 mmol, 1.1 equiv) in Dioxane:Water (4:1, 5 mL) was reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next reaction without further purification (160 mg). LCMS: 599[M+H]+

Step-3: Synthesis of N-(3-(2-aminoquinazolin-6-yl)-2,4-difluorophenyl)-4-chloro-2-(trifluoromethyl)benzenesulfonamide To a stirred solution of N-(6-(3-(4-chloro-2-(trifluoromethyl)phenylsulfonamido)-2,6-difluorophenyl)quinazolin-2-yl)pivalamide (160 mg, 0.267 mmol, 1.0 equiv) in ethanol (5 mL) was added 2M NaoH (2 mL) at room temperature. After addition, the reaction mixture was allowed to stir at 90 degree Celsius for 1 hr. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase chromatography to obtain as title compound N-(3-(2-aminoquinazolin-6-yl)-2,4-difluorophenyl)-3-chloro-5-(trifluoromethyl)benzenesulfonamide (15 mg), Analytical Data: LCMS: 515[M+H]$^+$, NMR: $^1$H NMR (400 MHz, DMSO-$d_6$) δ ppm 11.97 (br. s., 1H) 9.16 (s, 1H) 8.01-8.12 (m, 1H) 7.69-7.92 (m, 3H) 7.64 (d, J=8.33 Hz, 1H) 7.48 (d, J=8.77 Hz, 1H) 6.95 (br. s., 3H) 6.79 (br. s., 1H).

Compound 138

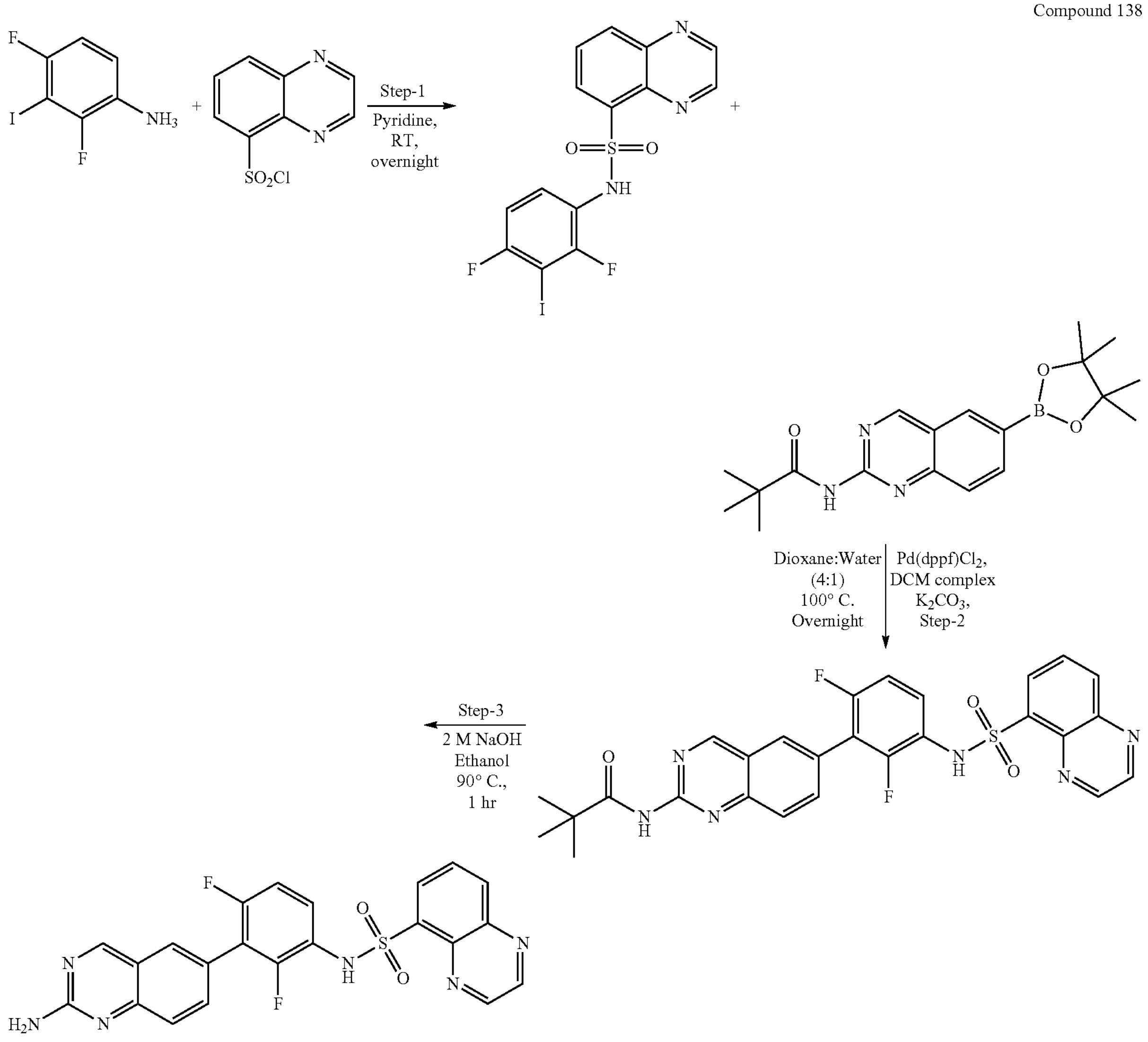

Step-1: Synthesis of N-(2,4-difluoro-3-iodophenyl)quinoxaline-5-sulfonamide

To a stirred solution of 2,4-difluoro-3-iodoaniline (100 mg, 0.392 mmol. 1.0 equiv.) in pyridine (1.0 mL) at room temperature was added quinoxaline-5-sulfonyl chloride (89.6 mg, 0.392 mmol. 1.0 equiv.) The resultant reaction mixture was stirred at room temperature for overnight. The progress of reaction was monitored through by TLC. After completion of the reaction, ice cold water was added to reaction mixture. The precipitate formed which was filtered by using Buchner funnel and washed the product with 1N HCl. This material was used in the next reaction without further purification (100 mg).

Step-2: Synthesis of N-(6-(2,6-difluoro-3-(quinoxaline-5-sulfonamido)phenyl)quinazolin-2-yl)pivalamide To a stirred solution of N-(2,4-difluoro-3-iodophenyl)quinoxaline-5-sulfonamide (100 mg, 0.223 mmol, 1.0 equiv) and N-(6-(4,4,5,5-tetramethyl-1,3,2-dioxaborolan-2-yl)quinazolin-2-yl)pivalamide (87 mg, 0.245 mmol, 1.1 equiv) in Dioxane:Water (4:1, 5 mL) was added $K_2CO_3$ (92 mg, 0.669 mmol, 3.0 equiv.). The resulting reaction mixture was purged with nitrogen for 15 minutes followed by the addition of Pd(dppf)$Cl_2$·DCM complex (9 mg, 0.0111 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next reaction without further purification (120 mg). LCMS: 549[M+H]$^+$ Step-3: Synthesis of N-(3-(2-aminoquinazolin-6-yl)-2,4-difluorophenyl)quinoxaline-5-sulfonamide To a stirred solution of N-(6-(2,6-difluoro-3-(quinoxaline-5-sulfonamido)phenyl)quinazolin-2-yl)pivalamide (120 mg, 0.21 mmol, 1.0 equiv) in ethanol (4 mL) was added 2M NaoH (1 mL). Then, the reaction mixture was allowed to stir at 90 degree Celsius for 1 hr. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase chromatography to obtain as title compound N-(3-(2-aminoquinazolin-6-yl)-2,4-difluorophenyl)quinoxaline-5-sulfonamide (15 mg), Analytical Data: LCMS: 465[M+H]$^+$, NMR: $^1$H NMR (400 MHz, DMSO-$d_6$) δ ppm 10.23 (br. s., 1H) 9.12 (s, 1H) 9.04 (s, 2H) 8.33 (d, J=6.58 Hz, 1H) 8.28 (d, J=7.89 Hz, 1H) 7.91 (t, J=7.89 Hz, 1H) 7.70 (s, 1H) 7.52 (d, J=8.33 Hz, 1H) 7.43 (d, J=8.77 Hz, 1H) 7.12-7.25 (m, 1H) 6.98 (s, 3H)

temperature was added 3-(trifluoromethoxy)benzene-1-sulfonyl chloride (204 mg, 0.784 mmol. 1.0 equiv.) The resultant reaction mixture was stirred at room temperature for overnight. The progress of reaction was monitored through by TLC. After completion of the reaction, ice cold water was added to reaction mixture. The precipitate formed which was filtered by using Buchner funnel and washed the product with 1N HCl. This material was used in the next reaction without further purification (300 mg).

Step-2: Synthesis of N-(6-(2,6-difluoro-3-(3-(trifluoromethoxy)phenylsulfonamido)phenyl)quinazolin-2-yl)pivalamide To a stirred solution of N-(2,4-difluoro-3-iodophenyl)-3-(trifluoromethoxy)benzenesulfonamide (300 mg, 0.626 mmol, 1.0 equiv) and N-(6-(4,4,5,5-tetramethyl-1,3,2-dioxaborolan-2-yl)quinazolin-2-yl)pivalamide (244 mg, 0.688 mmol, 1.1 equiv) in Dioxane:Water (8:2, 10 mL) was added $K_2CO_3$ (259 mg, 1.87 mmol, 3.0 equiv.). The resulting Compound 139

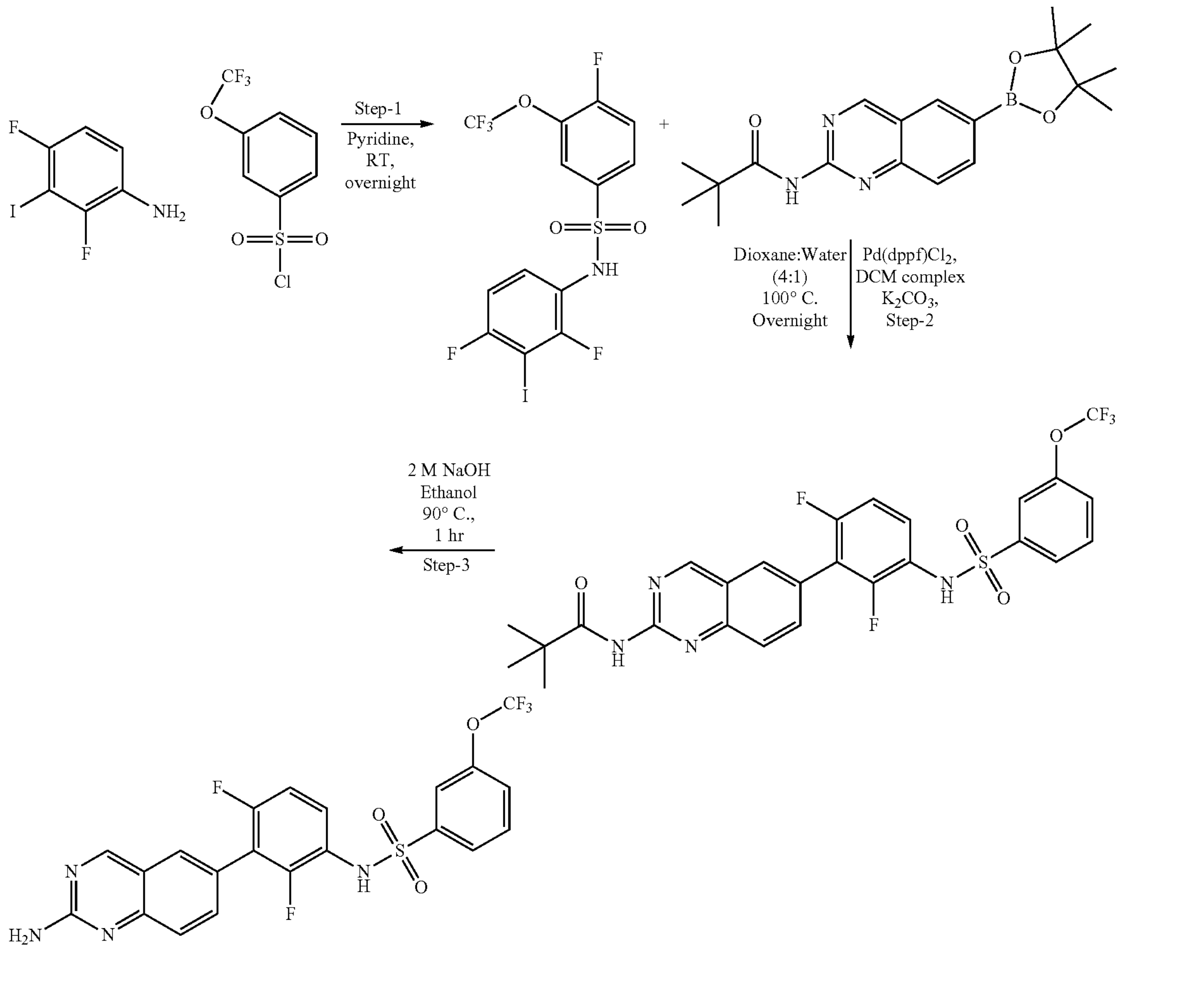

Step-1: Synthesis of N-(2,4-difluoro-3-iodophenyl)-3-(trifluoromethoxy)benzenesulfonamide To a stirred solution of 2,4-difluoro-3-iodoaniline (200 mg, 0.784 mmol. 1.0 equiv.) in pyridine (1.5 mL) at room reaction mixture was purged with nitrogen for 15 minutes followed by the addition of Pd(dppf)$Cl_2$·DCM complex (25 mg, 0.0313 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next reaction without further purification (350 mg). LCMS: 581[M+H]$^+$ Step-3: Synthesis of N-(3-(2-aminoquinazolin-6-yl)-2,4-difluorophenyl)-3-(trifluoromethoxy)benzenesulfonamide To a stirred solution of N-(6-(2,6-difluoro-3-(3-(trifluoromethoxy)phenylsulfonamido)phenyl)quinazolin-2-yl) pivalamide (350 mg, 0.602 mmol, 1.0 equiv) in ethanol (5 mL) was added 2M NaoH (1 mL). Then, the reaction mixture was allowed to stir at 90 degree Celsius for 1 hr. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase chromatography to obtain as title compound N-(3-(2-aminoquinazolin-6-yl)-2,4-difluorophenyl)-3-(trifluoromethoxy)benzenesulfonamide (25 mg), Analytical Data: LCMS: 497[M+H]$^+$, NMR: $^1$H NMR (400 MHz, DMSO-$d_6$) □ ppm 11.43 (br. s., 1H) 10.47 (s, 1H) 9.19 (s, 1H) 7.75 (s, 3H) 7.62 (s, 1H) 7.52-7.59 (m, 1H) 7.41-7.52 (m, 1H) 7.14-7.41 (m, 4H)

temperature was added thiophene-3-sulfonyl chloride (198 mg, 1.17 mmol. 2.0 equiv.) The resultant reaction mixture was stirred at room temperature for overnight. The progress of reaction was monitored through by TLC. After completion of the reaction, ice cold water had been added to reaction mixture. The precipitate formed which was filtered by using Buchner funnel and washed the product with 1N HCl. This material was used in the next reaction without further purification (180 mg).

Step-2: Synthesis of N-(6-(2,6-difluoro-3-(thiophene-3-sulfonamido)phenyl)quinazolin-2-yl)pivalamide To a stirred solution of N-(2,4-difluoro-3-iodophenyl) thiophene-3-sulfonamide (180 mg, 0.448 mmol, 1.0 equiv) and N-(6-(4,4,5,5-tetramethyl-1,3,2-dioxaborolan-2-yl)quinazolin-2-yl)pivalamide (174 mg, 0.492 mmol, 1.1 equiv) in Dioxane:Water (4:1, 5 mL) was added $K_2CO_3$ (185 mg, 1.344 mmol, 3.0 equiv.). The resulting reaction mixture was purged with nitrogen for 15 minutes followed by the addition of Pd(dppf)$Cl_2$·DCM complex (18.2 mg, 0.022 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, Compound 140

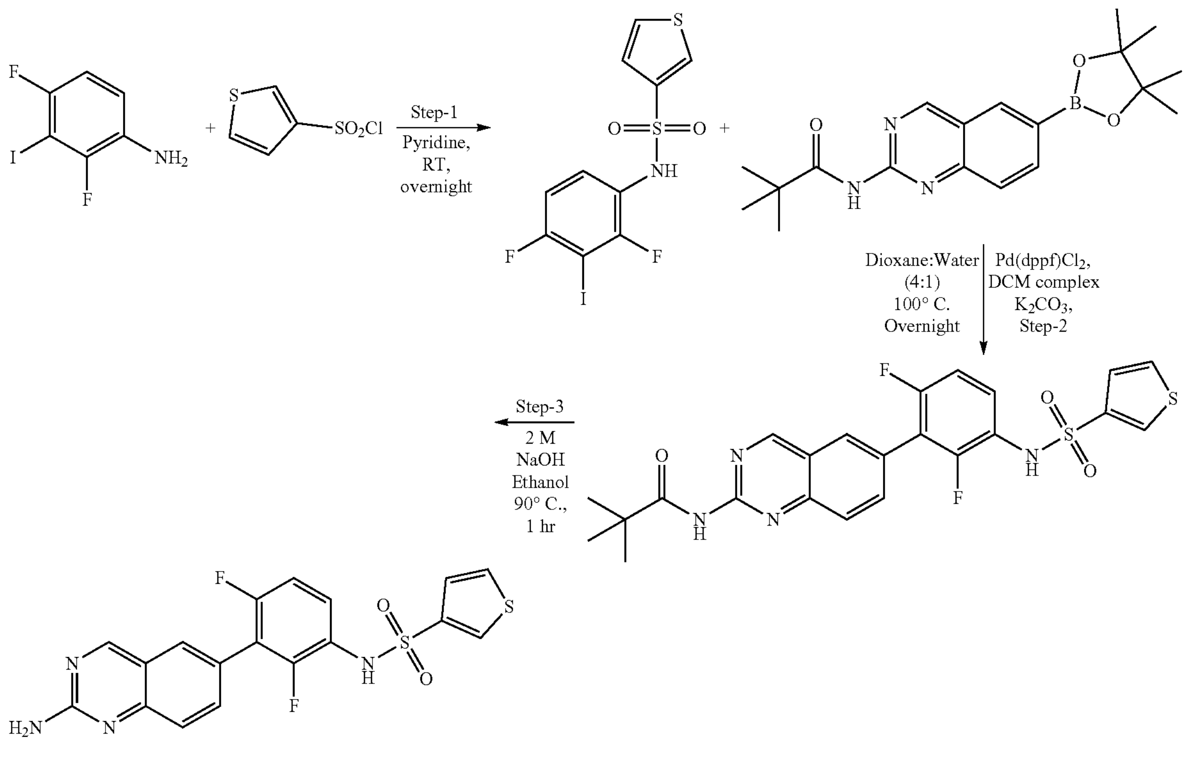

Step-1: Synthesis of N-(2,4-difluoro-3-iodophenyl) thiophene-3-sulfonamide

To a stirred solution of 2,4-difluoro-3-iodoaniline (150 mg, 0.588 mmol. 1.0 equiv.) in pyridine (1.0 mL) at room water was added to the reaction mixture, extracted with EtOAc (2×50 mL). The organic layers were combined, dried over anhydrous $Na_2SO_4$ and evaporated under reduced pressure. The crude product was used in the next reaction without further purification (290 mg). LCMS: 503[M+H]$^+$ Step-3: Synthesis of N-(3-(2-aminoquinazolin-6-yl)-2,4-difluorophenyl)thiophene-3-sulfonamide To a stirred solution of N-(6-(2,6-difluoro-3-(thiophene-3-sulfonamido)phenyl)quinazolin-2-yl)pivalamide (290 mg, 0.577 mmol, 1.0 equiv) in ethanol (5 mL) was added 2M NaoH (1 mL). Then, the reaction mixture was allowed to stir at 90 degree Celsius for 1 hr. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase chromatography to obtain as title compound N-(3-(2-aminoquinazolin-6-yl)-2,4-difluorophenyl)thiophene-3-sulfonamide (28 mg), Analytical Data: LCMS: 419[M+H]$^+$, NMR: $^1$H NMR (400 MHz, DMSO-$d_6$) □ ppm 11.31 (br. s., 1H) 9.15 (s, 1H) 7.84 (br. s., 1H) 7.79 (br. s., 1H) 7.62 (d, J=8.77 Hz, 1H) 7.55 (br. s., 1H) 7.47 (d, J=8.77 Hz, 1H) 7.13-7.29 (m, 2H) 6.97 (s, 2H) 6.85-6.93 (m, 1H).

Step-1: Synthesis of N-(2,4-difluoro-3-iodophenyl)-3-isopropylbenzenesulfonamide To a stirred solution of 2,4-difluoro-3-iodoaniline (150 mg, 0.5882 mmol. 1.0 equiv.) in pyridine (1.0 mL) at room temperature was added 3-isopropylbenzene-1-sulfonyl chloride (128.6 mg, 0.5882 mmol. 1.0 equiv.) The resultant reaction mixture was stirred at room temperature for overnight. The progress of reaction was monitored through by TLC. After completion of the reaction, ice cold water had been added to reaction mixture. The precipitate formed which was filtered by using Buchner funnel and washed the product with 1N HCl. This material was used in the next reaction without further purification (220 mg).

Step-2: Synthesis of N-(6-(2,6-difluoro-3-(3-isopropylphenylsulfonamido)phenyl)quinazolin-2-yl)pivalamide To a stirred solution of N-(2,4-difluoro-3-iodophenyl)-3-isopropylbenzenesulfonamide (200 mg, 0.4574 mmol, 1.0

Compound 141

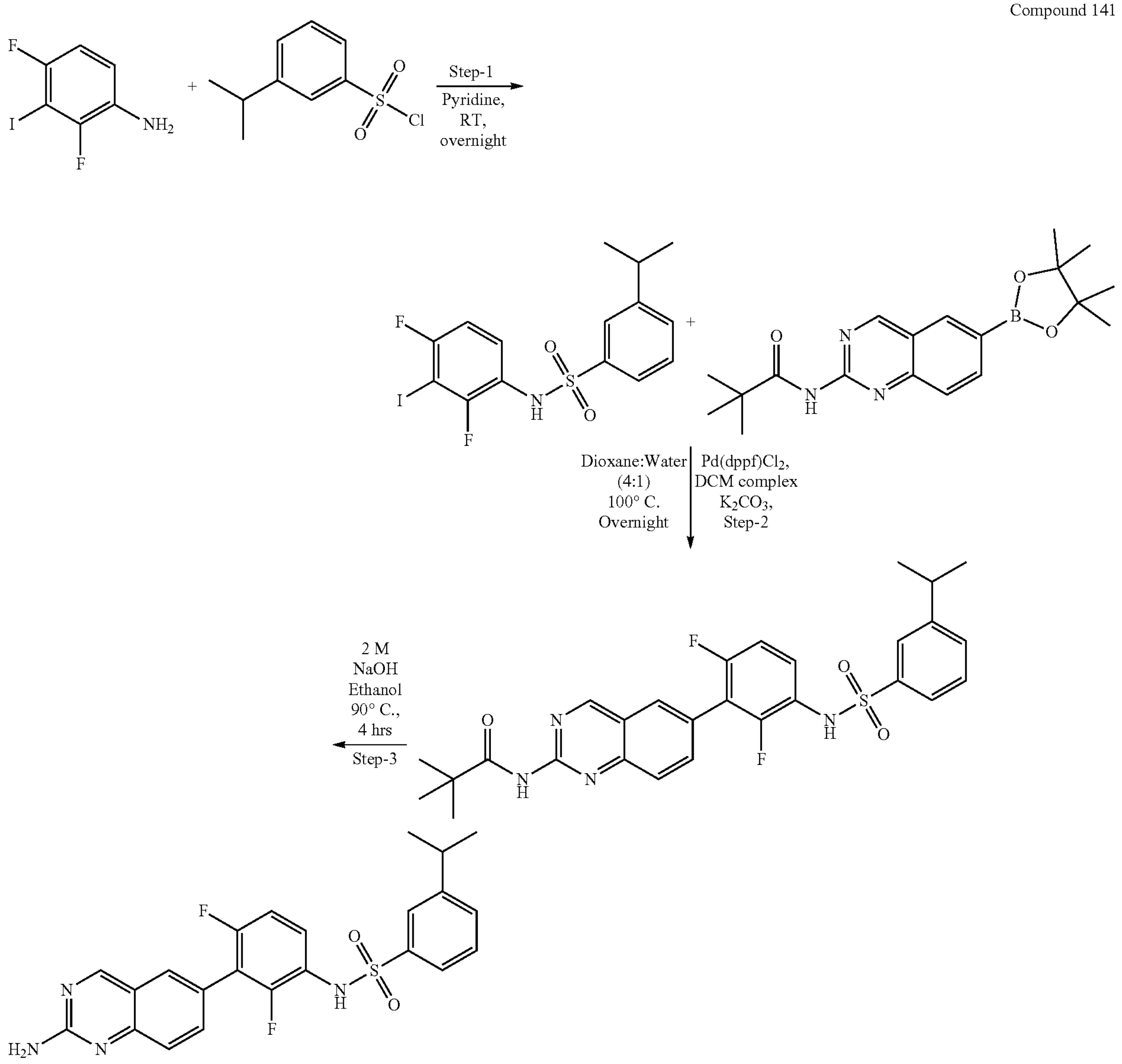

equiv) and N-(6-(4,4,5,5-tetramethyl-1,3,2-dioxaborolan-2-yl)quinazolin-2-yl)pivalamide (194.9 mg, 0.5488 mmol, 1.2 equiv) in Dioxane:Water (4:1, 5 mL) was added $K_2CO_3$ (189.6 mg, 1.3722 mmol, 3.0 equiv.). The resulting reaction mixture was purged with nitrogen for 10 minutes followed by the addition of Pd(dppf)$Cl_2$·DCM complex (18.6 mg, 0.0228 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used in the next reaction without further purification (400 mg). LCMS: 539.3 $[M+H]^+$ Step-3: Synthesis of N-(3-(2-aminoquinazolin-6-yl)-2,4-difluorophenyl)-3-isopropylbenzenesulfonamide To a stirred solution of N-(6-(2,6-difluoro-3-(3-isopropylphenylsulfonamido)phenyl)quinazolin-2-yl)pivalamide (400 mg, 0.7426 mmol, 1.0 equiv) in ethanol (6 mL) was added 2M NaOH (5 mL). Then, the reaction mixture was allowed to stir at 90 degree Celsius for 4 hrs. After completion of reaction, the solvent was evaporated and water was added to the reaction mixture, extracted with EtOAc (2×100 mL). The organic layers were combined, dried over anhydrous $Na_2SO_4$ and evaporated under reduced, evaporated under reduced and purified by reverse phase silica gel chromatography to obtain as title compound N-(3-(2-aminoquinazolin-6-yl)-2,4-difluorophenyl)-3-isopropylbenzenesulfonamide (35 mg), Analytical Data: LCMS: 455.4$[M+H]^+$, NMR: $^1H$ NMR (400 MHz, DMSO-$d_6$) δ ppm 10.17 (br. s., 1H) 9.13 (br. s., 1H) 7.70 (br. s., 1H) 7.51-7.47 (m, 7H) 7.27 (br. s., 1H) 7.17 (br. s., 1H) 7.02 (br. s., 2H) 1.13 (d, J=5.70 Hz, 6H).

Step-1: Synthesis of N-(2,4-difluoro-3-iodophenyl)thiophene-2-sulfonamide

To a stirred solution of 2,4-difluoro-3-iodoaniline (200 mg, 0.7843 mmol. 1.0 equiv.) in pyridine (1.0 mL) at room temperature was added thiophene-2-sulfonyl chloride (143.2 mg, 0.7843 mmol. 1.0 equiv.) The resultant reaction mixture was stirred at room temperature for overnight. The progress of reaction was monitored through by TLC. After completion of the reaction, ice cold water had been added to reaction mixture. The precipitate formed which was filtered by using Buchner funnel and washed the product with 1N HCl. This material was used in the next reaction without further purification (300 mg).

Step-2: Synthesis of N-(6-(2,6-difluoro-3-(thiophene-2-sulfonamido)phenyl)quinazolin-2-yl)pivalamide To a stirred solution of N-(2,4-difluoro-3-iodophenyl)thiophene-2-sulfonamide (300 mg, 0.7477 mmol, 1.0 equiv) and N-(6-(4,4,5,5-tetramethyl-1,3,2-dioxaborolan-2-yl)quinazolin-2-yl)pivalamide (318.7 mg, 0.8973 mmol, 1.2 equiv) in Dioxane:Water (5:2, 7 mL) was added $K_2CO_3$ (310 mg, 2.2433 mmol, 3.0 equiv.). The resulting reaction mixture was purged with nitrogen for 10 minutes followed by the addition of Pd(dppf)$Cl_2$·DCM complex (30.5 mg, 0.0373 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under Compound 142

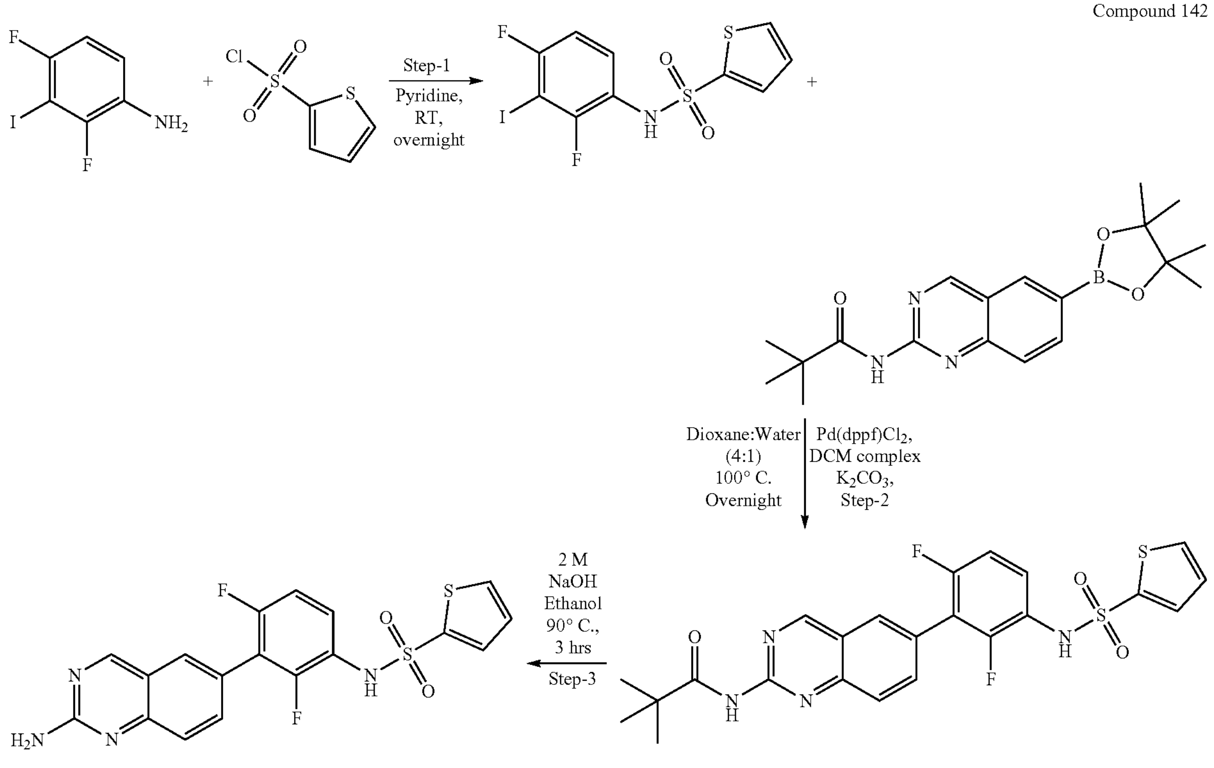

reduced pressure. The crude product was used in the next reaction without further purification (480 mg). LCMS: 503.02 $[M+H]^+$ Step-3: Synthesis of N-(3-(2-aminoquinazolin-6-yl)-2,4-difluorophenyl)thiophene-2-sulfonamide To a stirred solution of N-(6-(2,6-difluoro-3-(thiophene-2-sulfonamido)phenyl)quinazolin-2-yl)pivalamide (480 mg, 0.9551 mmol, 1.0 equiv) in ethanol (6 mL) was added 2M NaOH (6 mL). Then, the reaction mixture was allowed to stir at 90 degree Celsius for 3 hrs. After completion of reaction, the solvent was evaporated and water was added to the reaction mixture, extracted with EtOAc (2×100 mL). The organic layers were combined, dried over anhydrous $Na_2SO_4$ and evaporated under reduced, evaporated under reduced and purified by reverse phase silica gel chromatography to obtain as title compound N-(3-(2-aminoquinazolin-6-yl)-2,4-difluorophenyl)thiophene-2-sulfonamide (16 mg), Analytical Data: LCMS: 419.3$[M+H]^+$, NMR: $^1H$ NMR (400 MHz, DMSO-$d_6$) δ ppm 10.38 (br. s., 1H) 9.16 (s, 1H) 7.93 (br. s., 1H) 7.77 (s, 1H) 7.58 (d, J=8.33 Hz, 1H) 7.48 (d, J=7.02 Hz, 2H) 7.26-7.34 (m, 1H) 7.12-7.24 (m, 2H) 7.03 (s, 2H)

Compound 143

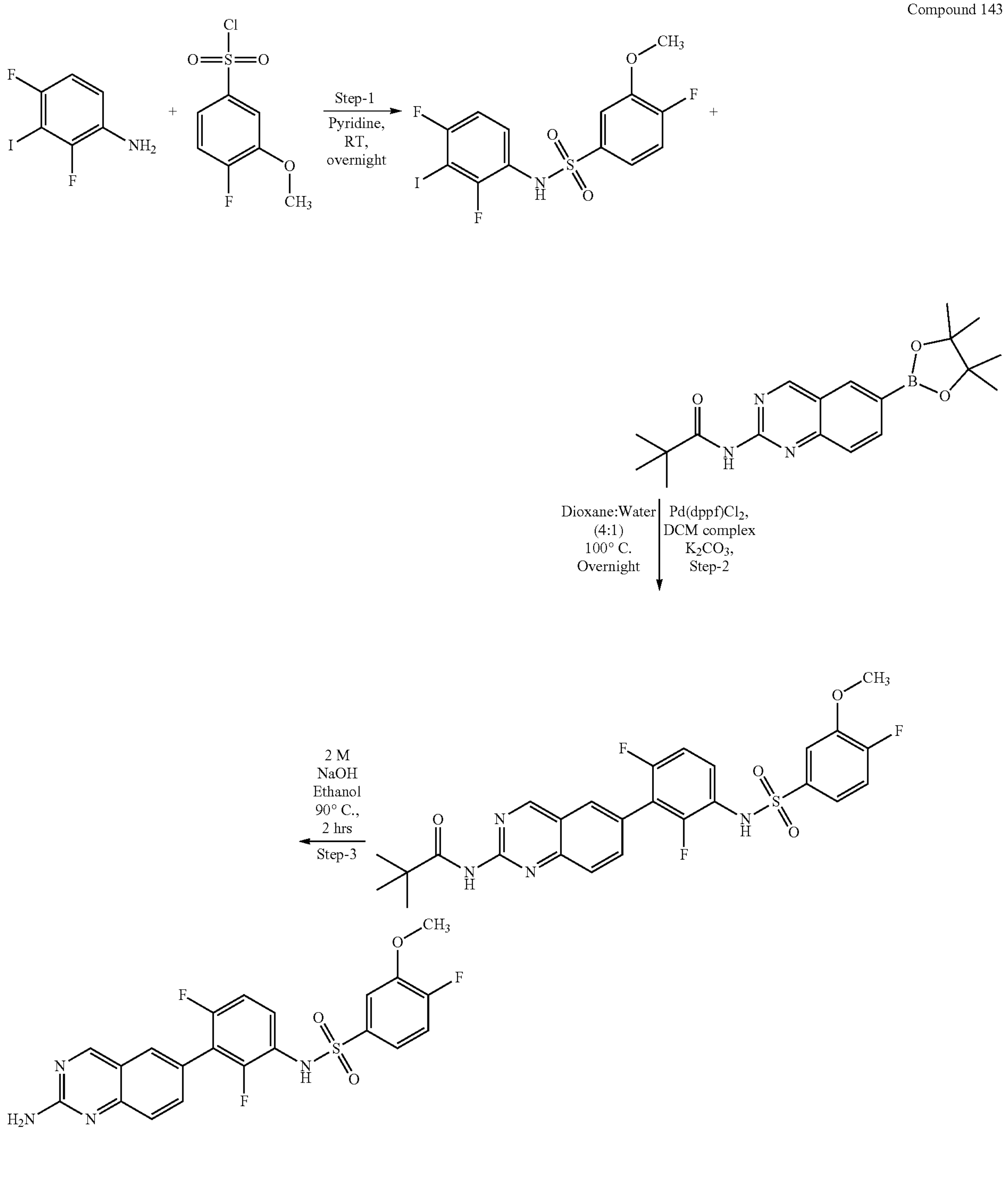

Step-1: Synthesis of N-(2,4-difluoro-3-iodophenyl)-4-fluoro-3-methoxybenzenesulfonamide To a stirred solution of 2,4-difluoro-3-iodoaniline (200 mg, 0.7842 mmol. 1.0 equiv.) in pyridine (1.0 mL) at room temperature was 4-fluoro-3-methoxybenzene-1-sulfonyl chloride (176.1 mg, 0.7843 mmol. 1.0 equiv.) The resultant reaction mixture was stirred at room temperature for overnight. The progress of reaction was monitored through by TLC. After completion of the reaction, ice cold water was added to reaction mixture. The precipitate formed which was filtered by using Buchner funnel and washed the product with 1N HCl. This material was used in the next reaction without further purification (300 mg).

Step-2: Synthesis of N-(6-(2,6-difluoro-3-(4-fluoro-3-methoxyphenylsulfonamido)phenyl)quinazolin-2-yl)pivalamide To a stirred solution of N-(2,4-difluoro-3-iodophenyl)-4-fluoro-3-methoxybenzenesulfonamide (300 mg, 0.6769 mmol, 1.0 equiv) and N-(6-(4,4,5,5-tetramethyl-1,3,2-dioxaborolan-2-yl)quinazolin-2-yl)pivalamide (288.5 mg, 0.8123 mmol, 1.2 equiv) in Dioxane:Water (5:2, 7 mL) was added $K_2CO_3$ (280.6 mg, 2.0307 mmol, 3.0 equiv.). The resulting reaction mixture was purged with nitrogen for 10 minutes followed by the addition of $Pd(dppf)Cl_2 \cdot DCM$ complex (27.6 mg, 0.0338 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used in the next reaction without further purification (620 mg). LCMS: 545.3[M+H]$^+$ Step-3: Synthesis of N-(3-(2-aminoquinazolin-6-yl)-2,4-difluorophenyl)-4-fluoro-3-methoxybenzenesulfonamide To a stirred solution of N-(6-(2,6-difluoro-3-(4-fluoro-3-methoxyphenylsulfonamido)phenyl)quinazolin-2-yl)pivalamide (620 mg, 1.1385 mmol, 1.0 equiv) in ethanol (6 mL) was added 2M NaOH (6 mL). Then, the reaction mixture was allowed to stir at 90 degree Celsius for 2 hrs. After completion of reaction, the solvent was evaporated and water was added to the reaction mixture, extracted with EtOAc (1×100 mL). The organic layers were combined, dried over anhydrous $Na_2SO_4$ and evaporated under reduced, evaporated under reduced and purified by reverse phase silica gel chromatography to obtain as title compound N-(3-(2-aminoquinazolin-6-yl)-2,4-difluorophenyl)-4-fluoro-3-methoxybenzenesulfonamide (38 mg), Analytical Data: LCMS: 461.4[M+H]$^+$, NMR: $^1$H NMR (400 MHz, DMSO-$d_6$) δ ppm 10.25 (br. s., 1H) 9.14 (s, 1H) 7.76 (s, 1H) 7.58 (d, J=8.33 Hz, 1H) 7.38-7.51 (m, 3H) 7.32 (br. s., 1H) 7.15-7.29 (m, 2H) 7.03 (s, 2H) 3.84 (s, 3H)

Compound 144

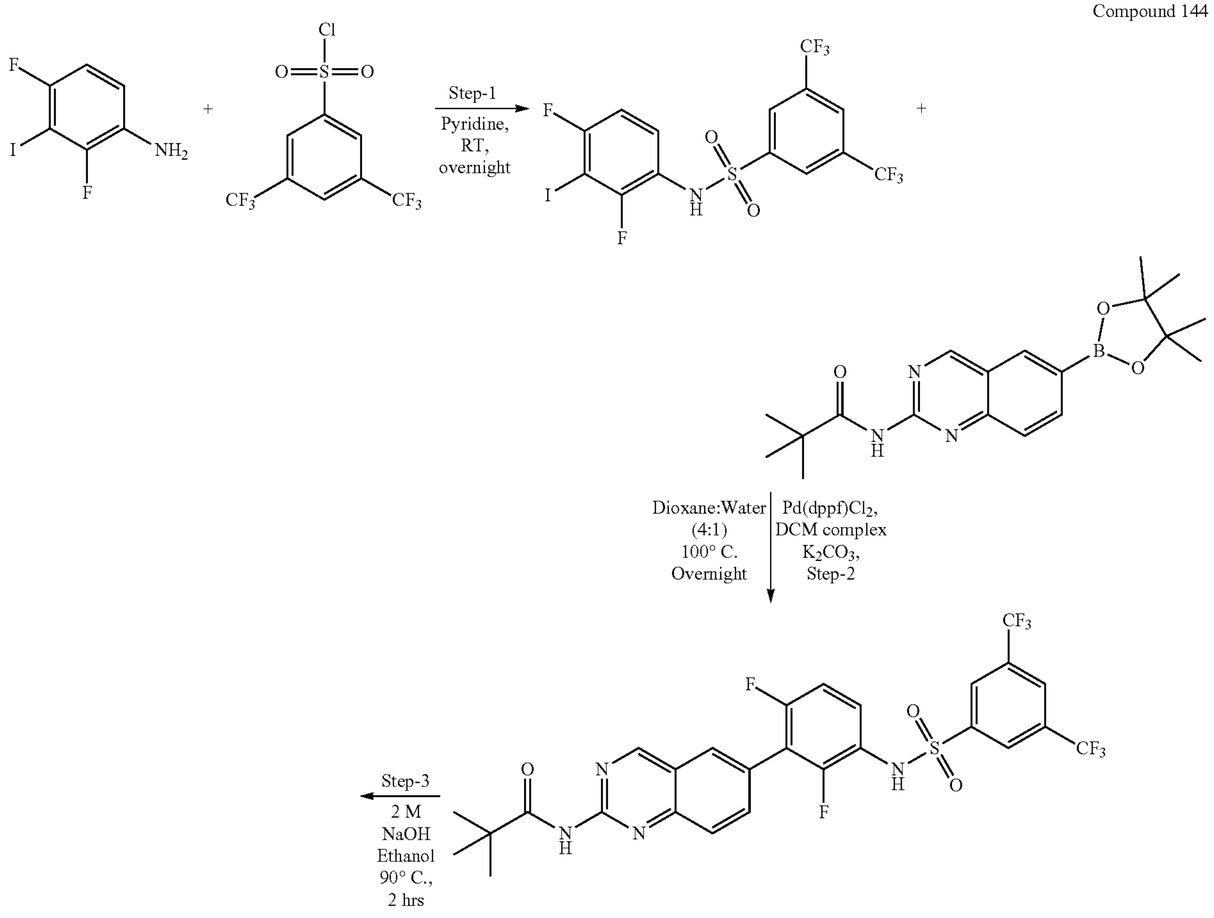

-continued

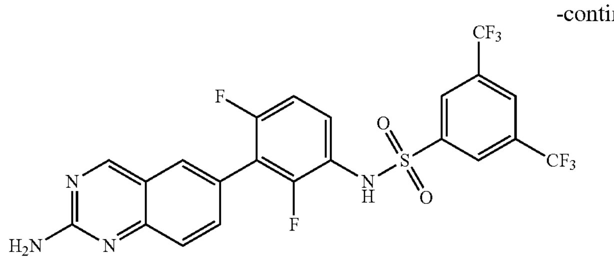

Step-1: Synthesis of N-(2,4-difluoro-3-iodophenyl)-3,5-bis(trifluoromethyl)benzenesulfonamide To a stirred solution of 2,4-difluoro-3-iodoaniline (200 mg, 0.7843 mmol. 1.0 equiv.) in pyridine (1 mL) at room temperature was added 3,5-bis(trifluoromethyl)benzene-1-sulfonyl chloride (245.1 mg, 0.7843 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc, dried over sodium sulphate and concentrated under vacuum to obtain crude product which was triturated with hexanes to obtain desired product N-(2,4-difluoro-3-iodophenyl)-3,5-bis(trifluoromethyl)benzenesulfonamide (270 mg).

Step-2: Synthesis of N-(6-(3-(3,5-bis(trifluoromethyl)phenylsulfonamido)-2,6-difluorophenyl)quinazolin-2-yl)pivalamide To a stirred solution of N-(2,4-difluoro-3-iodophenyl)-3,5-bis(trifluoromethyl)benzenesulfonamide (270 mg, 0.5083 mmol, 1.0 equiv) and N-(6-(4,4,5,5-tetramethyl-1,3,2-dioxaborolan-2-yl)quinazolin-2-yl)pivalamide (216.5 mg, 0.6099 mmol, 1.2 equiv) in dioxane:water (4:1, 5 mL) was added $K_2CO_3$ (210.7 mg, 1.5249 mmol, 3.0 equiv.). The resulting reaction mixture was purged with nitrogen for 10 minutes followed by the addition of Pd(dppf)$Cl_2$·DCM complex (20.7 mg, 0.0254 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure to obtain title product N-(6-(3-(3,5-bis(trifluoromethyl)phenylsulfonamido)-2,6-difluorophenyl)quinazolin-2-yl)pivalamide (450 mg). This product was used in next step without further purification. LCMS: 633.1[M+H]$^+$ Step-3: Synthesis of N-(3-(2-aminoquinazolin-6-yl)-2,4-difluorophenyl)-3,5-bis(trifluoromethyl)benzenesulfonamide To a stirred solution of N-(6-(3-(3,5-bis(trifluoromethyl)phenylsulfonamido)-2,6-difluorophenyl)quinazolin-2-yl)pivalamide (450 mg, 0.7114 mmol, 1.0 equiv) in ethanol (6 mL) at room temperature was added 2M NaOH (6 mL). Then, the reaction mixture was allowed to stir at 90° C. for 2 hrs. Progress of the reaction was monitored by TLC and LCMS. After completion of the reaction, RM was concentrated under reduced pressure to evaporate ethanol; water was added to crude, extracted with EtOAc (2×100 mL). The organic layers were combined, dried over anhydrous $Na_2SO_4$, evaporated under reduced pressure to obtain crude product which was purified by using reverse phase chromatography technique to obtain desired compound N-(3-(2-aminoquinazolin-6-yl)-2,4-difluorophenyl)-3,5-bis(trifluoromethyl)benzenesulfonamide (25 mg), Analytical Data: LCMS: 549.2 [M+H]$^+$, $^1$H NMR (400 MHz, DMSO-$d_6$) δ ppm 10.70 (br. s., 1H) 9.12 (s, 1H) 8.43 (br. s., 1H) 8.23 (s, 2H) 7.71 (s, 1H) 7.55 (d, J=8.77 Hz, 1H) 7.46 (d, J=8.77 Hz, 1H) 7.21-7.31 (m, 1H) 7.12 (t, J=8.99 Hz, 1H) 7.01 (s, 2H)

Compound 145

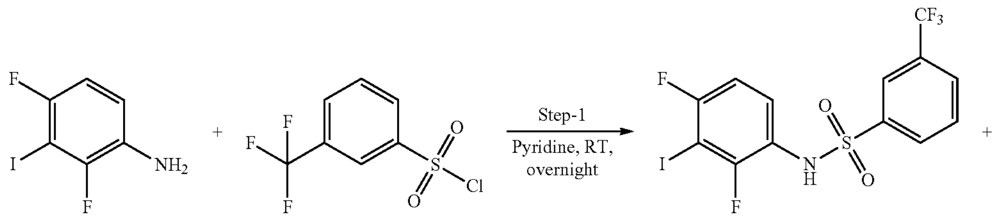

-continued

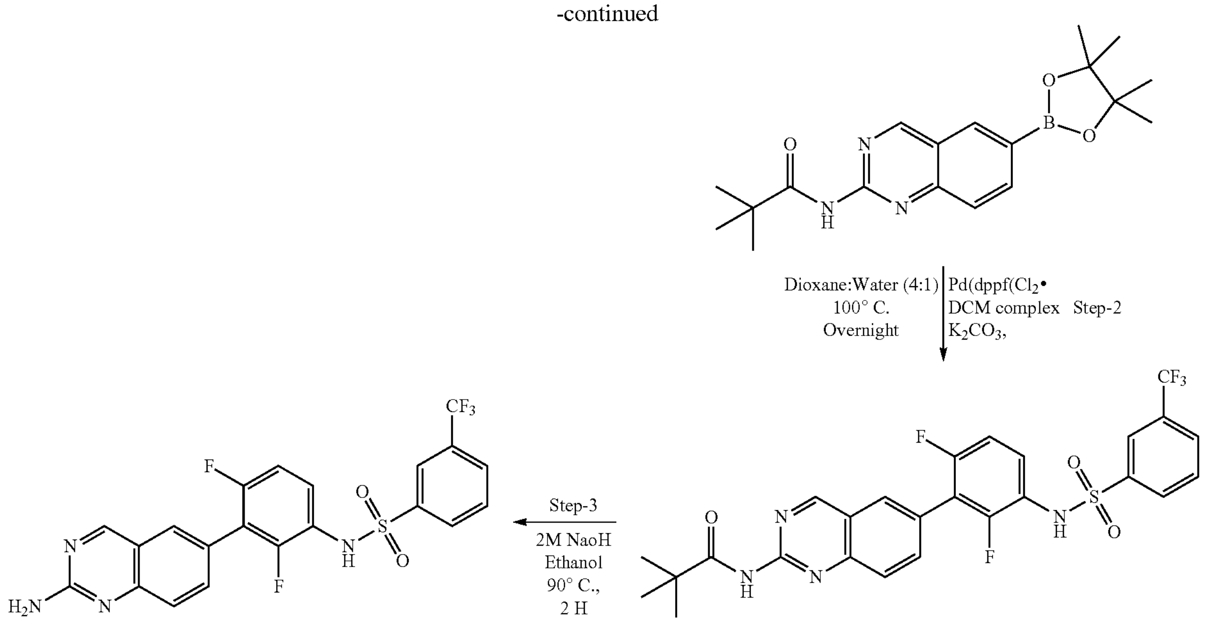

Step-1: Synthesis of N-(2,4-difluoro-3-iodophenyl)-3-(trifluoromethyl)benzenesulfonamide To a stirred solution of 2,4-difluoro-3-iodoaniline (200 mg, 0.7843 mmol. 1.0 equiv.) in pyridine (1.0 mL) at room temperature was added 3-(trifluoromethyl)benzene-1-sulfonyl chloride (191.8 mg, 0.7843 mmol. 1.0 equiv.) The resultant reaction mixture was stirred at room temperature for overnight. The progress of reaction was monitored through by TLC. After completion of the reaction, ice cold water was added to reaction mixture. The precipitate formed was filtered using Buchner funnel and washed the product with 1N HCl to remove pyridine. This material was used in the next reaction without further purification (224 mg).

Step-2: Synthesis of N-(6-(2,6-difluoro-3-(3-(trifluoromethyl)phenylsulfonamido)phenyl)quinazolin-2-yl)pivalamide To a stirred solution of N-(2,4-difluoro-3-iodophenyl)-3-(trifluoromethyl)benzenesulfonamide (220 mg, 0.4749 mmol, 1.0 equiv) and N-(6-(4,4,5,5-tetramethyl-1,3,2-dioxaborolan-2-yl)quinazolin-2-yl)pivalamide (202.3 mg, 0.5699 mmol, 1.2 equiv) in dioxane:Water (4:1, 5 mL) was added $K_2CO_3$ (196.9 mg, 1.4249 mmol, 3.0 equiv.). The resulting reaction mixture was purged with nitrogen for 10 minutes followed by the addition of Pd(dppf)$Cl_2$·DCM complex (19.39 mg, 0.0237 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used in the next reaction without further purification (452 mg), LCMS: 565.2 $[M+H]^+$.

Step-3: Synthesis of N-(3-(2-aminoquinazolin-6-yl)-2,4-difluorophenyl)-3-(trifluoromethyl)benzenesulfonamide To a stirred solution of N-(6-(2,6-difluoro-3-(3-(trifluoromethyl)phenylsulfonamido)phenyl)quinazolin-2-yl)pivalamide (200 mg, 0.3542 mmol, 1.0 equiv) in ethanol (4 mL) was added 2M NaoH (4 mL). Then, the reaction mixture was allowed to stir at 90° C. for 2 hrs. After completion of reaction, the solvent was evaporated and water was added to the reaction mixture, extracted with EtOAc (2×100 mL). The organic layers were combined, dried over anhydrous $Na_2SO_4$ and evaporated under reduced and purified by reverse phase HPLC to obtain as title compound N-(3-(2-aminoquinazolin-6-yl)-2,4-difluorophenyl)-3-(trifluoromethyl)benzenesulfonamide (13 mg), Analytical Data: LCMS: 481.3 $[M+H]^+$, NMR: $^1H$ NMR (400 MHz, DMSO-$d_6$) δ ppm 10.65 (s, 1H) 9.13 (s, 1H) 7.87-8.01 (m, 3H) 7.69-7.78 (m, 2H) 7.56 (d, J=8.33 Hz, 1H) 7.46 (d, J=8.77 Hz, 1H) 7.16-7.25 (m, 1H) 6.94-7.04 (m, 3H).

Compound 146

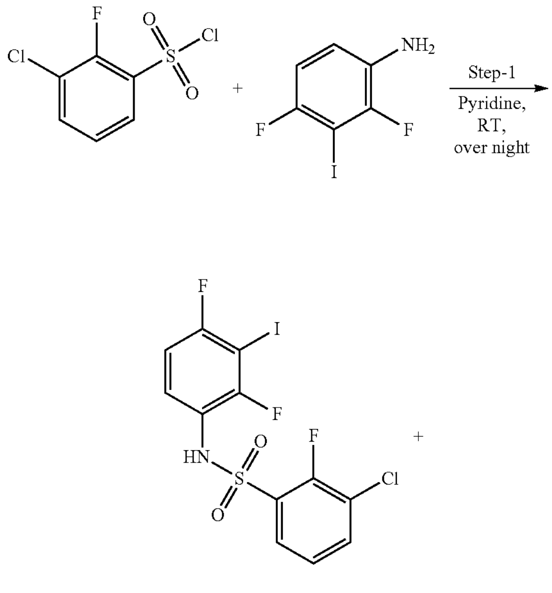

-continued

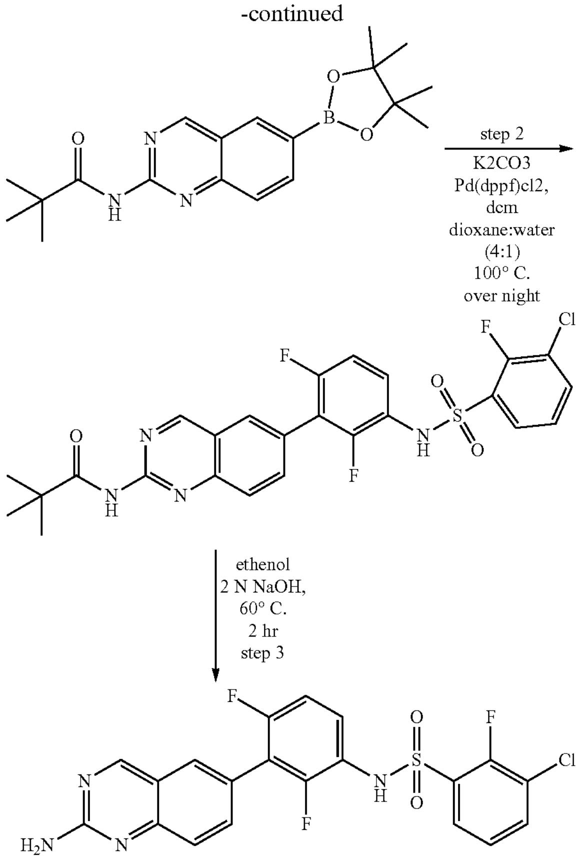

Step-1: Synthesis of 3-chloro-N-(2,4-difluoro-3-iodophenyl)-2-fluorobenzenesulfonamide To a stirred solution of 2,4-difluoro-3-iodoaniline (166 mg, 0.65 mmol, and 1.0 eq.) in pyridine (0.3 mL) at room temperature was added 3-chloro-2-fluorobenzene-1-sulfonyl chloride (150 mg, 0.65 mmol, 1.0 equiv.). After addition reaction mixture was stirred for overnight at room temperature. The progress of reaction was monitored through TLC and LCMS. After completion of reaction was added 2N HCl (5 mL) and the mixture were stirred at room temperature for 10 min reaction mass was diluted with water and extracted by Ethyl acetate (3×10 mL). The combined organic layers were dried over anhydrous $Na_2SO_4$ and concentrated under reduced pressure. This material was used in the next reaction without further purification (360 mg), Analytical Data: LCMS: 448 $[M+H]^+$

Step-2: Synthesis of N-(6-(3-(3-chloro-2-fluorophenylsulfonamido)-2,6-difluorophenyl)quinazolin-2-yl) pivalamide To the stirred solution of 3-chloro-N-(2,4-difluoro-3-iodophenyl)-2-fluorobenzenesulfonamide (350 mg, 0.78 mmol, 1.0 equiv.) and N-(6-(4,4,5,5-tetramethyl-1,3,2-dioxaborolan-2-yl)quinazolin-2-yl)pivalamide (306 mg, 0.86 mmol, and 1.1 eq.) in Dioxane:Water (4:1, 5 mL) was added $K_2CO_3$ (324 mg, 2.35 mmol, 3.0 equiv.). The resulting reaction mixture was purged with nitrogen for 15 minutes followed by the addition of $Pd(dppf)Cl_2 \cdot DCM$ complex (32 mg, 0.039 mmol, 0.05 equiv.). The reaction mixture was again purged with nitrogen for 5 minutes. The reaction mixture was heated to 100° C. for overnight. The progress of reaction was monitored by TLC and LCMS. After completion of reaction, water was added to the reaction mixture, extracted with EtOAc (2×15 mL). The organic layers were combined, dried over anhydrous $Na_2SO_4$ and evaporated under reduced pressure to obtain crude residue which was purified by flash chromatography to obtain title product N-(6-(3-(3-chloro-2-fluorophenylsulfonamido)-2,6-difluorophenyl)quinazolin-2-yl)pivalamide (420 mg), Analytical Data: LCMS: 549 $[M+H]^+$.

Step-3: Synthesis of N-(3-(2-aminoquinazolin-6-yl)-2,4-difluorophenyl)-3-chloro-2-fluorobenzenesulfonamide To a stirred solution of N-(6-(3-(3-chloro-2-fluorophenylsulfonamido)-2,6-difluorophenyl)quinazolin-2-yl)pivalamide (420 mg, 0.766 mmol, 1.0 equiv) in ethanol (5 mL) at room temperature was added 2N NaOH (2 mL). Then the reaction mixture was allowed to stir at 60° C. for 2 hr, Progress of the reaction was monitored by TLC and LCMS. After completion of the reaction, solvent was evaporated and water was added to the reaction mixture, extracted with EtOAc (2×10 mL). The organic layers were combined, dried over anhydrous $Na_2SO_4$, evaporated under reduced pressure to obtain crude product. This product was purified by using reverse phase chromatography technique to obtain desired N-(3-(2-aminoquinazolin-6-yl)-2,4-difluorophenyl)-3-chloro-2-fluorobenzenesulfonamide (50 mg), Analytical Data: LCMS: 465 $[M+H]^+$, $^1H$ NMR (400 MHz, DMSO-$d_6$) □ ppm 7.11 (m, 2H) 7.23 (t, J=9.21 Hz, 2H) 7.30-7.44 (m, 2H) 7.44-7.51 (m, 1H) 7.54-7.77 (m, 2H) 7.95 (t, J=6.80 Hz, 1H) 9.14 (s, 1H) 10.75 (br. s., 1H).

Compound 147

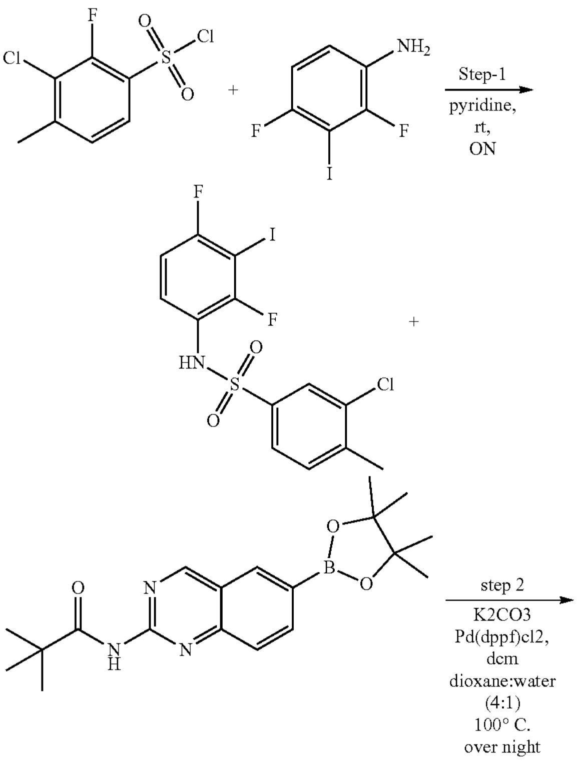

-continued

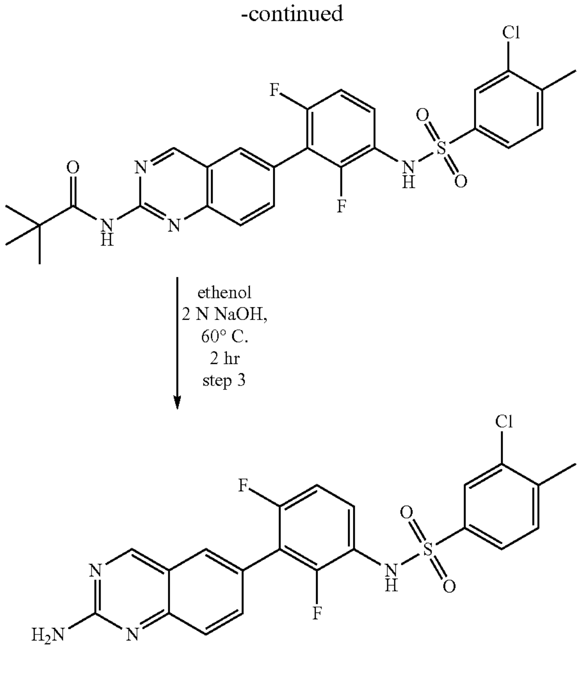

Step-1: Synthesis of 3-chloro-N-(2,4-difluoro-3-iodophenyl)-4-methylbenzenesulfonamide To a stirred solution of 2,4-difluoro-3-iodoaniline (169 mg, 0.664 mmol. 1.0 equiv.) in 2 mL pyridine at room was added 3-chloro-4-methylbenzene-1-sulfonyl chloride (150 mg, 0.66 mmol, and 1.0 eq), After addition reaction mixture was stirred at room temperature for overnight. The progress of reaction was monitored through TLC and LCMS, After completion of reaction added 2N HCl (5 mL) and the reaction mixture was stirred at room temperature for 10 min, reaction mass was diluted with water and extracted by Ethyl acetate (2×10 mL). The combined organic layers were dried over anhydrous $Na_2SO_4$ and concentrated under reduced pressure; this material was used in the next reaction without further purification (250 mg), Analytical Data: LCMS: 444 $[M+H]^+$.

Step-2: Synthesis of N-(6-(3-(3-chloro-4-methylphenylsulfonamido)-2,6-difluorophenyl)quinazolin-2-yl)pivalamide To a stirred solution of 3-chloro-N-(2,4-difluoro-3-iodophenyl)-4-methylbenzenesulfonamide (250 mg, 0.56 mmol. 1.0 equiv.) and N-(6-(4,4,5,5-tetramethyl-1,3,2-dioxaborolan-2-yl)quinazolin-2-yl)pivalamide (220 mg, 0.620 mmol, and 1.1 eq.) in Dioxane:Water (4:1, 5 mL) was added $K_2CO_3$ (233 mg, 1.69 mmol, 3.0 equiv.). The resulting reaction mixture was purged with nitrogen for 15 minutes followed by the addition of $Pd(dppf)Cl_2{\cdot}DCM$ complex (23 mg, 0.028 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×10 mL). The organic layers were combined, dried over anhydrous $Na_2SO_4$ and evaporated under reduced pressure to obtain crude residue which was purified by flash chromatography to obtain title product N-(6-(3-(3-chloro-4-methylphenylsulfonamido)-2,6-difluorophenyl)quinazolin-2-yl)pivalamide (351 mg), Analytical Data: LCMS: 545 $[M+H]^+$ Step-3: Synthesis of N-(3-(2-aminoquinazolin-6-yl)-2,4-difluorophenyl)-3-chloro-4-methylbenzenesulfonamide To a stirred solution of N-(6-(3-(3-chloro-4-methylphenylsulfonamido)-2,6-difluorophenyl)quinazolin-2-yl)pivalamide (351 mg, 0.64 mmol, 1.0 equiv) in ethanol (5 mL) at room temperature was added 2N NaOH (2 mL). Then the reaction mixture was allowed to stir at 60° C. for 2 hr, Progress of the reaction was monitored by TLC and LCMS. After completion of the reaction, solvent was evaporated and water was added to the reaction mixture, extracted with EtOAc (2×10 mL). The organic layers were combined, dried over anhydrous $Na_2SO_4$, evaporated under reduced pressure to obtain crude product which was purified by using reverse phase chromatography technique to obtain desired compound N-(3-(2-aminoquinazolin-6-yl)-2,4-difluorophenyl)-3-chloro-4-methylbenzenesulfonamide (60 mg), Analytical Data: LCMS: 461 $[M+H]^+$, $^1H$ NMR (400 MHz, DMSO-$d_6$) □ ppm 2.40 (br. s., 3H) 7.04 (br. s., 2H) 7.23 (d, J=9.65 Hz, 2H) 7.49 (br. s., 1H) 7.52-7.62 (m, 3H) 7.71 (br. s., 1H) 7.76 (br. s., 1H) 9.14 (br. s., 1H) 10.33 (br. s., 1H).

Compound 148

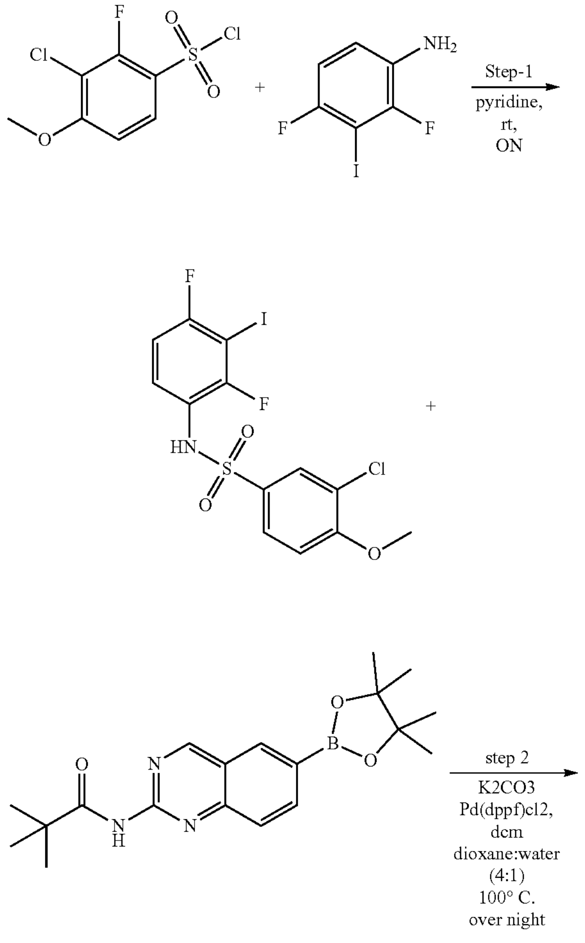

-continued

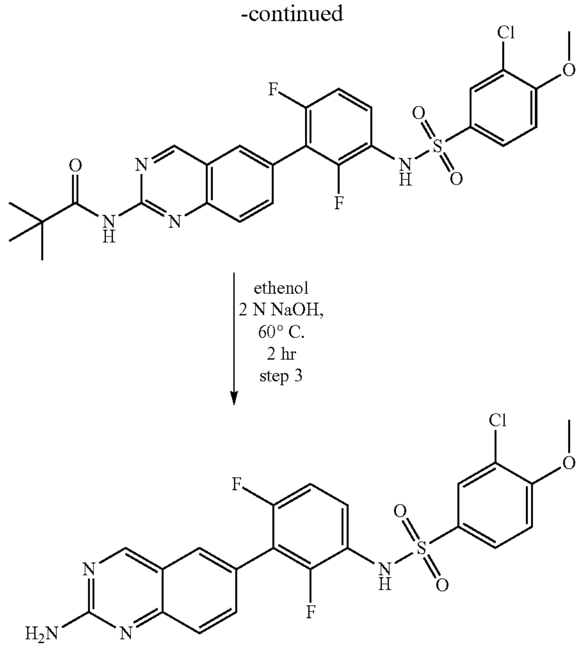

Step-1: Synthesis of 3-chloro-N-(2,4-difluoro-3-iodophenyl)-4-methoxybenzenesulfonamide To the stirred solution of 2,4-difluoro-3-iodoaniline (158 mg, 0.62 mmol. 1.0 equiv.) in pyridine (2 mL) at room temperature was added 3-chloro-4-methoxybenzene-1-sulfonyl chloride (150 mg, 0.62 mmol, 1.0 eq.), After addition reaction mixture was stirred for overnight at room temperature. The progress of reaction was monitored through TLC and LCMS, After completion of reaction added 2N HCl (5 mL) and the mixture was stirred at room temperature for 10 mms reaction mass was diluted with water and extracted by Ethyl acetate (2×15 mL). The combined organic layers were dried over anhydrous $Na_2SO_4$ and concentrated under reduced pressure, This material was used in the next reaction without further purification (200 mg).

Step-2: Synthesis of N-(6-(3-(3-chloro-4-methoxyphenylsulfonamido)-2,6-difluorophenyl)quinazolin-2-yl)pivalamide To the stirred solution of 3-chloro-N-(2,4-difluoro-3-iodophenyl)-4-methoxybenzenesulfonamide (200 mg, 0.435 mmol. 1.0 equiv.) and N-(6-(4,4,5,5-tetramethyl-1,3,2-dioxaborolan-2-yl)quinazolin-2-yl)pivalamide (170 mg, 0.47 mmol, and 1.1 eq.) in Dioxane:Water (4:1, 5 mL) was added $K_2CO_3$ (180 mg, 1.30 mmol, 3.0 equiv.). The resulting reaction mixture was purged with nitrogen for 15 minutes followed by the addition of $Pd(dppf)Cl_2$·DCM complex (17 mg, 0.021 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×10 mL). The organic layers were combined, dried over anhydrous $Na_2SO_4$ and evaporated under reduced pressure to obtain crude residue which was purified by flash chromatography to obtain title product of N-(6-(3-(3-chloro-4-methoxyphenylsulfonamido)-2,6-difluorophenyl)quinazolin-2-yl)pivalamide (285 mg), Analytical Data: LCMS: 561[M+H]$^+$

Step-3: Synthesis of N-(3-(2-aminoquinazolin-6-yl)-2,4-difluorophenyl)-3-chloro-4-methoxybenzenesulfonamide To a stirred solution of product of N-(6-(3-(3-chloro-4-methoxyphenylsulfonamido)-2,6-difluorophenyl)quinazolin-2-yl)pivalamide (285 mg, 0.508 mmol, 1.0 equiv) in ethanol (5 mL) at room temperature was added 2N NaOH (2 mL). Then the reaction mixture was allowed to stir at 60° C. for 2 h, Progress of the reaction was monitored by TLC and LCMS. After completion of the reaction, solvent was evaporated and water was added to the reaction mixture, extracted with EtOAc (2×10 mL), The organic layers were combined, dried over anhydrous $Na_2SO_4$, evaporated under reduced pressure to obtain crude product which was purified by using reverse phase chromatography technique to obtain N-(3-(2-aminoquinazolin-6-yl)-2,4-difluorophenyl)-3-chloro-4-methoxybenzenesulfonamide (19 mg), Analytical Data: LCMS: 477 [M+H]$^+$, $^1$H NMR (400 MHz, DMSO-$d_6$) □ ppm 3.85 (s, 3H) 6.75 (br. s., 2H) 6.93 (br. s., 2H) 7.13 (d, J=8.77 Hz, 2H) 7.46 (d, J=9.21 Hz, 1H) 7.58-7.66 (m, 3H) 7.78 (br. s., 1H) 9.14 (s, 1H).

Compound 149

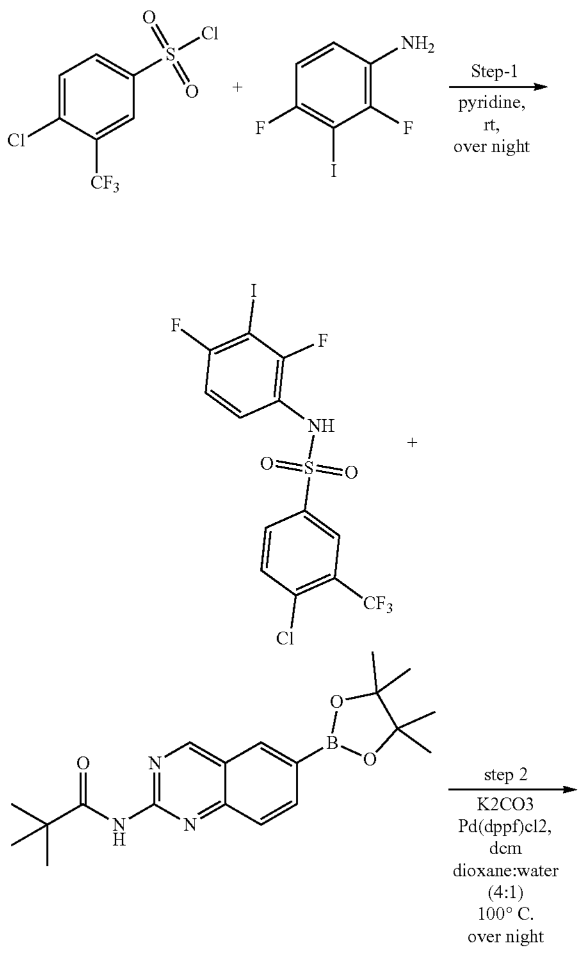

-continued

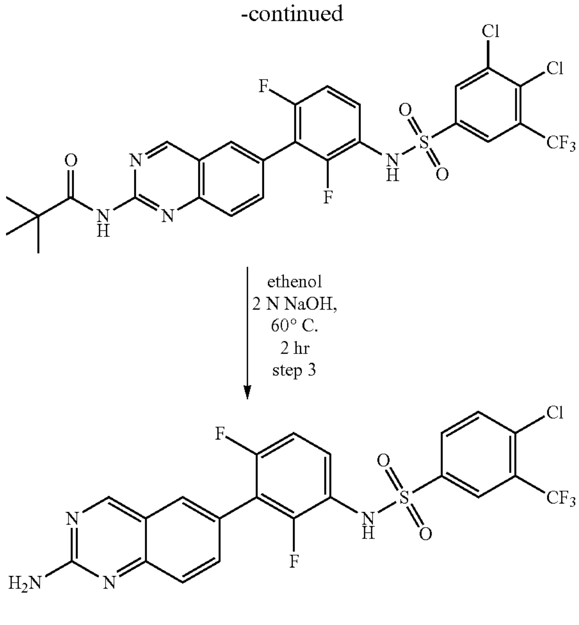

Step-1: Synthesis of 4-chloro-N-(2,4-difluoro-3-iodophenyl)-3-(trifluoromethyl)benzenesulfonamide To the stirred solution of 2,4-difluoro-3-iodoaniline (136 mg, 0.53 mmol. 1.0 equiv.) in pyridine (2 mL) at room temperature was added 4-chloro-3-(trifluoromethyl)benzene-1-sulfonyl chloride (150 mg, 0.53 mmol, 1.0 eq.), After addition reaction mixture was stirred for overnight at room temperature. The progress of reaction was monitored through TLC and LCMS, After completion of reaction added 2N HCl (5 mL) and the mixture was stirred at room temperature for 10 min reaction mass was diluted with water and extracted by Ethyl acetate (2×15 mL). The combined organic layers were dried over anhydrous $Na_2SO_4$ and concentrated under reduced pressure, This material was used in the next reaction without further purification (326 mg), Analytical Data: LCMS: 498 $[M+H]^+$

Step-2: Synthesis of N-(6-(3-(4-chloro-3-(trifluoromethyl)phenylsulfonamido)-2,6-difluorophenyl)quinazolin-2-yl)pivalamide To the stirred solution of 4-chloro-N-(2,4-difluoro-3-iodophenyl)-3-(trifluoromethyl)benzenesulfonamide (197 mg, 0.39 mmol. 1.0 equiv.) and N-(6-(4,4,5,5-tetramethyl-1,3,2-dioxaborolan-2-yl)quinazolin-2-yl)pivalamide (155 mg, 0.43 mmol, and 1.1 eq.) in Dioxane:Water (4:1, 5 mL) was added $K_2CO_3$ (164 mg, 1.19 mmol, 3.0 equiv.). The resulting reaction mixture was purged with nitrogen for 15 minutes followed by the addition of $Pd(dppf)Cl_2 \cdot DCM$ complex (16 mg, 0.019 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×10 mL). The organic layers were combined, dried over anhydrous $Na_2SO_4$ and evaporated under reduced pressure to obtain crude residue which was purified by flash chromatography to obtain title product of N-(6-(3-(4-chloro-3-(trifluoromethyl)phenylsulfonamido)-2,6-difluorophenyl)quinazolin-2-yl)pivalamide (326 mg), Analytical Data: LCMS: 599 $[M+H]^+$

Step-3: Synthesis of N-(3-(2-aminoquinazolin-6-yl)-2,4-difluorophenyl)-4-chloro-3-(trifluoromethyl)benzenesulfonamide To a stirred solution of N-(6-(3-(4-chloro-3-(trifluoromethyl)phenylsulfonamido)-2,6-difluorophenyl)quinazolin-2-yl)pivalamide (326 mg, 0.54 mmol, 1.0 equiv) in ethanol (5 mL) at room temperature was added 2N NaOH (2 mL). Then the reaction mixture was allowed to stir at 60° C. for 2 h, Progress of the reaction was monitored by TLC and LCMS. After completion of the reaction, solvent was evaporated and water was added to the reaction mixture, extracted with EtOAc (2×10 mL), The organic layers were combined, dried over anhydrous $Na_2SO_4$, evaporated under reduced pressure to obtain crude product which was purified by using reverse phase chromatography technique to obtain N-(3-(2-aminoquinazolin-6-yl)-2,4-difluorophenyl)-4-chloro-3-(trifluoromethyl)benzenesulfonamide (34 mg), Analytical Data: LCMS: 515 $[M+H]^+$, H NMR (400 MHz, DMSO-$d_6$) □ ppm 7.04 (s, 2H) 7.21-7.35 (m, 2H) 7.40-7.59 (m, 2H) 7.71 (s, 1H) 7.91-8.04 (m, 2H) 8.07 (s, 1H) 9.12 (s, 1H) 10.56 (br. s., 1H).

Compound 150

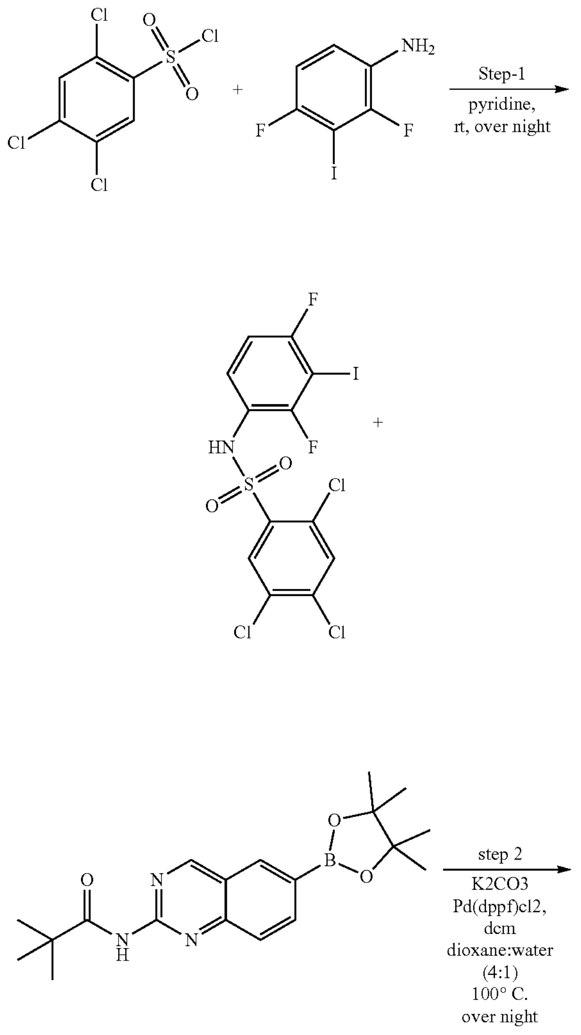

-continued

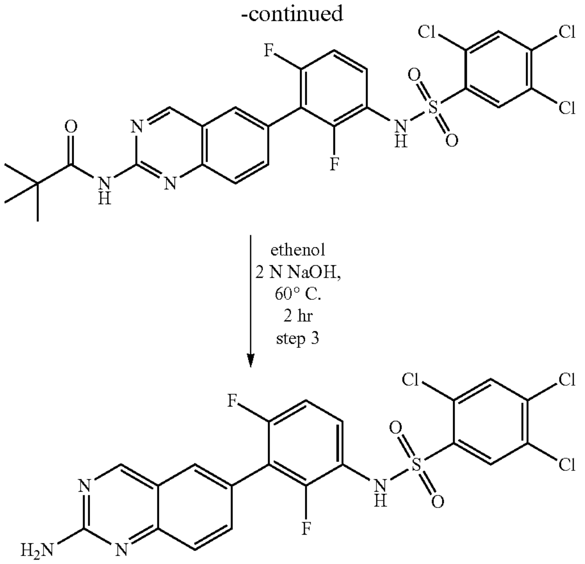

Step-1: Synthesis of 2,4,5-trichloro-N-(2,4-difluoro-3-iodophenyl)benzenesulfonamide To the stirred solution of 2,4-difluoro-3-iodoaniline (90 mg, 0.35 mmol. 1.0 equiv.) in pyridine (2 mL) at room temperature was added 2,4,5-trichlorobenzene-1-sulfonyl chloride (100 mg, 0.35 mmol, and 1.0 eq.), After addition reaction mixture was stirred for overnight at room temperature. The progress of reaction was monitored through TLC and LCMS, After completion of reaction added 2N HCl (5 mL) and the mixture was stirred at room temperature for 10 min reaction mass was diluted with water and extracted by Ethyl acetate (2×15 mL). The combined organic layers were dried over anhydrous $Na_2SO_4$ and concentrated under reduced pressure, This material was used in the next reaction without further purification (184 mg).

Step-2: Synthesis of N-(6-(2,6-difluoro-3-(2,4,5-trichlorophenylsulfonamido)phenyl)quinazolin-2-yl)pivalamide To the stirred solution of 2,4,5-trichloro-N-(2,4-difluoro-3-iodophenyl)benzenesulfonamide (184 mg, 0.37 mmol. 1.0 equiv.) and N-(6-(4,4,5,5-tetramethyl-1,3,2-dioxaborolan-2-yl)quinazolin-2-yl)pivalamide (144 mg, 0.408 mmol, and 1.1 eq.) in Dioxane:Water (4:1, 5 mL) was added $K_2CO_3$ (153 mg, 1.11 mmol, 3.0 equiv.). The resulting reaction mixture was purged with nitrogen for 15 minutes followed by the addition of $Pd(dppf)Cl_2$·DCM complex (15 mg, 0.018 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×10 mL). The organic layers were combined, dried over anhydrous $Na_2SO_4$ and evaporated under reduced pressure to obtain crude residue which was purified by flash chromatography to obtain title product of N-(6-(2,6-difluoro-3-(2,4,5-trichlorophenylsulfonamido)phenyl)quinazolin-2-yl)pivalamide (329 mg), Analytical Data: LCMS: 599 $[M+H]^+$ Step-3: Synthesis of N-(3-(2-aminoquinazolin-6-yl)-2,4-difluorophenyl)-2,4,5-trichlorobenzenesulfonamide To a stirred solution of N-(6-(2,6-difluoro-3-(2,4,5-trichlorophenylsulfonamido)phenyl)quinazolin-2-yl)pivalamide (329 mg, 0.55 mmol, 1.0 equiv) in ethanol (5 mL) at room temperature was added 2N NaOH (2 mL). Then the reaction mixture was allowed to stir at 60° C. for 2 h, Progress of the reaction was monitored by TLC and LCMS. After completion of the reaction, solvent was evaporated and water was added to the reaction mixture, extracted with EtOAc (2×10 mL), The organic layers were combined, dried over anhydrous $Na_2SO_4$, evaporated under reduced pressure to obtain crude product which was purified by using reverse phase chromatography technique to obtain N-(3-(2-aminoquinazolin-6-yl)-2,4-difluorophenyl)-2,4,5-trichlorobenzenesulfonamide (60 mg), Analytical Data: LCMS: 515 $[M+H]^+$, $^1H$ NMR (400 MHz, DMSO-$d_6$) □ ppm 10.61 (br. s., 1H) 9.13 (s, 1H) 8.31 (br. s., 1H) 8.02 (s, 1H) 7.91 (s, 1H) 7.73 (br. s., 1H) 7.55 (d, J=7.89 Hz, 1H) 7.47 (d, J=8.33 Hz, 1H) 7.23-7.34 (m, 1H) 7.04 (br. s., 2H).

Compound 153

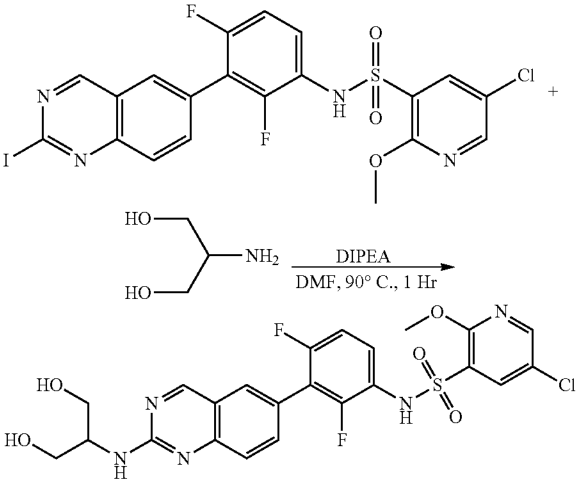

Step-1: Synthesis of 5-chloro-N-(3-(2-(1,3-dihydroxypropan-2-ylamino)quinazolin-6-yl)-2,4-difluorophenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (120 mg, 0.204 mmol, 1.0 equi.) in DMF (1.5 ml) was added 2-aminopropane-1,3-diol (46 mg, 0.51 mmol, 2.5 equi.), DIPEA (78 mg, 0.612 mmol, 3.0 equi.). After addition, reaction was heated at 90° C. for 1 h. Progress of reaction was monitored by TLC. After completion of reaction, water (50 ml) was added and extracted ethyl acetate (2×50 ml). The separated organic layer was dried over $Na_2SO_4$, filtered and concentrated. The crude product which was purified by reverse phase chromatography to obtain desired product (17 mg), Analytical Data: LCMS: 552$[M+H]^+$, NMR: $^1H$ NMR (400 MHz, DMSO-$d_6$) □=10.39 (br. s., 1H), 9.16 (br. s., 1H), 8.49 (d, J=2.2 Hz, 1H), 8.07 (d, J=2.6 Hz, 1H), 7.79 (s, 1H), 7.60 (d, J=8.3 Hz, 1H), 7.52 (d, J=8.8

Hz, 1H), 7.39-7.27 (m, 1H), 7.19 (t, J=9.0 Hz, 1H), 7.01 (br. s., 1H), 4.68 (t, J=5.5 Hz, 2H), 4.09 (br. s., 1H), 3.90 (s, 3H), 3.57 (br. s., 3H)

Compound 154

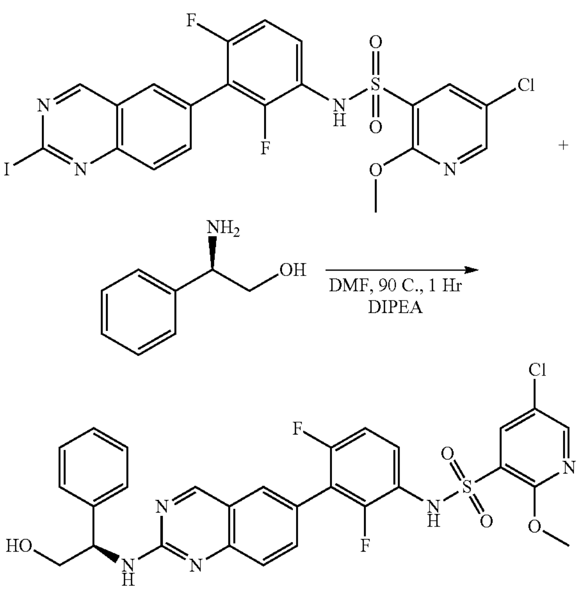

Step-1: Synthesis of (R)-5-chloro-N-(2,4-difluoro-3-(2-(2-hydroxy-1-phenylethylamino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (60 mg, 0.102 mmol, 1.0 equi.) in DMF (1.0 ml) was added (R)-2-amino-2-phenylethanol (28 mg, 0.204 mmol, 2.0 equi.), DIPEA (39.4 mg, 0.306 mmol, 3.0 equi.). After addition, reaction was heated at 90° C. for 1 h. Progress of reaction was monitored by TLC. After completion of reaction, water (20 ml) was added & extracted with ethyl acetate (2×50 ml). The separated organic layer was dried over $Na_2SO_4$, filtered and concentrated. The crude product which was purified by reverse phase chromatography to obtain desired product (7 mg), Analytical Data: LCMS: 598 $[M+H]^+$, $^1$H NMR (400 MHz, DMSO-$d_6$) □ ppm 10.22 (s, 1H) 9.15 (s, 1H) 8.20 (d, J=2.19 Hz, 1H) 7.97 (d, J=2.19 Hz, 1H) 7.84 (d, J=8.77 Hz, 1H) 7.78 (s, 1H) 7.62 (d, J=7.45 Hz, 1H) 7.45 (d, J=7.45 Hz, 3H) 7.30 (t, J=7.67 Hz, 2H) 7.17-7.23 (m, 1H) 7.07-7.16 (m, 1H) 6.83 (t, J=9.21 Hz, 1H) 5.18-5.26 (m, 1H) 4.90 (br. s., 1H) 3.78 (s, 3H) 3.71 (br. s., 2H).

Compound 155

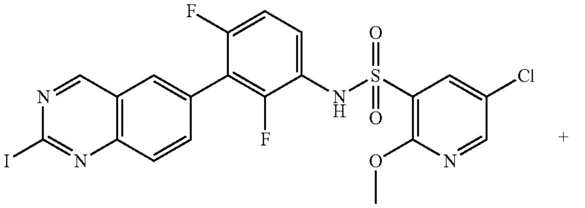

-continued

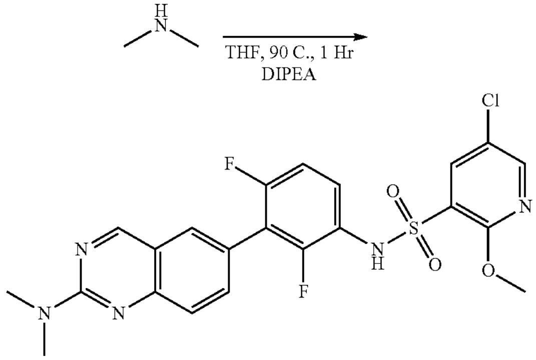

Step-1: Synthesis of 5-chloro-N-(3-(2-(dimethylamino)quinazolin-6-yl)-2,4-difluorophenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (60 mg, 0.102 mmol, 1.0 equi.) in THF (3.0 ml) was added Dimethyl amine (2.0 M in THF) (0.1 mL, 0.204 mmol, 2.0 equi.), DIPEA (39.4 mg, 0.306 mmol, 3.0 equi.). After addition, reaction was heated at 90° C. for 1 h. Progress of reaction was monitored by TLC. After completion of reaction, water (50 ml) was added and extracted with using ethyl acetate (1×50 ml). The separated organic layer was dried over $Na_2SO_4$, filtered and concentrated. The crude product which was purified by reverse phase chromatography to obtain desired product (22 mg). Analytical Data: LCMS: 506$[M+H]^+$, $^1$H NMR (400 MHz, DMSO-$d_6$) □=10.40 (s, 1H), 9.23 (s, 1H), 8.51 (d, J=2.2 Hz, 1H), 8.08 (d, J=1.8 Hz, 1H), 7.82 (s, 1H), 7.70-7.46 (m, 2H), 7.39-7.27 (m, 1H), 7.27-7.13 (m, 1H), 3.91 (s, 3H), 3.33 (s, 6H)

Compound 156

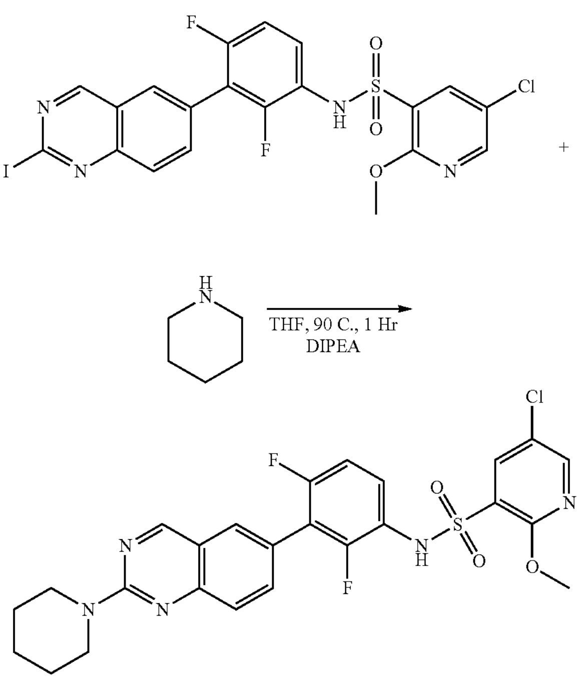

Step-1: Synthesis of 5-chloro-N-(2,4-difluoro-3-(2-(piperidin-1-yl)quinazolin-6-yl)phenyl)-2-methoxy-pyridine-3-sulfonamide To a stirred solution of 5-chloro-N-(2,4-difluoro-3-(2-iodoquinazolin-6-yl)phenyl)-2-methoxypyridine-3-sulfonamide (60 mg, 0.102 mmol, 1.0 equi.) in THE (4.0 ml) was added piperidine (17.3 mg, 0.204 mmol, 2.0 equi.), DIPEA (39.4 mg, 0.306 mmol, 3.0 equi.). After addition, reaction was heated at 90° C. for 1 h. Progress of reaction was monitored by TLC. After completion of reaction, work up of reaction had been carried out using ethyl acetate (1×50 ml) and water (20 ml). The separated organic layer was dried over $Na_2SO_4$, filtered and concentrated. The crude product was purified by reverse phase chromatography to obtain desired product (16 mg), Analytical Data: LCMS: 546[M+H]$^+$, $^1$H NMR (400 MHz, DMSO-$d_6$) □ ppm 10.44 (s, 1H) 9.22 (s, 1H) 8.39 (br. s., 1H) 8.04 (s, 1H) 7.81 (s, 1H) 7.62 (d, J=8.77 Hz, 1H) 7.53 (d, J=8.77 Hz, 1H) 7.24 (d, J=7.45 Hz, 1H) 6.99-7.10 (m, 1H) 3.76-3.99 (m, 7H) 1.67 (br. s., 2H) 1.57 (br. s., 4H)

Compound 157

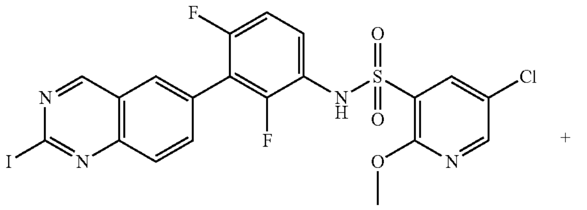

-continued

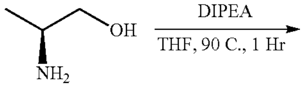

-continued

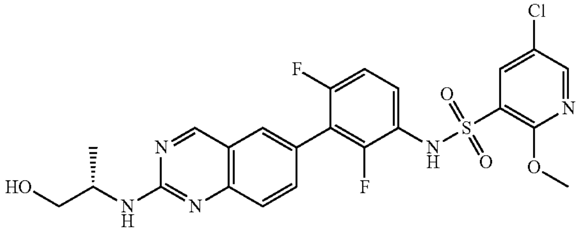

Step-1: Synthesis of (S)-5-chloro-N-(2,4-difluoro-3-(2-(1-hydroxypropan-2-ylamino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (70 mg, 0.119 mmol, 1.0 equi.) in THE (3.0 ml) was added (S)-2-aminopropan-1-ol (17.8 mg, 0.238 mmol, 2.0 equi.), DIPEA (46 mg, 0.357 mmol, 3.0 equi.). After addition, reaction was heated at 90° C. for 1 h. Progress of reaction was monitored by TLC. After completion of reaction, work up of reaction had been carried out using ethyl acetate (1×50 ml) and water (20 ml). The separated organic layer was dried over $Na_2SO_4$, filtered and concentrated. The crude product was purified by reverse phase chromatography to obtain desired product (28 mg), Analytical Data: LCMS: 536 [M+H]$^+$, $^1$H NMR (400 MHz, DMSO-$d_6$) □=10.41 (s, 1H), 9.22 (br. s., 1H), 8.51 (d, J=2.2 Hz, 1H), 8.08 (d, J=2.2 Hz, 1H), 7.85 (br. s., 1H), 7.61 (s, 1H), 7.65 (s, 1H), 7.43-7.29 (m, 2H), 7.29-7.17 (m, 1H), 4.17 (br. s., 1H), 3.91 (s, 3H), 3.53 (dd, J=5.3, 10.5 Hz, 3H), 1.32-1.07 (m, 3H)

Compound 158

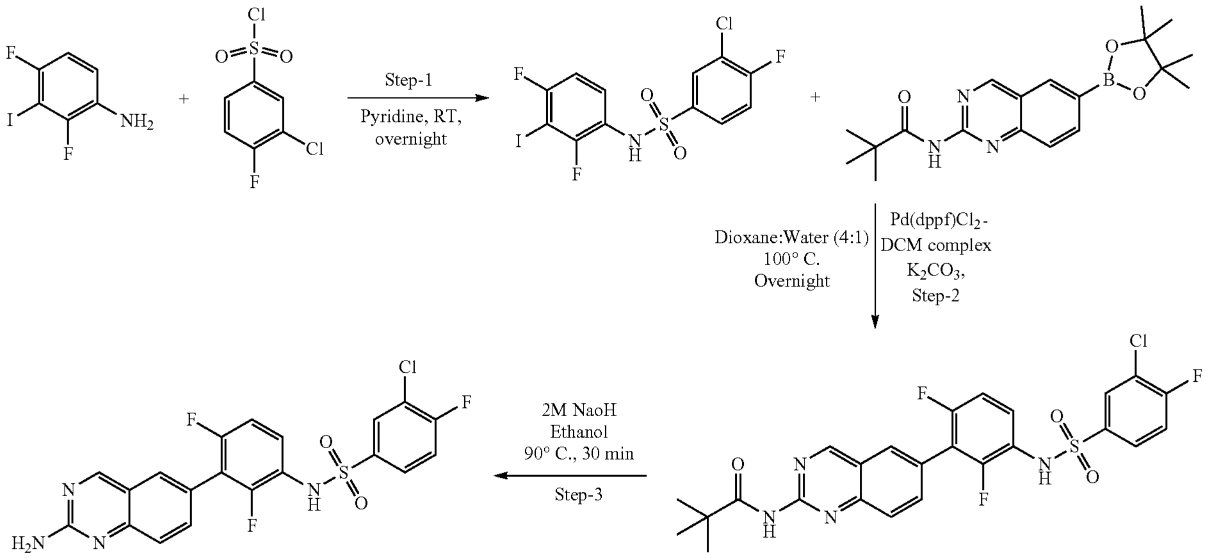

Step-1: Synthesis of 3-chloro-N-(2,4-difluoro-3-iodophenyl)-4-fluorobenzenesulfonamide To a stirred solution of 2,4-difluoro-3-iodoaniline (250 mg, 0.9803 mmol. 1.0 equiv.) in pyridine (1.0 mL) at room temperature was added 3-chloro-4-fluorobenzene-1-sulfonyl chloride (224.5 mg, 0.9803 mmol. 1.0 equiv.) The resultant reaction mixture was stirred at room temperature for overnight. The progress of reaction was monitored through by TLC. After completion of the reaction, ice cold water had been added to reaction mixture was filtered by using Buchner funnel and washed the product with 1N HCl. This material was used in the next reaction without further purification (243 mg).

Step-2: Synthesis of N-(6-(3-(3-chloro-4-fluorophenylsulfonamido)-2,6-difluorophenyl)quinazolin-2-yl) pivalamide To a stirred solution of 3-chloro-N-(2,4-difluoro-3-iodophenyl)-4-fluorobenzenesulfonamide (240 mg, 0.5361 mmol, 1.0 equiv) and N-(6-(4,4,5,5-tetramethyl-1,3,2-dioxaborolan-2-yl)quinazolin-2-yl)pivalamide (228.4 mg, 0.6434 mmol, 1.2 equiv) in Dioxane:Water (4:1, 5 mL) was added $K_2CO_3$ (222.3 mg, 1.6085 mmol, 3.0 equiv.). The resulting reaction mixture was purged with nitrogen for 10 minutes followed by the addition of Pd(dppf)$Cl_2$·DCM complex (21.8 mg, 0.0268 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product which was used in the next reaction without further purification (480 mg), LCMS: 549.2 $[M+H]^+$.

Step-3: Synthesis of N-(3-(2-aminoquinazolin-6-yl)-2,4-difluorophenyl)-3-chloro-4-fluorobenzenesulfonamide To a stirred solution of N-(6-(3-(3-chloro-4-fluorophenylsulfonamido)-2,6-difluorophenyl)quinazolin-2-yl)pivalamide (480 mg, 0.8744 mmol, 1.0 equiv) in ethanol (4 mL) was added 2M NaoH (1 mL). Then, the reaction mixture was allowed to stir at 90 degree Celsius for 30 min. After completion of reaction, the solvent was evaporated and water was added to the reaction mixture, extracted with EtOAc (2×100 mL). The organic layers were combined, dried over anhydrous $Na_2SO_4$ and evaporated under reduced, evaporated under reduced and purified by reverse phase silica gel chromatography to obtain as title compound N-(3-(2-aminoquinazolin-6-yl)-2,4-difluorophenyl)-3-chloro-4-fluorobenzenesulfonamide (27 mg), Analytical Data: LCMS: 465.3$[M+H]^+$, NMR: $^1H$ NMR (400 MHz, DMSO-$d_6$) □ ppm 10.42 (s, 1H) 9.14 (s, 1H) 7.85 (dd, J=7.02, 2.19 Hz, 1H) 7.78 (s, 1H) 7.71 (ddd, J=8.55, 4.60, 2.19 Hz, 1H) 7.51-7.64 (m, 2H) 7.47 (d, J=8.77 Hz, 1H) 7.14-7.25 (m, 1H) 6.93-7.08 (m, 3H).

Compound 159

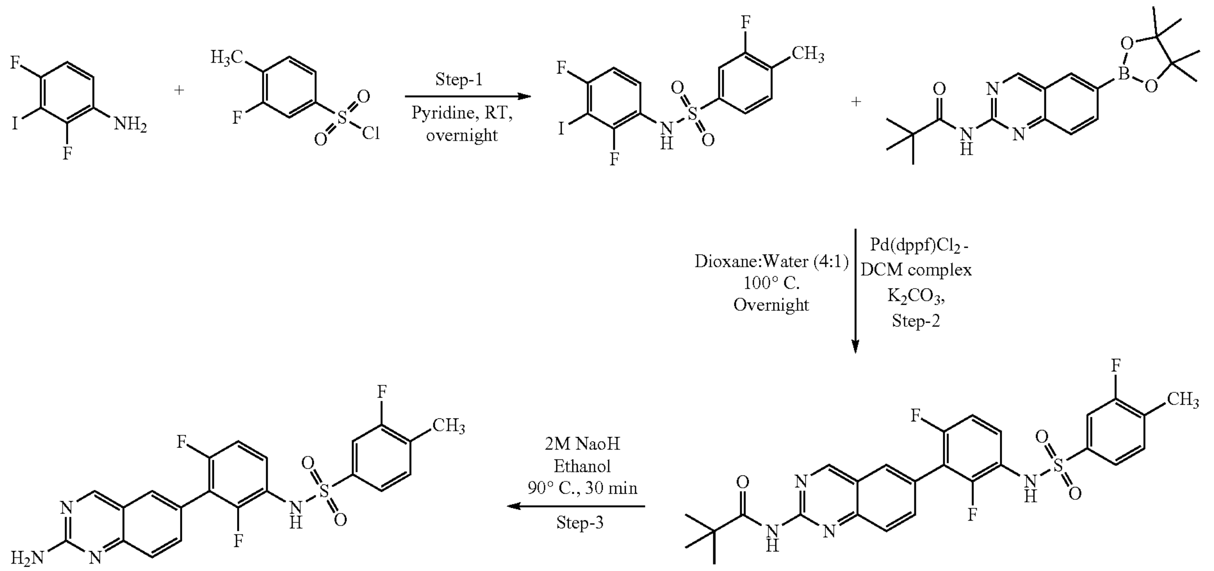

Step-1: Synthesis of N-(2,4-difluoro-3-iodophenyl)-3-fluoro-4-methylbenzenesulfonamide To a stirred solution of 2,4-difluoro-3-iodoaniline (300 mg, 1.1764 mmol. 1.0 equiv.) in pyridine (1.0 mL) at room temperature was added 3-fluoro-4-methylbenzene-1-sulfonyl chloride (368.18 mg, 1.764 mmol. 1.0 equiv.) The resultant reaction mixture was stirred at room temperature for overnight. The progress of reaction was monitored through by TLC. After completion of the reaction, ice cold water was added to reaction mixture, precipitate was filtered by using Buchner funnel and washed the product with 1N HC. This material was used in the next reaction without further purification (420 mg).

Step-2: Synthesis of N-(6-(2,6-difluoro-3-(3-fluoro-4-methylphenylsulfonamido)phenyl)quinazolin-2-yl) pivalamide To a stirred solution of N-(2,4-difluoro-3-iodophenyl)-3-fluoro-4-methylbenzenesulfonamide (150 mg, 0.3511 mmol, 1.0 equiv) and N-(6-(4,4,5,5-tetramethyl-1,3,2-dioxaborolan-2-yl)quinazolin-2-yl)pivalamide (149.5 mg, 0.4213 mmol, 1.2 equiv) in Dioxane:Water (3:1, 4 mL) was added $K_2CO_3$ (145.5 mg, 1.0534 mmol, 3.0 equiv.). The resulting reaction mixture was purged with nitrogen for 10 minutes followed by the addition of Pd(dppf)$Cl_2$·DCM complex (14.3 mg, 0.0175 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×50 mL). The organic layers were combined, dried over anhydrous $Na_2SO_4$ and evaporated under reduced pressure. The crude product was used in the next reaction without further purification (360 mg), LCMS: 529.2 $[M+H]^+$.

Step-3: Synthesis of N-(3-(2-aminoquinazolin-6-yl)-2,4-difluorophenyl)-3-fluoro-4-methylbenzenesulfonamide To a stirred solution of N-(6-(2,6-difluoro-3-(3-fluoro-4-methylphenylsulfonamido)phenyl)quinazolin-2-yl)pivalamide (360 mg, 0.6811 mmol, 1.0 equiv) in ethanol (3 mL) was added 2M NaoH (1 mL). Then, the reaction mixture was allowed to stir at 90 degree Celsius for 30 min. After completion of reaction, the solvent was evaporated and water was added to the reaction mixture, extracted with EtOAc (2×100 mL). The organic layers were combined, dried over anhydrous $Na_2SO_4$ and evaporated under reduced, evaporated under reduced pressure and purified by reverse phase silica gel chromatography to obtain as title compound N-(3-(2-aminoquinazolin-6-yl)-2,4-difluorophenyl)-3-fluoro-4-methylbenzenesulfonamide (15 mg), Analytical Data: LCMS: 445.3$[M+H]^+$, NMR: $^1H$ NMR (400 MHz, DMSO-$d_6$) □ ppm 10.27 (s, 1H) 9.14 (s, 1H) 7.77 (s, 1H) 7.58 (d, J=9.21 Hz, 1H) 7.37-7.52 (m, 4H) 7.16-7.27 (m, 1H) 7.10 (t, J=9.21 Hz, 1H) 7.01 (s, 2H) 2.24-2.36 (m, 3H).

overnight. The progress of reaction was monitored through by TLC. After completion of the reaction, ice cold water had been added to reaction mixture. The precipitate formed which was filtered by using Buchner funnel and washed the product with 1N HCl. This material was used in the next reaction without further purification (190 mg).

Step-2: Synthesis of N-(6-(2,6-difluoro-3-(4-fluoro-3-methylphenylsulfonamido)phenyl)quinazolin-2-yl) pivalamide To a stirred solution of N-(2,4-difluoro-3-iodophenyl)-4-fluoro-3-methylbenzenesulfonamide (190 mg, 0.4447 mmol, 1.0 equiv) and N-(6-(4,4,5,5-tetramethyl-1,3,2-dioxaborolan-2-yl)quinazolin-2-yl)pivalamide (189.6 mg, 0.5337 mmol, 1.2 equiv) in Dioxane:Water (4:1, 5 mL) was added $K_2CO_3$ (184.4 mg, 1.3343 mmol, 3.0 equiv.). The resulting reaction mixture was purged with nitrogen for 10 minutes followed by the addition of Pd(dppf)$Cl_2$·DCM complex (18.16 mg, 0.0222 mmol, 0.05 equiv.). The reaction mixture was again purged with nitrogen for 5 minutes. The reaction mixture was heated at 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure. The crude product was used in the next reaction without further purification (400 mg), LCMS: 529.3$[M+H]^+$.

Step-3: Synthesis of N-(3-(2-aminoquinazolin-6-yl)-2,4-difluorophenyl)-4-fluoro-3-methylbenzenesulfonamide To a stirred solution of N-(6-(2,6-difluoro-3-(4-fluoro-3-methylphenylsulfonamido)phenyl)quinazolin-2-yl)pival- Compound 160

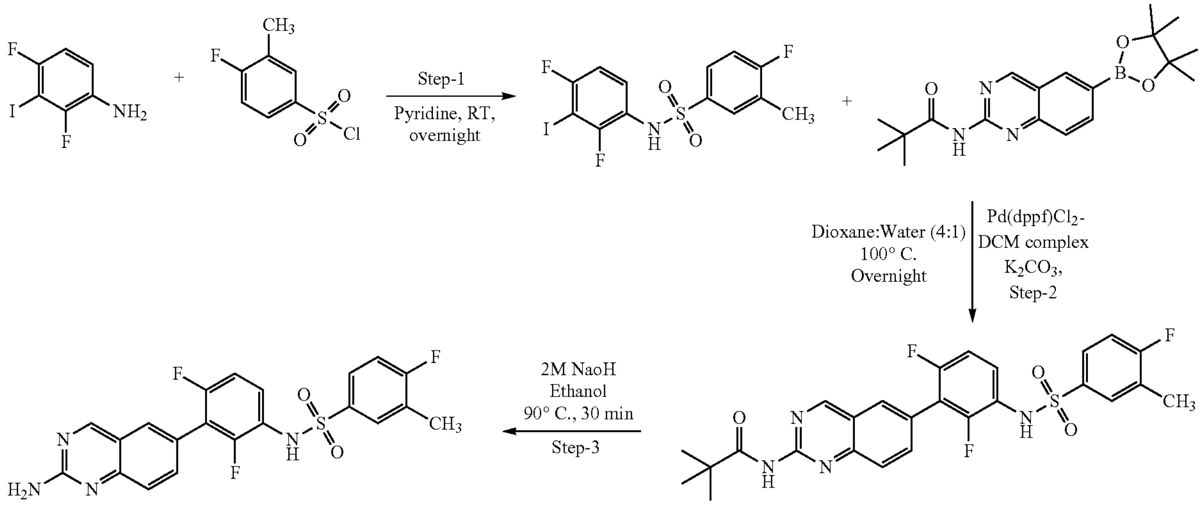

Step-1: Synthesis of N-(2,4-difluoro-3-iodophenyl)-4-fluoro-3-methylbenzenesulfonamide To a stirred solution of 2,4-difluoro-3-iodoaniline (91.6 mg, 0.3595 mmol. 0.5 equiv.) in pyridine (0.8 mL) at room temperature was added 4-fluoro-3-methylbenzene-1-sulfonyl chloride (150 mg, 0.7190 mmol. 1.0 equiv.) The resultant reaction mixture was stirred at room temperature for amide (400 mg, 0.7567 mmol, 1.0 equiv) in ethanol (3 mL) was added 2M NaOH (1 mL). Then, the reaction mixture was allowed to stir at 90 degree Celsius for 30 min. After completion of reaction, the solvent was evaporated and water was added to the reaction mixture, extracted with EtOAc (1×100 mL). The organic layers were combined, dried over anhydrous $Na_2SO_4$ and evaporated under reduced pressure and purified by reverse phase chromatography to obtain as title compound N-(3-(2-aminoquinazolin-6-yl)-2,4-difluorophenyl)-4-fluoro-3-methylbenzenesulfonamide (9 mg), Analytical Data: LCMS: 445.4[M+H]$^+$, NMR: $^1$H NMR (400 MHz, DMSO-$d_6$) □ ppm 10.47 (s, 1H) 9.14 (s, 1H) 7.78 (s, 1H) 7.58-7.68 (m, 2H) 7.55 (br. s., 1H) 7.47 (d, J=8.77 Hz, 1H) 7.05-7.21 (m, 2H) 6.96 (s, 2H) 6.85 (t, J=9.43 Hz, 1H) 2.24 (s, 3H).

Compound 161

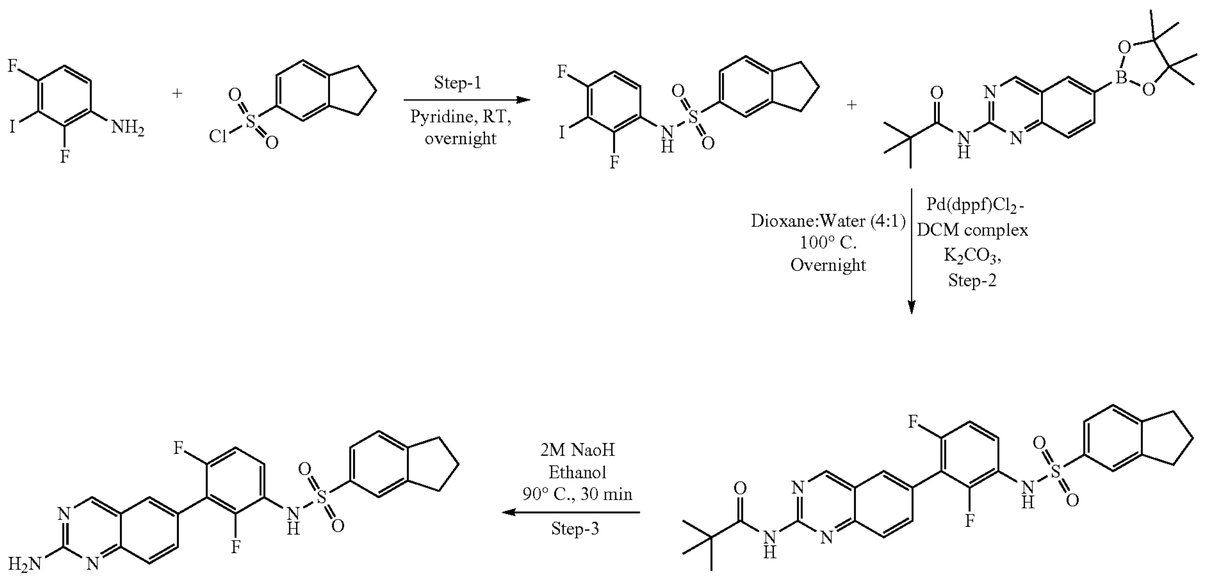

Step-1: Synthesis of N-(2,4-difluoro-3-iodophenyl)-2,3-dihydro-1H-indene-5-sulfonamide To a stirred solution of 2,4-difluoro-3-iodoaniline (200 mg, 0.7843 mmol. 1.0 equiv.) in pyridine (1 mL) at room temperature was added 2,3-dihydro-1H-indene-5-sulfonyl chloride (169.94 mg, 0.7843 mmol. 1.0 equiv.) The resultant reaction mixture was stirred at room temperature for overnight. The progress of reaction was monitored through TLC. After completion of the reaction, the solvent was concentrated under reduced pressure to obtain crude residue which was further purified by flash chromatography (20% EtOAc/hexane) to obtain title compound as liquid and the liquid was further treated with 1N HCl to remove pyridine. The product was extracted with EtOAc, dried over sodium sulphate and concentrated under vacuum to obtain crude product which was triturated with hexanes to obtain desired product N-(2,4-difluoro-3-iodophenyl)-2,3-dihydro-1H-indene-5-sulfonamide (348 mg).

Step 2: Synthesis of N-(6-(3-(2,3-dihydro-1H-indene-5-sulfonamido)-2,6-difluorophenyl)quinazolin-2-yl)pivalamide To a stirred solution of N-(2,4-difluoro-3-iodophenyl)-2,3-dihydro-1H-indene-5-sulfonamide (330 mg, 0.7582 mmol, 1.0 equiv) and N-(6-(4,4,5,5-tetramethyl-1,3,2-dioxaborolan-2-yl)quinazolin-2-yl)pivalamide (323.2 mg, 0.9098 mmol, 1.2 equiv) in dioxane:water (4:1, 5 mL) was added $K_2CO_3$ (314.3 mg, 2.2746 mmol, 3.0 equiv.). The resulting reaction mixture was purged with nitrogen for 10 minutes followed by the addition of Pd(dppf)$Cl_2$·DCM complex (30.9 mg, 0.0379 mmol, 0.05 equiv.). The reaction mixture was again purged with nitrogen for 5 minutes. The reaction mixture was heated to 100° C. for overnight. The progress of reaction was monitored through TLC and LCMS. After completion of reaction, water was added to the reaction mixture, extracted with EtOAc (2×100 mL). The organic layers were combined, dried over anhydrous $Na_2SO_4$ and evaporated under reduced pressure to obtain title product (340 mg). This product was used in next step without further purification. LCMS: 537.3[M+H]$^+$

Step-3: Synthesis of N-(3-(2-aminoquinazolin-6-yl)-2,4-difluorophenyl)-2,3-dihydro-1H-indene-5-sulfonamide To a stirred solution of N-(6-(3-(2,3-dihydro-1H-indene-5-sulfonamido)-2,6-difluorophenyl)quinazolin-2-yl)pivalamide (340 mg, 0.6336 mmol, 1.0 equiv) in ethanol (4 mL) at room temperature was added 2M NaOH (1 mL). Then, the reaction mixture was allowed to stir at 90° C. for 30 min. Progress of the reaction was monitored by TLC and LCMS. After completion of the reaction, RM was concentrated under reduced pressure to evaporate ethanol, extracted with EtOAc (2×100 mL). The organic layers were combined, dried over anhydrous $Na_2SO_4$, evaporated under reduced pressure to obtain crude product which was purified by using reverse phase chromatography technique to obtain desired compound N-(3-(2-aminoquinazolin-6-yl)-2,4-difluorophenyl)-2,3-dihydro-1H-indene-5-sulfonamide (22 mg), Analytical Data: LCMS: 453.4[M+H]$^+$, $^1$H NMR: $^1$H NMR (400 MHz, DMSO-$d_6$) □ ppm 10.47 (s, 1H) 9.14 (s, 1H) 7.77 (s, 1H) 7.52-7.61 (m, 2H) 7.48 (t, J=8.99 Hz, 2H) 7.32 (d, J=7.89 Hz, 1H) 7.19 (d, J=5.70 Hz, 1H) 6.99 (s, 3H) 2.88 (d, J=3.51 Hz, 4H) 1.96-2.09 (m, 2H)

Compound 162

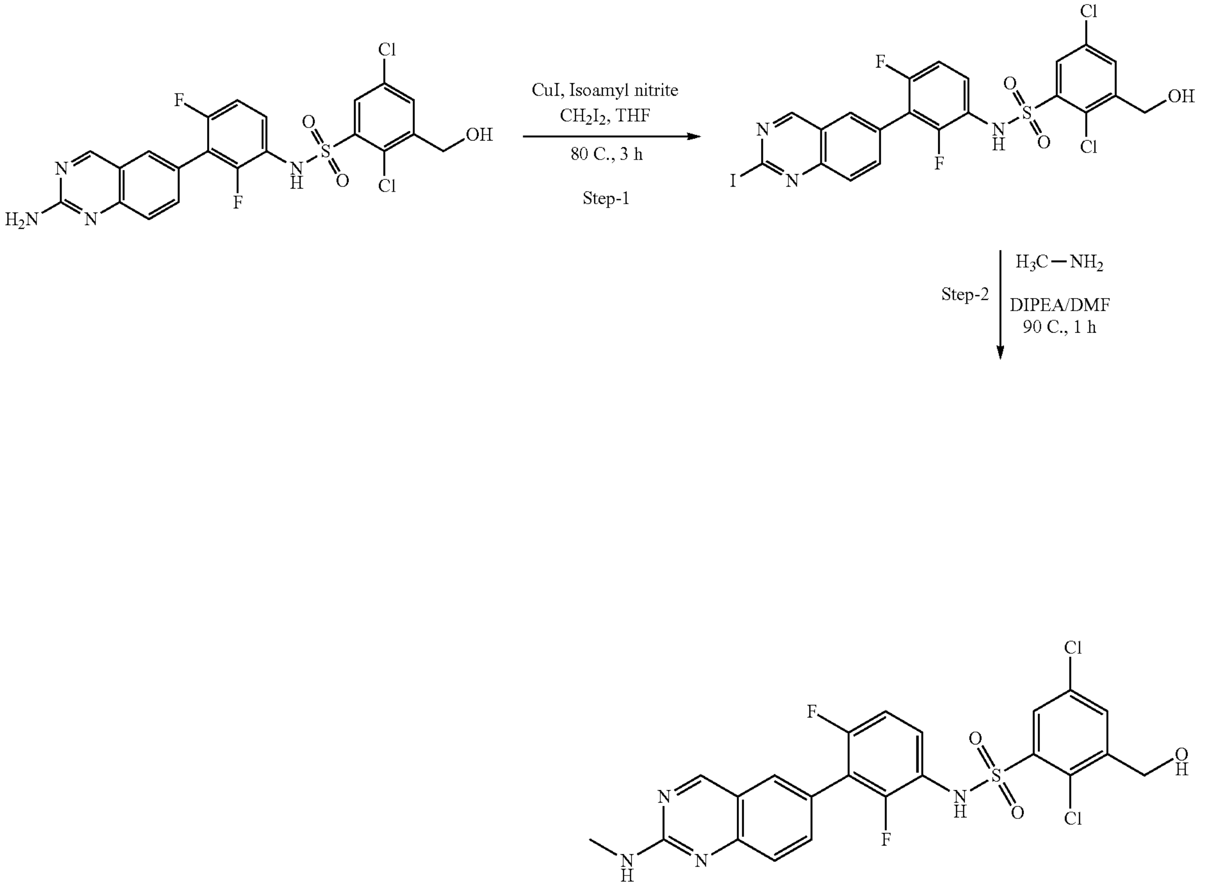

Step-1: Synthesis of 2,5-dichloro-N-(2,4-difluoro-3-(2-iodoquinazolin-6-yl)phenyl)-3-(hydroxymethyl) benzenesulfonamide To a stirred solution of N-(3-(2-aminoquinazolin-6-yl)-2,4-difluorophenyl)-2,5-dichloro-3-(hydroxymethyl)benzenesulfonamide (400 mg, 0.7822 mmol, 1.0 equiv u.) in THE (4 ml) and added CuI (223.47 mg, 1.1734 mmol, 1.5 equiv.) and purged with N2 gas. Under N2 atmosphere was added Isoamyl nitrite (137.4 mg, 1.1734 mmol, 1.5 equi.), diidomethane (0.37 ml, 4.6936 mmol, 6.0 equiv.) to reaction mixture. After addition, reaction mixture was allowed to stir at 80° C. for 3 h. After completion of reaction, reaction mixture was passed through celite, filtrate was added ice water and extracted with ethyl acetate (2×50 ml). The separated organic layer was dried over $Na_2SO_4$, filtered and concentrated under vacuum to obtain crude product which was purified by using combi-flash (Eluent System: 20% EA:Hexanes) to obtain desired product (190 mg)

Step-2: Synthesis of 2,5-dichloro-N-(2,4-difluoro-3-(2-(methylamino)quinazolin-6-yl)phenyl)-3-(hydroxymethyl)benzenesulfonamide To a stirred solution of 2,5-dichloro-N-(2,4-difluoro-3-(2-iodoquinazolin-6-yl)phenyl)-3-(hydroxymethyl)benzenesulfonamide (170 mg, 0.2732 mmol, 1.0 equiv.) in was added in DMF (2 ml) and added methylamine (28.1 mg, 0.5464 mmol, 2.0 equiv.), DIPEA (0.14 ml, 0.8196 mmol, 3.0 equiv.). After addition reaction was heated at 90° C. for 1 h. Progress of reaction was monitored by TLC. After completion of reaction, water was added & extracted ethyl acetate (2×50 ml). The separated organic layer was dried over $Na_2SO_4$, filtered and concentrated. The crude product was purified by reverse phase chromatography to obtain desired product (9 mg), Analytical Data: LCMS: 525.4[M+H]+NMR: $^{1}$H NMR (400 MHz, DMSO-$d_6$) □ ppm 10.51 (s, 1H) 9.12 (br. s., 1H) 7.79 (d, J=6.58 Hz, 3H) 7.47-7.64 (m, 3H) 7.20-7.29 (m, 1H) 7.16 (t, J=9.21 Hz, 1H) 5.75 (br. s., 1H) 4.55-4.63 (m, 2H) 2.91 (d, J=4.38 Hz, 3H).

Compound 163

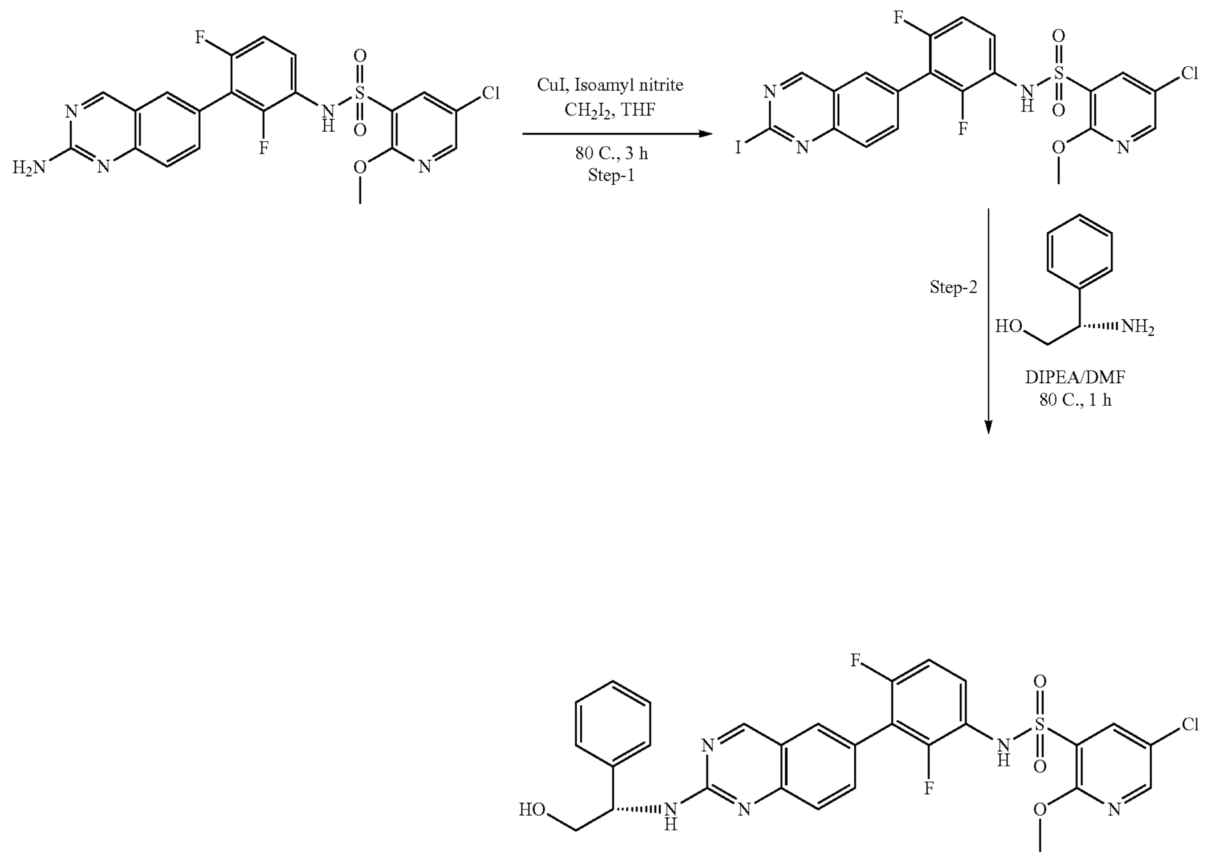

Step-1: Synthesis of 5-chloro-N-(2,4-difluoro-3-(2-iodoquinazolin-6-yl)phenyl)-2-methoxypyridine-3-sulfonamide To a stirred solution of N-(3-(2-aminoquinazolin-6-yl)-2,4-difluorophenyl)-5-chloro-2-methoxypyridine-3-sulfonamide (300 mg, 0.62 mmol, 1.0 equiv.) was added THF (2 ml) and added CuI (180 mg, 0.94 mmol, 1.5 equiv.) and purged with N2 gas. Under N2 atmosphere was added isoamyl nitrite (0.14 ml, 1.11 mmol, 1.8 equiv.), $CH_2I_2$ (0.3 ml, 3.72 mmol, 6.0 equiv.) to reaction mixture. After addition, reaction mixture was allowed to stir at 80° C. for 3 h. After completion of reaction, reaction mixture was passed through celite bed and added ice water and extracted with ethyl acetate (2×50 ml). The separated organic layer was dried over $Na_2SO_4$, filtered and concentrated under vacuum to obtain crude product which was purified by using combi-flash (Eluent System: 20% EA:Hexanes) to obtain desired product (120 mg)

Step-2: Synthesis of (S)-5-chloro-N-(2,4-difluoro-3-(2-(2-hydroxy-1-phenylethylamino)quinazolin-6-yl)phenyl)-2-methoxypyridine-3-sulfonamide To a stirred solution of 5-chloro-N-(2,4-difluoro-3-(2-iodoquinazolin-6-yl)phenyl)-2-methoxypyridine-3-sulfonamide (60 mg, 0.10 mmol, 1.0 equiv.) in was added in DMF (2 ml) and added (S)-2-amino-2-phenylethanol (28 mg, 0.20 mmol, 2.0 equiv.), DIPEA (0.05 ml, 0.30 mmol, 3.0 equiv.). After addition reaction mixture was heated at 90° C. for 1 h. Progress of reaction was monitored by TLC. After completion of reaction, was added water work up of reaction had been carried out using ethyl acetate (2×50 ml) and brine (20 ml). The separated organic layer was dried over $Na_2SO_4$, filtered and concentrated. The crude product was purified by reverse phase chromatography to obtain desired product (9 mg), Analytical Data: LCMS: −598.5 [M+H]+, NMR: 1H NMR (400 MHz, DMSO-$d_6$) d ppm $^1H$ NMR (400 MHz, DMSO-$d_6$) □ ppm 9.15 (s, 1H) 8.26 (br. s., 1H) 7.99 (br. s., 1H) 7.85 (br. s., 1H) 7.78 (br. s., 1H) 7.60 (br. s., 1H) 7.45 (d, J=7.45 Hz, 4H) 7.30 (t, J=7.67 Hz, 2H) 7.21 (d, J=6.14 Hz, 2H) 6.89 (br. s., 1H) 5.22 (d, J=6.58 Hz, 1H) 4.90 (br. s., 1H) 3.70 (br. s., 3H) 1.23 (br. s., 2H).

Compound 164

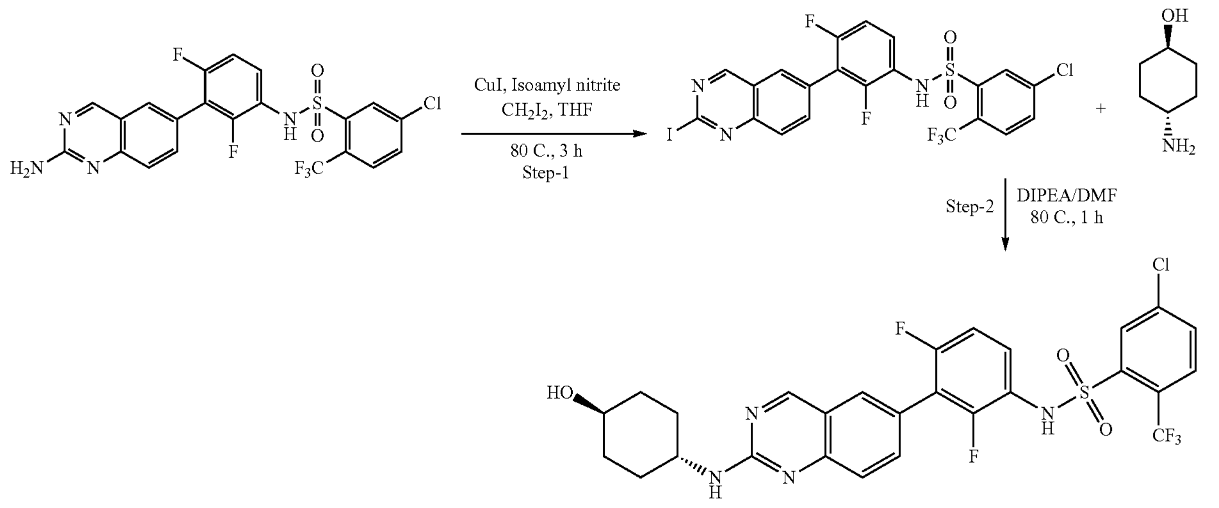

Step-1: Synthesis of 5-chloro-N-(2,4-difluoro-3-(2-iodoquinazolin-6-yl)phenyl)-2-(trifluoromethyl)benzenesulfonamide To a stirred solution of N-(3-(2-aminoquinazolin-6-yl)-2,4-difluorophenyl)-5-chloro-2-(trifluoromethyl)benzenesulfonamide (1 g, 1.94 mmol, 1.0 equiv.) was added THF (15 ml) and added CuI (556 mg, 2.91 mmol, 1.5 equiv.) and purged with N2 gas. Under N2 atmosphere was added isoamyl nitrite (0.42 ml, 3.49 mmol, 1.8 equiv.), $CH_2I_2$ (0.94 ml, 11.64 mmol, 6.0 equiv.) to reaction mixture. After addition, reaction mixture was allowed to stir at 80° C. for 3 h. After completion of reaction, reaction mixture was passed through celite and added ice water and extracted with ethyl acetate (2×50 ml). The separated organic layer was dried over Na2SO4, filtered and concentrated under vacuum to obtain crude product which was purified by using combi-flash (Eluent System: 20% EA:Hexanes) to obtain desired product (400 mg), LCMS: 626.20[M+H]$^+$

Step-2: Synthesis of 5-chloro-N-(2,4-difluoro-3-(2-((1r,4r)-4-hydroxycyclohexylamino)quinazolin-6-yl)phenyl)-2-(trifluoromethyl)benzenesulfonamide To a stirred solution of 5-chloro-N-(2,4-difluoro-3-(2-iodoquinazolin-6-yl)phenyl)-2-(trifluoromethyl)benzenesulfonamide (60 mg, 0.10 mmol, 1.0 equiv.) in was added in DMF (2 ml) and added trans-4-Aminocyclohexanol (34 mg, 0.28 mmol, 2.0 equi.), DIPEA (0.05 ml, 0.28 mmol, 3.0 equiv.). After addition reaction was heated at 90° C. for 1 h. Progress of reaction was monitored by TLC. After completion of reaction, was added water for work up of reaction had been carried out using ethyl acetate (2×50 ml) and brine (20 ml). The separated organic layer was dried over $Na_2SO_4$, filtered and concentrated. The crude product was purified by reverse phase chromatography to obtain desired product (16 mg), Analytical Data: LCMS: 613.5 [M+H]$^+$, NMR: 1H NMR (400 MHz, DMSO-$d_6$) d ppm $^1$H NMR (400 MHz, DMSO-$d_6$) □ ppm 10.66 (br. s., 1H) 9.11 (br. s., 1H) 7.98-8.05 (m, 1H) 7.97 (s, 1H) 7.90 (d, J=8.33 Hz, 1H) 7.73 (s, 1H) 7.49-7.62 (m, 1H) 7.42 (d, J=7.45 Hz, 1H) 7.25 (d, J=5.70 Hz, 1H) 7.15 (d, J=7.45 Hz, 1H) 4.56 (d, J=3.95 Hz, 1H) 3.83 (br. s., 2H) 3.42 (br. s., 1H) 1.77-2.02 (m, 4H) 1.17-1.45 (m, 4H).

Compound 165

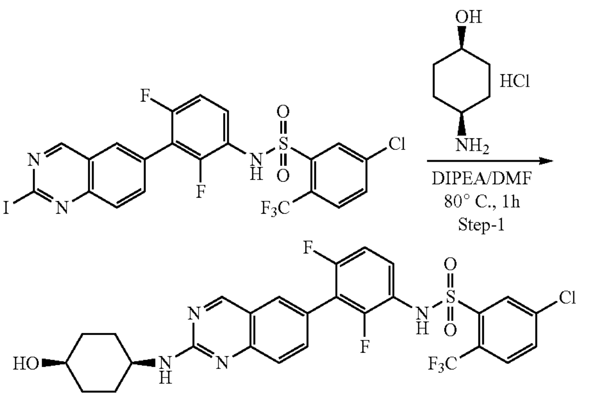

Step-1: Synthesis of 5-chloro-N-(2,4-difluoro-3-(2-((1s,4s)-4-hydroxycyclohexylamino)quinazolin-6-yl)phenyl)-2-(trifluoromethyl)benzenesulfonamide To a stirred solution of 5-chloro-N-(2,4-difluoro-3-(2-iodoquinazolin-6-yl)phenyl)-2-(trifluoromethyl)benzenesulfonamide (60 mg, 0.95 mmol, 1.0 equiv.) in was added in DMF (2 ml) and was added Cis-4-Aminocyclohexanol·HCl (43 mg, 0.29 mmol, 2.0 equiv.), DIPEA (0.05 ml, 0.28 mmol, 3.0 equiv.). After addition reaction was heated at 90° C. for 1 h. Progress of reaction was monitored by TLC. After completion of reaction, was added cold water for work up of reaction had been carried out using ethyl acetate (2×50 ml) and brine (20 ml). The separated organic layer was dried over $Na_2SO_4$, filtered and concentrated. The crude product was purified by reverse phase chromatography to obtain desired product (12 mg), Analytical Data: LCMS: 613.5 [M+H]$^+$, NMR: 1H NMR (400 MHz, DMSO-$d_6$) d ppm $^1$H NMR (400 MHz, DMSO-$d_6$) □ ppm 10.65 (br. s., 1H) 9.12 (br. s., 1H) 7.98 (s, 1H) 8.01 (s, 1H) 7.93 (br. s., 1H) 7.73 (br. s., 1H) 7.38-7.61 (m, 2H) 7.26 (br. s., 1H) 7.17 (br. s., 2H) 4.36 (br. s., 1H) 3.88 (br. s., 1H) 3.75 (br. s., 1H) 1.66 (br. s., 8H).

Compound 166

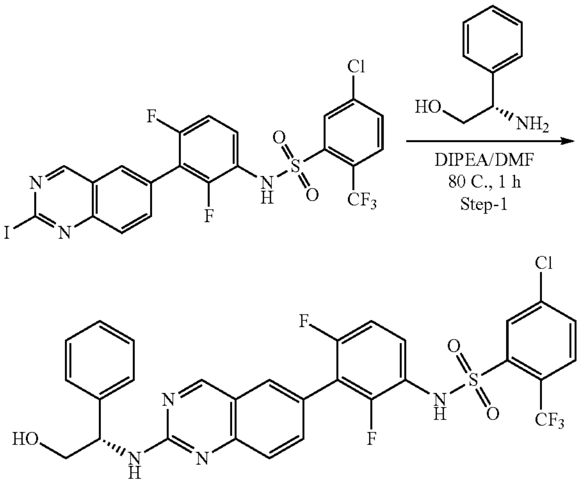

Step-1: Synthesis of (S)-5-chloro-N-(2,4-difluoro-3-(2-(2-hydroxy-1-phenylethylamino)quinazolin-6-yl)phenyl)-2-(trifluoromethyl)benzenesulfonamide To a stirred solution of 5-chloro-N-(2,4-difluoro-3-(2-iodoquinazolin-6-yl)phenyl)-2-(trifluoromethyl)benzenesulfonamide (50 mg, 0.08 mmol, 1.0 equiv.) in was added in DMF (2 ml) and added (S)-2-amino-2-phenylethanol (33 mg, 0.24 mmol, 2.0 equiv.), DIPEA (0.04 ml, 0.241 mmol, 3.0 equiv.). After addition reaction was heated at 90° C. for 1 h. Progress of reaction was monitored by TLC. After completion of reaction, was added cold water for work up of reaction had been carried out using ethyl acetate (2×50 ml) and brine (20 ml). The separated organic layer was dried over $Na_2SO_4$, filtered and concentrated. The crude product was purified by reverse phase chromatography to obtain desired product (12 mg), Analytical Data: LCMS: 635.5 [M+H]+NMR: 1H NMR (400 MHz, DMSO-$d_6$) d ppm $^{1}$H NMR (400 MHz, DMSO-$d_6$) □ ppm 9.16 (s, 1H) 8.03 (s, 1H) 7.70-7.81 (m, 2H) 7.60 (d, J=8.33 Hz, 1H) 7.46 (d, J=7.45 Hz, 5H) 7.30 (t, J=7.67 Hz, 3H) 7.15-7.26 (m, 2H) 7.11 (d, J=7.45 Hz, 1H) 5.3 (s, 1H) 5.19 (s, 1H) 3.69 (d, J=5.70 Hz, 2H)

Compound 167

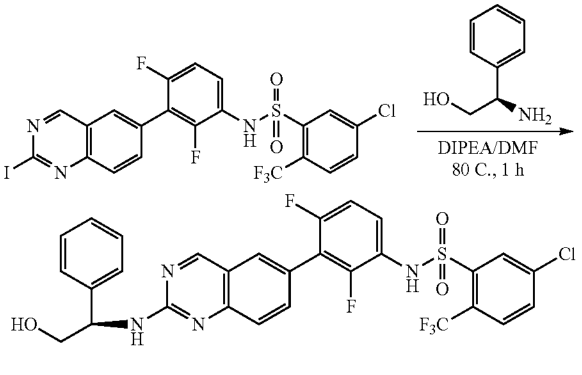

Step-1: Synthesis of (R)-5-chloro-N-(2,4-difluoro-3-(2-(2-hydroxy-1-phenylethylamino)quinazolin-6-yl)phenyl)-2-(trifluoromethyl)benzenesulfonamide To a stirred solution of 5-chloro-N-(2,4-difluoro-3-(2-iodoquinazolin-6-yl)phenyl)-2-(trifluoromethyl)benzenesulfonamide (50 mg, 0.080 mmol, 1.0 equiv.) in was added in DMF (2 ml) and added (R)-2-amino-2-phenylethanol (33 mg, 0.24 mmol, 2.0 equiv.), DIPEA (0.04 ml, 0.24 mmol, 3.0 equiv.). After addition reaction was heated at 90° C. for 1 h. Progress of reaction was monitored by TLC. After completion of reaction, was added cold water work up of reaction had been carried out using ethyl acetate (2×50 ml) and brine (20 ml). The separated organic layer was dried over $Na_2SO_4$, filtered and concentrated. The crude product was purified by reverse phase chromatography to obtain desired product (10 mg), Analytical Data: LCMS: 635.5 [M+H]+NMR: 1H NMR (400 MHz, DMSO-$d_6$) d ppm $^{1}$H NMR (400 MHz, DMSO-$d_6$) □ ppm 9.16 (s, 1H) 8.02 (s, 1H) 7.88 (d, J=8.33 Hz, 2H) 7.77 (br. s., 2H) 7.58 (br. s., 2H) 7.47 (br. s., 4H) 7.30 (t, J=7.67 Hz, 2H) 7.04-7.27 (m, 1H) 6.98 (br. s., 1H) 5.15-5.26 (m, 1H) 4.84-4.97 (m, 1H) 3.69 (d, J=5.70 Hz, 2H).

Compound 168

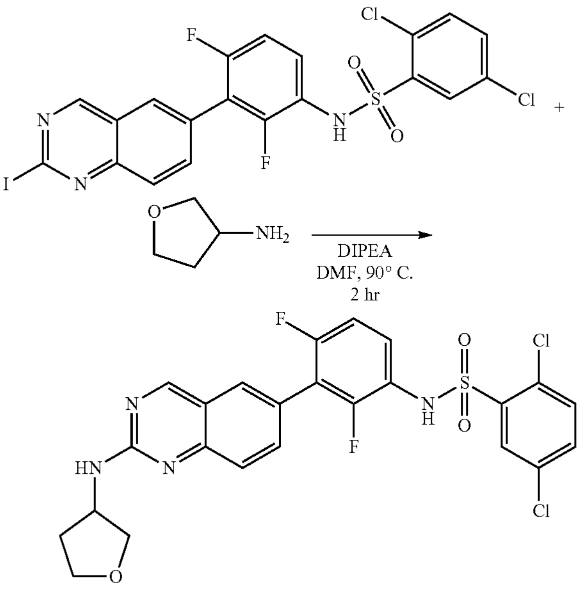

Step-1: Synthesis of 2,5-dichloro-N-(2,4-difluoro-3-(2-(tetrahydrofuran-3-ylamino)quinazolin-6-yl)phenyl)benzenesulfonamide To a stirred solution of 2,5-dichloro-N-(2,4-difluoro-3-(2-iodoquinazolin-6-yl)phenyl)benzenesulfonamide (100 mg, 0.169 mmol, 1.0 equiv.) in 5 mL DMF was added salt of tetrahydrofuran-3-amine methanesulfonate (0.0925 mg, 0.508 mmol, 3.0 equiv.) & DIPEA (0.0884 mL, 0.508 mmol, 3.0 equiv.). After addition reaction was heated at 90° C. for 2 hr. Progress of reaction was monitored by TLC. After completion of reaction, was added work up of reaction had been carried out using ethyl acetate (2×50 ml) and water (20 ml). The separated organic layer was dried over $Na_2SO_4$, filtered and concentrated. The crude product was purified by reverse phase chromatography to obtain desired product (15 mg), Analytical Data: LCMS: 551[M+H]$^1$H NMR (400 MHz, DMSO-$d_6$) □ ppm 10.68 (br. s., 1H) 9.17 (br. s., 1H) 7.88 (m, 2H) 7.80 (s, 1H) 7.71 (s, 1H) 7.61 (d, J=8.33 Hz, 1H) 7.54 (d, J=8.33 Hz, 1H) 7.31 (m, 1H) 7.19 (m, 1H) 4.52 (br. s., 1H) 3.99 (m, 1H) 3.87 (q, J=7.45 Hz, 1H) 3.80 (m, 1H) 3.61 (d, J=5.26 Hz, 1H), 2.9 (d, J=7 Hz, 1H), 2.25 (m, 1H) 1.88-2.00 (m, 1H).

Biological Activity

Example A

Evaluation of GCN2 Inhibitors in Primary CD4+ T Cells in Response to Tryptophan Starvation Primary CD4+ T cells were isolated by magnetic negative selection from leukocyte cones of healthy donors (e.g., using CD4+ T Cell Isolation Kit, human; Miltenyi Biotec). Purified CD4+ were fluorescently labelled (e.g., with Cell Proliferation Dye eFluor™ 450; ThermoFisher Scientific) according to manufacturer's instructions. Labelled cells were then seeded in U-bottom 96-well suspension culture microplates at a cell density of $1\times10^5$ cells/well.

CD4+ T cells were cultured in a matrix of Tryptophan-depleted RPMI media (RPMI 1640, w: L-glutamine, w/o: L-tryptophan, w: 2.0 g/L $NaHCO_3$; Pan Biotech UK Ltd, Cat No. #P04-17598) containing increasing amounts of tryptophan and GCN2 inhibitor, at a final concentration of $5\times10^5$ cells/ml. Concentrations of tryptophan ranged from low levels (0.3 μM and 3 μM), up to the concentration found in regular RPMI (30 μM). Titration of GCN2 inhibitor covered from 1 nM to 1 μM compound in 10-fold dilutions, including no compound condition (DMSO control). Cells were stimulated with anti-CD3/CD28 beads (Dynabeads™ Human T-Activator CD3/CD28; ThermoFisher Scientific) at a ratio of 2.5 beads per cell. Controls with unstimulated cells were included for all conditions. All conditions were tested in duplicate.

After 5 days of culture cell viability (e.g., using Fixable Viability Dye eFluor™ 780; ThermoFisher Scientific), proliferation and CD25 expression (Clone M-A251; BioLegend) were evaluated by flow cytometry. Samples were acquired using flow cytometry (e.g., using a Fortessa™ X-20 cytometer; BD Biosciences) and data were analyzed (e.g., using FlowJo software; BD Biosciences). Supernatants were analysed for IFN-γ and GranzymeB using multiplex immunoassays. IL-10 levels in supernatants were measured by ELISA (e.g., Human IL-10 DuoSet ELISA; R&D Systems). Data were plotted in GraphPad Prism software.

FIGS. 1A-1F shows representative results (mean) of one donor out of four associated with Example 1-1. After 5 days of culture in increasing amounts of tryptophan and GCN2 inhibitor cells were assessed for viability (FIG. 1A), proliferation (FIG. 1), and CD25 expression (FIG. 1C), and supernatants were analysed for Granzyme B (FIG. 1D), IFN-γ (FIG. 1E), and IL-10 (FIG. 1F).

Example B

GCN2 Inhibition Cell-Based Assay

Neuro 2a cells (N2a) were maintained at 37° C. and 5% $CO_2$ in DMEM/F12 medium (Fisher Scientific) supplemented with 10% fetal bovine serum and 1% penicillin-streptomycin (complete medium). 300,000 cells/well were seeded in flat bottom 6 well plates 48 hours before treatment with the compounds.

Testing compounds were prepared at different concentrations ranging from 10 μM to 0.1 nM on DMEM medium lacking L-cysteine and methionine (DMEM-CM) (Gibco) and supplemented with 1% penicillin-streptomycin. Complete medium was used as control of non-stressed condition. After 48 hours, the medium was removed from each well and 2 mL per well of each treatment was added. Cells were treated for 3 hours at 37° C. and 5% $CO_2$.

After the incubation time, each well was washed with sterile 1×PBS and then 100 μL of ice-cold lysis buffer supplemented with phosphatase and protease inhibitors was added. Lysates were transferred to 1.5 mL tubes and sonicated for 3 min, and total protein amounts were quantified using BCA assay (e.g., BCA Protein Assay Kit; Pierce) according to manufacturer instructions. Equal amount of proteins was loaded on SDS-PAGE gels for electrophoresis and then transferred onto 0.2 m filter pore PVDF membranes.

Membranes were then blocked in blocking buffer containing 3% BSA/0.1% Tween/1×Tris-buffered saline (TBS) for 1 hour and then incubated overnight at 4° C. with agitation with anti-pGCN2 primary antibody (Abcam ab-75836), diluted 1:1,000 in blocking buffer. Anti-O actin antibody (Sigma Aldrich) was used as a loading control.

Membranes were then incubated with the corresponding secondary antibody to detect immune-reactive bands using enhanced chemiluminescence (e.g., ECL Western Blotting Substrate Pierce).

Images were acquired (e.g., using Chemidoc™ equipment) and quantitated by densitometry using ImageJ software. $IC_{50}$ values were determined from a concentration-response curve using GraphPad prism software.

$IC_{50}$ values from P-GCN2 inhibition assay after induction with amino acid deprived media in the presence of different concentrations of test compounds are shown in Table 2. For $IC_{50}$ values: +++ refers to <10 nM of test compound; ++ refers to 10 nM to 100 nM of test compound; + refers to 100 nM to 1,000 nM of test compound and – refers to >1,000 nM of test compound.

TABLE 2

| Compound No. | $IC_{50}$ |
|---|---|
| Compound 1 | +++ |
| Compound 2 | +++ |
| Compound 3 | – |
| Compound 4 | – |
| Compound 5 | – |
| Compound 6 | – |
| Compound 7 | – |
| Compound 8 | – |
| Compound 9 | + |
| Compound 10 | +++ |
| Compound 11 | ++ |
| Compound 12 | – |
| Compound 13 | +++ |
| Compound 14 | – |
| Compound 15 | + |
| Compound 16 | + |
| Compound 17 | – |
| Compound 18 | – |
| Compound 19 | + |
| Compound 20 | – |
| Compound 44 | – |
| Compound 45 | – |
| Compound 46 | +++ |
| Compound 47 | +++ |
| Compound 51 | +++ |
| Compound 52 | +++ |
| Compound 58 | +++ |
| Compound 59 | +++ |
| Compound 63 | ++ |
| Compound 64 | +++ |
| Compound 65 | +++ |
| Compound 66 | +++ |

TABLE 2-continued

| Compound No. | $IC_{50}$ |
|---|---|
| Compound 67 | +++ |
| Compound 69 | +++ |
| Compound 76 | − |
| Compound 81 | − |
| Compound 105 | ++ |
| Compound 106 | +++ |
| Compound 107 | − |
| Compound 108 | +++ |
| Compound 109 | ++ |
| Compound 110 | − |
| Compound 111 | − |
| Compound 112 | − |
| Compound 113 | +++ |
| Compound 115 | ++ |
| Compound 116 | − |
| Compound 117 | − |
| Compound 118 | ++ |
| Compound 119 | − |
| Compound 120 | − |
| Compound 121 | +++ |
| Compound 122 | + |
| Compound 123 | − |
| Compound 124 | − |
| Compound 125 | − |
| Compound 128 | +++ |
| Compound 129 | +++ |
| Compound 130 | − |
| Compound 131 | ++ |
| Compound 132 | − |
| Compound 133 | ++ |
| Compound 134 | +++ |
| Compound 135 | + |
| Compound 136 | + |
| Compound 137 | ++ |
| Compound 138 | − |
| Compound 139 | + |
| Compound 140 | − |
| Compound 141 | − |
| Compound 142 | − |
| Compound 143 | + |
| Compound 144 | ++ |
| Compound 145 | − |
| Compound 146 | + |
| Compound 147 | + |
| Compound 148 | + |
| Compound 149 | + |
| Compound 150 | ++ |
| Compound 153 | ++ |
| Compound 154 | + |
| Compound 155 | + |
| Compound 156 | ++ |
| Compound 157 | +++ |
| Compound 158 | + |
| Compound 159 | ++ |
| Compound 160 | − |
| Compound 161 | − |
| Compound 162 | ++ |
| Compound 163 | + |
| Compound 164 | +++ |
| Compound 165 | ++ |
| Compound 166 | + |
| Compound 167 | + |
| Compound 168 | +++ |

Under GCN2-mediated stress conditions, resulting from an amino acid deprived medium, GCN2 is generally phosphorylated. Accordingly, inhibition of GCN2 phosphorylation as a result of the test compound indicates inhibition of the GCN2 pathway.

Example C

GCN2 Enzyme Inhibition Assay

In order to validate the above results, human GCN2 enzyme activity was measured in Reaction Biology Corp (EIF2AK4/GCN2 kinase assay). Compounds were tested in 5-dose $IC_{50}$ mode for non-active compounds and 10-dose $IC_{50}$ mode for active compounds with 3-fold serial dilution starting at 30 μM and 0.1 μM respectively. Control compound Staurosporine was tested in 10-dose $IC_{50}$ mode with 4-fold serial dilution starting at 20 μM. Reactions were carried out at 10 μM ATP using 20 μM peptide substrate [GRSRSRSRSR]. $IC_{50}$ values were determined from a concentration-response curve using GraphPad prism software and are shown in Table 3. For $IC_{50}$ values: +++ refers to <10 nM of test compound; ++ refers to 10 nM to 100 nM of test compound; + refers to 100 nM to 1,000 nM of test compound and − refers to >1,000 nM of test compound.

TABLE 3

| Compound No. | $IC_{50}$ |
|---|---|
| Compound 1 | ++ |
| Compound 3 | − |
| Compound 4 | + |
| Compound 5 | − |
| Compound 2 | +++ |
| Compound 6 | − |
| Compound 7 | − |

Example D

Recovery of Protein Synthesis Under GCN2-Mediated Stressed Condition

CHO cells were maintained in DMEM/F12 medium supplemented with 10% fetal bovine serum and 1% penicillin-streptomycin. 200,000 cells/well were seeded in flat bottom 6 well plates 48 hours before treatment with the compounds.

Testing compounds were prepared at 5 μM on 10 mM L-histidinol (Cayman Cat N° 18739) to measure the recovery of protein synthesis under G-CN2-mediated stress condition. 0.1% DMSO in supplemented DMEM/F12 with or without 10 mM L-histidinol were used as vehicles. The medium was removed from each well and 2 mL per well of each treatment was added. Cells were incubated for 2 hours at 37° C. and 5% $CO_2$.

Puromycin was prepared in supplemented DMEM/F12 at a final concentration of g/mL from a 10 mg/mL stock.

After the incubation time with the compounds, the medium was removed and 2 mL of 10 μg/mL puromycin was added to each well and incubated at 37° C. and 5% $CO_2$ for 30 minutes.

Once finished the incubation time, the medium was removed from each well and then 100 μL of ice-cold lysis buffer supplemented with phosphatase and protease inhibitors was added. The plates were then stored at −20° C. for 24 hours.

The wells were scraped and samples were collected in 1.5 mL centrifuge tubes, sonicated for 3 minutes and then centrifuged for 15 minutes at 15,000×g and 4° C. Supernatants were collected in clean centrifuge microtubes and maintained on ice for protein quantification using BCA assay (e.g., BCA Protein Assay Kit; Pierce) according to manufacturer instructions. Equal amount of proteins was loaded on SDS-PAGE gels for electrophoresis and then transferred onto 0.2 μm filter pore PVDF membranes.

Membranes were then blocked in blocking buffer containing 3% BSA/0.1% Tween/1×TBS buffer for 1 hour and then incubated overnight at 4° C. with agitation with the anti-Puromycin primary antibody, diluted 1:10,000 in blocking buffer. Anti-β actin antibody was used as a loading control.

Membranes were then incubated with the corresponding secondary antibody to detect immune-reactive bands using enhanced chemiluminescence (e.g., using ECL Western Blotting Substrate; Pierce).

Images were acquired using Chemidoc™ equipment and quantitated by densitometry using ImageJ software.

Percent recovery of protein synthesis in amino acid deprived condition (L-histidinol treatment) due to the test compounds at 5 μM is shown in Table 4. The levels were normalized to the media alone and to L-histidinol alone conditions, which correspond to 100% and 0% respectively. For % Recovery of protein synthesis (RPS): +++ refers to >80% RPS at 5 μM test compound; ++ refers to 50% to 80% RPS at 5 μM test compound; + refers to <50% RPS at 5 μM test compound.

TABLE 4

| Compound No. | Recovery of protein |
|---|---|
| Compound 1 | +++ |
| Compound 2 | +++ |
| Compound 3 | + |
| Compound 4 | ++ |
| Compound 5 | + |
| Compound 6 | + |
| Compound 7 | +++ |
| Compound 8 | ++ |
| Compound 9 | +++ |
| Compound 10 | +++ |
| Compound 11 | +++ |
| Compound 12 | + |
| Compound 13 | +++ |
| Compound 14 | +++ |
| Compound 15 | ++ |
| Compound 16 | +++ |
| Compound 17 | + |
| Compound 18 | + |
| Compound 19 | +++ |

Example E

Compounds Prevent GCN2 Activation Induced by Arginine Starvation

This example demonstrates that exemplary compounds, Compound 1 and Compound 2, prevent GCN2 activation.

Colorectal cancer cell lines HT29 and HCT116 were seeded at a concentration of $100\times10^3$ cells per well in 6 well plates, in SILAC DMEM Flex media supplemented with 10% fetal bovine serum, 1 g/L glucose, 2 mM glutamine, 800 μM lysine, and various concentrations of arginine in the absence or presence of Compound 1 and Compound 2 GCN2 inhibitors. Cells were cultured for 24 hours.

Following 24 hours of culture, expression of phosphorylated GCN2 (P-GCN2) and alpha-actinin loading control was assessed by Western blot. Briefly, cells were washed with cold PBS and dissolved in cell lysis buffer containing 1% Triton, supplemented with protease inhibitors and phosphatase inhibitors. All lysates were freshly prepared and normalized using a BCA protein assay before addition of LDS sample buffer and denaturation by boiling the samples for 5 minutes at 95° C. Proteins were separated on 4-12% Bis-Tris protein gels in MOPS SDS buffer and electrophoresis was performed (e.g., Novex NuPAGE® Gel Electrophoresis Systems; Invitrogen). Transfer of the protein samples was performed (e.g., using the Mini Trans-Blot Cell® system; Bio-Rad) with 0.45 μM pore Nitrocellulose/Filter paper sandwiches and transfer buffer at 350 mA for 90 minutes at 4° C. Membranes were blocked for 1 hour with 4% BSA in TBS-Tween at room temperature and incubated with 1:1,000 dilutions of anti-GCN2, phospho-GCN2, α-actinin1, and/or p21 (Waf/Cip1) antibodies overnight at 4° C. Afterwards, membranes were washed 3 times with TBS-Tween and incubated with HRP-conjugated secondary antibodies at 1:20,000 dilution for 1 hour at room temperature.

Depletion of arginine from the media of the colorectal cancer cell lines HT29 and HCT116 lead to the dose-dependent induction of GCN2 activation, demonstrated by detection of phosphorylated GCN2 (P-GCN2) in FIG. 2A. Treating cells with the GCN2 inhibitors Compound 1 or Compound 2 prevented the activation of GCN2 upon arginine depletion, as illustrated by the absence of P-GCN2 expression in FIG. 2B. Additionally, FIG. 2B demonstrates that p21 expression is induced in the presence of either Compound 1 or Compound 2, indicative of cell cycle arrest associated with GCN2 inactivation by the compounds.

Example F

Compounds Induce Cell Death in Colorectal Cancer Cells

This example demonstrates that exemplary compounds, Compound 1 and Compound 2, induce cell death and arrest the growth of colorectal tumor cells.

Proliferation and apoptosis of HT29 cells was determined in the presence of Compound 1 and Compound 2. Briefly, cells were seeded in 96-well flat bottom plates at 4,000 cells per well in 100 μL SILAC DMEM Flex media without phenol red, supplemented with 10% fetal bovine serum (FBS), 1 g/L glucose, 2 mM glutamine, 220 μM lysine, containing a physiological concentration of arginine (64 μM). After 24 hours, cells were treated with 10 μM vehicle control (Control; 0.1% DMSO), 10 μM Compound 1, or 10 μM Compound 2, together with 100 nM of fluorescent apoptosis stain (YO-PRO™-1 Iodide; Thermo Fisher) to detect apoptotic cells. Cells were placed in a live-cell imaging and analysis platform (IncuCyte ZOOM®; Essenbio) set up in a humidified incubator at 37° C. and the plates were scanned every 4 hours for up 96 hours, at 10× magnification to determine cell confluence and cell death. Experiments were performed in duplicate with 3 images collected per well and analyzed using live-cell imaging and analysis software (e.g., IncuCyte ZOOM® 2018A software; Essenbio).

As demonstrated in FIGS. 3A-3C, cells treated with Compound 1 or Compound 2 grew less dense (FIGS. 3A and 3C) and displayed an increased rate of apoptotic cell death (FIG. 3B), as compared to the untreated cells. The effect was particularly striking for Compound 2.

Example G

Compounds Prevent the Growth of Tumor Spheroids

This example demonstrates that exemplary compounds, Compound 1, Compound 2 and Compound 108, prevent growth of tumor spheroids.

The growth of tumor spheroids was evaluated following treatment of cells with Compound 1, Compound 2 and Compound 108. Briefly, HT29 cells were seeded at 5,000 cells/well in ultra-low attachment round bottom 96-well plates, in 100 μL SILAC DMEM Flex media without phenol red, supplemented with 10% fetal bovine serum (FBS), 1 g/L glucose, 2 mM glutamine, 220 μM lysine, and 64 μM arginine. The plates were centrifuged for 10 minutes at 125×g and put in a humidified incubator at 37° C. for 3 days before the onset of the experiment to allow spheroids to form.

Three days after seeding, 10 μM Compound 1, 10 μM Compound 2, 10 μM Compound 108 or 10 μM vehicle control (0.1% DMSO), were added together with 100 nM fluorescent apoptosis stain (e.g., YO-PRO™-1 Iodide; Thermo Fisher) to detect apoptotic cells and Nuclear-ID Red DNA Stain (1:100,000; ENZO Life Sciences) to detect live cells. Plates were placed in a live-cell imaging and analysis platform (e.g., IncuCyte ZOOM®; Essenbio) set up in a humidified incubator at 37° C. and scanned every 4 hours for up 120 hours, at 10× magnification, to determine relative spheroid size and cell death. Experiments were performed in quadruplicate and analyzed using live-cell imaging and analysis software (e.g., IncuCyte ZOOM® 2018A software; Essenbio).

As demonstrated in FIGS. 4A-4B, treating the spheroids with Compound 1 (FIGS. 4A-4B), Compound 2 (FIGS. 4A-4B), or Compound 108 (FIG. 4B), led to a relative reduction in spheroid size and viability in a dose-dependent manner, as compared to untreated spheroids.

Example H

Compounds Prevent the GCN2-Induction of CHOP

This example demonstrates that exemplary compounds, Compound 1, Compound 2 and Compound 108, prevent the induction of CHOP via GCN2 activation, by inhibiting GCN2 activation.

To further demonstrate the specificity of the exemplary compounds, Compound 1, Compound 2 and Compound 108, wild type (WT) or GCN2 knock-out (KO) murine 3T3 fibroblasts stably transduced with a CHOP (DDIT3) reporter construct were evaluated for cell growth (e.g., proliferation) and cell death (e.g., apoptosis). The CHOP construct comprised the 3' untranslated region (UTR) of mouse DDIT3 mRNA fused to a sequence encoding the fluorescent protein mCherry.

Cells were seeded at 5,000 cells per well in flat bottom 96-well plates in 100 μL DMEM low glucose media without phenol red, and supplemented with 10% FBS and 2 mM glutamine. After 24 hours, the exemplary compounds, and either tunicamycin, halofuginone, or histidinol, were added together with 100 nM of fluorescent apoptosis stain (YO-PRO™-1 Iodide; Thermo Fisher) to detect apoptotic cells. Cells were placed in a live-cell imaging and analysis platform (IncuCyte ZOOM®; Essenbio) set up in a humidified incubator at 37° C. and the plates were scanned every 4 hours for up 120 hours, at 10× magnification, to determine cell confluence and cell death. Experiments were performed in duplicate with 3 images collected per well, and analyzed using live-cell imaging and analysis software (IncuCyte ZOOM® 2018A software; Essenbio).

Treatment of the cells with either halofuginone or histidinol induced GCN2 activation, and induction of CHOP (mCherry) could be observed in the WT cells, but not in the GCN2 knockout cells (FIGS. 5A-5D). This indicates that halofuginone or histidinol induces CHOP activation via the activation of GCN2, since CHOP is not activated in the absence of GCN2. However, treating the cells with the ER-stress inducing compound tunicamycin, which activates PERK, led to significant induction of CHOP in both the WT and GCN2 knockout cell lines (FIGS. 7A-7B). Thus, when PERK is activated, CHOP may be induced regardless of the presence of GCN2.

Treatment of the cells with increasing concentrations of Compound 1, Compound 2 or Compound 108 reduced GCN2 activation, shown as a fraction of cell confluence (e.g., cell growth) in FIGS. 5A-5D. This decrease in overall GCN2 activation by the exemplary compounds resulted in a corresponding decrease of GCN2-included CHOP activation, in the presence of halofuginone or histidinol (FIGS. 5A-5D).

In contrast, co-treatment of the compounds with tunicamyin increased CHOP activation by tunicamyin (FIGS. 7A-7B). This increase in CHOP activation suggests that compounds specifically target GCN2, and therefore have no effect on PERK driven CHOP induction.

Evaluation of apoptosis was performed to determine the effect of Compound 1, Compound 2 or Compound 108 co-treatment with halofuginone or histidinol (FIGS. 6A-6D). As shown in FIGS. 6A-6D, the exemplary compounds effectively inhibited apoptosis induced by treatment of the WT cells with halofuginone (FIG. 6A and FIG. 6C), but increased late-stage apoptosis induced by treatment of the WT cells with histidinol (FIG. 6B and FIG. 6D). This can be partially attributed to the fact that cell growth, which was inhibited by histidinol treatment, was initially rescued by treatment with the compounds (FIG. 5B and FIG. 5D), leading to more apoptosis upon prolonged treatment (FIGS. 6B and 6D). Alternatively, this may suggest a different mode of cell death induced by histidinol treatment as compared to halofuginone treatment. Apoptosis induction by histidinol in the presence of the exemplary compounds occurs independent of GCN2, as demonstrated by the apoptosis of GCN2 KO cells (FIG. 6D).

BRIEF DESCRIPTION OF THE FIGURES

FIG. 5A shows the relative increase of CHOP positive (mCherry) murine 3T3 wildtype (WT) fibroblasts stably transduced with a CHOP reporter construct. Cells were treated with increasing amounts of Compound 1 (left), Compound 2 (middle), or Compound 108 (right), and 1 μM halofuginone. The increase of CHOP positive cells is expressed as a fraction of cell confluence determined by a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

FIG. 5B shows the relative increase of CHOP positive (mCherry) murine 3T3 wildtype (WT) fibroblasts stably transduced with a CHOP reporter construct. Cells were treated with increasing amounts of Compound 1 (left), Compound 2 (middle), or Compound 108 (right), and 5 mM histidinol. The increase of CHOP positive cells is expressed as a fraction of cell confluence determined by a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

FIG. 5C shows increase of CHOP positive (mCherry) murine 3T3 GCN2 knock out (KO) stably transduced with a CHOP reporter construct. Cells were treated with increasing amounts of Compound 1 (left), Compound 2 (middle), or Compound 108 (right), and 1 μM halofuginone. The increase of CHOP positive cells is expressed as a fraction of cell confluence determined by a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

FIG. 5D shows increase of CHOP positive (mCherry) murine 3T3 GCN2 knock out (KO) stably transduced with a CHOP reporter construct. Cells were treated with increasing amounts of Compound 1 (left), Compound 2 (middle), or Compound 108 (right), and 5 mM histidinol. The increase of CHOP positive cells is expressed as a fraction of cell confluence determined by a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

FIG. 6A shows the relative increase of fluorescent apoptosis stain (e.g., YO-PRO™-1 Iodide; Thermo Fisher) positive cells in murine 3T3 wildtype (WT) fibroblasts stably transduced with a CHOP reporter construct. Cells were treated with increasing amounts of Compound 1 (left), Compound 2 (middle), or Compound 108 (right), and 1 μM halofuginone. The increase of CHOP positive cells is expressed as a fraction of cell confluence determined by in a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

FIG. 6B shows the relative increase of fluorescent apoptosis stain (e.g., YO-PRO™-1 Iodide; Thermo Fisher) positive cells in murine 3T3 wildtype (WT) fibroblasts stably transduced with a CHOP reporter construct. Cells were treated with increasing amounts of Compound 1 (left), Compound 2 (middle), or Compound 108 (right), and 5 mM histidinol. The increase of CHOP positive cells is expressed as a fraction of cell confluence determined by in a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

FIG. 6C shows the relative increase of fluorescent apoptosis stain (e.g., YO-PRO™-1 Iodide; Thermo Fisher) positive cells in murine 3T3 GCN2 knock out (KO) fibroblasts stably transduced with a CHOP reporter construct. Cells were treated with increasing amounts of Compound 1 (left), Compound 2 (middle), or Compound 108 (right), and 1 μM halofuginone. The increase of CHOP positive cells is expressed as a fraction of cell confluence determined by in a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

FIG. 6D shows the relative increase of fluorescent apoptosis stain (e.g., YO-PRO™-1 Iodide; Thermo Fisher) positive cells in murine 3T3 GCN2 knock out (KO) fibroblasts stably transduced with a CHOP reporter construct. Cells were treated with increasing amounts of Compound 1 (left), Compound 2 (middle), or Compound 108 (right), and 5 mM histidinol. The increase of CHOP positive cells is expressed as a fraction of cell confluence determined by in a live-cell imaging and analysis platform (e.g., IncuCyte ZOOM®; Essenbio). An untreated control (Ctrl, grey inverted triangles) was also included. The data represents the mean±SEM of three technical replicates, with three images collected per well, per time point.

EMBODIMENTS

Set 1

Figure 1A:
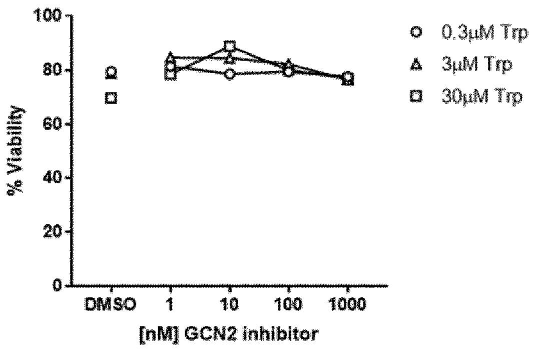
FIG. 1A shows the viability of primary CD4+ T cells treated with Compound 1, in response to tryptophan (Trp) starvation. Cell viability was assessed following five days of culture in increasing amounts of tryptophan and GCN2 inhibitor. Provided are representative results (mean) of one donor out of four associated with Compound 1.
Figure 1B:
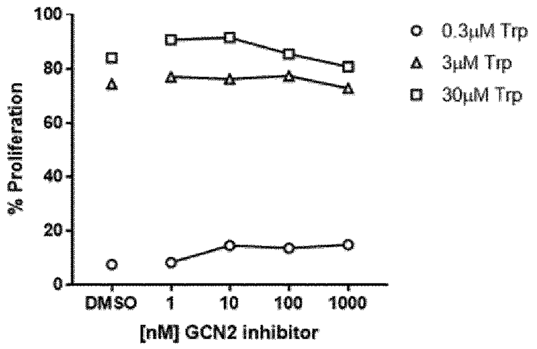
FIG. 1B shows the proliferation of primary CD4+ T cells treated with Compound 1 in response to tryptophan (Trp) starvation. Cell proliferation was assessed following five days of culture in increasing amounts of tryptophan and GCN2 inhibitor. Provided are representative results (mean) of one donor out of four associated with Compound 1.
Figure 1C:
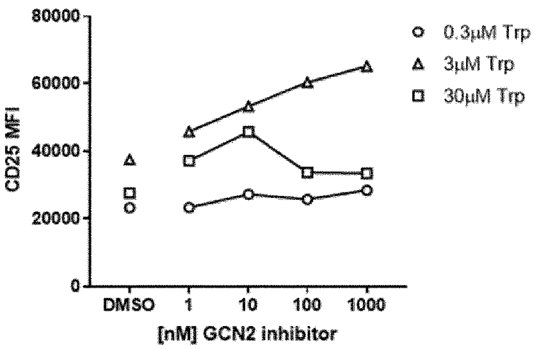
FIG. 1C shows the CD25 expression of primary CD4+ T cells treated with Compound 1 in response to tryptophan (Trp) starvation. Cell CD25 expression was assessed following five days of culture in increasing amounts of tryptophan and GCN2 inhibitor. Provided are representative results (mean) of one donor out of four associated with Compound 1. MFI is mean fluoresce intensity.
Figure 1D:
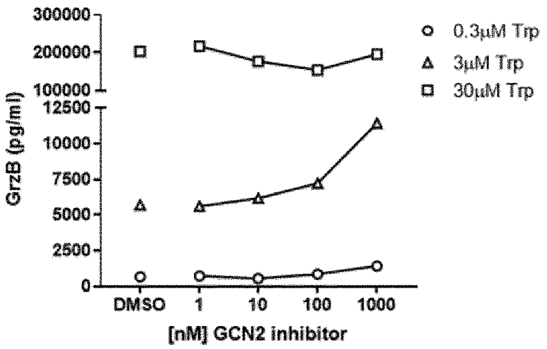
FIG. 1D shows the Granzyme B concentration in the supernatant of primary CD4+ T cells treated with Compound 1 in response to tryptophan starvation. The supernatant of cells was analysed for Granzyme B following five days of culture in increasing amounts of tryptophan and GCN2 inhibitor. Provided are representative results (mean) of one donor out of four associated with Compound 1.
Figure 1E:
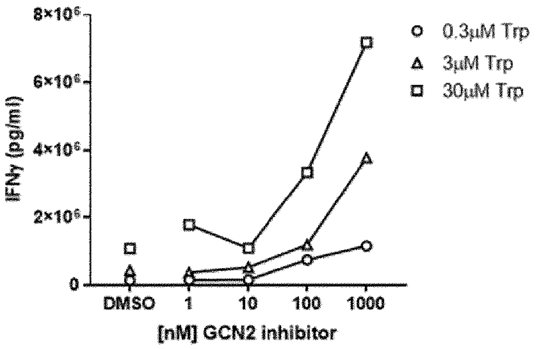
FIG. 1E shows the IFN-γ concentration in the supernatant of primary CD4+ T cells treated with Compound 1 in response to tryptophan (Trp_starvation. The supernatant of cells was analysed for IFN-γ following five days of culture in increasing amounts of tryptophan and GCN2 inhibitor. Provided are representative results (mean) of one donor out of four associated with Compound 1.
Figure 1F:
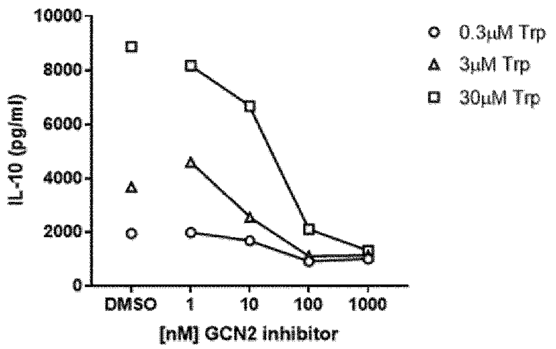
FIG. 1F shows the IL-10 concentration in the supernatant of primary CD4+ T cells treated with Compound 1 in response to tryptophan (Trp) starvation. The supernatant of cells was analysed for IL-10 following five days of culture in increasing amounts of tryptophan and GCN2 inhibitor. Provided are representative results (mean) of one donor out of four associated with Compound 1.
Figure 2A:
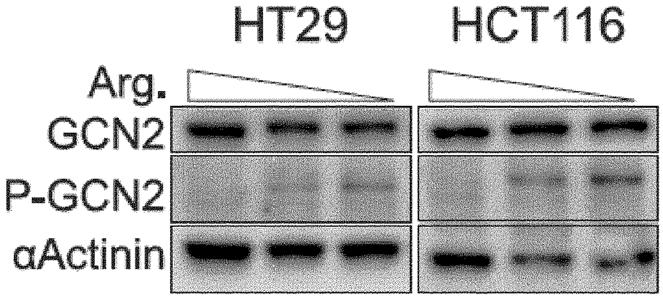
FIG. 2A shows phosphorylated GCN2 (P-GCN2) expression in colorectal cancer cell lines HT29 and HCT116. Cells were cultured in medium containing decreasing concentrations of arginine (256 μM, 64 μM, or 4 μM, respectively) for 24 hours before samples were harvested and analyzed via Western blot. Alpha-actinin was used as a loading control.
Figure 2B:
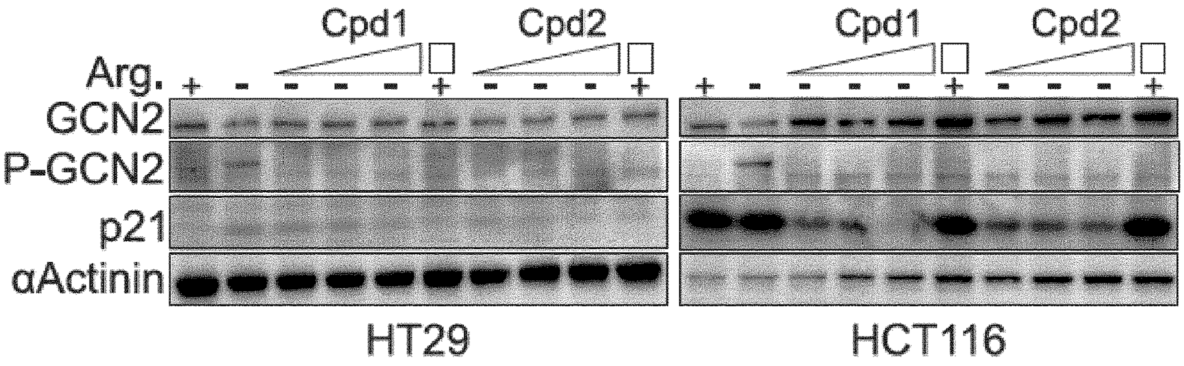
FIG. 2B shows total GCN2, phosphorylated GCN2 (P-GCN2), and p21 expression in colorectal cancer cell lines HT29 (left) and HCT116 (right). Cells were cultured in the presence (+) or absence (−) of the indicated compounds for 24 hours before samples were harvested and analyzed via Western blot. Alpha-actinin was used as a loading control.
Figure 3A:
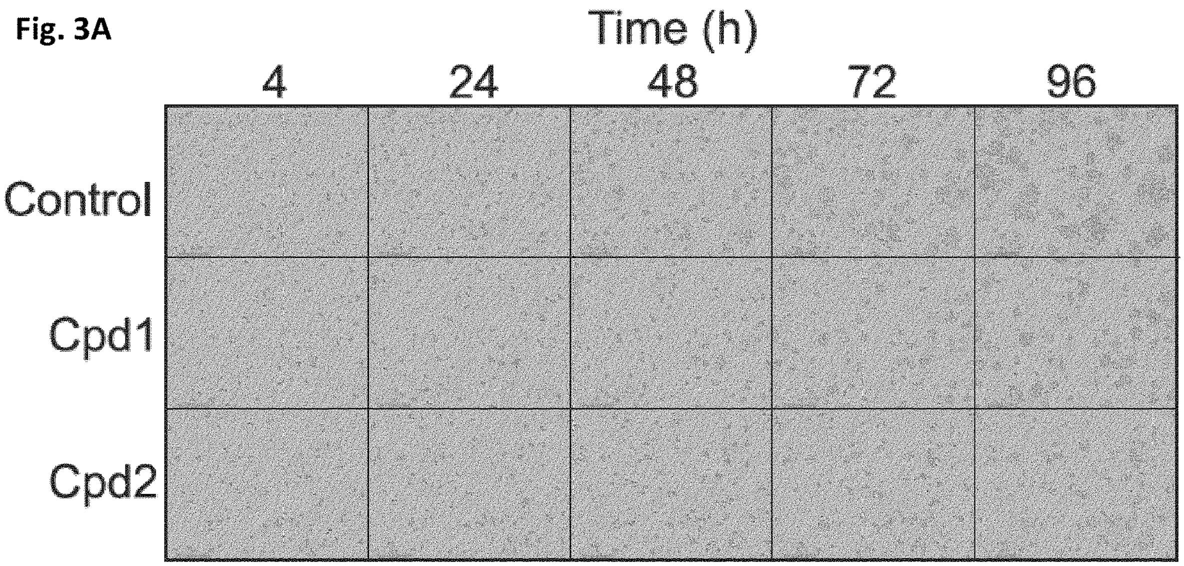
FIG. 3A shows HT29 cell density and morphology following treatment with Compound 1 or Compound 2. HT29 cells were seeded at 4,000 cells/well in 96-well flat bottom plates in media containing a physiological concentration of arginine (64 μM). After 24 hours, cells were treated with 10 μM vehicle control (Control; 0.1% DMSO), 10 μM Compound 1, or 10 μM Compound 2, in addition to 100 nM fluorescent apoptosis stain (e.g., YO-PRO™-1 Iodide; Thermo Fisher) uptake to detect apoptotic cells. The plates were placed in an live-cell imaging and analysis platform (e.g., IncuCyte ZOOM®; Essenbio), and scanned every 4 hours for up to 96 hours. Representative images at 10× magnification are shown.
Figure 3B:
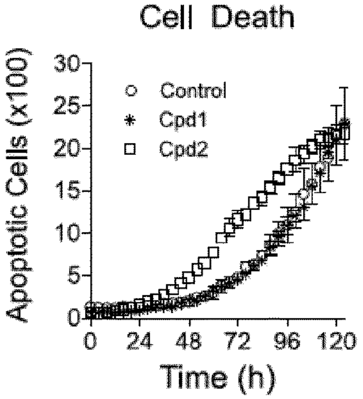
FIG. 3B shows the number of apoptotic HT29 cells, as indicated by fluorescent apoptosis stain (e.g., YO-PRO™-1 Iodide; Thermo Fisher) uptake, per well over time. Cells were treated with vehicle control (0.1% DMSO; open circles), 10 μM Compound 1 (asterisks), or 10 μM Compound 2 (open squares). Data represent the mean±SEM of three technical replicates, with three images collected per well, per time point.
Figure 3C:
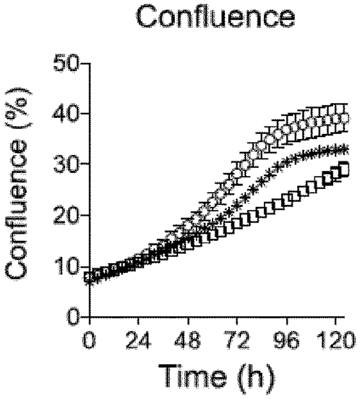
FIG. 3C shows the confluence of HT29 cells per well over time. Cells were treated with vehicle control (0.1% DMSO; open circles), 10 μM Compound 1 (asterisks) or 10 μM Compound 2 (open squares). Data represent the mean±SEM of three technical replicates, with three images collected per well, per time point.
Figure 4A:
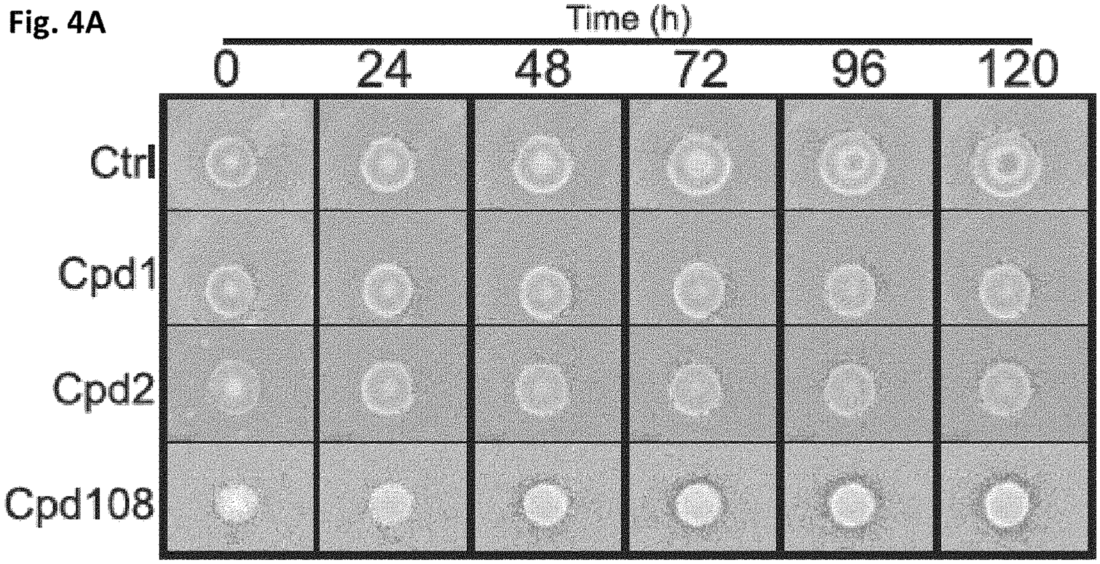
FIG. 4A shows the relative spheroid size and morphology of HT29 cells following treatment with Compound 1 or Compound 2. HT29 cells were seeded at 5,000 cells/well in 96-well ultra-low adherence round bottom plates in media containing a physiological concentration of arginine (64 μM). Spheroids were allowed to form for three days before addition of the indicated compounds (Compound 1 or Compound 2; 10 μM) or vehicle control (Ctrl; 0.1% DMSO), in addition a DNA stain to stain live cells (e.g., Nuclear ID®-Red; Enzo Life Sciences) and determine relative spheroid size. Plates were placed in a live-cell imaging and analysis platform (e.g., IncuCyte ZOOM®; Essenbio) and the plates were scanned every 4 hours for up to 120 hours. Representative images at 10× magnification are shown.
Figure 4B:
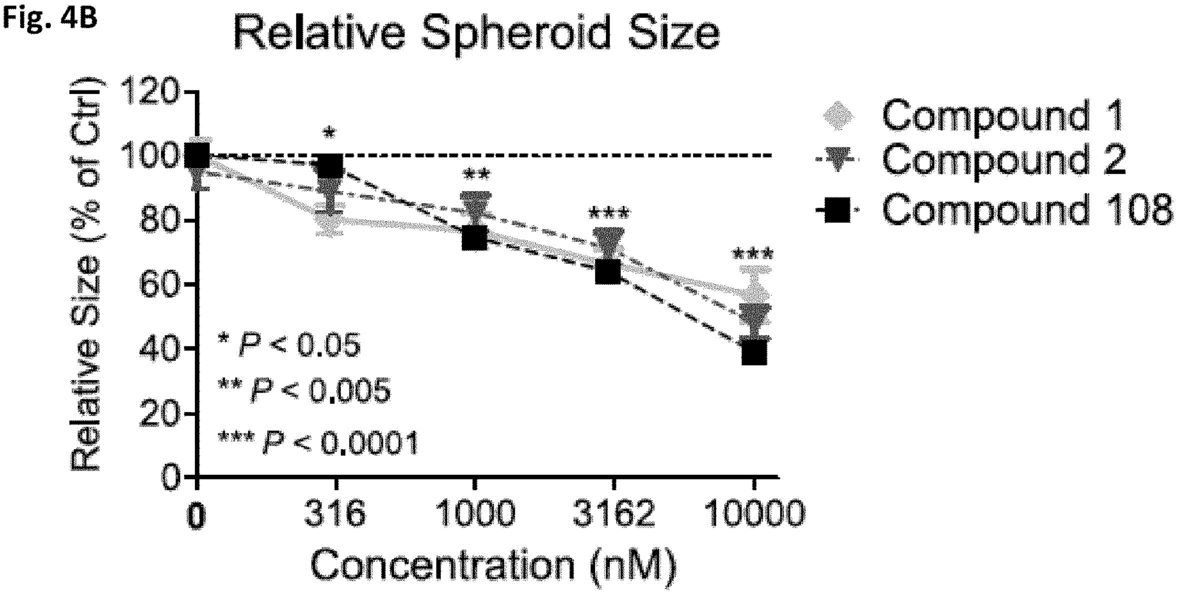
FIG. 4B shows the relative quantification of spheroid size of HT29 cells following treatment with Compound 1 (diamonds), Compound 2 (inverted triangles), or Compound 108 (squares), expressed as a percentage of the vehicle control spheroid over time. The relative quantification was calculated by determining the total surface area of DNA stained (e.g., Nuclear ID®-Red; Enzo Life Sciences) cells. Data represent the mean±SEM of three individual experiments performed in quadruplicate. A student's t-test was performed for each time point to determine whether each compound had a significant effect on spheroid size relative to the vehicle control-treated spheroids (set at 100%, as indicated by the dotted line).
Figure 7A:
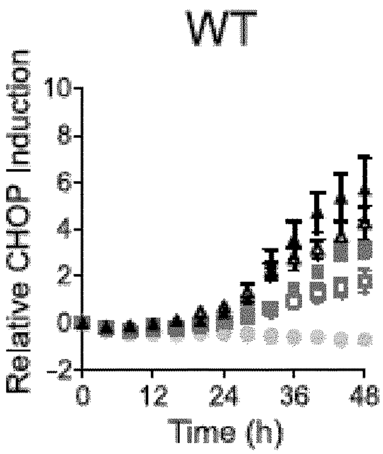
FIG. 7A shows CHOP induction by tunicamycin treatment in murine 3T3 wildtype (WT) fibroblasts stably transduced with a CHOP reporter construct. WT 3T3 cells were either treated with vehicle control (circles; ○/●), 3 nM tunicamycin (squares; □/■) or 10 nM tunicamycin (triangles; Δ/▲), after 24 h pre-treatment with vehicle (open symbols) or 1 μM Compound 1 (closed symbols). The data represents the mean±SEM of three technical replicates, with three images collected per well, per time point.
Figure 7B:
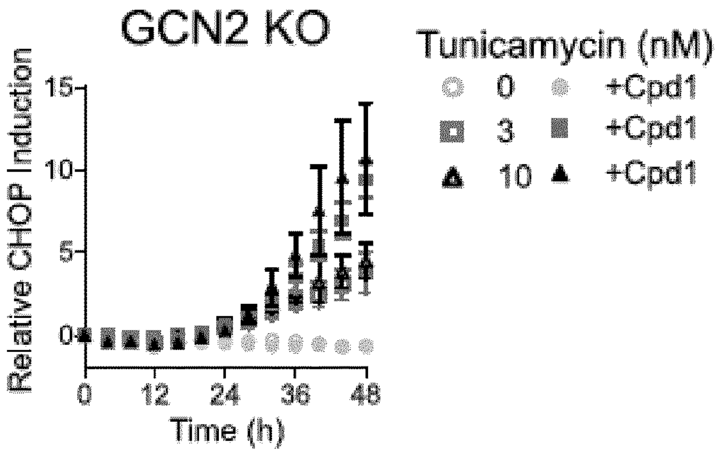
FIG. 7B shows CHOP induction by tunicamycin treatment in murine 3T3 GCN2 knock out (KO) cells stably transduced with a CHOP reporter construct. KO 3T3 cells were either treated with vehicle control (circles; ○/●), 3 nM tunicamycin (squares; □/■) or 10 nM tunicamycin (triangles; Δ/▲), after 24 h pre-treatment with vehicle (open symbols) or 1 μM Compound 1 (closed symbols). The data represents the mean±SEM of three technical replicates, with three images collected per well, per time point.

Embodiment 1. A compound according to Formula (1):

(1)

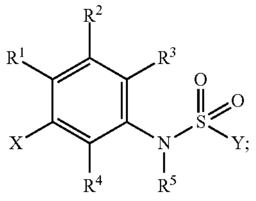

or a salt thereof, wherein;

X is an optionally substituted 9 or 10-membered fused heterobicyclic ring system comprising 1-4 N heteroatoms;

Y is an optionally substituted 6-membered carbocyclic or heterocyclic ring; or $NH_2$;

$R^1$, $R^2$ and $R^3$ are independently selected from H, halo and $C_{1-3}$ alkyl optionally substituted with 1-6 fluorine atoms;

$R^4$ is selected from H, halo and $C_{1-3}$ alkyl optionally substituted with 1-6 fluorine atoms; or is joined to $R^5$ to form an optionally substituted ring;

$R^5$ is selected from H and $C_{1-3}$ alkyl optionally substituted with 1-6 fluorine atoms; or is joined to $R^4$ to form an optionally substituted ring.

Embodiment 2. The compound according to embodiment 1, wherein X is selected from the group consisting of:

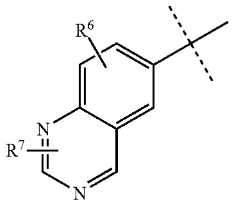
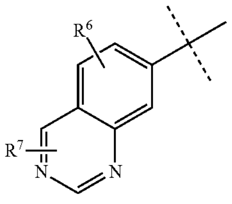
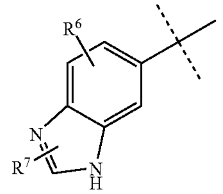
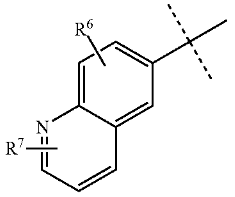
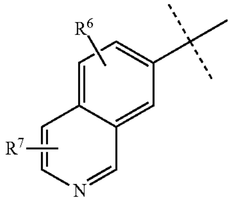
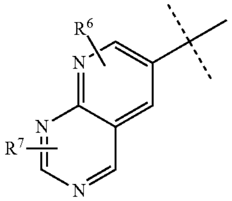
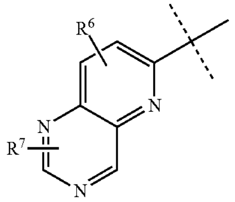
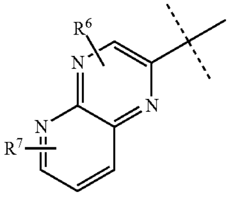
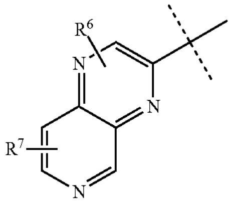
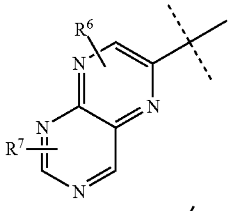
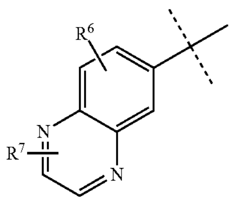
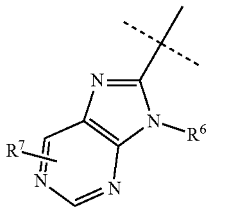

-continued

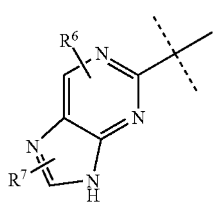

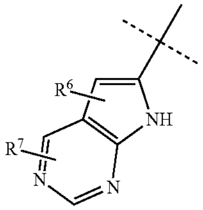

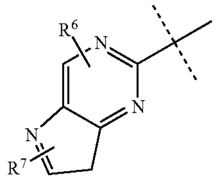

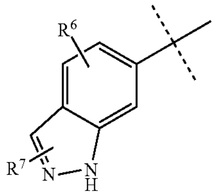

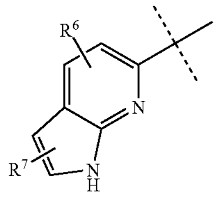

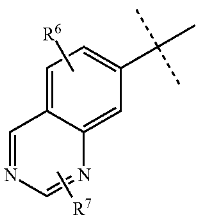

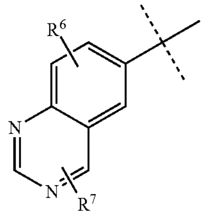

wherein $R^6$ and $R^7$ may be attached at any available position of the bicyclic ring system and are independently selected from H, $NR^8R^9$ and halo;

wherein $R^8$ and $R^9$ are independently selected from H and $C_{1-6}$ alkyl optionally substituted with 1 to 6 fluorine atoms or optionally substituted with OH.

Embodiment 3. The compound according to embodiment 2, wherein $R^6$ and $R^7$ are independently selected from: H, $NH_2$, $NHCH_3$, F, $NHCH_2CH_2OH$, $NHCH(CH_3)CH_2OH$ and

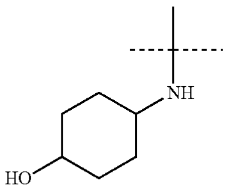

Embodiment 4. The compound according to embodiment 2, wherein $R^6$ is H and $R^7$ is $NH_2$.

Embodiment 5. The compound according to embodiment 1, wherein X is selected from the group consisting of:

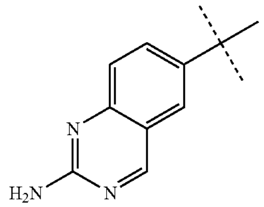

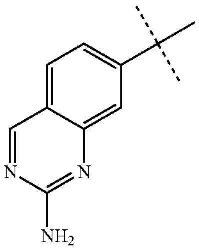

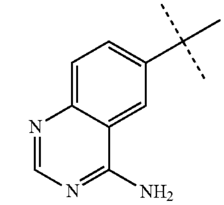

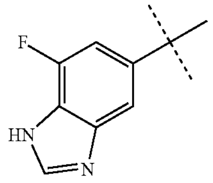

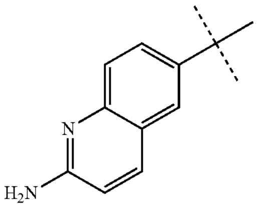

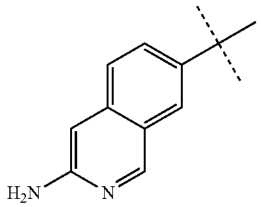

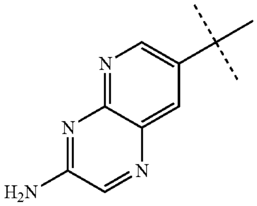

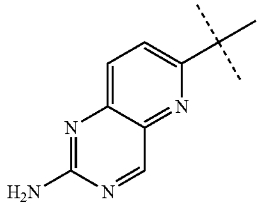

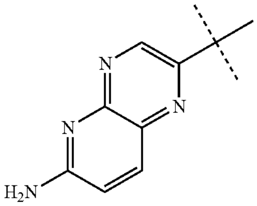

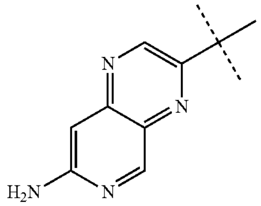

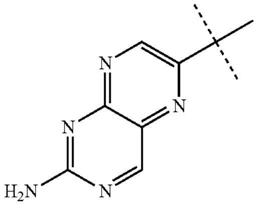

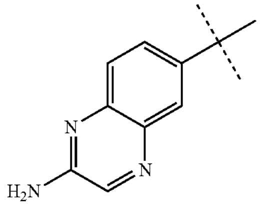

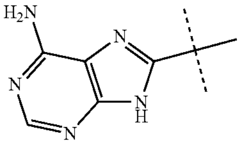

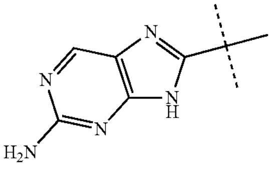

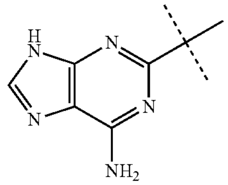

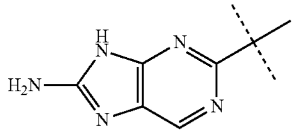

-continued

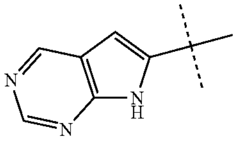

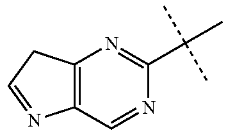

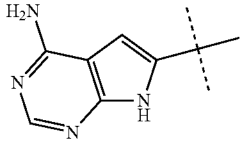

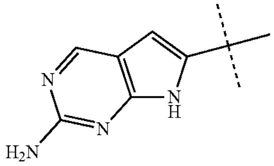

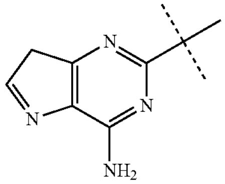

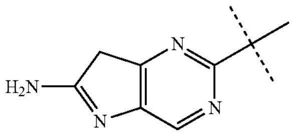

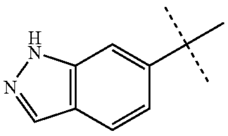

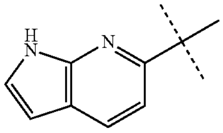

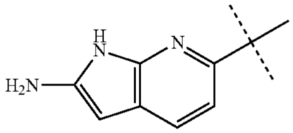

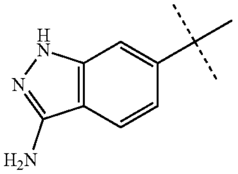

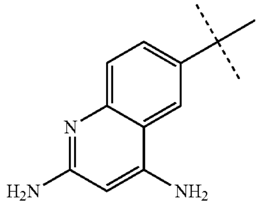

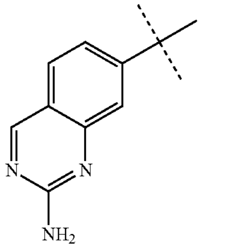

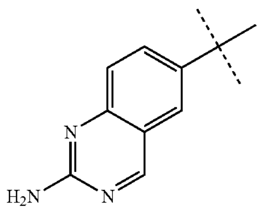

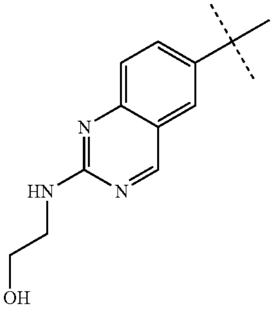

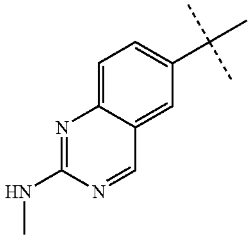

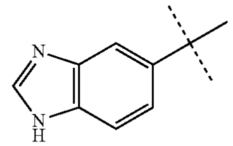

-continued

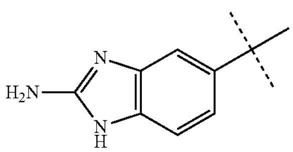

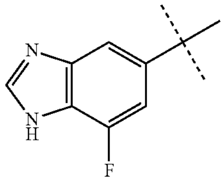

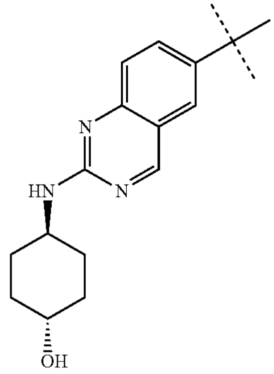

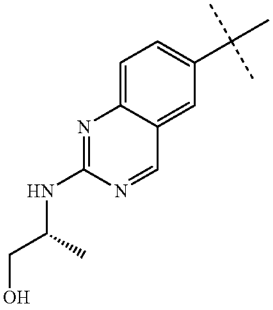

Embodiment 6. The compound according to embodiment 1, which is a compound of formula (2):

(2)

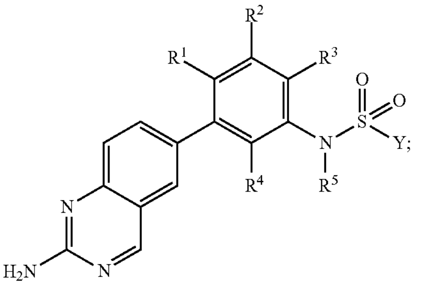

or a salt thereof.

Embodiment 7. The compound according to any one of embodiments 1 to 6, wherein Y is selected from: an optionally substituted phenyl ring, an optionally substituted pyridyl ring, an optionally substituted cyclohexane ring, an optionally substituted piperidine ring, an optionally substituted piperazine ring, an optionally substituted tetrahydropyran ring, an optionally substituted thiane ring, an optionally substituted morpholine ring and an optionally substituted thiomorpholine ring;

wherein the optional substituents are the groups $R^{10}$, $R^{11}$ and $R^{12}$ which are themselves independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$; wherein $R^{13}$ and $R^{14}$ are independently H or $C_{1-3}$ alkyl.

Embodiment 8. The compound according to embodiment 7, wherein Y is a group of formula:

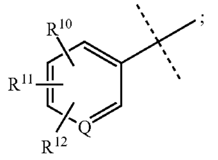

wherein Q is C or N.

Embodiment 9. The compound according to embodiment 1, which is a compound of formula (3):

(3)

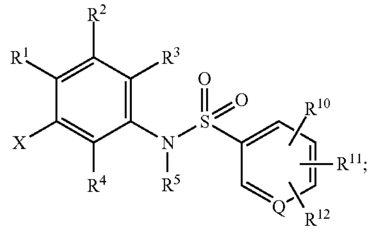

or a salt thereof, wherein;

Q is C or N;

$R^{10}$, $R^{11}$ and $R^{12}$ are independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$;

wherein $R^{13}$ and $R^{14}$ are independently H or $C_{1-3}$ alkyl.

Embodiment 10. The compound according to embodiment 1, which is a compound of formula (3a):

(3a)

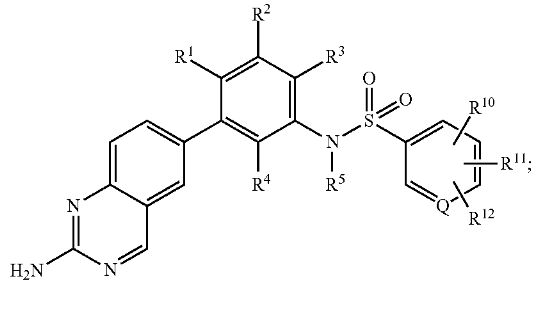

or a salt thereof, wherein;

Q is C or N;

$R^{10}$, $R^{11}$ and $R^{12}$ are independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$;

wherein $R^{13}$ and $R^{14}$ are independently H or $C_{1-3}$ alkyl.

Embodiment 11. The compound according to any one of embodiments 7 to 10, wherein $R^{10}$, $R^{11}$ and $R^{12}$ are independently selected from the group consisting of: H, Cl, F, $OCH_3$, $CF_3$, $CH_3$, $CH_2OH$, OH, $CONH_2$, COOH, $CONHCH_3$ and $COOCH_3$.

Embodiment 12. The compound according to any one of embodiments 1 to 7, wherein Y is selected from the group consisting of:

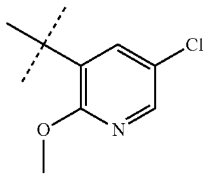
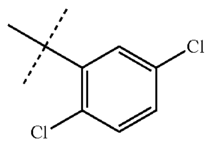
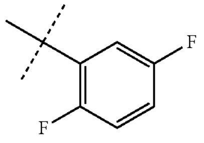
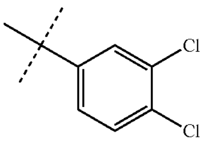
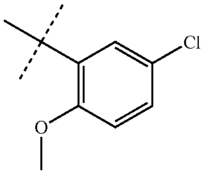
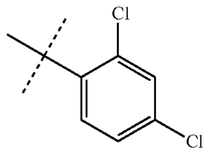
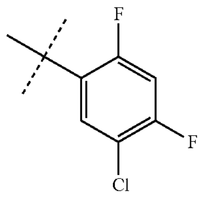
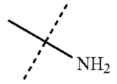
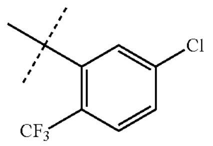
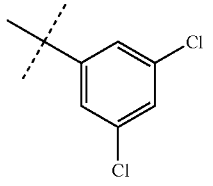
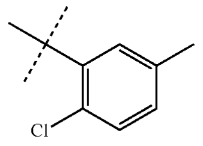
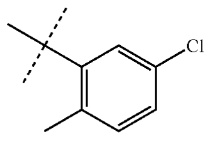
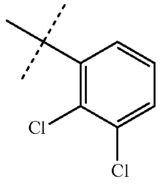
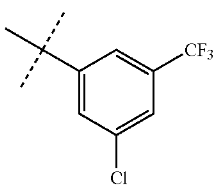
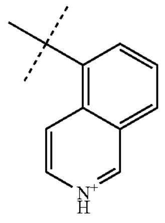
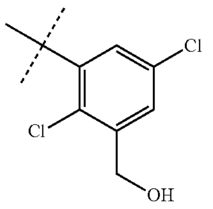
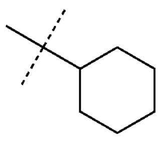
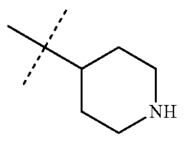
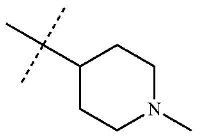
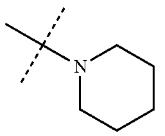
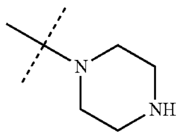

-continued

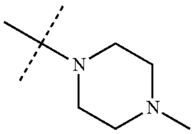
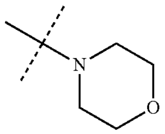
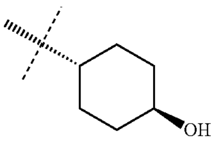
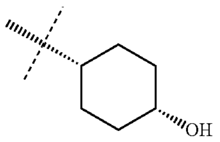
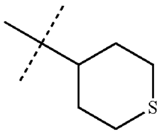
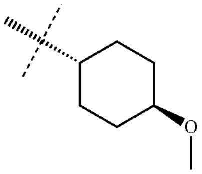
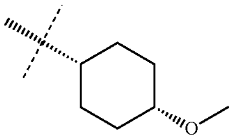
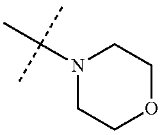
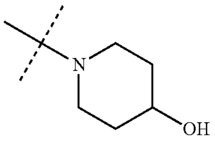
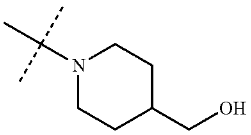
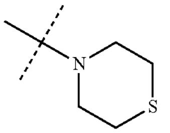
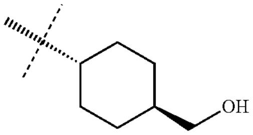
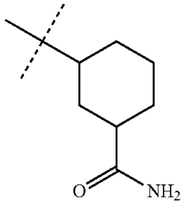
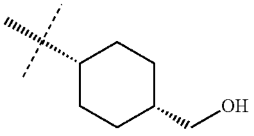
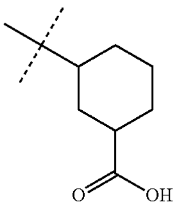
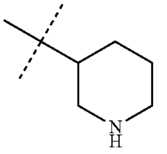
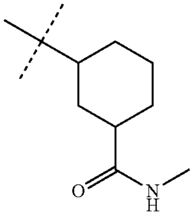
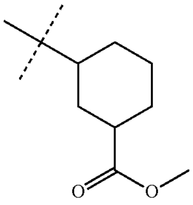
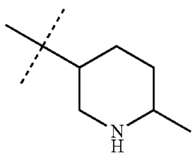

Embodiment 13. The compound according to embodiment 12, wherein Y is:

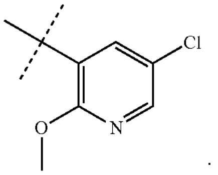

Embodiment 14. The compound according to any one of embodiments 1 to 13, wherein $R^1$, $R^2$, $R^3$ and $R^4$ are independently selected from H, F and $CH_3$.

Embodiment 15. The compound according to embodiment 14, wherein $R^1$ and $R^4$ are F and $R^2$ and $R^3$ are H.

Embodiment 16. The compound according to any one of embodiments 1 to 15, wherein $R^5$ is H.

Embodiment 17. The compound according to embodiment 1 which is a compound of formula (4):

(4)

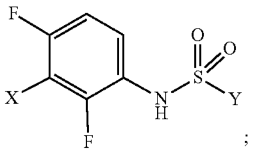

;

or a salt thereof.

Embodiment 18. The compound according to embodiment 1 which is a compound of formula (4a):

(4a)

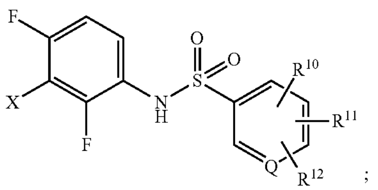

;

or a salt thereof, wherein;

Q is C or N;

$R^{10}$, $R^{11}$ and $R^{12}$ are independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$;

wherein $R^{13}$ and $R^{14}$ are independently H or $C_{1-3}$ alkyl.

Embodiment 19. The compound according to embodiment 1 which is a compound of formula (4b):

(4b)

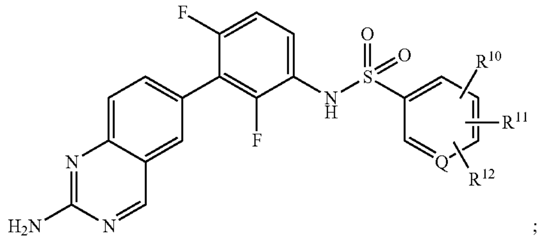

;

or a salt thereof, wherein;

Q is C or N;

$R^{10}$, $R^{11}$ and $R^{12}$ are independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$;

wherein $R^{13}$ and $R^{14}$ are independently H or $C_{1-3}$ alkyl.

Embodiment 20. The compound according to any one of embodiments 1 to 13, wherein $R^1$, $R^2$ and $R^3$ are independently selected from H, F and $CH_3$ and $R^4$ is joined to $R^5$ to form a ring.

Embodiment 21. The compound according to embodiment 1 which is a compound of formula (5) or (5a):

(5)

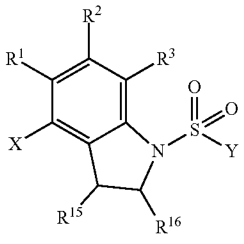

;

(5a)

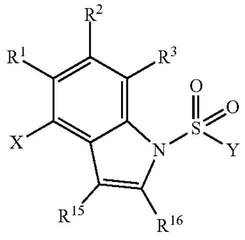

;

or a salt thereof; wherein;

$R^{15}$ and $R^{16}$ are independently selected from H, halo and $C_{1-3}$ alkyl optionally substituted with 1 to 6 fluorine atoms.

Embodiment 22. The compound according to embodiment 1 which is a compound of formula (5b) or (5c):

(5b)

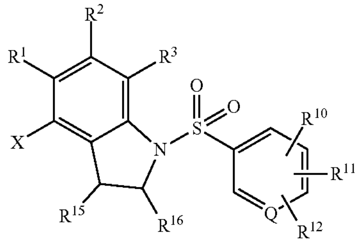

;

(5c)

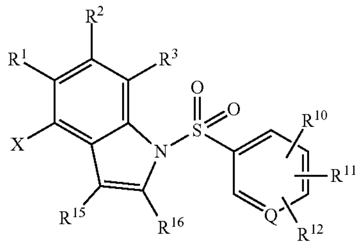

;

or a salt thereof, wherein;

Q is C or N;

$R^{10}$, $R^{11}$ and $R^{12}$ are independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$;

wherein $R^{13}$ and $R^{14}$ are independently H or $C_{1-3}$ alkyl;

and $R^{15}$ and $R^{16}$ are independently selected from H, halo and $C_{1-3}$ alkyl optionally substituted with 1 to 6 fluorine atoms.

Embodiment 23. The compound according to embodiment 1 which is a compound of formula (5d) or (5e):

(5d)

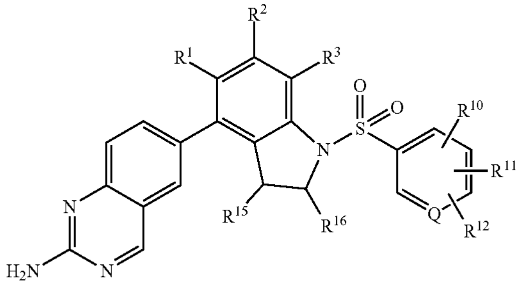

;

-continued (5e)

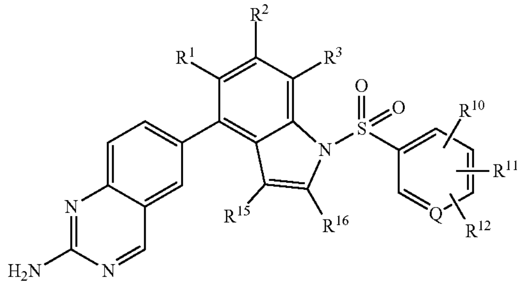

;

or a salt thereof, wherein;

Q is C or N;

$R^{10}$, $R^{11}$ and $R^{12}$ are independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$;

wherein $R^{13}$ and $R^{14}$ are independently H or $C_{1-3}$ alkyl;

and $R^{15}$ and $R^{16}$ are independently selected from H, halo and $C_{1-3}$ alkyl optionally substituted with 1 to 6 fluorine atoms.

Embodiment 24. A pharmaceutically acceptable salt of a compound according to any one of embodiments 1 to 23.

Embodiment 25. A pharmaceutical composition comprising a compound as defined in any one of embodiments 1 to 24 and a pharmaceutically acceptable excipient.

Embodiment 26. The compound or composition according to any one of embodiments 1 to 25 for use in the treatment of a disease or disorder characterised by activation of GCN2.

Embodiment 27. The compound or composition according to any one of embodiments 1 to 25 for use in the treatment of cancer, a neurodegenerative disease, or chronic infections.

Embodiment 28. The compound or composition according to any one of embodiments 1 to 25 for use in the treatment of cancer.

Embodiment 29. The compound or composition for use according to embodiment 28, wherein the cancer is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, adenocarcinoma, hepatocellular carcinoma, thyroid cancer, multiple myeloma, cancer of secretory cells, myelodysplastic syndrome, myeloproliferative neoplasm, malignant glioma, non-Hodgkin's lymphoma, Hodgkin's lymphoma, Burkitt's lymphoma, chronic lymphocytic leukemia, chronic myeloid leukemia, hairy cell leukemia, monoclonal gammopathy of undetermined significance (MGUS), plasmacytoma, lymphoplasmacytic lymphoma, acute lymphoblastic leukemia, acute myeloid leukemia, chronic myelomonocytic leukemia, juvenile myelomonocytic leukemia, large granular lymphocytic leukemia, B-cell prolymphocytic leukemia, T-cell prolymphocytic leukemia. small cell lung cancer, malignant pleural mesothelioma, Head and neck squamous cell carcinoma, glioblastoma multiforme, sarcoma or pediatric neuroblastoma.

Embodiment 30. The compound or composition for use according to any one of embodiments 26 to 29, wherein the compound or composition is administered in combination with a second therapeutic agent.

Embodiment 31. The compound or composition for use according to embodiment 30, wherein the second therapeutic agent is PEG-arginase, asparaginase, anti-angiogenic factors, cysteinase or sulfasalazine.

Set 2

Clause 1. A compound according to Formula (3):

(3)

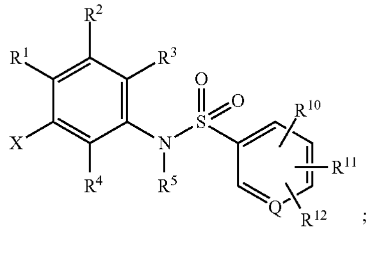

;

or a salt thereof, wherein;

Q is C or N;

$R^1$, $R^2$ and $R^3$ are independently selected from H, halo and $C_{1-3}$ alkyl optionally substituted with 1-6 fluorine atoms;

$R^4$ is selected from H, halo and $C_{1-3}$ alkyl optionally substituted with 1-6 fluorine atoms; or is joined to $R^5$ to form an optionally substituted ring;

$R^5$ is selected from H and $C_{1-3}$ alkyl optionally substituted with 1-6 fluorine atoms; or is joined to $R^4$ to form an optionally substituted ring;

$R^{10}$, $R^{11}$ and $R^{12}$ are independently selected from the group consisting of: H, halo, CN, $C_{1-6}$ alkyl optionally substituted with 1 to 6 fluorine atoms or optionally substituted with OH, $C_{1-6}$ alkoxy optionally substituted with 1 to 6 fluorine atoms, $CONR^{13}R^{14}$, $NR^{13}COR^{14}$ and $COOR^{13}$;

wherein $R^{13}$ and $R^{14}$ are independently H or $C_{1-3}$ alkyl;

X is selected from the group consisting of:

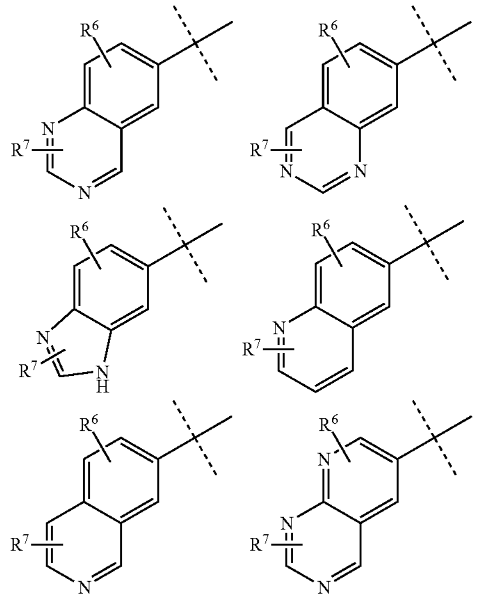

-continued

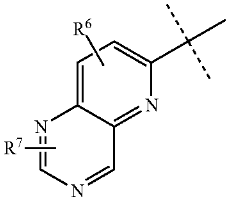
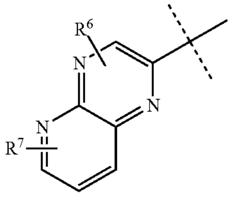
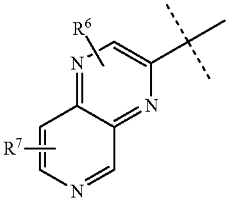
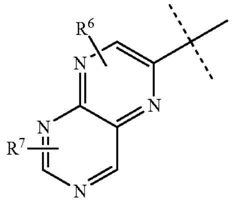
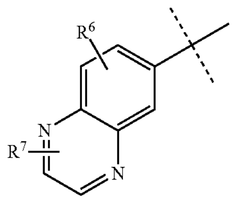
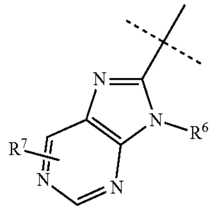
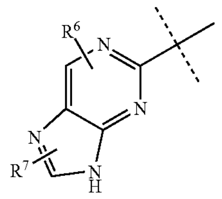
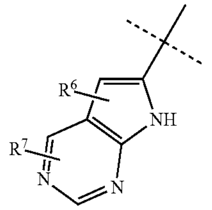
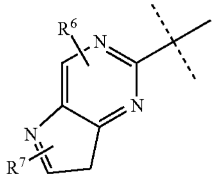
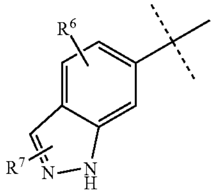
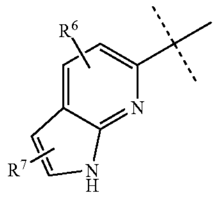
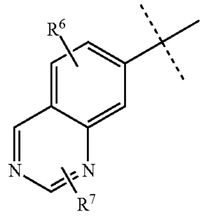
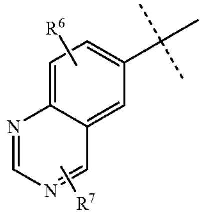

wherein $R^6$ and $R^7$ may be attached at any available position of the bicyclic ring system and are independently selected from H, $NR^8R^9$ and halo;

wherein $R^8$ and $R^9$ are independently selected from H, $C_{1-6}$ alkyl optionally substituted with 1 to 6 fluorine atoms or optionally substituted with OH and —C(O)—$C_{1-6}$ alkyl optionally substituted with 1 to 6 fluorine atoms or optionally substituted with OH.

Clause 2. The compound according to clause 1, wherein X is:

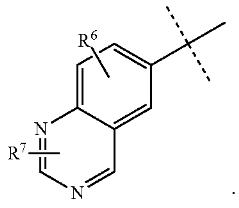

Clause 3. The compound according to clause 1 or clause 2, wherein $R^6$ and $R^7$ are independently selected from: H, $NH_2$, $NHCH_3$, F, $NHCH_2CH_2OH$, $NHCH(CH_3)CH_2OH$, $NHCOCH_3$, $NHCOCH_2CH_3$, $NHCOCH(CH_3)_2$, $NHCOC(CH_3)_3$ and

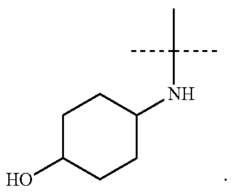

Clause 4. The compound according to clause 1 or clause 2, wherein $R^6$ is H and $R^7$ is $NH_2$.

Clause 5. The compound according to clause 1, wherein X is selected from the group consisting of:

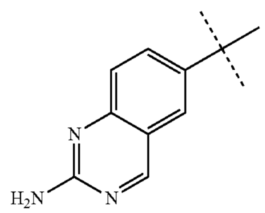
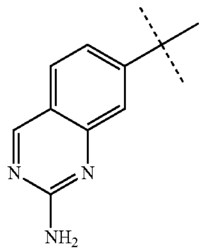
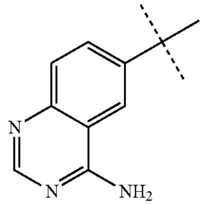
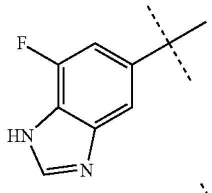
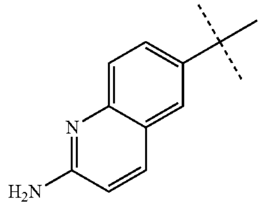
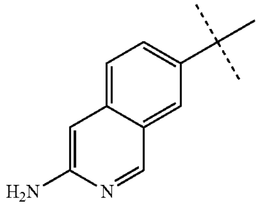
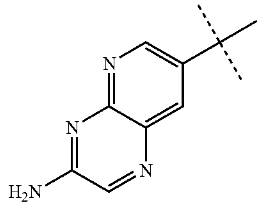
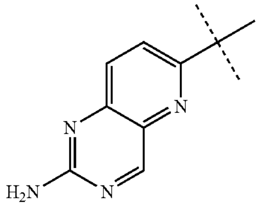

-continued
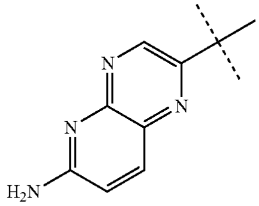
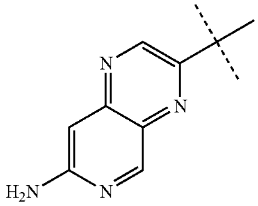
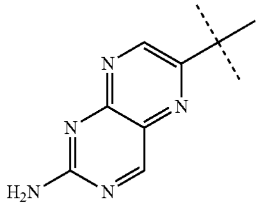
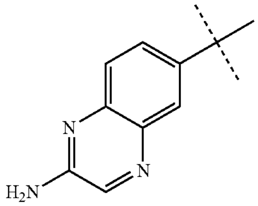
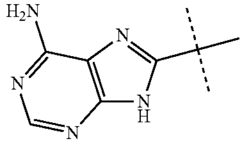
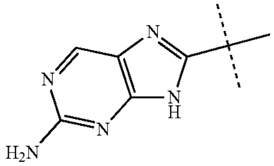
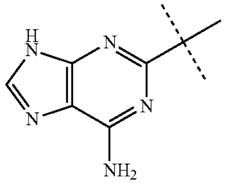
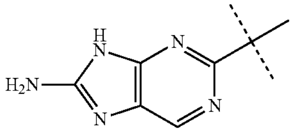
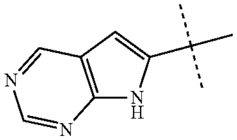
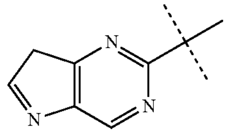
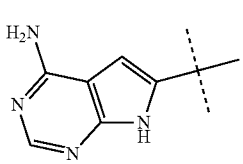
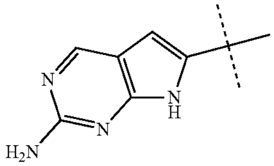
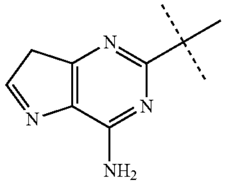
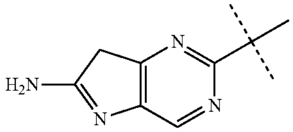
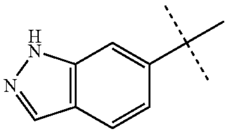
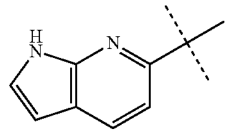
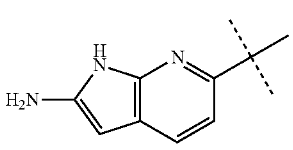
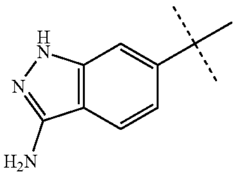
-continued
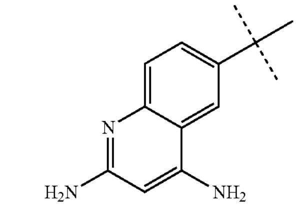
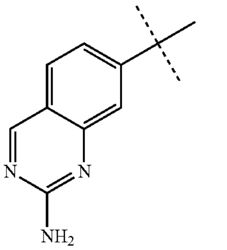
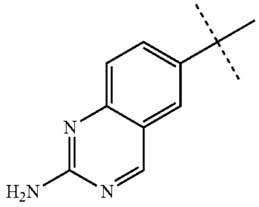
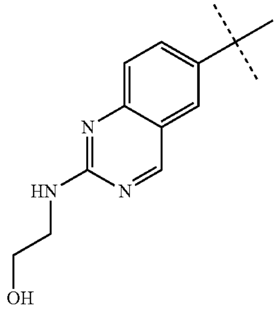
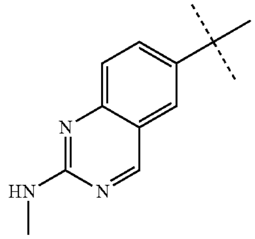
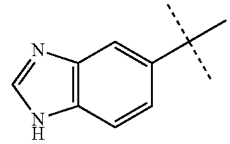
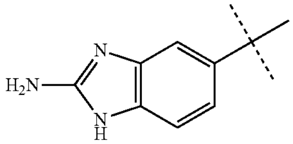
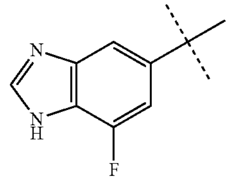
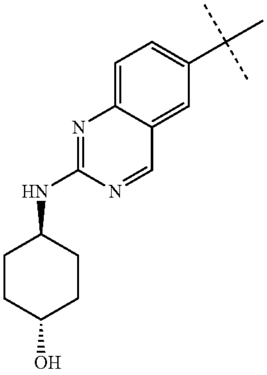
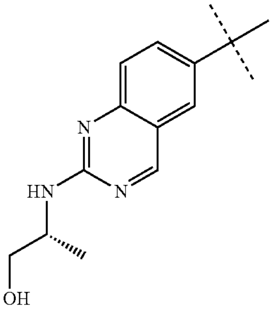
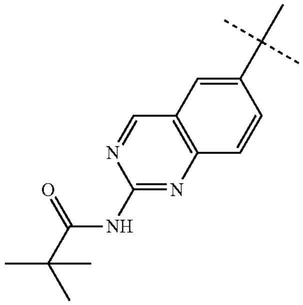
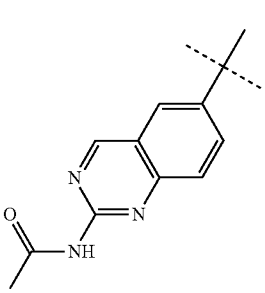

Clause 6. The compound according to clause 1, which is a compound of formula (3a):

(3a)

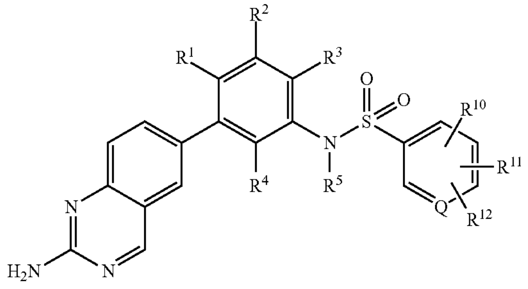

;

or a salt thereof.

Clause 7. The compound according to any one of clauses 1 to 6, wherein $R^{10}$, $R^{11}$ and $R^{12}$ are independently selected from the group consisting of: H, Cl, F, $OCH_3$, $CF_3$, $CH_3$, $CH_2OH$, OH, $CONH_2$, COOH, $CONHCH_3$ and $COOCH_3$.

Clause 8. The compound according to any one of clauses 1 to 7, wherein Q is N.

Clause 9. The compound according to any one of clauses 1 to 6, wherein the moiety:

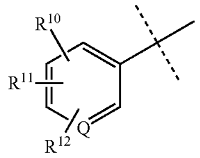

is selected from the group consisting of:

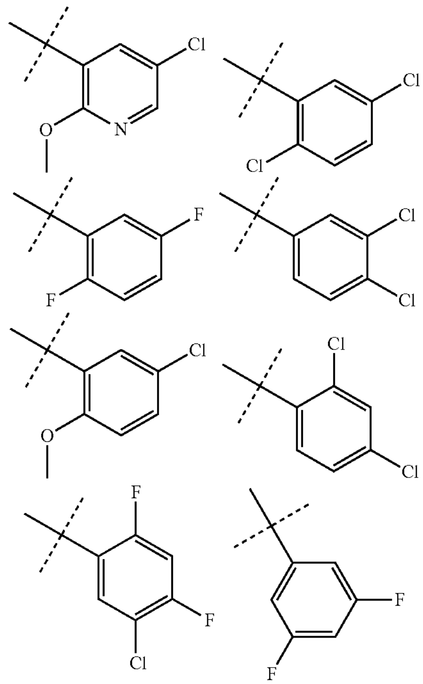

-continued

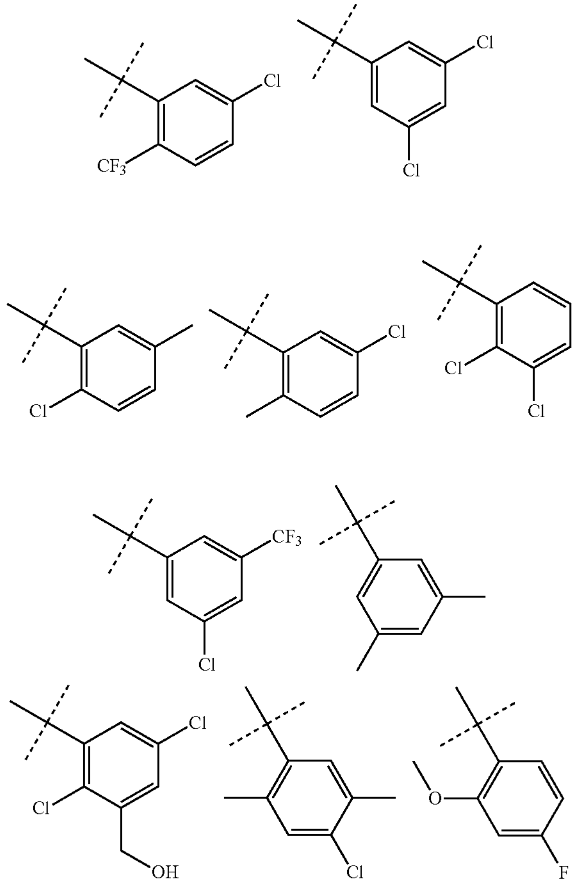

Clause 10. The compound according to clause 9, wherein the moiety:

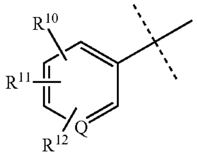

is:

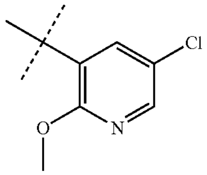

.

Clause 11. The compound according to any one of clauses 1 to 10, wherein $R^1$, $R^2$, $R^3$ and $R^4$ are independently selected from H, F and $CH_3$.

Clause 12. The compound according to clause 11, wherein $R^1$ and $R^4$ are F and $R^2$ and $R^3$ are H.

Clause 13. The compound according to any one of clauses 1 to 12, wherein $R^5$ is H.

Clause 14. The compound according to clause 1 which is a compound of formula (4a):

(4a)

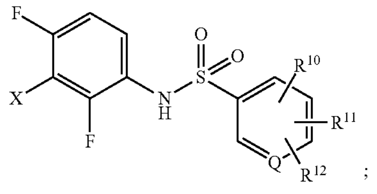

or a salt thereof.

Clause 15. The compound according to clause 1 which is a compound of formula (4b):

(4b)

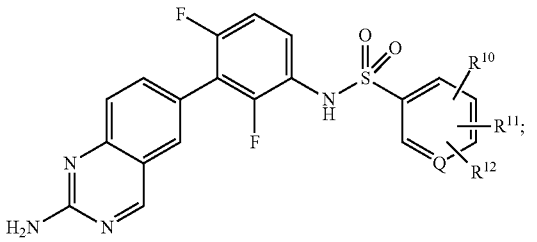

or a salt thereof.

Clause 16. The compound according to clause 1 which is a compound of formula (5b) or (5c):

(5b)

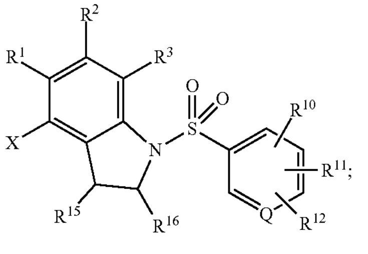

(5c)

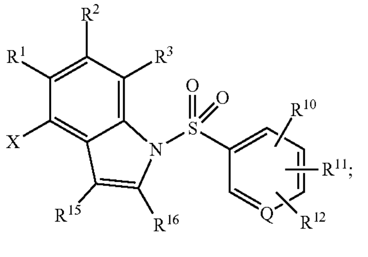

or a salt thereof.

Clause 17. The compound according to clause 1 which is a compound of formula (5d) or (5e):

(5d)

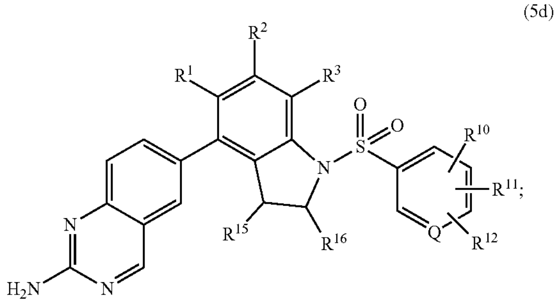

(5e)

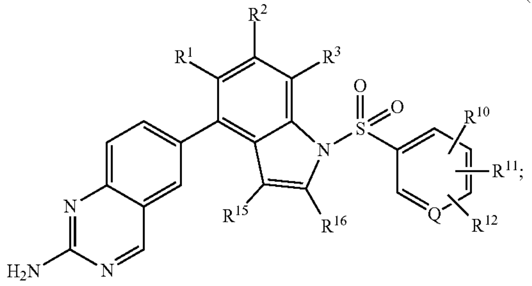

or a salt thereof.

Clause 18. A pharmaceutically acceptable salt of a compound according to any one of clauses 1 to 17.

Clause 19. A pharmaceutical composition comprising a compound as defined in any one of clauses 1 to 18 and a pharmaceutically acceptable excipient.

Clause 20. The compound or composition according to any one of clauses 1 to 19 for use in the treatment of a disease or disorder characterised by activation of GCN2.

Clause 21. The compound or composition according to any one of clauses 1 to 20 for use in the treatment of cancer, a neurodegenerative disease, or chronic infections.

Clause 22. The compound or composition according to any one of clauses 1 to 20 for use in the treatment of cancer.

Clause 23. The compound or composition for use according to clause 22, wherein the cancer is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, adenocarcinoma, hepatocellular carcinoma, thyroid cancer, multiple myeloma, cancer of secretory cells, myelodysplastic syndrome, myeloproliferative neoplasm, malignant glioma, non-Hodgkin's lymphoma, Hodgkin's lymphoma, Burkitt's lymphoma, chronic lymphocytic leukemia, chronic myeloid leukemia, hairy cell leukemia, monoclonal gammopathy of undetermined significance (MGUS), plasmacytoma, lymphoplasmacytic lymphoma, acute lymphoblastic leukemia, acute myeloid leukemia, chronic myelomonocytic leukemia, juvenile myelomonocytic leukemia, large granular lymphocytic leukemia, B-cell prolymphocytic leukemia, T-cell prolymphocytic leukemia. small cell lung cancer, malignant pleural mesothelioma, Head and neck squamous cell carcinoma, glioblastoma multiforme, sarcoma or pediatric neuroblastoma.

Clause 24. The compound or composition for use according to any one of clauses 20 to 23, wherein the compound or composition is administered in combination with a second therapeutic agent, wherein the second therapeutic agent is PEG-arginase, asparaginase, anti-angiogenic factors, cysteinase or sulfasalazine.

The invention claimed is:

1. A compound according to Formula (I):

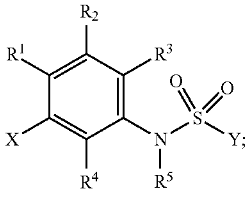

(1)

or a salt thereof, wherein;

$R^1$, $R^2$, $R^3$ and $R^4$ are independently selected from the group consisting of H, halo and $C_{1-3}$ alkyl optionally substituted with 1-6 fluoro, wherein at least one of $R^1$, $R^2$, $R^3$, and $R^4$is halo or $C_{1-3}$ alkyl optionally substituted with 1-6 fluoro, or $R^4$ is joined to $R^5$ to form 5 or 6-membered heterocyclic ring, wherein the 5 or 6-membered heterocyclic ring is optionally substituted with halo and $C_{1-3}$ alkyl optionally substituted with 1-6 fluoro;

$R^5$ is selected from the group consisting of H and $C_{1-3}$ alkyl optionally substituted with 1-6 fluoro;

X is a 9 or 10-membered fused heterobicyclic ring comprising 1-4 annular heteroatoms being nitrogen, wherein the 9 or 10-membered fused heterobicyclic ring is substituted with $NR^8R^9$ and optionally further substituted with halo, $C_{1-3}$ alkyl or $NH_2$;

$R^8$ and $R^9$ are independently selected from the group consisting of H, $C_{1-6}$ alkyl, —C(O)$NH_2$, —C(O)—$C_{1-6}$ alkyl, and 5 or 6-membered carbocyclic or heterocyclic ring, wherein the $C_{1-6}$ alkyl, —C(O)—$C_{1-6}$ alkyl, and 5 or 6-membered carbocyclic or heterocyclic ring are independently optionally substituted with 1-6 substituents selected from the group consisting halo, OH and phenyl, or $R^8$ and $R^9$ taken together with the nitrogen form a 6-membered heterocyclic ring;

Y is a 5, 6, 9 or 10-membered carbocyclic or heterocyclic ring; or $NH_2$, wherein the 5, 6, 9 or 10-membered carbocyclic or heterocyclic ring is optionally substituted with 1-3 substituents selected from the group consisting of halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH;

$R^{13}$ and $R^{14}$ are independently H or $C_{1-3}$ alkyl; and provided that when X is a 9-membered fused heterobicyclic ring comprising 1-4 annular heteroatoms being nitrogen, then the 9 membered fused heterobicyclic ring is substituted with $NR^8R^9$ only, and Y is a 6-membered heterocyclic ring comprising 1-4 annular heteroatoms being nitrogen, wherein the 6-membered heterocyclic ring is optionally substituted with 1-3 substituents selected from the group consisting of halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH; and when X is a 10-membered fused heterobicyclic ring comprising 1-4 annular heteroatoms being nitrogen, wherein the 10 membered fused heterobicyclic ring is substituted with $NH_2$ only, one of $R^1$, $R^2$, $R^3$ and $R^4$ is halo or $C_{1-3}$ alkyl, the remainder of $R^1$, $R^2$, $R^3$ and $R^4$ are H, $R^5$ is H, and Y is 5 or 6-membered carbocyclic or heterocyclic ring, then the 5 or 6-membered carbocyclic or heterocyclic ring is substituted with 2 or 3 substituents selected from the group consisting of halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH.

2. The compound of claim 1, wherein X is selected from the group consisting of:

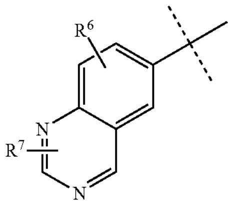,
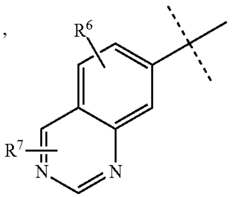,
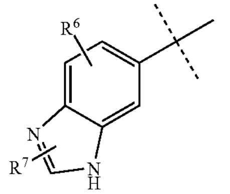,
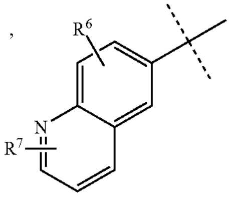,
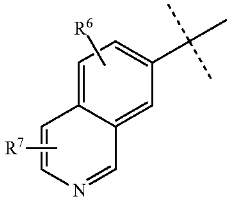,
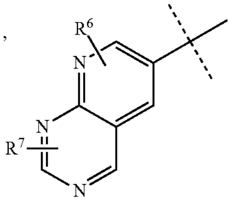,
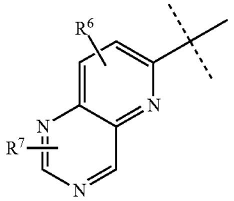,
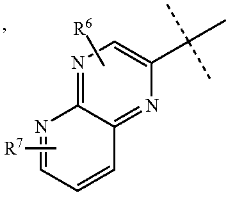,
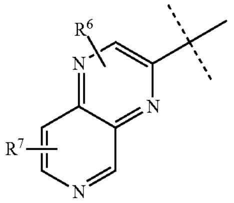,
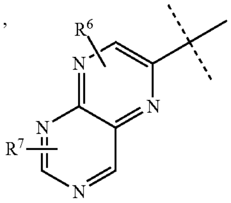,
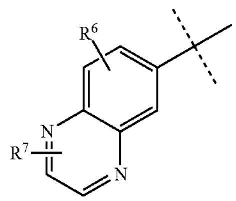,
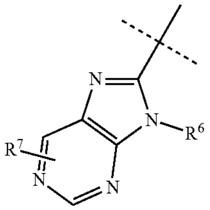, -continued

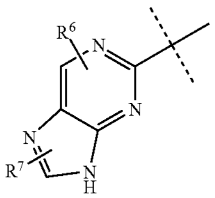
,
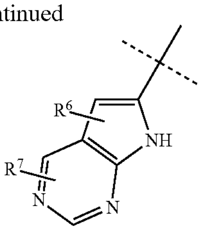
,
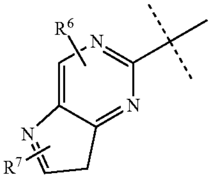
,
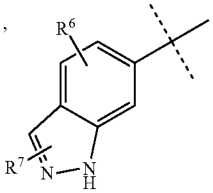
,
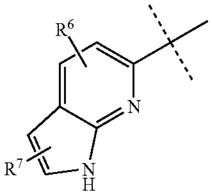
,
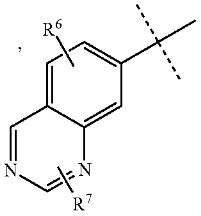
, and
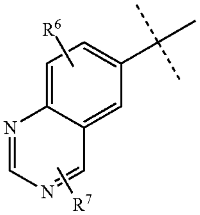
.

wherein $R^6$ and $R^7$ may be attached at any available position of the heterobicyclic ring, one of $R^6$ and $R^7$ is $NR^8R^9$ and the other is H, $NH_2$ or halo.

3. The compound of claim 2, wherein X is:

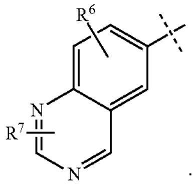
.

4. The compound of claim 1, wherein $NR^8R^9$ is selected from the group consisting of $NH_2$, $NHCH_3$, $N(CH_3)_2$, $NHCH_2CH_2OH$, $NHCH(CH_3)CH_2OH$, $NHCH(CH_2OH)_2$, $NHCH(CH_2OH)(C_6H_5)$, $NHCOCH_3$, $NHCOCH_2CH_3$, $NHCOCH(CH_3)_2$, $NHCOC(CH_3)_3$,

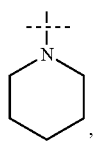
,
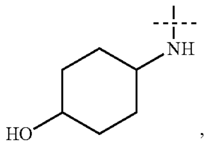
, and
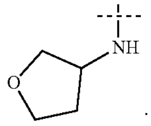
.

5. The compound of claim 2, wherein $R^6$ is H and $R^7$ is $NR^8R^9$.

6. The compound of claim 5, wherein $R^6$ is H and $R^7$ is $NH_2$.

7. The compound of claim 1, wherein X is selected from the group consisting of:

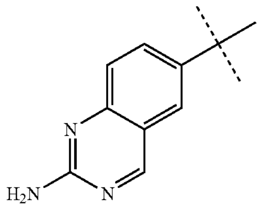
,
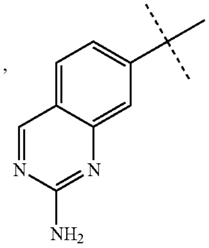
,
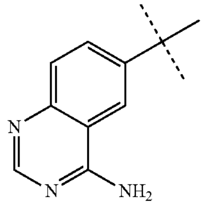
,
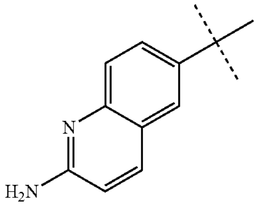
,
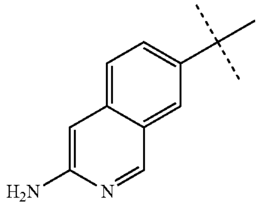
,
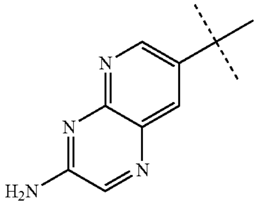
,
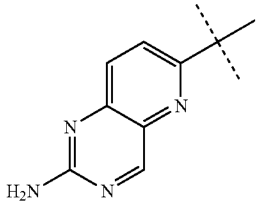
,
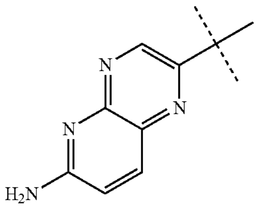
,
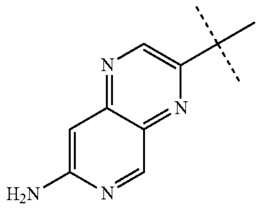
,
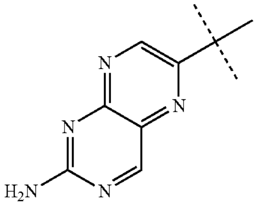
,
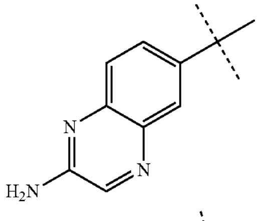
,
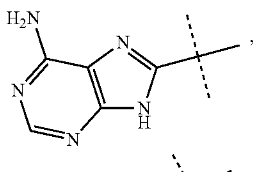
,
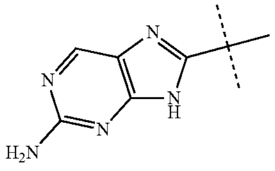
,
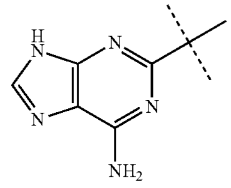

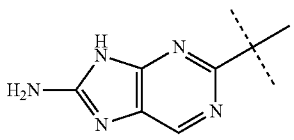

-continued
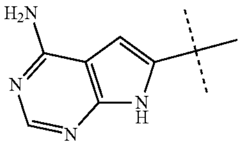
,
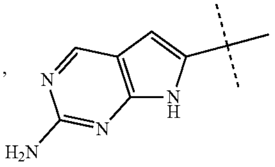
,
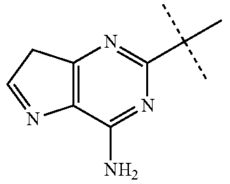
,
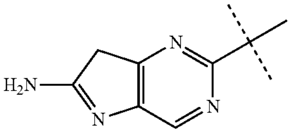
,
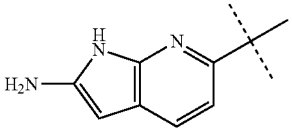
,
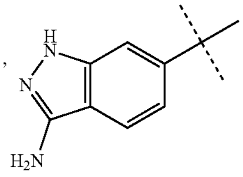
,
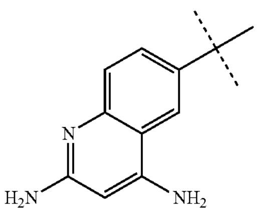
,
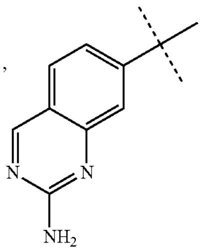
,
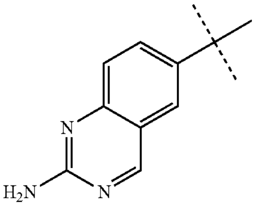
,
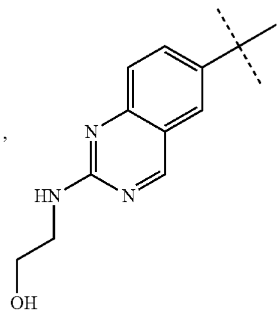
,
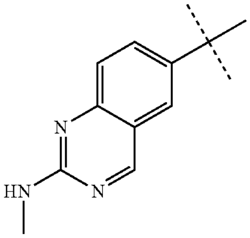
,
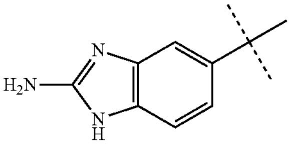
,
-continued
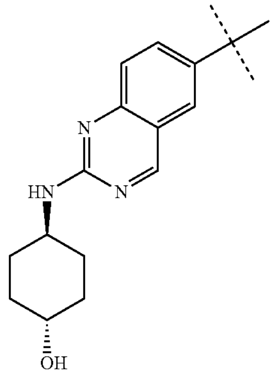
,
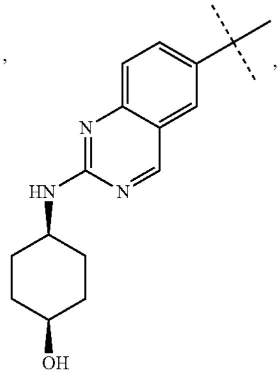
,
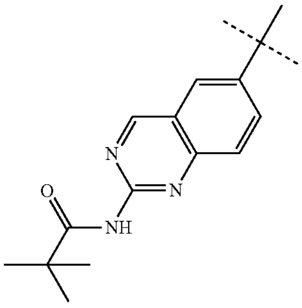
,
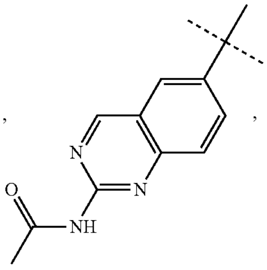
,
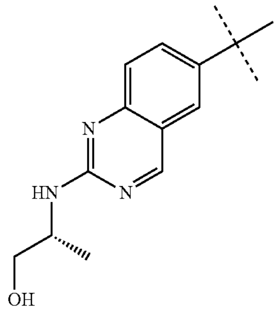
,
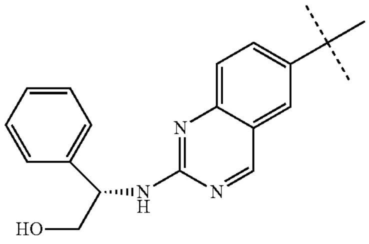
, and
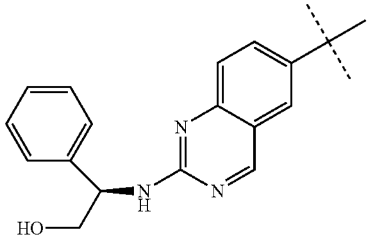
.

8. The compound of claim 1, wherein Y is selected from the group consisting of:
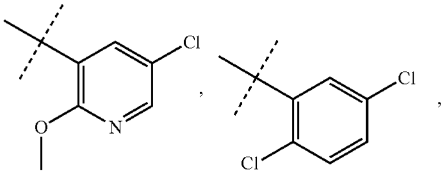
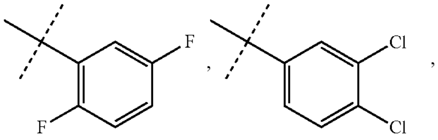
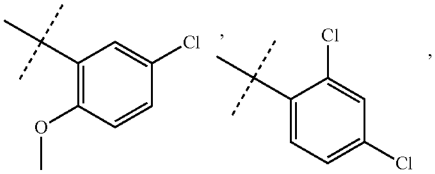
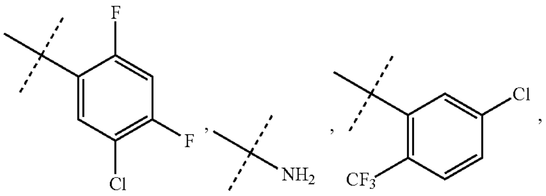
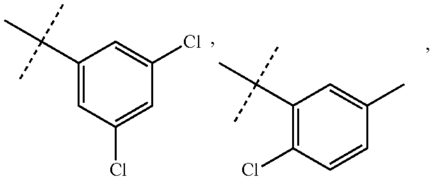
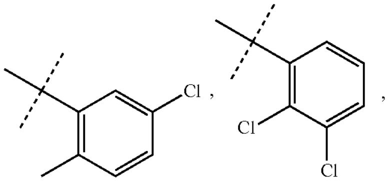
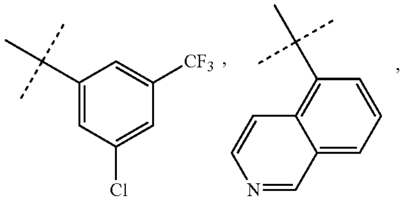
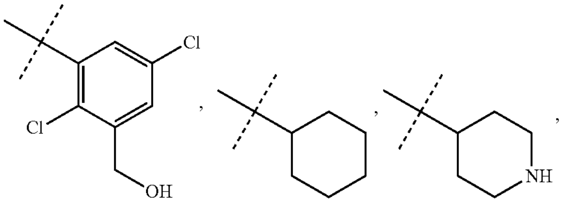
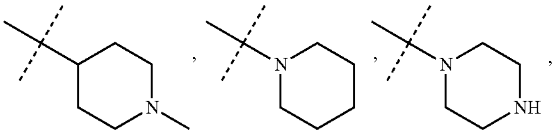
-continued
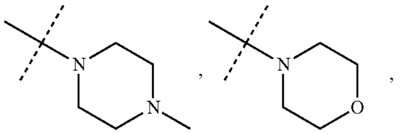
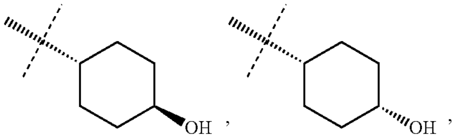
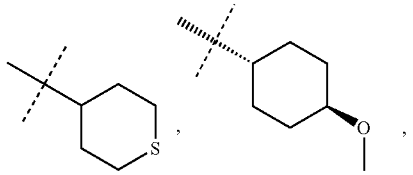
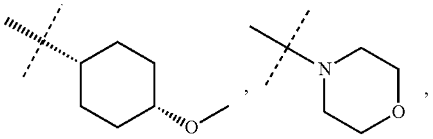
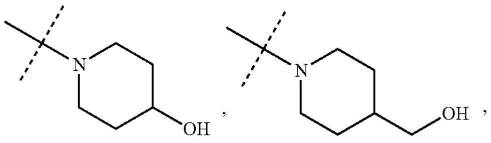
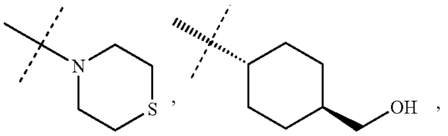
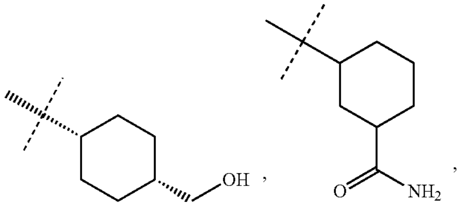
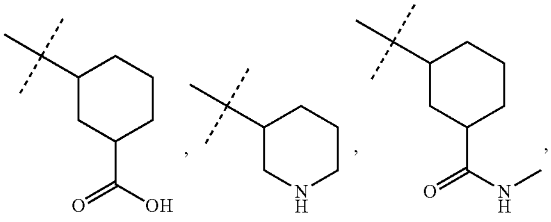
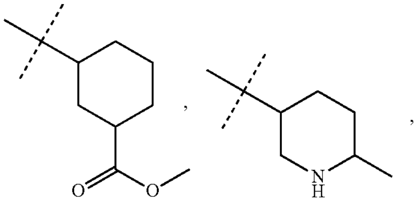
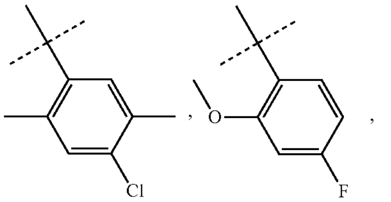

-continued

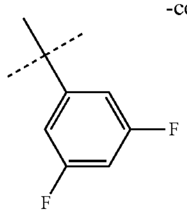

, and

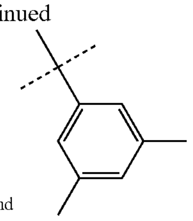

.

9. The compound of claim 1, which is a compound of formula (1b):

(1b)

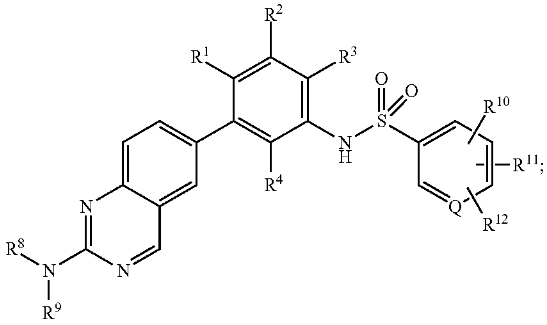

or a salt thereof, wherein

Q is N, C or CH, and $R^{10}$, $R^{11}$ and $R^{12}$ are independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH, wherein $R^{13}$ and $R^{14}$ are independently H or $C_{1-3}$ alkyl.

10. The compound of claim 1, which is a compound of formula (3a):

(3a)

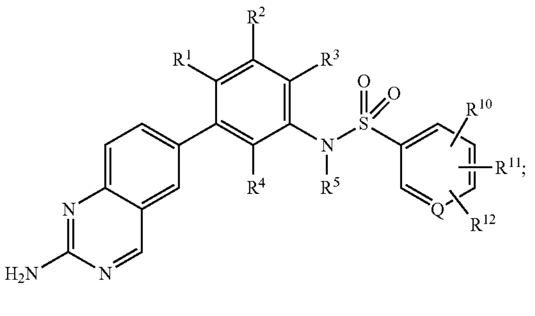

or a salt thereof, wherein

Q is N, C or CH, and $R^{10}$, $R^{11}$ and $R^{12}$ are independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH, wherein $R^{13}$ and $R^{14}$ are independently H or $C_{1-3}$ alkyl.

11. The compound of claim 1, which is a compound of formula (4a):

(4a)

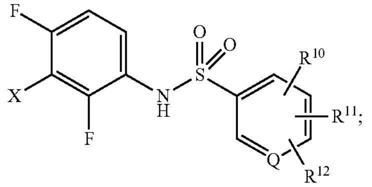

or a salt thereof, wherein

Q is N, C or CH, and $R^{10}$, $R^{11}$ and $R^{12}$ are independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH, wherein $R^{13}$ and $R^{14}$ are independently H or $C_{1-3}$ alkyl.

12. The compound of claim 1, which is a compound of formula (4b):

(4b)

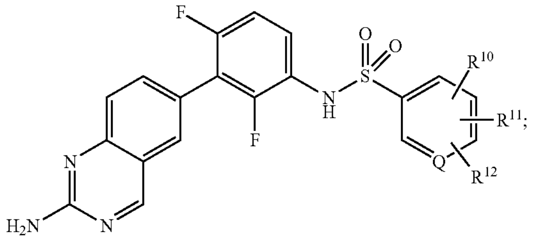

or a salt thereof, wherein

Q is N, C or CH, and $R^{10}$, $R^{11}$ and $R^{12}$ are independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH, wherein $R^{13}$ and $R^{14}$ are independently H or $C_{1-3}$ alkyl.

13. The compound of claim 1, wherein Q is N.

14. The compound of claim 1, wherein $R^{10}$, $R^{11}$ and $R^{12}$ are independently selected from the group consisting of: H, Cl, F, $OCH_3$, $CF_3$, $CH_3$, $CH_2OH$, OH, $CONH_2$, COOH, $CONHCH_3$ and $COOCH_3$.

15. The compound of claim 1, wherein the moiety:

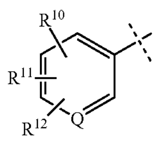

is selected from the group consisting of:

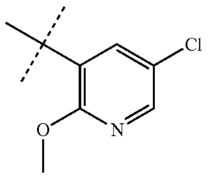 , 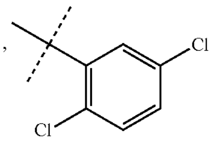 ,

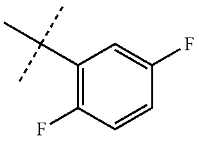 , 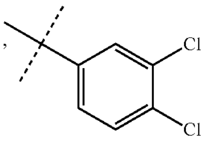 ,

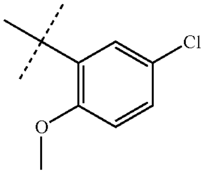 , 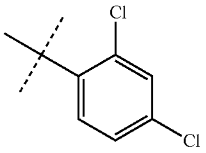 ,

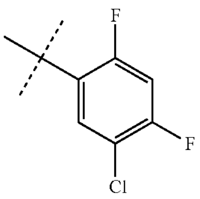 , 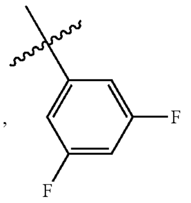 ,

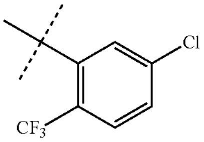 , 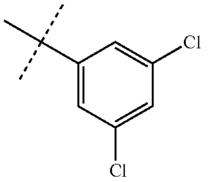 ,

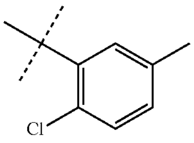 , 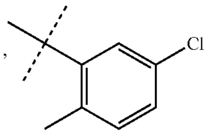 , 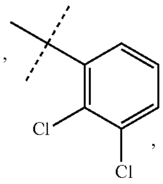 ,

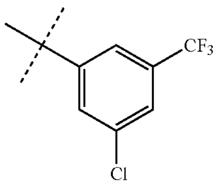 , 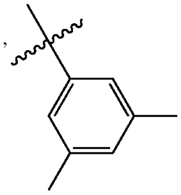 ,

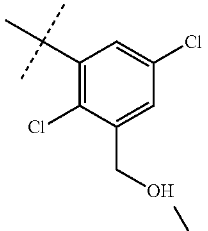 , 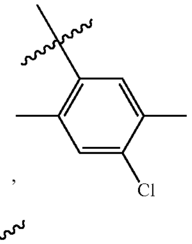 , and

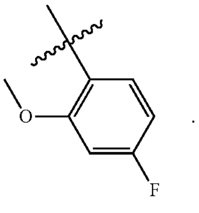 .

16. The compound of claim 15, wherein the moiety:

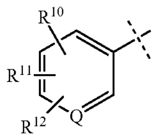

is:

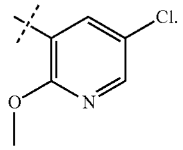

17. The compound of claim 1, wherein $R^1$, $R^2$, $R^3$ and $R^4$ are independently selected from the group consisting of H, F and $CH_3$.

18. The compound of claim 17, wherein $R^1$ and $R^4$ are F and $R^2$ and $R^3$ are H.

19. The compound of claim 1, wherein $R^5$ is H.

20. The compound of claim 1, which is a compound of formula (5b) or (5c):

(5b)

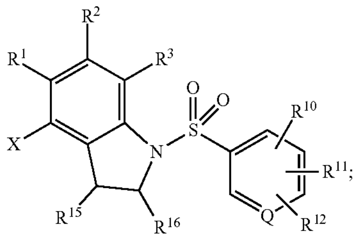

(5c)

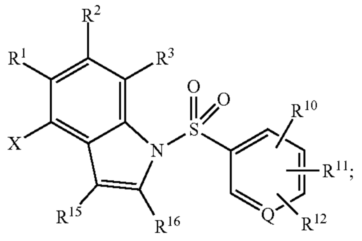

or a salt thereof, wherein

Q is N, C or CH;

$R^{10}$, $R^{11}$ and $R^{12}$ are independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH, wherein $R^{13}$ and $R^{14}$ are independently H or $C_{1-3}$ alkyl; and $R^{15}$ and $R^{16}$ are independently selected from H, halo and $C_{1-3}$ alkyl optionally substituted with 1 to 6 fluoro.

21. The compound according to claim 1, which is a compound of formula (5d) or (5e):

(5d)

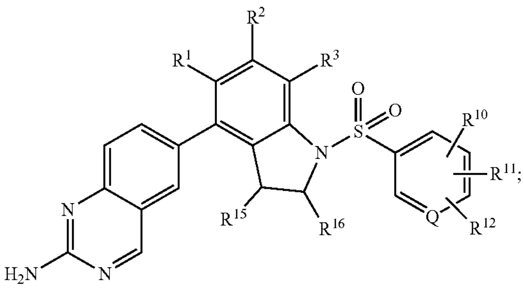

-continued (5e)

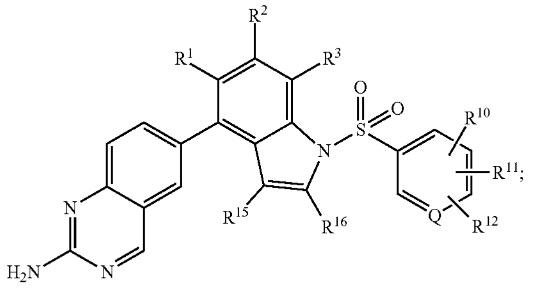

or a salt thereof, wherein

Q is N, C or CH;

$R^{10}$, $R^{11}$ and $R^{12}$ are independently selected from the group consisting of: H, halo, OH, CN, —C(O)$NR^{13}R^{14}$, —$NR^{13}COR^{14}$, —C(O)$OR_{13}$, $C_{1-6}$ alkyl, $C_{1-6}$ alkoxy, wherein the $C_{1-6}$ alkyl and $C_{1-6}$ alkoxy are optionally substituted with 1-6 substituents selected from the group consisting of halo and OH, wherein $R^{13}$ and $R^{14}$ are independently H or $C_{1-3}$ alkyl; and $R^{15}$ and $R^{16}$ are independently selected from H, halo and $C_{1-3}$ alkyl optionally substituted with 1 to 6 fluoro.

22. A compound selected from the group consisting of:

N-(3-(2-aminoquinazolin-6-yl)-2,4-difluorophenyl)-5-chloro-2-methoxypyridine-3-sulfonamide
N-[3-(2-aminoquinazolin-6-yl)-2,4-difluorophenyl]-2,5-dichlorobenzene-1-sulfonamide
N-{3-[(2-aminopyrimidin-5-yl)ethynyl]-2,4-difluorophenyl}-5-chloro-2-methoxypyridine-3-carboxamide
N-{3-[6-(2-aminopyrimidin-5-yl)pyridin-3-yl]-2,4-difluorophenyl}-5-chloro-2-methoxypyridine-3-sulfonamide
N-[3-(2-aminoquinazolin-7-yl)-2,4-difluorophenyl]-2,5-dichlorobenzene-1-sulfonamide
N-[3-(2-aminoquinazolin-7-yl)-2,4-difluorophenyl]-5-chloro-2-methoxypyridine-3-sulfonamide
5-({3-[5-(5-chloro-2-methoxypyridin-3-yl)-1,3,4-oxadiazol-2-yl]-2,6-difluorophenyl}ethynyl)pyrimidin-2-amine
N-[3-(2-aminoquinazolin-6-yl)-2,4-difluorophenyl]-2,5-difluorobenzene-1-sulfonamide
N-[3-(2-aminoquinazolin-6-yl)-2,4-difluorophenyl]-3,4-dichlorobenzene-1-sulfonamide
N-[3-(2-aminoquinazolin-6-yl)-2,4-difluorophenyl]-5-chloro-2-methoxybenzene-1-sulfonamide
N-[3-(2-aminoquinazolin-6-yl)-2-methylphenyl]-2,5-dichlorobenzene-1-sulfonamide
N-[3-(2-aminoquinazolin-6-yl)-2,6-difluorophenyl]-2,5-dichlorobenzene-1-sulfonamide
N-[3-(2-aminoquinazolin-6-yl)-2-fluorophenyl]-2,5-dichlorobenzene-1-sulfonamide
N-[3-(2-aminoquinazolin-6-yl)-5-fluorophenyl]-2,5-dichlorobenzene-1-sulfonamide
N-[3-(2-aminoquinazolin-6-yl)-2,4-difluorophenyl]-2,4-dichlorobenzene-1-sulfonamide
N-[3-(2-aminoquinazolin-6-yl)-4-methylphenyl]-2,5-dichlorobenzene-1-sulfonamide
N-[3-(4-aminoquinazolin-6-yl)-2,4-difluorophenyl]-2,5-dichlorobenzene-1-sulfonamide
2,5-dichloro-N-[2,4-difluoro-3-(7-fluoro-1H-benzimidazol-5-yl)phenyl]benzene-1-sulfonamide
N-[3-(2-aminoquinazolin-6-yl)-4-fluorophenyl]-5-chloro-2-methoxypyridine-3-sulfonamide
N-[3-(2-aminoquinolin-6-yl)-2,4-difluorophenyl]-5-chloro-2-methoxypyridine-3-sulfonamide
N-[3-(3-aminoisoquinolin-7-yl)-2,4-difluorophenyl]-5-chloro-2-methoxypyridine-3-sulfonamide
N-[3-(2-aminopyrido[2,3-d]pyrimidin-6-yl)-2,4-difluorophenyl]-5-chloro-2-methoxypyridine-3-sulfonamide
N-[3-(2-aminopyrido[3,2-d]pyrimidin-6-yl)-2,4-difluorophenyl]-5-chloro-2-methoxypyridine-3-sulfonamide
N-[3-(6-aminopyrido[2,3-b]pyrazin-2-yl)-2,4-difluorophenyl]-5-chloro-2-methoxypyridine-3-sulfonamide
N-[3-(7-aminopyrido[3,4-b]pyrazin-3-yl)-2,4-difluorophenyl]-5-chloro-2-methoxypyridine-3-sulfonamide
N-[3-(2-aminopteridin-6-yl)-2,4-difluorophenyl]-5-chloro-2-methoxypyridine-3-sulfonamide
N-[3-(2-aminoquinoxalin-6-yl)-2,4-difluorophenyl]-5-chloro-2-methoxypyridine-3-sulfonamide
N-[3-(6-amino-9H-purin-8-yl)-2,4-difluorophenyl]-5-chloro-2-methoxypyridine-3-sulfonamide
N-[3-(2-amino-9H-purin-8-yl)-2,4-difluorophenyl]-5-chloro-2-methoxypyridine-3-sulfonamide -continued N-[3-(6-amino-9H-purin-2-yl)-2,4-difluorophenyl]-5-chloro-2-methoxypyridine-3-sulfonamide
N-[3-(8-amino-9H-purin-2-yl)-2,4-difluorophenyl]-5-chloro-2-methoxypyridine-3-sulfonamide
5-chloro-N-[2,4-difluoro-3-(7H-pyrrolo[2,3-d]pyrimidin-6-yl)phenyl]-2-methoxypyridine-3-sulfonamide
5-chloro-N-[2,4-difluoro-3-(7H-pyrrolo[3,2-d]pyrimidin-2-yl)phenyl]-2-methoxypyridine-3-sulfonamide
N-[3-(4-amino-7H-pyrrolo[2,3-d]pyrimidin-6-yl)-2,4-difluorophenyl]-5-chloro-2-methoxypyridine-3-sulfonamide
N-[3-(2-amino-7H-pyrrolo[2,3-d]pyrimidin-6-yl)-2,4-difluorophenyl]-5-chloro-2-methoxypyridine-3-sulfonamide
N-[3-(4-amino-7H-pyrrolo[3,2-d]pyrimidin-2-yl)-2,4-difluorophenyl]-5-chloro-2-methoxypyridine-3-sulfonamide
N-[3-(6-amino-7H-pyrrolo[3,2-d]pyrimidin-2-yl)-2,4-difluorophenyl]-5-chloro-2-methoxypyridine-3-sulfonamide
5-chloro-N-[2,4-difluoro-3-(1H-indazol-6-yl)phenyl]-2-methoxypyridine-3-sulfonamide
5-chloro-N-[2,4-difluoro-3-(1H-pyrrolo[2,3-b]pyridin-6-yl)phenyl]-2-methoxypyridine-3-sulfonamide
N-[3-(2-amino-1H-pyrrolo[2,3-b]pyridin-6-yl)-2,4-difluorophenyl]-5-chloro-2-methoxypyridine-3-sulfonamide
N-[3-(4-aminoquinazolin-6-yl)-2,4-difluorophenyl]-5-chloro-2-methoxypyridine-3-sulfonamide
N-[3-(3-amino-1H-indazol-6-yl)-2,4-difluorophenyl]-5-chloro-2-methoxypyridine-3-sulfonamide
5-chloro-N-[3-(2,4-diaminoquinolin-6-yl)-2,4-difluorophenyl]-2-methoxypyridine-3-sulfonamide
N-[3-(2-aminoquinazolin-8-yl)-2,4-difluorophenyl]-5-chloro-2-methoxypyridine-3-sulfonamide
N-[3-(2-aminoquinazolin-5-yl)-2,4-difluorophenyl]-5-chloro-2-methoxypyridine-3-sulfonamide
5-chloro-N-(2,4-difluoro-3-{2-[(2-hydroxyethyl)amino]quinazolin-6-yl}phenyl)-2-methoxypyridine-3-sulfonamide
5-chloro-N-{2,4-difluoro-3-[2-(methylamino)quinazolin-6-yl]phenyl}-2-methoxypyridine-3-sulfonamide
N-[3-(1H-benzimidazol-5-yl)-2,4-difluorophenyl]-5-chloro-2-methoxypyridine-3-sulfonamide
N-[3-(2-amino-1H-benzimidazol-5-yl)-2,4-difluorophenyl]-5-chloro-2-methoxypyridine-3-sulfonamide
5-chloro-N-[2,4-difluoro-3-(7-fluoro-1H-benzimidazol-5-yl)phenyl]-2-methoxypyridine-3-sulfonamide
N-[3-(2-aminoquinazolin-6-yl)-2-methylphenyl]-5-chloro-2-methoxypyridine-3-sulfonamide
N-[3-(2-aminoquinazolin-6-yl)-2-fluorophenyl]-5-chloro-2-methoxypyridine-3-sulfonamide
N-[3-(2-aminoquinazolin-6-yl)-5-fluorophenyl]-5-chloro-2-methoxypyridine-3-sulfonamide
N-[3-(2-aminoquinazolin-6-yl)-2,6-difluorophenyl]-5-chloro-2-methoxypyridine-3-sulfonamide
N-[3-(2-aminoquinazolin-6-yl)-2,4-difluorophenyl]-5-chloro-2,4-difluorobenzene-1-sulfonamide
N-[3-(2-aminoquinazolin-6-yl)-2,4-difluorophenyl]sulfuric diamide
N-[3-(2-aminoquinazolin-6-yl)-4-fluorophenyl]-2,5-dichlorobenzene-1-sulfonamide
N-[3-(2-aminoquinazolin-6-yl)-2,4-difluorophenyl]-5-chloro-2-(trifluoromethyl)benzene-1-sulfonamide
N-[3-(2-aminoquinazolin-6-yl)-2,4-difluorophenyl]-3,5-dichlorobenzene-1-sulfonamide
N-[3-(2-aminoquinazolin-6-yl)-2,4-difluorophenyl]-2-chloro-5-methylbenzene-1-sulfonamide
N-[3-(2-aminoquinazolin-6-yl)-2,4-difluorophenyl]-5-chloro-2-methylbenzene-1-sulfonamide
N-[3-(2-aminoquinazolin-6-yl)-2,4-difluorophenyl]-2,3-dichlorobenzene-1-sulfonamide
N-[3-(2-aminoquinazolin-6-yl)-2,4-difluorophenyl]-3-chloro-5-(trifluoromethyl)benzene-1-sulfonamide
N-[3-(2-aminoquinazolin-6-yl)-2,4-difluorophenyl]isoquinoline-5-sulfonamide
5-chloro-N-[2,4-difluoro-3-(2-{[(1r,4r)-4-hydroxycyclohexyl]amino}quinazolin-6-yl)phenyl]-2-methoxypyridine-3-sulfonamide
5-chloro-N-[2,4-difluoro-3-(2-{[(2R)-1-hydroxypropan-2-yl]amino}quinazolin-6-yl)phenyl]-2-methoxypyridine-3-sulfonamide
2,5-dichloro-N-[2,4-difluoro-3-(2-{[(1r,4r)-4-hydroxycyclohexyl]amino}quinazolin-6-yl)phenyl]benzene-1-sulfonamide
2,5-dichloro-N-[2,4-difluoro-3-(2-{[(2R)-1-hydroxypropan-2-yl]amino}quinazolin-6-yl)phenyl]benzene-1-sulfonamide
2,5-dichloro-N-[2,4-difluoro-3-(2-{[(1r,4r)-4-hydroxycyclohexyl]amino}quinazolin-6-yl)phenyl]-3-(hydroxymethyl)benzene-1-sulfonamide
2,5-dichloro-N-[2,4-difluoro-3-(2-{[(2R)-1-hydroxypropan-2-yl]amino}quinazolin-6-yl)phenyl]-3-(hydroxymethyl)benzene-1-sulfonamide
6-[1-(5-chloro-2-methoxypyridine-3-sulfonyl)-5-fluoro-1H-indol-4-yl]quinazolin-2-amine
6-[1-(5-chloro-2-methoxypyridine-3-sulfonyl)-1H-indol-4-yl]quinazolin-2-amine -continued

| |
|---|
| 6-[1-(5-chloro-2-methoxypyridine-3-sulfonyl)-5-fluoro-2,3-dihydro-1H-indol-4-yl]quinazolin-2-amine |
| 6-[1-(5-chloro-2-methoxypyridine-3-sulfonyl)-2,3-dihydro-1H-indol-4-yl]quinazolin-2-amine |
| 6-[1-(2,5-dichlorobenzene-1-sulfonyl)-5-fluoro-1H-indol-4-yl]quinazolin-2-amine |
| 6-[1-(2,5-dichlorobenzene-1-sulfonyl)-1H-indol-4-yl]quinazolin-2-amine |
| {3-[4-(2-aminoquinazolin-6-yl)-5-fluoro-1H-indole-1-sulfonyl]-2,5-dichlorophenyl}methanol |
| 6-[1-(2,5-dichlorobenzene-1-sulfonyl)-5-fluoro-2,3-dihydro-1H-indol-4-yl]quinazolin-2-amine |
| 6-[1-(2,5-dichlorobenzene-1-sulfonyl)-2,3-dihydro-1H-indol-4-yl]quinazolin-2-amine |
| {3-[4-(2-aminoquinazolin-6-yl)-5-fluoro-2,3-dihydro-1H-indole-1-sulfonyl]-2,5-dichlorophenyl}methanol |
| N-[3-(2-aminoquinazolin-6-yl)-2,4-difluorophenyl]cyclohexanesulfonamide |
| N-[3-(2-aminoquinazolin-6-yl)-2,4-difluorophenyl]piperidine-4-sulfonamide |
| N-[3-(2-aminoquinazolin-6-yl)-2,4-difluorophenyl]-1-methylpiperidine-4-sulfonamide |
| N-[3-(2-aminoquinazolin-6-yl)-2,4-difluorophenyl]piperidine-1-sulfonamide |
| N-[3-(2-aminoquinazolin-6-yl)-2,4-difluorophenyl]piperazine-1-sulfonamide |
| N-[3-(2-aminoquinazolin-6-yl)-2,4-difluorophenyl]-4-methylpiperazine-1-sulfonamide |
| N-[3-(2-aminoquinazolin-6-yl)-2,4-difluorophenyl]oxane-4-sulfonamide |
| (1r,4r)-N-[3-(2-aminoquinazolin-6-yl)-2,4-difluorophenyl]-4-hydroxycyclohexane-1-sulfonamide |
| (1s,4s)-N-[3-(2-aminoquinazolin-6-yl)-2,4-difluorophenyl]-4-hydroxycyclohexane-1-sulfonamide |
| N-[3-(2-aminoquinazolin-6-yl)-2,4-difluorophenyl]thiane-4-sulfonamide |
| (1r,4r)-N-[3-(2-aminoquinazolin-6-yl)-2,4-difluorophenyl]-4-methoxycyclohexane-1-sulfonamide |
| (1s,4s)-N-[3-(2-aminoquinazolin-6-yl)-2,4-difluorophenyl]-4-methoxycyclohexane-1-sulfonamide |
| N-[3-(2-aminoquinazolin-6-yl)-2,4-difluorophenyl]morpholine-4-sulfonamide |
| N-[3-(2-aminoquinazolin-6-yl)-2,4-difluorophenyl]-4-hydroxypiperidine-1-sulfonamide |
| N-[3-(2-aminoquinazolin-6-yl)-2,4-difluorophenyl]-4-(hydroxymethyl)piperidine-1-sulfonamide |
| N-[3-(2-aminoquinazolin-6-yl)-2,4-difluorophenyl]thiomorpholine-4-sulfonamide |
| (1r,4r)-N-[3-(2-aminoquinazolin-6-yl)-2,4-difluorophenyl]-4-(hydroxymethyl)cyclohexane-1-sulfonamide |
| (1s,4s)-N-[3-(2-aminoquinazolin-6-yl)-2,4-difluorophenyl]-4-(hydroxymethyl)cyclohexane-1-sulfonamide |
| 3-{[3-(2-aminoquinazolin-6-yl)-2,4-difluorophenyl]sulfamoyl}cyclohexane-1-carboxamide |
| 3-{[3-(2-aminoquinazolin-6-yl)-2,4-difluorophenyl]sulfamoyl}cyclohexane-1-carboxylic acid |
| N-[3-(2-aminoquinazolin-6-yl)-2,4-difluorophenyl]piperidine-3-sulfonamide |
| 3-{[3-(2-aminoquinazolin-6-yl)-2,4-difluorophenyl]sulfamoyl}-N-methylcyclohexane-1-carboxamide |
| methyl 3-{[3-(2-aminoquinazolin-6-yl)-2,4-difluorophenyl]sulfamoyl}cyclohexane-1-carboxylate |
| N-[3-(2-aminoquinazolin-6-yl)-2,4-difluorophenyl]-6-methylpiperidine-3-sulfonamide |
| N-(6-(3-((5-chloro-2-methoxypyridine)-3-sulfonamido)-2,6-difluorophenyl)quinazolin-2-yl)pivalamide |
| N-(6-(3((2,5-dichlorophenyl)sulfonamido)2,6-difluorophenyl)quinazolin-2-yl)acetamide |
| N-(3-(2-aminoquinolin-6-yl)-2,4-difluorophenyl)-2,5-dichlorobenzenesulfonamide |
| N-(3-(2-aminoquinazolin-6-yl)-2,4-difluorophenyl)-2,5-dichloro-3-(hydroxymethyl)benzenesulfonamide |
| N-(3-(2-aminoquinazolin-6-yl)-2,4-difluorophenyl)-4-chloro-2,5-dimethylbenzenesulfonamide |
| N-(3-(2-aminoquinazolin-6-yl)-2,4-difluorophenyl)-5-fluoro-2-methoxybenzenesulfonamide |
| N-(3-(2-aminoquinazolin-5-yl)-2,4-difluorophenyl)-2,5-dichlorobenzenesulfonamide |
| N-(3-(2-aminoquinazolin-6-yl)-2,4-difluorophenyl)-3,5-difluorobenzenesulfonamide |
| N-(3-(2-aminoquinazolin-6-yl)-2,4-difluorophenyl)-3,5-dimethylbenzenesulfonamide |
| N-(5-(3-((5-chloro-2-methoxypyridine)-3-sulfonamido)-2,6-difluorophenyl)quinazolin-2-yl)pivalamide |
| N-(3-(2-aminoquinazolin-6-yl)-2,4-difluorophenyl)-3,4-dimethoxybenzenesulfonamide |
| N-(3-(2-aminoquinazolin-6-yl)-2,4-difluorophenyl)-3-fluorobenzenesulfonamide |
| N-(3-(2-aminoquinazolin-6-yl)-2,4-difluorophenyl)-4-methoxy-3-methylbenzenesulfonamide |
| N-(3-(2-aminoquinazolin-6-yl)-2,4-difluorophenyl)-2-methoxy-5-methylbenzenesulfonamide |
| N-(3-(2-aminoquinazolin-6-yl)-2,4-difluorophenyl)-2,5-dimethoxybenzenesulfonamide |
| N-(3-(2-aminoquinazolin-6-yl)-2,4-difluorophenyl)-5-ethyl-2-methoxybenzenesulfonamide |
| N-(3-(2-aminoquinazolin-6-yl)-2,4-difluorophenyl)-2,5-bis(trifluoromethyl)benzenesulfonamide |
| N-(3-(2-aminoquinazolin-6-yl)-2,4-difluorophenyl)benzofuran-5-sulfonamide |
| N-(3-(2-aminoquinazolin-6-yl)-2,4-difluorophenyl)-3-fluoro-5-(trifluoromethyl)benzenesulfonamide |
| N-(3-(2-aminoquinazolin-6-yl)-2,4-difluorophenyl)-2,3-difluorobenzenesulfonamide |
| N-(3-(2-aminoquinazolin-6-yl)-2,4-difluorophenyl)-3-methylbenzenesulfonamide |

-continued

| |
|---|
| 2,5-dichloro-N-(3,5-difluoro-4-(2-((2-hydroxyethyl)amino)quinazolin-6-yl)pyridin-2-yl)benzenesulfonamide |
| 5-chloro-N-(2,4-difluoro-3-(2-(((1s,4s)-4-hydroxycyclohexyl)amino)quinazolin-6-yl)phenyl)-2-methoxypyridine-3-sulfonamide |
| N-(3-(2-aminoquinazolin-6-yl)-2,4-difluorophenyl)pyridine-3-sulfonamide |
| N-(3-(2-aminoquinazolin-6-yl)-2,4-dichlorophenyl)-5-chloro-2-methoxypyridine-3-sulfonamide |
| N-(3-(2-aminoquinazolin-6-yl)-2,4-difluorophenyl)-3,4-difluorobenzenesulfonamide |
| N-(3-(2-aminoquinazolin-6-yl)-2,4-difluorophenyl)-5-fluoro-2-methylbenzenesulfonamide |
| 2,5-dichloro-N-(2,4-difluoro-3-(2-((2-hydroxyethyl)amino)quinazolin-6-yl)phenyl)-3-(hydroxymethyl)benzenesulfonamide |
| N-(3-(2-aminoquinazolin-6-yl)-2,4-difluorophenyl)-2-fluoro-5-(trifluoromethyl)benzenesulfonamide |
| N-(3-(2-aminoquinazolin-6-yl)-2,4-difluorophenyl)-4-fluoro-3-(trifluoromethyl)benzenesulfonamide |
| N-(3-(2-aminoquinazolin-6-yl)-2,4-difluorophenyl)-4-chloro-2-(trifluoromethyl)benzenesulfonamide |
| N-(3-(2-aminoquinazolin-6-yl)-2,4-difluorophenyl)quinoxaline-5-sulfonamide |
| N-(3-(2-aminoquinazolin-6-yl)-2,4-difluorophenyl)-3-(trifluoromethoxy)benzenesulfonamide |
| N-(3-(2-aminoquinazolin-6-yl)-2,4-difluorophenyl)thiophene-3-sulfonamide |
| N-(3-(2-aminoquinazolin-6-yl)-2,4-difluorophenyl)-3-isopropylbenzenesulfonamide |
| N-(3-(2-aminoquinazolin-6-yl)-2,4-difluorophenyl)thiophene-2-sulfonamide |
| N-(3-(2-aminoquinazolin-6-yl)-2,4-difluorophenyl)-4-fluoro-3-methoxybenzenesulfonamide |
| N-(3-(2-aminoquinazolin-6-yl)-2,4-difluorophenyl)-3,5-bis(trifluoromethyl)benzenesulfonamide |
| N-(3-(2-aminoquinazolin-6-yl)-2,4-difluorophenyl)-3-(trifluoromethyl)benzenesulfonamide |
| N-(3-(2-aminoquinazolin-6-yl)-2,4-difluorophenyl)-4-chloro-3-fluorobenzenesulfonamide |
| N-(3-(2-aminoquinazolin-6-yl)-2,4-difluorophenyl)-3-chloro-4-methylbenzenesulfonamide |
| N-(3-(2-aminoquinazolin-6-yl)-2,4-difluorophenyl)-3-chloro-4-methoxybenzenesulfonamide |
| N-(3-(2-aminoquinazolin-6-yl)-2,4-difluorophenyl)-4-chloro-3-(trifluoromethyl)benzenesulfonamide |
| N-(3-(2-aminoquinazolin-6-yl)-2,4-difluorophenyl)-2,4,5-trichlorobenzenesulfonamide |
| 5-chloro-N-(3-(2-((1,3-dihydroxypropan-2-yl)amino)quinazolin-6-yl)-2,4-difluorophenyl)-2-methoxypyridine-3-sulfonamide |
| (R)-5-chloro-N-(2,4-difluoro-3-(2-((2-hydroxy-1-phenylethyl)amino)quinazolin-6-yl)phenyl)-2-methoxypyridine-3-sulfonamide |
| 5-chloro-N-(3-(2-(dimethylamino)quinazolin-6-yl)-2,4-difluorophenyl)-2-methoxypyridine-3-sulfonamide |
| 5-chloro-N-(2,4-difluoro-3-(2-(piperidin-1-yl)quinazolin-6-yl)phenyl)-2-methoxypyridine-3-sulfonamide |
| (S)-5-chloro-N-(2,4-difluoro-3-(2-((1-hydroxypropan-2-yl)amino)quinazolin-6-yl)phenyl)-2-methoxypyridine-3-sulfonamide |
| N-(3-(2-aminoquinazolin-6-yl)-2,4-difluorophenyl)-3-chloro-4-fluorobenzenesulfonamide |
| N-(3-(2-aminoquinazolin-6-yl)-2,4-difluorophenyl)-3-fluoro-4-methylbenzenesulfonamide |
| N-(3-(2-aminoquinazolin-6-yl)-2,4-difluorophenyl)-4-fluoro-3-methylbenzenesulfonamide |
| N-(3-(2-aminoquinazolin-6-yl)-2,4-difluorophenyl)-2,3-dihydro-1H-indene-5-sulfonamide |
| 2,5-dichloro-N-(2,4-difluoro-3-(2-(methylamino)quinazolin-6-yl)phenyl)-3-(hydroxymethyl)benzenesulfonamide |
| (S)-5-chloro-N-(2,4-difluoro-3-(2-((2-hydroxy-1-phenylethyl)amino)quinazolin-6-yl)phenyl)-2-methoxypyridine-3-sulfonamide |
| 5-chloro-N-(2,4-difluoro-3-(2-(((1r,4r)-4-hydroxycyclohexyl)amino)quinazolin-6-yl)phenyl)-2-(trifluoromethyl)benzenesulfonamide |
| 5-chloro-N-(2,4-difluoro-3-(2-(((1s,4s)-4-hydroxycyclohexyl)amino)quinazolin-6-yl)phenyl)-2-(trifluoromethyl)benzenesulfonamide |
| (S)-5-chloro-N-(2,4-difluoro-3-(2-((2-hydroxy-1-phenylethyl)amino)quinazolin-6-yl)phenyl)-2-(trifluoromethyl)benzenesulfonamide |
| (R)-5-chloro-N-(2,4-difluoro-3-(2-((2-hydroxy-1-phenylethyl)amino)quinazolin-6-yl)phenyl)-2-(trifluoromethyl)benzenesulfonamide |
| 2,5-dichloro-N-(2,4-difluoro-3-(2-((tetrahydrofuran-3-yl)amino)quinazolin-6-yl)phenyl)benzenesulfonamide |

or a salt thereof.

23. A pharmaceutically acceptable salt of a compound of claim 1.

24. A pharmaceutical composition comprising a compound of claim 1, or a salt thereof, and a pharmaceutically acceptable excipient.

25. A method of treating a disease or disorder characterized by activation of GCN2 in an individual in need thereof, comprising administering to the individual an effective amount of a compound of claim 1, a salt thereof.

26. The method of claim 25, wherein the disease or disorder is cancer, a neurodegenerative disease, or a chronic infection.

27. The method of claim 25, further comprising administering a second therapeutic agent, wherein the second therapeutic agent is PEG-arginase, asparaginase, anti-angiogenic factors, cysteinase or sulfasalazine.

* * * * *